US012715878B2

(12) United States Patent
Stansfield et al.

(10) Patent No.: US 12,715,878 B2
(45) Date of Patent: Aug. 25, 2026

(54) TRICYCLIC PYRIMIDINES AS CYCLIN-DEPENDENT KINASE 7 (CDK7) INHIBITORS

(71) Applicant: JANSSEN PHARMACEUTICA NV, Beerse (BE)

(72) Inventors: Ian Stansfield, Saint-Germain-en-Laye (FR); Yannick Aimé Eddy Ligny, Sotteville-les-Rouen (FR); Yvan René Ferdinand Simonnet, Princeton, NJ (US); Nathalie Claudie Isabelle Amblard, Crestot (FR)

(73) Assignee: Janssen Pharmaceutica NV, Beerse (BE)

( * ) Notice: Subject to any disclaimer, the term of this patent is extended or adjusted under 35 U.S.C. 154(b) by 455 days.

(21) Appl. No.: 18/258,605

(22) PCT Filed: Dec. 17, 2021

(86) PCT No.: PCT/EP2021/086552

§ 371 (c)(1),
(2) Date: Jun. 21, 2023

(87) PCT Pub. No.: WO2022/136174

PCT Pub. Date: Jun. 30, 2022

(65) Prior Publication Data

US 2024/0109912 A1 Apr. 4, 2024

(30) Foreign Application Priority Data

Dec. 21, 2020 (EP) .................................... 20216100

(51) Int. Cl.

| | |
|---|---|
| *C07D 498/04* | (2006.01) |
| *A61P 35/02* | (2006.01) |
| *C07D 498/14* | (2006.01) |
| *C07D 519/00* | (2006.01) |

(52) U.S. Cl.

CPC ............ *C07D 498/04* (2013.01); *A61P 35/02* (2018.01); *C07D 498/14* (2013.01); *C07D 519/00* (2013.01)

(58) Field of Classification Search

CPC .. C07D 498/04; C07D 498/14; C07D 519/00; A61P 35/02

USPC .................................................... 514/210.18

See application file for complete search history.

(56) References Cited

U.S. PATENT DOCUMENTS

| | | | |
|---|---|---|---|
| 2007/0249583 | A1 | 10/2007 | Stein et al. |
| 2015/0018329 | A1 | 1/2015 | Eickhoff et al. |
| 2018/0110778 | A1 | 4/2018 | Gray et al. |
| 2018/0319801 | A1 | 11/2018 | Gray et al. |
| 2019/0315753 | A1 | 10/2019 | Ferguson et al. |
| 2024/0254138 | A1 | 8/2024 | Stansfield et al. |

FOREIGN PATENT DOCUMENTS

| | | | |
|---|---|---|---|
| CN | 104910137 | A | 9/2015 |
| CN | 116964061 | A | 10/2023 |
| JP | 2015-511952 | A | 4/2015 |
| JP | 2018-515434 | A | 6/2018 |
| JP | 2018-522866 | A | 8/2018 |
| JP | 2019-530724 | A | 10/2019 |
| JP | 2024-509864 | A | 3/2024 |
| WO | 2013/128028 | A1 | 9/2013 |
| WO | 2014/063068 | A1 | 4/2014 |
| WO | 2016/201370 | A1 | 12/2016 |

OTHER PUBLICATIONS

Berge et al., "Pharmaceutically Acceptable Salts," J. Pharm. Sci., vol. 66, 1997, ••-19.
Cahn et al., "Specification of Molecular Chirality", Angew. Chem. Int. Ed. Engl., vol. 5, 1966, 38••-415.
Gaoyuan et al., "Advances in Research on a Novel Antitumor Target CDK7 and its Inhibitors", vol. 45, No. 369, 2018, 129-132 (English Abstract Available).
Liang et al., "Recent progress in development of cyclin-dependent kinase 7 inhibitors for cancer therapy", Expert Opinion on Investigational Drugs, vol. 30, No. 1, Jan. 2, 2021, 61-76.
Sava et al., "CDK7 inhibitors as anticancer drugs," Cancer Metastasis and Review, vol. 39, No. 3, May 8, 2020, 805-823.

*Primary Examiner* — Kahsay Habte
(74) *Attorney, Agent, or Firm* — BakerHostetler

(57) ABSTRACT

The invention relates to pharmaceutical compounds of formula (I) and pharmaceutical compositions comprising said compounds, to processes for the preparation of said compounds and to the use of said compounds as inhibitors of cyclin-dependent kinase 7 (CDK7) and to their use in the treatment of diseases, e.g., cancer.

(I)

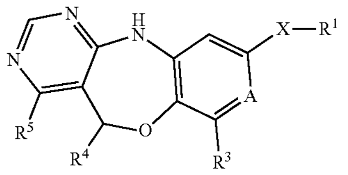

20 Claims, No Drawings

TRICYCLIC PYRIMIDINES AS CYCLIN-DEPENDENT KINASE 7 (CDK7) INHIBITORS

CROSS-REFERENCE TO RELATED APPLICATIONS

This application is the National Stage of International Patent Application No. PCT/EP2021/086552, filed Dec. 17, 2021, which claims the benefit of European Patent Application No. 20216100.6, filed Dec. 21, 2020, the entirety of which is Incorporated herein for any and all purposes.

FIELD OF THE INVENTION

The invention relates to pharmaceutical compounds and pharmaceutical compositions comprising said compounds, to processes for the preparation of said compounds and to the use of said compounds as inhibitors of cyclin-dependent kinase 7 (CDK7) and to their use in the treatment of diseases, e.g. cancer.

BACKGROUND OF THE INVENTION

The members of the cyclin-dependent kinase (CDK) family play critical regulatory roles in proliferation. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression. In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation. Together, the two functions of CDK7, i.e., CAK and CTD phosphorylation, support critical facets of cellular proliferation, cell cycling, and transcription.

Disruption of RNAP II CTD phosphorylation has been shown to preferentially affect proteins with short half-lives, including those of the anti-apoptotic BCL-2 family. Cancer cells have demonstrated ability to circumvent pro-cell death signaling through upregulation of BCL-2 family members. Therefore, inhibition of human CDK7 kinase activity is likely to result in anti-proliferative activity.

The discovery of selective inhibitors of CDK7 has been hampered by the high sequence and structural similarities of the kinase domain of CDK family members. Therefore, there is a need for the discovery and development of selective CDK7 inhibitors. Such CKD7 inhibitors hold promise as therapeutic agents for the treatment of chronic lymphocytic leukemia and other cancers.

SUMMARY OF THE INVENTION

The present invention relates to a compound of formula (I), including any tautomeric and stereochemically isomeric form, isotopically labeled derivative, or a pharmaceutically acceptable salt or solvate thereof:

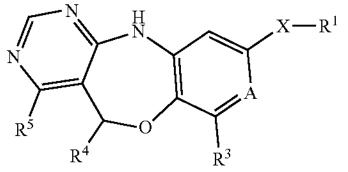

(I)

wherein,

X is a 4-7 membered non-aromatic heterocycle, a 4-10 membered non-aromatic bridged heterocycle, $C_{3-7}$cycloalkyl, $C_{5-7}$cycloalkenyl; wherein each of the cycles, independently, may be optionally substituted with —$C_{1-3}$alkyl;

$R^1$ is a 4-7 membered non-aromatic heterocycle having at least one nitrogen atom, wherein the at least one nitrogen atom is substituted with —C(═O)—CH═CH—$R^6$, or —C(═O)—CH—CH—$R^7$, and wherein the 4-7 membered non-aromatic heterocycle is optionally substituted with $C_{1-3}$alkyl, halo, or D; or $R^1$ is $C_{1-3}$alkyl substituted with —NH—C(═O)—CH═CH—$R^6$ or —NH—C(═O)—CH—CH—$R^7$;

A is a $CR^2$ or N;

$R^2$ is H, $C_{1-3}$alkyl, cyano, halo, or $C_{2-3}$alkynyl;

$R^3$ is $C_{1-3}$alkyl, H, halogen, $C_{2-3}$alkenyl, $C_{2-3}$alkynyl, cyano, $C_{3-7}$cycloalkyl; $C_{1-3}$ alkyl substituted with one, two, or three halo, hydroxy, carboxyl, amino, mono- or di($C_{1-6}$alkyl)amino; 1-imidazolyl, 2-imidazolyl, or 4-imidazolyl;

$R^4$ is $C_{1-3}$alkyl; $C_{1-3}$alkyl substituted with one, two, or three halo; H;

$R^5$ is a 4-7 membered saturated or partially unsaturated heterocycle, a 5-6 membered heteroaryl, or a 6-12 membered spiro-bicyclic heterocycle; wherein each of the cycles have one, two, or three heteroatoms selected from sulphur, nitrogen, and oxygen; and wherein, said sulphur, if present, is substituted with dioxo, or with oxo and imino;

said one, two, or three nitrogens, if present, may, each independently, be optionally substituted with $C_{1-3}$alkyl;

any one of the carbon atoms of the cycles may be optionally substituted with $C_{1-3}$alkyl, hydroxy$C_{1-3}$ alkyl, $C_{1-3}$alkoxy, oxo, $C_{1-3}$alkylsulfonyl, cyano, hydroxy, halo, carboxyl, mono- or di($C_{1-6}$alkyl) amino, polyhalo$C_{1-3}$alkyl, polyhalo$C_{1-3}$alkoxy, $C_{2-3}$alkenyl, and $C_{2-3}$alkynyl;

$R^6$ is H; —$C_{1-3}$alkyl optionally substituted with one, two, or three substituents selected from halo, D, and —$NR^{7a}R^{7b}$; wherein each of $R^{7a}$ and $R^{7b}$ is, independently, $C_{1-3}$alkyl; or $R^{7a}$ and $R^{7b}$ taken together form a heterocycle; and $R^7$ is —$C_{1-3}$alkyl optionally substituted with one, two, or three substituents selected from halo, D, and —$NR^{7a}R^{7b}$; wherein each of $R^{7a}$ and $R^{7b}$ is, independently, $C_{1-3}$alkyl, or $R^{7a}$ and $R^{7b}$ taken together form a heterocycle.

The present invention also relates to the compound of formula (I), including any tautomeric and stereochemically isomeric form, isotopically labeled derivative, or a pharmaceutically acceptable salt or solvate thereof, wherein, X is a 4-7 membered non-aromatic heterocycle, a 4-10 membered non-aromatic bridged heterocycle, $C_{4-7}$cycloalkyl, $C_{5-7}$cycloalkenyl; wherein each of the cycles, independently, may be optionally substituted with —$C_{1-3}$alkyl;

$R^1$ is a 4-7 membered non-aromatic heterocycle having at least one nitrogen atom, wherein the at least one nitrogen atom is substituted with —C(═O)—CH═CH—$R^6$, or —C(═O)—CH—CH—$R^7$, and wherein the 4-7 membered non-aromatic heterocycle is optionally substituted with $C_{1-3}$alkyl, halo, or D; or $R^1$ is $C_{1-3}$alkyl substituted with —NH—C(═O)—CH═CH—$R^6$ or —NH—C(═O)—CH—CH—$R^7$;

A is a $CR^2$ or N;

$R^2$ is H, $C_{1-3}$alkyl, or cyano;

$R^3$ is $C_{1-3}$alkyl, H, halogen, cyano, $C_{3-7}$cycloalkyl; or $C_{1-3}$alkyl substituted with one, two, or three halo;

$R^4$ is methyl or H;

$R^5$ a 4-7 membered saturated or partially unsaturated heterocycle, a 5-6 membered heteroaryl, or a 6-12 membered spiro-bicyclic heterocycle;

wherein each of the cycles have one, two, or three heteroatoms selected from sulphur, nitrogen, and oxygen; and wherein, said sulphur, if present, is substituted with dioxo, or with oxo and imino;

said one, two, or three nitrogens, if present, may, each independently, be optionally substituted with $C_{1-3}$alkyl;

any one of the carbon atoms of the cycles may be optionally substituted with $C_{1-3}$alkyl, hydroxy$C_{1-3}$alkyl, $C_{1-3}$alkoxy, oxo, $C_{1-3}$alkylsulfonyl, cyano, hydroxy, halo, carboxyl, mono- or di($C_{1-6}$alkyl)amino, polyhalo$C_{1-3}$alkyl, polyhalo$C_{1-3}$alkoxy, $C_{2-3}$alkenyl, and $C_{2-3}$alkynyl;

$R^6$ is H; —$C_{1-3}$alkyl optionally substituted with one, two, or three substituents selected from halo, D, and —$NR^{7a}R^{7b}$; wherein each of $R^{7a}$ and $R^{7b}$ is, independently, $C_{1-3}$alkyl; or $R^{7a}$ and $R^{7b}$ taken together form a heterocycle; and $R^7$ is —$C_{1-3}$alkyl optionally substituted with one, two, or three substituents selected from halo, D, and —$NR^{7a}R^{7b}$; wherein each of $R^{7a}$ and $R^{7b}$ is, independently, $C_{1-3}$alkyl; or $R^{7a}$ and $R^{7b}$ taken together form a heterocycle.

The compound may be a compound of formula (II), including any tautomeric and stereochemically isomeric form, isotopically labeled derivative, or a pharmaceutically acceptable salt or solvate thereof, (II)

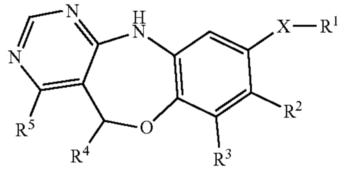

wherein each of X, $R^1$, $R^2$, $R^3$, $R^4$, and $R^5$, independently, is as defined herein above.

The compound may be a compound of formula (IIa), (IIb), (IIc), (IId), (IIe), or (IIf), including any tautomeric and stereochemically isomeric form, isotopically labeled derivative, or a pharmaceutically acceptable salt or solvate thereof:

(IIa)

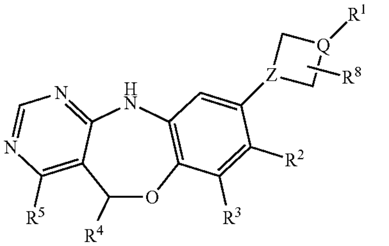

(IIb)

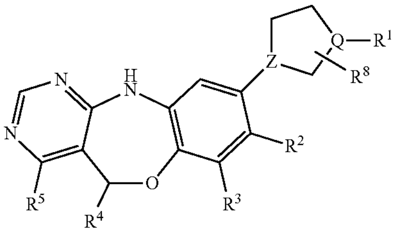

(IIc)

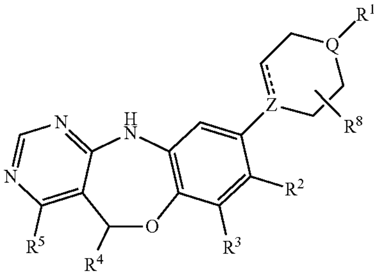

(IId)

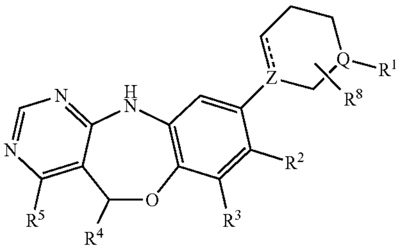

(IIe)

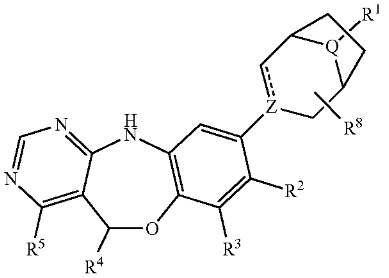

(IIf)

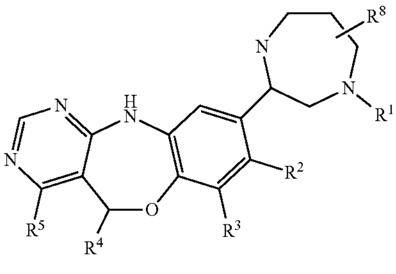

wherein in each of the compounds of formula (IIa), (IIb), (IIc), (IId), (IIe), or (IIf), each Q is, independently, CH or N;

each Z is, independently, CH or N;

each of $R^1$, $R^2$, $R^3$, $R^4$, and $R^5$, independently, is as defined herein above;

each $R^8$ is, independently, H or $-C_{1-3}$alkyl; and said $R^8$ may be bound to any carbon or nitrogen atom of the cycle; and each dashed bond is, independently, an optional double bond.

The compound may be a compound of formula (I), (II), (IIa), (IIb), (IIc), (IId), (IIe), or (IIf), with the substituents as defined herein above, wherein $R^1$ is selected from

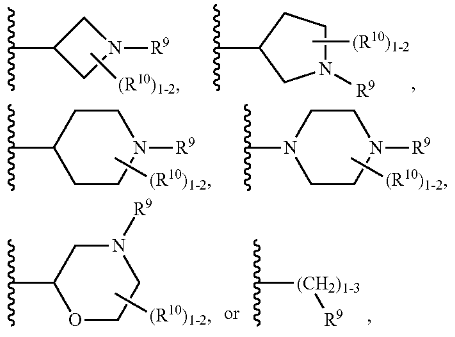

wherein each $R^9$ is, independently, $-C(=O)-CH=CH-R^6$, or $-C(=O)-CH-CH-R^7$;

each $R^{10}$ is, independently, H, $-C_{1-3}$alkyl, halo, or D; and said $R^{10}$ may be bound to any carbon atom of the cycle; and $R^5$ is selected from

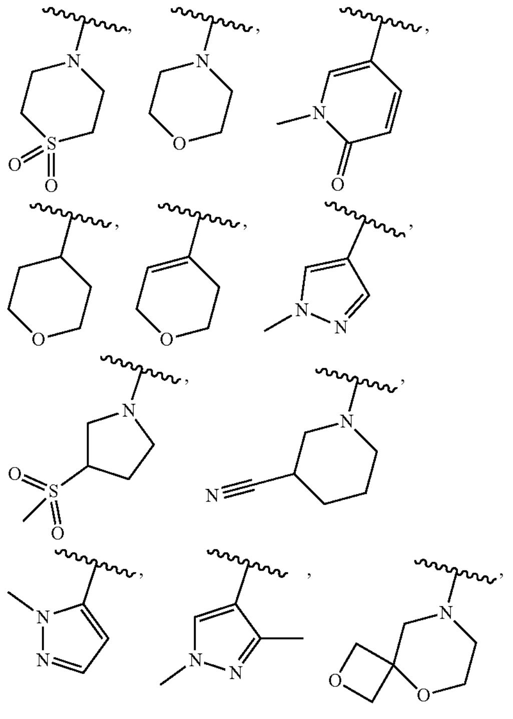

-continued

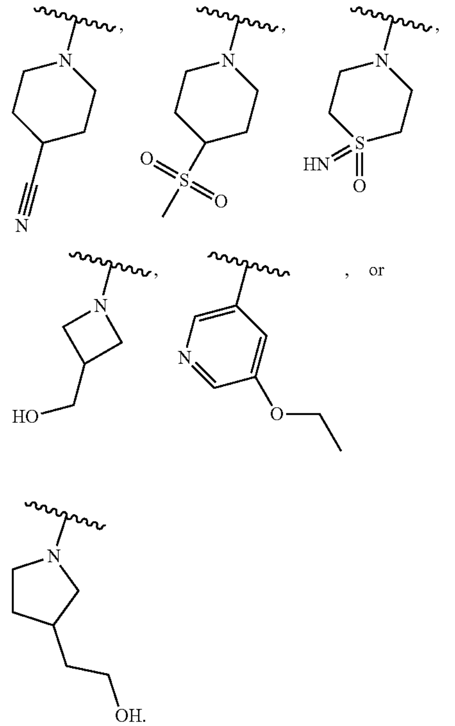

The compound may be a compound of formula (IIIa), (IIIb), (IIIc), (IIId), (IIIe), or (IIIf), including any tautomeric and stereochemically isomeric form, isotopically labeled derivative, or a pharmaceutically acceptable salt or solvate thereof:

(IIIa)

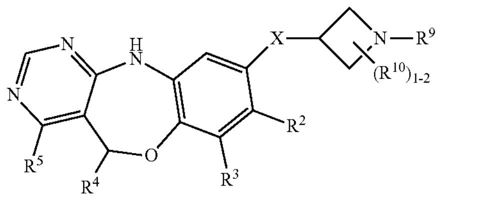

(IIIb)

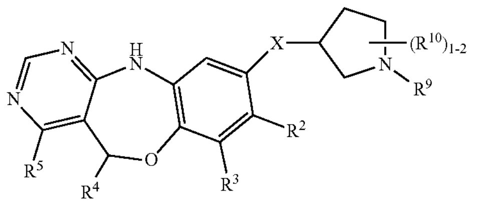

(IIIc)

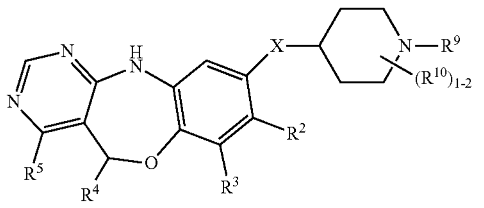

-continued (IIId)

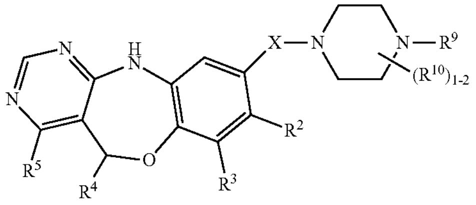

(IIIe)

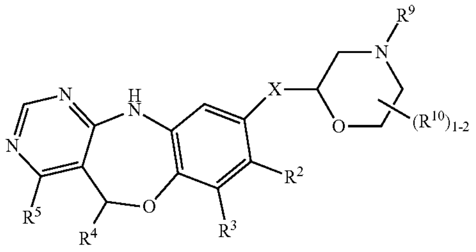

(IIIf)

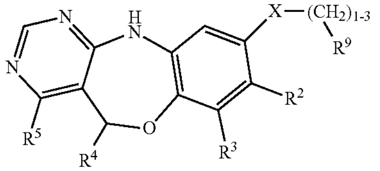

wherein each $R^9$ is, independently, —C(=O)—CH=CH—$R^6$, or —C(=O)—CH—CH—$R^7$; each $R^{10}$ is, independently, H, —$C_{1-3}$alkyl, halo, or D; and said $R^{10}$ may be bound to any carbon atom of the cycle; and each of $R^2$, $R^3$, $R^4$, $R^5$, $R^6$, and $R^7$, independently, is as defined herein above.

The compound may be a compound of formula (IVa), (IVb), (IVc), (IVd), (IVe), (IVf), (IVg), (IVh), (IVi), (IVj), (IVk), (IVl), (IVm), (IVn), (Ivo), (IVp), or (IVq), including any tautomeric and stereochemically isomeric form, isotopically labeled derivative, or a pharmaceutically acceptable salt or solvate thereof:

(IVa)

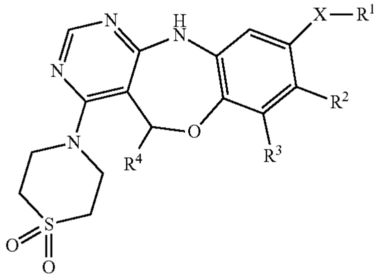

(IVb)

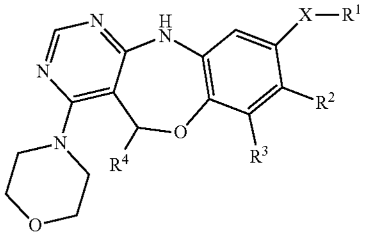

-continued (IVc)

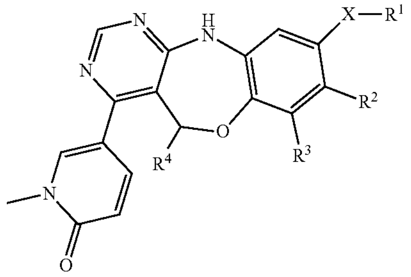

(IVd)

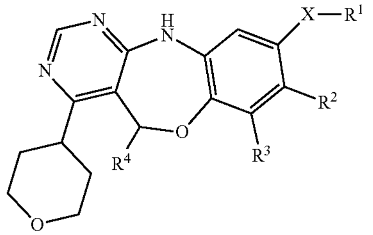

(IVe)

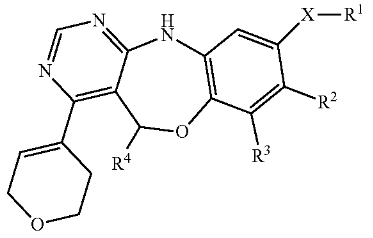

(IVf)

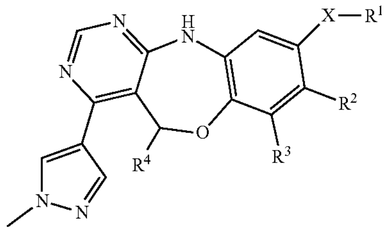

(IVg)

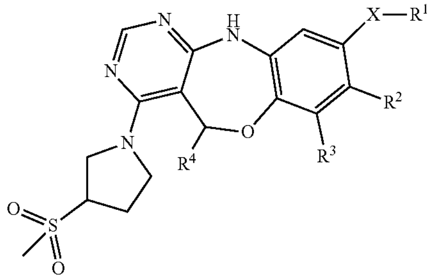

(IVh)

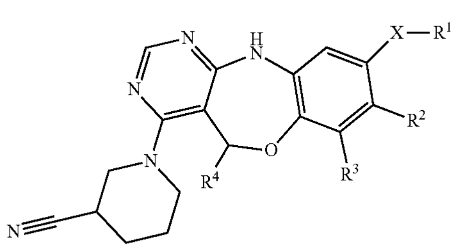

-continued (IVi)

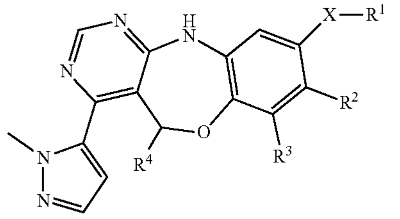

(IVj)

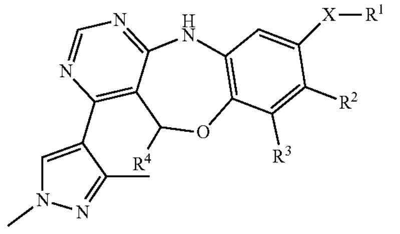

(IVk)

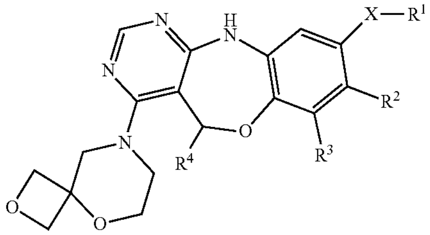

(IVl)

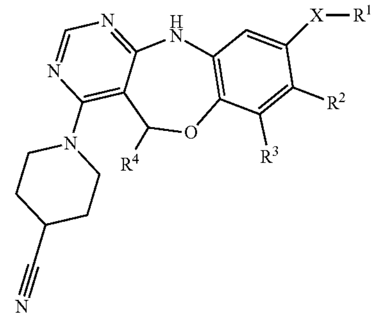

(IVm)

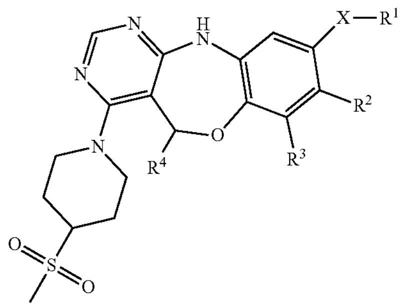

(IVn)

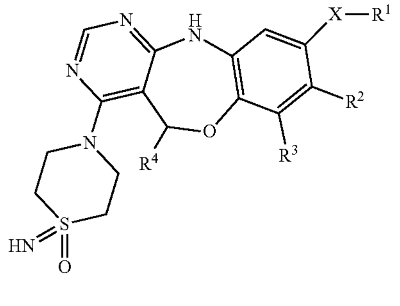

-continued (IVo)

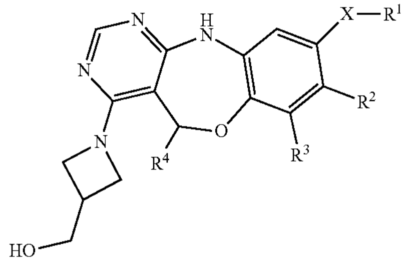

(IVp)

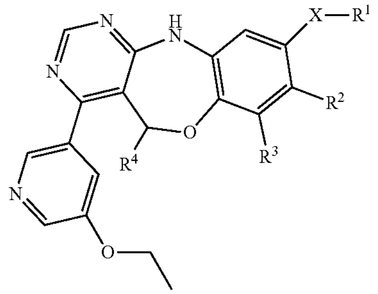

(IVq)

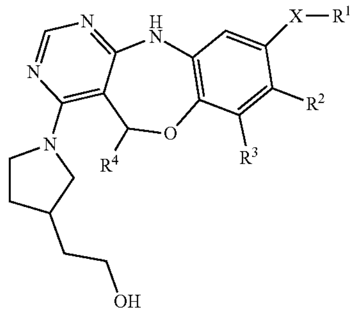

wherein each of X, $R^1$, $R^2$, $R^3$, and $R^4$, independently, is as defined herein above.

The compound may be a compound of formula (Va) or (Vb), including any tautomeric and stereochemically isomeric form, isotopically labeled derivative, or a pharmaceutically acceptable salt or solvate thereof:

(Va)

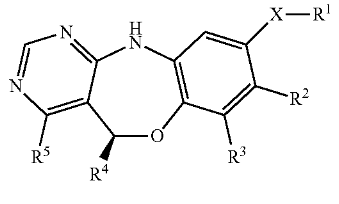

(Vb)

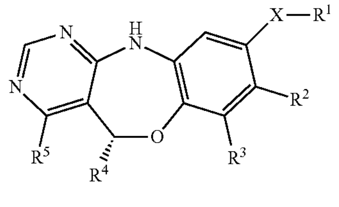

wherein, each of X, $R^1$, $R^2$, $R^3$, $R^4$, and $R^5$, independently, is as defined herein above.

The present invention also relates to a compound of formula (VI), including any tautomeric and stereochemically isomeric form, isotopically labeled derivative, or a pharmaceutically acceptable salt or solvate thereof, (VI)

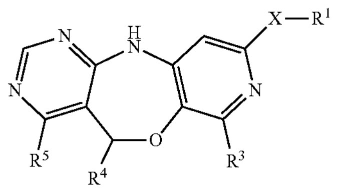

wherein,

X is a 4-7 membered non-aromatic heterocycle, a 4-10 membered non-aromatic bridged heterocycle, $C_{3-7}$cycloalkyl, $C_{5-7}$cycloalkenyl; wherein each of the cycles, independently, may be optionally substituted with —$C_{1-3}$alkyl;

$R^1$ is a 4-7 membered non-aromatic heterocycle having at least one nitrogen atom, wherein the at least one nitrogen atom is substituted with —C(═O)—CH═CH—$R^6$, or —C(═O)—CH—CH—$R^7$, and wherein the 4-7 membered non-aromatic heterocycle is optionally substituted with $C_{1-3}$alkyl, halo, or D; or $R^1$ is $C_{1-3}$alkyl substituted with —NH—C(═O)—CH═CH—$R^6$ or —NH—C(═O)—CH—CH—$R^7$;

$R^3$ is $C_{1-3}$alkyl, H, halogen, $C_{2-3}$alkenyl, $C_{2-3}$alkynyl, cyano, $C_{3-7}$cycloalkyl; $C_{1-3}$ alkyl substituted with one, two, or three halo, hydroxy, carboxyl, amino, mono- or di($C_{1-6}$alkyl)amino; 1-imidazolyl, 2-imidazolyl, or 4-imidazolyl;

$R^4$ is $C_{1-3}$alkyl; $C_{1-3}$alkyl substituted with one, two, or three halo; H;

$R^5$ is a 4-7 membered saturated or partially unsaturated heterocycle, a 5-6 membered heteroaryl, or a 6-12 membered spiro-bicyclic heterocycle;

wherein each of the cycles have one, two, or three heteroatoms selected from sulphur, nitrogen, and oxygen; and wherein, said sulphur, if present, is substituted with dioxo, or with oxo and imino;

said one, two, or three nitrogens, if present, may, each independently, be optionally substituted with $C_{1-3}$alkyl;

any one of the carbon atoms of the cycles may be optionally substituted with $C_{1-3}$alkyl, hydroxy$C_{1-3}$ alkyl, $C_{1-3}$alkoxy, oxo, $C_{1-3}$alkylsulfonyl, cyano, hydroxy, halo, carboxyl, mono- or di($C_{1-6}$alkyl) amino, polyhalo$C_{1-3}$ alkyl, polyhalo$C_{1-3}$alkoxy, $C_{2-3}$alkenyl, and $C_{2-3}$alkynyl;

$R^6$ is H; —$C_{1-3}$alkyl optionally substituted with one, two, or three substituents selected from halo, D, and —$NR^{7a}R^{7b}$; wherein each of $R^{7a}$ and $R^{7b}$ is, independently, $C_{1-3}$alkyl; or $R^{7a}$ and $R^{7b}$ taken together form a heterocycle; and $R^7$ is —$C_{1-3}$alkyl optionally substituted with one, two, or three substituents selected from halo, D, and —$NR^{7a}R^{7b}$; wherein each of $R^{7a}$ and $R^{7b}$ is, independently, $C_{1-3}$alkyl, or $R^{7a}$ and $R^{7b}$ taken together form a heterocycle.

The present invention also relates to a compound of formula (VI), including any tautomeric and stereochemically isomeric form, isotopically labeled derivative, or a pharmaceutically acceptable salt or solvate thereof, wherein, X is a 4-7 membered non-aromatic heterocycle, a 4-10 membered non-aromatic bridged heterocycle, $C_{4-7}$cycloalkyl, $C_{5-7}$cycloalkenyl; wherein each of the cycles, independently, may be optionally substituted with —$C_{1-3}$alkyl;

$R^1$ is a 4-7 membered non-aromatic heterocycle having at least one nitrogen atom, wherein the at least one nitrogen atom is substituted with —C(═O)—CH═CH—$R^6$, or —C(═O)—CH—CH—$R^7$, and wherein the 4-7 membered non-aromatic heterocycle is optionally substituted with $C_{1-3}$alkyl, halo, or D; or $R^1$ is $C_{1-3}$alkyl substituted with —NH—C(═O)—CH═CH—$R^6$ or —NH—C(═O)—CH—CH—$R^7$;

$R^3$ is $C_{1-3}$alkyl, H, halogen, cyano, $C_{3-7}$cycloalkyl; or $C_{1-3}$alkyl substituted with one, two, or three halo;

$R^4$ is methyl or H;

$R^5$ a 4-7 membered saturated or partially unsaturated heterocycle, a 5-6 membered heteroaryl, or a 6-12 membered spiro-bicyclic heterocycle;

wherein each of the cycles have one, two, or three heteroatoms selected from sulphur, nitrogen, and oxygen; and wherein, said sulphur, if present, is substituted with dioxo, or with oxo and imino;

said one, two, or three nitrogens, if present, may, each independently, be optionally substituted with $C_{1-3}$alkyl;

any one of the carbon atoms of the cycles may be optionally substituted with $C_{1-3}$alkyl, hydroxy$C_{1-3}$alkyl, $C_{1-3}$alkoxy, oxo, $C_{1-3}$alkylsulfonyl, cyano, hydroxy, halo, carboxyl, mono- or di($C_{1-6}$alkyl) amino, polyhalo$C_{1-3}$alkyl, polyhalo$C_{1-3}$alkoxy, $C_{2-3}$alkenyl, and $C_{2-3}$alkynyl;

$R^6$ is H; —$C_{1-3}$alkyl optionally substituted with one, two, or three substituents selected from halo, D, and —$NR^{7a}R^{7b}$; wherein each of $R^{7a}$ and $R^{7b}$ is, independently, $C_{1-3}$alkyl; or $R^{7a}$ and $R^{7b}$ taken together form a heterocycle; and $R^7$ is —$C_{1-3}$alkyl optionally substituted with one, two, or three substituents selected from halo, D, and —$NR^{7a}R^{7b}$; wherein each of $R^{7a}$ and $R^{7b}$ is, independently, $C_{1-3}$alkyl; or $R^{7a}$ and $R^{7b}$ taken together form a heterocycle.

The present invention also relates to a compound of formula (VI), including any tautomeric and stereochemically isomeric form, isotopically labeled derivative, or a pharmaceutically acceptable salt or solvate thereof, wherein, X is a 4-7 membered non-aromatic heterocycle;

$R^1$ is a 4-7 membered non-aromatic heterocycle having at least one nitrogen atom, wherein the at least one nitrogen atom is substituted with —C(═O)—CH═CH—$R^6$, or —C(═O)—CH≡CH—$R^7$;

$R^3$ is $C_{1-3}$alkyl, H, halogen, cyano, $C_{3-7}$cycloalkyl; or $C_{1-3}$alkyl substituted with one, two, or three halo;

$R^4$ is methyl or H;

$R^5$ is a 4-7 membered saturated or partially unsaturated heterocycle, a 5-6 membered heteroaryl, or a 6-12 membered spiro-bicyclic heterocycle;

wherein each of the cycles have one, two, or three heteroatoms selected from sulphur, nitrogen, and oxygen; and wherein, said sulphur, if present, is substituted with dioxo, or with oxo and imino;

said one, two, or three nitrogens, if present, may, each independently, be optionally substituted with $C_{1-3}$alkyl;

any one of the carbon atoms of the cycles may be optionally substituted with $C_{1-3}$alkyl, hydroxy$C_{1-3}$ alkyl, $C_{1-3}$alkoxy, oxo, $C_{1-3}$alkylsulfonyl, cyano, hydroxy, halo, carboxyl, mono- or di($C_{1-6}$alkyl) amino, polyhalo$C_{1-3}$alkyl, polyhalo$C_{1-3}$alkoxy, $C_{2-3}$alkenyl, and $C_{2-3}$alkynyl;

$R^6$ is H; —$C_{1-3}$alkyl optionally substituted with one, two, or three substituents selected from halo, D, and —$NR^{7a}R^{7b}$; wherein each of $R^{7a}$ and $R^{7b}$ is, independently, $C_{1-3}$alkyl; or $R^{7a}$ and $R^{7b}$ taken together form a heterocycle; and $R^7$ is —$C_{1-3}$alkyl optionally substituted with one, two, or three substituents selected from halo, D, and —$NR^{7a}R^{7b}$; wherein each of $R^{7a}$ and $R^{7b}$ is, independently, $C_{1-3}$alkyl; or $R^{7a}$ and $R^{7b}$ taken together form a heterocycle.

The compound may be a compound of formula (VIIa), (VIIb), (VIIc), (VIId), (VIIe), or (VIIf), including any tautomeric and stereochemically isomeric form, isotopically labeled derivative, or a pharmaceutically acceptable salt or solvate thereof:

(VIIa)

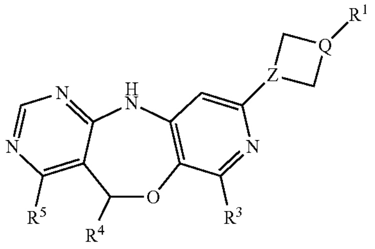

(VIIb)

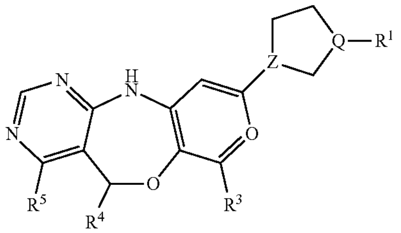

(VIIc)

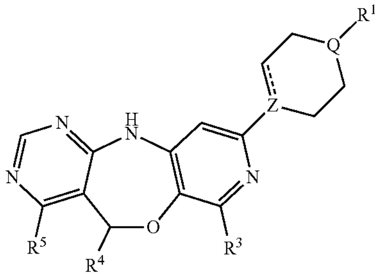

(VIId)

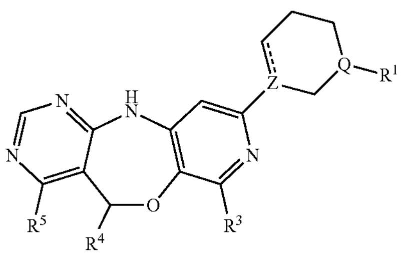

-continued (VIIe)

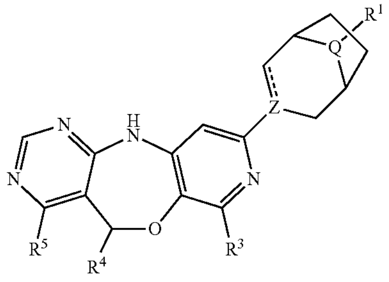

(VIIf)

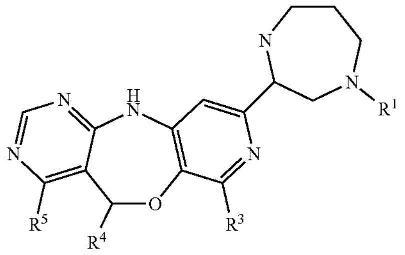

wherein, each Q is, independently, CH or N;

each Z is, independently, CH or N;

each of $R^1$, $R^3$, $R^4$, and $R^5$, independently, is as defined above for the compound of formula (VI).

The compound may be a compound of formula (VIIIa), (VIIIb), (VIIIc), (VIIId), (VIIIe), or (VIIIf) including any tautomeric and stereochemically isomeric form, isotopically labeled derivative, or a pharmaceutically acceptable salt or solvate thereof:

(VIIIa)

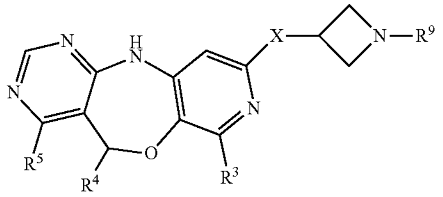

(VIIIb)

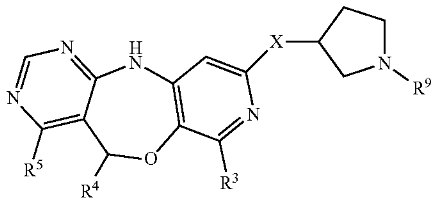

(VIIIc)

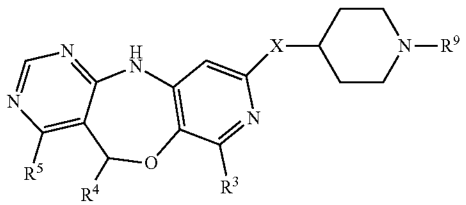

-continued (VIIId)

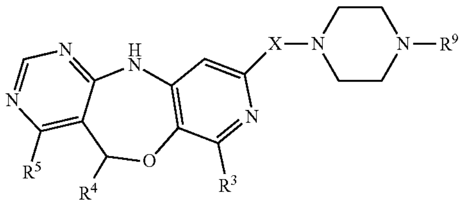

(VIIIe)

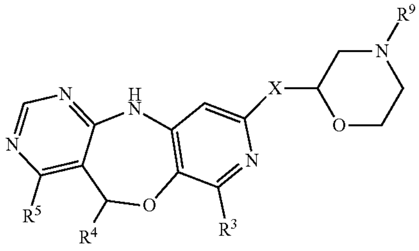

(VIIIf)

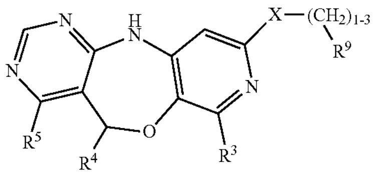

wherein $R^9$ is —C(=O)—CH=CH—$R^6$, or —C(=O)—CH≡CH—$R^7$; and each of X, $R^3$, $R^4$, $R^5$, $R^6$, and $R^7$, independently, is as defined above for the compound of formula (VI).

The compound may be a compound of formula (IXa), (IXb), (IXc), (IXd), (IXe), (IXf), (IXg), (IXh), (IXi), (IXj), (IXk), (IXl), (IXm), (IXn), (IXo), (IXp), or (IXq), including any tautomeric and stereochemically isomeric form, isotopically labeled derivative, or a pharmaceutically acceptable salt or solvate thereof:

(IXa)

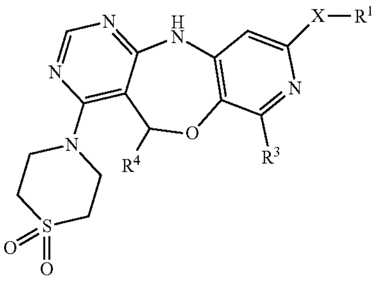

(IXb)

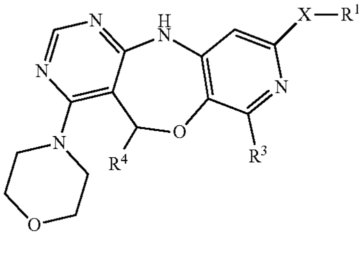

-continued (IXc)

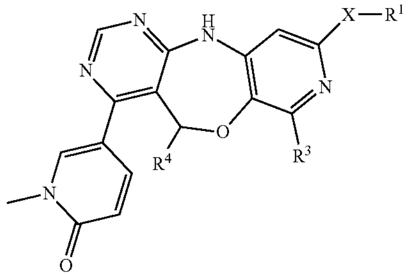

(IXd)

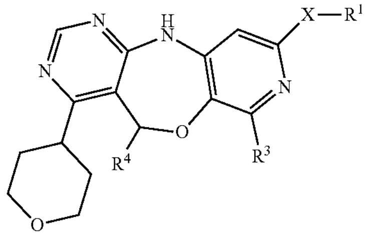

(IXe)

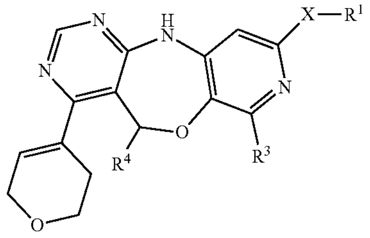

(IXf)

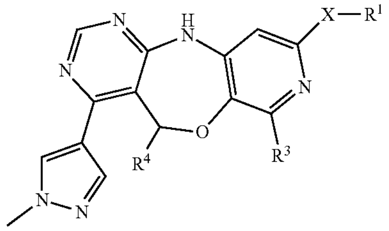

(IXg)

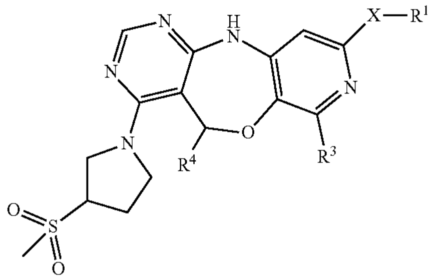

(IXh)

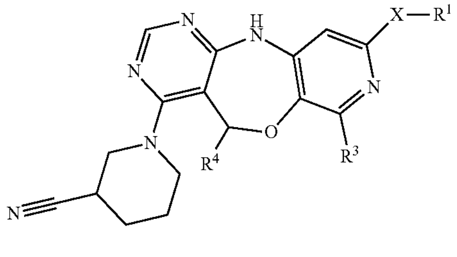

-continued (IXi)

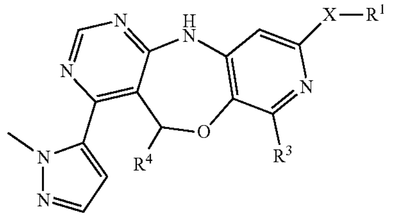

(IXj)

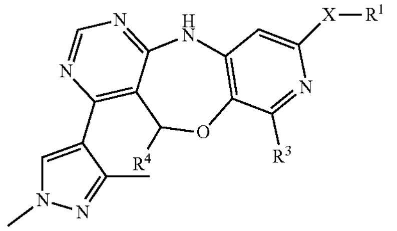

(IXk)

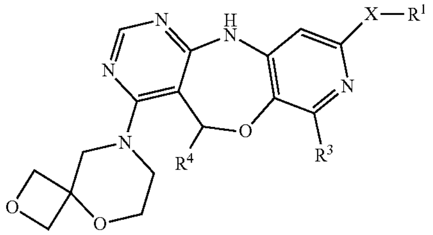

(IXl)

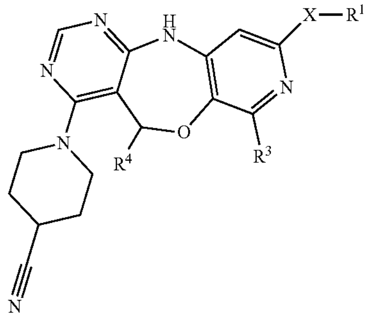

(IXm)

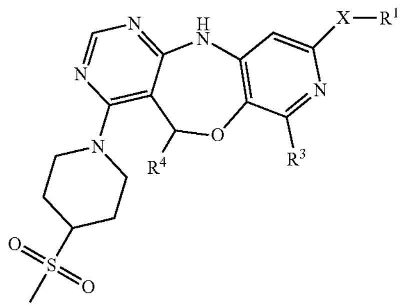

(IXn)

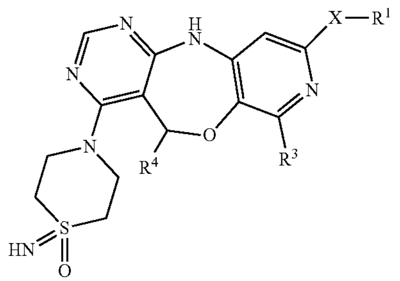

-continued (IXo)

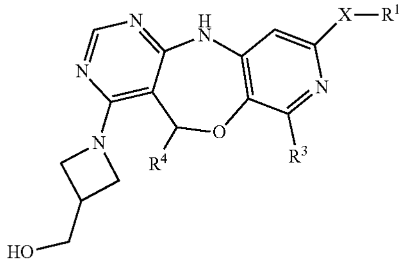

(IXp)

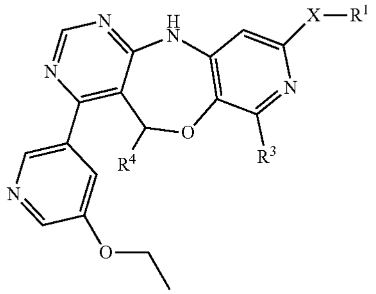

(IXq)

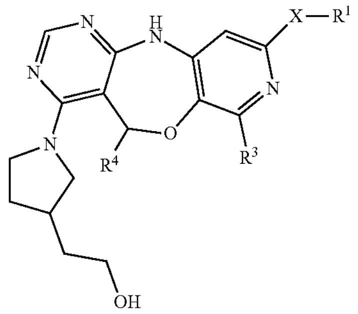

wherein, each of X, $R^1$, $R^3$, and $R^4$ independently, is as defined above for the compound of formula (VI).

In the compounds of formula (VI), (VIIa), (VIIb), (VIIc), (VIId), (VIIe), (VIIf), (VIIIa), (VIIIb), (VIIIc), (VIIId), (VIIIe), (VIIIf), (IXa), (IXb), (IXc), (IXd), (IXe), (IXf), (IXg), (IXh), (IXi), (IXj), (IXk), (IXi), (IXm), (IXn), (IXo), (IXp), or (IXq), including any tautomeric and stereochemically isomeric form, isotopically labeled derivative, or a pharmaceutically acceptable salt or solvate thereof $R^5$ is

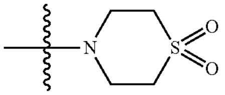 or 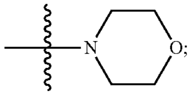;

and each of X, $R^1$, $R^3$, and $R^4$, independently, is as defined herein above.

The compound may be a compound of formula (Xa) or (Xb), including any tautomeric and stereochemically isomeric form, isotopically labeled derivative, or a pharmaceutically acceptable salt or solvate thereof:

(Xa)

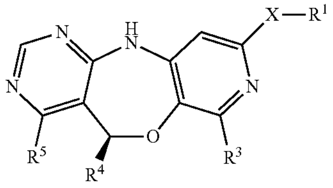

-continued (Xb)

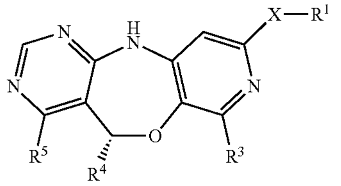

wherein, each of X, $R^1$, $R^3$, $R^4$, and $R^5$, independently, is as defined herein above.

The present invention particularly relates to a compound, including any tautomeric and stereochemically isomeric form, isotopically labeled derivative, or a pharmaceutically acceptable salt or solvate thereof, wherein the compound is selected from

| Cpd # | Structure |
|---|---|
| 1 | 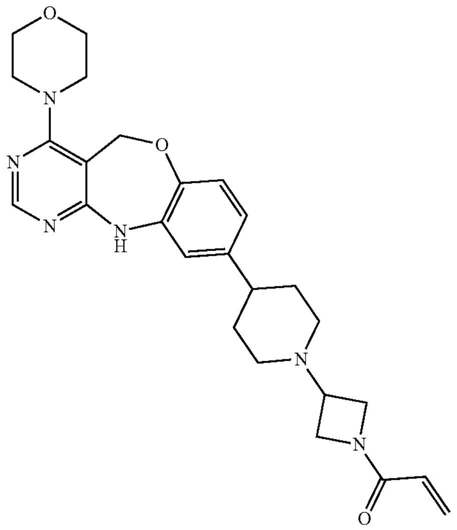 [SMILES: C=CC(=O)N1CC(N2CCC(c3ccc4c(c3)Nc3ncnc(N5CCOCC5)c3CO4)CC2)C1] |
| 4 | 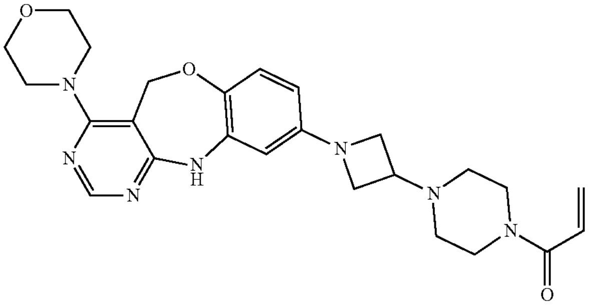 [SMILES: C=CC(=O)N1CCN(C2CN(c3ccc4c(c3)Nc3ncnc(N5CCOCC5)c3CO4)C2)CC1] |

-continued
| Cpd # | Structure |
|---|---|
| 2 | 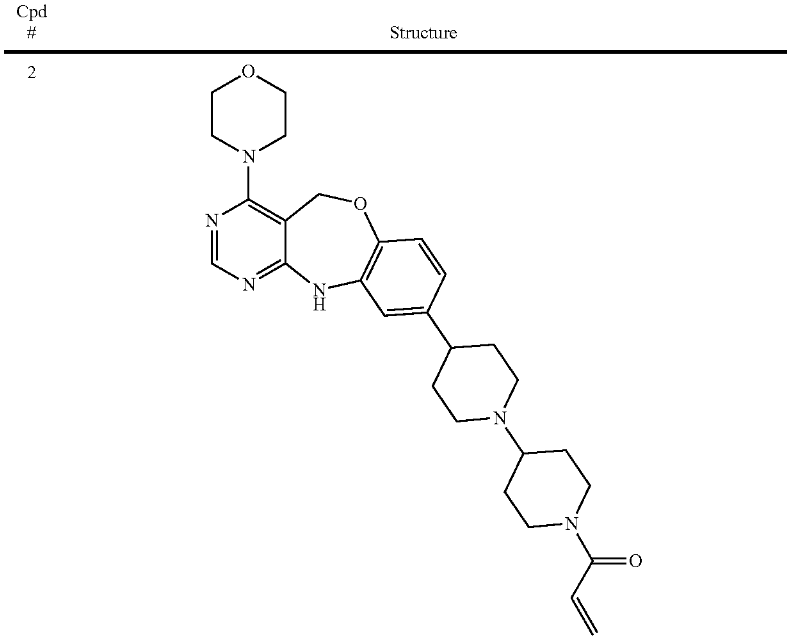 |
| 5 | 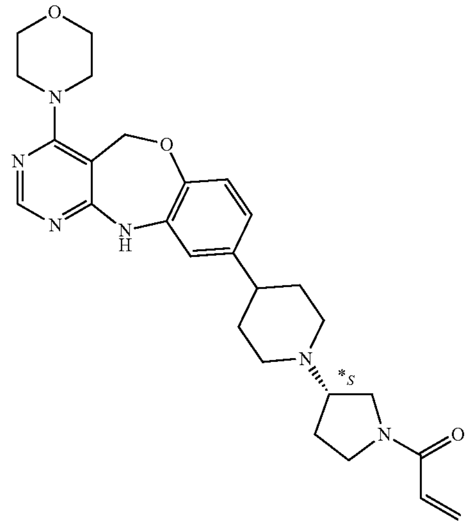 [SMILES: C=CC(=O)N1CC[C@H](N2CCC(c3ccc4c(c3)Nc3ncnc(N5CCOCC5)c3CO4)CC2)C1] |
| 3 | 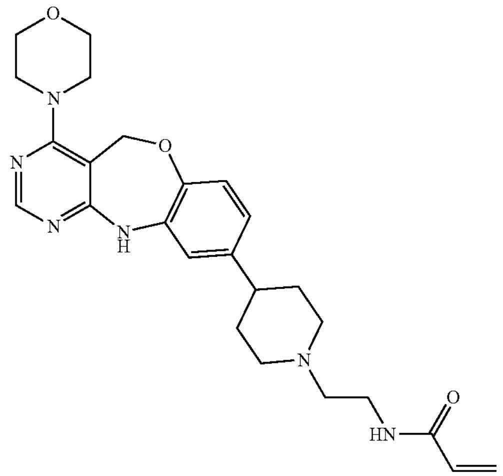 [SMILES: C=CC(=O)NCCN1CCC(c2ccc3c(c2)Nc2ncnc(N4CCOCC4)c2CO3)CC1] |

-continued
| Cpd # | Structure |
|---|---|
| 6 | 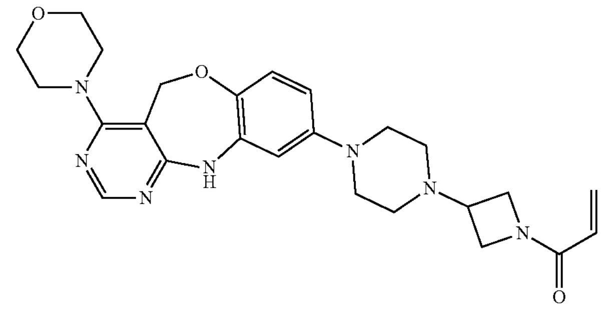 |
| 7 | 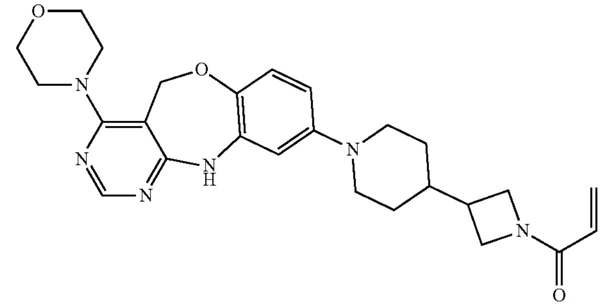 [SMILES: C=CC(=O)N1CC(C2CCN(c3ccc4c(c3)Nc3ncnc(N5CCOCC5)c3CO4)CC2)C1] |
| 10 | 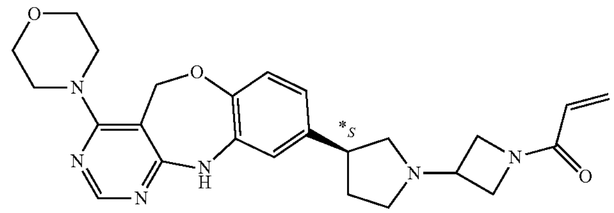 [SMILES: C=CC(=O)N1CC(N2CC[C@@H](c3ccc4c(c3)Nc3ncnc(N5CCOCC5)c3CO4)C2)C1] |
| 8 | 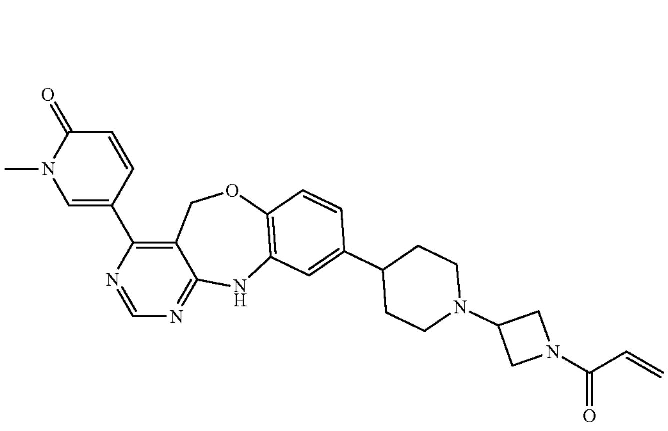 [SMILES: C=CC(=O)N1CC(N2CCC(c3ccc4c(c3)Nc3ncnc(-c5ccc(=O)n(C)c5)c3CO4)CC2)C1] |

-continued
| Cpd # | Structure |
| --- | --- |
| 11 | 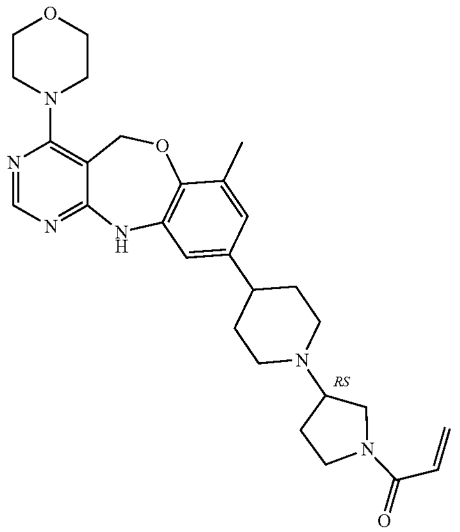 [SMILES: C=CC(=O)N1CCC(N2CCC(c3cc(C)c4c(c3)Nc3ncnc(N5CCOCC5)c3CO4)CC2)C1] |
| 9 | 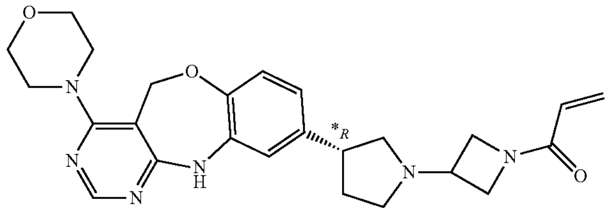 [SMILES: C=CC(=O)N1CC(N2CC[C@H](c3ccc4c(c3)Nc3ncnc(N5CCOCC5)c3CO4)C2)C1] |
| 12 | 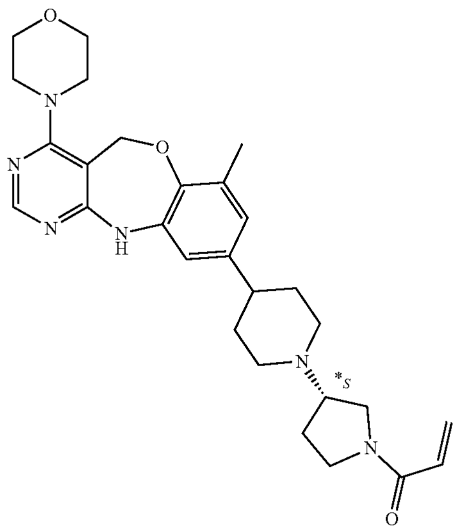 [SMILES: C=CC(=O)N1CC[C@H](N2CCC(c3cc(C)c4c(c3)Nc3ncnc(N5CCOCC5)c3CO4)CC2)C1] |

-continued
| Cpd # | Structure |
|---|---|
| 13 | 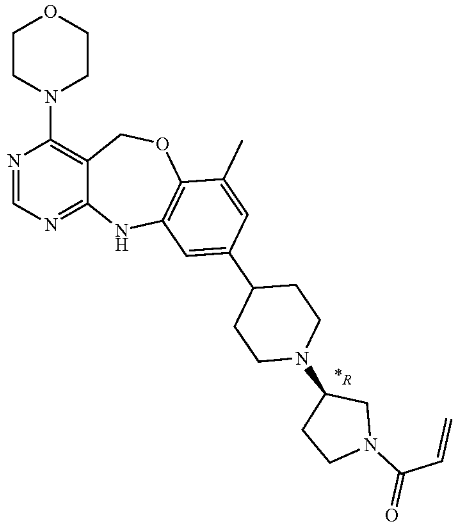 [SMILES: C=CC(=O)N1CC[C@@H](N2CCC(c3cc(C)c4c(c3)Nc3ncnc(N5CCOCC5)c3CO4)CC2)C1] |
| 16 | 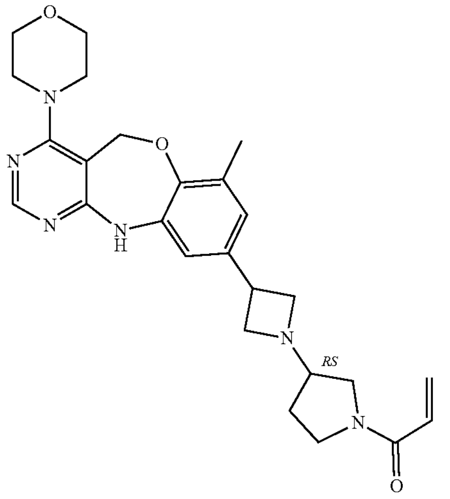 [SMILES: C=CC(=O)N1CCC(N2CC(c3cc(C)c4c(c3)Nc3ncnc(N5CCOCC5)c3CO4)C2)C1] |
| 14 | 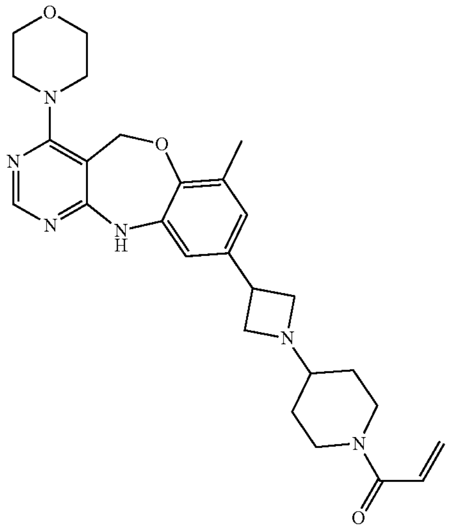 [SMILES: C=CC(=O)N1CCC(N2CC(c3cc(C)c4c(c3)Nc3ncnc(N5CCOCC5)c3CO4)C2)CC1] |

-continued
| Cpd # | Structure |
| --- | --- |
| 17 | 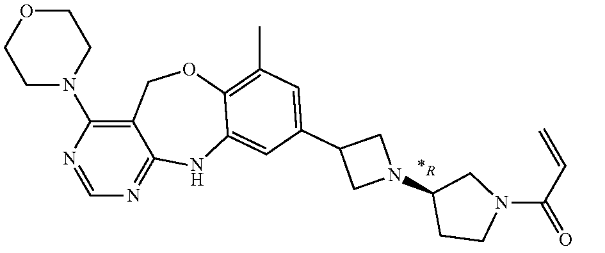 [SMILES: C=CC(=O)N1CC[C@@H](N2CC(c3cc(C)c4c(c3)Nc3ncnc(N5CCOCC5)c3CO4)C2)C1] |
| 15 | 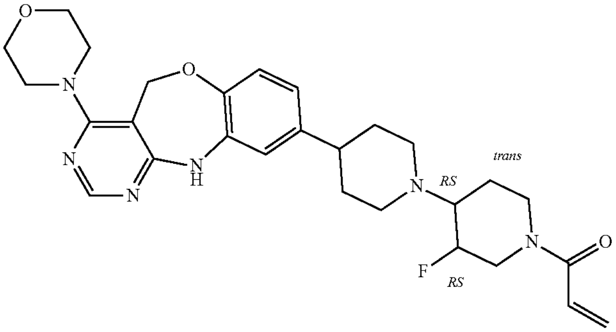 [SMILES: C=CC(=O)N1CCC(N2CCC(c3ccc4c(c3)Nc3ncnc(N5CCOCC5)c3CO4)CC2)C(F)C1] |
| 18 | 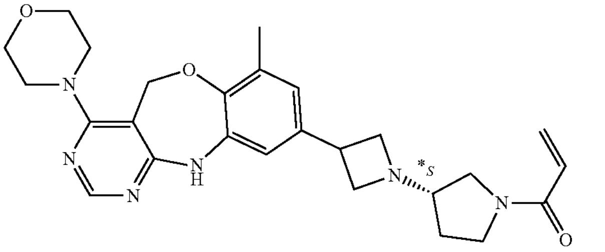 [SMILES: C=CC(=O)N1CC[C@H](N2CC(c3cc(C)c4c(c3)Nc3ncnc(N5CCOCC5)c3CO4)C2)C1] |
| 19 | 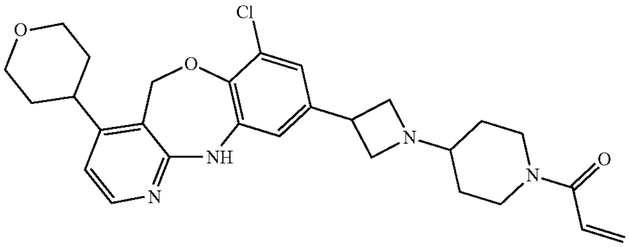 [SMILES: C=CC(=O)N1CCC(N2CC(c3cc(Cl)c4c(c3)Nc3nccc(C5CCOCC5)c3CO4)C2)CC1] |
| 22 | 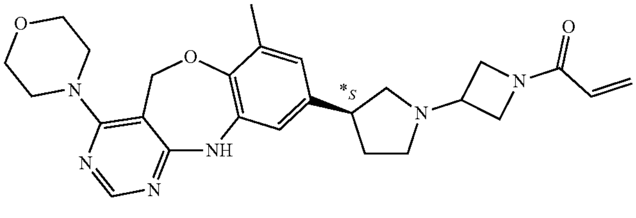 [SMILES: C=CC(=O)N1CC(N2CC[C@@H](c3cc(C)c4c(c3)Nc3ncnc(N5CCOCC5)c3CO4)C2)C1] |
| 20 | 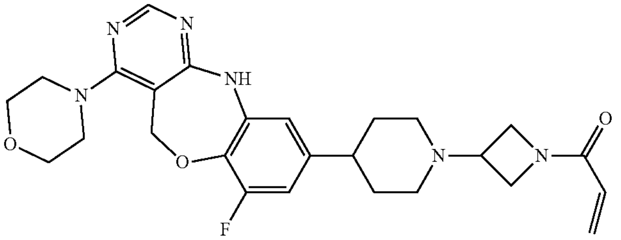 [SMILES: C=CC(=O)N1CC(N2CCC(c3cc(F)c4c(c3)Nc3ncnc(N5CCOCC5)c3CO4)CC2)C1] |

-continued
| Cpd # | Structure |
|---|---|
| 23 | 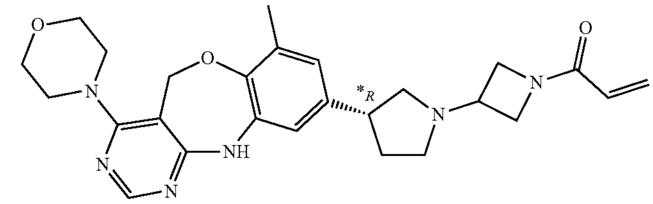 [SMILES: C=CC(=O)N1CC(N2CC[C@H](c3cc(C)c4c(c3)Nc3ncnc(N5CCOCC5)c3CO4)C2)C1] |
| 21 | 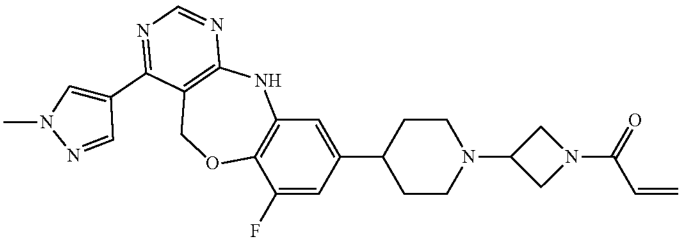 [SMILES: C=CC(=O)N1CC(N2CCC(c3cc(F)c4c(c3)Nc3ncnc(-c5cnn(C)c5)c3CO4)CC2)C1] |
| 24 | 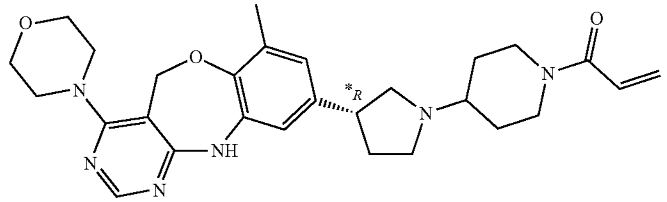 [SMILES: C=CC(=O)N1CCC(N2CC[C@H](c3cc(C)c4c(c3)Nc3ncnc(N5CCOCC5)c3CO4)C2)CC1] |
| 25 | 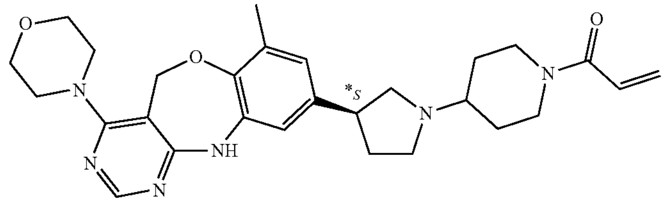 [SMILES: C=CC(=O)N1CCC(N2CC[C@@H](c3cc(C)c4c(c3)Nc3ncnc(N5CCOCC5)c3CO4)C2)CC1] |
| 28 | 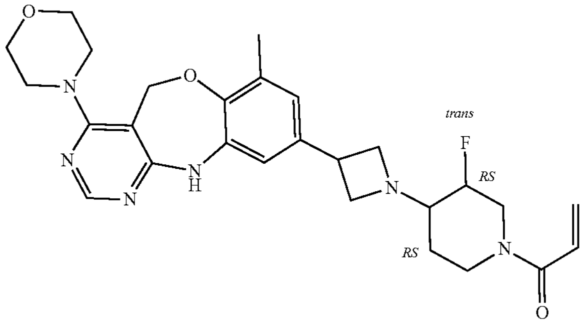 [SMILES: C=CC(=O)N1CCC(N2CC(c3cc(C)c4c(c3)Nc3ncnc(N5CCOCC5)c3CO4)C2)C(F)C1] |
| 26 | 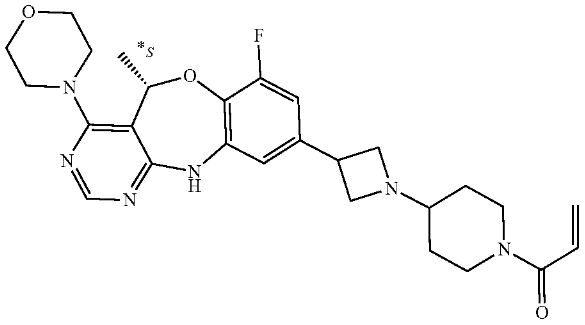 [SMILES: C=CC(=O)N1CCC(N2CC(c3cc(F)c4c(c3)Nc3ncnc(N5CCOCC5)c3[C@H](C)O4)C2)CC1] |

-continued
| Cpd # | Structure |
|---|---|
| 29 | 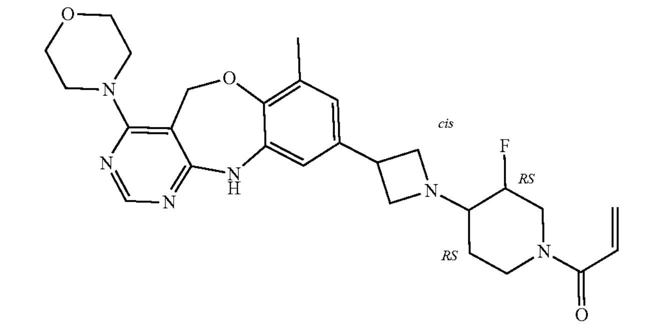 [SMILES: C=CC(=O)N1CCC(N2CC(c3cc(C)c4c(c3)Nc3ncnc(N5CCOCC5)c3CO4)C2)C(F)C1] |
| 27 | 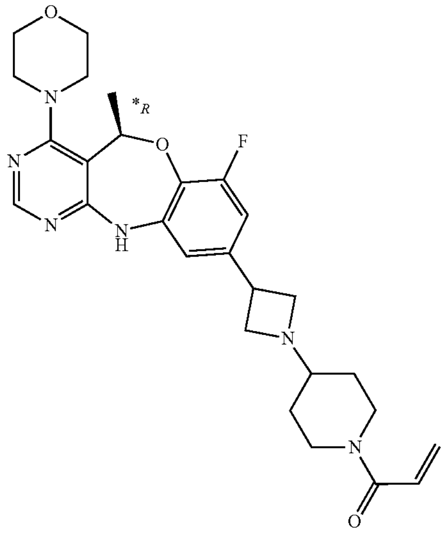 [SMILES: C=CC(=O)N1CCC(N2CC(c3cc(F)c4c(c3)Nc3ncnc(N5CCOCC5)c3[C@@H](C)O4)C2)CC1] |
| 30 | 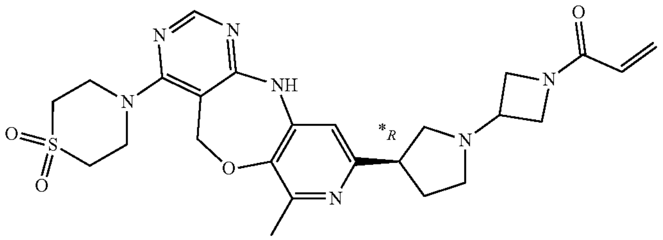 [SMILES: C=CC(=O)N1CC(N2CC[C@@H](c3cc4c(c(C)n3)OCc3c(ncnc3N3CCS(=O)(=O)CC3)N4)C2)C1] |
| 31 | 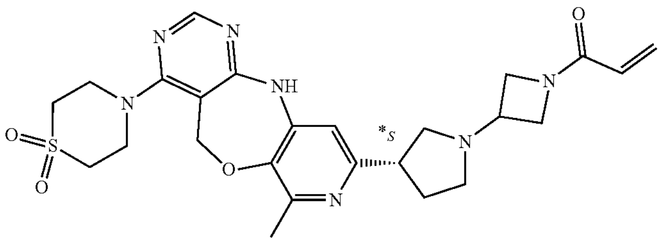 [SMILES: C=CC(=O)N1CC(N2CC[C@H](c3cc4c(c(C)n3)OCc3c(ncnc3N3CCS(=O)(=O)CC3)N4)C2)C1] |

-continued
| Cpd # | Structure |
|---|---|
| 34 | 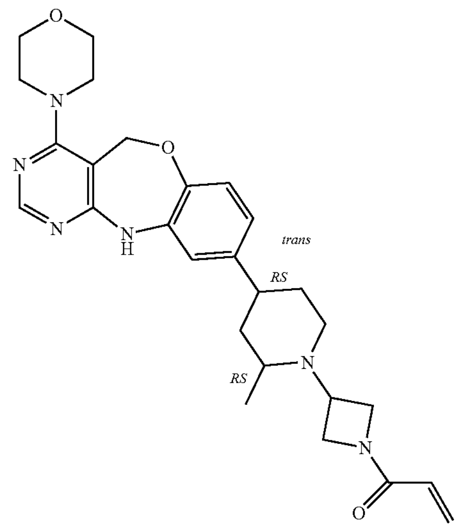 [SMILES: C=CC(=O)N1CC(N2CCC(c3ccc4c(c3)Nc3ncnc(N5CCOCC5)c3CO4)CC2C)C1] |
| 32 | 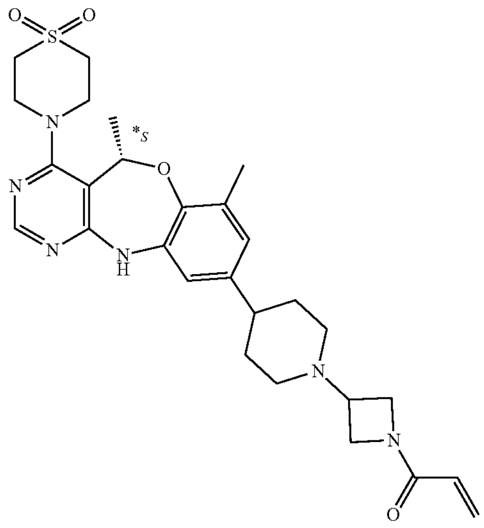 [SMILES: C=CC(=O)N1CC(N2CCC(c3cc(C)c4c(c3)Nc3ncnc(N5CCS(=O)(=O)CC5)c3[C@H](C)O4)CC2)C1] |
| 35 | 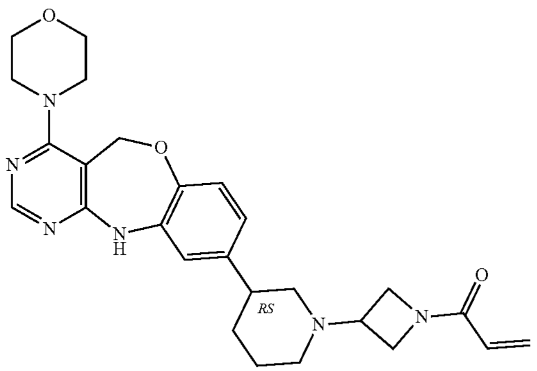 [SMILES: C=CC(=O)N1CC(N2CCCC(c3ccc4c(c3)Nc3ncnc(N5CCOCC5)c3CO4)C2)C1] |

-continued
| Cpd # | Structure |
|---|---|
| 33 | 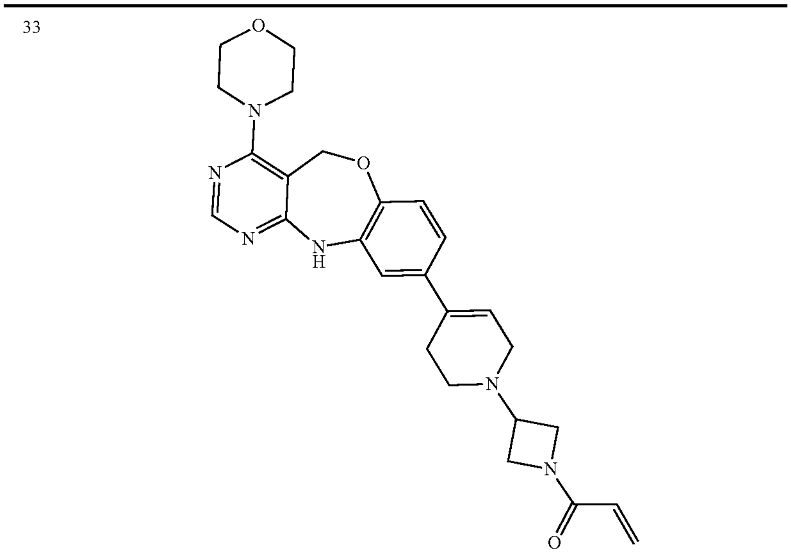 |
| 36 | 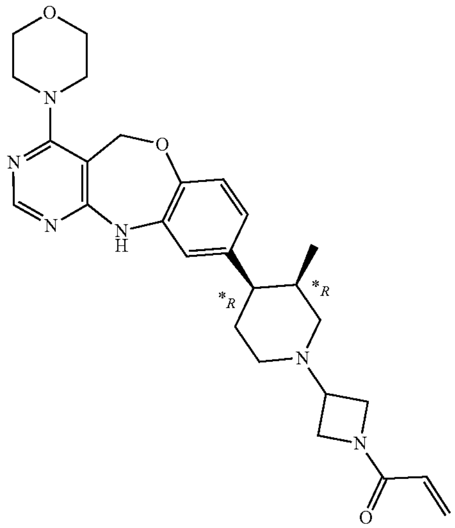 [SMILES: C=CC(=O)N1CC(N2CC[C@@H](c3ccc4c(c3)Nc3ncnc(N5CCOCC5)c3CO4)[C@@H](C)C2)C1] |
| 37 | 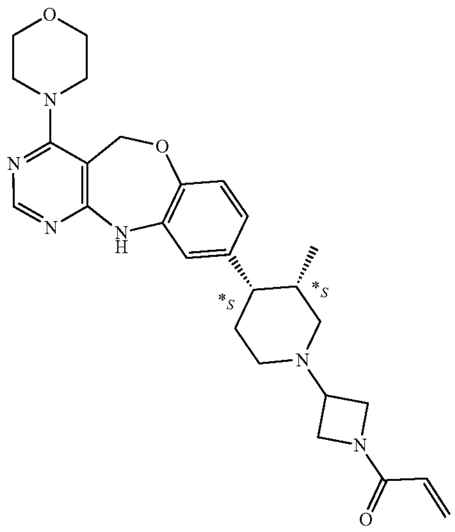 [SMILES: C=CC(=O)N1CC(N2CC[C@H](c3ccc4c(c3)Nc3ncnc(N5CCOCC5)c3CO4)[C@H](C)C2)C1] |

-continued
| Cpd # | Structure |
| --- | --- |
| 40 | 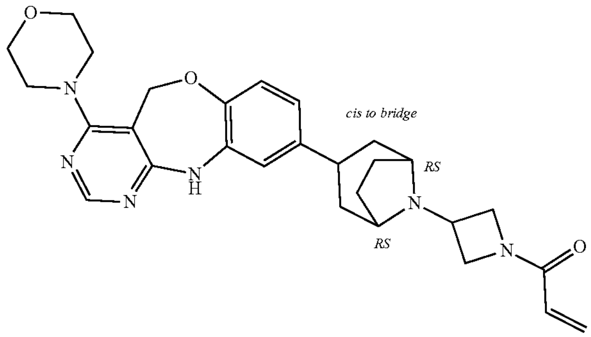 [SMILES: C=CC(=O)N1CC(N2C3CCC2CC(c2ccc4c(c2)Nc2ncnc(N5CCOCC5)c2CO4)C3)C1] |
| 38 | 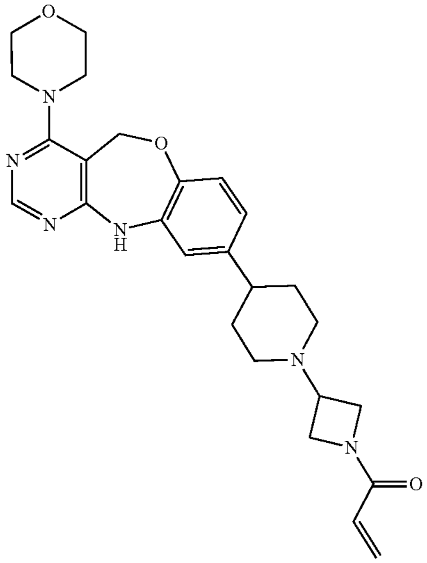 [SMILES: C=CC(=O)N1CC(N2CCC(c3ccc4c(c3)Nc3ncnc(N5CCOCC5)c3CO4)CC2)C1] |
| 41 | 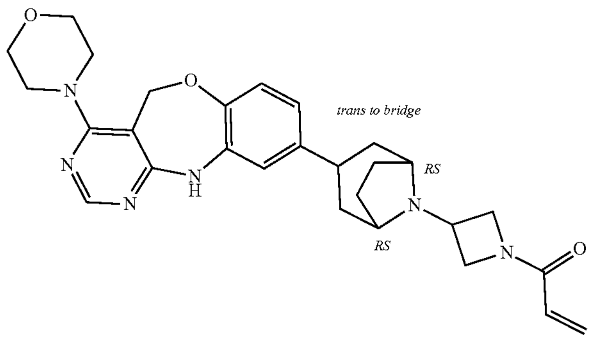 [SMILES: C=CC(=O)N1CC(N2C3CCC2CC(c2ccc4c(c2)Nc2ncnc(N5CCOCC5)c2CO4)C3)C1] |

-continued
| Cpd # | Structure |
|---|---|
| 39 | 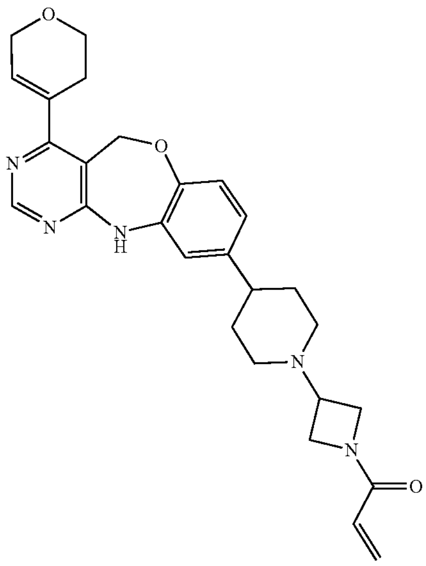 [SMILES: C=CC(=O)N1CC(N2CCC(c3ccc4c(c3)Nc3ncnc(C5=CCOCC5)c3CO4)CC2)C1] |
| 42 | 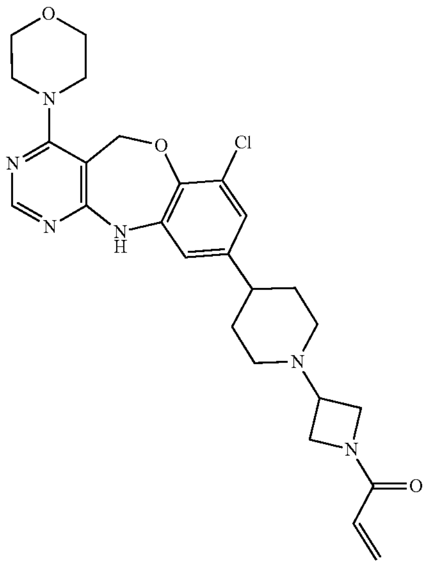 [SMILES: C=CC(=O)N1CC(N2CCC(c3cc(Cl)c4c(c3)Nc3ncnc(N5CCOCC5)c3CO4)CC2)C1] |

-continued
| Cpd # | Structure |
|---|---|
| 43 | 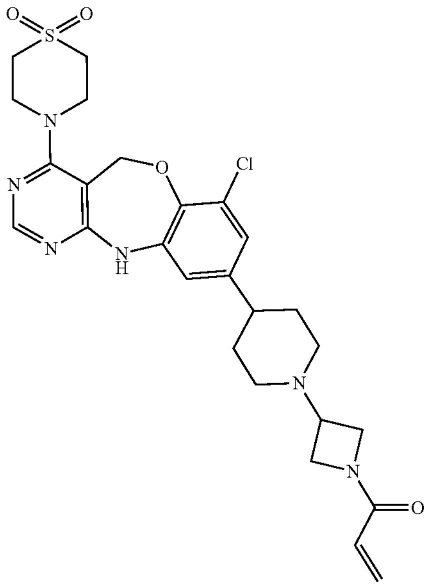 [SMILES: C=CC(=O)N1CC(N2CCC(c3cc(Cl)c4c(c3)Nc3ncnc(N5CCS(=O)(=O)CC5)c3CO4)CC2)C1] |
| 46 | 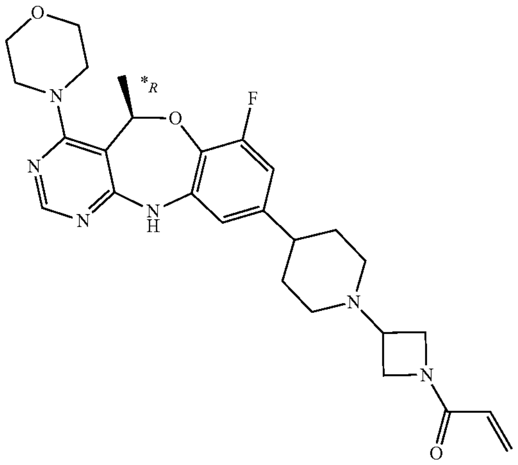 [SMILES: C=CC(=O)N1CC(N2CCC(c3cc(F)c4c(c3)Nc3ncnc(N5CCOCC5)c3[C@@H](C)O4)CC2)C1] |
| 44 | 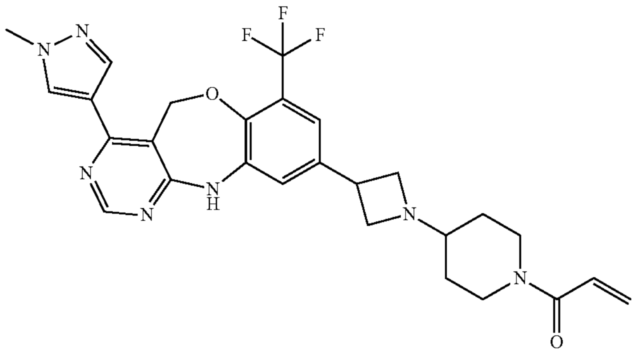 [SMILES: C=CC(=O)N1CCC(N2CC(c3cc4c(c(C(F)(F)F)c3)OCc3c(ncnc3-c3cnn(C)c3)N4)C2)CC1] |

-continued
| Cpd # | Structure |
| --- | --- |
| 47 | 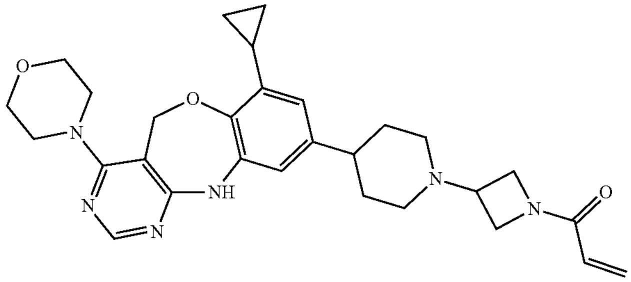 [SMILES: C=CC(=O)N1CC(N2CCC(c3cc4c(c(C5CC5)c3)OCc3c(ncnc3N3CCOCC3)N4)CC2)C1] |
| 45 | 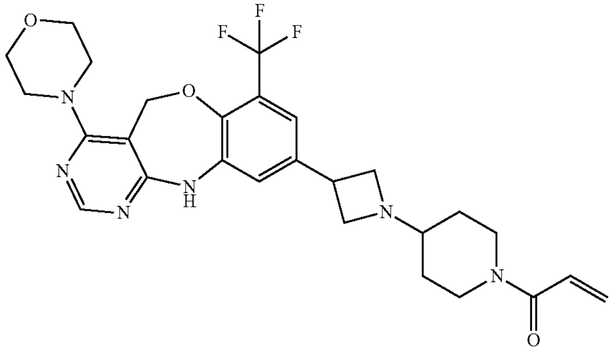 [SMILES: C=CC(=O)N1CCC(N2CC(c3cc4c(c(C(F)(F)F)c3)OCc3c(ncnc3N3CCOCC3)N4)C2)CC1] |
| 48 | 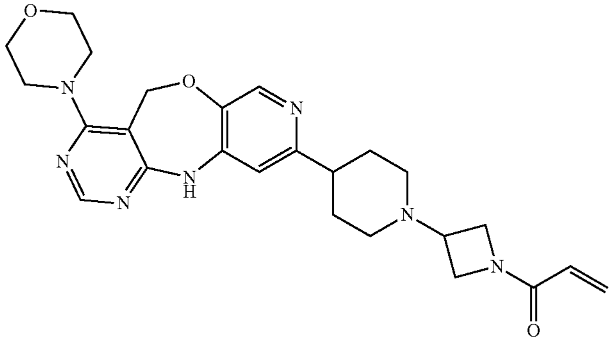 [SMILES: C=CC(=O)N1CC(N2CCC(c3cc4c(cn3)OCc3c(ncnc3N3CCOCC3)N4)CC2)C1] |
| 49 | 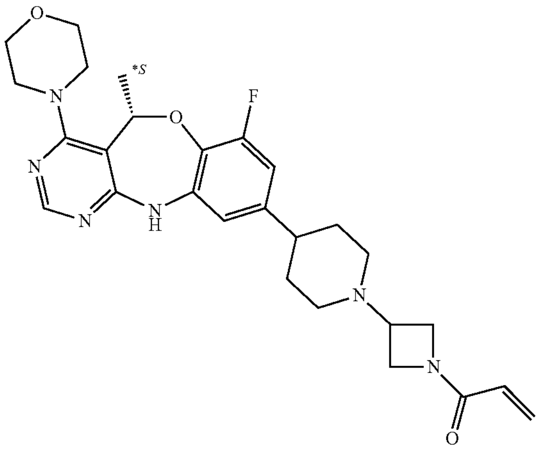 [SMILES: C=CC(=O)N1CC(N2CCC(c3cc(F)c4c(c3)Nc3ncnc(N5CCOCC5)c3[C@H](C)O4)CC2)C1] |

-continued
| Cpd # | Structure |
|---|---|
| 52 | 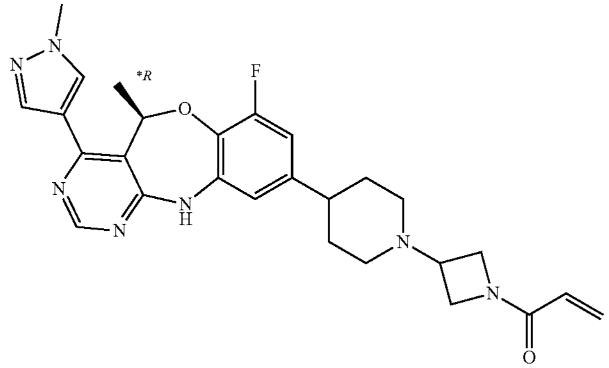 [SMILES: C=CC(=O)N1CC(N2CCC(c3cc(F)c4c(c3)Nc3ncnc(-c5cnn(C)c5)c3[C@@H](C)O4)CC2)C1] |
| 50 | 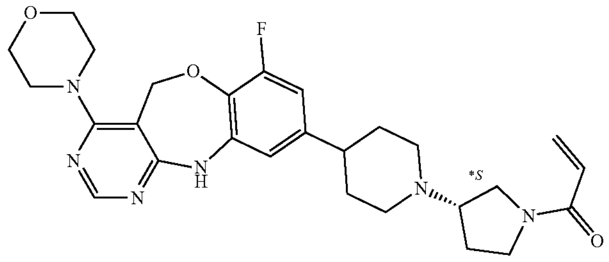 [SMILES: C=CC(=O)N1CC[C@H](N2CCC(c3cc(F)c4c(c3)Nc3ncnc(N5CCOCC5)c3CO4)CC2)C1] |
| 53 | 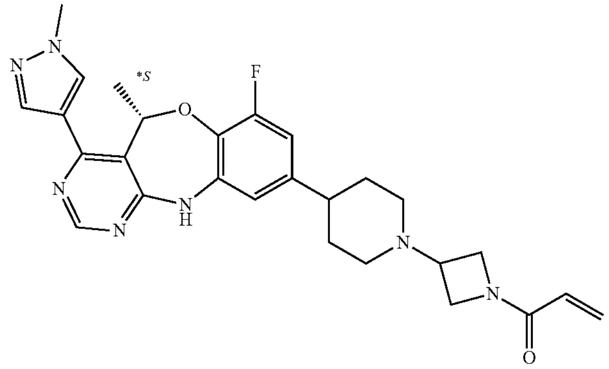 [SMILES: C=CC(=O)N1CC(N2CCC(c3cc(F)c4c(c3)Nc3ncnc(-c5cnn(C)c5)c3[C@H](C)O4)CC2)C1] |
| 51 | 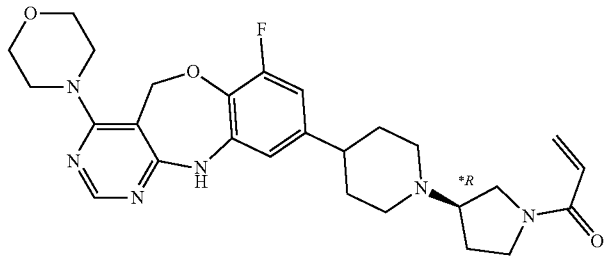 [SMILES: C=CC(=O)N1CC[C@@H](N2CCC(c3cc(F)c4c(c3)Nc3ncnc(N5CCOCC5)c3CO4)CC2)C1] |
| 54 | 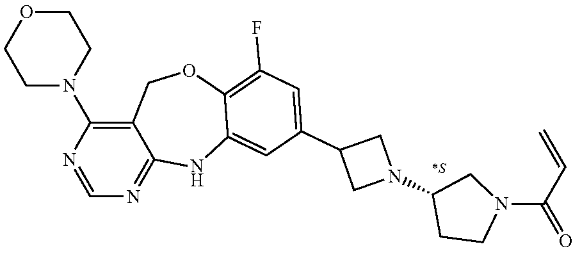 [SMILES: C=CC(=O)N1CC[C@H](N2CC(c3cc(F)c4c(c3)Nc3ncnc(N5CCOCC5)c3CO4)C2)C1] |

-continued
| Cpd # | Structure |
|---|---|
| 55 | 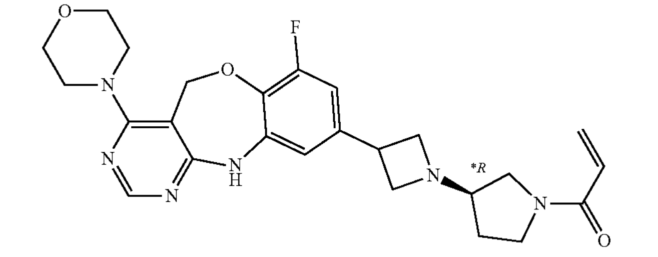 [SMILES: C=CC(=O)N1CC[C@@H](N2CC(c3cc(F)c4c(c3)Nc3ncnc(N5CCOCC5)c3CO4)C2)C1] |
| 58 | 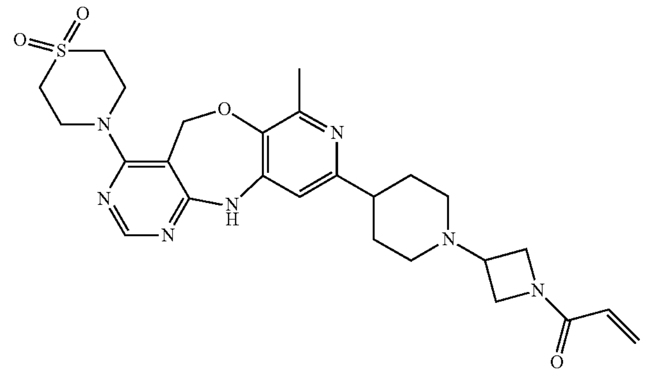 [SMILES: C=CC(=O)N1CC(N2CCC(c3cc4c(c(C)n3)OCc3c(ncnc3N3CCS(=O)(=O)CC3)N4)CC2)C1] |
| 56 | 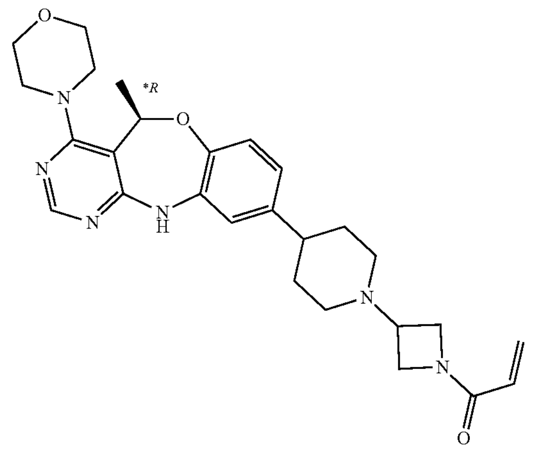 [SMILES: C=CC(=O)N1CC(N2CCC(c3ccc4c(c3)Nc3ncnc(N5CCOCC5)c3[C@@H](C)O4)CC2)C1] |
| 59 | 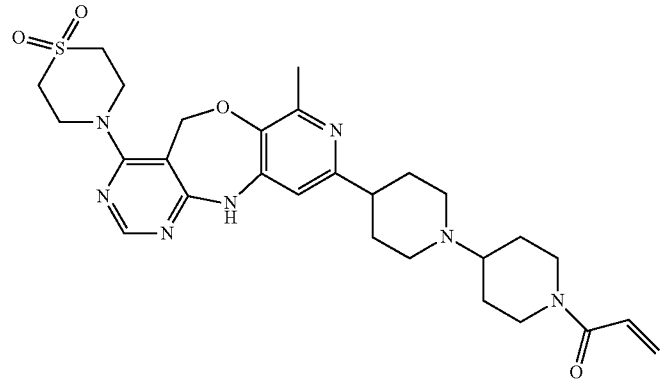 [SMILES: C=CC(=O)N1CCC(N2CCC(c3cc4c(c(C)n3)OCc3c(ncnc3N3CCS(=O)(=O)CC3)N4)CC2)CC1] |

-continued
| Cpd # | Structure |
| --- | --- |
| 57 | 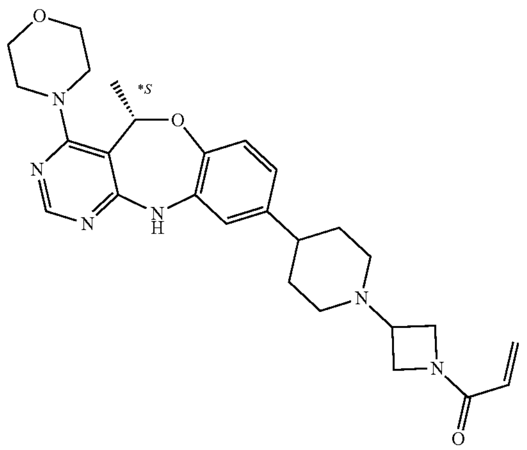 [SMILES: C=CC(=O)N1CC(N2CCC(c3ccc4c(c3)Nc3ncnc(N5CCOCC5)c3[C@H](C)O4)CC2)C1] |
| 60 | 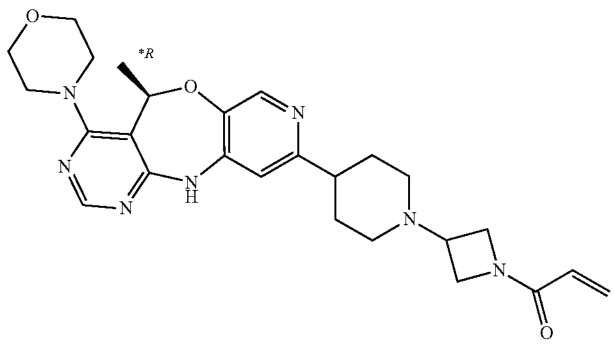 [SMILES: C=CC(=O)N1CC(N2CCC(c3cc4c(cn3)O[C@H](C)c3c(ncnc3N3CCOCC3)N4)CC2)C1] |
| 61 | 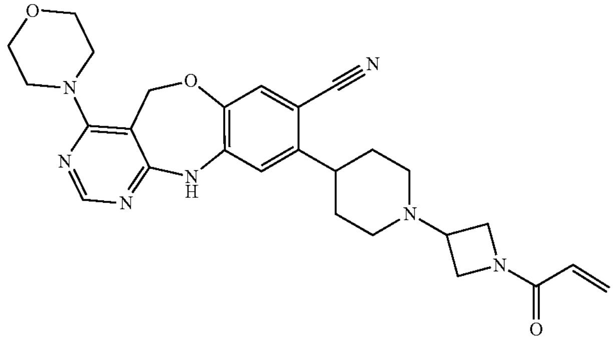 [SMILES: C=CC(=O)N1CC(N2CCC(c3cc4c(cc3C#N)OCc3c(ncnc3N3CCOCC3)N4)CC2)C1] |
| 64 | 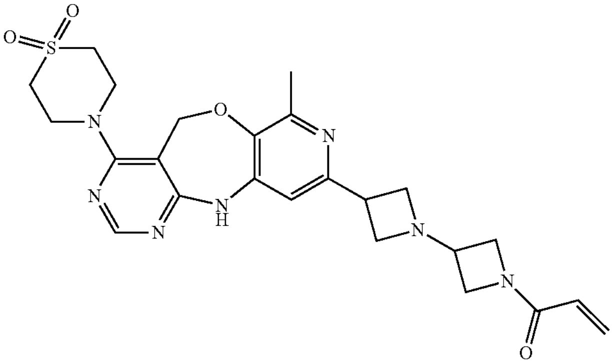 [SMILES: C=CC(=O)N1CC(N2CC(c3cc4c(c(C)n3)OCc3c(ncnc3N3CCS(=O)(=O)CC3)N4)C2)C1] |

-continued
| Cpd # | Structure |
|---|---|
| 62 | 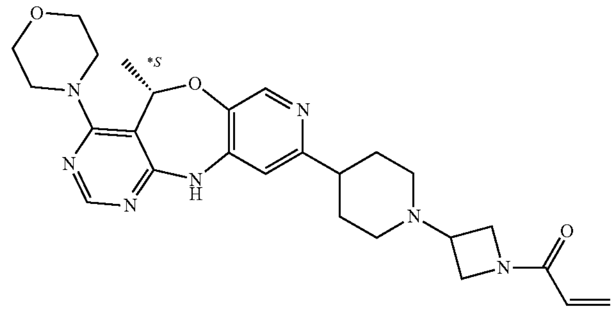 [SMILES: C=CC(=O)N1CC(N2CCC(c3cc4c(cn3)O[C@@H](C)c3c(ncnc3N3CCOCC3)N4)CC2)C1] |
| 65 | 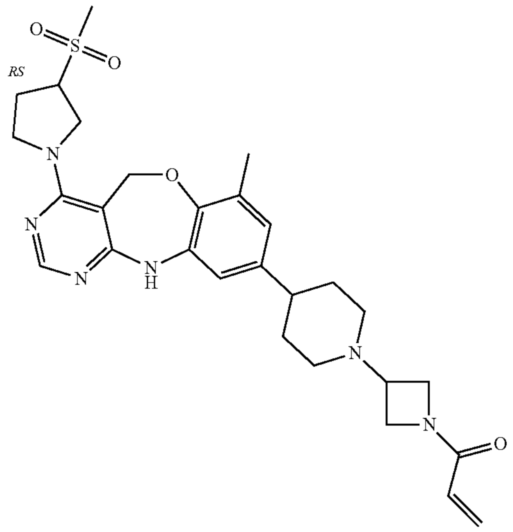 [SMILES: C=CC(=O)N1CC(N2CCC(c3cc(C)c4c(c3)Nc3ncnc(N5CCC(S(C)(=O)=O)C5)c3CO4)CC2)C1] |
| 63 | 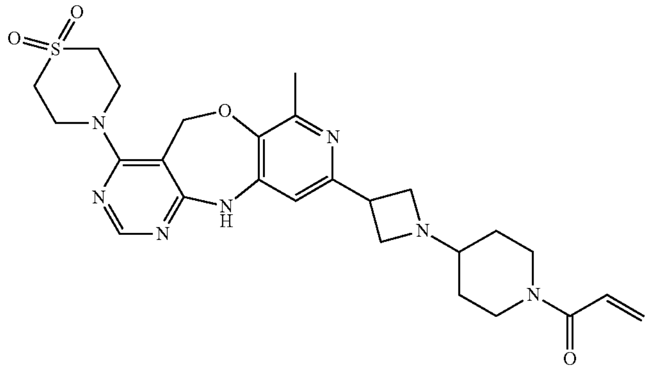 [SMILES: C=CC(=O)N1CCC(N2CC(c3cc4c(c(C)n3)OCc3c(ncnc3N3CCS(=O)(=O)CC3)N4)C2)CC1] |
| 66 | 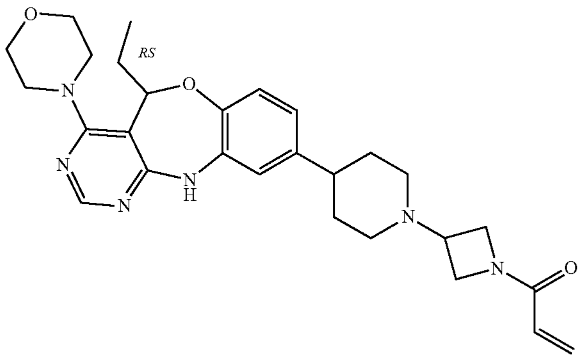 [SMILES: C=CC(=O)N1CC(N2CCC(c3ccc4c(c3)Nc3ncnc(N5CCOCC5)c3C(CC)O4)CC2)C1] |

-continued
| Cpd # | Structure |
| --- | --- |
| 67 | 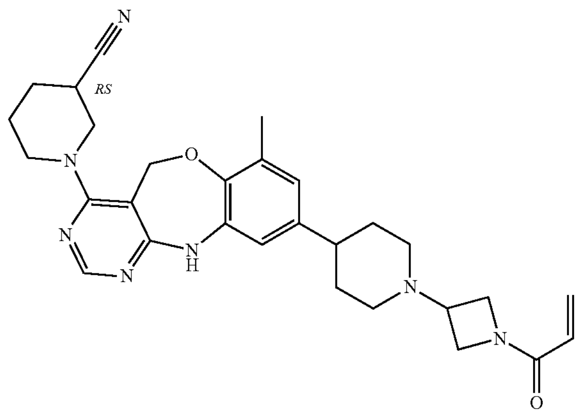 [SMILES: C=CC(=O)N1CC(N2CCC(c3cc(C)c4c(c3)Nc3ncnc(N5CCCC(C#N)C5)c3CO4)CC2)C1] |
| 70 | 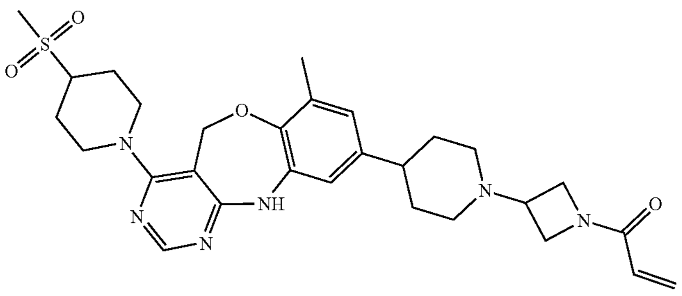 [SMILES: C=CC(=O)N1CC(N2CCC(c3cc(C)c4c(c3)Nc3ncnc(N5CCC(S(C)(=O)=O)CC5)c3CO4)CC2)C1] |
| 68 | 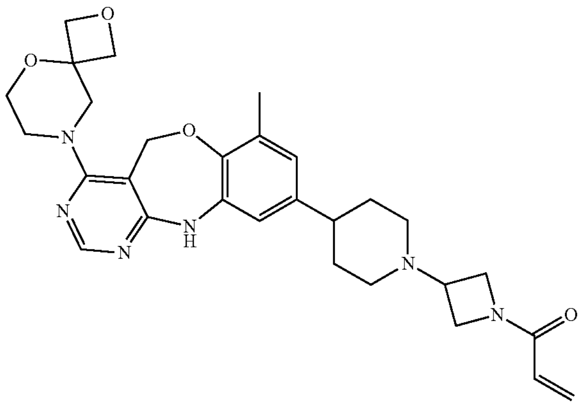 [SMILES: C=CC(=O)N1CC(N2CCC(c3cc(C)c4c(c3)Nc3ncnc(N5CCOC6(COC6)C5)c3CO4)CC2)C1] |
| 71 | 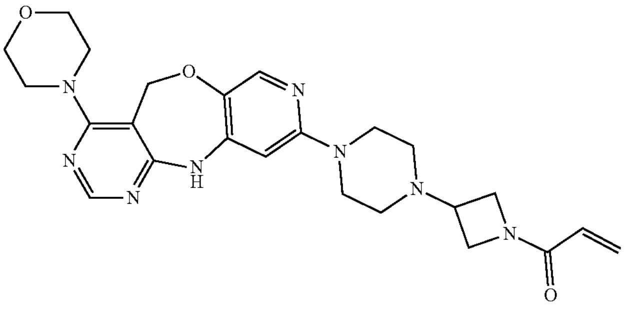 [SMILES: C=CC(=O)N1CC(N2CCN(c3cc4c(cn3)OCc3c(ncnc3N3CCOCC3)N4)CC2)C1] |

-continued
| Cpd # | Structure |
|---|---|
| 69 | 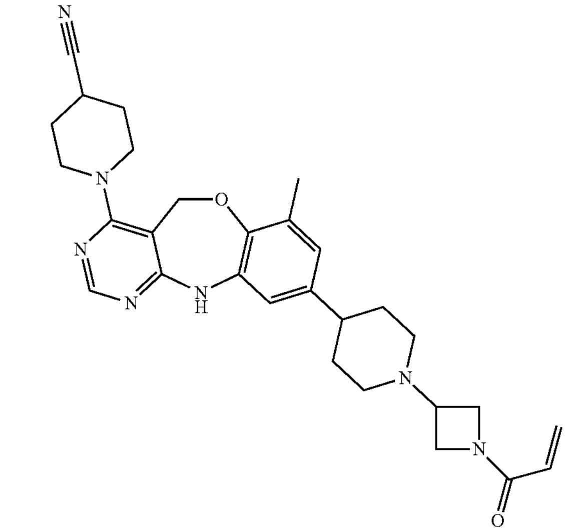 [SMILES: C=CC(=O)N1CC(N2CCC(c3cc(C)c4c(c3)Nc3ncnc(N5CCC(C#N)CC5)c3CO4)CC2)C1] |
| 72 | 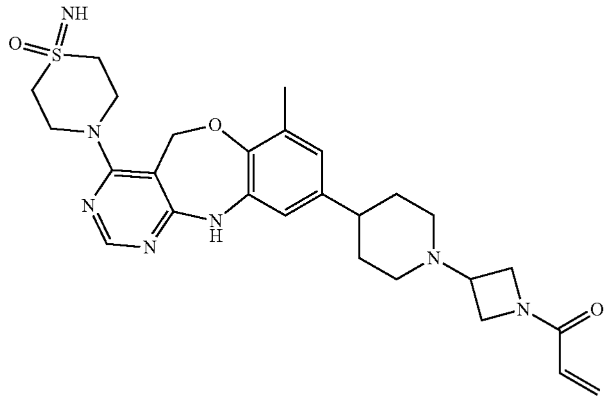 [SMILES: C=CC(=O)N1CC(N2CCC(c3cc(C)c4c(c3)Nc3ncnc(N5CCS(=N)(=O)CC5)c3CO4)CC2)C1] |
| 73 | 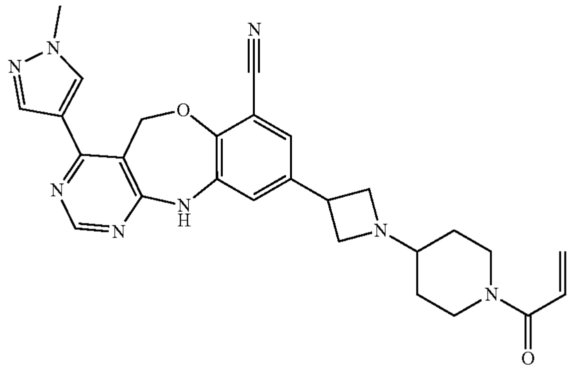 [SMILES: C=CC(=O)N1CCC(N2CC(c3cc(C#N)c4c(c3)Nc3ncnc(-c5cnn(C)c5)c3CO4)C2)CC1] |

-continued
| Cpd # | Structure |
| --- | --- |
| 76 | 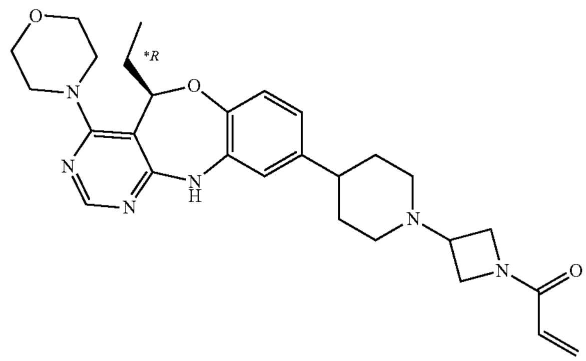 [SMILES: C=CC(=O)N1CC(N2CCC(c3ccc4c(c3)Nc3ncnc(N5CCOCC5)c3[C@@H](CC)O4)CC2)C1] |
| 74 | 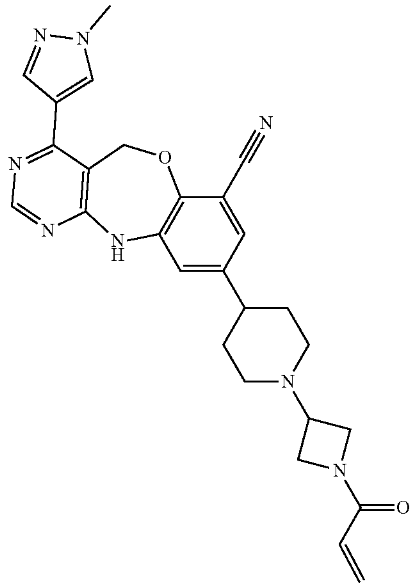 [SMILES: C=CC(=O)N1CC(N2CCC(c3cc(C#N)c4c(c3)Nc3ncnc(-c5cnn(C)c5)c3CO4)CC2)C1] |
| 77 | 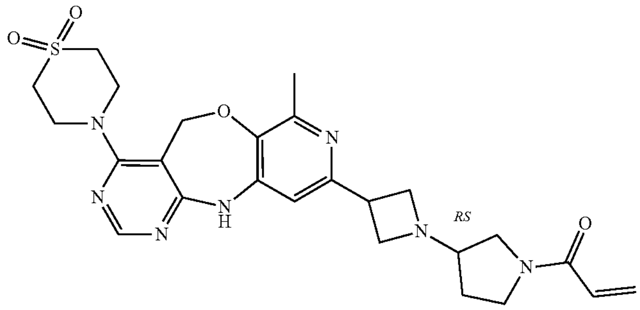 [SMILES: C=CC(=O)N1CCC(N2CC(c3cc4c(c(C)n3)OCc3c(ncnc3N3CCS(=O)(=O)CC3)N4)C2)C1] |

-continued
| Cpd # | Structure |
|---|---|
| 75 | 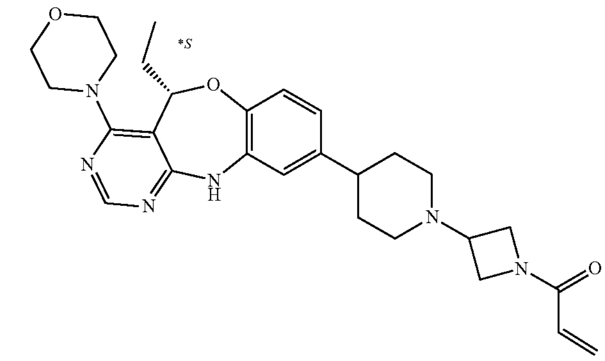 [SMILES: C=CC(=O)N1CC(N2CCC(c3ccc4c(c3)Nc3ncnc(N5CCOCC5)c3[C@H](CC)O4)CC2)C1] |
| 78 | 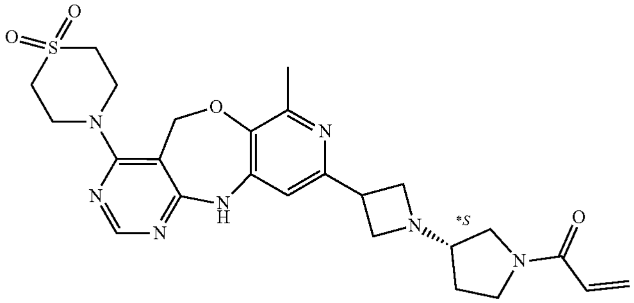 [SMILES: C=CC(=O)N1CC[C@H](N2CC(c3cc4c(c(C)n3)OCc3c(ncnc3N3CCS(=O)(=O)CC3)N4)C2)C1] |
| 79 | 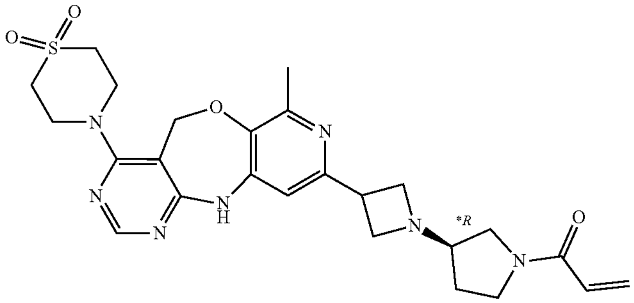 [SMILES: C=CC(=O)N1CC[C@@H](N2CC(c3cc4c(c(C)n3)OCc3c(ncnc3N3CCS(=O)(=O)CC3)N4)C2)C1] |
| 82 | 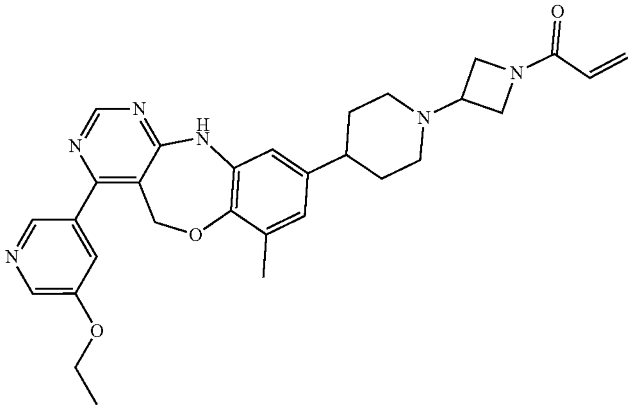 [SMILES: C=CC(=O)N1CC(N2CCC(c3cc(C)c4c(c3)Nc3ncnc(-c5cncc(OCC)c5)c3CO4)CC2)C1] |

-continued
| Cpd # | Structure |
| --- | --- |
| 80 | 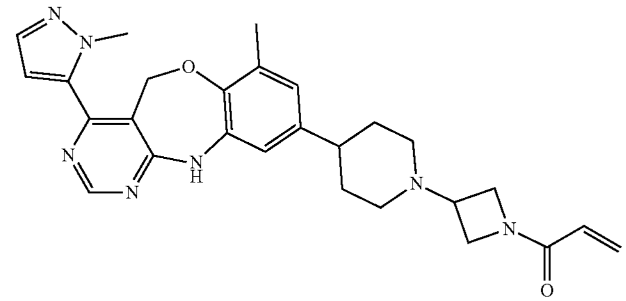 [SMILES: C=CC(=O)N1CC(N2CCC(c3cc(C)c4c(c3)Nc3ncnc(-c5ccnn5C)c3CO4)CC2)C1] |
| 83 | 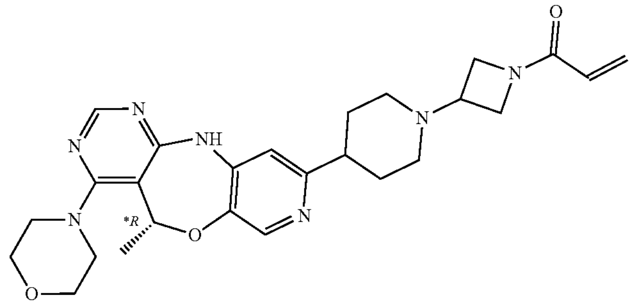 [SMILES: C=CC(=O)N1CC(N2CCC(c3cc4c(cn3)O[C@H](C)c3c(ncnc3N3CCOCC3)N4)CC2)C1] |
| 81 | 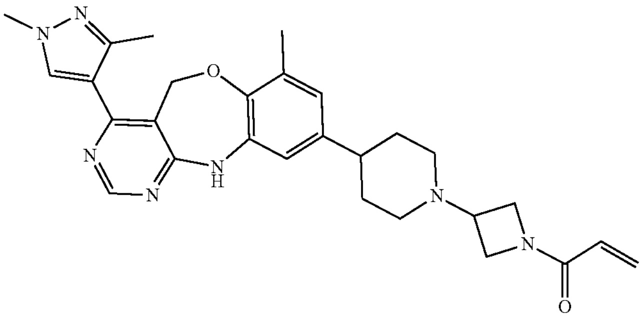 [SMILES: C=CC(=O)N1CC(N2CCC(c3cc(C)c4c(c3)Nc3ncnc(-c5cn(C)nc5C)c3CO4)CC2)C1] |
| 84 | 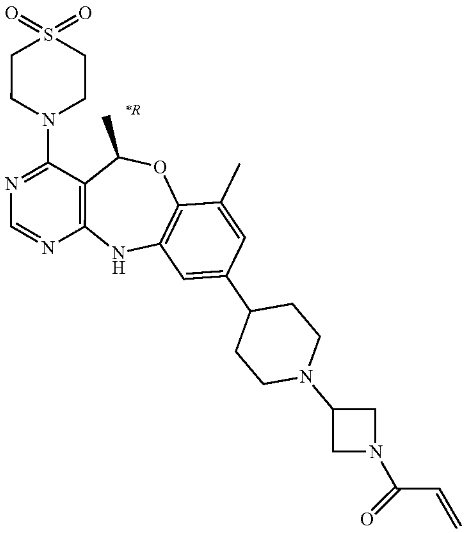 [SMILES: C=CC(=O)N1CC(N2CCC(c3cc(C)c4c(c3)Nc3ncnc(N5CCS(=O)(=O)CC5)c3[C@@H](C)O4)CC2)C1] |

-continued
| Cpd # | Structure |
|---|---|
| 85 | 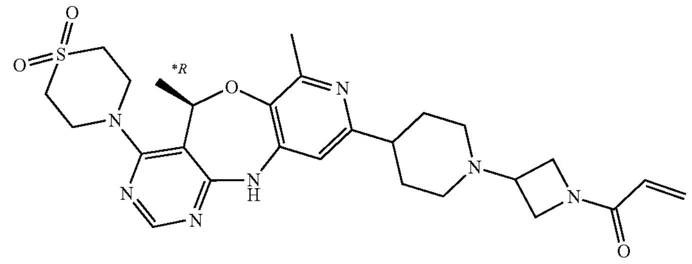 [SMILES: C=CC(=O)N1CC(N2CCC(c3cc4c(c(C)n3)O[C@H](C)c3c(ncnc3N3CCS(=O)(=O)CC3)N4)CC2)C1] |
| 88 | 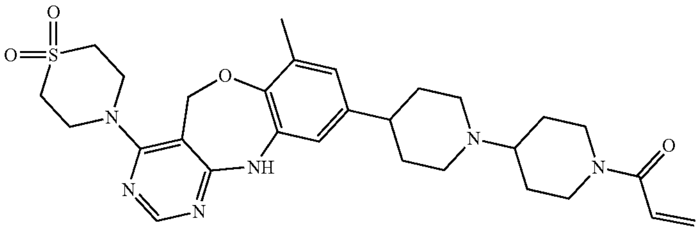 [SMILES: C=CC(=O)N1CCC(N2CCC(c3cc(C)c4c(c3)Nc3ncnc(N5CCS(=O)(=O)CC5)c3CO4)CC2)CC1] |
| 86 | 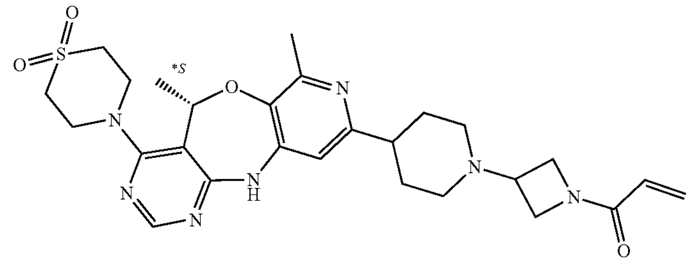 [SMILES: C=CC(=O)N1CC(N2CCC(c3cc4c(c(C)n3)O[C@@H](C)c3c(ncnc3N3CCS(=O)(=O)CC3)N4)CC2)C1] |
| 89 | 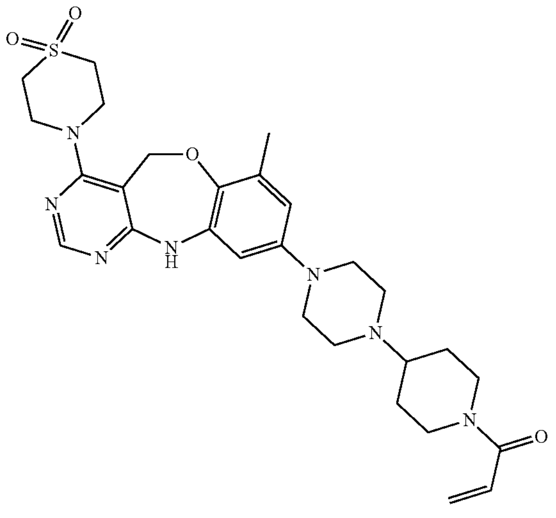 [SMILES: C=CC(=O)N1CCC(N2CCN(c3cc(C)c4c(c3)Nc3ncnc(N5CCS(=O)(=O)CC5)c3CO4)CC2)CC1] |

-continued
| Cpd # | Structure |
|---|---|
| 87 | 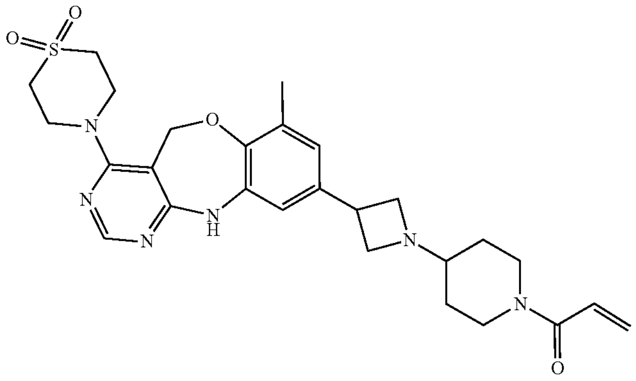 [SMILES: C=CC(=O)N1CCC(N2CC(c3cc(C)c4c(c3)Nc3ncnc(N5CCS(=O)(=O)CC5)c3CO4)C2)CC1] |
| 90 | 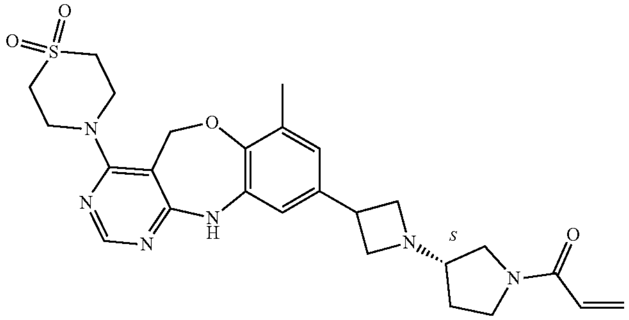 |
| 91 | 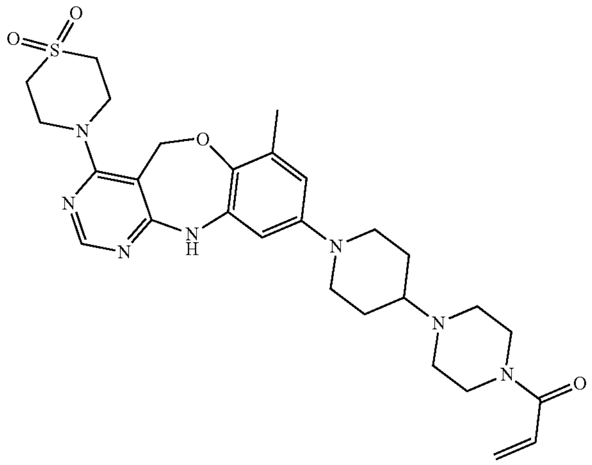 [SMILES: C=CC(=O)N1CCN(C2CCN(c3cc(C)c4c(c3)Nc3ncnc(N5CCS(=O)(=O)CC5)c3CO4)CC2)CC1] |
| 94 | 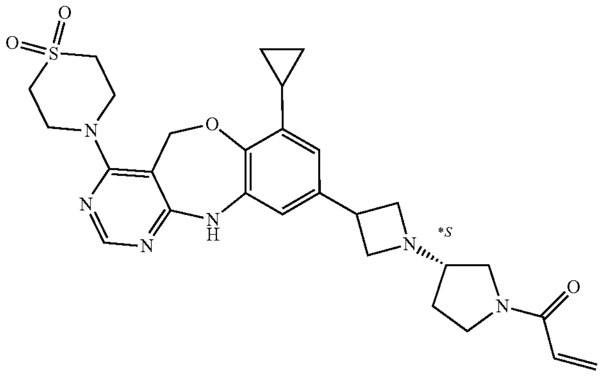 [SMILES: C=CC(=O)N1CC[C@H](N2CC(c3cc4c(c(C5CC5)c3)OCc3c(ncnc3N3CCS(=O)(=O)CC3)N4)C2)C1] |

-continued
| Cpd # | Structure |
| --- | --- |
| 92 | 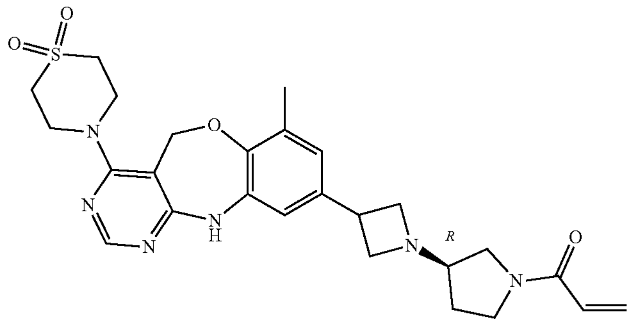 |
| 95 | 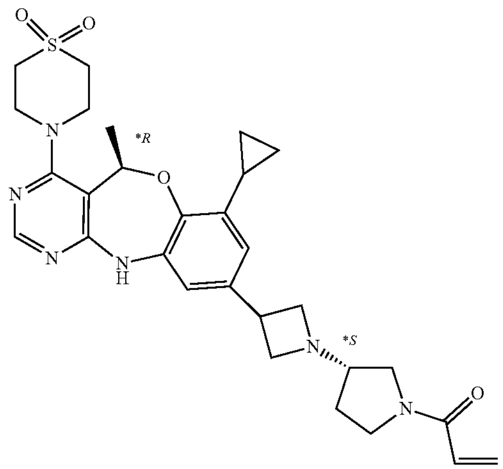 [SMILES: C=CC(=O)N1CC[C@H](N2CC(c3cc4c(c(C5CC5)c3)O[C@H](C)c3c(ncnc3N3CCS(=O)(=O)CC3)N4)C2)C1] |
| 93 | 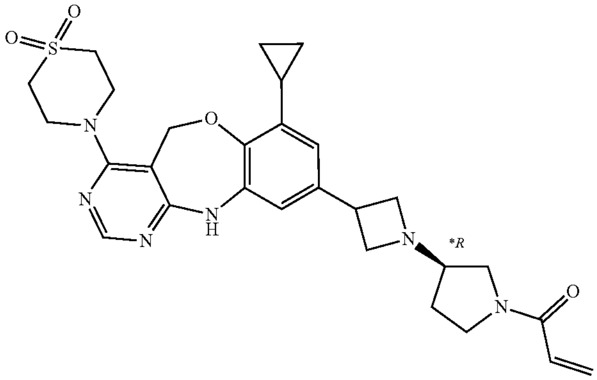 [SMILES: C=CC(=O)N1CC[C@@H](N2CC(c3cc4c(c(C5CC5)c3)OCc3c(ncnc3N3CCS(=O)(=O)CC3)N4)C2)C1] |

-continued
| Cpd # | Structure |
|---|---|
| 96 | 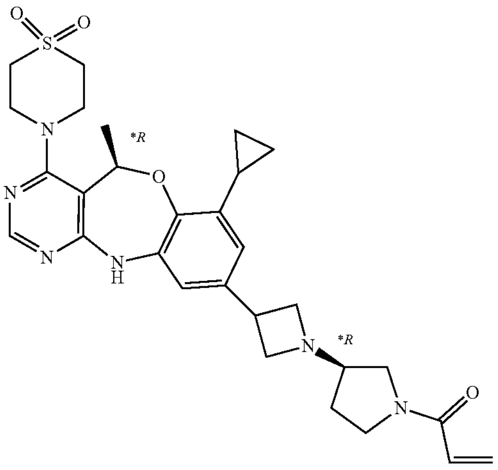 [SMILES: C=CC(=O)N1CC[C@@H](N2CC(c3cc4c(c(C5CC5)c3)O[C@H](C)c3c(ncnc3N3CCS(=O)(=O)CC3)N4)C2)C1] |
| 97 | 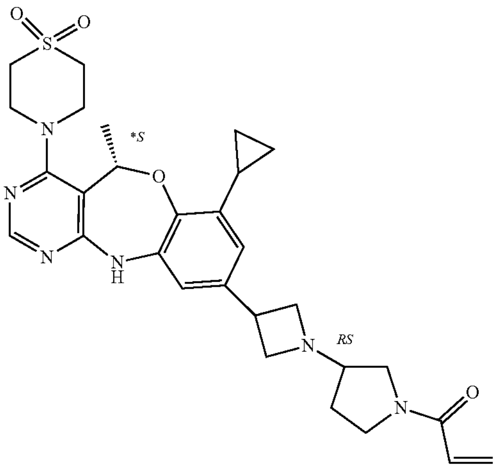 [SMILES: C=CC(=O)N1CCC(N2CC(c3cc4c(c(C5CC5)c3)O[C@@H](C)c3c(ncnc3N3CCS(=O)(=O)CC3)N4)C2)C1] |
| 100 | 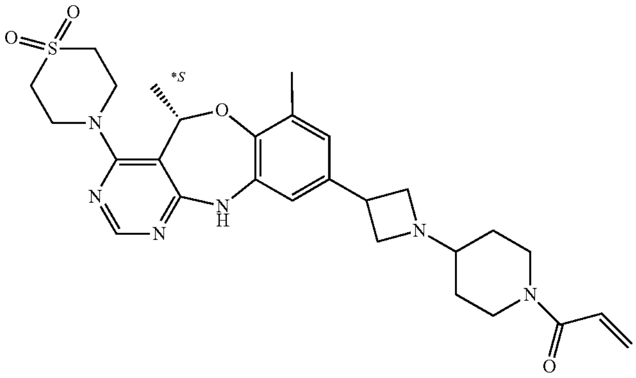 [SMILES: C=CC(=O)N1CCC(N2CC(c3cc(C)c4c(c3)Nc3ncnc(N5CCS(=O)(=O)CC5)c3[C@H](C)O4)C2)CC1] |

-continued
| Cpd # | Structure |
|---|---|
| 98 | 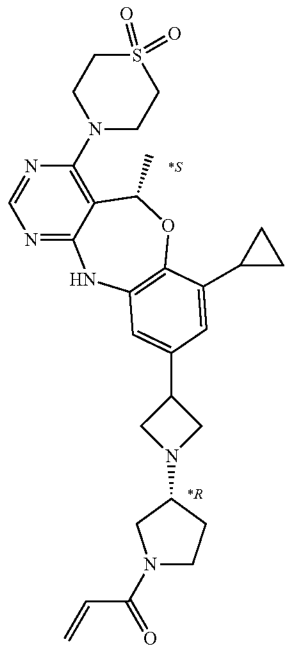 [SMILES: C=CC(=O)N1CC[C@@H](N2CC(c3cc4c(c(C5CC5)c3)O[C@@H](C)c3c(ncnc3N3CCS(=O)(=O)CC3)N4)C2)C1] |
| 101 | 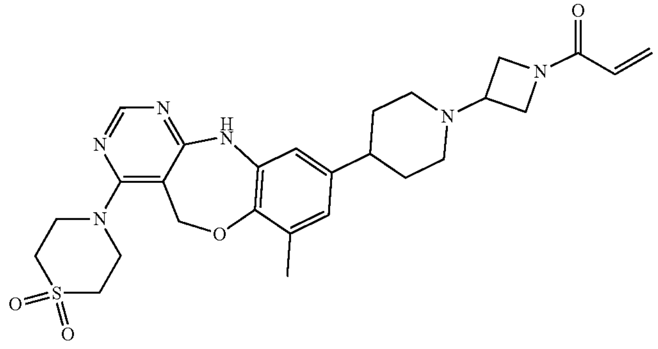 [SMILES: C=CC(=O)N1CC(N2CCC(c3cc(C)c4c(c3)Nc3ncnc(N5CCS(=O)(=O)CC5)c3CO4)CC2)C1] |

-continued
| Cpd # | Structure |
|---|---|
| 99 | 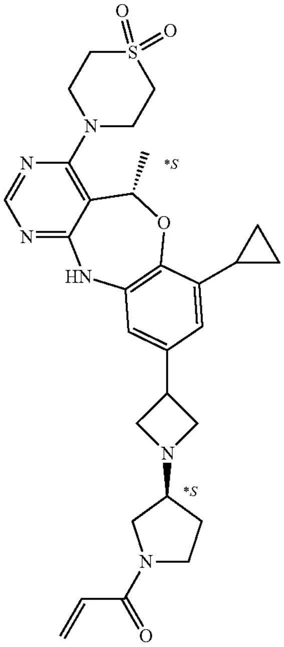 [SMILES: C=CC(=O)N1CC[C@H](N2CC(c3cc4c(c(C5CC5)c3)O[C@@H](C)c3c(ncnc3N3CCS(=O)(=O)CC3)N4)C2)C1] |
| 102 | 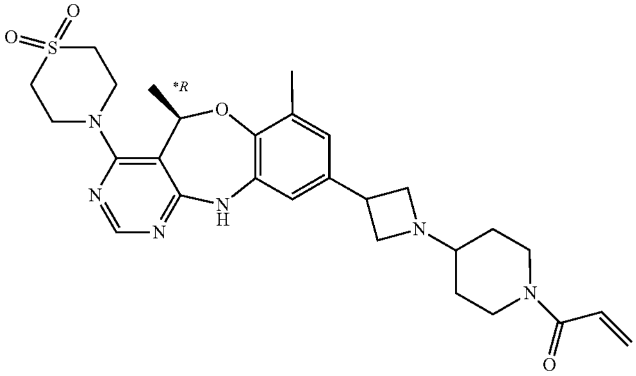 [SMILES: C=CC(=O)N1CCC(N2CC(c3cc(C)c4c(c3)Nc3ncnc(N5CCS(=O)(=O)CC5)c3[C@@H](C)O4)C2)CC1] |
| 103 | 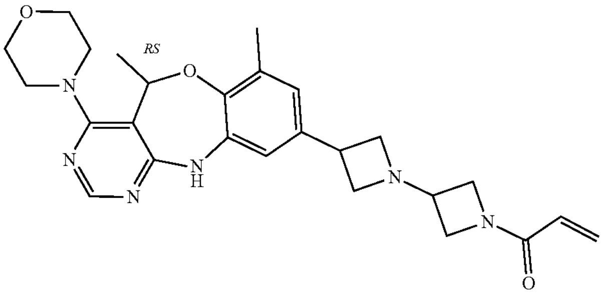 [SMILES: C=CC(=O)N1CC(N2CC(c3cc(C)c4c(c3)Nc3ncnc(N5CCOCC5)c3C(C)O4)C2)C1] |

-continued
| Cpd # | Structure |
|---|---|
| 106 | 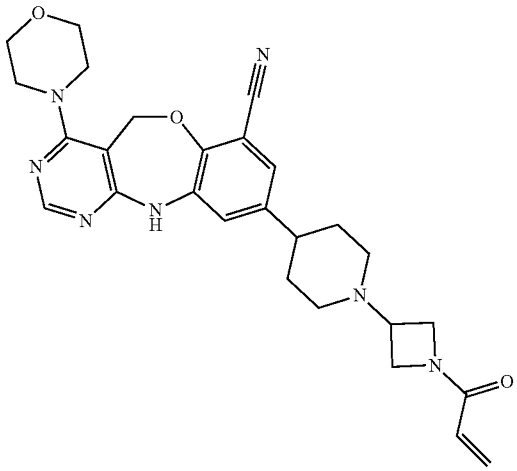 [SMILES: C=CC(=O)N1CC(N2CCC(c3cc(C#N)c4c(c3)Nc3ncnc(N5CCOCC5)c3CO4)CC2)C1] |
| 104 | 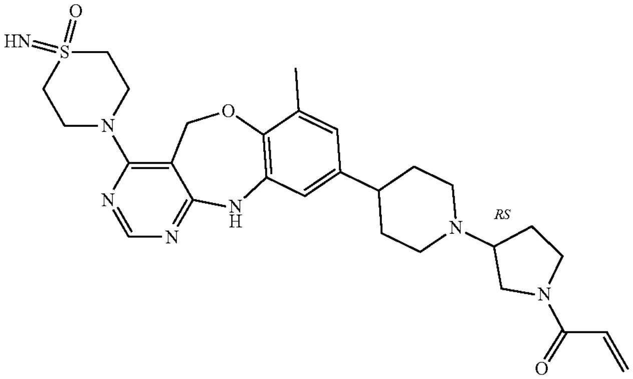 [SMILES: C=CC(=O)N1CCC(N2CCC(c3cc(C)c4c(c3)Nc3ncnc(N5CCS(=N)(=O)CC5)c3CO4)CC2)C1] |
| 107 | 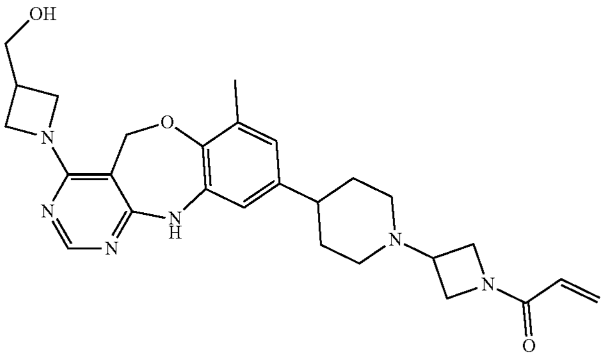 [SMILES: C=CC(=O)N1CC(N2CCC(c3cc(C)c4c(c3)Nc3ncnc(N5CC(CO)C5)c3CO4)CC2)C1] |
| 105 | 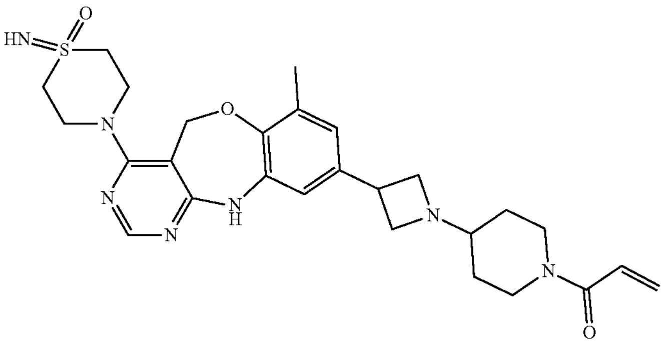 [SMILES: C=CC(=O)N1CCC(N2CC(c3cc(C)c4c(c3)Nc3ncnc(N5CCS(=N)(=O)CC5)c3CO4)C2)CC1] |

-continued
| Cpd # | Structure |
| --- | --- |
| 108 | 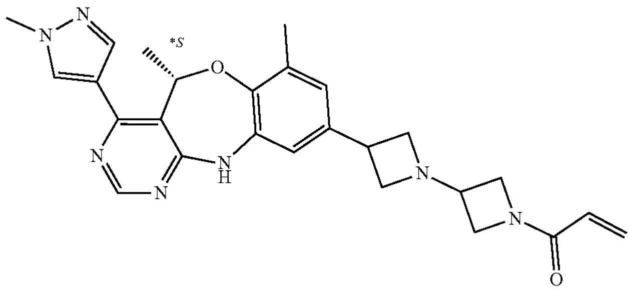 [SMILES: C=CC(=O)N1CC(N2CC(c3cc(C)c4c(c3)Nc3ncnc(-c5cnn(C)c5)c3[C@H](C)O4)C2)C1] |
| 109 | 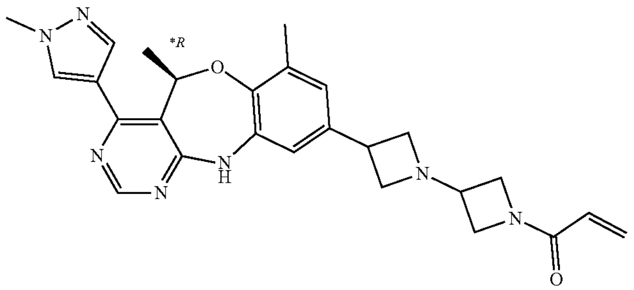 [SMILES: C=CC(=O)N1CC(N2CC(c3cc(C)c4c(c3)Nc3ncnc(-c5cnn(C)c5)c3[C@@H](C)O4)C2)C1] |
| 112 | 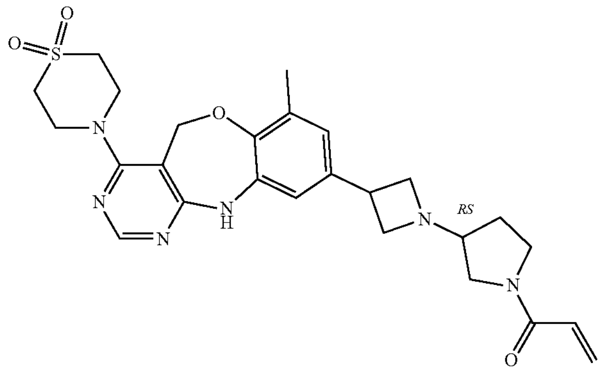 [SMILES: C=CC(=O)N1CCC(N2CC(c3cc(C)c4c(c3)Nc3ncnc(N5CCS(=O)(=O)CC5)c3CO4)C2)C1] |
| 110 | 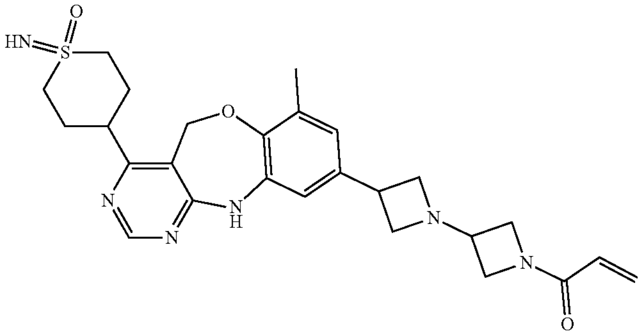 [SMILES: C=CC(=O)N1CC(N2CC(c3cc(C)c4c(c3)Nc3ncnc(C5CCS(=N)(=O)CC5)c3CO4)C2)C1] |

-continued
| Cpd # | Structure |
| --- | --- |
| 113 | 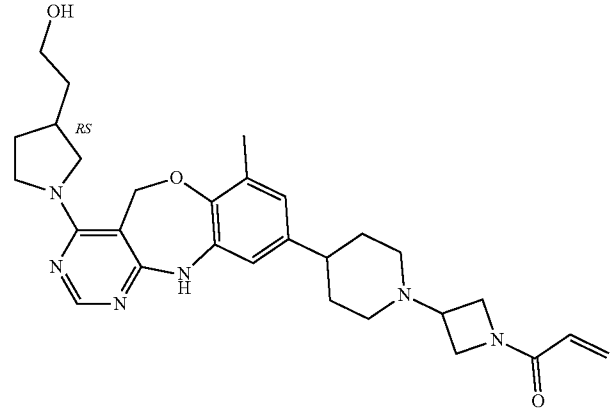 [SMILES: C=CC(=O)N1CC(N2CCC(c3cc(C)c4c(c3)Nc3ncnc(N5CCC(CCO)C5)c3CO4)CC2)C1] |
| 111 | 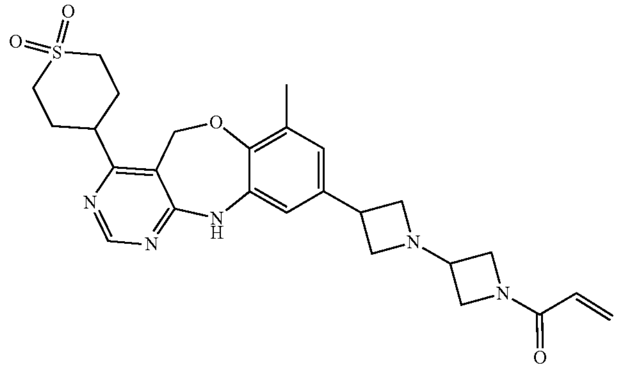 [SMILES: C=CC(=O)N1CC(N2CC(c3cc(C)c4c(c3)Nc3ncnc(C5CCS(=O)(=O)CC5)c3CO4)C2)C1] |
| 114 | 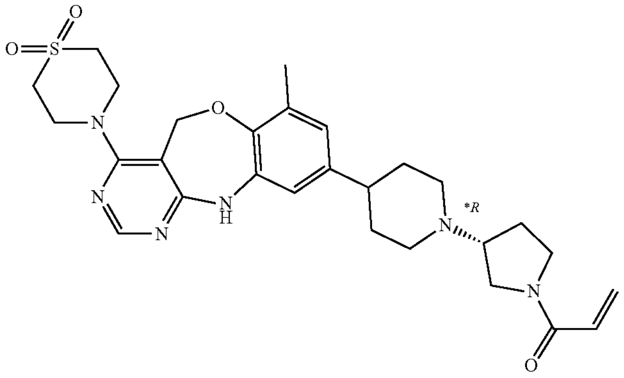 [SMILES: C=CC(=O)N1CC[C@@H](N2CCC(c3cc(C)c4c(c3)Nc3ncnc(N5CCS(=O)(=O)CC5)c3CO4)CC2)C1] |
| 115 | 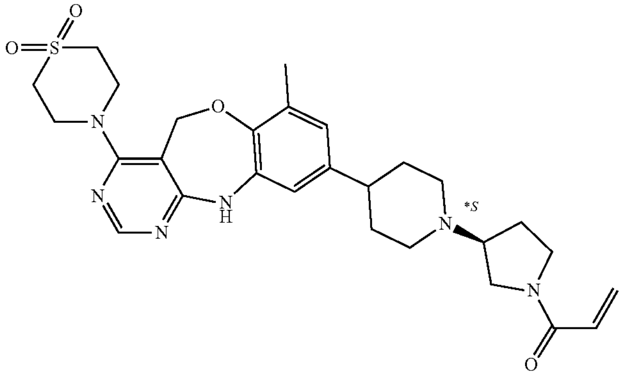 [SMILES: C=CC(=O)N1CC[C@H](N2CCC(c3cc(C)c4c(c3)Nc3ncnc(N5CCS(=O)(=O)CC5)c3CO4)CC2)C1] |

-continued
| Cpd # | Structure |
|---|---|
| 118 | 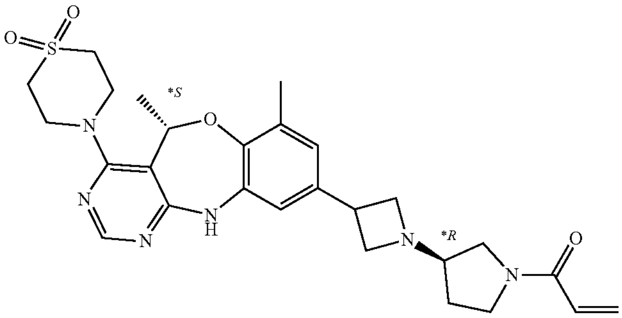 [SMILES: C=CC(=O)N1CC[C@@H](N2CC(c3cc(C)c4c(c3)Nc3ncnc(N5CCS(=O)(=O)CC5)c3[C@H](C)O4)C2)C1] |
| 116 | 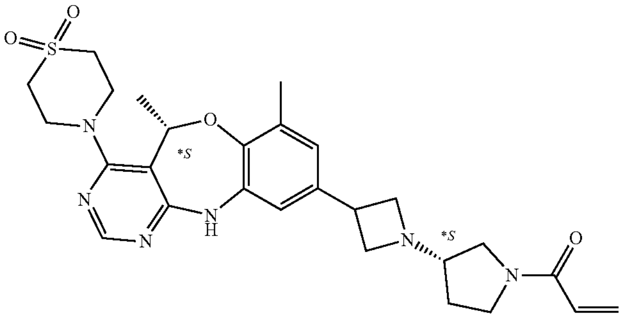 [SMILES: C=CC(=O)N1CC[C@H](N2CC(c3cc(C)c4c(c3)Nc3ncnc(N5CCS(=O)(=O)CC5)c3[C@H](C)O4)C2)C1] |
| 119 | 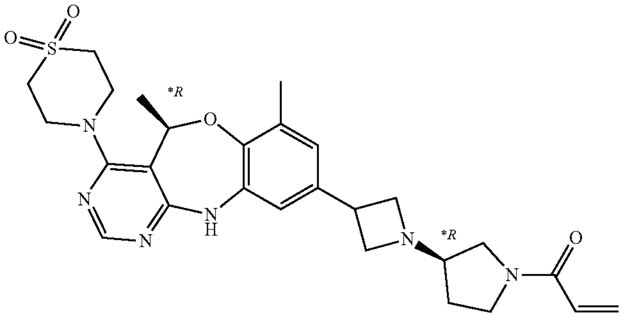 [SMILES: C=CC(=O)N1CC[C@@H](N2CC(c3cc(C)c4c(c3)Nc3ncnc(N5CCS(=O)(=O)CC5)c3[C@@H](C)O4)C2)C1] |
| 117 | 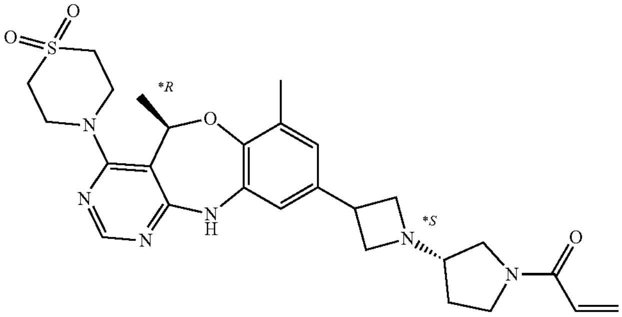 [SMILES: C=CC(=O)N1CC[C@H](N2CC(c3cc(C)c4c(c3)Nc3ncnc(N5CCS(=O)(=O)CC5)c3[C@@H](C)O4)C2)C1] |

-continued
| Cpd # | Structure |
|---|---|
| 120 | 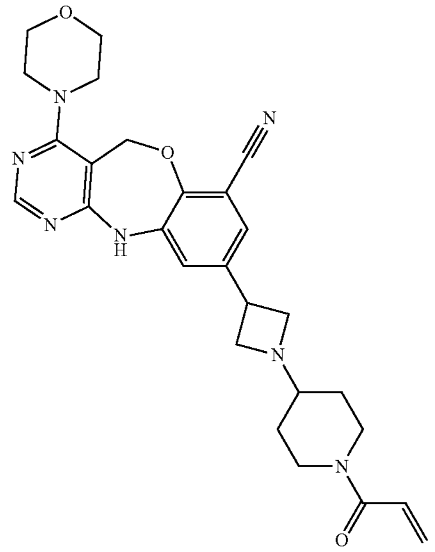 [SMILES: C=CC(=O)N1CCC(N2CC(c3cc(C#N)c4c(c3)Nc3ncnc(N5CCOCC5)c3CO4)C2)CC1] |
| 121 | 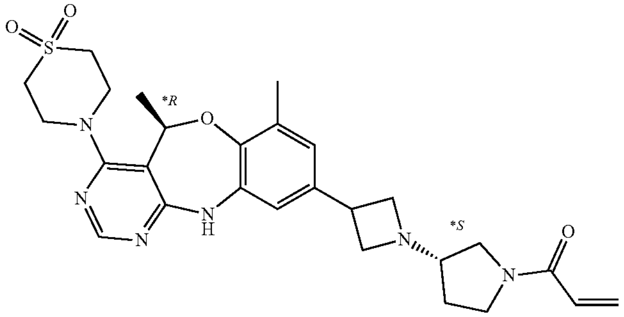 [SMILES: C=CC(=O)N1CC[C@H](N2CC(c3cc(C)c4c(c3)Nc3ncnc(N5CCS(=O)(=O)CC5)c3[C@@H](C)O4)C2)C1] |
| 124 | 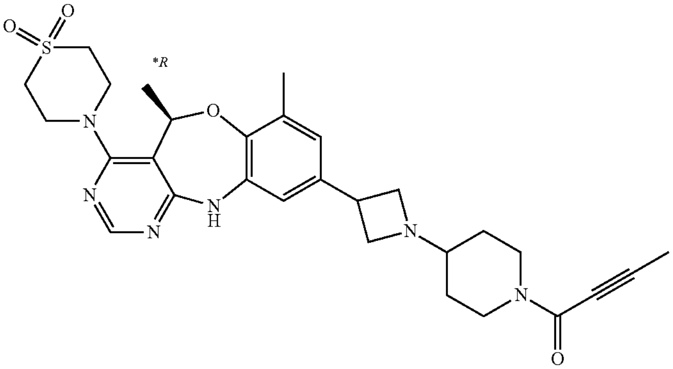 [SMILES: CC#CC(=O)N1CCC(N2CC(c3cc(C)c4c(c3)Nc3ncnc(N5CCS(=O)(=O)CC5)c3[C@@H](C)O4)C2)CC1] |
| 122 | 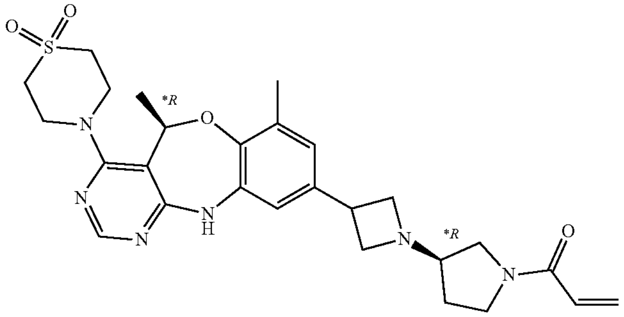 [SMILES: C=CC(=O)N1CC[C@@H](N2CC(c3cc(C)c4c(c3)Nc3ncnc(N5CCS(=O)(=O)CC5)c3[C@@H](C)O4)C2)C1] |

-continued
| Cpd # | Structure |
|---|---|
| 125 | 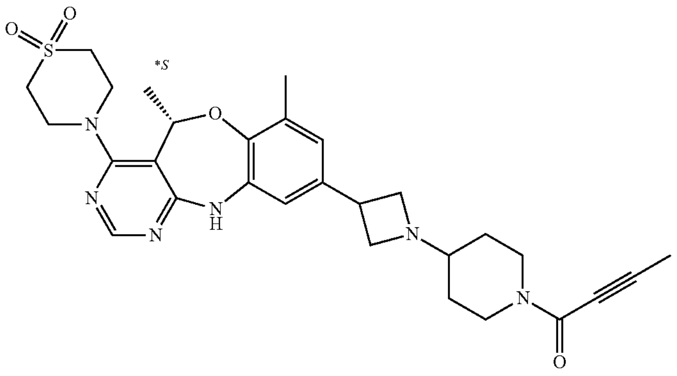 [SMILES: CC#CC(=O)N1CCC(N2CC(c3cc(C)c4c(c3)Nc3ncnc(N5CCS(=O)(=O)CC5)c3[C@H](C)O4)C2)CC1] |
| 123 | 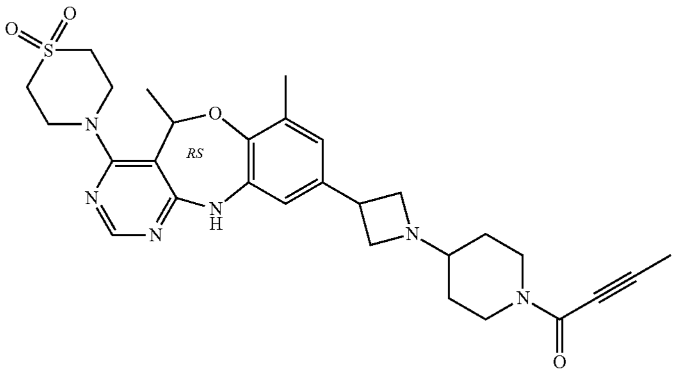 [SMILES: CC#CC(=O)N1CCC(N2CC(c3cc(C)c4c(c3)Nc3ncnc(N5CCS(=O)(=O)CC5)c3C(C)O4)C2)CC1] |
| 126 | 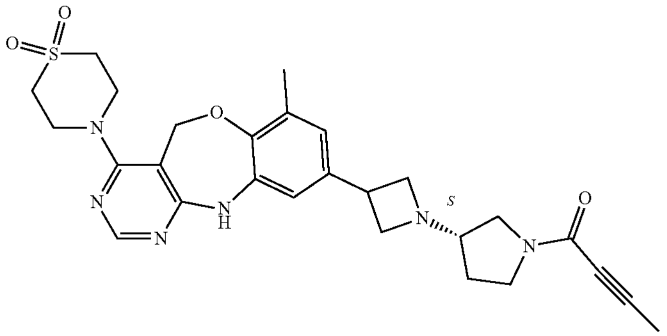 |
| 127 | 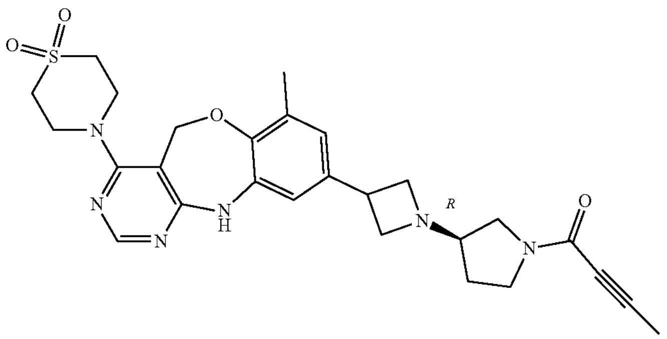 |

-continued
| Cpd # | Structure |
|---|---|
| 130 | 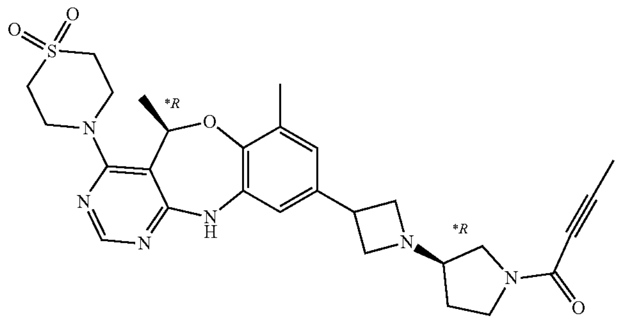 [SMILES: CC#CC(=O)N1CC[C@@H](N2CC(c3cc(C)c4c(c3)Nc3ncnc(N5CCS(=O)(=O)CC5)c3[C@@H](C)O4)C2)C1] |
| 128 | 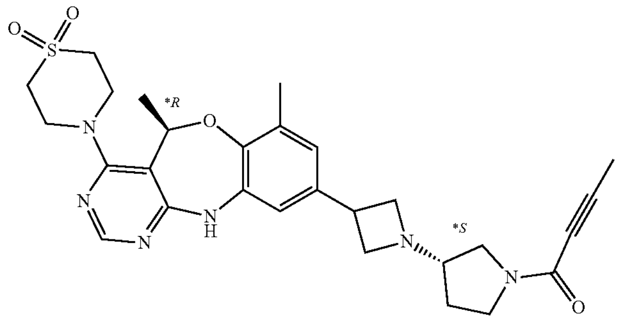 [SMILES: CC#CC(=O)N1CC[C@H](N2CC(c3cc(C)c4c(c3)Nc3ncnc(N5CCS(=O)(=O)CC5)c3[C@@H](C)O4)C2)C1] |
| 131 | 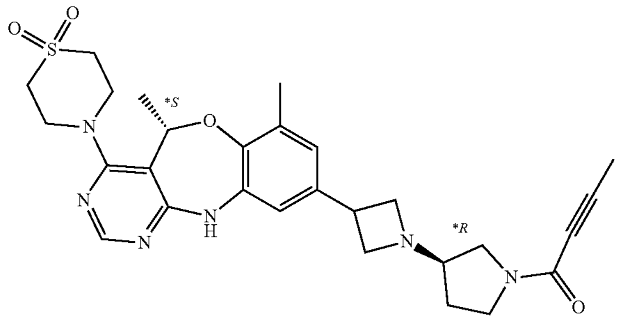 [SMILES: CC#CC(=O)N1CC[C@@H](N2CC(c3cc(C)c4c(c3)Nc3ncnc(N5CCS(=O)(=O)CC5)c3[C@H](C)O4)C2)C1] |
| 129 | 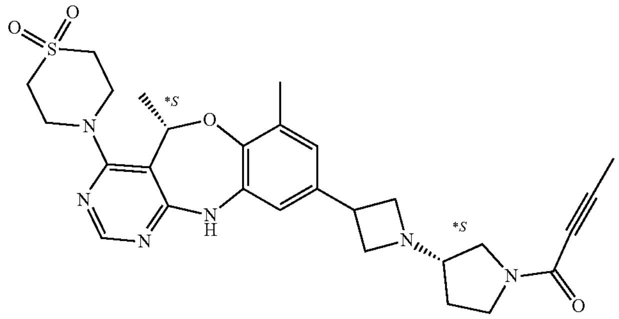 [SMILES: CC#CC(=O)N1CC[C@H](N2CC(c3cc(C)c4c(c3)Nc3ncnc(N5CCS(=O)(=O)CC5)c3[C@H](C)O4)C2)C1] |

-continued
| Cpd # | Structure |
|---|---|
| 132 | 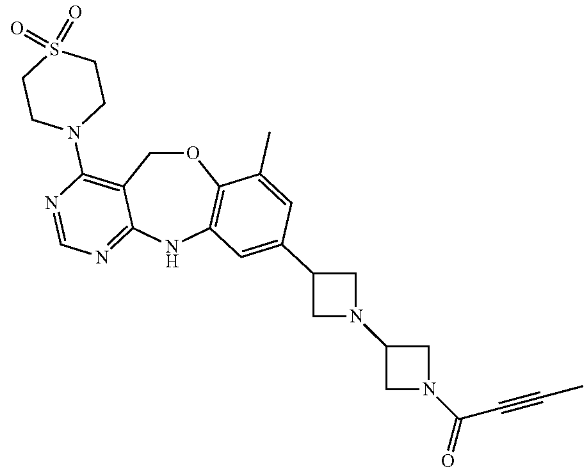 [SMILES: CC#CC(=O)N1CC(N2CC(c3cc(C)c4c(c3)Nc3ncnc(N5CCS(=O)(=O)CC5)c3CO4)C2)C1] |
| 133 | 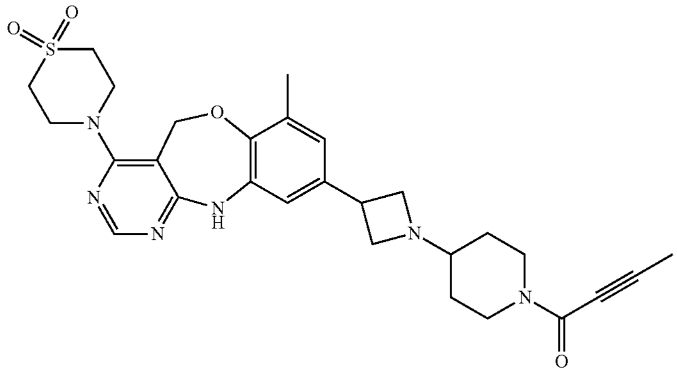 [SMILES: CC#CC(=O)N1CCC(N2CC(c3cc(C)c4c(c3)Nc3ncnc(N5CCS(=O)(=O)CC5)c3CO4)C2)CC1] |
| 136 | 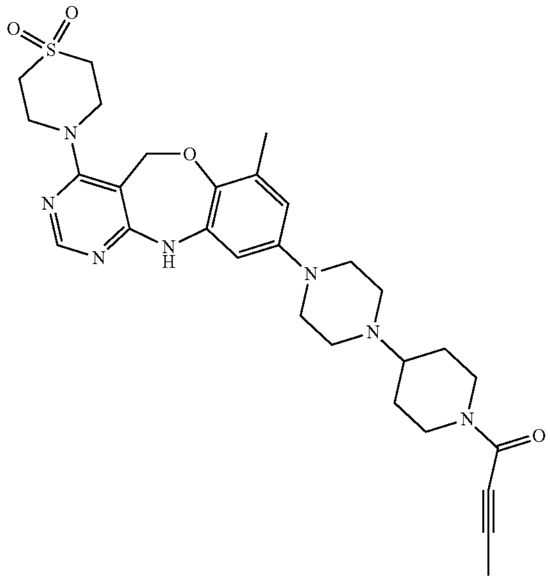 [SMILES: CC#CC(=O)N1CCC(N2CCN(c3cc(C)c4c(c3)Nc3ncnc(N5CCS(=O)(=O)CC5)c3CO4)CC2)CC1] |

-continued
| Cpd # | Structure |
|---|---|
| 134 | 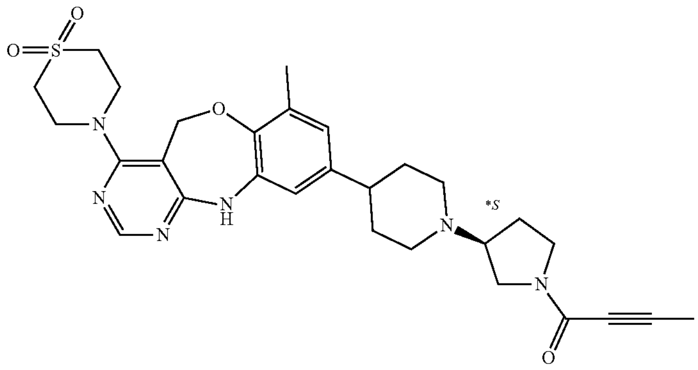 |
| 137 | 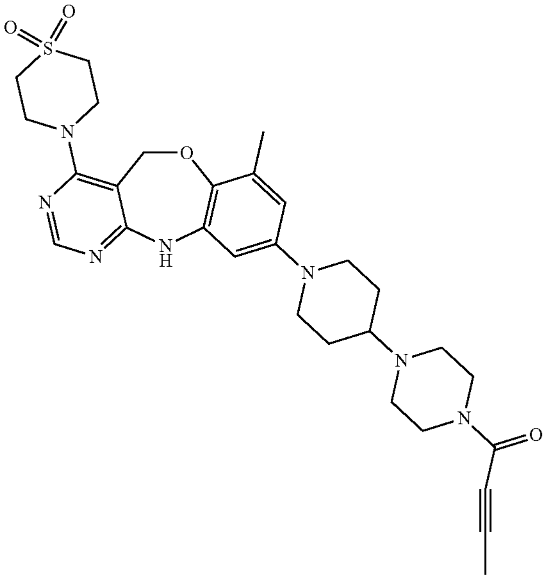 [SMILES: CC#CC(=O)N1CCN(C2CCN(c3cc(C)c4c(c3)Nc3ncnc(N5CCS(=O)(=O)CC5)c3CO4)CC2)CC1] |
| 135 | 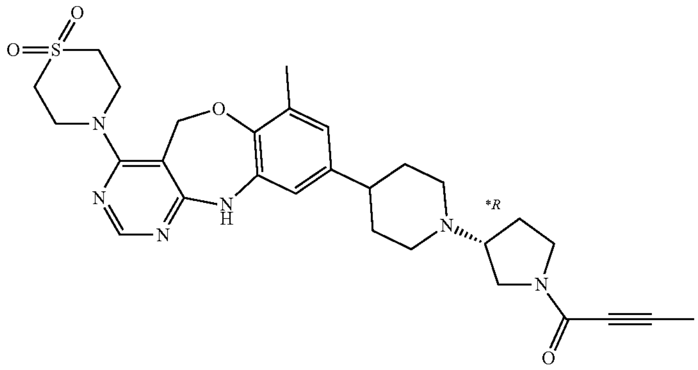 |

-continued
| Cpd # | Structure |
|---|---|
| 138 | 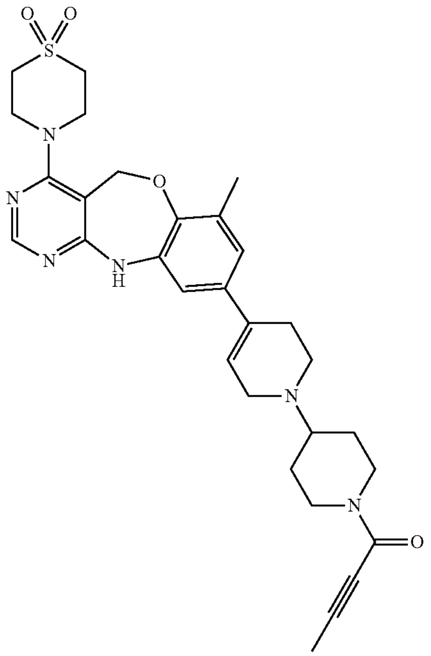 [SMILES: CC#CC(=O)N1CCC(N2CC=C(c3cc(C)c4c(c3)Nc3ncnc(N5CCS(=O)(=O)CC5)c3CO4)CC2)CC1] |
| 139 | 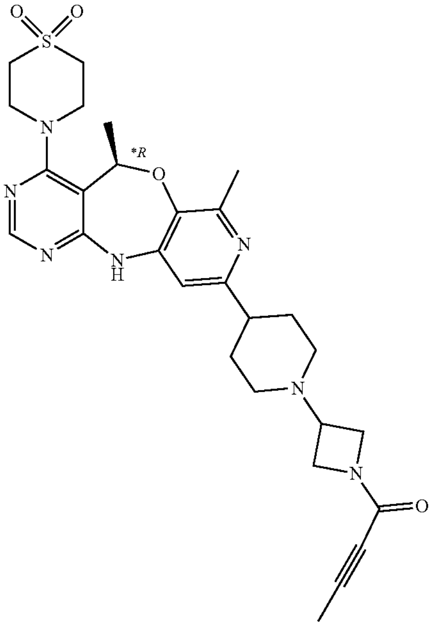 [SMILES: CC#CC(=O)N1CC(N2CCC(c3cc4c(c(C)n3)O[C@H](C)c3c(ncnc3N3CCS(=O)(=O)CC3)N4)CC2)C1] |

-continued
| Cpd # | Structure |
|---|---|
| 142 | 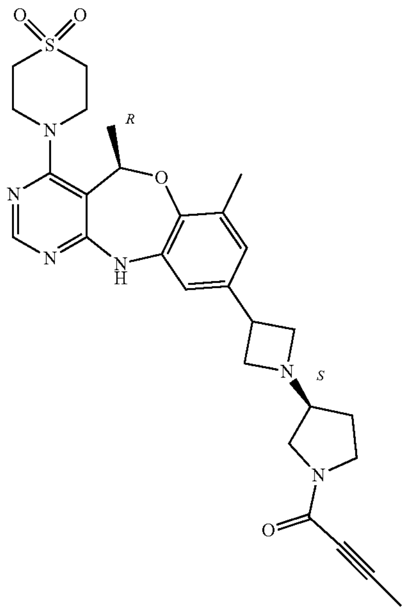 |
| 140 | 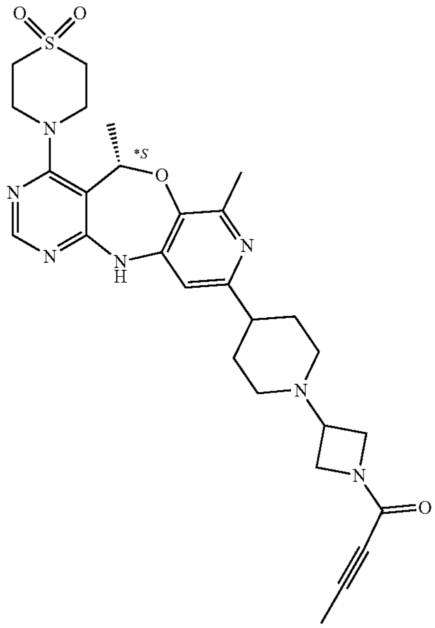 [SMILES: CC#CC(=O)N1CC(N2CCC(c3cc4c(c(C)n3)O[C@@H](C)c3c(ncnc3N3CCS(=O)(=O)CC3)N4)CC2)C1] |
| 143 | 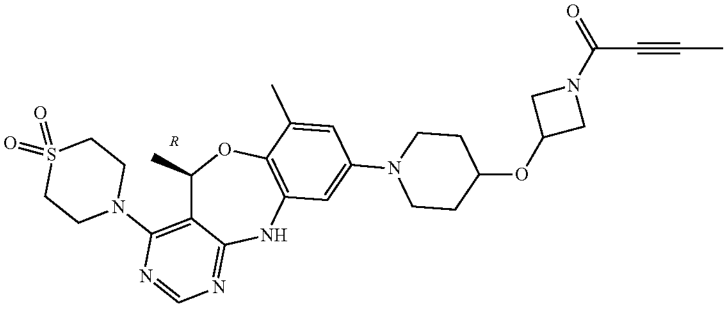 |

-continued
| Cpd # | Structure |
|---|---|
| 141 | 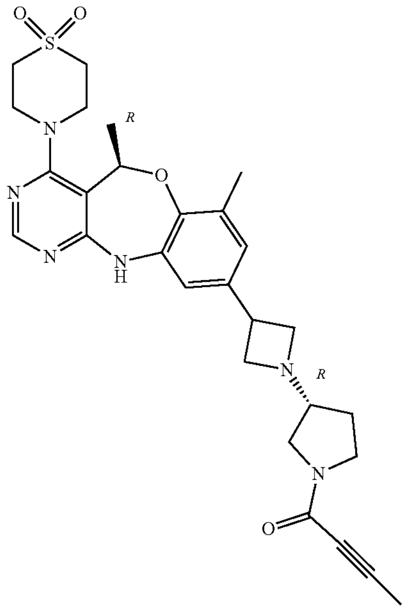 |
| 144 | 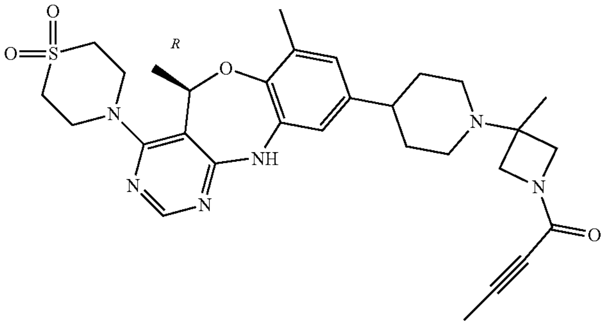 |
| 145 | 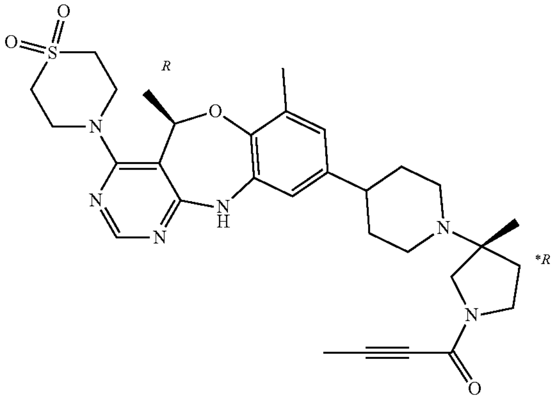 |

-continued
| Cpd # | Structure |
| --- | --- |
| 148 | 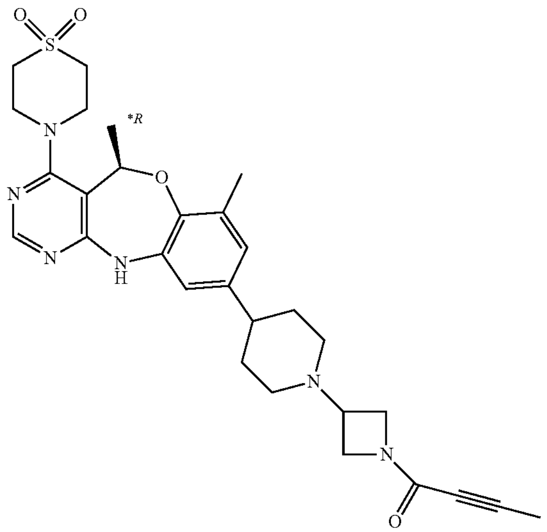 |
| 146 | 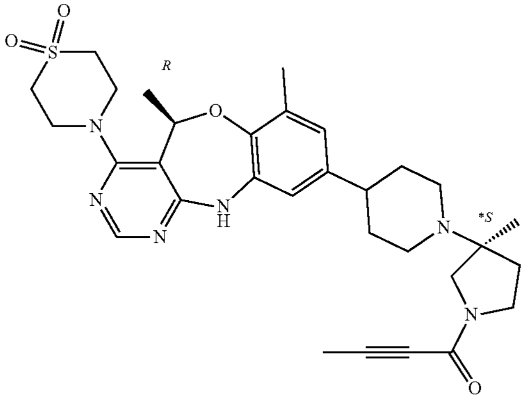 |
| 150 | 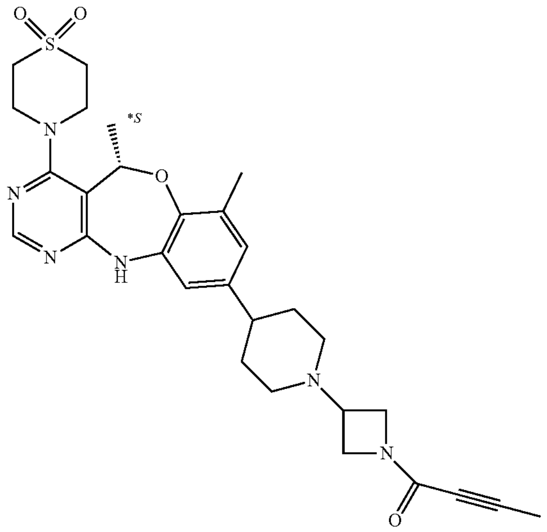 |

-continued
| Cpd # | Structure |
| --- | --- |
| 147 | 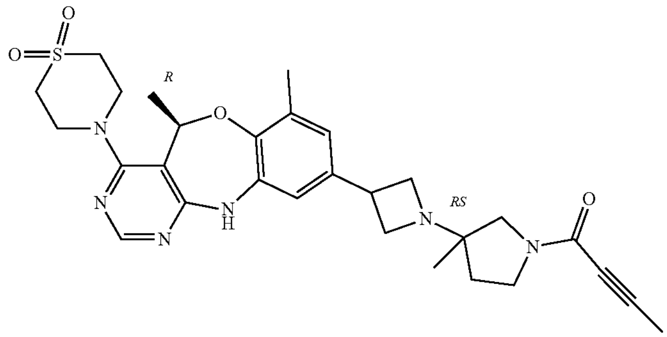 |
| 151 | 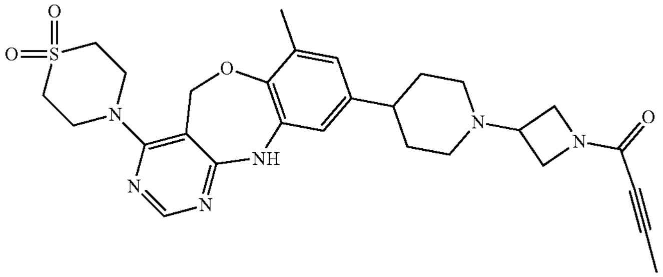 [SMILES: CC#CC(=O)N1CC(N2CCC(c3cc(C)c4c(c3)Nc3ncnc(N5CCS(=O)(=O)CC5)c3CO4)CC2)C1] |
| 152 | 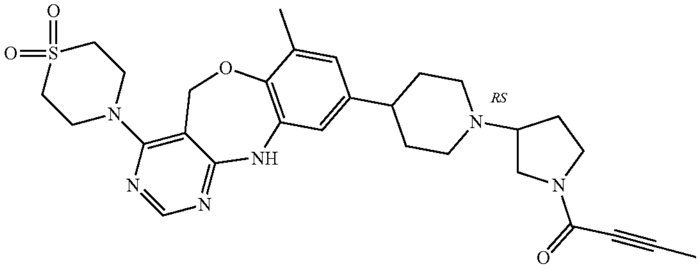 [SMILES: CC#CC(=O)N1CCC(N2CCC(c3cc(C)c4c(c3)Nc3ncnc(N5CCS(=O)(=O)CC5)c3CO4)CC2)C1] |
| 155 | 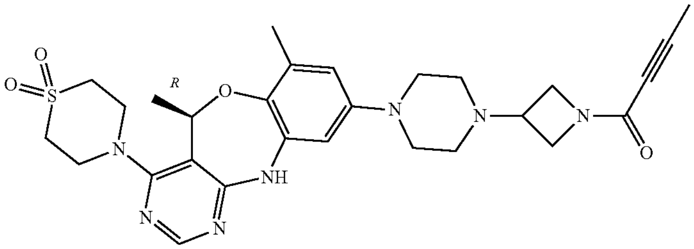 |
| 154 | 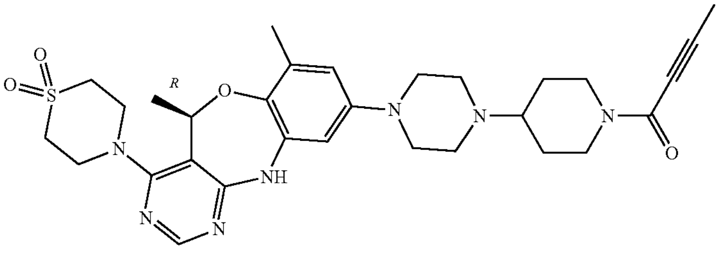 |

-continued
| Cpd # | Structure |
| --- | --- |
| 156 | 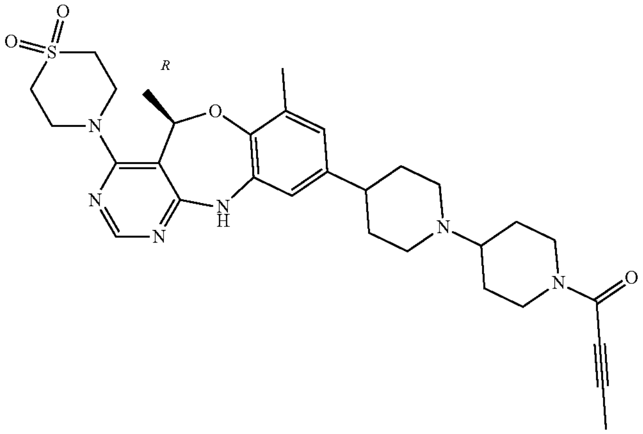 |
| 157 | 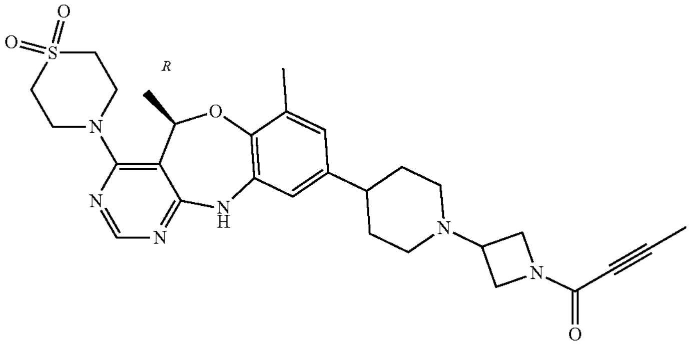 |
| 160 | 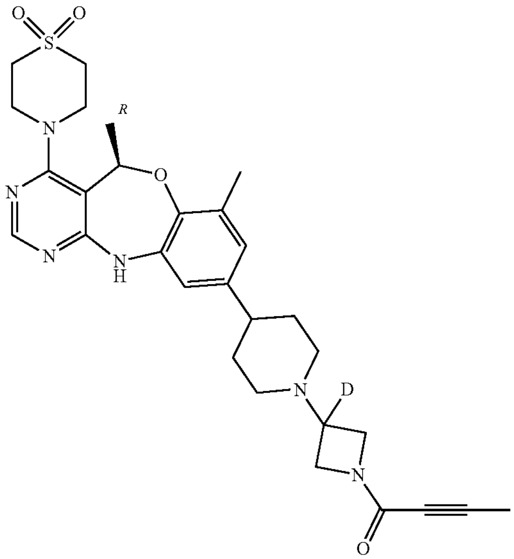 |

-continued
| Cpd # | Structure |
|---|---|
| 1581 | 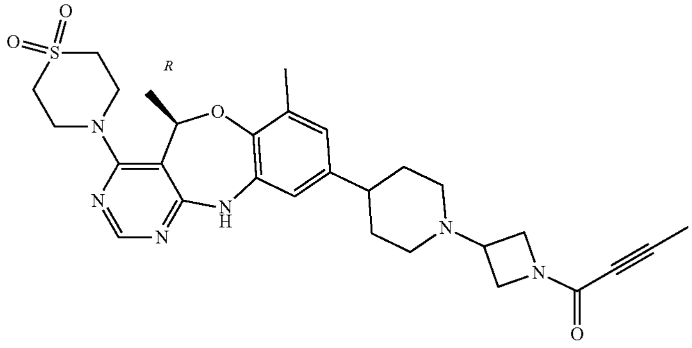 |
| 161 | 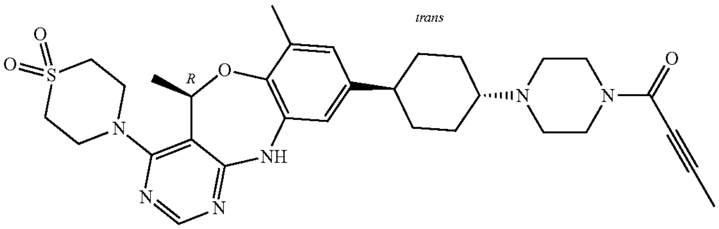 |
| 159 | 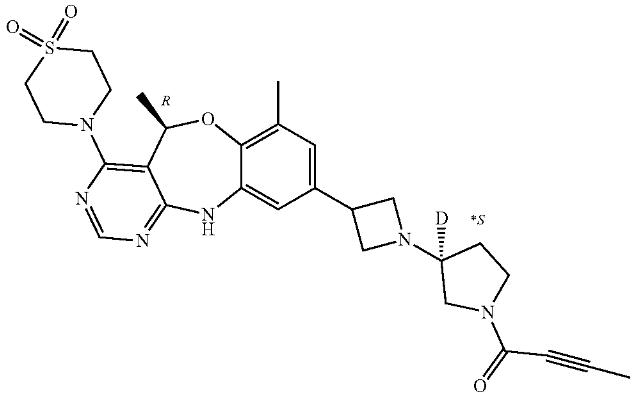 |
| 162 | 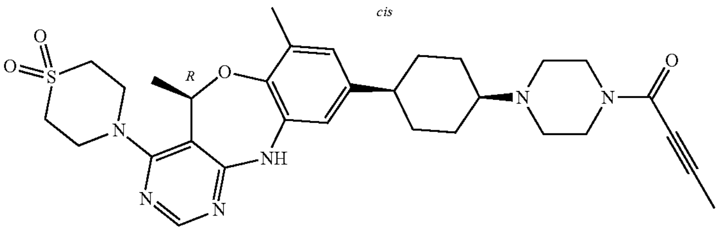 |

-continued
| Cpd # | Structure |
|---|---|
| 163 | 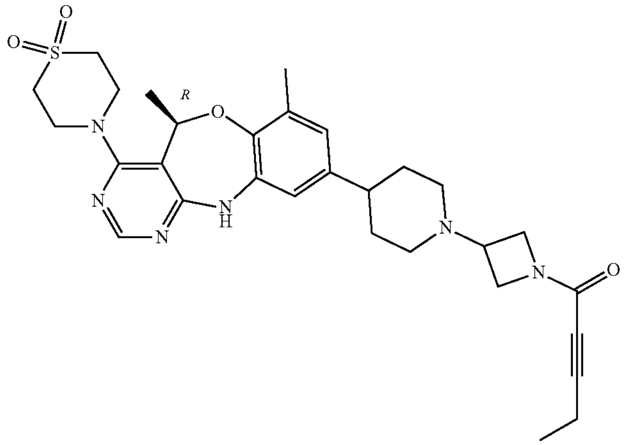 |
| 166 | 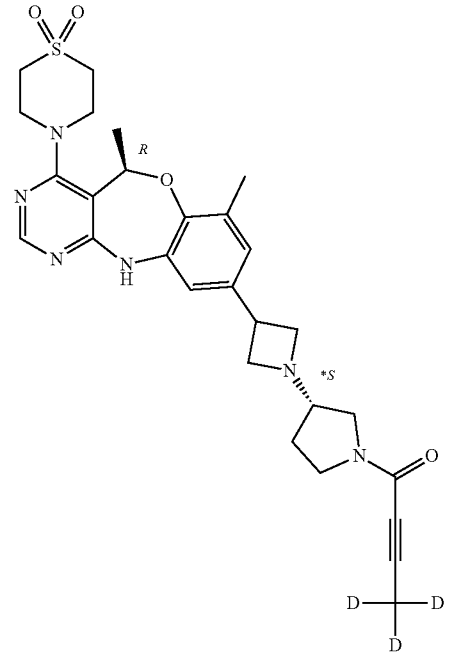 |

-continued
| Cpd # | Structure |
|---|---|
| 164 | 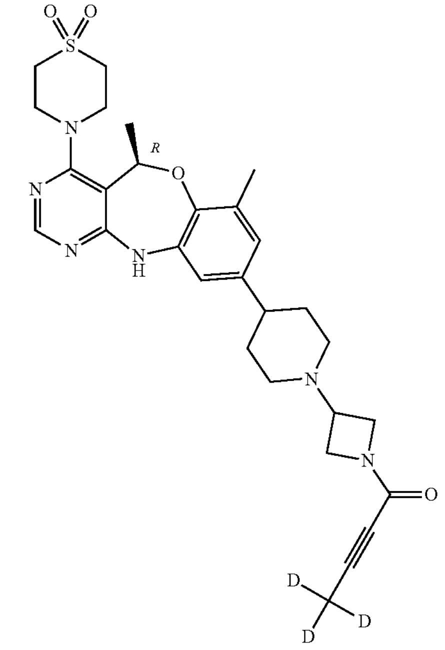 |
| 167 | 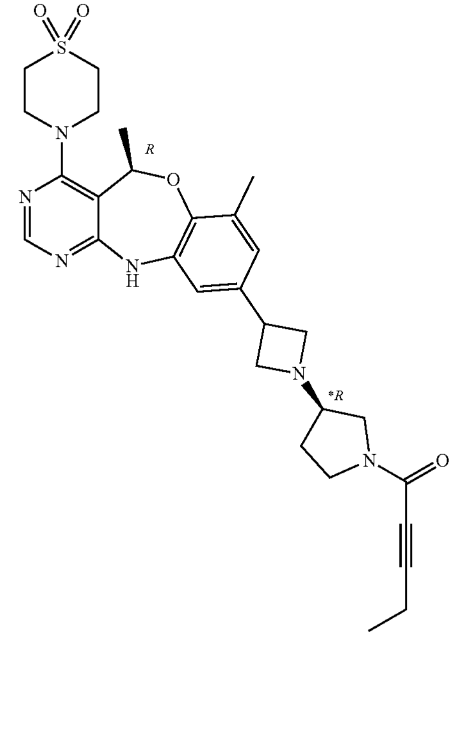 |

-continued
| Cpd # | Structure |
|---|---|
| 165 | 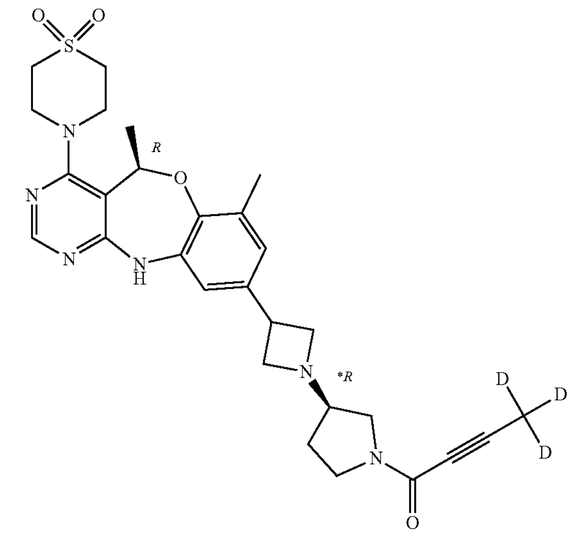 |
| 168 | 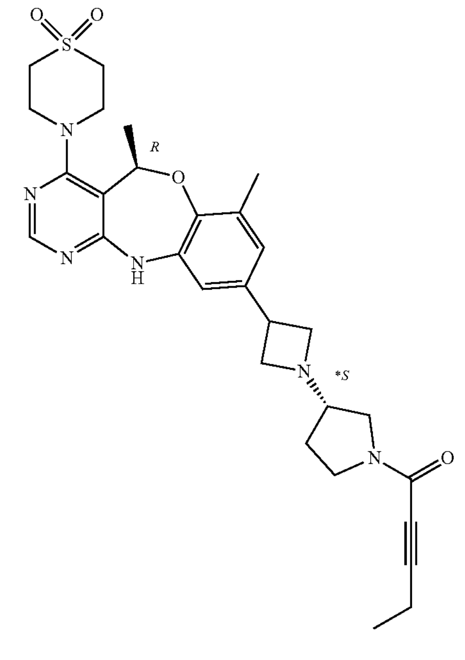 |

-continued
| Cpd # | Structure |
| --- | --- |
| 169 | 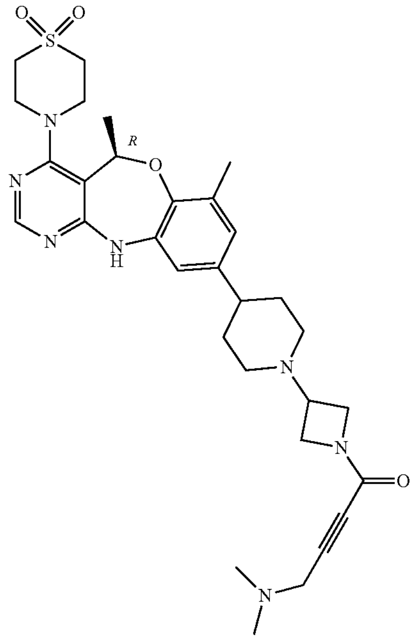 |
| 172 | 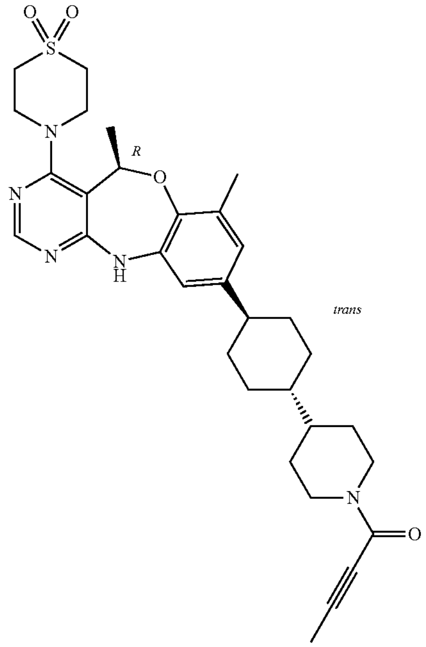 |

-continued
| Cpd # | Structure |
|---|---|
| 170 | 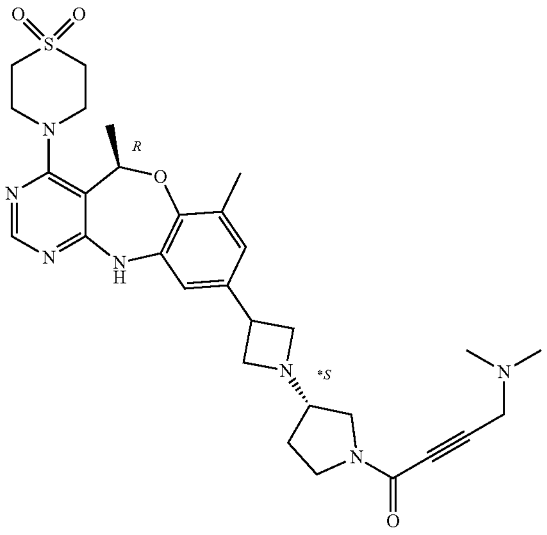 |
| 173 | 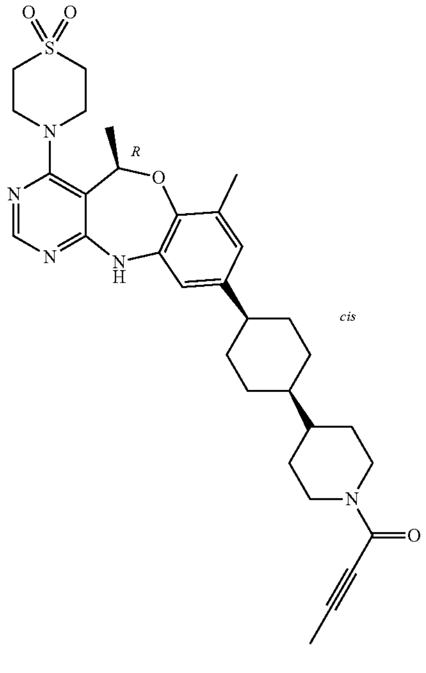 |

-continued
| Cpd # | Structure |
|---|---|
| 171 | 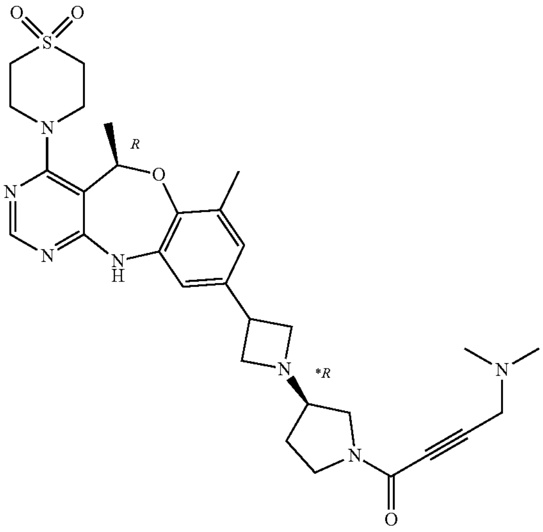 |
| 174 | 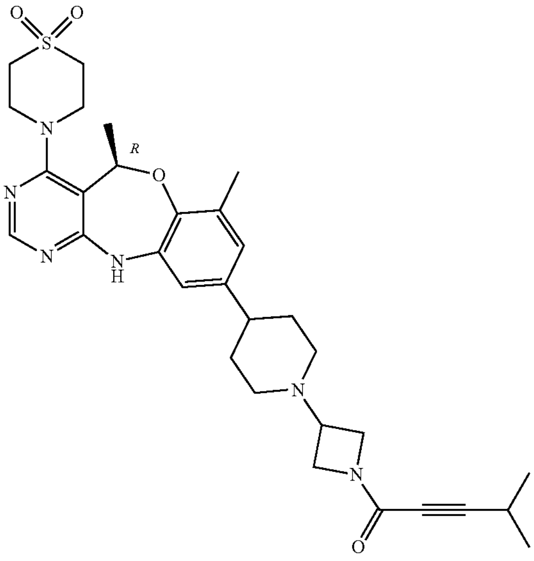 |

-continued
| Cpd # | Structure |
| --- | --- |
| 175 | 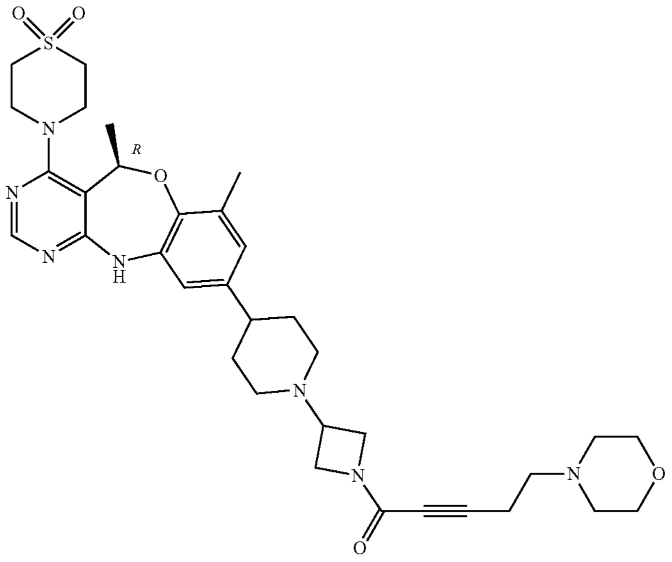 |
| 178 | 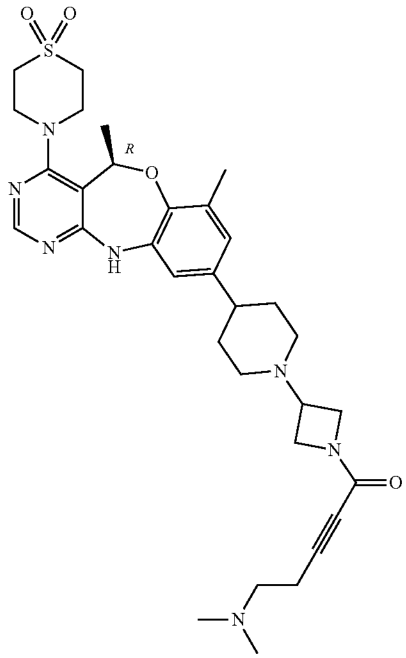 |

-continued
| Cpd # | Structure |
| --- | --- |
| 176 | 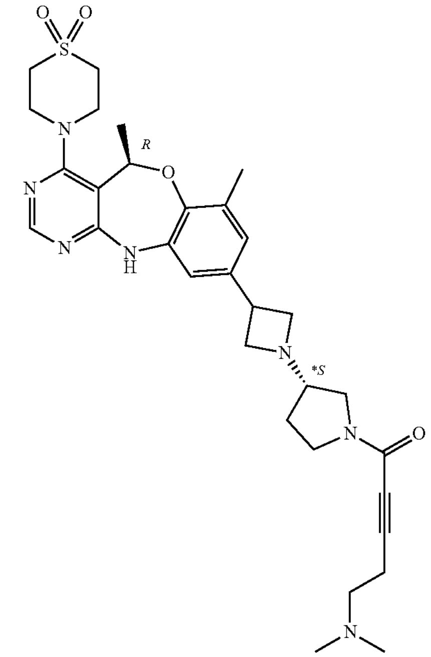 |
| 179 | 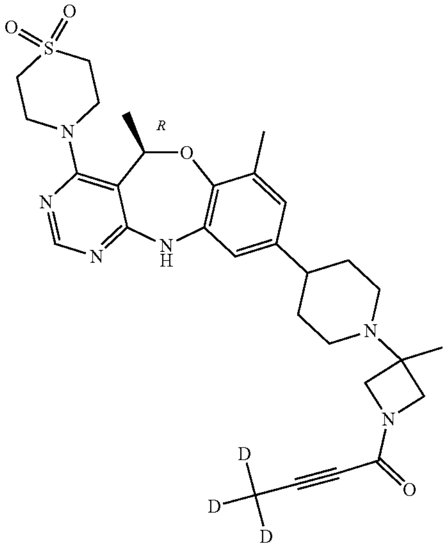 |

-continued
| Cpd # | Structure |
|---|---|
| 177 | 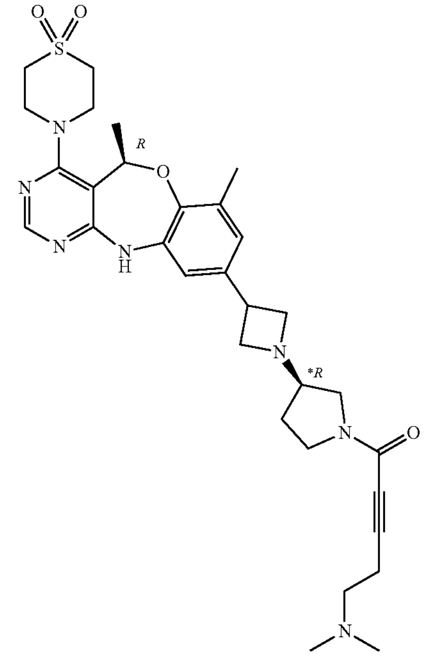 |
| 180 | 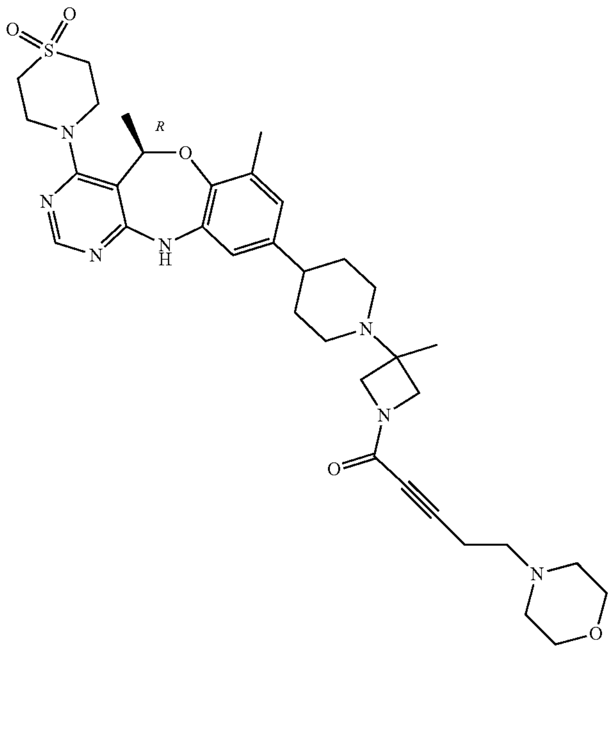 |

-continued
| Cpd # | Structure |
|---|---|
| 181 | 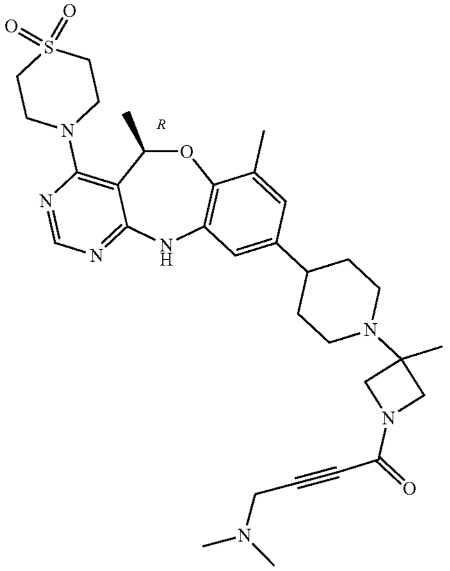 |
| 184 | 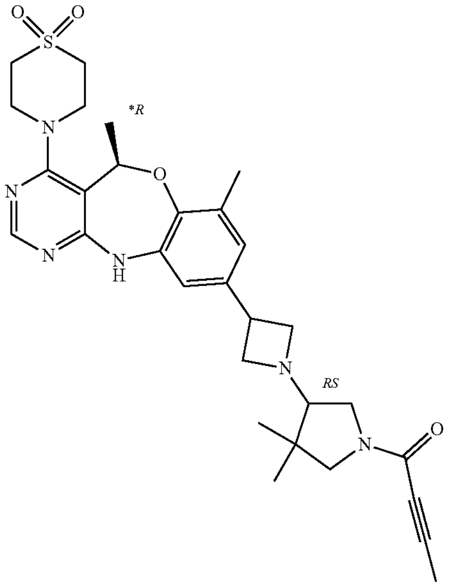 |

-continued
| Cpd # | Structure |
|---|---|
| 182 | 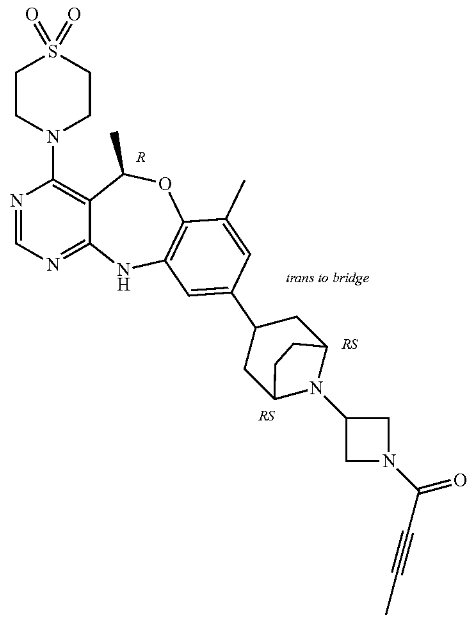 |
| 185 | 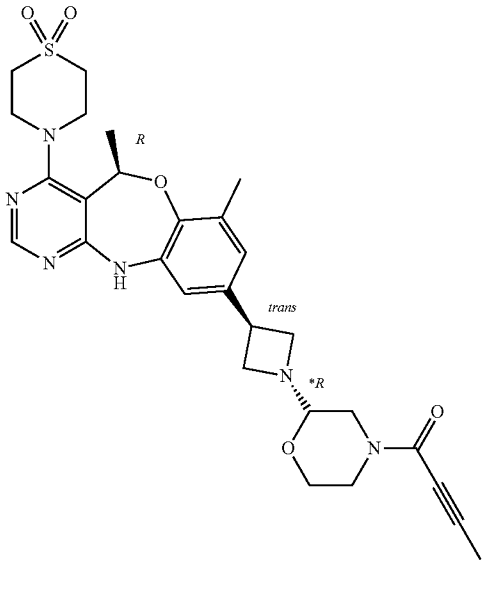 |

-continued
| Cpd # | Structure |
|---|---|
| 183 | 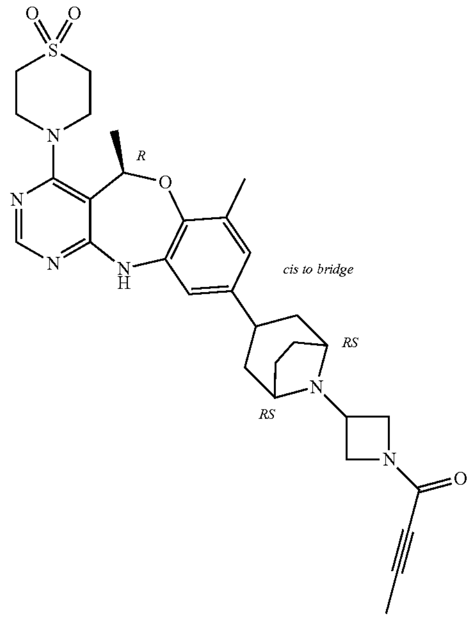 |
| 186 | 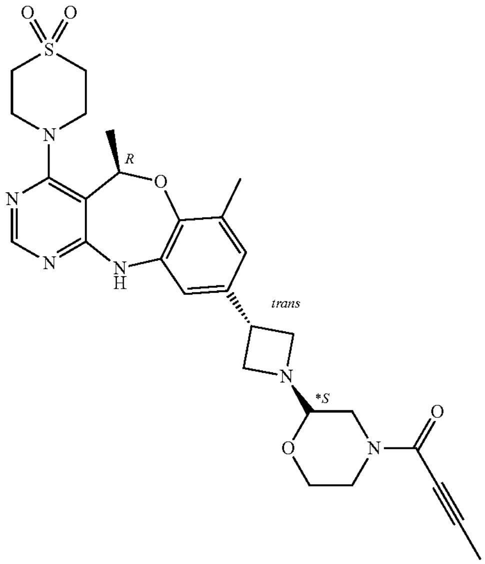 |

-continued
| Cpd # | Structure |
|---|---|
| 187 | 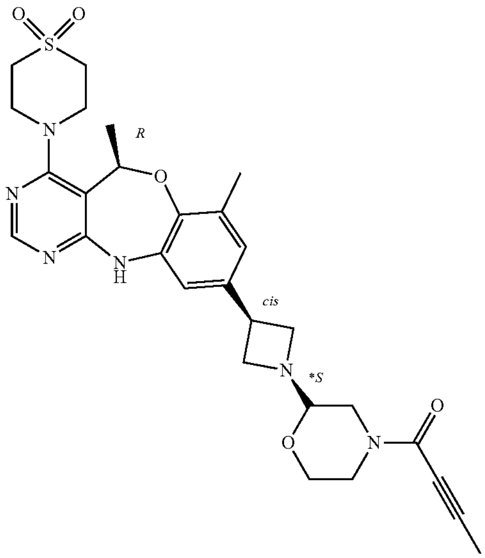 |
| 190 | 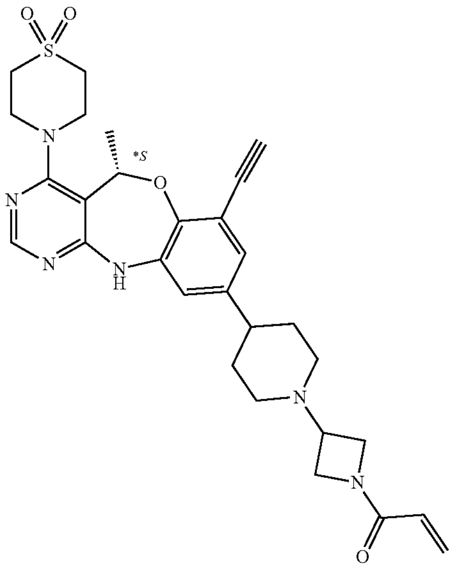 |

-continued
| Cpd # | Structure |
|---|---|
| 188 | 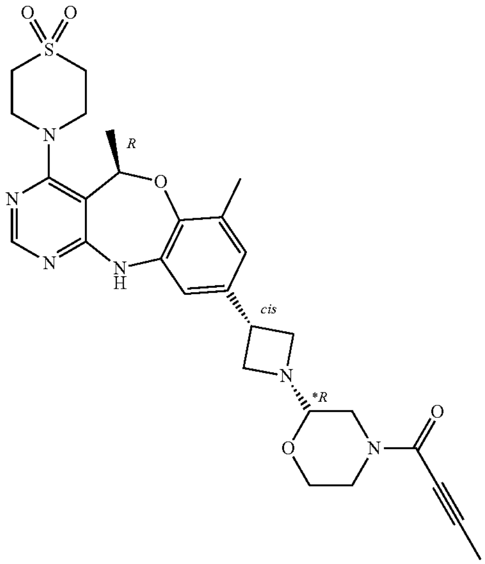 |
| 191 | 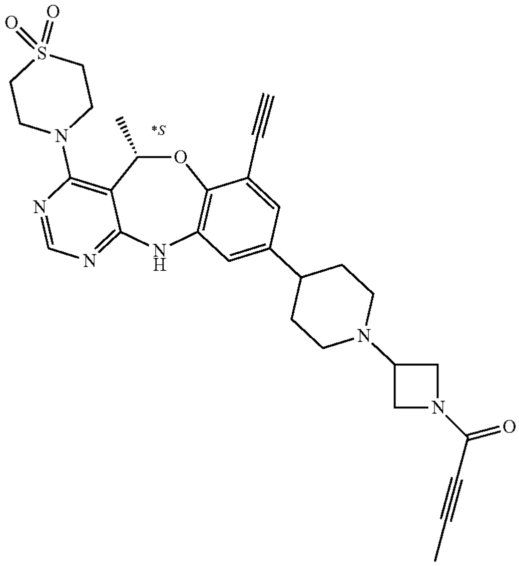 |

-continued
| Cpd # | Structure |
|---|---|
| 189 | 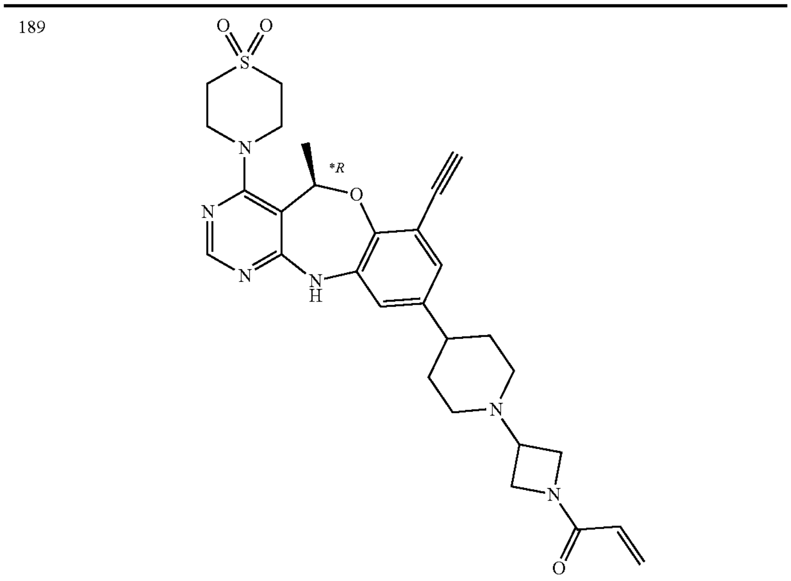 |
| 192 | 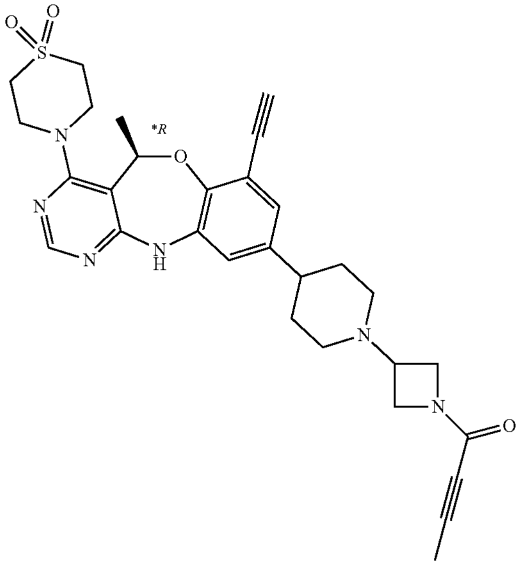 |
| 193 | 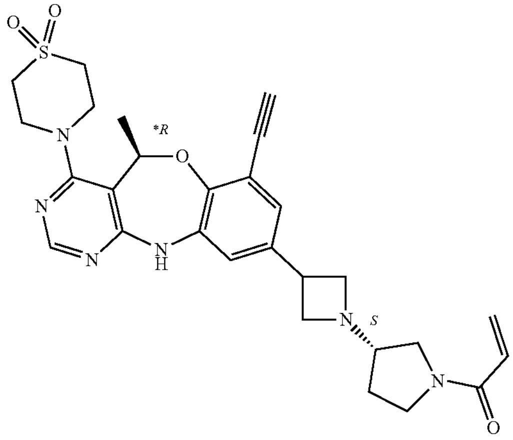 |

-continued
| Cpd # | Structure |
| --- | --- |
| 195 | 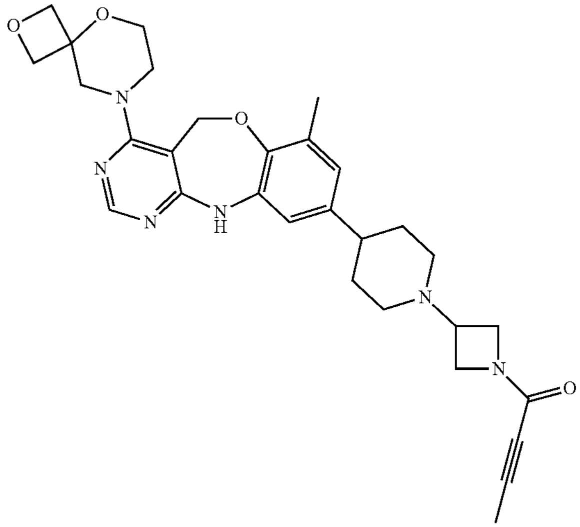 [SMILES: CC#CC(=O)N1CC(N2CCC(c3cc(C)c4c(c3)Nc3ncnc(N5CCOC6(COC6)C5)c3CO4)CC2)C1] |
| 194 | 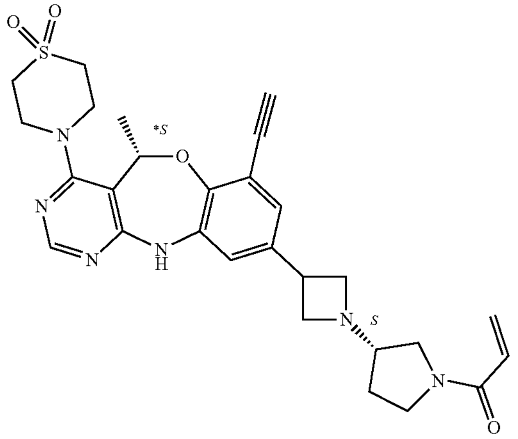 |
| 149 | 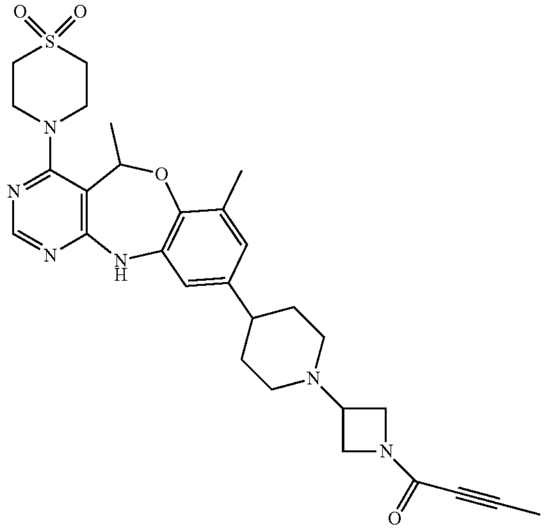 [SMILES: CC#CC(=O)N1CC(N2CCC(c3cc(C)c4c(c3)Nc3ncnc(N5CCS(=O)(=O)CC5)c3C(C)O4)CC2)C1] |

The present invention further relates to a pharmaceutical composition comprising a compound as disclosed herein, and a pharmaceutically acceptable carrier.

The present invention further relates to any compound disclosed herein, for use in therapy.

The present invention further relates to any compound disclosed herein, for use in the prophylaxis and/or treatment of a disease state or condition mediated by a cyclin-dependent kinase 7 (CDK7).

The present invention further relates to any of the compounds for the use disclosed herein above, wherein the disease state or condition mediated by CDK7 is a proliferative disease selected from cancer, leukemia, acute myeloid leukemia (AML), chronic myelogenous leukemia (CML), lymphoma, B cell lymphoma, chronic lymphocytic leukemia (CLL), acute lymphoblastic leukemia (ALL), T-cell acute lymphoblastic leukemia (T-ALL), Hodgkin's lymphoma, non-Hodgkin's lymphoma, melanoma, multiple myeloma, bone cancer, osteosarcoma, Ewing's sarcoma, breast cancer, triple-negative breast cancer (TNBC), brain cancer, neuroblastoma, lung cancer, small cell lung cancer (SCLC), large cell lung cancer, benign neoplasm, angiogenesis, an inflammatory disease, rheumatoid arthritis, an autoinflammatory disease, or an autoimmune disease.

The present invention also relates to the use of any compound disclosed herein for the manufacture of a medicament for the prophylaxis or treatment of a proliferative disease.

The proliferative disease may be cancer, leukemia, acute myeloid leukemia (AML), chronic myelogenous leukemia (CML), lymphoma, B cell lymphoma, chronic lymphocytic leukemia (CLL), acute lymphoblastic leukemia (ALL), T-cell acute lymphoblastic leukemia (T-ALL), Hodgkin's lymphoma, non-Hodgkin's lymphoma, melanoma, multiple myeloma, bone cancer, osteosarcoma, Ewing's sarcoma, breast cancer, triple-negative breast cancer (TNBC), brain cancer, neuroblastoma, lung cancer, small cell lung cancer (SCLC), large cell lung cancer, benign neoplasm, angiogenesis, an inflammatory disease, rheumatoid arthritis, an autoinflammatory disease, or an autoimmune disease.

The present invention relates as well to a method for the prophylaxis or treatment of a disease state or condition mediated by a CDK7, which method comprises administering to a subject in need thereof an effective amount of a compound as disclosed herein.

The disease or condition is selected from a proliferative disease, cancer, leukemia, acute myeloid leukemia (ANIL), chronic myelogenous leukemia (CML), lymphoma, B cell lymphoma, chronic lymphocytic leukemia (CLL), acute lymphoblastic leukemia (ALL), T-cell acute lymphoblastic leukemia (T-ALL), Hodgkin's lymphoma, non-Hodgkin's lymphoma, melanoma, multiple myeloma, bone cancer, osteosarcoma, Ewing's sarcoma, breast cancer, triple-negative breast cancer (TNBC), brain cancer, neuroblastoma, lung cancer, small cell lung cancer (SCLC), large cell lung cancer, benign neoplasm, angiogenesis, an inflammatory disease, rheumatoid arthritis, an autoinflammatory disease, or an autoimmune disease.

The subject may be a mammal.

The present invention also relates to an in vitro method of modulating CDK7 activity comprising contacting the CDK7 protein, or a portion thereof, with a compound as disclosed herein.

INCORPORATION BY REFERENCE

All publications, patents, patent applications, and published nucleotide and amino acid sequences (e.g., sequences available in GenBank or other databases) mentioned in this specification are herein incorporated by reference to the same extent as if each individual publication, patent, patent application, or published nucleotide and amino acid sequence, was specifically and individually indicated to be incorporated by reference.

DETAILED DESCRIPTION OF THE INVENTION

Definitions

Unless defined otherwise, all technical and scientific terms used herein have the same meaning as is commonly understood to which the claimed subject matter belongs. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed.

In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

Some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions and acceptable error margins, for such given value.

As used herein, the expression "one or more" refers to at least one, for example one, two, three, four, five or more, whenever possible and depending on the context.

Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry 4$^{th}$ Ed." Vols. A (2000) and B (2001), Plenum Press, New York.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

Hereinbefore and hereinafter, the term "compound of formula (I)" is meant to include the addition salts, the solvates and the stereoisomers thereof.

As used herein, "$C_{x-y}$" (where x and y are integers) refers to the number of carbon atoms that make up the moiety to which it designates (excluding optional substituents). Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term "halo" or, alternatively, "halogen" means fluoro, chloro, bromo and iodo.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_{1-6}$alkyl" or similar designations.

By way of example, the term "$C_{1-4}$alkyl", or "$C_{1-6}$alkyl" as used herein as a group or part of a group refers to a linear or branched saturated hydrocarbon group containing from 1 to 4 or 1 to 6 carbon atoms, respectively. Examples of such groups include methyl, ethyl, n-propyl, isopropyl, n-butyl, isobutyl, sec-butyl, tert-butyl, n-pentyl, isopentyl, neopentyl, hexyl, and the like.

The term "alkenyl" refers to a type of alkyl group in which at least two atoms of the alkyl group form a double bond that is not part of an aromatic group. Non-limiting examples of an alkenyl group include $-CH{=}CH_2$, $-C(CH_3){=}CH_2$, $-CH{=}CHCH_3$, $-CH{=}C(CH_3)_2$ and $-C(CH_3){=}CHCH_3$. The alkenyl moiety may be branched or a straight chain. Alkenyl groups may have 2 to 6 carbons. Alkenyl groups can be substituted or unsubstituted. Depending on the structure, an alkenyl group can be a monoradical or a diradical (i.e., an alkenylene group). Examples of "alkenyl" include also "$C_{2-4}$alkenyl" or "$C_{2-6}$alkenyl".

The term "alkynyl" refers to a type of alkyl group in which at least two atoms of the alkyl group form a triple bond. Non-limiting examples of an alkynyl group include $-C{\equiv}CH$, $-C{\equiv}CCH_3$, $-C{\equiv}CCH_2CH_3$ and $-C{\equiv}CCH_2CH_2CH_3$. The alkynyl moiety may be branched or a straight chain. An alkynyl group can have 2 to 6 carbons. Alkynyl groups can be substituted or unsubstituted. Depending on the structure, an alkynyl group can be a monoradical or a diradical (i.e., an alkynylene group). Examples of "alkynyl" include also "$C_{2-4}$alkynyl" or "$C_{2-6}$alkynyl".

An "alkoxy" refers to a "—O-alkyl" group, where alkyl is as defined herein.

The term "$C_{1-4}$alkoxy" or "$C_{1-6}$alkoxy" as used herein as a group or part of a group refers to an $-O-C_{1-4}$alkyl group or an $-O-C_{1-6}$alkyl group wherein $C_{1-4}$alkyl and $C_{1-6}$alkyl are as defined herein. Examples of such groups include methoxy, ethoxy, propoxy, butoxy, and the like.

The term "hydroxy$C_{1-4}$alkyl" or "hydroxy$C_{1-6}$alkyl" as used herein as a group or part of a group refers to a $C_{1-4}$alkyl or $C_{1-6}$alkyl group as defined herein wherein one or more than one hydrogen atoms are replaced with a hydroxyl group. The terms "hydroxy$C_{1-4}$alkyl" or "hydroxy$C_{1-6}$alkyl" therefore include monohydroxy$C_{1-4}$alkyl, monohydroxy$C_{1-6}$alkyl and also polyhydroxy$C_{1-4}$alkyl and polyhydroxy$C_{1-6}$alkyl. There may be one, two, three or more hydrogen atoms replaced with a hydroxyl group, so the hydroxy$C_{1-4}$alkyl or hydroxy$C_{1-6}$alkyl may have one, two, three or more hydroxyl groups. Examples of such groups include hydroxymethyl, hydroxyethyl, hydroxypropyl and the like.

The term "haloalkyl" refers to an alkyl group as defined herein wherein one or more than one hydrogen atom is replaced with one or more halogens. The term "haloalkyl" includes "halo$C_{1-4}$alkyl", "halo$C_{1-6}$alkyl", monohalo$C_{1-4}$alkyl, monohalo$C_{1-6}$alkyl, polyhalo$C_{1-4}$ alkyl, and polyhalo$C_{1-6}$alkyl. There may be one, two, three or more hydrogen atoms replaced with a halogen, so the halo$C_{1-4}$alkyl or halo$C_{1-6}$alkyl may have one, two, three or more halogens. The halogens may the same or they may be different. Non-limiting examples of haloalkyls include $-CH_2Cl$, $-CF_3$, $-CHF_2$, $-CH_2CF_3$, $-CF_2CF_3$, $-CF(CH_3)_2$, fluoroethyl, fluoromethyl, trifluoroethyl, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, $-CH_2-O-CH_3$, $-CH_2-CH_2-O-CH_3$, $-CH_2-NH-CH_3$, $-CH_2-CH_2-NH-CH_3$, $-CH_2-N(CH_3)-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH_2-NH-OCH_3$, $-CH_2-O-Si(CH_3)_3$, $-CH_2-CH{=}N-OCH_3$, and $-CH{=}CH-N(CH_3)-CH_3$. In addition, up to two heteroatoms may be consecutive, such as, by way of example, $-CH_2-NH-OCH_3$ and $-CH_2-O-Si(CH_3)_3$. Excluding the number of heteroatoms, a "heteroalkyl" may have from 1 to 6 carbon atoms.

The term "halo$C_{1-4}$alkoxy" or "halo$C_{1-6}$alkoxy" as used herein as a group or part of a group refers to a $-O-C_{1-}$ 4alkyl group or a —O—$C_{1-6}$ alkyl group as defined herein wherein one or more than one hydrogen atom is replaced with a halogen. The terms "halo$C_{1-4}$alkoxy" or "halo$C_{1-6}$alkoxy" therefore include monohalo$C_{1-4}$alkoxy, monohalo$C_{1-6}$alkoxy and also polyhalo$C_{1-4}$alkoxy and polyhalo$C_{1-6}$alkoxy. There may be one, two, three or more hydrogen atoms replaced with a halogen, so the halo$C_{1-4}$alkoxy or halo$C_{1-6}$alkoxy may have one, two, three or more halogens. Examples of such groups include fluoroethyloxy, difluoromethoxy, or trifluoromethoxy and the like.

The terms "fluoroalkyl" and "fluoroalkoxy" include alkyl and alkoxy groups, respectively, that are substituted with one or more fluorine atoms. Non-limiting examples of fluoroalkyls include $—CF_3$, $—CHF_2$, $—CH_2F$, $—CH_2CF_3$, $—CF_2CF_3$, $—CF_2CF_2CF_3$, $—CF(CH_3)_3$, and the like. Non-limiting examples of fluoroalkoxy groups, include $—OCF_3$, $—OCHF_2$, $—OCH_2F$, $—OCH_2CF_3$, $—OCF_2CF_3$, $—OCF_2CF_2CF_3$, $—OCF(CH_3)_2$, and the like.

The term "cyano$C_{1-4}$alkyl" or "cyano$C_{1-6}$alkyl" as used herein refers to a $C_{1-4}$alkyl or $C_{1-6}$alkyl group as defined herein which is substituted with one or two cyano groups, in particular with one cyano group.

"Amino" refers to a $—NH_2$ group.

The term "alkylamine" or "alkylamino" refers to the $—N(alkyl)_xH_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a $—N(alkyl)_2$ group, where alkyl is as defined herein.

The terms "carboxy" or "carboxyl" refer to $—CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

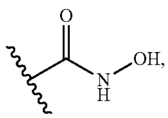,
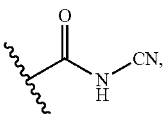,
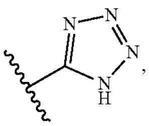,
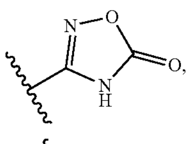,
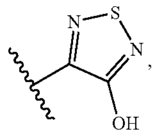,
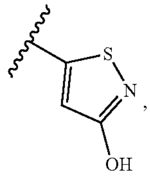,
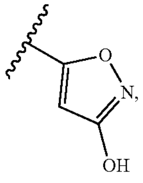,
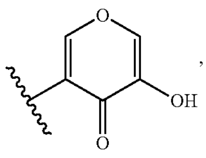, and the like.

The term "carbocyclyl" as used herein, unless the context indicates otherwise, includes aromatic, non-aromatic, unsaturated, partially saturated, and fully saturated carbon ring systems. In general, unless the context indicates otherwise, such ring systems may be monocyclic or bicyclic or bridged and may contain, for example, 3 to 12 ring members, or 4 to 10 ring members, or more usually 5 to 10 ring members. Reference to 3 to 6 ring members include 3, 4, 5, or 6 atoms in the ring, reference to 4 to 7 ring members include 4, 5, 6 or 7 atoms in the ring, and reference to 4 to 6 ring members include 4, 5, or 6 atoms in the ring. Examples of monocyclic carbocyclyl ring systems are ring systems containing 3, 4, 5, 6, 7 and 8 ring members, more usually 3 to 7, and preferably 4, 5, 6 or 7 ring members, more preferably 5 or 6 ring members. Examples of bicyclic carbocyclyl ring systems are those containing 8, 9, 10, 11 and 12 ring members, and more usually 9 or 10 ring members. Where reference is made herein to a carbocyclyl ring system, the carbocyclyl ring can, unless the context indicates otherwise, be optionally substituted (i.e. unsubstituted or substituted) by one or more substituents as discussed herein. Particular examples of 3 to 12 membered carbocycles include cyclopropyl, cyclobutyl, cyclopentyl, cyclyhexyl, cycloheptyl, cyclooctyl, phenyl naphthyl, indenyl, tetrahydronaphthyl, azulenyl, norbornane (1,4-endo-methylene-cyclohexane), adamantane ring systems.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

The term "non-aromatic group" embraces, unless the context indicates otherwise, unsaturated ring systems without aromatic character, partially saturated and fully saturated heterocyclyl ring systems.

The terms "unsaturated" and "partially saturated" refer to rings wherein the ring structure(s) contains atoms sharing more than one valence bond i.e. the ring contains at least one multiple bond e.g. a C≡C, C≡C or N═C bond.

The term "fully saturated" refers to rings where there are no multiple bonds between ring atoms. Saturated heterocyclyl groups include piperidine, morpholine, thiomorpholine, piperazine. Partially saturated heterocyclyl groups include pyrazolines, for example 2-pyrazoline and 3-pyrazoline.

The carbocyclyl ring systems can be aryl ring systems.

The term "aryl" as used herein refers to carbocyclyl aromatic groups and embraces polycyclic (e.g. bicyclic) ring systems wherein one or more rings are non-aromatic, provided that at least one ring is aromatic. In such polycyclic systems, the ring system may be attached to the remainder of the compound by an aromatic ring or by a non-aromatic ring. The term "aryl" includes phenyl, naphthyl or naphthalenyl, indenyl, and tetrahydronaphthyl groups. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. An example of a "cycloalkyl" is "$C_{3-6}$cycloalkyl". Cycloalkyls may be fused with an aromatic ring (in which case the cycloalkyl is bonded through a non-aromatic ring carbon atom). Cycloalkyl groups include groups having from 3 to 10 ring atoms.

Illustrative examples of cycloalkyl groups include, but are not limited to, the following moieties:

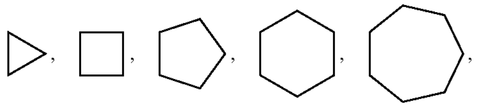

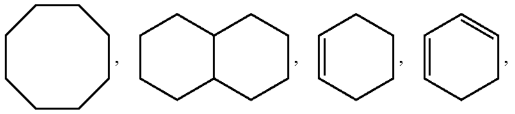

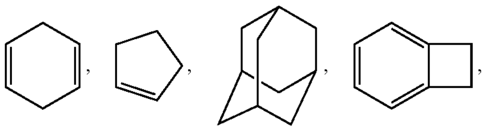

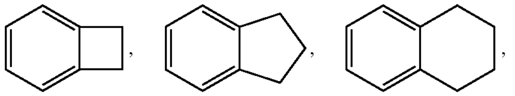

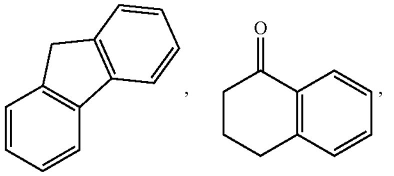

and the like.

The term "heterocyclyl", "heterocycloalkyl", or "heteroalicyclic" group refers to a carbocyclyl, as defined herein, containing at least one heteroatom typically selected from nitrogen, oxygen or sulphur, in particular containing up to 5, up to 4, up to 3, up to 2, or a single heteroatom. Where reference is made herein to a heterocyclyl ring system, the heterocyclyl ring can, unless the context indicates otherwise, be optionally substituted (i.e. unsubstituted or substituted) by one or more substituents as discussed herein. The radicals may be fused with an aryl or heteroaryl. Illustrative examples of heterocycloalkyl groups, also referred to as non-aromatic heterocycles, include

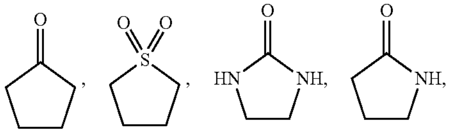

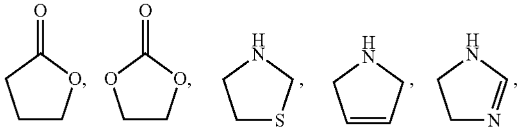

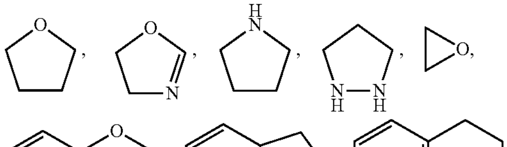

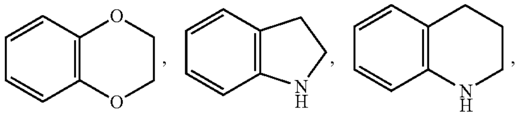

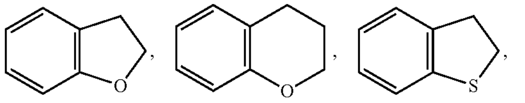

-continued

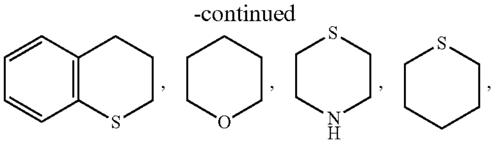

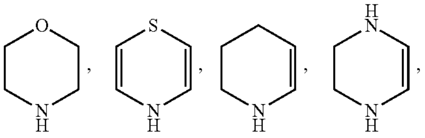

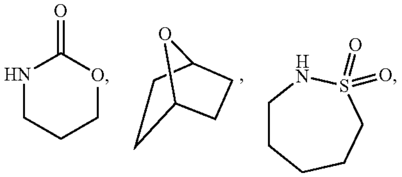

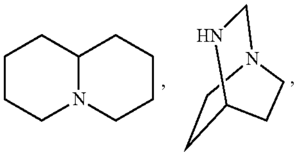

and the like.

The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The heterocyclyl ring systems can be heteroaryl ring systems having from 5 to 12 ring members, more usually from 5 to 10 ring members.

The term "heteroaryl" is used herein to denote a heterocyclyl ring system having aromatic character. The term "heteroaryl" embraces polycyclic (e.g. bicyclic) ring systems wherein one or more rings are non-aromatic, provided that at least one ring is aromatic. In such polycyclic systems, the ring system may be attached to the remainder of the compound by an aromatic ring or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. The heteroaryl ring system may contain up to about five heteroatoms typically selected from nitrogen, oxygen and sulphur. Typically, the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of five membered heteroaryl groups include but are not limited to pyrrolyl, furanyl, thienyl, imidazolyl, oxazolyl, oxadiazolyl, oxatriazole, isoxazolyl, thiazolyl, thiadiazolyl, isothiazolyl, pyrazolyl, triazolyl and tetrazolyl groups. In particular, examples of five membered heteroaryl groups include but are not limited to pyrrolyl, furanyl, thienyl, imidazolyl, oxazolyl, oxadiazolyl, isoxazolyl, thiazolyl, thiadiazolyl, isothiazolyl, pyrazolyl and triazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from: a benzene ring fused to a 5- or 6-membered ring containing 1, 2 or 3 ring heteroatoms; a pyridine ring fused to a 5- or 6-membered ring containing 0, 1, 2 or 3 ring heteroatoms; a pyrimidine ring fused to a 5- or 6-membered ring containing 0, 1 or 2 ring heteroatoms; a pyrrole ring fused to a 5- or 6-membered ring containing 0, 1, 2 or 3 ring heteroatoms; a pyrazole ring fused to a 5- or 6-membered ring containing 0, 1 or 2 ring heteroatoms; an imidazole ring fused to a 5- or 6-membered ring containing 0, 1 or 2 ring heteroatoms; an oxazole ring fused to a 5- or 6-membered ring containing 0, 1 or 2 ring heteroatoms; an isoxazole ring fused to a 5- or 6-membered ring containing 0, 1 or 2 ring heteroatoms; a thiazole ring fused to a 5- or 6-membered ring containing 0, 1 or 2 ring heteroatoms; an isothiazole ring fused to a 5- or 6-membered ring containing 0, 1 or 2 ring heteroatoms; a thiophene ring fused to a 5- or 6-membered ring containing 0, 1, 2 or 3 ring heteroatoms; a furan ring fused to a 5- or 6-membered ring containing 0, 1, 2 or 3 ring heteroatoms; a cyclohexyl ring fused to a 5- or 6-membered aromatic ring containing 1, 2 or 3 ring heteroatoms; and a cyclopentyl ring fused to a 5- or 6-membered aromatic ring containing 1, 2 or 3 ring heteroatoms.

Particular examples of bicyclic heteroaryl groups containing a five membered ring fused to another five membered ring include but are not limited to imidazothiazolyl (e.g. imidazo[2,1-b]thiazole) and imidazoimidazolyl (e.g. imidazo[1,2-a]imidazole).

Particular examples of bicyclic heteroaryl groups containing a six membered ring fused to a five membered ring include but are not limited to benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, purinyl, indazolyl, pyrazolopyrimidinyl (e.g. pyrazolo[1,5-a]pyrimidine), triazolopyrimidinyl (e.g. [1,2,4]triazolo[1,5-a]pyrimidine), benzodioxolyl, imidazopyrazinyl, imidazopyridazinyl, imidazopyridinyl and pyrazolopyridinyl (e.g. pyrazolo[1,5-a]pyridine) groups.

Particular examples of bicyclic heteroaryl groups containing two fused six membered rings include but are not limited to quinolizinyl, quinolinyl, isoquinolinyl, cinnolinyl, chromanyl, isochromanyl, thiochromanyl, benzopyranyl, benzodioxanyl, benzoxazinyl, pyridopyridinyl, quinoxalinyl, quinazolinyl, phthalazinyl, naphthyridinyl and pteridinyl groups.

Particular examples of bicyclic heteroaryl groups containing two fused six membered rings include but are not limited to quinolizinyl, quinolinyl, isoquinolinyl, benzopyranyl, benzodioxanyl, benzoxazinyl, pyridopyridinyl, quinoxalinyl, quinazolinyl, phthalazinyl, naphthyridinyl, and pteridinyl groups.

Examples of polycyclic heteroaryl groups containing an aromatic ring and a non-aromatic ring include, tetrahydroisoquinolinyl, tetrahydroquinolinyl, dihydrobenzothienyl, dihydrobenzofuranyl, 2,3-dihydro-benzo[1,4]dioxinyl, benzo[1,3]dioxolyl, 4,5,6,7-tetrahydrobenzofuranyl, tetrahydrotriazolopyrazinyl (e.g. 5,6,7,8-tetrahydro-[1,2,4]triazolo[4,3-a]pyrazinyl), and indolinyl.

A nitrogen-containing heteroaryl ring must contain at least one ring nitrogen atom. Each ring may, in addition, contain up to about four other heteroatoms typically selected from nitrogen, sulphur and oxygen. Typically, the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazolyl, benzthiazolyl and benzisothiazole, indolyl, 3H-indolyl, isoindolyl, indolizinyl, isoindolinyl, purinyl, indazolyl, quinolizinyl, benzoxazinyl, pyridopyridinyl, quinoxalinyl, quinazolinyl, cinnolinyl, phthalazinyl, naphthyridinyl, and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), and combinations thereof (e.g. thiomorpholine).

Particular examples include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), azetidinyl, pyranyl (2H-pyranyl or 4H-pyranyl), dihydrothiophenyl, dihydropyranyl, dihydrofuranyl, dihydrothiazolyl, tetrahydrofuranyl, tetrahydrothiophenyl, dioxanyl, dioxolanyl, tetrahydropyranyl, imidazolinyl, oxazolinyl, oxazolidinyl, oxetanyl, thiazolinyl, 2-pyrazolinyl, pyrazolidinyl and piperazinyl. In general, preferred non-aromatic heterocyclyl groups include saturated groups such as piperidinyl, pyrrolidinyl, azetidinyl, morpholinyl and piperazinyl. In general, preferred non-aromatic heterocyclyl groups include saturated groups such as piperidinyl, pyrrolidinyl, azetidinyl, morpholinyl and piperazinyl.

In a nitrogen-containing non-aromatic heterocyclyl ring the ring must contain at least one ring nitrogen atom.

Particular examples of nitrogen-containing non-aromatic heterocyclyl groups include aziridinyl, morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), dihydrothiazolyl, imidazolinyl, oxazolinyl, thiazolinyl, 2-pyrazolinyl, 3-pyrazolinyl, pyrazolidinyl and piperazinyl.

Particular examples of 3 to 6 membered monocyclic saturated heterocyclyls include morpholinyl, thiomorpholinyl, dioxanyl, piperidinyl (e.g. 1-piperidinyl, 2-piperidinyl, 3-piperidinyl and 4-piperidinyl), piperazinyl, pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, tetrahydrofuranyl, tetrahydrothiophenyl, tetrahydropyranyl (e.g. 4-tetrahydro pyranyl), dithianyl, trioxanyl, trithianyl, aziridinyl, oxiranyl, thiiranyl, diaziridinyl, dioxarinyl, oxetanyl, azetidinyl, thietanyl, dioxetanyl ring systems.

Particular examples of 3 to 6 membered monocyclic heterocyclyls include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, piperazinyl, tetrahydrofuranyl, tetrahydrothiophenyl, dioxanyl, tetrahydropyranyl (e.g. 4-tetrahydro pyranyl), dithianyl, trioxanyl, trithianyl, aziridinyl, oxiranyl, thiiranyl, diaziridinyl, dioxarinyl, oxetanyl, azetidinyl, thietanyl, dioxetanyl, azirinyl, azetyl, 1,2-dithietyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl ring systems.

Particular examples of 3 to 12 membered heterocycles include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, piperazinyl, tetrahydrofuranyl, tetrahydrothiophenyl, dioxanyl, tetrahydropyranyl (e.g. 4-tetrahydropyranyl), dithianyl, trioxanyl, trithianyl, aziridinyl, oxiranyl, thiiranyl, diaziridinyl, dioxarinyl, oxetanyl, azetidinyl, thietanyl, dioxetanyl, azirinyl, azetyl, 1,2-dithietyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl, azepanyl, oxepanyl, thiepanyl, 1,2-diazepanyl, 1,4-diazepanyl, diazepinyl, thiazepinyl, azocanyl, azocinyl, imidazothiazolyl (e.g. imidazo[2,1-b]thiazolyl), imidazo-imidazolyl (e.g. imidazo[1,2-a]imidazolyl), benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, purinyl, indazolyl, pyrazolopyrimidinyl (e.g. pyrazolo[1,5-a]pyrimidinyl), triazolopyrimidinyl (e.g. [1,2,4]triazolo[1,5-a]pyrimidinyl), benzodioxolyl, imidazopyridinyl and pyrazolopyridinyl (e.g. pyrazolo[1,5-a]pyridinyl), quinolinyl, isoquinolinyl, chromanyl, thiochromanyl, isochromanyl, benzodioxanyl, quinolizinyl, benzoxazinyl, pyridopyridinyl, quinoxalinyl, quinazolinyl, cinnolinyl, phthalazinyl, naphthyridinyl, pteridinyl, tetrahydroisoquinolinyl, tetrahydroquinolinyl, dihydrobenzthienyl, dihydrobenzfuranyl, 2,3-dihydro-benzo[1,4]dioxinyl, benzo[1,3]dioxolyl, 4,5,6,7-tetrahydrobenzofuranyl, tetrahydrotriazolopyrazinyl (e.g. 5,6,7,8-tetrahydro-[1,2,4]triazolo[4,3-a]pyrazinyl), 8-oxa-3-azabicyclo[3.2.1]octanyl, 2-oxa-5-azabicyclo[2.2.1]heptanyl, 3-oxa-8-azabicyclo[3.2.1]octanyl, 3,6-diazabicyclo[3.1.1]heptanyl ring systems.

Particular examples of 5 to 6 membered aromatic heterocycles include but are not limited to pyrrolyl, furanyl, thiophenyl, imidazolyl, furazanyl, oxazolyl, oxadiazolyl, oxatriazolyl, isoxazolyl, thiazolyl, thiadiazolyl, isothiazolyl, pyrazolyl, triazolyl, tetrazolyl, pyridinyl, pyrazinyl, pyridazinyl, pyrimidinyl and triazinyl ring systems.

The heterocyclyl and carbocyclyl rings also include bridged ring systems such as for example bridged cycloalkanes, such as for example norbornane (1,4-endo-methylene-cyclohexane), adamantane, oxa-adamantane; bridged morpholine rings such as for example 8-oxa-3-azabicyclo[3.2.1]octane, 2-oxa-5-azabicyclo[2.2.1]heptane, 3-oxa-8-azabicyclo[3.2.1]octane; bridged piperazine rings such as for example 3,6-diazabicyclo[3.1.1]heptane; bridged piperidine rings such as for example 1,4-ethylenepiperidine. For an explanation of the distinction between fused and bridged ring systems, see Advanced Organic Chemistry, by Jerry March, $4^{th}$ Edition, Wiley Interscience, pages 131-133, 1992.

Lines drawn into ring systems indicate that the bond may be attached to any of the suitable and available ring atoms.

The term "optional" or "optionally" means the event described subsequent thereto may or may not happen. This term encompasses the cases that the event may or may not happen.

In the compounds of the present disclosure the carbon atom indicated with a "*" in the drawn formula, is a chiral center. When the carbon atom is indicated with "(R*)", it means that it is a pure enantiomer but that it is unknown whether is it an R or S enantiomer. Similarly, when the carbon atom is indicated with "(S*)", it means that it is a pure enantiomer but that it is unknown whether is it an R or S enantiomer.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted", if not explicitly defined, means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkynyl, $C_{1-6}$alkylalkynyl, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —$N(R)_2$), and the protected derivatives thereof. In some embodiments, optional substituents are independently selected from halogen, —CN, —$NH_2$, —$NH(CH_3)$, —$N(CH_3)_2$, —OH, —$CO_2H$, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, —$NH_2$, —OH, —$NH(CH_3)$, —$N(CH_3)_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The term a "therapeutically effective amount" as used herein refers to the amount of active compound or pharmaceutical agent that, when administered to a mammal in need, is effective to at least partially ameliorate or to at least partially prevent diseases, disorders or conditions described herein.

As used herein, the term "composition" is intended to encompass a product comprising specified ingredients in specified amounts, as well as any product which results, directly or indirectly, from combinations of the specified ingredients in the specified amounts.

As used herein, the term "expression" includes the process by which polynucleotides are transcribed into mRNA and translated into peptides, polypeptides, or proteins.

The term "activator" is used in this specification to denote any molecular species that results in activation of the indicated receptor, regardless of whether the species itself binds to the receptor or a metabolite of the species binds to the receptor. Thus, the activator can be a ligand of the receptor or it can be an activator that is metabolized to the ligand of the receptor, i.e., a metabolite that is formed in tissue and is the actual ligand.

The term "antagonist" as used herein, refers to a small-molecule agent that binds to a receptor and subsequently decreases the agonist induced transcriptional activity of the receptor.

The term "agonist" as used herein, refers to a small-molecule agent that binds to a receptor and subsequently increases receptor transcriptional activity in the absence of a known agonist.

The term "inverse agonist" as used herein, refers to a small-molecule agent that binds to a receptor and subsequently decreases the basal level of receptor transcriptional activity that is present in the absence of a known agonist.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. Those skilled in the art recognize that a therapy which reduces the severity of a pathology in one species of mammal is predictive of the effect of the therapy on another species of mammal.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "proliferative disease" refers to a disease that occurs due to abnormal growth or extension by the multiplication of cells. A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

As used herein, the term "cancer" refers to a malignant neoplasm. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barre syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behget's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

Isomers, Salts, N-Oxides, Solvates, Polymorphs, Prodrugs, Isotopically Labeled Derivatives Hereinbefore and hereinafter, the term "compound of formula (I), (II), (IIIa), (IIIb), (IVa), (IVb), (Va), (Vb)", "compounds of the present disclosure or invention", "compounds presented herein", or similar terms, is meant to include the addition salts, the solvates and the stereoisomers thereof.

In certain embodiments, the compounds presented herein possess one or more stereocenters and each center independently exists in either the R or S configuration. The compounds presented herein include all diastereomeric, enantiomeric, atropisomers, and epimeric forms as well as the appropriate mixtures thereof. Stereoisomers are obtained, if desired, by methods such as, stereoselective synthesis and/or the separation of stereoisomers by chiral chromatographic columns. In some embodiments, a compound of the present disclosure is used as a single enantiomer. In some embodiments, a compound of the present disclosure is used as a racemic mixture. In some embodiments, a compound of the present disclosure possesses hindered rotation about a single bond resulting in atropisomers.

In some situations, compounds may exist as tautomers. All tautomers are included within the scope of the compounds presented herein.

For the avoidance of doubt, where a compound can exist in one of several geometric isomeric or tautomeric forms and only one is specifically described or shown, all others are nevertheless embraced. Examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol and nitro/aci-nitro.

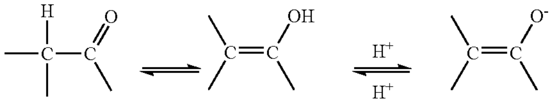

keto enol enolate

Such forms in so far as they may exist, are intended to be included within the scope of the compounds presented herein. It follows that a single compound may exist in both stereoisomeric and tautomeric form.

Where compounds described herein contain one or more chiral centres, and can exist in the form of two or more optical isomers, references to the compounds described herein include all optical isomeric forms thereof (e.g. enantiomers, epimers and diastereoisomers), either as individual optical isomers, or mixtures (e.g. racemic mixtures) of two or more optical isomers, unless the context requires otherwise. When a compound has more than one chiral centre, and one chiral centre is indicated as having an absolute stereoconfiguration, the other chiral centre(s) include all optical isomeric forms, either as individual optical isomers, or mixtures (e.g. racemic mixtures) of two or more optical isomers, thereof, unless the context requires otherwise. The optical isomers may be characterized and identified by their optical activity (i.e. as + and − isomers depending on the direction in which they rotate plane polarized light, or d and l isomers) or they may be characterized in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog (1966) *Angew. Chem. Int. Ed. Engl.*, 5, 385-415. For instance, resolved enantiomers whose absolute configuration is not known can be designated by (+) or (−) depending on the direction in which they rotate plane polarized light.

Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds exist as two or more isomeric forms, one isomeric form, e.g. one enantiomer in a pair of enantiomers, may exhibit advantages over the other isomeric form, e.g. over the other enantiomer, for example, in terms of biological activity. Thus, in certain circumstances, it may be desirable to use as a therapeutic agent only one of a pair of enantiomers, or only one of a plurality of diastereoisomers.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound described herein is for instance specified as (S), this means that the compound is substantially free of the (R) isomer; when a compound described herein is for instance specified as E, this means that the compound is substantially free of the Z isomer; when a compound described herein is for instance specified as cis, this means that the compound is substantially free of the trans isomer.

As used herein, any chemical formula with bonds shown only as solid lines and not as solid wedged or hashed wedged bonds, or otherwise not indicated as having a particular configuration (e.g. R, S) around one or more atoms, contemplates each possible stereoisomer, or mixture of two or more stereoisomers.

The terms “stereoisomers”, “stereoisomeric forms” or “stereochemically isomeric forms” hereinbefore or hereinafter are used interchangeably.

Enantiomers are stereoisomers that are non-superimposable mirror images of each other.

A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds described herein are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the present disclosure includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The methods and formulations described herein include the use of N-oxides (if appropriate), crystalline forms (also known as polymorphs), solvates and hydrates (also known as pseudo-polymorphs), pharmaceutically acceptable salts, and combinations thereof, of compounds having the structures presented herein, as well as active metabolites of these compounds having the same type of activity.

In some embodiments, compounds described herein, are in various forms, including but not limited to, amorphous forms, milled forms and nano-particulate forms. In addition, compounds described herein include crystalline forms, also known as polymorphs.

Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

In specific embodiments, the compounds described herein exist in solvated forms with pharmaceutically acceptable solvents such as water, ethanol, and the like. In other embodiments, the compounds described herein exist in unsolvated form.

In some embodiments, the compounds described herein include solvent addition forms or crystal forms thereof, particularly solvates or polymorphs. As used herein, the term “solvate” means a physical association of the compounds of the present invention with one or more solvent molecules, as well as pharmaceutically acceptable addition salts thereof. This physical association involves varying degrees of ionic and covalent bonding, including hydrogen bonding. In certain instances, the solvate will be capable of isolation, for example when one or more solvent molecules are incorporated in the crystal lattice of the crystalline solid. The term “solvate” is intended to encompass both solution-phase and isolatable solvates. Solvates contain either stoichiometric or non-stoichiometric amounts of a solvent, and may be formed during the process of crystallization with pharmaceutically acceptable solvents such as water, ethanol, isopropanol, methanol, DMSO, ethyl acetate, acetic acid, ethanolamine and the like. Hydrates are formed when the solvent is water, or alcoholates are formed when the solvent is alcohol. The compounds described herein may exert their biological effects whilst they are in solution.

The salt forms of the compounds presented herein are typically pharmaceutically acceptable salts, and examples of pharmaceutically acceptable salts are discussed in Berge et al. (1977) “Pharmaceutically Acceptable Salts,” J. Pharm. Sci., Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The pharmaceutically acceptable salts include pharmaceutically acceptable acid and base addition salts and are meant to comprise the therapeutically active non-toxic acid and base addition salt forms that the compounds described herein are able to form.

The salts of the present disclosure can be synthesized from the parent compound that contains a basic or acidic moiety by conventional chemical methods such as methods described in "Pharmaceutical Salts: Properties, Selection, and Use", P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

The pharmaceutically acceptable acid addition salts can conveniently be obtained by treating the base form with such appropriate inorganic acid (such as hydrochloric acid, hydrobromic acid, sulfuric acid, nitric acid, phosphoric acid and the like) or organic acids such (as acetic acid, methanesulfonic acid, maleic acid, tartaric acid, citric acid and the like) in an anion form.

Appropriate anions comprise, for example, acetate, 2,2-dichloroacetate, adipate, alginate, ascorbate (e.g. L-ascorbate), L-aspartate, benzenesulfonate, benzoate, 4-acetamidobenzoate, butanoate, bicarbonate, bitartrate, bromide, (+) camphorate, camphor-sulphonate, (+)-(1S)-camphor-10-sulphonate, calcium edetate, camsylate, caprate, caproate, caprylate, carbonate, chloride, cinnamate, citrate, cyclamate, dihydrochloride, dodecylsulphate, edetate, estolate, esylate, ethane-1,2-disulphonate, ethanesulphonate, formate, fumarate, galactarate, gentisate, glucoheptonate, gluceptate, gluconate, D-gluconate, glucuronate (e.g. D-glucuronate), glutamate (e.g. L-glutamate), α-oxoglutarate, glycolate, glycollylarsanilate, hexylresorcinate, hippurate, hydrabamine, hydrobromide, hydrochloride, hydriodate, 2-hydroxy-ethane-sulphonate, hydroxynaphthoate, iodide, isethionate, lactate (e.g. (+)-L-lactate, (±)-DL-lactate), lactobionate, malate, (−)-L-malate, maleate, malonate, mandelate, (±)-DL-mandelate, mesylate, methansulfonate, methylbromide, methylnitrate, methylsulfate, mucate, naphthalene-sulphonate (e.g. naphthalene-2-sulphonate), naphthalene-1,5-disulphonate, 1-hydroxy-2-naphthoate, napsylate, nicotinate, nitrate, oleate, orotate, oxalate, palmitate, pamoate (embonate), pantothenate, phosphate/diphosphate, propionate, polygalacturonate, L-pyroglutamate, pyruvate, salicylate, 4-amino-salicylate, sebacate, stearate, subacetate, succinate, sulfate, tannate, tartrate, (+)-L-tartrate, teoclate, thiocyanate, toluenesulphonate (e.g. p-toluenesulphonate), tosylate, triethiodide, undecylenate, valeric acids, as well as acylated amino acids and cation exchange resins. Conversely said salt forms can be converted by treatment with an appropriate base into the free base form.

The compounds of the present disclosure containing an acidic proton may also be converted into their nontoxic metal or amine addition salt forms by treatment with appropriate organic and inorganic bases in a cation form. Appropriate basic salts comprise those formed with organic cations such as arginine, benzathine, benzylamine, butylamine, chloroprocaine, choline, diethanolamine, dicyclohexylamine, diethanolamine, diethylamine, ethanolamine, ethylamine, ethylenediamine, lysine, meglumine, phenylbenzylamine, piperazine, procaine, triethylamine, tromethamine, and the like; those formed with ammonium ion (i.e., $NH_4^+$), quaternary ammonium ion $N(CH_3)_4^+$, and substituted ammonium ions (e.g., $NH_3R^+$, $NH_2R_2^+$, $NHR_3^+$, $NR_4^+$); and those formed with metallic cations such as aluminum, calcium, lithium, magnesium, potassium, sodium, zinc, and the like. Where the compounds described herein contain an amine function, these may form quaternary ammonium salts, for example by reaction with an alkylating agent according to methods well known to the skilled person. Such quaternary ammonium compounds are within the scope of the compounds presented herein.

Conversely said salt forms can be converted by treatment with an appropriate acid into the free form.

The screening and characterization of the pharmaceutically acceptable salts, polymorphs and/or solvates may be accomplished using a variety of techniques including, but not limited to, thermal analysis, X-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravimetric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). Solid State NMR (SS-NMR) is also known as Magic Angle Spinning NMR or MAS-NMR. The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Vivekkumar K. and Bari S. "Prodrug Design", Academic Press, 2016; Rautio, J. and Laine, K. "Prodrugs in Drug Design and Development" in "Textbook of Drug Design and Development", Strømgaard, Krogsgaard-Larsen, and Madsen, Ed. 5, 2017, Chapter 10; and Di and Kerns, "Prodrugs" in "Drug-Like Properties", 2016, 2nd. Ed. 471-485, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like.

Prodrug forms of the herein described compounds, wherein the prodrug is metabolized in vivo to produce a compound of the present disclosure, as set forth herein, are included within the scope of the claims. In some cases, some of the herein-described compounds may be a prodrug for another derivative or active compound.

In some embodiments, sites on the compounds disclosed herein are susceptible to various metabolic reactions. Therefore, incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

The compounds of the present disclosure include compounds that are isotopically labeled, i.e., with one or more isotopic substitutions. These compounds are identical to those recited in the various formulae and structures presented herein, but for the fact that one or more atoms are replaced by an atom having an atomic mass or mass number different from the atomic mass or mass number usually found in nature. A reference to a particular element includes within its scope all isotopes of the element, either naturally occurring or synthetically produced, either with natural abundance or in an isotopically enriched form. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment of the invention, the compounds contain no radioactive isotopes. In another embodiment, the compound may contain one or more radioisotopes. Compounds containing such radioisotopes may also be useful in a diagnostic context. Radiolabeled compounds described herein may comprise a radioactive isotope selected from the group of $^{2}H$, $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention. In some embodiments, metabolic sites on the compounds described herein are deuterated.

Throughout the specification, groups and substituents thereof can be chosen to provide stable moieties and compounds.

Synthesis of Compounds

The synthesis of compounds described herein, particularly in the Examples section, are accomplished using means described in the chemical literature, using the methods described herein, or by a combination thereof. In addition, solvents, temperatures, and other reaction conditions presented herein may vary. Techniques and materials recognized in the field are described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified using appropriate reagents and conditions, for the introduction of the various moieties found in the formulae as provided herein.

The starting materials and reagents used for the synthesis of the compounds described herein may be synthesized or obtained from commercial sources, such as, but not limited to, Sigma-Aldrich, FischerScientific (Fischer Chemicals), and AcrosOrganics. In the reactions described herein, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyl dimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as acetyl, trifluoroacetyl, t-butoxycarbonyl (Boc), benzyloxycarbonyl (CBz), and 9-fluorenylmethyleneoxycarbonyl (Fmoc). Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a $Pd^{0}$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

Me

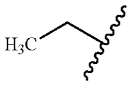

Et

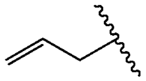

allyl

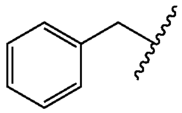

Bn

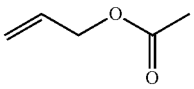

alloc

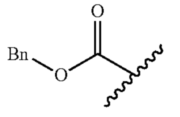

Cbz

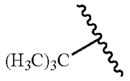

t-butyl

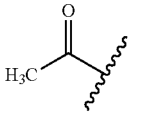

acetyl

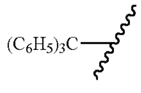

trityl

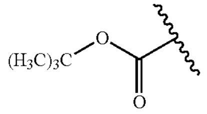

Boc

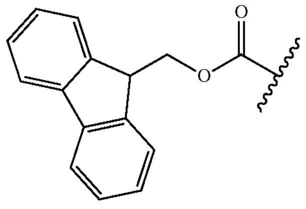

Fmoc

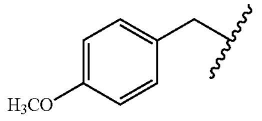

PMB

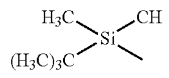

TBDMS

Other protecting groups, plus a detailed description of techniques applicable to the creation of protecting groups and their removal are described in T. W. Greene and P. G. M. Wuts, Protective Groups in Organic Synthesis, 4th ed., Wiley, Hoboken, New Jersey, 2007, which is incorporated herein by reference for such disclosure.

The skilled person will realize that intermediates and final compounds shown in the schemes below may be further functionalized according to methods well-known by the person skilled in the art.

The compounds of formula (I) may also be converted into each other via art-known reactions or functional group transformations. For instance, substituents like —C(═O)—O—$C_{1-6}$alkyl or $C_{1-6}$alkyl-O—C(═O)—, can be converted into HOOC—$C_{1-6}$alkyl or carboxyl in the presence of lithium hydroxide, and in the presence of a suitable solvent, such as for example tetrahydrofuran or an alcohol, e.g. methanol.

The skilled person will realize that in the reactions described herein, in certain cases it may be advisable or necessary to perform the reaction under an inert atmosphere, such as for example under $N_2$-gas atmosphere.

It will be apparent for the skilled person that it may be necessary to cool the reaction mixture before reaction work-up, meaning those series of manipulations required to isolate and purify the product(s) of a chemical reaction such as for example quenching, column chromatography, or extraction.

The skilled person will realize that heating the reaction mixture under stirring may enhance the reaction outcome. In some reactions microwave heating may be used instead of conventional heating to shorten the overall reaction time.

The compounds of the invention as prepared in the processes described herein may be synthesized in the form of mixtures of enantiomers, in particular racemic mixtures of enantiomers, that can be separated from one another following art-known resolution procedures. Racemic compounds of formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I), and the pharmaceutically acceptable addition salts and solvates thereof, involves liquid chromatography using a chiral stationary phase e.g. by supercritical fluid chromatography. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In all these preparations, the reaction products may be isolated from the reaction medium and, if necessary, further purified according to methodologies generally known in the art such as, for example, extraction, crystallization, trituration and chromatography. The purity of the reaction products may be determined according to methodologies generally known in the art such as for example LC-MS, TLC, HPLC.

Methods of Treatment and Medical Uses, Pharmaceutical Compositions, and Combinations The present invention also provides methods for the treatment or prevention of a proliferative disease (e.g., cancer, benign neoplasm, angiogenesis, inflammatory disease, autoinflammatory disease, or autoimmune disease) or an infectious disease (e.g., a viral disease) in a subject. Such methods comprise the step of administering to the subject in need thereof an effective amount of a compound of the present disclosure, or a pharmaceutically acceptable salt, solvate, hydrate, tautomer, stereoisomer, or isotopically labeled derivative thereof, or a pharmaceutical composition thereof.

The subject being treated is a mammal. The subject may be a human. The subject may be a domesticated animal, such as a dog, cat, cow, pig, horse, sheep, or goat. The subject may be a companion animal such as a dog or cat. The subject may be a livestock animal such as a cow, pig, horse, sheep, or goat. The subject may be a zoo animal. The subject may be a research animal such as a rodent, dog, or non-human primate. The subject may be a non-human transgenic animal such as a transgenic mouse or transgenic pig.

The proliferative disease to be treated or prevented using the compounds of Formula (I) or Formula (II) will typically be associated with aberrant activity of CDK7. Aberrant activity of CDK7 may be an elevated and/or an inappropriate (e.g., abnormal) activity of CDK7. In certain embodiments, CDK7 is not overexpressed, and the activity of CDK7 is elevated and/or inappropriate. In certain other embodiments, CDK7 is overexpressed, and the activity of CDK7 is elevated and/or inappropriate. The compounds of the present disclosure, and pharmaceutically acceptable salts, solvates, hydrates, tautomers, stereoisomers, isotopically labeled derivatives, and compositions thereof, may inhibit the activity of CDK7 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Inhibition of the activity of CDK7 is expected to cause cytotoxicity via induction of apoptosis. The compounds of the present disclosure, and pharmaceutically acceptable salts, solvates, hydrates, tautomers, stereoisomers, isotopically labeled derivatives, and compositions thereof, may induce apoptosis, and therefore, be useful in treating and/or preventing proliferative diseases.

Cancers that may benefit from a treatment with CDK7 inhibitors of the invention include lymphomas, leukemias, carcinomas, and sarcomas, e.g. non-Hodgkin's lymphoma, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chronic lymphocytic leukemia (CLL), lymphoblastic T cell leukemia, chronic myelogenous leukemia (CML), hairy-cell leukemia, acute lymphoblastic T cell leukemia (T-ALL), Plasmacytoma, Immunoblastic large cell leukemia, megakaryoblastic leukemia, acute megakaryocytic leukemia, acute myeloid leukemia (AML) promyelocytic leukemia, erytholeukemia, brain (gliomas), glioblastomas, breast cancer, colorectal/colon cancer, prostate cancer, lung cancer including small-cell and non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head&neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount may be from about 0.005 mg/kg to 50 mg/kg body weight. The amount of a compound according to the present invention, also referred to here as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment, the compounds according to the invention are preferably formulated prior to administration. As described herein below, suitable pharmaceutical formulations are prepared by known procedures using well known and readily available ingredients.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences ($18^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, or a nose spray. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The methods described herein may also comprise the additional step of administering one or more additional pharmaceutical agents in combination with the compound of the present invention, a pharmaceutically acceptable salt thereof, or compositions comprising such compound or pharmaceutically acceptable salt thereof. Such additional pharmaceutical agents include, but are not limited to, anti-proliferative agents, anti-cancer agents, anti-diabetic agents, anti-inflammatory agents, immunosuppressant agents, and a pain-relieving agent. The additional pharmaceutical agent(s) may synergistically augment inhibition of CDK7 or CDK12 and/or CDK13 induced by the inventive compounds or compositions of this invention in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations. For the treatment of the above conditions, the compounds of the invention may be advantageously employed in combination with one or more other medicinal agents, more particularly, with other anti-cancer agents or adjuvants in cancer therapy.

Examples of anti-cancer agents or adjuvants (supporting agents in the therapy) include but are not limited to

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
  - tetracarcin derivatives for example tetrocarcin A;
  - glucocorticoids, for example prednisone or prednisolone;
  - antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, carminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, venetoclax, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- famesyltransferase inhibitors for example tipifarnib;
- histone deacetylase (HDAC) inhibitors for example sodium butyrate, suberoylanilide hydroxamic acid (SAHA), depsipeptide (FR 901228), NVP-LAQ824, R306465, quisinostat, trichostatin A, vorinostat;
- Inhibitors of the ubiquitin-proteasome pathway for example PS-341, Velcade (MLN-341) or bortezomib;
- Yondelis;
- Telomerase inhibitors for example telomestatin;
- Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b;
MAPK inhibitors;
Retinoids for example alitretinoin, bexarotene, tretinoin;
Arsenic trioxide;
Asparaginase;
Steroids for example dromostanolone propionate, megestrol acetate, nandrolone (decanoate, phenpropionate), dexamethasone;
Gonadotropin releasing hormone agonists or antagonists for example abarelix, goserelin acetate, histrelin acetate, leuprolide acetate;
Thalidomide, lenalidomide;
Mercaptopurine, mitotane, pamidronate, pegademase, pegaspargase, rasburicase;
BH3 mimetics for example ABT-199;
MEK inhibitors for example PD98059, AZD6244, CI-1040;
colony-stimulating factor analogs for example filgrastim, pegfilgrastim, sargramostim; erythropoietin or analogues thereof (e.g. darbepoetin alfa);
interleukin 11; oprelvekin; zoledronate, zoledronic acid; fentanyl;
bisphosphonate; palifermin;
a steroidal cytochrome P450 17alpha-hydroxylase-17,20-lyase inhibitor (CYP17), e.g. abiraterone, abiraterone acetate;
mTOR inhibitors such as rapamycins and rapalogs, and mTOR kinase inhibitors;
PI3K inhibitors and dual mTOR/PI3K inhibitors; PI3K delta inhibitors for example idelalisib and duvelisib;
BTK inhibitors for example Ibrutinib, ONO-4059, ACP-196;
R-CHOP (Rituxan added to CHOP—Cyclophosphamide, Doxorubicin, Vincristine and Prednisolone);
daratumumab;
BRD4 inhibitors;
CDK9 inhibitors;
SYK inhibitors;
PKC inhibitors;
JAK inhibitors;
PIM kinase inhibitors;
immune cell redirection agents (e.g. Blinatumomab or CAR T cells); and
immunomodulatory agents (e.g. anti-PD1 antibodies).

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

EXAMPLES

The following examples are offered for purposes of illustration and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

When a stereocenter is indicated with 'RS' this means that a racemic mixture was obtained.

For intermediates that may be used in a next reaction step as a crude or as a partially purified intermediate, theoretical mol amounts may be indicated in the reaction protocols described below.

Hereinafter, the terms: 'ACN' means acetonitrile, 'AcOH' means acetic acid, 'Ar' means argon, 'BINAP' means 2,2'-bis(diphenylphosphino)-1,1'-binaphthyl, 'BOC' means tert-butyloxycarbonyl, '$Boc_2O$' means di-tert-butyl dicarbonate, 'Celite®' means diatomaceous earth, 'DCM' means dichloromethane, 'DIPEA' means diisopropylethylamine, 'h' means hours(s), 'min' means minute(s), 'Int.' means intermediate; 'aq.' Means aqueous; 'DMAP' means dimethylaminopyridine, 'DMF' means dimethylformamide, '$Et_2O$' means diethylether, 'EtOAc' means ethyl acetate, 'HPLC' means High-performance Liquid Chromatography, 'iPrOH' means isopropyl alcohol, 'HATU' means 1-[bis(dimethylamino)methylene]-1H-[1,2,3]triazolo[4,5-b]pyridin-1-ium 3-oxide hexafluorophosphate, 'LC/MS' means Liquid Chromatography/Mass Spectrometry, 'Me-THF' means methyltetrahydrofuran, 'MeOH' means methanol, 'EtOH' means ethanol, 'NBS' means N-bromosuccinimide, 'NCS' means N-chlorosuccinimide, 'NMR' means Nuclear Magnetic Resonance, 'Pd/C 10%' means palladium on carbon loading 10%, '$Pd(OAc)_2$' means palladium (II) acetate, '$Pd(PPh_3)_4$' means tetrakis(triphenylphosphine)palladium (0), 'rt' means room temperature, 'SFC' means supercritical fluid chromatography, 'ee' means enantiomeric excess, 'TBAF' means tetrabutylammonium fluoride, 'TBDMS' or 'SMDBT' means tert-butyldimethylsilyl, 'TEA' means triethylamine, 'TFA' means trifluoroacetic acid, 'THF' means tetrahydrofuran, 'CV' means column volumes, 'Quant.' means quantitative, 'equiv.' means equivalent(s), 'M.P.' or 'm.p.' means melting point, 'OR' means optical rotation, 'DIPE' means diisopropyl ethylether, 'RaNi' means Raney Nickel, '$NaHCO_3$' means sodium hydrogenocarbonate, 'BRETT-PHOS' means 2-(dicyclohexylphosphino)-3,6-dimethoxy-2', 4', 6'-triisopropyl-1,1'-biphenyl, 'DMSO' means dimethylsulfoxide, '$NaBH_3(OAc)_3$' means sodium triacetoxyborohydride, 'DMA-DMF' means N,N-dimethylformamidedimethylacetal, 'v/v' means volume/volume percent, 'T' means temperature, '$iPrNH_2$' means isopropylamine.

A. Preparation of the Intermediates

Example A1

Preparation of Intermediate 1

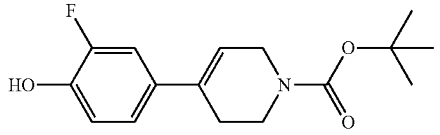 [SMILES: CC(C)(C)OC(=O)N1CC=C(c2ccc(O)c(F)c2)CC1]

In schlenk reactor, a mixture of 4-bromo-2-fluorophenol (2.8 mL, 1.74 g/mL, 25.508 mmol), N-Boc-1,2,3,6-tetrahydropyridine-4-boronic acid pinacol ester (8.38 g, 27.101 mmol), potassium phosphate tribasic (10.9 g, 51.351 mmol), Tris(dibenzylideneacetone)dipalladium(0) (0.468 g, 0.511 mmol), tricyclohexylphosphine (0.286 g, 1.02 mmol) in 1,4-dioxane (190 mL, 1.033 g/mL, 2227.65 mmol) and distilled water (25 mL, 0.998 g/mL, 1384.935 mmol) was stirred at 100° C. for 2 hours. The reaction was allowed to cool to room temperature, before being poured into water and extracted three times with EtOAc. The organic layer was decanted and the solvent was evaporated until dryness to afford 7.85 g of crude material, which was purified by preparative LC (Irregular SiOH 15-40 μm 120 g GraceResolv®, mobile phase: 90% Heptane, 10% EtOAc to 60% Heptane, 40% EtOAc). The fractions containing the pure compound were collected and the solvent was evaporated until dryness to afford the product (5.34 g; 71%).

The intermediate in the Table below were prepared by using an analogous method starting from the respective starting materials.

| Inter-mediate number | Structure | Mass (mg) | Yield (%) |
|---|---|---|---|
| Inter-mediate 2 | 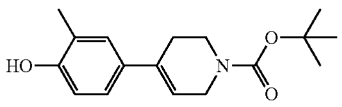 [SMILES: Cc1cc(C2=CCN(C(=O)OC(C)(C)C)CC2)ccc1O] from 2-Methyl,4-bromo-phenol and N-Boc-1,2,3,6-tetrahydropyridine-4-boronic acid pinacol ester | 58500 | 82 (94% pure) |

Example A2

Preparation of Intermediate 3

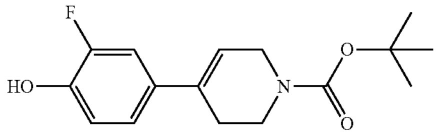 [SMILES: CC(C)(C)OC(=O)N1CC=C(c2ccc(O)c(F)c2)CC1]

Intermediate 1 (5.3 g, 18.068 mmol) was hydrogenated at atmospheric pressure in EtOAc (100 mL) and MeOH (75 mL) with Pd/C (10%) (1.2 g, 1.128 mmol) as a catalyst. After leaving the reaction overnight, the catalyst was removed by filtering the reaction mixture through a pad of Cellite® and the filtrate was evaporated until dryness, affording the product (5.10 g; 96%). The product was used as is for the next step.

The intermediates in the Table below were prepared by using an analogous method

| Inter-mediate number | Structure | Mass (mg) | Yield (%) |
|---|---|---|---|
| Inter-mediate 2a | 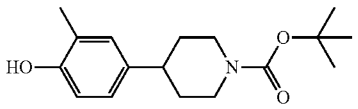 [SMILES: Cc1cc(C2CCN(C(=O)OC(C)(C)C)CC2)ccc1O] from intermediate 2, 3 bars, 6 h | 22400 | 94 |

Example A3

Preparation of Intermediate 4

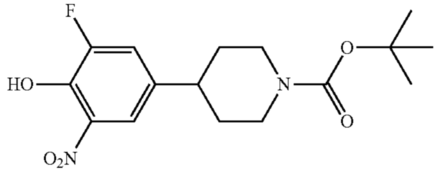 [SMILES: CC(C)(C)OC(=O)N1CCC(c2cc(F)c(O)c([N+](=O)[O-])c2)CC1]

At 0° C., nitric acid (1.3 mL, 1.4 g/mL, 18.774 mmol) and distilled water were added dropwise to a stirred solution of intermediate 3 (5.1 g, 17.267 mmol) in AcOH (25 mL) keeping the temperature between 10-15° C. The reaction was allowed to warm to room temperature and stirred at room temperature for 3 hours. The reaction was poured onto water and this mixture was extracted with EtOAc twice. The combined organics were evaporated until dryness to afford the crude product. This crude was purified by preparative LC (Irregular SiOH 15-40 μm 120 g GraceResolv, mobile phase gradient from: 80% Heptane, 20% EtOAc to 60% Heptane, 40% EtOAc). The fractions containing pure compound were combined and the solvent was evaporated until dryness to give the product (5.17 g; 88%).

The intermediates in the Table below were prepared by using an analogous method starting from the respective starting materials.

| Intermediate number | Structure | Mass (mg) | Yield (%) |
|---|---|---|---|
| Intermediate 5 | 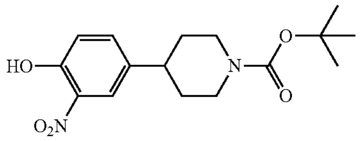 from 4-bromo-phenol and N-Boc-1,2,3,6-tetrahydropyridin-4-boronic acid pinacol ester | 9000 | 66 |

Example A4

Preparation of Intermediate 6

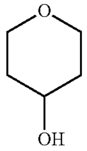

A mixture of tetrahydro-4H-pyran-4-one (2 g; 19.98 mmol) in MeOH (100 mL) was cooled won to 0° C. under $N_2$ atmosphere. Sodium borohydride (1.51 g; 39.95 mmol) was added and the resulting solution was stirred at rt for 2 hours. The reaction mixture was was concentrated in vacuo. The residue was dissolved with EtOAc, washed with 1M $Na_2CO_3$ solution and brine (50 ml). The organic layer was dried over $MgSO_4$, filtered and concentrated to dryness under vacuum. The residue was purified by flash column chromatography ($SiO_2$, from 100% Heptane—0% EtOAc to 0% Heptane—100% EtOAc). Fractions containing the compound were combined and concentrated under reduced pressure to afford the product (1.71 g; 83%) as a clear oil.

Preparation of Intermediate 7

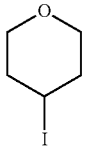

To a solution of intermediate 6 (1.71 g; 16.69 mmol), imidazole (1.36 g; 20.03 mmol) and $PPh_3$ (4.60 g; 17.53 mmol) in THF (40 mL) at 0° C. under a $N_2$ atmosphere was added dropwise a solution of $I_2$ (5.09 g; 20.03 mmol) in THF (30 mL) over 30 minutes. Once complete addition, the mixture was allowed to warm up to rt and stirred for overnight. The reaction mixture was diluted with EtOAc and washed with a sat. $Na_2S_2O_3$ aqueous solution and with brine. The organic layer was dried over $MgSO_4$, filtered and concentrated under vacuum. The residue was purified by column chromatography over silica gel ($SiO_2$; from 100% Heptane—0% EtOAc to 40% Heptane—60% EtAOc). The desired fractions were combined and concentrated under reduced pressure to give the product (2.12 g; 59%) as a clear oil.

The intermediates in the Table below were prepared by using an analogous method

| Intermediate number | Structure | Mass (mg) | Yield (%) |
|---|---|---|---|
| Intermediate 8 | 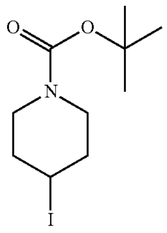 from 1-Boc-4-hydroxypiperidine | 4100 | 88 |

Preparation of Intermediate 9

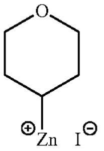

1,2-dibromoethane (0.035 mL; 2.173 g/mL; 0.406 mmol) was added to a suspension of Zn (354 mg; 5.408 mmol) in DMA (4 mL) under $N_2$ atmosphere. The mixture was heated briefly with heat gun and allowed to cool to rt (3 times). TMS-Cl (0.034 mL; 0.859 g/mL; 0.27 mmol) was added slowly and the mixture was stirred for 30 minutes at rt. Intermediate 7 in DMA (4 mL) was added dropwise at such a rate that the temperature did not exceed 50° C. (5 minutes) and the stirring was maintained for 30 minutes. The solution was used in the next step (molarity calculation based on complete conversion).

The intermediates in the Table below were prepared by using an analogous method starting from the respective starting materials.

| Intermediate number | Structure | Molarity (mol/L) | Yield (%) |
|---|---|---|---|
| Intermediate 10 | 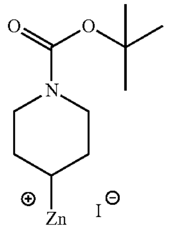 from intermediate 8 | 0.13 | quant. |
| Intermediate 11 | 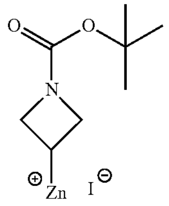 from 1-Boc-3-Iodoazetidine | 0.40 | quant. |

Example A5

Preparation of Intermediate 12

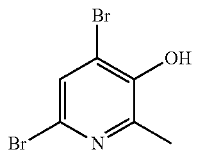

N-bromo-succinimide (163 g, 916 mmol) was added to a solution of 2-methyl-3-hydroxypyridine (50 g, 458 mmol) in acetonitrile (500 mL). The resulting mixture was refluxed for 1.5 h. The volatiles were removed in vacuo. The residue thus obtained was diluted with EtOAc and washed sequentially with water and brine. The organic extract was then dried over $MgSO_4$, filtered and the filtrate concentrated in vacuo. The crude product thus obtained was purified on silica gel (eluting with a solvent gradient of 0 to 35% EtOAc in hexanes). Product fractions were collected and concentrated in vacuum to give intermediate 12 (64.1 g, 52%).

Preparation of Intermediate 13

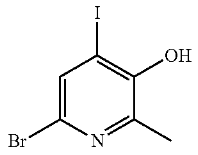

A 2.5 M solution of nBuLi in hexanes (211 mL, 528 mmol) was added dropwise during 10 min to a solution of intermediate 12 (64.1 g, 240 mmol) in THF (550 mL) at −90° C. under nitrogen. The mixture was stirred 30 min at −90° C., then a solution of iodine (73 g, 288 mmol) in THF (180 mL) was added dropwise. The mixture was stirred for 30 min, then water (100 ml) was added to quench the mixture. The mixture was diluted with ethyl acetate and saturated aqueous ammonium chloride. Sodium hydrogenosulfite saturated solution (15 mL) was added to remove excess of iodine. The mixture was acified by slow addition of HCl 3 M to a pH of around 5. Layers were separated, the organic layer was washed with brine, then dried ($MgSO_4$) and concentrated to give intermediate 13 (65.8 g, 87%).

Preparation of Intermediate 14

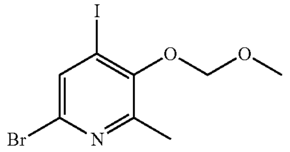

60% sodium hydride dispersion (7.9 g, 197.3 mmol) was added to a solution of intermediate 13 (51.6 g, 164.4 mmol) in DMF (360 mL) at 0° C. under nitrogen atmosphere. The mixture was stirred for 10 min, then chloromethyl methyl ether (16.2 mL, 213.7 mmol) was added dropwise and the mixture was stirred at rt overnight. The reaction was quenched with water. Brine was added and the mixture was extracted with ethyl acetate. The combined organic layers were dried over $MgSO_4$, filtered and concentrated. The crude was purified by flash chromatography (silica; heptane/EtOAc gradient). The desired fractions were collected and concentrated to afford intermediate 14 (48.8 g, 83%) as a white solid.

Preparation of Intermediate 15

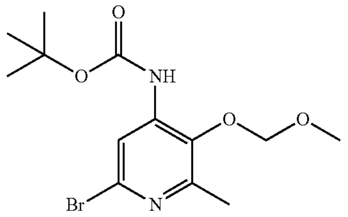 [SMILES: COCOc1c(NC(=O)OC(C)(C)C)cc(Br)nc1C]

Intermediate 14 (23.2 g, 64.81 mmol), 4,5-bis(diphenylphosphino)-9,9-dimethylxanthene (1.88 g, 3.24 mmol) and cesium carbonate (42.2 g, 129.62 mmol) were dissolved in toluene (200 mL) and the mixture was degassed by bubbling nitrogen for 15 min. Palladium(II) acetate (0.73 g, 3.24 mmol) was added under nitrogen, followed by tert-butyl carbamate (8.35 g, 71.29 mmol) and the mixture was stirred at rt for 15 min and then heated at 50° C. for 16 h. The mixture was then allowed to cool to rt, diluted with water (100 mL) and extracted with ethyl acetate (2*150 mL). The combined organic layers were dried over $MgSO_4$, filtered and concentrated. The crude was purified by flash chromatography (silica; heptane/EtOAc gradient). The desired fraction was collected and concentrated to afford intermediate 15 (10.6 g, 47%).

Preparation of Intermediate 16

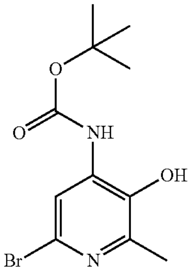

37% aqueous HCl (2.8 mL, 33.6 mmol) was added to a solution of intermediate 15 (10.6 g, 30.5 mmol) in 2-propanol (250 mL). The mixture was stirred at rt for 72 h. Saturated aqueous $NaHCO_3$ was added until pH=7. The mixture was extracted with dichloromethane, dried over $MgSO_4$, filtered and concentrated to afford intermediate 16 (9.3 g, quant).

Example A6

Preparation of Intermediate 17

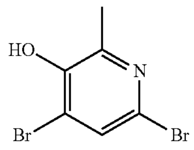

To a solution of 2-methyl-3-hydroxypyridine (20 g; 183.3 mmol) in $CH_3CN$ (400 mL) was added NBS (65.2 g; 366.5 mmol). The resulting mixture was heated at reflux for 2 hours. The volatiles were removed in vacuo. The residue was diluted with $Et_2O$ and washed sequentially with water and brine. The organic layer was dried over $Na_2SO_4$, filtered and the filtrate concentrated under vacuum. The residue was purified by column chromatography over silica gel ($SiO_2$, from 100% Heptane to 65% Heptane—35% EtOAc) to afford the product (23.2 g; 47%) as a white solid.

Preparation of Intermediate 18

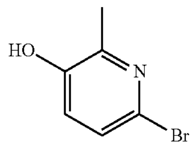

A solution of intermediate 17 (8.29 g; 31.06 mmol) in THF (150 mL) was cooled to −90° C. n-BuLi (27.33 mL; 2.5 mol/L; 68.33 mmol) was added dropwise over 15 minutes. The mixture was stirred for 30 minutes and then quenched with distilled water (10 mL). The mixture was diluted with EtOAc and saturated $NH_4Cl$ was added. The organic layer was dried over MgSO4, filtered and concentrated under vacuum. The residue was purified by chromatography over silica gel ($SiO_2$, Heptane/EtOAc from 100/0 to 50/50) to give the product (5.09 g; 85%) as a white solid.

Preparation of Intermediate 13

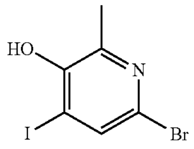

To a solution of intermediate 17 (41 g; 153.6 mmol) in THF (450 mL) at −90° C. under nitrogen, n-BuLi (135.2 mL; 2.5 mol/L; 337.9 mmol) was added dropwise during 10 min. The mixture was stirred for 30 min at −90° C., then a solution of iodine (46.78 g; 184.33 mmol) in THF (150 mL) was added dropwise. The mixture was stirred for 30 min., then water (100 ml) was added to quench the mixture. The mixture was diluted with ethylacetate and saturated aqueous ammonium chloride. Sodium hydrogensulfite saturated solution (5 ml) was added to remove excess of iodine. The pH was made acidic by slow addition of HCl(aq) 3N to attain a pH of around 5. The phases were separated, the organic layer was washed with brine, then dried ($MgSO_4$), filtered and concentrated in vacuo. The resultant product (47 g; 97%) was used as such or next reaction.

Preparation of Intermediate 19

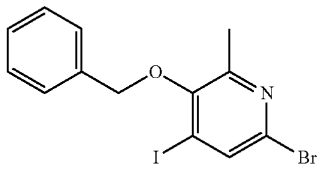 [SMILES: Cc1nc(Br)cc(I)c1OCc1ccccc1]

Benzyl bromide (21.37 mL; 1.438 g/mL; 179.67 mmol) was added to a mixture of intermediate 13 (47 g; 149.72 mmol) and $K_2CO_3$ (41.39 g; 299.44 mmol) in DMF (200 mL), and the mixture was stirred at room temperature for 2 hr. The reaction mixture was poured onto saturated aqueous NaCl solution. A solid precipitated, which was filtered and washed with water twice. The solid was then extracted with dichloromethane and washed with brine. The organic layers were dried ($MgSO_4$), filtered and concentrated in vacuo. Purification was by flash chromatography (silica; heptane/EtOAc from 95/5 to 80/20). The desired fractions were collected and concentrated until a solid started to precipitate. The solid was collected by filtration and washed with heptane, then dried to afford the product (29.1 g; 48%). The mother liquors were also concentrated and the residue purified by flash chromatography (silica; heptane/EtOAc from 95/5 to 80/20). The desired fractions were combined and concentrated in vacuo, to yield a further batch of product (8.4 g; 14%).

Preparation of Intermediate 20

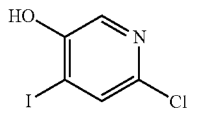

Following the protocol used for the preparation of intermediate 40 and starting from intermediate 25, the intermediate 20 (23.4 g; 64%) was obtained.

Preparation of Intermediate 21

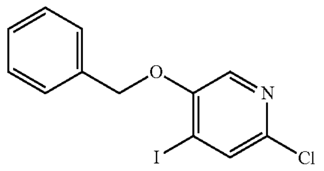 [SMILES: Clc1cc(I)c(OCc2ccccc2)cn1]

Following the protocol used for the preparation of intermediate 43 and starting from intermediate 20, the intermediate 21 (20.3 g; 60%) was obtained.

Preparation of Intermediate 22

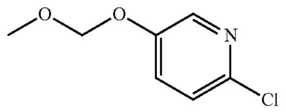

NaH (6.02 g; 60% dispersion, 150.5 mmol) was added portionwise in a solution of 2-chloro-5-hydroxypyridine (16.3 g; 125.4 mmol) in DMF (200 mL) at 0° C. and stirred for 1 hour, then chloromethyl methyl ether (19.1 mL; 1.06 g/mL; 250.9 mmol) was added and the mixture was stirred overnight at rt. The reaction mixture was quenched by addition of water in an ice bath and extracted with EtOAc. The organic layer was dried over $MgSO_4$, filtered and concentrated under vacuum. The residue was purified by column chromatography ($SiO_2$; Heptane/EtOAc) to afford the product (15.2 g; 70%).

The intermediates in the Table below were prepared by using an analogous method starting from the respective starting materials.

| compound number | Structure | Mass (mg) | Yield (%) |
|---|---|---|---|
| Intermediate 23 | 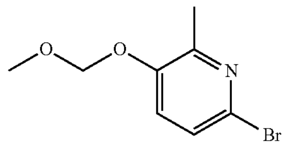 from intermediate 18 | 5810 | 91 |

Example A7

Preparation of Intermediate 24

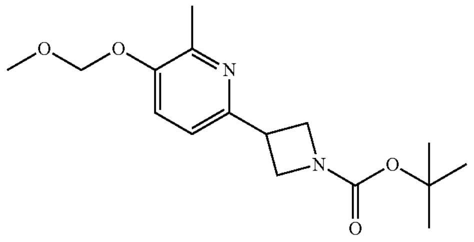 [SMILES: COCOc1ccc(C2CN(C(=O)OC(C)(C)C)C2)nc1C]

Intermediate 23 (56.4 g; 243.025 mmol), Pd(dppf)$Cl_2 \cdot CH_2Cl_2$ adduct (5.954 g; 7.291 mmol) and CuI (4.628 g; 24.302 mmol) were added to the solution of h59 in DMA (702 mL; 0.45 M; 315.932 mmol) at room temperature under a nitrogen atmosphere. The resulting mixture was heated at 80° C. for 1 hour. The mixture was allowed to cool to room temperature and solvent removed in vacuo. The dark residue was taken up in ethylacetate (500 ml) and water (500 ml). 25% $NH_4OH$ (50 ml) and sodium cyanide (NaCN, 1 g) were added. The insolubles were filtered off through a pad of Celite, and organic layer was separated. The organics were extracted with more ethylacetate (2×200 ml). The combined organic layers were washed with brine, dried over $MgSO_4$, filtered and concentrated to afford the crude product as a viscous brownish oil. Chromatography over silica gel (gradient of ethylacetate in heptane from 0 to 30%) gave the product as a yellowish oil that crystallized upon standing (70.94 g; 90%).

Example A8

Preparation on Intermediate 25

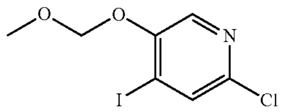

A solution of n-BuLi in hexane (38.5 mL; 2.5 mol/L; 96.3 mmol) was added dropwise in a solution of intermediate 22 (15.2 g; 87.6 mmol) in THF (40 mL) at −78° C. and stirred at this temperature for 1 hour. Then, a solution of $I_2$ (26.7 g; 105.1 mmol) in THF (15 mL) was added, and the mixture was stirred for 1 hour at −78° C. The reaction was quenched with water and extracted with EtOAc. The organic layer was dried over $MgSO_4$, filtered and concentrated under vacuum. The residue was purified by column chromatography ($SiO_2$; Heptane/EtOAc) to afford the product (15.5 g; 38%).

The intermediates in the Table below were prepared by using an analogous method

| compound number | Structure | Mass (mg) | Yield (%) |
|---|---|---|---|
| Intermediate 26 | 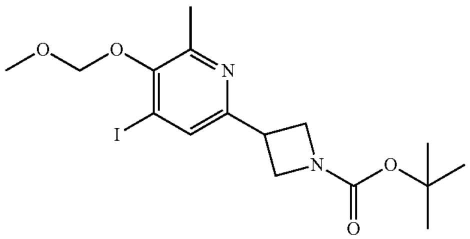 [SMILES: COCOc1c(I)cc(C2CN(C(=O)OC(C)(C)C)C2)nc1C] from intermediate 24 | 8470 | 81 |

Example A9

Preparation of Intermediate 27

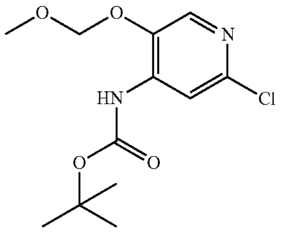 [SMILES: COCOc1cnc(Cl)cc1NC(=O)OC(C)(C)C]

Intermediate 25 (15.5 g; 31.1 mmol), $Cs_2CO_3$ (20.2 g; 62.1 mmol), Xantphos (1.80 g; 3.11 mmol) and $Pd_2(dba)_3$ (2.84 g; 3.11 mmol) were mixed in toluene (250 mL) under $N_2$ atmosphere and the mixture was stirred for 10 min at rt, then tert-butyl carbamate (4.08 g; 34.2 mmol) was added and stirred for 3 hours at 100° C. The crude mixture was partitioned between EtOAc and brine. The organic layer was dried over $MgSO_4$, filtered and concentrated under reduced pressure. Another batch (scale: 5.5 g) was combined with this batch to carry out the purification. The residue was purified by column chromatography ($SiO_2$; Heptane/EtOAc) to afford the product (14.5 g; 90%).

The intermediates in the Table below were prepared by using an analogous method starting from the respective starting materials.

| compound number | Structure | Mass (mg) | Yield (%) |
|---|---|---|---|
| Intermediate 28 | 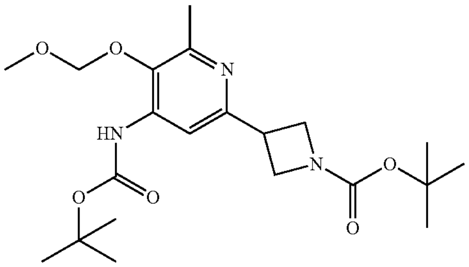 [SMILES: COCOc1c(NC(=O)OC(C)(C)C)cc(C2CN(C(=O)OC(C)(C)C)C2)nc1C] from intermediate 26 | 7900 | 95 |
| Intermediate 29 | 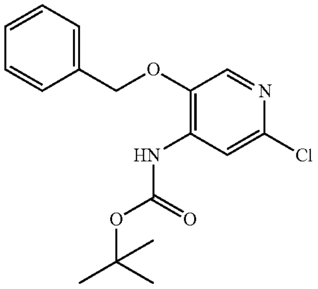 [SMILES: CC(C)(C)OC(=O)Nc1cc(Cl)ncc1OCc1ccccc1] from intermediate 21 | 10600 | quant. |

-continued

| compound number | Structure | Mass (mg) | Yield (%) |
| --- | --- | --- | --- |
| Intermediate 30 | 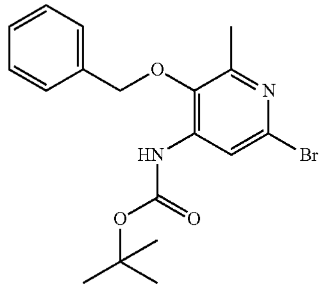 [SMILES: Cc1nc(Br)cc(NC(=O)OC(C)(C)C)c1OCc1ccccc1] from intermediate 19 and tert-butyl carbamate | 16800 | 56 |

Example A10

Preparation of Intermediate 31

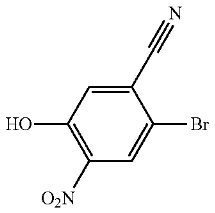 [SMILES: N#Cc1cc(O)c([N+](=O)[O-])cc1Br]

To a solution of 2-bromo-5-hydroxybenzonitrile (9.7 g; 48.99 mmol) and $H_2SO_4$ (137.4 µL; 1.84 g/mL; 2.45 mmol) in acetic acid (380 mL) was added dropwise at rt a solution of $HNO_3$ in acetic acid (100 mL). The reaction mixture was stirred at rt for 20 hours. The reaction mixture was partitioned between EtOAc and brine. The organic layer was dried over $MgSO_4$, filtered and concentrated under vacuum. The residue was purified by column chromatography over silica gel ($SiO_2$; heptane/EtOAc from 100/0 to 0/100) to afford the product (4.78 g; 39%) as a white solid.

Example A11

Preparation of Intermediate 32

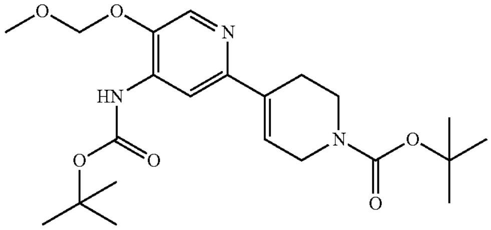

To a suspension of intermediate 27 (7 g; 24.2 mmol), N-boc-1,2,3,6-tetrahydropyridine-4-boronic acid pinacol ester (12.2 g; 31.5 mmol) and $K_3PO_4$ (10.3 g; 48.5 mmol) in a mixture of 1,4-dioxane (180 mL) and distilled water (30 mL) under $N_2$ atmosphere, [1,1'-bis(diphenylphosphino)ferrocene]dichloropalladium(II) (992 mg; 1.21 mmol) was added and the mixture was stirred overnight at 80° C. under nitrogen. The reaction mixture was partitioned between EtOAc and brine. The organic layer was concentrated and the residue was purified by column chromatography ($SiO_2$; Heptane/EtOAc) to afford the product (7.34 g; 70%).

The intermediates in the Table below were prepared by using an analogous method starting from the respective starting materials.

| compound number | Structure | Mass (mg) | Yield (%) |
|---|---|---|---|
| Intermediate 33 | 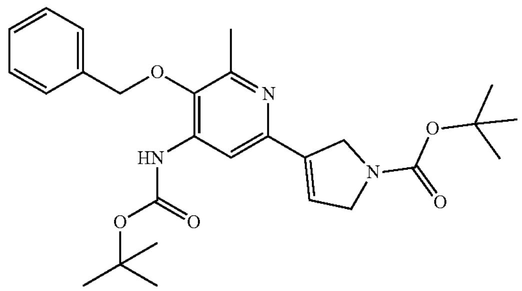 [SMILES: Cc1nc(C2=CCN(C(=O)OC(C)(C)C)C2)cc(NC(=O)OC(C)(C)C)c1OCc1ccccc1] from intermediate 30 and 1-BOC-2,5-dihydro-1H-pyrrole-3-boronic acid, pinacol ester | 14900 | 76 |
| Intermediate 34 | 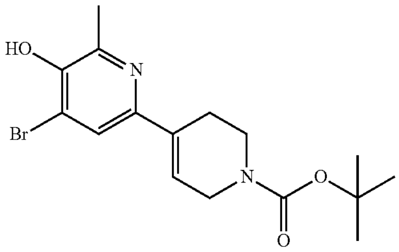 [SMILES: Cc1nc(C2=CCN(C(=O)OC(C)(C)C)CC2)cc(Br)c1O] from intermediate 17 and N-boc-1,2,3,6-tetrahydropyridine-4-boronic acid pinacol ester | 1372 | 50 |
| Intermediate 35 | 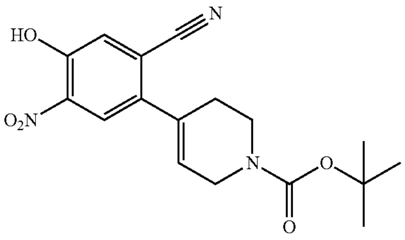 [SMILES: CC(C)(C)OC(=O)N1CC=C(c2cc([N+](=O)[O-])c(O)cc2C#N)CC1] from intermediate 31 and N-boc-1,2,3,6-tetrahydropyridine-4-boronic acid pinacol ester | 1942 | 30 |

Example A12

Preparation of Intermediate 36

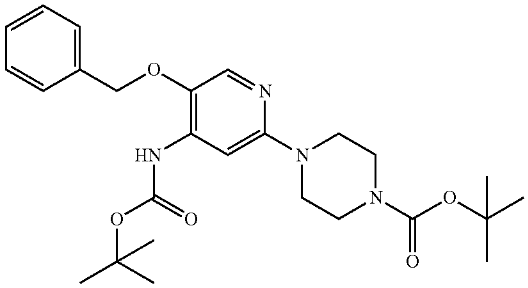 [SMILES: CC(C)(C)OC(=O)Nc1cc(N2CCN(C(=O)OC(C)(C)C)CC2)ncc1OCc1ccccc1]

Intermediate 29 (7.62 g; 22.76 mmol), 1-Boc-piperazine (8.48 g; 45.52 mmol), $Pd_2(dab)_3$ (1.04 g; 1.138 mmol), XPhos (1.09 g; 2.276 mmol) and $Cs_2CO_3$ (11.12 g; 34.14 mmol) were placed in toluene (100 mL) while bubbling nitrogen. The mixture was then stirred at reflux under nitrogen atmosphere for 16 hours. The reaction mixture was allowed to cool to room temperature and diluted with EtOAc. The mixture filtered through a pad of Celite and filtrate washed with water. The organic layer was dried over $MgSO_4$, filtered and concentrated under vacuum. The residue was purified by column chromatography over silica gel ($SiO_2$; Heptane/EtOAc from 100/0 to 65/35) to afford the product (1.92 g; 15%) as a beige solid.

Example A13

Preparation of Intermediate 37

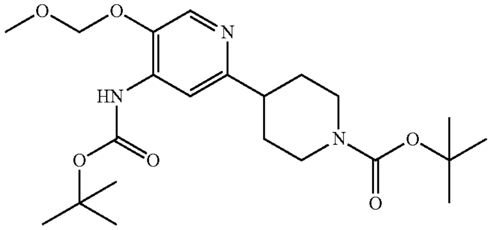 [SMILES: COCOc1cnc(C2CCN(C(=O)OC(C)(C)C)CC2)cc1NC(=O)OC(C)(C)C]

10% Pd/C (34.0 mg) was added in a solution of intermediate 32 (7.34 g; 16.9 mmol) in MeOH (50 mL) under $N_2$ atmosphere at 0° C. The resulting suspension was hydrogenated at atmospheric pressure at rt for overnight. The mixture was filtered over a pad of Celite®. The filtrate was concentrated under reduced pressure to afford the product (6.87 g; 93%) which was used in next step without further purification.

The intermediates in the Table below were prepared by using an analogous method starting from the respective starting materials.

| compound number | Structure | Mass (mg) | Yield (%) |
|---|---|---|---|
| Intermediate 38 | 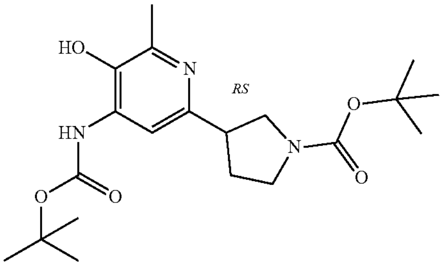 [SMILES: Cc1nc(C2CCN(C(=O)OC(C)(C)C)C2)cc(NC(=O)OC(C)(C)C)c1O] from intermediate 33; solvent MeOH: THF, 2:1 | 12800 | quant |
| Intermediate 39 | 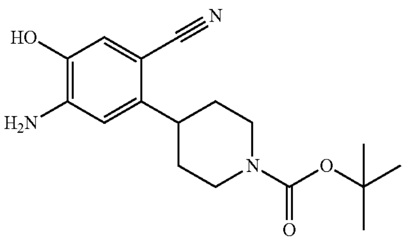 [SMILES: CC(C)(C)OC(=O)N1CCC(c2cc(N)c(O)cc2C#N)CC1] from intermediate 35 | 1848 | 89 |

Example A14

Preparation of Intermediate 40

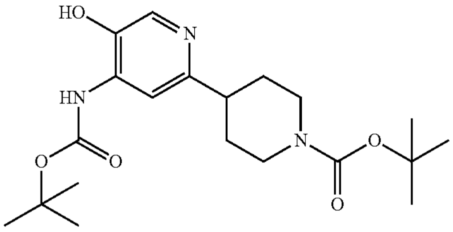 [SMILES: CC(C)(C)OC(=O)Nc1cc(C2CCN(C(=O)OC(C)(C)C)CC2)ncc1O]

To a solution of intermediate 37 (6.6 g; 15.1 mmol) in a mixture iPrOH:THF (1:1; 450 mL), HCl (75.4 mL; 6 mol/L; 226.3 mmol) were added and the mixture was stirred for 24 hours at rt. The reaction mixture was diluted with EtOAc and neutralised with AcONa water solution to pH 4-5. The organic layer was washed with brine and concentrated under vacuum. The residue was purified by column chromatography ($SiO_2$; DCM/MeOH) to afford the product (2.19 g; 37%).

The intermediates in the Table below were prepared by using an analogous method starting from the respective starting materials.

| compound number | Structure | Mass (mg) | Yield (%) |
|---|---|---|---|
| Intermediate 41 | 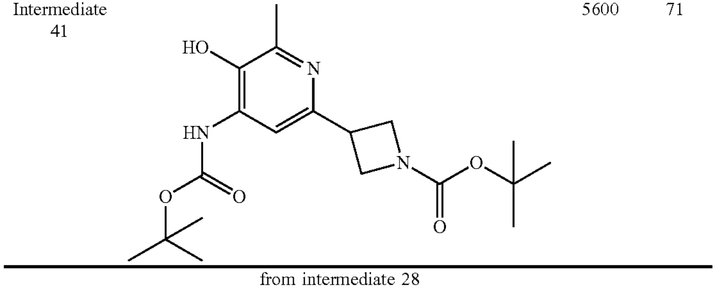 from intermediate 28 | 5600 | 71 |

Example A15

Preparation of Intermediate 42

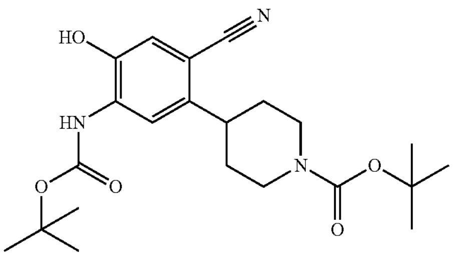 [SMILES: CC(C)(C)OC(=O)Nc1cc(C2CCN(C(=O)OC(C)(C)C)CC2)c(C#N)cc1O]

To a solution of intermediate 39 (1.95 g; 6.16 mmol), DMAP (38.0 mg; 0.308 mmol) and TEA (1.29 mL; 0.726 g/mL; 9.24 mmol) in DCM (40 mL), Boc2O (1.84 g; 8.00 mmol) was added and the mixture was stirred at rt for 1 hour. The reaction mixture was partitioned between DCM and brine. The organic layer was dried over $MgSO_4$, filtered and concentrated under vacuum. The residue was purified by column chromatography over silica gel ($SiO_2$; heptane/EtOAc from 100/0 to 50/50) to afford the product (2.36 g; 70%).

Example A16

Preparation of Intermediate 43

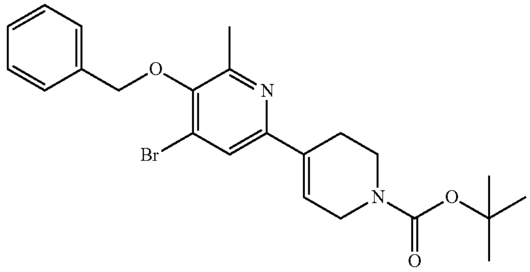 [SMILES: Cc1nc(C2=CCN(C(=O)OC(C)(C)C)CC2)cc(Br)c1OCc1ccccc1]

To a solution of intermediate 34 (343 mg; 0.929 mmol) and $K_2CO_3$ (154 mg; 1.115 mmol) in acetone (10 mL), benzyl bromide (166 μL; 1.438 g/mL; 1.393 mmol) was added and the mixture was stirred at 50° C. for 15 hours. The reaction mixture was cooled down to rt, partitioned between EtOAc and brin. The organic layer was dried over $MgSO_4$, filtered and concentrated under reduced pressure. The residue was purified by column chromatography over silica gel ($SiO_2$, from 100% Heptane to 80% Heptane-20% EtOAc) to afford the product (389 mg; 91%) as a white solid.

Example A17

Preparation of Intermediate 44

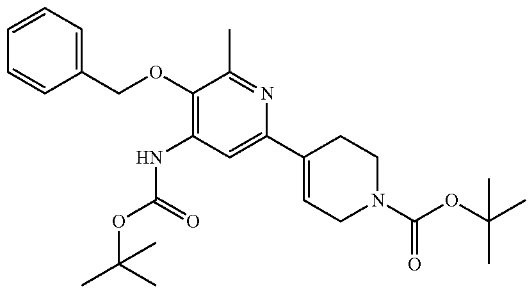 [SMILES: Cc1nc(C2=CCN(C(=O)OC(C)(C)C)CC2)cc(NC(=O)OC(C)(C)C)c1OCc1ccccc1]

Intermediate 43 (8.0 g; 17.4 mmol), $Cs_2CO_3$ (11.3 g; 34.7 mmol), Xantphos (1.00 g; 1.74 mmol) and $Pd_2(dba)_3$ (1.59 g; 1.74 mmol) were mixed in toluene (220 mL) under $N_2$ atmosphere and the mixture was stirred for 10 min at rt, then tert-butyl carbamate (2.64 g; 22.6 mmol) was added and stirred for 16 hours at 100° C. The crude mixture was partitioned between EtOAc and brine. The organic layer was dried over $MgSO_4$, filtered and concentrated under reduced pressure. The residue was purified by column chromatography ($SiO_2$; Heptane/EtOAc) to afford the product (6.7 g; 78%).

Example A18

Preparation of Intermediate 45

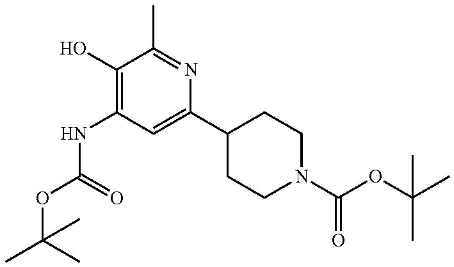 [SMILES: Cc1nc(C2CCN(C(=O)OC(C)(C)C)CC2)cc(NC(=O)OC(C)(C)C)c1O]

10% Pd/C (560 mg) was added in a solution of intermediate 44 (6.69 g; 13.5 mmol) in MeOH (350 mL) under $N_2$ atmosphere. The resulting suspension was hydrogenated at atmospheric pressure at rt for overnight. The mixture was filtered over a pad of Celite®. The filtrate was concentrated under reduced pressure to afford the product (5.4 g; 98%) which was used in next step without further purification.

The intermediates in the Table below were prepared by using an analogous method starting from the respective starting materials.

| compound number | Structure | Mass (mg) | Yield (%) |
| --- | --- | --- | --- |
| Intermediate 46 | 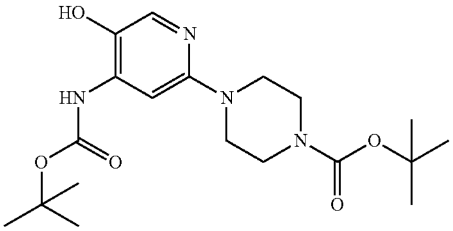 from intermediate 36 | 911 | 57 |

Example A19

Preparation of Intermediate 49

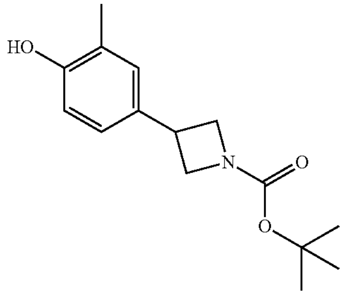 [SMILES: Cc1cc(C2CN(C(=O)OC(C)(C)C)C2)ccc1O]

2 batches were prepared.

To a solution of intermediate 11 (theoretical molarity 0.86 M, 500 mL)) was added a mixture of 4-bromo-2-methylphenol (37 g, 198 mmol), palladium (II) acetate (2.2 g, 9.9 mmol) and CPhos (4.3 g, 9.9 mmol) under N2 at 28° C. The light brown suspension was stirred at 28° C. for 16 h. The mixture was diluted with ethyl acetate (600 mL) and $H_2O$ (0.8 L) and filtered through a celite pad. The aqueous layer of the filtrate was extracted with ethyl acetate (800 mL). The combined organic layers were washed with $H_2O$ (3*0.8 L), brine (0.5 L), dried over MgSO4, filtered and concentrated. The 2 batches were combined, diluted with petroleum ether/methyl t-butyl ether (1/1) (80 mL) and stirred at room temperature for 10 min. Light brown precipitate was observed. The precipitate was filtered off, washed with petroleum ether (2*50 mL) and dried (high vacuum, 50° C., 30 min) to give intermediate 49 (76.5 g, 73%) of a yellow solid.

The filtrate was concentrated to give crude (100 g) as brown oil, which was purified by flash column chromatography over silica gel (eluent: Ethyl acetate/petroleum ether, from 0/100 to 25/75, gradient). The product fractions were collected and the solvent was evaporated to give 25 g of intermediate 49 (purity 60%) as brown oil.

The intermediates in the Table below were prepared by using an analogous method starting from the respective starting materials.

| Intermediate number | Structure | Mass (mg) | Yield (%) |
|---|---|---|---|
| Intermediate 50 | 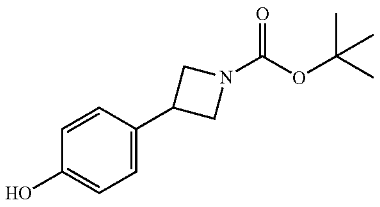 [SMILES: CC(C)(C)OC(=O)N1CC(c2ccc(O)cc2)C1] from 4-bromophenol and intermediate 11 | 15000 | 69 |

Intermediate 50

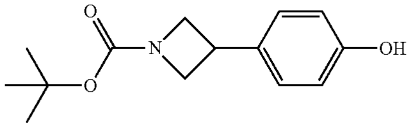 [SMILES: CC(C)(C)OC(=O)N1CC(c2ccc(O)cc2)C1]

To a solution of intermediate 11 (theoretical molarity 0.86 M, 500 mL)) was added a mixture of 4-bromophenol (37 g; 213.864 mmol), $Pd(OAc)_2$ (2.401 g; 10.693) and CPhos (4.669; 10.693 mmol) at 28° C. The resultant light brown suspension was stirred at 28° C. under $N_2$ for 16 h. A dark suspension was observed. The mixture was diluted with ethyl acetate (600 mL) and $H_2O$ (0.8 L). The mixture was filtered through a celite pad. The aqueous layer of the filtrate was extracted with ethyl acetate (800 mL). The combined organic layers were washed with $H_2O$ (3*0.8 L), brine (0.8 L), before being dried over $MgSO_4$, filtered and concentrated to give the crude product as a brown oil, which solidified after standing over night. The mixture was diluted with methyl t-butyl ether (50 mL). The mixture was stirred at room temperature (25° C.) for 10 min. The precipitate was filtered off, washed with methyl t-butyl ether (2*30 mL) and dried (high vacuum, 50° C., 30 min) to give a batch of product as a yellow solid. The filtrate was concentrated to give a crude residue (48 g) as brown oil, which was purified by flash column chromatography over a 330 g silica gel (eluent: Ethyl acetate/petroleum ether, from 0/100 to 25/75, gradient). Fractions containing pure product were collected and the solvent was evaporated to give product as a yellow solid. The product batches were combined to give intermediate 46 as a yellow solid (45 g; 84%).

Example A20

Preparation of Intermediate 51

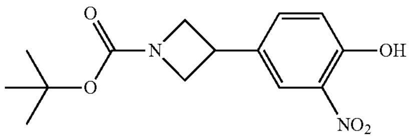

To a yellow suspension of intermediate 46 (45 g; 180.5 mmol) in AcOH (700 mL) was added nitric acid (13.367 mL; 1.44 g/mL; 198.55 mmol) dropwise at 40° C. (inner temperature 30° C.), leading to a dark brown solution. The mixture was stirred at 40° C. for 20 min. A black solution resulted. The mixture was diluted with ethyl acetate (1.5 L).

The mixture was washed with a solution of sat. $Na_2CO_3$(aq) (3*700 mL), $H_2O$ (1 L), and brine (0.8 L), before being dried ($MgSO_4$), filtered and concentrated to give the crude product as a brown oil, which solidified after standing at room temperature for 16 h. The mixture was diluted with methyl t-butyl ether (50 mL). The mixture was stirred for 5 min and filtered. The filter cake was rinsed with methyl t-butyl ether (2*30 mL) and dried under high vacuum (50° C., 0.5 h) to give a batch of the product as a yellow solid. The filtrate was concentrated under vacuum to give a residue (30 g) as a brown oil, which was purified by flash column chromatography over 330 g silica gel (eluent: ethyl acetate/petroleum ether from 0/100 to 18/82, gradient). Fractions containing pure product were collected and the solvent was evaporated to give product as a yellow solid. The product batches were combined to give intermediate 51 as a yellow solid (39 g; 73%).

Preparation of Intermediate 52

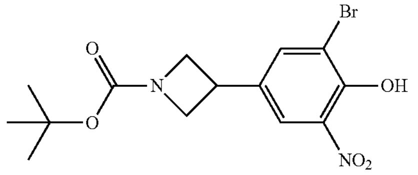

2 reactions (6 g & 34 g scale) were run in parallel and combined for purification. The protocol is described for the 34 g reaction. NBS (20.383 g; 114.522 mmol) was added portionwise to a suspension of intermediate 51 (34 g; 114.522 mmol) and silica (210 g) in $CH_2Cl_2$ (1100 mL) at −15° C. The mixture was stirred at −15° C. for 30 min. The mixture was filtered. The filter cake was rinsed with DCM (3*800 mL). The filtrate was concentrated to give the crude product as a yellow gum. Purification was by flash column chromatography over silica gel (eluent: ethyl acetate/petroleum ether from 0/100 to 18/82, gradient). Fractions containing the pure product were combined and the solvent was evaporated to give the product as a yellow solid (35.45 g; 69%, based on two batches).

Preparation of Intermediate 53

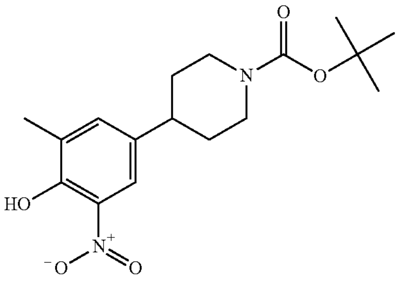

To a yellow suspension of intermediate tert-butyl 4-(4-hydroxy-3-methylphenyl)piperidine-1-carboxylate [1852496-93-5] (100 g, 323 mmol) in AcOH (1.1 L) was added nitric acid (density about 1.4 g/mL) (23.9 mL, 355 mmol) dropwise at 40° C. Dark brown solution was observed. The mixture was stirred at 40° C. for 20 min. The mixture was diluted with ethyl acetate (1500 mL) and poured into sat. aq. $NaHCO_3$ (1.3 L) slowly. The separated aqueous layer was extracted with ethyl acetate (300 mL). The combined organic layers were washed with a solution of $H_2O$/brine (1/1) (2 L), dried (MgSO4), filtered and concentrated to give a brown liquid, which was purified by flash column chromatography on silica gel (eluent: petroleum ether/ethyl acetate from 100/0 to 90/10, gradient, 35 min). The desired fractions were collected and the solvent was evaporated under vacuum to give intermediate 53 (91.8 g; 84%) as light yellow gum, which was solidified after standing.

The intermediates in the Table below were prepared by using an analogous method starting from the respective starting materials.

| Intermediate number | Structure | Mass (mg) | Yield (%) |
|---|---|---|---|
| Intermediate 54 | 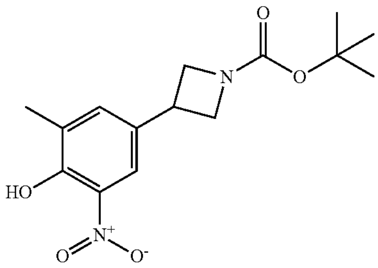 [SMILES: Cc1cc(C2CN(C(=O)OC(C)(C)C)C2)cc([N+](=O)[O-])c1O] from intermediate 49, at 25° C. | 74000 | 82 |
| Intermediate 51 | 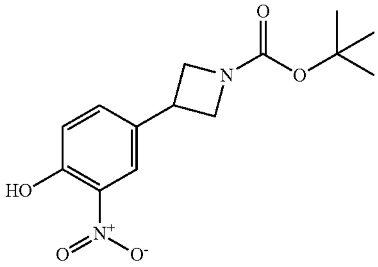 [SMILES: CC(C)(C)OC(=O)N1CC(c2ccc(O)c([N+](=O)[O-])c2)C1] from intermediate 50 | 14500 | 82 |

Example A21

Preparation of Intermediate 55

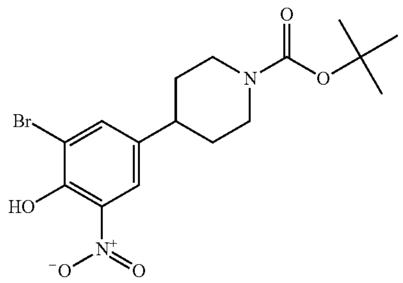

Method A: To a solution of intermediate 2a (43.4 g, 135 mmol) in DMF (218 mL) was added portionwise N-Bromosuccinimide (28.8 g, 162 mmol). The mixture was stirred at room temperature overnight. Water (400 mL) was added and the mixture was extracted with ethyl acetate (400 mL*2). The organic layers were combined, washed with brine (400 mL), dried over $Na_2SO_4$, evaporated to give a yellow solid (60 g). The crude was purified by flash column chromatography over silica gel (eluent: petroleum ether/ethyl acetate from 100/0 to 70/30). The desired fractions were collected and the solvent was concentrated to dryness in vacuum to give intermediate 55 (26.5 g, 47%, purity 96%) as a yellow solid.

Method B

At 0° C., a solution of bromine (2.8 mL, 3.119 g/mL, 54.6 mmol) in AcOH (40 ml) was added dropwise to a solution of intermediate 2a (11.8 g, 36.6 mmol) in AcOH (130 mL) and MeOH (135 mL). The reaction was stirred for 7 hours at room temperature. The reaction mixture was diluted with water (2×200 ml) and extracted three times with EtOAc. The combined organic layer was decanted and evaporated until dryness.

The crude was taken up into DCM, triturated and filtered. The solvent was evaporated until dryness to give intermediate 55 (9 g, 61%)

Preparation of Intermediate 52

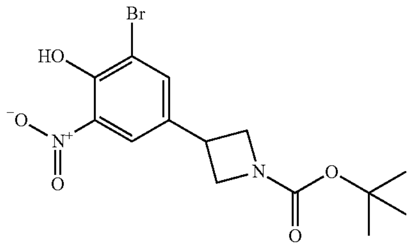

NBS (20.4 g, 115 mmol) was added portionwise to a suspension of intermediate 51 (34 g, 115 mmol) and silica gel (210 g) in DCM (1.1 L) at −15° C. The mixture was stirred at −15° C. for 30 min. The mixture was filtered. The filter cake was rinsed with DCM (3*800 mL). The filtrate was concentrated to give a yellow gum (60 g). The crude was purified by flash column chromatography over silica gel (eluent: ethyl acetate/petroleum ether from 0/100 to 18/82, gradient). The product fractions were collected and the solvent was evaporated to give intermediate 52 (35.4 g, 69%, 86% pure) as a yellow solid.

Example A22

Preparation of Intermediate 655

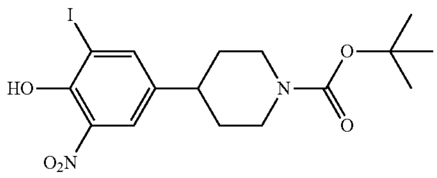

N-iodosuccinimide (3.49 g, 15.51 mmol) was added portionwise to a suspension of intermediate 5 (5.0 g, 15.51 mmol) and silica (30 g) in DCM (180 mL) at −15° C. The mixture was stirred at −15° C. for 15 min and at 25° C. for 2 h. The mixture was concentrated under vacuum and purified by flash column chromatography over 40 g silica gel (eluent: ethyl acetate/petroleum ether from 0/100 to 25/75, gradient). The desired fractions were collected and the solvent was evaporated to give intermediate 655 (6.2 g, 89%) as light yellow gum.

Example A23

Preparation of Intermediate 656

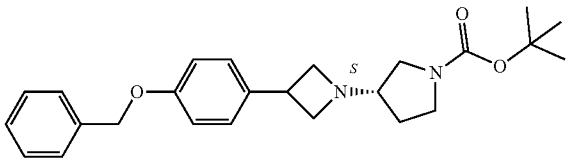

Nickel(II) chloride, ethylene glycol dimethyl ether complex (16.6 mg, 0.075 mmol) and [4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate (169 mg, 0.15 mmol) were added to a suspension of 4-benzyloxybromobenzene (2.00 g, 7.53 mmol), intermediate 101 (2.53 g, 8.28 mmol), tris(trimethylsilyl)silane (2.06 g, 8.28 mmol), 4,4'-di-tert-butyl-2,2'-bipyridine (24.3 mg, 0.09 mmol) and sodium carbonate (1.60 g, 15.06 mmol) in DME (50 mL). The solution was degassed with nitrogen and stirred at 40° C. under 72 W royal blue LED irradiation for 48 h. The mixture was filtered and the filter cake was rinsed with ethyl acetate (3*80 mL). The filtrate was concentrated under vacuum. The crude material was purified by flash column chromatography over 40 g silica gel (eluent: petroleum ether/ethyl acetate from 100/0 to 50/50, gradient). The desired fractions were collected the solvent was evaporated under vacuum to give intermediate 656 (960 mg, 31%).

Preparation of Intermediate 657

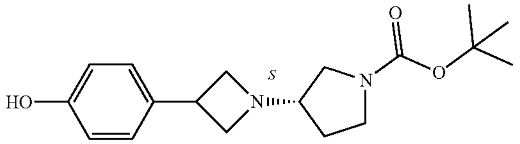

A mixture of intermediate 656 (960 mg, 2.31 mmol) and 10% Pd/C (1.0 g) in methanol/ethyl acetate 1/1 (50 mL) was hydrogenated at rt (50 psi) for 16 h. The catalyst was filtered off and the filtrate was concentrated to give intermediate 657 (700 mg, 90%).

Preparation of Intermediate 658

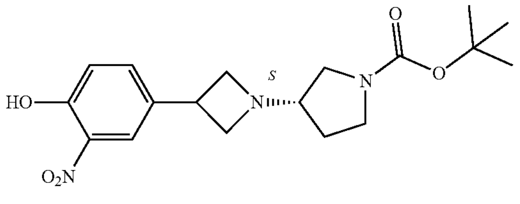

Nitric acid (0.15 mL, 2.29 mmol) was added dropwise to a solution of intermediate 657 (700 mg, 2.09 mmol) in acetic acid at 40° C. The mixture was stirred at 40° C. for 10 min, then poured into a mixture of ice-water (15 mL) and ethyl acetate (15 mL). The aqueous layer was extracted with ethyl acetate (3*15 mL). The combined organic layers were slowly treated with sat. aq. $Na_2CO_3$ (20 mL), washed with brine (20 mL), dried over MgSO4 and concentrated. The crude material was purified by flash column chromatography over 12 g silica gel (eluent: ethyl acetate/petroleum ether from 0/100 to 90/10, gradient). The product fractions were collected and the solvent was evaporated under vacuum to give intermediate 658 (220 mg, 28%).

Preparation of Intermediate 659

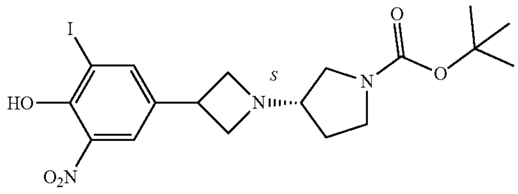

N-iodosuccinimide (136 mg, 0.61 mmol) was added portionwise to a suspension of intermediate 658 (220 mg, 0.61 mmol) and silica (1.2 g) in DCM (7 mL) at −15° C. The mixture was stirred at −15° C. for 15 min and at 25° C. for 16 h, then concentrated under vacuum. The crude was purified by flash column chromatography over 4 g silica gel (eluent: ethyl acetate/petroleum ether from 0/100 to 100/0, gradient). The desired fractions were collected and the solvent was evaporated to give intermediate 659 (90 mg, 27%).

Example A24

Preparation of Intermediate 56

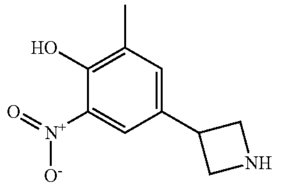

Intermediate 54 (31.5 g, 102 mmol) was dissolved in DCM (350 mL). TFA (53 mL, 715 mmol) was added at 25° C. The orange solution was stirred at 25° C. for 16 h. The mixture was concentrated under vacuum to give a residue, which was coevaporated with toluene (2*200 mL) to give intermediate 56 (45 g, quant) as an orange liquid, which was solidified after standing.

The intermediates in the Table below were prepared by using an analogous method starting from the respective starting materials.

| compound number | Structure | Mass (mg) | Yield (%) |
|---|---|---|---|
| Intermediate 57 | 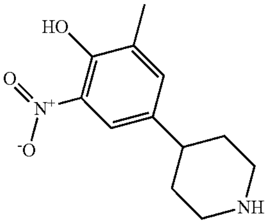 from intermediate 53 | 83000 | quant |
| Intermediate 58 | 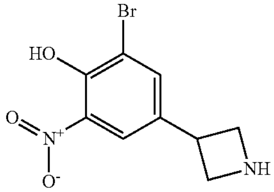 [SMILES: O=[N+]([O-])c1cc(C2CNC2)cc(Br)c1O] from intermediate 52 | | |

Example A25

Preparation of Intermediate 59

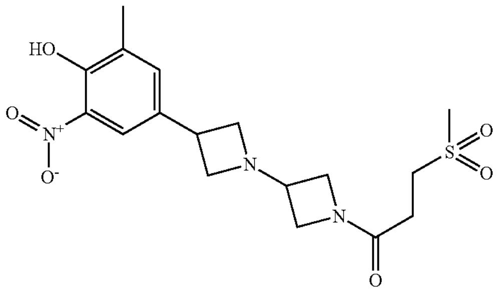 [SMILES: Cc1cc(C2CN(C3CN(C(=O)CCS(C)(=O)=O)C3)C2)cc([N+](=O)[O-])c1O]

A solution of intermediate 56 (3.9 g, 11.4 mmol), TEA (3.16 g, 22.8 mmol), intermediate 89 (2.8 g, 13.7 mmol) in DCE (40 mL) was stirred at room temperature for 1 hour. Sodium triacetoxy borohydride (3.1 g, 14.8 mmol) was added and the reaction was stirred at room temperature overnight. The reaction mixture was concentrated. The crude compound was dissolved in CH2Cl2 (300 mL), washed with Sat.$NaHCO_3$ (100 mL), brine (50 mL), dried over $Na_2SO_4$, filtered, and evaporated in vacuum to give 10 g of crude. It was purified by flash column chromatography over silica gel (eluent: CH2Cl2/MeOH from 100/0 to 80/20). The desired fractions were collected and the solvent was concentrated to dryness under vacuum to give intermediate 59 (2.9 g, 63%).

Preparation of Intermediate 60

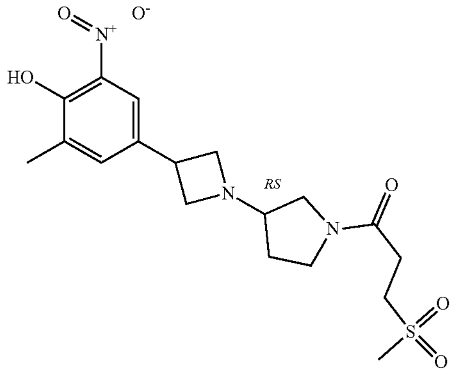

DIPEA (35.9 mL, 206 mmol) was added to a solution of intermediate 56 (45 g, 103 mmol) in EtOH (500 mL). Intermediate 90 (24 g, 109 mmol) and AcOH (10.2 mL, 186 mmol) were added under nitrogen. The mixture was stirred at 30° C. for 1 h. Sodium cyanoborohydride (13 g, 206 mmol) was added portionwise and slowly. The mixture was stirred at 30° C. for 16 hr. The mixture was concentrated under reduced pressure. The residue was diluted with CH2Cl2 (1 L), washed with sat. aq. $NaHCO_3$ (11*700 mL), dried over MgSO4, filtered and concentrated under vacuum to give an orange liquid (50 g). The residue was dissolved in CH2Cl2 (30 mL) and purified by column chromatography over 330 g silica gel (eluent: MeOH/CH2Cl2 from 0/100 to 1/99, gradient). The desired fractions were collected and the solvent was evaporated to give intermediate 60 (32.7 g, 71%) as an orange solid.

The intermediates in the Table below were prepared by using an analogous method starting from the respective starting materials.

| compound number | Structure | Mass (mg) | Yield (%) |
|---|---|---|---|
| Intermediate 61 | 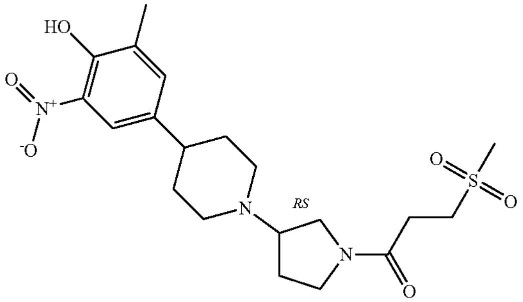 from intermediate 57 and intermediate 90, 25° C., 16 h | 61000 | 57 |

Example A26

Preparation of Intermediate 62

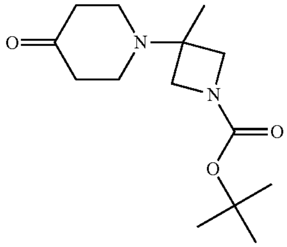 [SMILES: CC(C)(C)OC(=O)N1CC(C)(N2CCC(=O)CC2)C1]

tert-Butyl 3-amino-3-methylazetidine-1-carboxylate (3.5 g, 19 mmol) and K2CO3 (260 mg, 1.88 mmol) in EtOH (51 mL) was stirred at 80° C. 1-Ethyl-1-methyl-4-oxopiperidin-1-ium iodide (intermediate 108) (10.1 g, 37.6 mmol) in water (23 mL) was added and the reaction mixture was stirred at reflux for 18 h. Water, aq $NH_4Cl$ sat. and DCM were added. The organic layer was separated, dried over MgSO4, filtered and evaporated under vacuum. The crude was purified by preparative LC (Irregular SiOH 15-40 µm 220 g Buchi, mobile phase: 100% DCM to DCM:95, MeOH: 5, NH4OH: 0.5. The fractions containing products were evaporated under vacuum to give intermediate 62 (4.51 g, 89%).

Example A27

Preparation of Intermediate 63

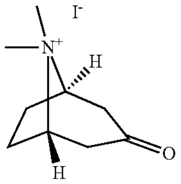

To a solution of tropinone (5.00 g, 35.9 mmol) in acetone (20 mL) was added via a dropping funnel a solution of iodomethane (2.46 mL, 39.5 mmol) in acetone (20 mL) at room temperature. The reaction was stirred at room temperature for 4 hours, then filtered on a glass frit. The solid was washed with acetone, then with Et2O. The solid was collected and dried in vacuo to afford intermediate 63 (9.12 g, 90%).

Preparation of Intermediate 63

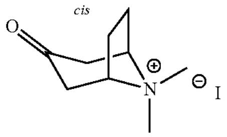

To a solution of tropinone (8.72 g; 62.6 mmol) in acetone (70 mL) was added dropwise for 45 min $CH_3I$ (4.7 mL; 2.27 g/mL; 75.2 mmol). The resulting suspension was stirred for 1 hour at rt. The precipitate was filtered off, washed with acetone and with a mixture of Heptane/EtOAc (6/4). The resulting solid was then dried under vacuum to give the product (16.6 g; 94%) as a light brown powder.

Example A28

Preparation of Intermediate 64

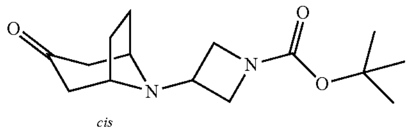 [SMILES: CC(C)(C)OC(=O)N1CC(N2C3CCC2CC(=O)C3)C1]

A solution of intermediate 63 (4.9 g; 17.42 mmol) and 3-amino-1-N-Boc-azetidine (3 g; 17.42 mmol) in EtOH (39 mL) and distilled water (39 mL) was heated to reflux temperature. $K2CO_3$ (7.2 g; 52.26 mmol) was added portion wise for 15 minutes and the mixture was then refluxed for 14 hours. The mixture was cooled down to rt and extracted with DCM. The organic layer was washed with brine, dried over MgSO4 and concentrated under reduced pressure. The residue was purified by flash chromatography (SiO2, Heptane/EtOAc) to afford the product (2.8 g; 58%).

The intermediates in the Table below were prepared by using an analogous method starting from the respective starting materials.

| compound number | Structure | Mass (mg) | Yield (%) |
|---|---|---|---|
| Intermediate 64 | 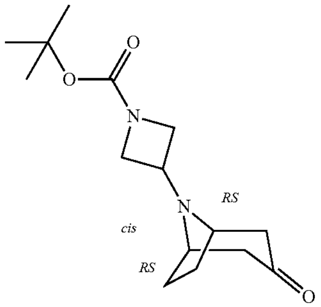 [SMILES: CC(C)(C)OC(=O)N1CC(N2C3CCC2CC(=O)C3)C1] from intermediate 63 | 2680 | 61 |

Example A29

Preparation of Intermediate 65

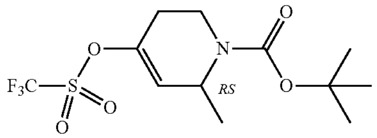

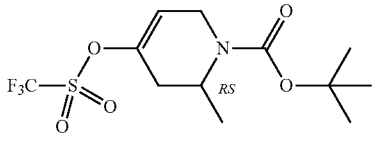

At −78° C., lithium bis(trimethylsilyl)amide solution (7.033 mL; 1 mol/L; 7.033 mmol) was added dropwise to a solution of 2-methyl-4-oxo-piperidine-1-carboxylic acid tert-butyl ester (1 g; 4.689 mmol) in THF (20 mL) under $N_2$. After stirring the solution at −78° C. for 20 minutes, a solution of N,N-bis(trifluoromethylsulfonyl)aniline (2.01 g; 5.627 mmol) in THF (20 mL) was added and the resulting solution was allowed to warm to 0° C. and stirred overnight. The reaction mixture was concentrated under vacuum and the residue was dissolved in diethyl ether and washed with water, 1 M NaOH solution and brine. The organic phase was dried over $MgSO_4$, filtered, concentrated under reduce pressure and purified by flash chromatography ($SiO_2$; Hexane/EtOAc). The desired fractions were combined and concentrated in vacuo to afford the product (1.03 g; 32%).

The intermediates in the Table below were prepared by using an analogous method starting from the respective starting materials.

| compound number | Structure | Mass (mg) | Yield (%) |
|---|---|---|---|
| Intermediate 66 | 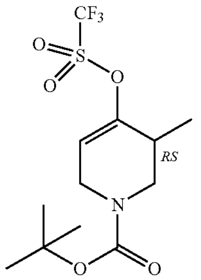 [SMILES: CC1CN(C(=O)OC(C)(C)C)CC=C1OS(=O)(=O)C(F)(F)F] from tert-Butyl 3-methyl-4-oxopiperidine-1-carboxylate | 2606 | 49 |
| Intermediate 67 | 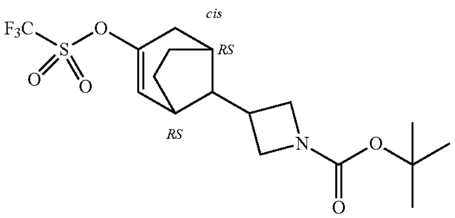 [SMILES: CC(C)(C)OC(=O)N1CC(C2C3C=C(OS(=O)(=O)C(F)(F)F)CC2CC3)C1] from intermediate 64 | 3429 | 82 |

Preparation of Intermediate 67

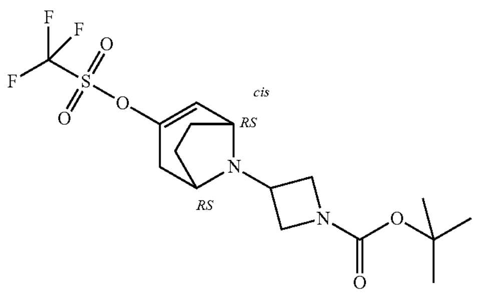 [SMILES: CC(C)(C)OC(=O)N1CC(N2C3C=C(OS(=O)(=O)C(F)(F)F)CC2CC3)C1]

To a solution of intermediate 64 (2.8 g, 10.1 mmol) in THF (3 ml) under nitrogen at −60° C., lithium bis(trimethylsilyl)-amide 1M in THF (17.2 mL, 17.2 mmol) was added and the mixture was stirred at −60° C. for 15 min. Then a solution of N-Phenyl-bis(trifluoro-methanesultonimide (4.7 g, 13.1 mmol) in THF (2 ml) was added and the mixture was stirred for 30 min at −60° C., then allowed to warm to rt during 2 hr. The mixture was poured onto $NaHCO_3$ saturated solution and extracted with ethylacetate. The organic layer was washed with brine, dried with MgSO and concentrated. The crude was purified by flash chromatography (SiO2, Hexane/Ethyl acetate gradient) to give intermediate 67 (3.43 g, 82%).

Example A30

Preparation of Intermediate 68

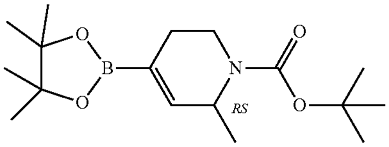

-continued

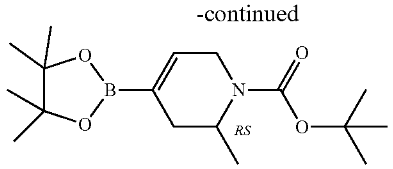

Bis(pinacolato)diboron (808.88 mg; 3.185 mmol), [1,1'-bis(diphenylphosphino)ferrocene]dichloropalladium(II), complex with dichloromethane (94.59 mg; 0.116 mmol), potassium acetate (852.65 mg; 8.687 mmol) and 1,1'-bis(diphenylphosphino)ferrocene (64.17 mg; 0.116 mmol) were added to a solution of intermediate 65 in 1,4-dioxane (37 mL) while $N_2$ was bubbling. The reaction mixture was stirred at 80° C. for 14 hours. Then, the mixture was diluted with brine and extracted with EtOAc (3×). The combined organic layers were washed with brine, dried over $MgSO_4$, filtered and the solvent was evaporated in vacuo. The residue was purified by flash chromatography ($SiO_2$; 0-10% EtOAc in Heptane). The desired fractions were combined and concentrated in vacuo to afford the product (700 mg; 37%) as a white solid.

Example A31

Preparation of Intermediate 69

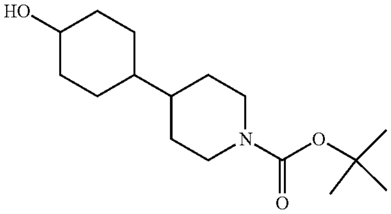 [SMILES: CC(C)(C)OC(=O)N1CCC(C2CCC(O)CC2)CC1]

At 0° C., NaBH4 (134 mg, 3.55 mmol) was added portionwise to a solution of Tert-butyl-4-(4-oxocyclohexyl)piperidine-1-carboxylate (1 g, 3.55 mmol) in dry MeOH (35 mL) and the solution was allowed to stir to rt for 20 h. Most of the solvent was removed under reduced pressure and the residue was diluted with EtOAc and then a 1M aqueous solution of HCl was added. The layers were separated and the aqueous layer was extracted with EtOAc (twice). The combined organic layers were dried over MgSO4, filtered and the solvent was removed under reduced pressure to give intermediate 69 (944 mg, 94%) as a colourless oil.

The intermediates in the Table below were prepared by using an analogous method starting from the respective starting materials.

| compound number | Structure | Mass (mg) | Yield (%) |
| --- | --- | --- | --- |
| Intermediate 70 | 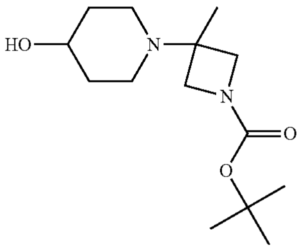 [SMILES: CC(C)(C)OC(=O)N1CC(C)(N2CCC(O)CC2)C1] from intermediate 62 | 4520 | quant |

Example A32

Preparation of Intermediate 71

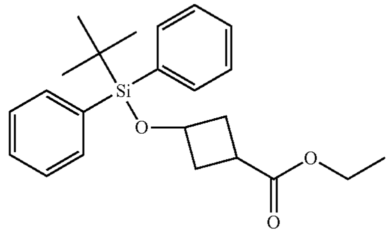 [SMILES: CCOC(=O)C1CC(O[Si](c2ccccc2)(c2ccccc2)C(C)(C)C)C1]

At room temperature, tert-butylchlorodiphenylsilane (24.4 mL; 95.4 mmol) was added dropwise to a solution of ethyl-3-hydroxycyclobutanecarboxylate (12.5 g; 86.7 mmol), imidazole (6.49 g; 95.4 mmol) and DMAP (1.06 g; 8.67 mmol) in DCM (500 mL) and the solution was stirred at rt for 20 h. The reaction mixture was diluted with DCM and treated with an aqueous saturated solution of NaHCO3. The layers were separated and the aqueous layer was extracted with DCM (once). The combined organic layers were dried over MgSO4, filtered and the solvent was removed under reduced pressure to give 34.7 g. The crude was purified by preparative LC (irregular SiOH 40 μm, 220 g Buchi, liquid injection (DCM), mobile phase gradient: from Heptane/EtOAc 100/0 to 50/50). The fractions containing pure product were combined to give intermediate 71 (20.5 g, 62%) of a colourless oil.

Preparation of Intermediate 72

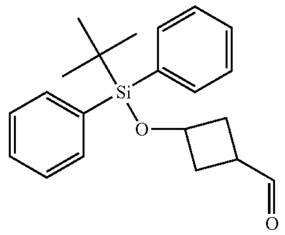 [SMILES: CC(C)(C)[Si](OC1CC(C=O)C1)(c1ccccc1)c1ccccc1]

At −78° C., DIBAL (1.2M in toluene) (45 mL; 54 mmol) was slowly added to a solution of intermediate 71 (20.5 g; 53.6 mmol) in dry DCM (587 mL) and the solution was stirred at −78° C. for 1 h. MeOH (30 mL) was added, the mixture was stirred at rt for 5 minutes and DCM was added. The layers were separated and the aqueous layer was extracted with EtOAc (twice). The combined organic layers were dried over MgSO4, filtered and concentrated to give intermediate 72 (1555 g,&86%) of a colourless oil.

Preparation of Intermediate 73

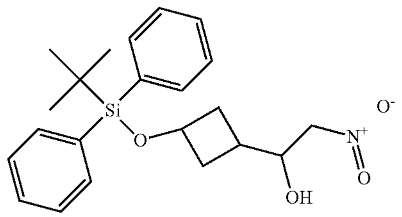

A solution of intermediate 72 (15.5 g, 37.5 mmol), nitromethane (101 mL) and TEA (26.1 mL, 188 mmol) was stirred at rt for 2 h. Water, brine and EtOAc were added to the crude. The layers were separated and the aqueous layer was extracted with EtOAc (twice). The combined organic layers were dried over MgSO4, filtered and evaporated in vacuo to give intermediate 73 (16.1 g, quant) as a yellow oil (Quant., 93% purity).

Purity was calculated to give a quantitative yield.

Preparation of Intermediate 74

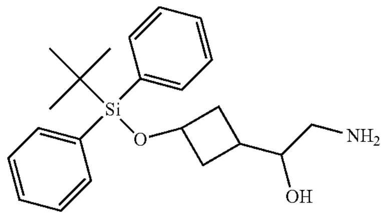 [SMILES: CC(C)(C)[Si](OC1CC(C(O)CN)C1)(c1ccccc1)c1ccccc1]

Pd/C (10%) (2.4 g, 2.27 mmol, 0.15 eq.) was added to a solution of intermediate 73 (6.49 g, 15.1 mmol) in EtOH (227 mL) and the mixture was hydrogenated (1 bar of H2) at rt for 20 h. The reaction mixture was diluted with MeOH and was then filtered on a pad of celite. The celite was washed with MeOH and the filtrate was concentrated under reduced pressure to give intermediate 74 (5.4 g, 97%).

was used as such in the next step.

Preparation of Intermediate 75

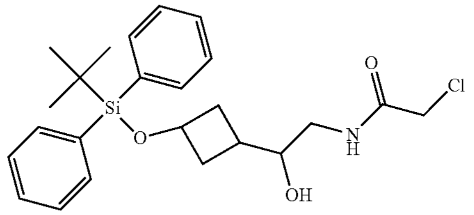 [SMILES: CC(C)(C)[Si](OC1CC(C(O)CNC(=O)CCl)C1)(c1ccccc1)c1ccccc1]

To a mixture of intermediate 74 (6.08 g, 16.5 mmol) and TEA (5.7 mL, 41.1 mmol) in THF (260 mL) was added chloroacetyl chloride (1.31 mL, 16.5 mmol) at 0° C. The mixture was allowed to stir at rt for 1 h 30. Water and EtOAc were added. The layers were separated and the aqueous layer was extracted with EtOAc (twice). The combined organic layers were dried over MgSO4, filtered and the solvent was removed in vacuo to give intermediate 75 (7.3 g, quant) as a yellow oil.

Preparation of Intermediate 76

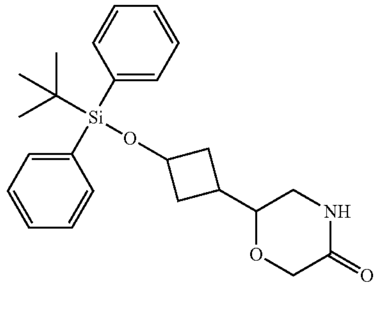 [SMILES: CC(C)(C)[Si](OC1CC(C2CNC(=O)CO2)C1)(c1ccccc1)c1ccccc1]

A solution of potassium tert butoxide (7.35 g, 65.5 mmol) in iPrOH (200 mL) was added dropwise to a solution of intermediate 75 (7.30 g, 16.4 mmol) in DCM (200 mL) at 0° C. The mixture was allowed to stir to rt for 2 h. An aqueous saturated solution of $NH_4Cl$ was added. The layers were separated and the aqueous layer was extracted with EtOAc (twice). The combined organic layers were washed with brine, dried over MgSO4, filtered and the solvent was removed in vacuo to give intermediate 76 (6.28 g, 94%) as a yellow oil.

Preparation of Intermediate 77

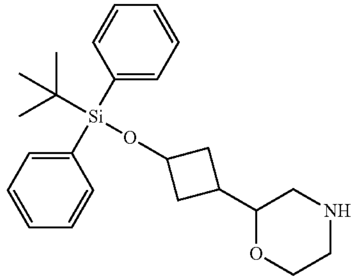 [SMILES: CC(C)(C)[Si](OC1CC(C2CNCCO2)C1)(c1ccccc1)c1ccccc1]

Under N2, LAH (1M in THF) (30.5 mL, 30.5 mmol) was added dropwise to a solution of intermediate 76 (6.25 g, 15.2 mmol) in dry THF (323 mL) at 0° C. The mixture was allowed to stir at rt for 30 min and was then stirred at 50° C. for 30 min. The resulting reaction was cooled to rt and the reaction mixture was quenched by addition of with water (1.2 mL), then 3M aqueous NaOH (1.2 mL) and water (3.6 mL) (Fieser's method). EtOAc was added, as well as MgSO4. The mixture was filtered on a glass frit and the filtrate was evaporated to give 5.35 g of a yellow oil. The crude was purified by preparative LC (irregular SiOH 15-40 μm, 80 g Buchi, liquid loading (DCM), mobile phase gradient: from CH2Cl2/MeOH: 97/3 to 80/20, 15 CV, collect all). The pure fractions were combined to give intermediate 77 (2.87 g, 48%) of a pale yellow oil.

Preparation of Intermediate 78

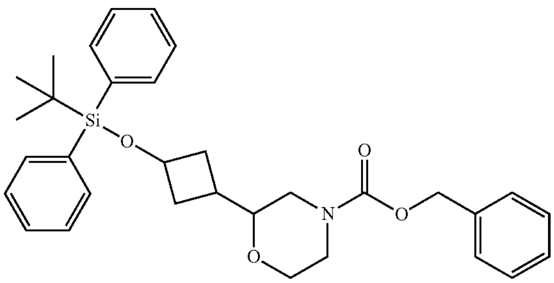 [SMILES: CC(C)(C)[Si](OC1CC(C2CN(C(=O)OCc3ccccc3)CCO2)C1)(c1ccccc1)c1ccccc1]

Benzylchloroformate (1.09 mL, 7.62 mmol) was added dropwise to a solution of intermediate 77 (2.87 g, 7.25 mmol), DIPEA (1.44 mL, 8.34 mmol) and DMAP (27 mg, 0.22 mmol) in dry DCM (34 mL) at 0° C. The reaction mixture was then allowed to stir to rt for 20 h. The reaction mixture was quenched by addition of water and was stirred for 5 minutes at room temperature. DCM and a saturated aqueous solution of $NaHCO_3$ was added. The layers were separated and the aqueous layer was extracted with DCM (once). The organic layers were combined, dried over MgSO4, filtered and evaporated to give intermediate 78 (3.47 g, 90%) of as a yellow oil.

Preparation of Intermediate 79

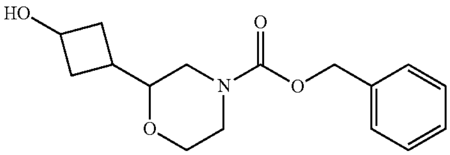 [SMILES: O=C(OCc1ccccc1)N1CCOC(C2CC(O)C2)C1]

TBAF (1M in THF) (7.9 mL, 7.9 mmol) was added dropwise to a solution of intermediate 78 (3.47 g, 6.55 mmol) in THF (174 mL). The reaction mixture was then allowed to stir to rt for 20 h. The reaction mixture was diluted with EtOAc and water. The layers were separated and the aqueous layer was extracted with EtOAc (once). The organic layers were combined, dried over MgSO4, filtered and evaporated. The crude was purified by preparative LC (irregular SiOH 15-40 μm, 40 g Buchi, liquid injection (CH2Cl2), mobile phase gradient: from Heptane/EtOAc 100/0 to 0/100, collect all). The fractions containing products were evaporated to give intermediate 79 (1.58 g, 83%) as a colourless oil.

Example A33

Preparation of Intermediate 80

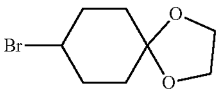 [SMILES: BrC1CCC2(CC1)OCCO2]

To the solution of 1,4-dioxaspiro[4.5]decan-8-ol (1.00 g, 1.174 g/mL, 6.32 mmol), triphenylphosphine (1.74 g, 6.64 mmol) and imidazole (0.495 g, 7.27 mmol) in dry DCM (15 mL) was added carbon tetrabromide (2.20 g, 6.64 mmol) at 0° C. The reaction mixture was stirred at RT for 18 h. The volatiles were evaporated under reduced pressure and the residue was purified by preparative LC (irregular SiOH 15-40 μm, 40 g Buchi, liquid loading (DCM), mobile phase gradient: from Heptane/EtOAc 99/1 to 90/10 in 10 Column Volumes) the fractions containing product were combined and evaporated to give the product as a colourless liquid (916 mg; 66%).

The intermediates in the Table below were prepared by using an analogous method starting from the respective starting materials.

| compound number | Structure | Mass (mg) | Yield (%) |
|---|---|---|---|
| Intermediate 81 | 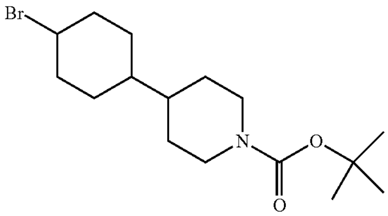 [SMILES: CC(C)(C)OC(=O)N1CCC(C2CCC(Br)CC2)CC1] from intermediate 69 | 270 | 34 Purity 53% |

Preparation of Intermediate 82

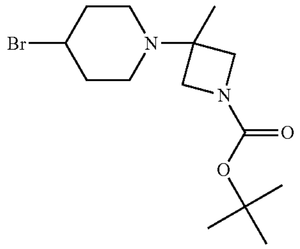 [SMILES: CC(C)(C)OC(=O)N1CC(C)(N2CCC(Br)CC2)C1]

To a solution of intermediate 70 (2.0 g, 7.4 mmol) in THF (75 mL), triphenylphosphine (5.8 g, 22 mmol) was added, then a solution of tetrabromomethane (7.4 g, 22 mmol) in THF (11 mL) was added dropwise and the mixture was stirred at room temperature for 18 hours. The mixture was poured into $NaHCO_3$ aqueous solution, extracted twice with DCM, dried over MgSO4, filtered and evaporated. The crude was purified by preparative LC (irregular SiOH 15-40 μm, 80 g Buchi, liquid loading (DCM), mobile phase gradient: from Heptane/EtOAc 99/1 to 1/1, 10 CV). The fractions containing products were evaporated to give intermediate 82 (2.05 g, 83%).

Preparation of Intermediate 83

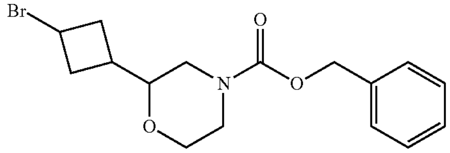 [SMILES: O=C(OCc1ccccc1)N1CCOC(C2CC(Br)C2)C1]

To the solution of intermediate 79 (1.58 g, 5.42 mmol), triphenyphosphine (1.49 g, 5.69 mmol) in dry DCM (9 mL) was added carbon tetrabromide (1.89 g, 5.69 mmol) at 0° C. The reaction mixture was stirred at rt for 20 h. The solvent was removed under reduced pressure and purified by preparative LC (irregular SiOH 15-40 μm, 120 g Buchi, dry load (Celite), mobile phase gradient: from Heptane/EtOAc 95/5 to 0/100, 20 CV). The fractions containing products were evaporated to give intermediate 83 (1.12 g, 46%) as a pale yellow oil.

Example A34

Preparation of Intermediate 84

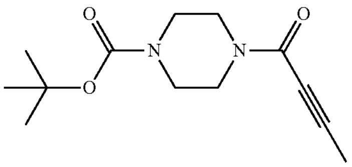 [SMILES: CC#CC(=O)N1CCN(C(=O)OC(C)(C)C)CC1]

A mixture of 1-Boc-piperazine (2.50 g, 13.4 mmol) 2-butynoic acid (1.36 g, 16.2 mmol) and di-isopropylethylamine (11.5 mL, 0.75 g/mL, 66.5 mmol) in DCM (45 mL) was stirred at 0° C. 1-Propanephosphonic anhydride (T3P) (20 mL, 1.069 g/mL, 33.7 mmol) was added slowly at 0° C. The mixture was stirred at 0° C. for 10 min then at rt for 1 h. A sat. solution of $NaHCO_3$(aq) and EtOAc were added. An extraction was performed. The organic layer was washed with an aqueous 1M solution of HCl (aq), then brine, before being dried ($MgSO_4$) and evaporated to give the product as a pale yellow solid (3.54 g; quant.).

Preparation of Intermediate 85

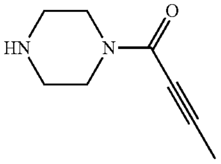

TFA (1.5 mL, 1.49 g/mL, 19.6 mmol) was added to a solution of intermediate 84 (200 mg, 0.793 mmol) in DCM (10 mL). The reaction mixture was stirred at rt for 1 h. The reaction mixture was evaporated under reduced pressure to give the product as a pale yellow oil (332 mg; quant.). The product was used without further elaboration in subsequent steps.

Example A35

Preparation of Intermediate 86

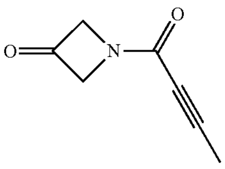

2-Butynoic acid (4.3 g; 51.144 mmol) and triethylamine (19.441 mL; 0.726 g/mL; 139.484 mmol) was dissolved in DCM (250 mL) and stirred at 0° C. 3-Azetidinone hydrochloride (5 g; 46.495 mmol) was added to the reaction mixture in one portion, before 1-propanephosphonic anhydride (T3P—50% wt in EtOAc) (34.113 mL; 1.301 g/mL; 69.742 mmol) was then added slowly. The mixture was stirred at 0° C. for 4 hours. $H_2O$ (100 mL) was added slowly to the mixture and the cooling bath was removed. The mixture was extracted with the solvent mixture ($CH_2Cl_2$:MeOH=10:1, 3*100 mL). The organic layers were dried ($MgSO_4$) and concentrated to afford the crude product as a red oil. The residue was purified by column chromatography over silica gel (eluent: petroleum ether/ethyl acetate=100:0:−30:70). The desired fractions were evaporated in vacuum to afford the product as a yellow solid (4.28 g; 48%).

Preparation of Intermediate 87

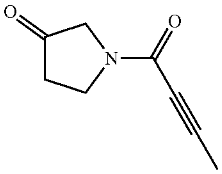

2-Butynoic acid (7.608 g; 90.487 mmol) and triethylamime, 57.327 mL; 0.726 g/mL; 411.303 mmol) was dissolved in DCM (200 mL) and stirred at 0° C. 3-Pyrrolidinone hydrochloride (10 g; 82.261 mmol) was added to the reaction mixture in one portion, before 1-propanephosphonic anhydride (T3P—50% wt in EtOAc) (40.236 mL; 1.301 g/mL; 82.261 mmol) was then added slowly. The mixture was stirred at 35° C. overnight. Ethyl acetate (100 mL) was added to the reaction, stirred for 30 min, filtered and rinsed with ethyl acetate (50 mL*3). The filtrate was evaporated in vacuum to give the crude product as an oil. The crude product was purified by column chromatography over silica gel (eluent: petroleum ether/ethyl acetate=100:0-10:90). The pure fractions were collected and the solvent was removed in vacuum to give the product as oil (2.3 g; 18%).

The intermediates in the Table below were prepared by using an analogous method starting from the respective starting materials.

| compound number | Structure | Mass (mg) | Yield (%) |
|---|---|---|---|
| Intermediate 88 | 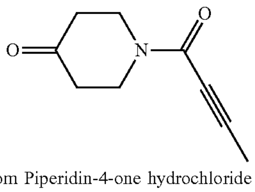 from Piperidin-4-one hydrochloride & 2-butynoic acid; 2 hrs reaction time at 0° C. | 9200 | 73 |

Example A36

Preparation of Intermediate 89

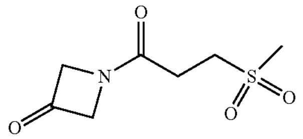

A mixture of 3-(methylsulfonyl)propionic acid (50 g; 329 mmol), 1-(3-dimethylaminopropyl)-3-ethylcarbodiimide hydrochloride (126 g; 657 mmol), 1-benzotriazolol (64.4 g; 476 mmol) and triethylamine (100.8 mL; 0.726 g/mL; 723 mmol) in DCM (1000 mL) was stirred at 5° C. for 60 min. Then 3-azetidinone hydrochloride (35.3 g; 329 mmol) was added, and the mixture was stirred at room temperature for 12 hours. Ethyl acetate (1500 mL) was added to the reaction, stirred for 30 min, filtered and rinsed with ethyl acetate (100 mL*3). The filtrate was evaporated in vacuum to afford 131 g of crude. It was purified by column chromatography over silica gel (eluent: ethyl acetate/MeOH=100/0-95/5). The desired fractions were evaporated in vacuum to afford 40 g of white solid. THF (50 mL) was added and the mixture was stirred for 15 min and the solid was filtered off and dried in vacuum to afford a white solid (32 g; 47.5%).

The intermediates in the Table below were prepared by using an analogous method starting from the respective starting materials.

| compound number | Structure | Mass (mg) | Yield (%) |
|---|---|---|---|
| Intermediate 90 | 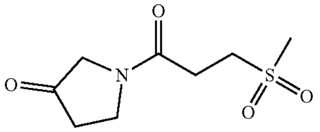 from 3-(methylsulfonyl)propionic acid and 3-pyrrolidinone, hydrochloride | 69.9 | 48 |
| Intermediate 91 | 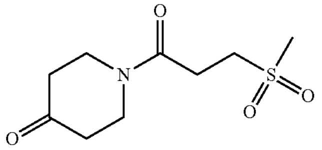 from 3-(methylsulfonyl)propionic acid and piperidin-4-one hydrochloride | 33 | 42 |

Example A37

Preparation of Intermediate 92

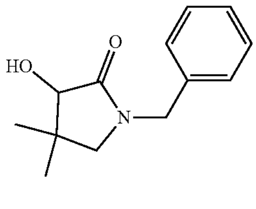 [SMILES: CC1(C)CN(Cc2ccccc2)C(=O)C1O]

A mixture of DL-pantolactone (8.00 g, 61.5 mmol), benzenemethanamine (8.07 mL, 73.8 mmol) and PTSA (1.06 g, 6.15 mmol) was stirred at 235° C. using a single mode microwave (Biotage initiator60) with a power output ranging from 0 to 400 W for 2 h30 [fixed hold time]. The reaction mixture was cooled down and the mixture was diluted with ethyl acetate. The organic layer was washed with 1N aqeuous HCl three times, then with a saturated solution of $NaHCO_3$ then with brine, dried and concentrated in vacuo to give an oil which was purified by preparative LC (irregular SiOH 40 μm, 120 g Buchi, dry loading (celite), mobile phase gradient: Heptane/AcOEt from 80/20 to 50/50, 12 CV). The fraction containing product were combined and evaporated to give intermediate 92 (4.67 g, 35%).

Preparation of Intermediate 93

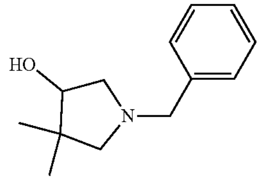

Under nitrogen, a solution of intermediate 92 (3.5 g, 16.0 mmol) in dry THF (17.5 mL) was treated dropwise with LAH 1M in THF (32.0 mL, 32.0 mmol) and stirred at 50° C. for 2 hours. The reaction mixture was cooled down to rt, diluted with Et2O and quenched by the slow addition of water (1.20 mL), a 3M aqueous solution of NaOH (1.20 mL) and water (3.60 mL). The reaction mixture was stirred at rt for 5 minutes. MgSO4 was then added and the reaction mixture was filtered on a glass frit. The filtrate was evaporated in vacuo to give intermediate 93 (3.08 g, 94%).

Preparation of Intermediate 94

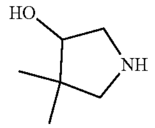

A solution of intermediate 93 (900 mg, 4.38 mmol) in EtOH (10 mL) was hydrogenated in a bomb under hydrogen (8 bar) at room temperature for 17 hours in presence of a catalytic amount of palladium hydroxide on carbon (308 mg, 0.22 mmol).

The reaction mixture was diluted in DCM, filtered through a pad of celite and evaporated to give intermediate 94 (500 mg, quant.).

Preparation of Intermediate 95

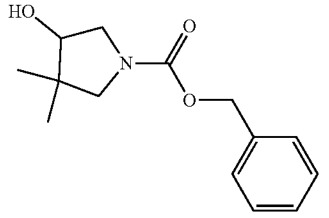 [SMILES: CC1(C)CN(C(=O)OCc2ccccc2)CC1O]

Benzylchloroformate (2.12 mL, 14.8 mmol) was added dropwise to a solution of intermediate 94 (1.8 g, 15.6 mmol) and NaOH (1M in $H_2O$) (16.4 mL, 16.4 mmol) in DCM (35 mL). The reaction mixture was then stirred ar rt for 20 h. DCM was added and the layers were separated and the aqueous layer was extracted with DCM (once). The organic layers were combined, dried over MgSO4, filtered and evaporated to give intermediate 95 (3.1 g, 80%).

Preparation of Intermediate 96

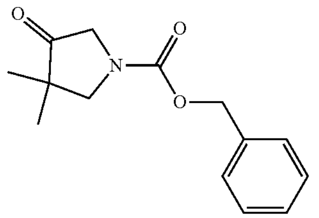 [SMILES: CC1(C)CN(C(=O)OCc2ccccc2)CC1=O]

To a mixture of intermediate 95 (3.1 g, 12.4 mmol) and TEA (8.8 mL, 63.4 mmol) in DMSO (11 mL) and DCM (50 mL) was added PYRIDINE SULFUR TRIOXIDE (48-50%) (7.9 g, 50 mmol) at rt and the resulting mixture was stirred at rt for 20 h. A saturated aq. solution of $NaHCO_3$ and DCM were added. The layers were separated and the aqueous layer was extracted with DCM (twice). The combined organic layers were dried over MgSO4, filtered and the solvent was removed in vacuo. The residue was purified by preparative LC (irregular SiOH 15-40 μm, 80 g Grace, liquid loading (DCM), mobile phase gradient: from Heptane/EtOAc: 100/0 to 20/80). The fractions containing product were combined to give intermediate 96 (1.46 g, 47%).

Example 38

Preparation of Intermediate 97

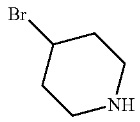

To a solution of 1-Boc-4-Bromopiperidine (15 g, 57 mmol) in DCM (15 mL), HCl 4N in dry Dioxane (35.5 mL, 142 mmol) was added and the mixture was stirred for 4 hr at rt. Diethylether was added, a solid precipitated. The mixture was stirred at rt for 30 min, then filtered, washed with ether and dried to give intermediate 97 (10.3 g, 91%, HCl salt)

Preparation of Intermediate 98

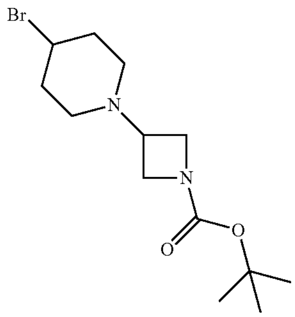 [SMILES: CC(C)(C)OC(=O)N1CC(N2CCC(Br)CC2)C1]

A solution of intermediate 97 (10 g, 51.4 mmol), N-Boc-3-oxoazetidine (11 g, 64.2 mmol) and TEA (7.1 mL, 51.4 mmol) in DCE (480 mL) was stirred at room temperature for 30 minutes. Sodium triacetoxyborohydride (16.4, 77 mmol) was then added and reaction continued for 3 hours. 1M $Na_2CO_3$ was added. The phases were separated. The aqueous layer was extracted with DCM. The combined organic layers were dried over MgSO4, filtered and evaporated in vacuo. The residue was purified by flash column chromatography (silice:AcOEt in heptane 0/100 to 100/0). The desired fractions were collected and concentrated in vacuo to afford intermediate 98 (15.8 g, 96 mmol).

Example A39

Preparation of Intermediate 99

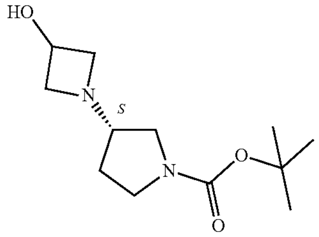

To a mixture of S-(−)-Boc-3-aminopyrrolidine (7.22 g; 38.75 mmol) and $Na_2CO_3$ (6.51 g; 77.49 mmol) in MeCN (77.4 mL), epichlorhydrin (5.08 mL; 1.18 g/mL; 46.50 mmol) was added and the mixture was stirred at 80° C. for 16 hours. The reaction mixture was basified with $NaHCO_3$ and extracted with EtOAc. The organic layer was washed with brine, dried over $MgSO_4$, filtered and evaporated under vacuum. The residue was purified by column chromatography over silica gel ($SiO_2$; DCM/MeOH) to afford the product (3.75 g; 40%).

The intermediates in the Table below were prepared by using an analogous method starting from the respective starting materials.

| compound number | Structure | Mass (mg | Yield (%) |
| --- | --- | --- | --- |
| Intermediate 100 | 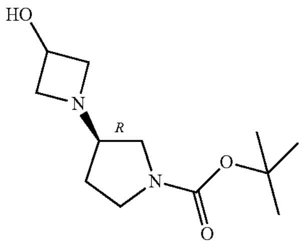 from R-(+)-Boc-3-aminopyrrolidine | 7253 | 42 |

Preparation of Intermediate 101

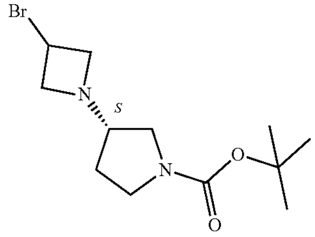

To a solution of intermediate 99 (3.62 g; 14.94 mmol) in THF (75 mL), PPh3 (11.76 g; 44.82 mmol) was added, then a solution of CBr4 (14.86 g; 44.82 mmol) in THF (75 mL) was drooped and the mixture was stirred at rt for 2 hours under nitrogen. A solution of NaHCO3 1M was added and the mixture was extracted with EtOAc. The organic layer was washed with water, dried over MgSO4, filtered and evaporated under vacuum. The residue was purified by column chromatography over silica gel ($SiO_2$; DCM/MeOH) to afford the product (3.43 g; 75%).

The intermediates in the Table below were prepared by using an analogous method starting from the respective starting materials.

| compound number | Structure | Mass (mg) | Yield (%) |
| --- | --- | --- | --- |
| Intermediate 102 | 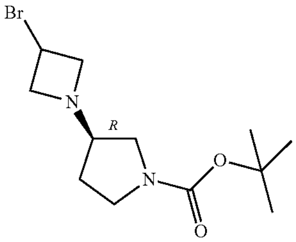 from intermediate 100 | 798 | 63 |

Preparation of Intermediate 99

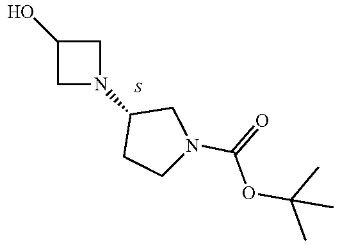

Sodium bicarbonate (135.3 g, 1610.7 mmol) was added to a solution of (S)-(−)-1-Boc-3-aminopyrrolidine (100.0 g, 536.9 mmol) in acetonitrile (1000 mL). Epichlorhydrin (59.6 g, 644.3 mmol) was added in small portions and the mixture was stirred at 90° C. overnight. The mixture was filtered and the filtrate was concentrated to give intermediate 99 (140.6 g, quant) as yellow oil.

Preparation of Intermediate 101

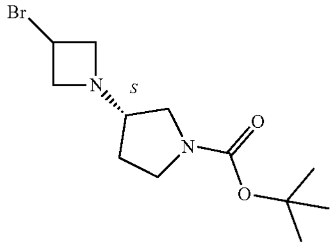

Triphenylphoshine (197.8 g, 754.3 mmol) and tetrabromomethane (250.2 g, 754.3 mmol) were successively added to a solution of intermediate 99 (140.6 g, 580.2 mmol) in THF (1500 mL). The reaction mixture was stirred at rt for 2 h, then filtered and the filtrate was concentrated. The residue was purified by silica gel column chromatography (gradient eluent: petroleum ether/ethyl acetate from 100/0 to 70/30). The pure fractions were collected and the solvent was evaporated under vacuum to give intermediate 101 (53.1 g, 30%).

Preparation of Intermediate 100

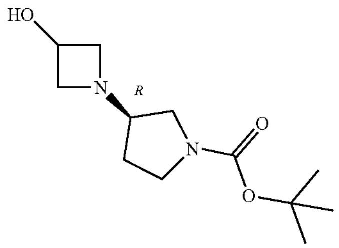

Sodium bicarbonate (162.4 g, 1932.9 mmol) was added to a solution of (R)-(+)-1-Boc-3-aminopyrrolidine (120.0 g, 644.3 mmol) in acetonitrile (1000 mL). Epichlorhydrin (71.5 g, 773.2 mmol) was added in small portions and the mixture was stirred at 90° C. overnight. The mixture was filtered and the filtrate was concentrated. The crude product was purified by silica gel chromatography (eluent: DCM/MeOH, from 100/0 to 80/20). The desired fractions were collected and the solvent was evaporated to give intermediate 100 (100.0 g, 64%) as yellow oil.

Preparation of Intermediate 102

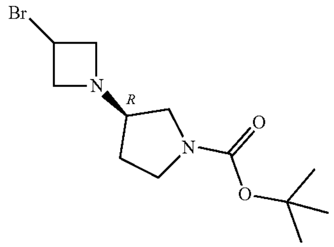

Triphenylphoshine (142.9 g, 544.8 mmol) and a solution of tetrabromomethane (180.7 g, 544.8 mmol) in THF (200 mL) were successively added to a solution of intermediate 100 (66.0 g, 272.4 mmol) in THF (1000 mL). The reaction mixture was stirred at rt for 2 h. The reaction mixture was diluted with ethyl acetate (500 mL) and the organic layer was washed with saturated aqueous $NaHCO_3$ (400 mL), water (3*300 mL) and brine (500 mL). The organic layer was concentrated, the crude product was purified by silica gel chromatography (eluent: petroleum ether/ethyl acetate, from 100/0 to 60/40). The desired fractions were collected and the solvent was evaporated to give intermediate 102 (43.0 g, 52%) as yellow oil.

Example A40

Preparation of Intermediate 103

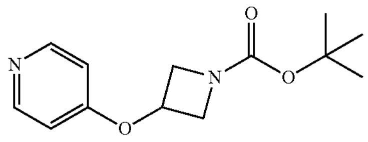 [SMILES: CC(C)(C)OC(=O)N1CC(Oc2ccncc2)C1]

To a solution of 4-hydroxypyridine (1.0 g, 11 mmol) in THF (35 mL) at rt were added 1-Boc-3-hydroxyazetidine (2.28 g, 13.1 mmol) and triphenylphosphine (3.45 g, 13.1 mmol). Then diisopropyl azodicarboxylate (2.6 mL, 13.1 mmol) was added dropwise and the mixture was heated at 55° C. for 16 h. The solvent was evaporated in vacuo. The resulting oil was taken up with a 1 M HCl aqueous solution. The acidic mixture was washed twice with DCM. The combined DCM washings were re-extracted with a 1 M HCl aqueous solution and water. The aqueous layer were combined, basified to pH~12 using a 1 M NaOH aqueous solution, and extracted with DCM three times. The organic extracts were washed with brine, dried over $MgSO_4$, filtered and concentrated in vacuo. The crude material was purified by preparative LC (irregular $SiO_2$ 40 μm, 40 g Buchi, liquid loading (DCM), mobile phase gradient: from DCM 99%, iPrOH 1% to DCM 85%, iPrOH 15%). The fractions containing product were combined and evaporated under vacuum to give intermediate 103 (2.25 g, 85%).

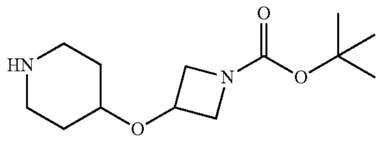 [SMILES: CC(C)(C)OC(=O)N1CC(OC2CCNCC2)C1]

Preparation of Intermediate 104

A solution of intermediate 103 (2.0 g, 8.0 mmol) in dry ethanol (44 mL) was degassed with $N_2$. Platinum (IV) dioxide (454 mg, 2.00 mmol) was added. The mixture was degassed again. p-Toluenesulfonic acid monohydrate (1.52 g, 8.00 mmol) was then added. The resulting mixture was degassed a third time and hydrogenated under an atmospheric pressure of $H_2$ at rt for 18 h. The mixture was poured into 50 mL of an ice cold 1 M NaOH aqueous solution, rinsed with a small volume of DCM, and filtered through a Celite® pad. The filtrate was concentrated in vacuo to remove ethanol, and the remaining aqueous solution was extracted with DCM three times. The combined organic extracts were washed with brine, dried over $MgSO_4$, filtered and concentrated in vacuo. The crude material was purified by preparative LC (irregular $SiO_2$ 40 μm, 40 g Buchi, liquid loading (DCM), mobile phase gradient: from DCM 90%, ($MeOH/NH_4OH$: 10/0.2) 10% to DCM 50%, ($MeOH/NH_4OH$: 10/0.2) 50%). The fractions containing product were combined and evaporated under vacuum to give intermediate 104 (1.65 g, 72%).

Example A41

Preparation of Intermediate 105

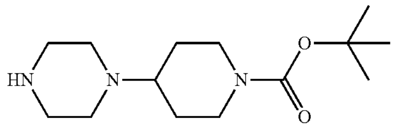 [SMILES: CC(C)(C)OC(=O)N1CCC(N2CCNCC2)CC1]

1-tert-butoxycarbonyl-4-hydroxypiperidine (7.83 g; 38.89 mmol) and TEA (8.11 mL; 0.728 g/mL; 58.34 mmol) was dissolved in MeCN (300 mL), and the mixture was stirred at rt for 10 minutes. Then methanesulfonyl chloride (3.31 mL; 1.48 g/mL; 42.78 mmol) was added in a water-ice bath, and the reaction was stirred at 0° C. for 1 hour. Piperazine (13.4 g; 155.57 mmol) and $K_2CO_3$ (21.50 g; 155.57 mmol) were added and the mixture was stirred at 80° C. for overnight. The reaction mixture was partitioned between EtOAc and sat. $NaHCO_3$ solution. The combined organic layers were dried over $MgSO_4$, filtered and concentrated under vacuum. The residue was purified by flash column chromatography over silica gel ($SiO_2$, DCM/MeOH) to afford the product (3.8 g; 36%).

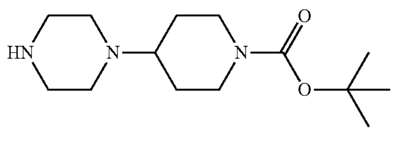 [SMILES: CC(C)(C)OC(=O)N1CCC(N2CCNCC2)CC1]

Preparation of Intermediate 105

1-tert-Butoxycarbonyl-4-hydroxypiperidine (7.83 g, 38.89 mmol) and triethylamine (8.11 mL, 58.34 mmol) were dissolved in acetonitrile (300 mL) and the mixture was stirred at rt for 10 min, then cooled to 0° C. Methanesulfonyl chloride (3.31 mL, 42.78 mmol) was added and the reaction was stirred at 0° C. for 1 h. Piperazine (13.4 g, 155.57 mmol) and potassium carbonate (21.5 g, 155.57 mmol) were added and the mixture was stirred at 80° C. for two days. The reaction mixture was partitioned between EtOAc and saturated aqueous $NaHCO_3$ solution. The combined organic layers were dried ($MgSO_4$), filtered and concentrated. Product was purified by flash chromatography (DCM-MeOH) Pure fractions were combined and concentrated to afford intermediate 105 (1.70 g, 16%).

Example A42

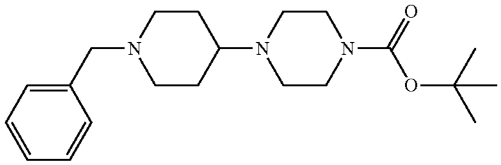 [SMILES: CC(C)(C)OC(=O)N1CCN(C2CCN(Cc3ccccc3)CC2)CC1]

Preparation of Intermediate 106

1-Benzyl-4-piperidone (7.1 g, 37.6 mmol) was added to a solution of 1-Boc-piperazine (7.0 g, 37.6 mmol) in THF (64 mL). The mixture was acidified with acetic acid (2.2 mL, 37.6 mmol) and the mixture was cooled at 0° C. Then, sodium triacetoxyborohydride (8.0 g, 37.6 mmol) was added portionwise and the mixture was stirred at rt for 16 h. The mixture was adjusted with aqueous potassium carbonate solution to pH 8. The organic phase was separated off, dried with $MgSO_4$ and concentrated in vacuo. The residue was purified by flash chromatography (silica; DCM-DCM/MeOH) to give intermediate 106 (9.4 g, 70%).

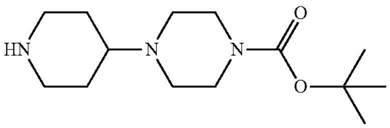 [SMILES: CC(C)(C)OC(=O)N1CCN(C2CCNCC2)CC1]

Preparation of Intermediate 107

Palladium hydroxide on carbon 20% (2.0 g, 2.8 mmol) was added to a solution of intermediate 106 (9.4 g, 26.2 mmol) in methanol (90 mL) under $N_2$, then purged with $H_2$ and the mixture was stirred for 72 h at rt under $H_2$. The mixture was filtered over a pad of celite, and the solvent was removed under reduced pressure to give intermediate 107 (7.2 g, quant).

Example A43

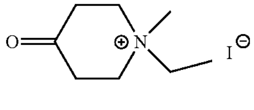

Preparation of Intermediate 108

To a solution of 1-methyl-4-piperidone (1.45 g, 12.82 mmol) in acetone (15 mL) was added ethyl iodide (2.4 g, 15.39 mmol) dropwise under $N_2$ atmosphere and the mixture was stirred at rt for 18 h. The mixture was filtered, washed with acetone then Et2O and dried to afford intermediate 108 (2.41 g, 70%).

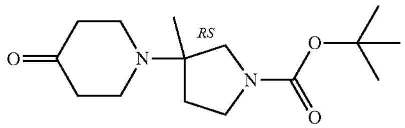 [SMILES: CC(C)(C)OC(=O)N1CCC(C)(N2CCC(=O)CC2)C1]

Preparation of Intermediate 109

A solution of intermediate 108 (2.1 g, 7.80 mmol) in water (5 mL) was added to a solution of tert-butyl 3-amino-3-methyl-pyrrolidine-1-carboxylate (781 mg, 3.90 mmol) and potassium carbonate (54 mg, 0.39 mmol) in ethanol (10 mL) at 80° C. The mixture was refluxed for 3 h. Water, $NH_4Cl$ and DCM were added. The organic layer was separated, dried over $MgSO_4$, filtered and evaporated. The residue was purified by preparative LC (Irregular $SiO_2$ 15-40 μm 40 g GraceResolv®, mobile phase: 100% DCM to 96% DCM, 4% MeOH (2% $NH_4OH$)) to afford intermediate 109 (600 mg, 54%).

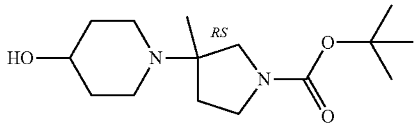 [SMILES: CC(C)(C)OC(=O)N1CCC(C)(N2CCC(O)CC2)C1]

Preparation of Intermediate 110

Sodium borohydride (161 mg, 4.25 mmol) was added to a solution of intermediate 109 (600 mg, 2.13 mmol) in methanol (7 mL) at rt. The mixture was stirred at rt for 3 h. Water, $NH_4Cl$ and DCM were added. The mixture was stirred at rt for 1 h, the organic layer was separated, dried over $MgSO_4$, filtered and evaporated to afford intermediate 110 (550 mg, 91%).

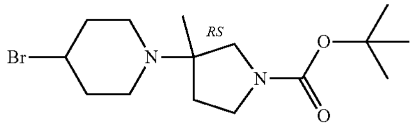 [SMILES: CC(C)(C)OC(=O)N1CCC(C)(N2CCC(Br)CC2)C1]

Preparation of Intermediate 111

Triphenylphosphine (1.522 g, 5.80 mmol) and a solution of tetrabromomethane (1.924 g, 5.802 mmol) in THF (4 mL) were successively added to a solution of intermediate 110 (550 mg, 1.93 mmol) in THF (20 mL). The mixture was stirred at rt for 4 h, then poured onto a saturated aqueous $NaHCO_3$ solution, extracted twice with DCM and dried over $MgSO_4$, filtered and evaporated to dryness. A purification was performed via preparative LC (Stationary phase: irregular $SiO_2$ 40 µm 24 g, Mobile phase: gradient from 100% Heptane to 50% Heptane, 50% AcOEt) to afford intermediate 111 (238 mg, 35%).

Example A44

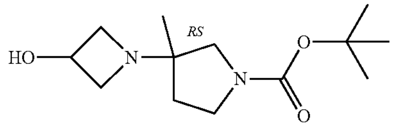 [SMILES: CC(C)(C)OC(=O)N1CCC(C)(N2CC(O)C2)C1]

Preparation of Intermediate 112

Epichlorhydrin (873 µL, 7.99 mmol) was added to a mixture of tert-butyl 3-amino-3-methyl-pyrrolidine-1-carboxylate (800 mg, 3.99 mmol) and sodium bicarbonate (1.007 g, 11.98 mmol) in acetonitrile (20 mL), and the mixture was stirred at 80° C. for 16 h. Epichlorhydrin (437 µL, 3.99 mmol) and sodium bicarbonate (336 mg, 3.99 mmol) were added and the mixture was stirred at 80° C. for 16 h more. Aqueous $Na_2CO_3$ was added until pH 8-9 and the aqueous layer was extracted with ethyl acetate. The organic phase was washed with brine, then dried over $MgSO_4$, filtered and evaporated to dryness. The crude was purified by flash column chromatography (eluting with a gradient of Methanol-dichloromethane) to afford intermediate 112 (499 mg, 49%).

Preparation of Intermediate 113

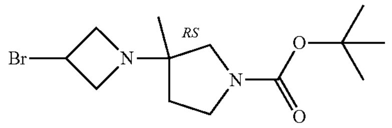 [SMILES: CC(C)(C)OC(=O)N1CCC(C)(N2CC(Br)C2)C1]

Triphenylphosphine (1.29 g, 4.92 mmol) was added to a solution of intermediate 112 (420 mg, 1.64 mmol) in THF (5 mL). A solution of tetrabromomethane (1.63 g, 4.92 mmol) in THF (5 mL) was added and the mixture was stirred overnight at rt. Aqueous $NaHCO_3$ was added and the aqueous layer was extracted with EtOAc. The organic layer was washed with water, dried over MgSO4, filtered and evaporated to dryness. The residue was purified by flash chromatography (AcOEt/Heptane) to give intermediate 113 (411 mg, 79%).

Example A45

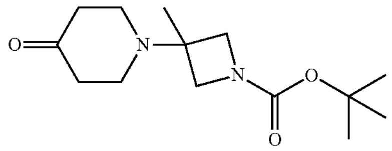 [SMILES: CC(C)(C)OC(=O)N1CC(C)(N2CCC(=O)CC2)C1]

Preparation of Intermediate 114

A solution of intermediate 108 (5.78 g, 21.48 mmol) in water (13 mL) was added to a solution of tert-Butyl 3-amino-3-methylazetidine-1-carboxylate (2.00 g, 10.74 mmol) and potassium carbonate (148 mg, 1.07 mmol) in ethanol (29 mL) at 80° C. The mixture was refluxed for 2 h. Water, $NH_4Cl$ and DCM were added. The organic layer was separated, dried over $MgSO_4$, filtered and evaporated. The residue was purified by preparative LC (Irregular $SiO_2$ 15-40 µm 80 g GraceResolv®, mobile phase: 100% DCM to 96% DCM, 4% MeOH (2% $NH_4OH$)) to give intermediate 114 (910 mg, 32%).

Preparation of Intermediate 115

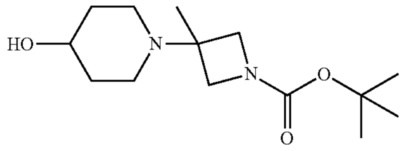 [SMILES: CC(C)(C)OC(=O)N1CC(C)(N2CCC(O)CC2)C1]

Sodium borohydride (451 mg, 11.92 mmol) was added portionwise to a stirred solution of intermediate 114 (1600 mg, 5.96 mmol) in methanol (20 mL) at 5° C. The mixture was stirred at rt for 3 h. Water, $NH_4Cl$ and DCM were added. The mixture was stirred at rt for 1 h, the organic layer was separated, dried over $MgSO_4$, filtered and evaporated to give intermediate 115 (1.39 g, 86%).

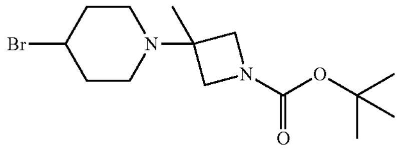 [SMILES: CC(C)(C)OC(=O)N1CC(C)(N2CCC(Br)CC2)C1]

Preparation of Intermediate 116

Triphenylphosphine (4.05 g, 15.42 mmol) and a solution of tetrabromomethane (5.12 g, 15.42 mmol) in THF (10 mL) were successively added to a solution of intermediate 115 (1.39 g, 5.14 mmol) in THF (50 mL). The mixture was stirred at rt for 4 h, then poured onto a saturated aqueous $NaHCO_3$ solution, extracted twice with DCM and dried over $MgSO_4$, filtered and evaporated to dryness. A purification was performed via preparative LC (Stationary phase: irregular $SiO_2$ 40 µm 120 g, Mobile phase: gradient from 100% Heptane to 50% Heptane, 50% EtOAc) to give intermediate 116 (1.15 g, 67%).

Example A46

Preparation of Intermediate 117

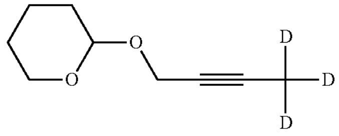 [SMILES: [2H]C([2H])([2H])C#CCOC1CCCCO1]

n-BuLi (1.6M in hexane) (14 mL, 22.4 mmol) was added to a solution of tetrahydro-2-(2-propynyloxy)-2H-pyran (3.0 mL, 21.3 mmol) in THF (43 mL) at −78° C. After being stirred for 10 min, the reaction mixture was warmed to 0° C. and iodomethane-$D_3$ (1.5 mL, 24 mmol) was added. The reaction mixture was allowed to warm to room temperature overnight. The reaction was then quenched by the addition of sat. aqueous $NH_4Cl$ solution. The layers were separated and the aqueous layer was extracted with DCM three times. The combined organic layers were dried over MgSO4, filtered, concentrated under vacuum. The crude was purified by preparative LC (irregular SiOH 40 μm, 80 g Buchi, liquid loading (heptane), mobile phase gradient: from heptane 100%, EtOAc 0% to Heptane 80%, EtOAc 20%). The fractions containing product were combined and evaporated under vacuum to give intermediate 117 (2.79 g, 83%).

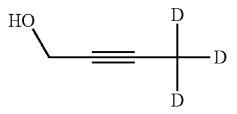

Preparation of Intermediate 118

To a solution of the intermediate 117 (2.79 g, 17.8 mmol) in MeOH (17 mL) was added TPSA,H2O (338 mg, 1.8 mmol) and the reaction mixture was stirred for 18 h. $K2CO_3$ (245 mg, 1.8 mmol) was added and the resulting suspension was stirred at rt for 30 min, then the mixture was filtered over ®Celite, concentrated. The crude was purified by preparative LC (irregular SiOH 15-40 μm, 40 g Buchi, dry load (Celite), mobile phase gradient: from Pentane/Et2O 90/10 to 60/40). The fractions containing product were evaporated to give intermediate 118 (717 mg, 55%) as a colourless oil.

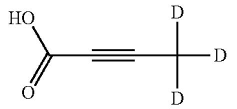

Preparation of Intermediate 119: 0 D

To a solution of copper(I) chloride (15 mg, 0.15 mmol) in ACN (6 mL) and intermediate 118 (220 mg, 3.01 mmol) was slowly added tert-butyl hydroperoxide solution 70% in water (2.1 mL, 15 mmol). The resulting mixture was stirred at rt for 18 h Water was added, the pH of the reaction mixture was adjusted to 8.0-8.5 with saturated aq $NaHCO_3$. The aqueous layer was then extracted with Et2O twice. The aqueous layer was acidified to pH 2.0 using 1 N HCl and extracted 4 times with Et2O. The combined organic layer was dried over MgSO4, filtered and concentrated under vacuum to give intermediate 119 (108 mg, 41%).

Example A47

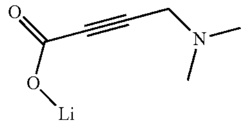

Preparation of Intermediate 120

A solution of 1-dimethylamino-2-propyne (1.00 g, 12.0 mmol) and n-BuLi (1.6M in hexane) (8.3 mL, 13.2 mmol) in THF (21 mL) was kept in a carboglace/acetone bath. After 1 h at −78° C., dry $CO_2$* was bubbled in reaction mixture for 18 h. The reaction mixture was diluted with water then washed with EtOAc. The aqueous layer was evaporated. The residue was dissolved in MeOH and the insoluble salts were removed via filtration. The filtrate was evaporated to give intermediate 120 (1.7 g, quant).

dry $CO_2$ was obtained by bubbling through $H_2SO_4$ before bubbling in to the reaction mixture.

The intermediates in the Table below were prepared by using an analogous method starting from the respective starting materials.

| Intermediate number | Structure | Mass (mg) | Yield (%) |
|---|---|---|---|
| Intermediate 121 | 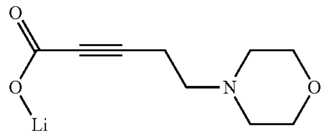 From 4-(but-3-yn-1-yl)morpholine | 1900 | 85 |
| Intermediate 122 | 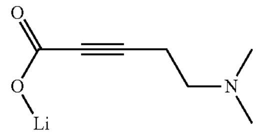 From (but-3-yn-1-yl)dimethylamine | 1900 | 85 |

Example A48

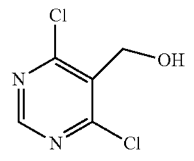

Preparation of Intermediate 123

To a solution of 4,6-dichloropyrimidine-5-carbaldehyde (80 g; 452 mmol) in THF (100 mL) at −78° C. was added dropwise over 30 mins a solution of diisobutyl aluminium hydride (1.0 M solution in toluene; 587.6 mL; 587.6 mmol). The mixture was stirred for 2 hours at −78° C. A saturated aqueous solution of Rochelle's salt (800 mL) was added and the dry ice/acetone bath was removed. The reaction mixture was allowed to warm to room temperature and stirred overnight. The mixture was extracted with $CH_2Cl_2$ (4×1000 mL), the organic layers were combined, dried over $Na_2SO_4$, filtered, and the filtrate was concentrated under reduced pressure to give product as yellow solid (63.8 g; 79%). The product was used in the next step without any further purification.

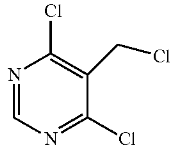

Preparation of Intermediate 124

At 0° C. thionyl chloride (7.62 mL; 105.02 mmol) was added dropwise to a solution of intermediate 123 (4.70 g; 26.25 mmol) in DCM (130 mL). The reaction was allowed to warm to rt overnight. After evaporation under reduce pressure, the solid residue was purified by flash chromatography on a silica gel column using a mixture of cyclohexane/EtOAc (7/3) as eluant to give the title compound as a white solid (4.57 g, 87%).

Example A49

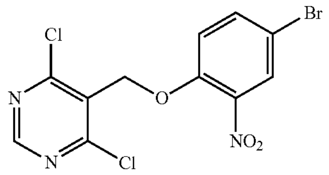 [SMILES: O=[N+]([O-])c1cc(Br)ccc1OCc1c(Cl)ncnc1Cl]

Preparation of Intermediate 125

At 0° C. under nitrogen atmosphere, intermediate 123 (20 g; 111.73 mmol) then triphenylphosphine (35.16 g; 134.075 mmol) was added to a solution of 4-bromo-2-nitrophenol (24.35 g; 111.73 mmol) in THF (400 mL). Diisopropyl azodicarboxylate (27.11 g; 134.08 mmol) was added dropwise. The mixture was allowed to warm to room temperature and stirred overnight. The mixture was evaporated to give the crude product as yellow oil, which was purified by flash column chromatography over silica gel (eluent: petroleum ether/ethyl acetate from 100/0 to 50/50). The desired fractions were combined and the solvent was concentrated to dryness in vacuo to give intermediate 125 as yellow solid (45 g; >100%). The product was used in the next step without any further purification.

The intermediates in the Table below were prepared by using an analogous method starting from the respective starting materials.

| Intermediate number | Structure | Mass (mg) | Yield (%) |
|---|---|---|---|
| Intermediate 126 | 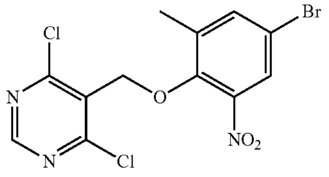 [SMILES: Cc1cc(Br)cc([N+](=O)[O-])c1OCc1c(Cl)ncnc1Cl] from intermediate 123 and 4-bromo-2-methyl-6-nitrophenol | 14300 | 93 |

-continued

| Intermediate number | Structure | Mass (mg) | Yield (%) |
|---|---|---|---|
| Intermediate 127 | 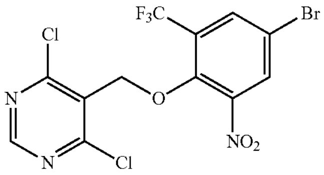 [SMILES: O=[N+]([O-])c1cc(Br)cc(C(F)(F)F)c1OCc1c(Cl)ncnc1Cl] from intermediate 123 and 4-bromo-2-nitro-6-(trifluoromethyl)phenol | 4260 | 57 |
| Intermediate 128 | 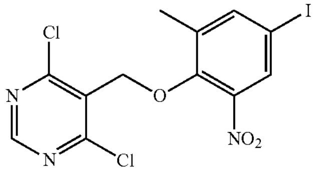 [SMILES: Cc1cc(I)cc([N+](=O)[O-])c1OCc1c(Cl)ncnc1Cl] from intermediate 123 and 4-iodo-2-methyl-6-nitrophenol | 50000 | >100 |
| Intermediate 129 | 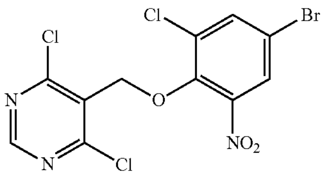 from intermediate 123 and 4-bromo-2-chloro-6-nitrophenol | 4650 | 37 |

Example A50

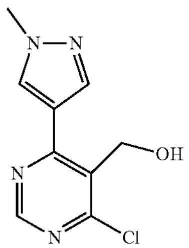

Preparation of Intermediate 130

To a solution of intermediate 123 (17 g; 94.97 mmol) in 1,4-dioxane (500 mL) were added $Na_2CO_3$ (119 mL; 2 mol/L; 238 mmol) and 1-methylpyrazole-4-boronic acid pinacol ester (20.52 g; 98.60 mmol) under $N_2$ and stirred at rt for 10 minutes. Then tetrakis(triphenylphosphine)palladium(0) (7.86 g; 6.80 mmol) was added and the reaction mixture was heated to 140° C. and stirred for 1 hour. After cooling, the mixture was concentrated under vacuum. The residue was purified by column chromatography on silica gel ($SiO_2$; petroleum ether/EtOAc from 100/0 to 40/60) to afford the product (23 g; quant.) as a white solid.

Example A51

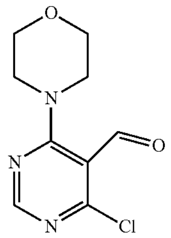

Preparation of Intermediate 131

4,6-Dichloropyrimidine-5-carboxaldehyde (30 g; 169.50 mmol) was suspended in DCM (250 mL) and TEA (24.74 mL; 0728 g/mL; 177.98 mmol) was added. The dissolution was cooled in bath-ice to 0° C. Morpholine (14.77 g; 169.51 mmol) dissolved in DCM (50 mL) was added dropwise. The reaction mixture was allowed to warm to RT and then stirred for 20 hours. 1M $Na_2CO_3$ was added and the phases separated. The combined organic layers were dried over $MgSO_4$, filtered and evaporated in vacuo. The residue was purified by flash chromatography ($SiO_2$; heptane/EtOAc from 100/0 to 50/50) to afford the product (19.8 g; 87%).

Example A52

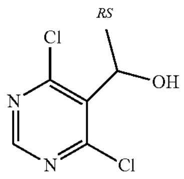

Preparation of Intermediate 132

4,6-dichloropyrimidine-5-carbaldehyde (30 g; 169.5 mmol) was dissolved in THF (500 mL) and the reaction mixture cooled at 0° C. under nitrogen. Methyl magnesium bromide (1.4 M in THF/toluene (⅓); 145.3 mL; 203.4 mmol) was added dropwise at 0° C. and the reaction mixture was stirred at 0° C. for 10 minutes and then at room temperature for 30 minutes. Further (0.1 eq) methyl magnesium bromide (1.4 M in THF/toluene (⅓); 12.1 mL; 16.94 mmol) was added and mixture was stirred overnight. A mixture of water and acetic acid (220 mmol) was added and the mixture was extracted with ethyl acetate. The organic layers were washed with water and brine, dried with $MgSO_4$, filtered and evaporated. The crude was purified by flash chromatography ($SiO_2$, Ethylacetate-heptane gradient). Fractions containing the pure product were combined and evaporated in vacuo to afford the product (21.0 g; 64%).

The intermediates in the Table below were prepared by using an analogous method starting from the respective starting materials.

| Intermediate number | Structure | Mass (mg) | Yield (%) |
|---|---|---|---|
| Intermediate 133 | 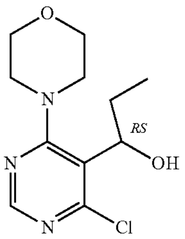 [SMILES: CCC(O)c1c(Cl)ncnc1N1CCOCC1] from intermediate 131 and ethyl magnesium bromide (3 M in diethylether) | 5670 | 83 |

Preparation of Intermediate 134

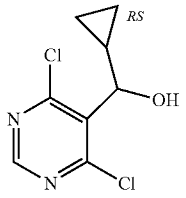 [SMILES: OC(c1c(Cl)ncnc1Cl)C1CC1]

4,6-dichloropyrimidine-5-carbaldehyde (2.5 g; 13.7 mmol) was dissolved in THF (55 mL) and the reaction mixture cooled at −5° C. under nitrogen. Cyclopropyl magnesium bromide (0.5 M in THF; 27.4 mL; 13.7 mmol) was added dropwise at −5° C. and the reaction mixture was stirred at −5° C. for 1 hr before being allowed to reach room temperature over 1 hr. The reaction mixture was partitioned between EtOAc and sat. $NH_4Cl$(aq) solution. The combined organic layers were dried ($MgSO_4$), filtered and concentrated in vacuo. The product was purified by flash chromatography (silica; EtOAc/heptane gradient from 0/100 to 70/30). The desired fractions were combined and concentrated in vacuo to afford the product as a transparent oil (1.12 g; 36%).

Example A53

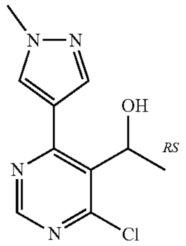 [SMILES: CC(O)c1c(Cl)ncnc1-c1cnn(C)c1]

Preparation of Intermediate 135

To a solution of intermediate 132 (42 g, 218 mmol) in THF (800 mL) and water (80 mL) was added 1-methylpyrazole-4-boronic acid pinacol ester (45.3 g, 218 mmol) and sodium carbonate (27.7 g, 261 mmol). Bis(triphenylphosphine)palladium(II) dichloride was added under N2 atmosphere. The mixture was heated to 60° C. and stirred overnight. The mixture was filtered through Celite, rinsed with ethyl acetate (500 mL).

The filtrate was evaporated in vacuum to give a yellow oil (100 g). The crude compound was purified by column chromatography over silica gel (eluent: Petroleum ether/ethyl acetate=100/0-0/100). The desired fractions were evaporated in vacuum to give intermediate 135 as a yellow solid (19 g, 37%).

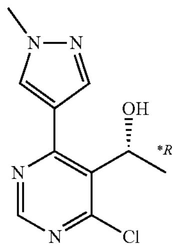

and

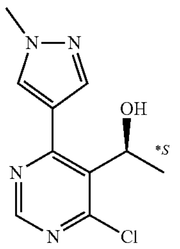

Preparation of Intermediate 136 and Intermediate 137

Chiral separation on 3 g scale: A purification was performed via chiral SFC (Stationary phase: Chiralpak IG 5 μm 250*20 mm, Mobile phase: 75% CO2, 25% mixture of EtOH/DCM 80/20 v/v) to give intermediate 136 (1.5 g) and intermediate 137 (1.5 g)

Example A54

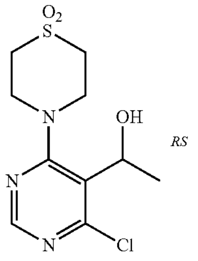 [SMILES: CC(O)c1c(Cl)ncnc1N1CCS(=O)(=O)CC1]

Preparation of Intermediate 138

A light brown suspension of intermediate 132 (55.5 g, 287 mmol), thiomorpholine-1,1-dioxide (38.9 g, 287.5 mmol) and $Et_3N$ (120 mL, 863 mmol) in Et2O (500 mL) was stirred at 50° C. for 16 h. The mixture was concentrated to give a yellow solid. Water (400 mL) and MTBE (300 mL) were added. The mixture was stirred at room temperature for 30 min. The solid was filtered off and dried to afford a light yellow solid. This was combined with the test reaction done on 2 g scale of intermediate 132 to afford the intermediate 138 (58 g; 69%).

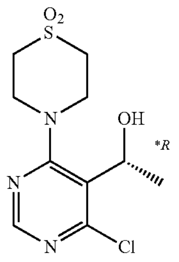

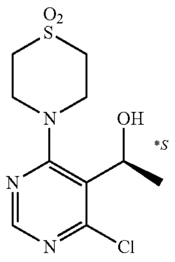

Preparation of Intermediate 139 and Intermediate 140

A separation (on 6 g scale) was performed on intermediate 138 via chiral SFC (Stationary phase: CHIRALPAK AS-H 5 μm 250*20 mm, Mobile phase: 60% CO2, 40% EtOH) to give intermediate 139 (2.9 g, 48%) and intermediate 140 (2.95 g, 49%)

Identification of Absolute Configurations of Intermediate 139 and Intermediate 140 Via VCD Spectroscopic Technique:

intermediate 139 was determined to be the R enantiomer namely intermediate 660 (check EE purity by SFC (RT: 0.68, 1.00, Area %: 100.00, 0.00, MW: 291, BPM1: 292, BPM2:290, Method::UPCC_AS3_ ETOH_NEAT_30_6MIN))

intermediate 140 was determined to be the S enantiomer namely intermediate 661 (check EE purity (RT: 0.68, 0.99, Area %: 0.16, 99.84, MW: 291, BPM1: 292, BPM2: 290, Method::UPCC_AS3_ ETOH_NEAT_30_6MIN))

Example A55

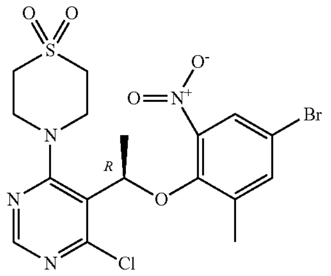

Preparation of Intermediate 662

Intermediate 660 (200 mg; 0.69 mmol), 5-bromo-2-fluoro-3-nitrotoluene (241 mg; 1.03 mmol) and $K2CO_3$ (190 mg; 1.37 mmol) in DMSO (1 mL). The reaction mixture was stirred at rt for 18 h. The mixture was poured onto water and DCM. The mixture was extracted with DCM (3×). The organic layer was combined, dried over MgSO4, filtered and the solvent was evaporated to give 405 mg of orange oil. The residue was purified by chromatography over silica gel ($SiO_2$, Buchi, 24 g, eluent: from 90% heptane, 10% EtOAc to 30% heptane, 70% EtOAc). The pure fractions were collected and the solvent was evaporated to give intermediate 662 (195 mg, 45%).

The intermediate in the Table below was prepared by using an analogous method starting from the respective starting materials.

| Intermediate number | Structure | Mass (mg) | Yield (%) |
|---|---|---|---|
| Intermediate 663 | 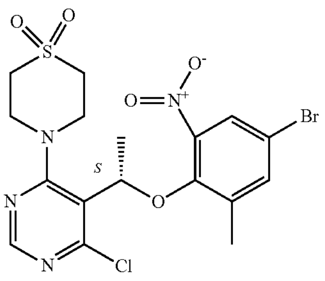 from intermediate 661 | 246 | 57 Pure at 81% |

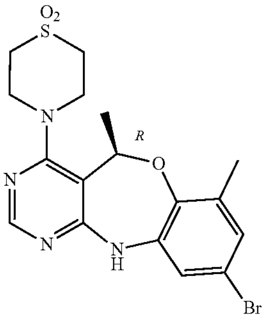

Preparation of Intermediate 664

Iron (86 mg, 1.54 mmol) was added to mixture of intermediate 662 (195 mg; 0.31 mmol) and ammonium chloride (168 mg; 3.15 mmol) in THF (1.3 mL), MeOH (1.3 mL) and water (0.8 mL). The reaction mixture was stirred at 90° C. for 12 h. After cooling down to rt, the mixture was diluted with DCM, filtered through Chromabond® and the filtrate was evaporated to give 182 mg of yellow oil. The residue was purified by chromatography over silica gel (SiO2, Buchi, 4 g, eluent: from 100% DCM to 98% DCM, 2% MeOH, 0.2% $NH_4OH$). The pure fractions were collected and the solvent was evaporated to give intermediate 664 (110 mg, 81%).

The intermediate in the Table below was prepared by using an analogous method starting from the respective starting materials.

| Intermediate number | Structure | Mass (mg) | Yield (%) |
|---|---|---|---|
| Intermediate 665 | 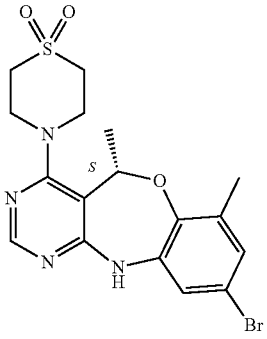 from intermediate 663 | 229 | quantitative |

Example A56

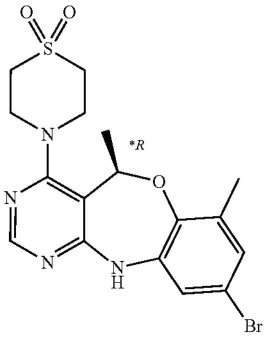

Preparation of Intermediate 667

620 mg SiO2 35-70 μm was added to a solution of intermediate 259 (100 mg; 0.19 mmol) in toluene (7.9 mL) at rt. The reaction mixture was stirred at reflux (111° C.) overnight. After cooling down to rt, $SiO_2$ was filtered off, washed with DCM/MeOH 50/50 and the filtrate was evaporated to give intermediate 667 (81 mg, quant), which was shown to be identical to intermediate 664.

The intermediate in the Table below was prepared by using an analogous method starting from the respective starting materials.

| Intermediate number | Structure | Mass (mg) | Yield (%) |
|---|---|---|---|
| Intermediate 668 | 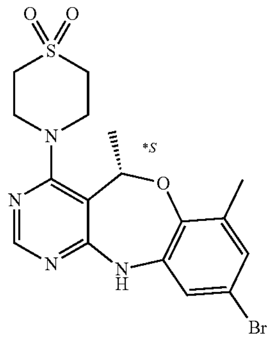 from intermediate 260, which was shown to be identical to intermediate 665 | 81 | quantitative |

Analytical Data

| Intermediate number | Structure | OR | SFC |
|---|---|---|---|
| Intermediate 664 | 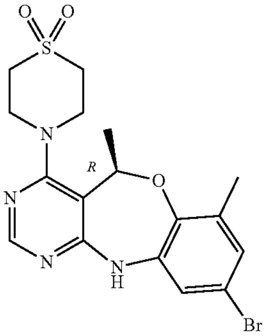 | −48° (589 nm, c 0.25 w/v %, DMF, 20° C.) | check EE purity (RT: 1.63, 1.98, Area %: 0.00, 100.00, MW: 438, BPM1: 439, Method: :UPCC_IC3_ETOH_40_3MIN) |
| Intermediate 665 | 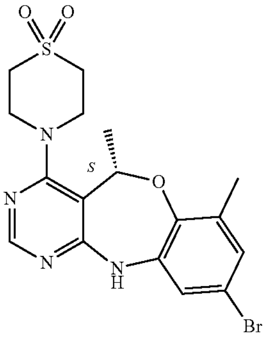 | +41.29° (589 nm, c 0.31 w/v %, DMF, 20° C.) | check EE purity (RT: 179, 2.16, Area %: 100.00, 0.00, MW: 438, BPM1: 439, Method: :UPCC_IC3_ETOH_40_3MIN) |
| Intermediate 667 | 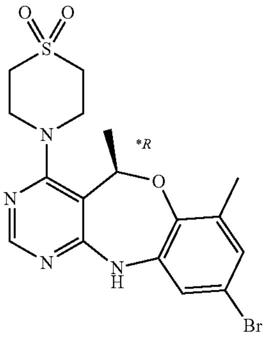 | | Check EE purity (RT: 1.63, 1.97, Area %: 0.84, 99.16, MW: 438, BPM1: 439, Method: :UPCC_IC3_ETOH_40_3MIN) |

-continued

| Intermediate number | Structure | OR | SFC |
| --- | --- | --- | --- |
| Intermediate 668 | 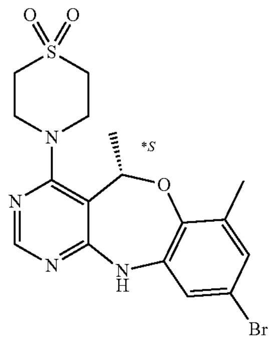 | | RT: 1.63, 1.97, Area %: 98.33, 1.67, MW: 438, BPM1: 439, Method: :UPCC_IC3_ETOH_403_MIN) |

Example A57

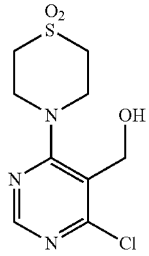

Preparation of Intermediate 141

A solution of intermediate 123 (30 g, 168 mmol), thiomorpholine 1,1-dioxide (23.3 g, 173 mmol) and TEA (50.9 g, 503 mmol) in THF (300 mL) was stirred at 90° C. overnight. The crude compound was evaporated, taken up into EtOAc (300 mL) and stirred for 1 hour. The mixture was filtered. The filter cake poured into H2O (300 mL) and stirred for 1 hour. The mixture was filtered and the filter cake was dried to give intermediate 141 (38.3 g, 79%, purity 960%) as a white solid.

Example A58

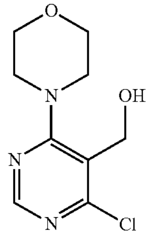

Preparation of Intermediate 142

Sodium borohydride (1.5 g, 40 mmol) was added portionwise at 0° C. to a solution of 4-chloro-6-(morpholin-4-yl)pyrimidine-5-carboxaldehyde [54503-94-5] (6.55 g, 29 mmol) in MeOH (71 mL) and the reaction mixture was stirred at room temperature for 2 hours. The reaction mixture was partitioned between EtOAc and brine. The combined organic layers were dried with MgSO4, filtered and concentrated.

The crude of reaction was purified by flash chromatography (Heptano/Ethyl acetate 0-100%). The desired fractions were collected and concentrated in vacuo to intermediate 142 (5.6 g, 84%)

Example A59

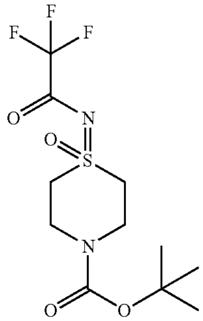 [SMILES: CC(C)(C)OC(=O)N1CCS(=O)(=NC(=O)C(F)(F)F)CC1]

Preparation of Intermediate 143

(Diacetoxyiodo)benzene (57.3 g, 178 mmol) was added to a solution of 4-thiomorpholinecarboxylic acid, 1,1-dimethylethyl ester, 1-oxide [278788-74-2] (26 g, 119 mmol), trifluoroacetamide (20.1 g, 178 mmol), magnesium oxide (19.1 g, 474 mmol) and Rhodium(II) acetate dimer (2.62 g, 11.9 mmol) in DCM (300 mL). The reaction mixture was stirred at rt overnight. The reaction mixture was filtered through a pad of Celite. The filtrate was concentrated under vacuum to give crude product.

The crude product was purified by column chromatography over silica gel (petroleum ether/ethyl acetate=100:0 to petroleum ether/ethyl acetate=30:70) The desired fractions were collected and the solvent was evaporated under vacuum to give intermediate 143 (36 g, 92%) as a white solid.

Preparation of Intermediate 144

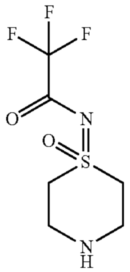

TFA (200 mL) was added to a solution of intermediate 143 (36 g, 109 mmol) in DCM (300 mL). The mixture was stirred at rt overnight. The solvent was concentrated under vacuum to give intermediate 144 (38 g, quantitative) as a yellow oil.

Preparation of Intermediate 145

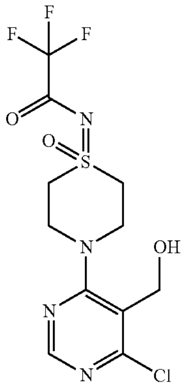 [SMILES: O=C(N=S1(=O)CCN(c2ncnc(Cl)c2CO)CC1)C(F)(F)F]

TEA (48.7 mL, 351 mmol) was added to a solution of intermediate 144 (38 g, 110 mmol) in DCM (400 mL). intermediate 123 (18 g, 100 mmol) was added to the reaction mixture. The reaction mixture was stirred at 50° C. for 48 h.

Water (500 mL) was added and the reaction mixture was extracted with DCM (800 mL*3). The combined organic layer was dried over Mg2SO4 and concentrated in vacuo to give the crude product. The crude product was washed with CH2Cl2 (100 mL*2) to afford intermediate 145 (22 g, 57%) as a white solid.

Example A60

Preparation of Intermediate 146

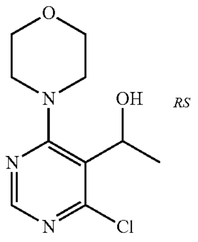 [SMILES: CC(O)c1c(Cl)ncnc1N1CCOCC1]

Under a nitrogen atmosphere, 4-chloro-6-(morpholin-4-yl)pyrimidine-5-carboxaldehyde (15 g, 65 mmol) was dissolved in THF (200 mL), then cooled to −78° C., then methylmagnesium bromide solution 3.0 M in diethyl ether (43.5 mL, 130.5 mmol) was added dropwise. The reaction mixture was stirred at −78° C. for 1.5 hours. The mixture was quenched with sat. $NH_4Cl$(aq) solution and combined with another batch from 1.5 g of 4-chloro-6-(morpholin-4-yl)pyrimidine-5-carboxaldehyde. The combined experiments were extracted with ethyl acetate (300 mL*2). The organic layers were dried with $Na_2SO_4$, filtered and concentrated to give 15 g of a white solid. Methyl tert-butyl ether (25 mL) was added to the residue. The mixture was stirred at room temperature for 20 min and the insoluble was filtered off and dried under vacuum to give intermediate 146 (12.3 g; 70%) as a white solid.

Preparation of Intermediate 147 and Intermediate 148

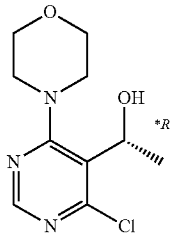

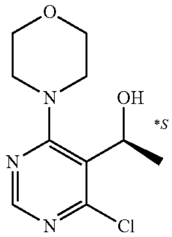

A separation was performed of intermediate 146 via chiral SFC (Stationary phase: Lux Cellulose-2 5 μm 250*30 mm, Mobile phase: 85% CO2, 15% EtOH) to give intermediate 147 (3 g; 25%) and intermediate 148 (3.1 g; 26%).

Example A61

Preparation of Intermediate 149

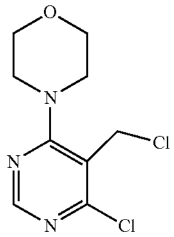 [SMILES: ClCc1c(Cl)ncnc1N1CCOCC1]

Intermediate 142 (560 mg; 2.44 mmol) was dissolved in DCM (6 mL) at 0° C. and $SOCl_2$ (265 μL; 1.64 g/mL; 3.66 mmol) was slowly added. The reaction mixture was stirred at rt for 3 hours. The solvents were removed in vacuo. The residue was partitioned between DCM and brine. The combined organic layers were dried over $MgSO_4$, filtered and concentrated to afford the product (605 mg; quant.).

The intermediates in the Table below were prepared by using an analogous method starting from the respective starting materials.

| Intermediate number | Structure | Mass (mg) | Yield (%) |
|---|---|---|---|
| Intermediate 150 | 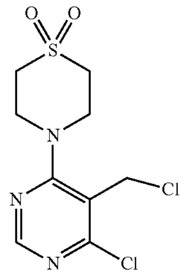 [SMILES: O=S1(=O)CCN(c2ncnc(Cl)c2CCl)CC1] from intermediate 151a | 4530 | 76 |

Example A62

Preparation of Intermediate 151

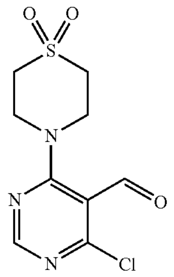 [SMILES: O=Cc1c(Cl)ncnc1N1CCS(=O)(=O)CC1]

Triethylamine (21.4 mL, 154.3 mmol) was added to a suspension of 4,6-dichloropyrimidine-5-carbaldehyde (26.0 g, 146.9 mmol) in DCM (390 mL). The mixture was cooled to 0° C. and thiomorpholine N,N-dioxide (19.9 g, 146.9 mmol) was added portionwise. The reaction mixture was allowed to warm to rt and then stirred for 5 h. A 1 M aqueous solution of $Na_2CO_3$ was added and the phases separated. The aqueous layer was extracted with DCM. The combined organic layers were dried over MgSO4, filtered and evaporated in vacuo. The residue was purified by flash chromatography (silica; DCM-DCM/MeOH) to give intermediate 151 (18.0 g, 44%).

Preparation of Intermediate 151a

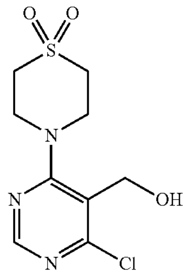 [SMILES: O=S1(=O)CCN(c2ncnc(Cl)c2CO)CC1]

Sodium borohydride (3.46 g, 91.4 mmol) was added portionwise to a solution of intermediate 151 (18.0 g, 65.29 mmol) in methanol (175 mL) at 0° C. and the reaction mixture was stirred at rt for 16 h. The reaction mixture was partitioned between EtOAc and brine, and the aqueous layer was extracted with DCM. The combined organic layers were dried (MgSO4), filtered and concentrated to give intermediate 151a (14.4 g, 79%).

Preparation of Intermediate 150

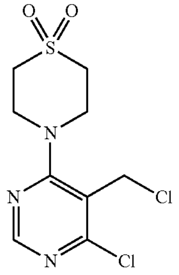 [SMILES: O=S1(=O)CCN(c2ncnc(Cl)c2CCl)CC1]

Thionyl chloride was slowly added to a solution of intermediate 151a (7.2 g, 25.9 mmol) in DCM (70 mL) at 0° C. The mixture was stirred overnight at rt. Heptane was added and the mixture was stirred for 5 min, then the mixture was filtered and the solid was dried under vacuum to afford intermediate 150 (7.7 g, quant).

Example A63

Preparation of Intermediate 152

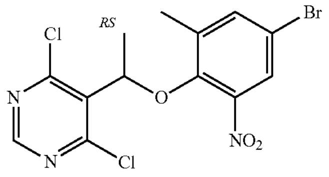 [SMILES: Cc1cc(Br)cc([N+](=O)[O-])c1OC(C)c1c(Cl)ncnc1Cl]

Under a nitrogen atmosphere, intermediate 132 (20.5 g; 106.2 mmol), triphenylphosphine (39 g; 148.7 mmol) and 4-bromo-2-methyl-6-nitrophenol (24.6 g; 106.2 mmol) were mixed in THF (300 mL). Diisopropyl azodicarboxylate (29.3 mL; 148.7 mmol) was added dropwise and the reaction mixture stirred at RT for 1 hour. The mixture was evaporated and the crude product dry-loaded with silica onto a column for purification by flash chromatography (SiO2; 40% EtOAt/heptane). The desired fractions were combined and concentrated to afford the product (30.1 g; 69%).

The intermediates in the Table below were prepared by using an analogous method starting from the respective starting materials.

| Intermediate number | Structure | Mass (mg) | Yield (%) |
|---|---|---|---|
| Intermediate 153 | 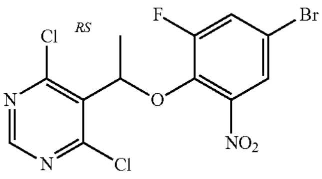 [SMILES: CC(Oc1c(F)cc(Br)cc1[N+](=O)[O-])c1c(Cl)ncnc1Cl] from intermediate 132 and 4-bromo-2-fluoro-6-nitrophenol | 12200 | 57 |

-continued

| Intermediate number | Structure | Mass (mg) | Yield (%) |
|---|---|---|---|
| Intermediate 154 | 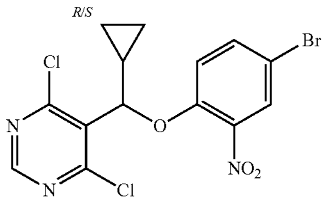 [SMILES: O=[N+]([O-])c1cc(Br)ccc1OC(c1c(Cl)ncnc1Cl)C1CC1] from intermediate 134 and 4-bromo-2-nitrophenol | 135 | 25 |
| Intermediate 155 | 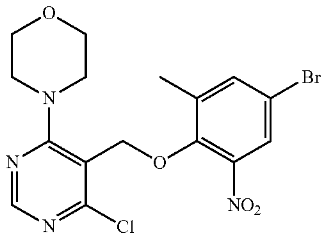 [SMILES: Cc1cc(Br)cc([N+](=O)[O-])c1OCc1c(Cl)ncnc1N1CCOCC1] from intermediate 142 and 4-Bromo-2-methyl-6-nitrophenol; using di-tert-butyl azodicarboxylate | 2110 | 30 |
| Intermediate 156 | 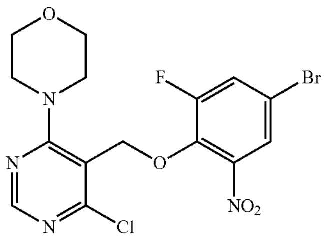 [SMILES: O=[N+]([O-])c1cc(Br)cc(F)c1OCc1c(Cl)ncnc1N1CCOCC1] from intermediate 142 and 4-Bromo-2-fluoro-6-nitrophenol | 11600 | 57 |

-continued

| Intermediate number | Structure | Mass (mg) | Yield (%) |
|---|---|---|---|
| Intermediate 157 | 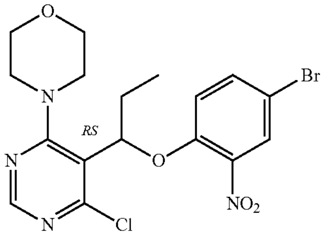 [SMILES: CCC(Oc1ccc(Br)cc1[N+](=O)[O-])c1c(Cl)ncnc1N1CCOCC1] from intermediate 133 and 4-Bromo-2-nitrophenol | 7635 | 82 |

Example A64

Preparation of Intermediate 158

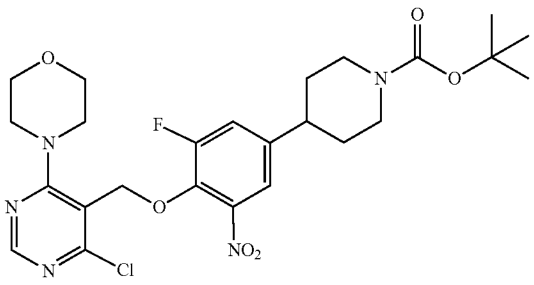

To a solution of intermediate 142 (0.877 g, 3.82 mmol), intermediate 4 (1.3 g, 3.82 mmol) and $PPh_3$ (1.503 g, 5.729 mmol) in THF (10.9 mL) at 0-5° C. under $N_2$ was added dropwise DIAD (1.115 mL, 1.039 g/mL, 5.729 mmol). The resulting solution was stirred at 0-5° C. for 30 minutes. Volatiles were removed under reduced pressure and the residue was purified by column chromatography ($SiO_2$; from 90% Heptane—10% EtOAc to 40% Heptane—600% EtOAc) to afford the product (1.89 g; 90%).

The intermediates in the Table below were prepared by using an analogous method starting from the respective starting materials.

| compound number | Structure | Mass (mg) | Yield (%) |
|---|---|---|---|
| Intermediate 159 | 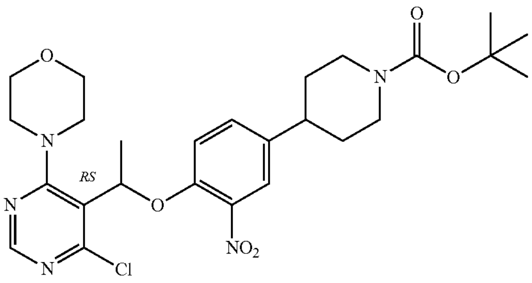 [SMILES: CC(Oc1ccc(C2CCN(C(=O)OC(C)(C)C)CC2)cc1[N+](=O)[O-])c1c(Cl)ncnc1N1CCOCC1] from intermediate 5 and intermediate 146 | 1750 | 78 |

-continued

| compound number | Structure | Mass (mg) | Yield (%) |
|---|---|---|---|
| Intermediate 160 | 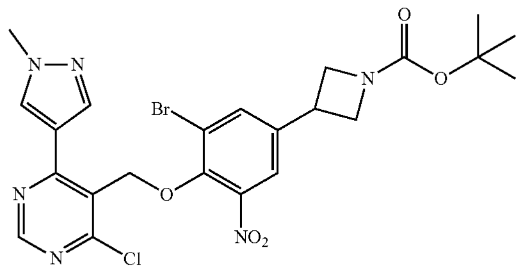 [SMILES: Cn1cc(-c2ncnc(Cl)c2COc2c(Br)cc(C3CN(C(=O)OC(C)(C)C)C3)cc2[N+](=O)[O-])cn1] from intermediate 130 and intermediate 52 | 3090 | quant. |
| Intermediate 161 | 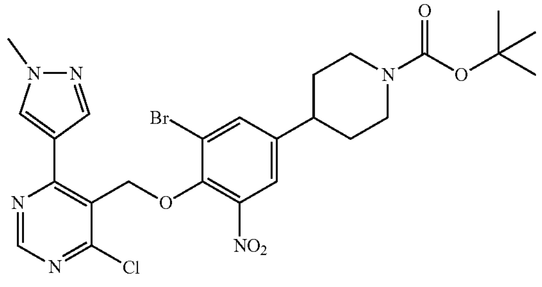 [SMILES: Cn1cc(-c2ncnc(Cl)c2COc2c(Br)cc(C3CCN(C(=O)OC(C)(C)C)CC3)cc2[N+](=O)[O-])cn1] from intermediate 130 and intermediate 55 | 2000 | 44 |
| Intermediate 162 | 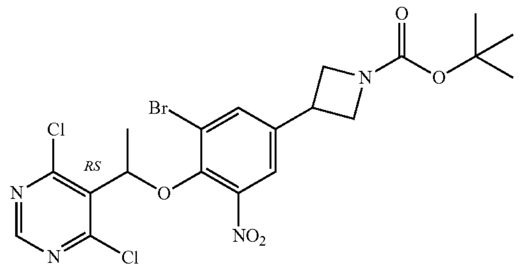 [SMILES: CC(Oc1c(Br)cc(C2CN(C(=O)OC(C)(C)C)C2)cc1[N+](=O)[O-])c1c(Cl)ncnc1Cl] from intermediate 132 and intermediate 52 | 2580 | 78 |

Preparation of Intermediate 163

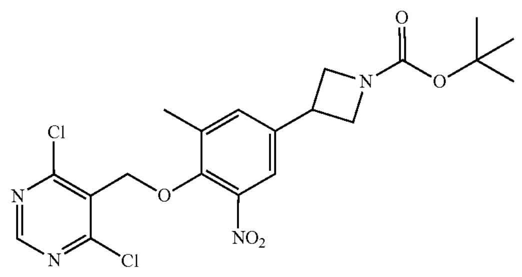 [SMILES: Cc1cc(C2CN(C(=O)OC(C)(C)C)C2)cc([N+](=O)[O-])c1OCc1c(Cl)ncnc1Cl]

Diisopropyl azodicarboxylate (86.2 mL, 435.19 mmol) was added to a solution of intermediate 123 (40.9 g, 228.47 mmol), intermediate 54 (67.09 g, 217.59 mmol) and triphenylphosphine (62.78 g, 239.35 mmol) in THF (650 mL) at 0° C. The mixture was stirred at rt for 16 h, then concentrated to give a brown oil, which was diluted with petroleum ether/ethyl acetate (2.5/1) (1190 mL) and stirred for 0.5 h. Yellow precipitate was filtered off and washed with petroleum ether/ethyl acetate (2.5/1) (350 mL), then treated with ethanol (100 mL) and stirred for 5 min. The mixture was filtered. The solid was washed with ethanol (30 mL) and dried under high vacuum to give intermediate 163 (97 g, 95%) as a light yellow solid.

Preparation of Intermediate 164

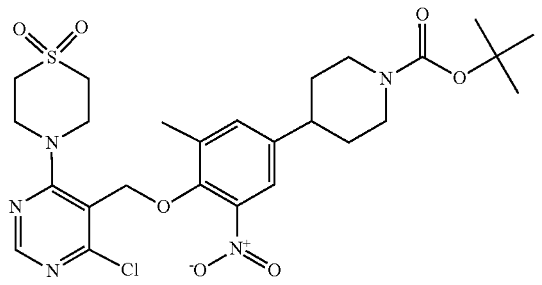

Diisopropyl azodicarboxylate (31 mL, 1.039 g/mL, 159 mmol) was added dropwise to a stirred solution of intermediate 53 (35.8 g, 106.3 mmol), intermediate 151a (31 g, 111.6 mmol) and triphenylphosphine (41.8 g, 159.5 mmol) in THF (796 mL) at rt. The reaction was stirred at et for 3 h. The volatiles were evaporated. A purification was performed via preparative LC solid deposit (Stationary phase: irregular SiOH 15-40 m 2× 750 g Grace, Mobile phase: gradient from 100% DCM to 9500 DCM, 5% MeOH, 0.50% $NH_4OH$). The pure fractions were combined and the solvent was evaporated to give 51 g of expected compound. It was crystallized from CH3CN, filtered, rinsed with dipe and dried to give intermediate 164 (27.9 g, yield 44%).

The intermediates in the Table below were prepared by using an analogous method starting from the respective starting materials.

| Intermediate number | Structure | Mass (mg) | Yield (%) |
|---|---|---|---|
| Intermediate 165 | 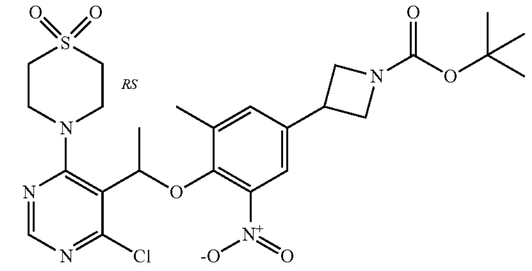 from intermediate 54 and intermediate 138 | 2340 | 92 (70% pure) |
| Intermediate 166 | 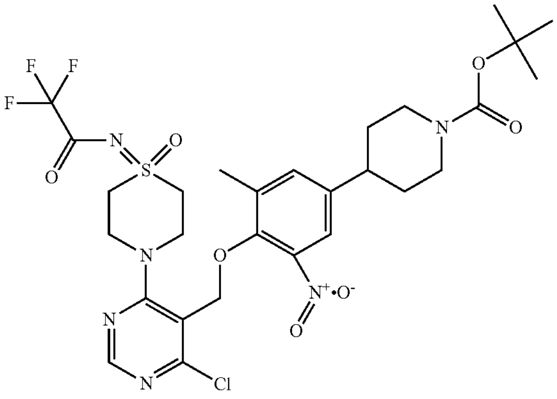 from intermediate 145 and intermediate 53 for 15', rt | 2470 | 85 |
| Intermediate 167 | 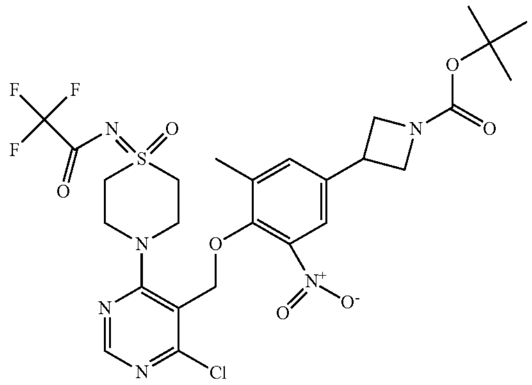 [SMILES: Cc1cc(C2CN(C(=O)OC(C)(C)C)C2)cc([N+](=O)[O-])c1OCc1c(Cl)ncnc1N1CCS(=O)(=NC(=O)C(F)(F)F)CC1] from intermediate 145 and intermediate 54 for 15', rt | 3360 | 63 |

-continued
| Intermediate number | Structure | Mass (mg) | Yield (%) |
| --- | --- | --- | --- |
| Intermediate 168 | 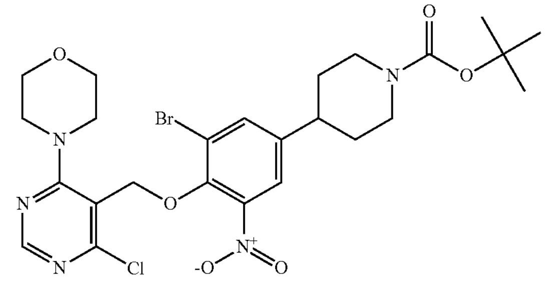 from intermediate 55 and intermediate 142 o.n, rt | 2000 | 44 |
| Intermediate 169 | 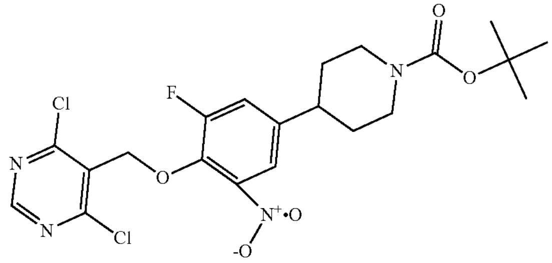 from intermediate 123 and intermediate 4; 0° C., then rt overnight | 255 | 22 |
| Intermediate 170 | 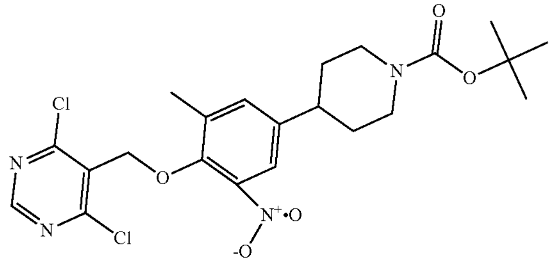 from intermediate 123 and intermediate 53 0° C., for 1 h | 7050 | 57 |
| Intermediate 171 | 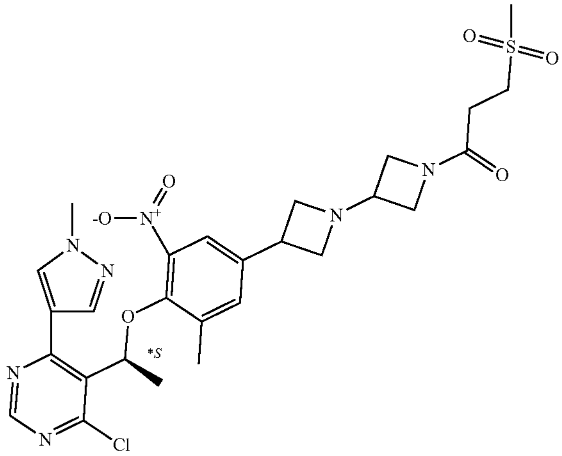 from intermediate 136 and intermediate 59 rt, 12 h | 222 | 42 |

-continued
| Intermediate number | Structure | Mass (mg) | Yield (%) |
|---|---|---|---|
| Intermediate 172 | 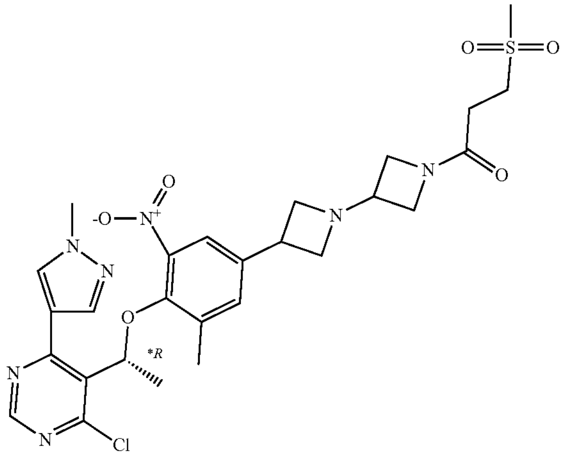 from intermediate 137 and intermediate 59 rt, 12 h | 96 | 18 |
| Intermediate 173 | 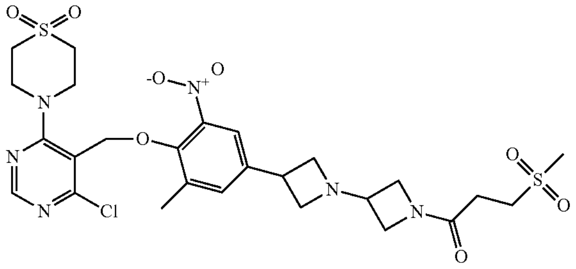 from intermediate 151a and intermediate 59 rt, 12 h | 260 | 68 |
| Intermediate 174 | 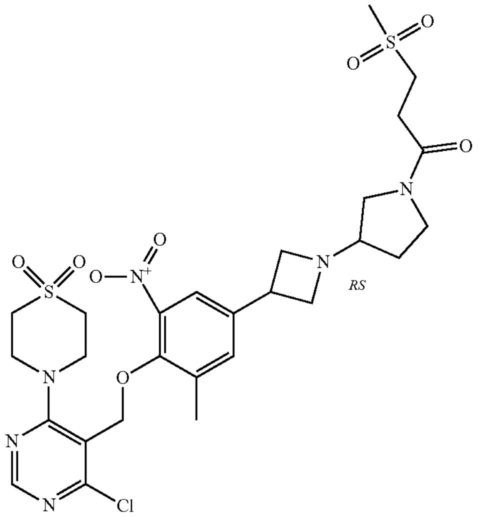 from intermediate 151a and intermediate 60 rt, 3 h | 1670 | 36 |

-continued
| Intermediate number | Structure | Mass (mg) | Yield (%) |
|---|---|---|---|
| Intermediate 175 | 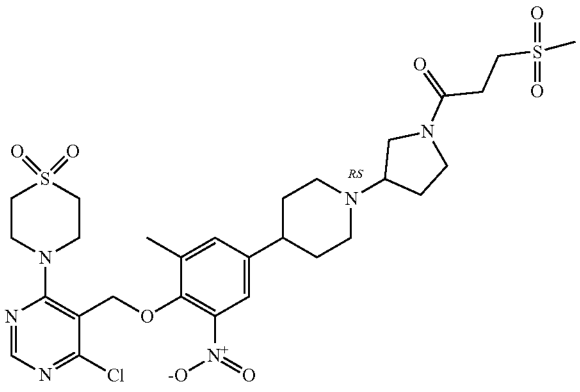 from intermediate 151a and intermediate 61 rt, 3 h | 5060 | 54 |
| Intermediate 176 | 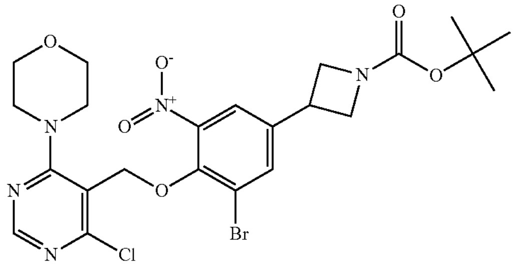 [SMILES: CC(C)(C)OC(=O)N1CC(c2cc(Br)c(OCc3c(Cl)ncnc3N3CCOCC3)c([N+](=O)[O-])c2)C1] from intermediate 142 and intermediate 52 rt, 2 d | 5200 | 95 |
| Intermediate 669 | 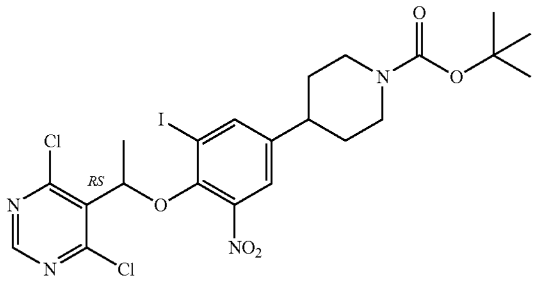 [SMILES: CC(Oc1c(I)cc(C2CCN(C(=O)OC(C)(C)C)CC2)cc1[N+](=O)[O-])c1c(Cl)ncnc1Cl] from intermediate 132 and intermediate 655 | 6500 | 75 |
| Intermediate 670 | 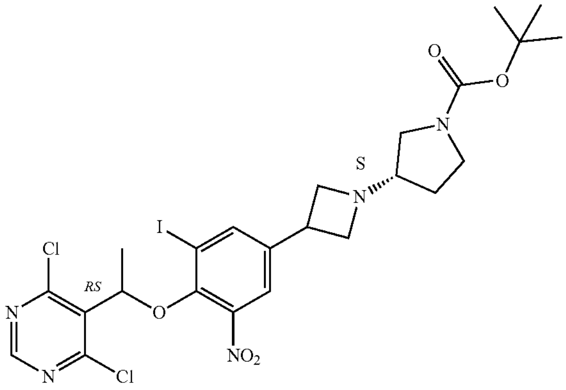 from intermediate 132 and intermediate 659 | 5200 | 43 |

Preparation of Intermediate 177 and Intermediate 178

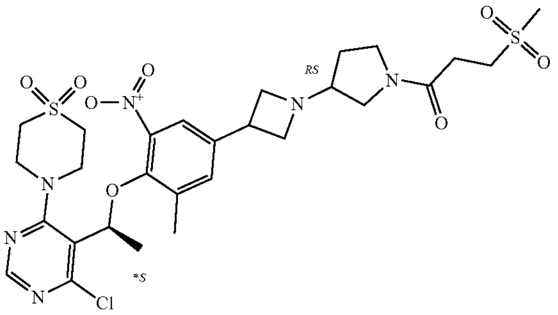

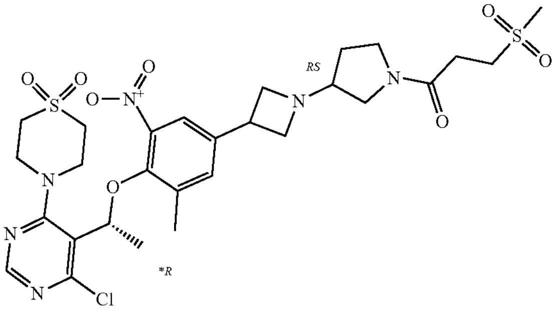

From intermediate 139: Diisopropyl azodicarboxylate (0.46 mL, 2.34 mmol) was added dropwise to a stirred solution of intermediate 60 (712 mg, 1.56 mmol), intermediate 139 (500 mg, 1.71 mmol) and triphenylphosphine (613 mg, 2.34 mmol) in THF (11.7 mL, 143 mmol) at rt. The reaction was stirred at rt for 3 h. DCM and water were added. The organic layer was separated, dried over MgSO4, filtered and evaporated. A purification was performed via preparative LC (Stationary phase: irregular SiOH 15-40 μm 120 g Grace, Mobile phase: gradient from 100% DCM to 90% DCM, 10% MeOH (2% $NH_4OH$)). The purest fractions were combined and the solvent was evaporated. A purification was performed via reverse phase (solid deposit) (Stationary phase: YMC-DispoPack AT ODS-25:40 g, Mobile phase: gradient from 90% HCCONH3 0.2% in water, 10% ACN to 50% HCCONH3 0.2% in water, 50% ACN). The pure fractions were combined and the solvent was evaporated to give a mixture of intermediate 177 and intermediate 178 (total 550 mg).

A chiral purification was performed via Prep SFC (Stationary phase: Chiralcel Diacel OJ 20×250 mm, Mobile phase: CO2, MeOH+0.4 iPrNH2) to afford intermediate 178 (97 mg; 9%) and intermediate 177 (280 mg; 26%).

From intermediate 140: Diisopropyl azodicarboxylate (0.46 mL, 2.34 mmol) was added dropwise to a stirred solution of intermediate 60 (712 mg, 1.56 mmol), intermediate 140 (500 mg, 1.71 mmol) and triphenylphosphine (613 mg, 2.34 mmol) in THF (11.7 mL, 143 mmol) at rt. The reaction was stirred at rt for 3 h. DCM and water were added. The organic layer was separated, dried over MgSO4, filtered and evaporated. A purification was performed via preparative LC (Stationary phase: irregular SiOH 15-40 μm 120 g Grace, Mobile phase: gradient from 100% DCM to 90% DCM, 10% MeOH (2% NH4OH)). The purest fractions were combined and the solvent was evaporated. A purification was performed via reverse phase (solid deposit) (Stationary phase: YMC-DispoPack AT ODS-25:40 g, Mobile phase: gradient from 90% HCCONH3 0.2% in water, 10% ACN to 50% HCCONH3 0.2% in water, 50% ACN). The pure fractions were combined and the solvent was evaporated to give a mixture of intermediate 177 and intermediate 178 (380 mg). A chiral purification was performed via Prep SFC (Stationary phase: Chiralcel Diacel OJ 20×250 mm, Mobile phase: CO2, MeOH+0.4 iPrNH2) to afford intermediate 178 (222 mg; 21%) and intermediate 177 (80 mg; 7%).

Preparation of Intermediate 179

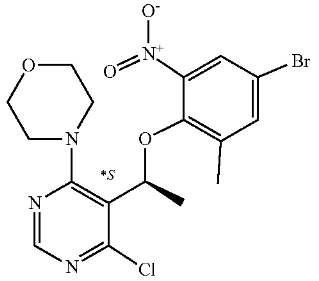 [SMILES: Cc1cc(Br)cc([N+](=O)[O-])c1O[C@@H](C)c1c(Cl)ncnc1N1CCOCC1]

To a solution of intermediate 148 (1.6 g, 6.566 mmol) and 5-bromo-2-fluoro-3-nitrotoluene (2.31 g, 9.9 mmol) in THF (19 mL) at rt under nitrogen, lithium bis(trimethylsilyl) amide (9.9 mL, 1 M, 9.9 mmol) was added and the mixture was stirred at reflux for 15 hr. The reaction mixture was quenched with $NH_4Cl$ solution and diluted with DCM. Layers were separated, the organic layer was washed with brine. The aqueous layers were reextracted with ethylacetate. The combined organic layers were concentrated under vacuum. A purification was performed via preparative LC (Stationary phase: irregular SiOH 35-70 μm 80 g, Mobile phase: gradient from 100% DCM to 97% DCM, 3% MeOH (2% NH4OH)). The pure fractions were collected and the solvent was evaporated to give intermediate 179 (2.25 g, yield 75%)

Example A65

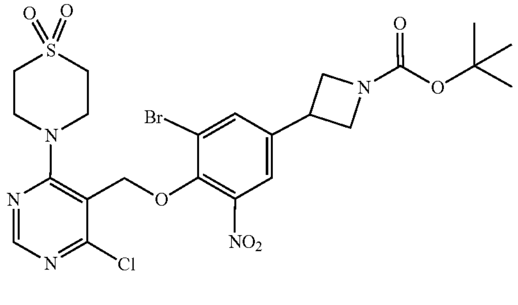 [SMILES: CC(C)(C)OC(=O)N1CC(c2cc(Br)c(OCc3c(Cl)ncnc3N3CCS(=O)(=O)CC3)c([N+](=O)[O-])c2)C1]

Preparation of Intermediate 180

To a suspension of intermediate 52 (2.1 g; 5.627 mmol) in DMF (125 mL), $K_2CO_3$ (1.56 g; 11.25 mmol) was added. Then intermediate 150 (2 g; 6.752 mmol) was added and the mixture was stirred at rt for overnight. The reaction mixture was diluted with EtOAc and washed with brine. The organic layer was concentrated and dried under high vacuum to afford the product (3.56 g; quant.) which was used in the next step without further purification.

Preparation of Intermediate 181

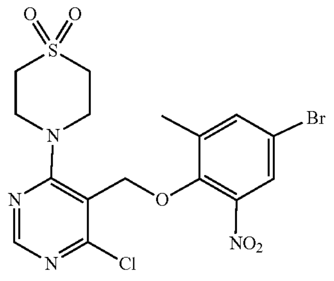 [SMILES: Cc1cc(Br)cc([N+](=O)[O-])c1OCc1c(Cl)ncnc1N1CCS(=O)(=O)CC1]

Intermediate 150 (3.6 g, 12.2 mmol) was added to a suspension of 4-bromo-2-methyl-6-nitrophenol (2.4 g, 10.1 mmol) and potassium carbonate (2.8 g, 20.3 mmol) in DMF (45 mL). The mixture was stirred at rt overnight, then diluted with ethyl acetate. The organic layer was washed with brine (5 times). The organic layer was concentrated and dried under high vacuum to give intermediate 181 (4.3 g, 86%).

Example A66

Preparation of Intermediate 182

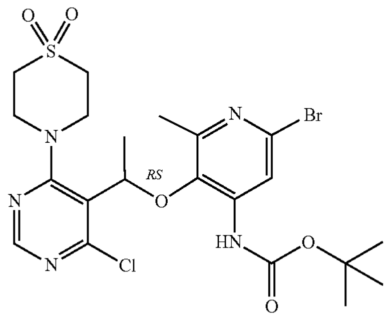 [SMILES: Cc1nc(Br)cc(NC(=O)OC(C)(C)C)c1OC(C)c1c(Cl)ncnc1N1CCS(=O)(=O)CC1]

The reaction was performed on four batches (13.71 mmol and 3*17.14 mmol), which were combined for purification.

Diisopropyl azodicarboxylate (4.5 mL, 22.85 mmol) and triphenylphosphine (5.99 g, 22.85 mmol) were mixed in THF (55 mL) under nitrogen at 0° C. When a solid precipitated, intermediate 138 (5.0 g, 17.14 mmol) was added and after 5 min intermediate 16 (3.46 g, 11.43 mmol) was added. The reaction mixture was stirred at rt for 16 h. Saturated aqueous $NaHCO_3$ was added and the mixture was extracted with ethyl acetate. The organic layer was dried over $MgSO_4$, concentrated, combined with the 3 other batches and purified by flash chromatography (Hexane:DCM (9:1)-ethyl acetate gradient) to afford intermediate 182 (18.69 g, 50%).

Example A67

Preparation of Intermediate 183

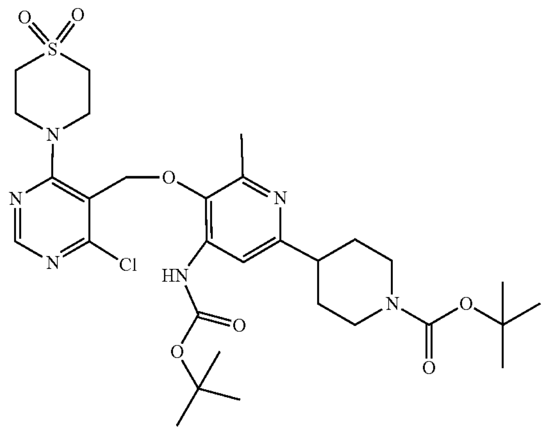 [SMILES: Cc1nc(C2CCN(C(=O)OC(C)(C)C)CC2)cc(NC(=O)OC(C)(C)C)c1OCc1c(Cl)ncnc1N1CCS(=O)(=O)CC1]

Under a nitrogen atmosphere, intermediate 45 (1.4 g; 3.44 mmol), triphenylphosphine (1.80 g; 6.87 mmol) and intermediate 151a (954 mg; 3.44 mmol) were mixed in THF (50 mL). Diisopropyl azodicarboxylate (1.38 mL; 1.027 g/mL; 6.87 mmol) was added dropwise and the reaction mixture stirred at RT for 20 hours. The mixture was evaporated and the crude product dry-loaded with silica onto a column for purification by flash chromatography ($SiO_2$; Hexane-DCM/EtOAc) to afford the product (1.46 g; 57%).

The intermediates in the Table below were prepared by using an analogous method starting from the respective starting materials.

| compound number | Structure | Mass (mg) | Yield (%) |
|---|---|---|---|
| Intermediate 184 | 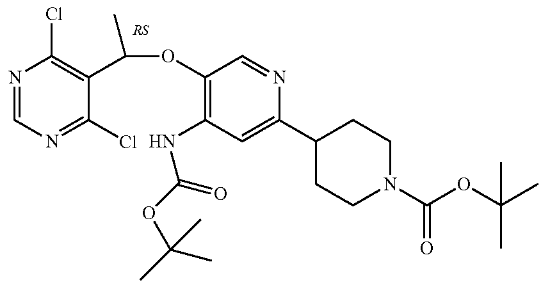 [SMILES: CC(Oc1cnc(C2CCN(C(=O)OC(C)(C)C)CC2)cc1NC(=O)OC(C)(C)C)c1c(Cl)ncnc1Cl] from intermediate 132 and intermediate 40 | 545 | 32 |

-continued

| compound number | Structure | Mass (mg) | Yield (%) |
|---|---|---|---|
| Intermediate 185 | 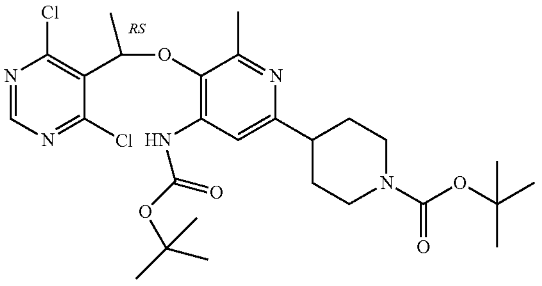 [SMILES: Cc1nc(C2CCN(C(=O)OC(C)(C)C)CC2)cc(NC(=O)OC(C)(C)C)c1OC(C)c1c(Cl)ncnc1Cl] from intermediate 132 and intermediate 45 | 1837 | 43 |

Example A68

Preparation of Intermediate 186

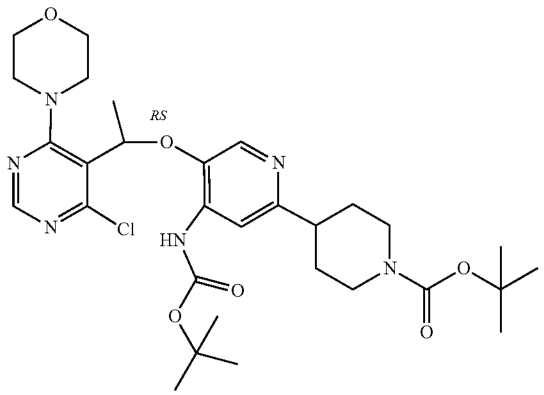 [SMILES: CC(Oc1cnc(C2CCN(C(=O)OC(C)(C)C)CC2)cc1NC(=O)OC(C)(C)C)c1c(Cl)ncnc1N1CCOCC1]

To a solution of intermediate 184 (545 mg; 0.959 mmol) in DCM (20 mL), TEA (0.2 mL; 0.728 g/mL; 1.44 mmol) followed by morpholine (125 mg; 1.44 mmol) were added. The mixture was stirred at rt for 20 hours. The mixture was diluted with DCM and washed with brine. The organic layer was dried over $MgSO_4$, filtered and concentrated under vacuum. The residue was purified by column chromatography over silica gel (SiO2; from 95% Heptane—5% EtOAc to 10% Heptane—90% EtOAc) to afford the product (350 mg; 59%).

The intermediates in the Table below were prepared by using an analogous method starting from the respective starting materials.

| compound number | Structure | Mass (mg) | Yield (%) |
|---|---|---|---|
| Intermediate 187 | 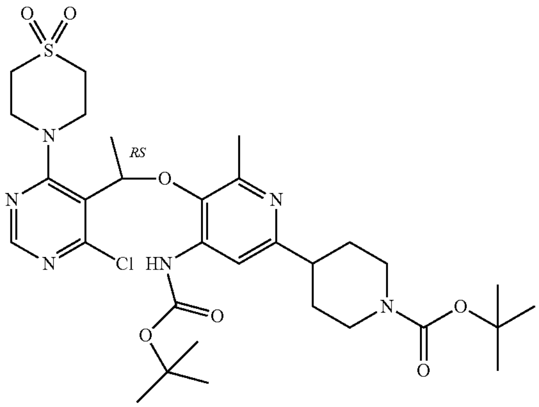 [SMILES: Cc1nc(C2CCN(C(=O)OC(C)(C)C)CC2)cc(NC(=O)OC(C)(C)C)c1OC(C)c1c(Cl)ncnc1N1CCS(=O)(=O)CC1] from intermediate 185 and Thiomorpholine 1,1-Dioxide | 669 | 32 |

Example A69

Preparation of Intermediate 188

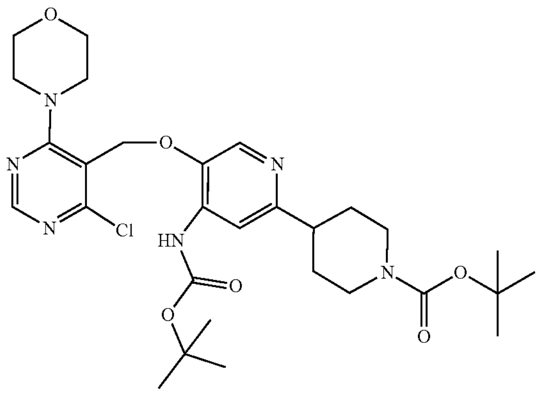 [SMILES: CC(C)(C)OC(=O)Nc1cc(C2CCN(C(=O)OC(C)(C)C)CC2)ncc1OCc1c(Cl)ncnc1N1CCOCC1]

To a solution of intermediate 149 (605 mg; 2.44 mmol) and intermediate 40 (960 mg; 2.44 mmol) in DMF (15 mL), $K_2CO_3$ (674 mg; 0.88 mmol) was added. The reaction mixture was stirred at 60° C. under N2 for 20 hours. The reaction mixture was partitioned between EtOAc and brine. The organic layer was dried over $MgSO_4$, filtered and concentrated in vacuo. The residue was purified by column chromatography ($SiO_2$; Heptane/EtOAc) to afford the product (880 mg; 58%) as a white solid.

The intermediates in the Table below were prepared by using an analogous method starting from the respective starting materials.

| compound number | Structure | Mass (mg) | Yield (%) |
|---|---|---|---|
| Intermediate 189 | 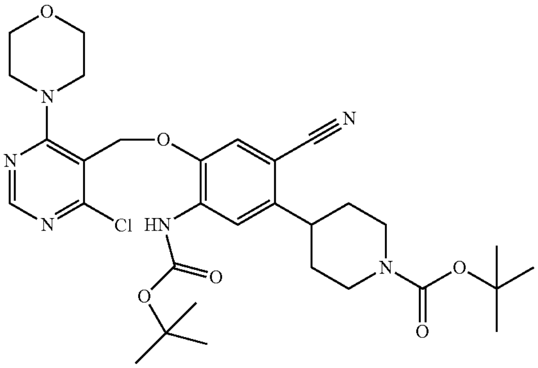 [SMILES: CC(C)(C)OC(=O)Nc1cc(C2CCN(C(=O)OC(C)(C)C)CC2)c(C#N)cc1OCc1c(Cl)ncnc1N1CCOCC1] from intermediate 149 and intermediate 42 | 1031 | 55 |
| Intermediate 190 | 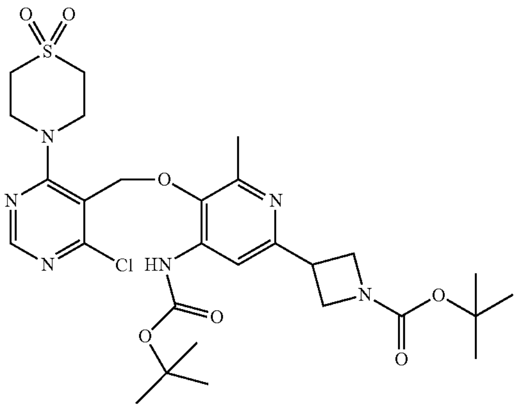 [SMILES: Cc1nc(C2CN(C(=O)OC(C)(C)C)C2)cc(NC(=O)OC(C)(C)C)c1OCc1c(Cl)ncnc1N1CCS(=O)(=O)CC1] from intermediate 150 and intermediate 41 | 3268 | quant. |

-continued

| compound number | Structure | Mass (mg) | Yield (%) |
|---|---|---|---|
| Intermediate 191 | 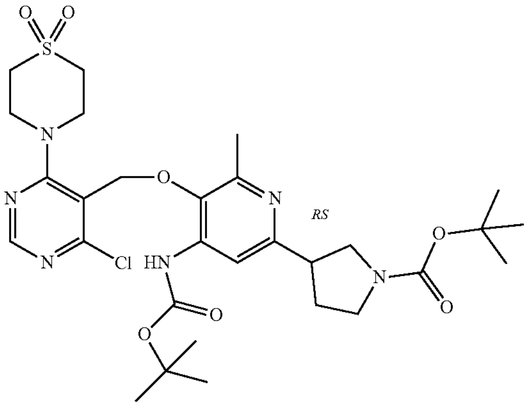 [SMILES: Cc1nc(C2CCN(C(=O)OC(C)(C)C)C2)cc(NC(=O)OC(C)(C)C)c1OCc1c(Cl)ncnc1N1CCS(=O)(=O)CC1] from intermediate 150 and intermediate 38 | 1877 | 64 |
| Intermediate 192 | 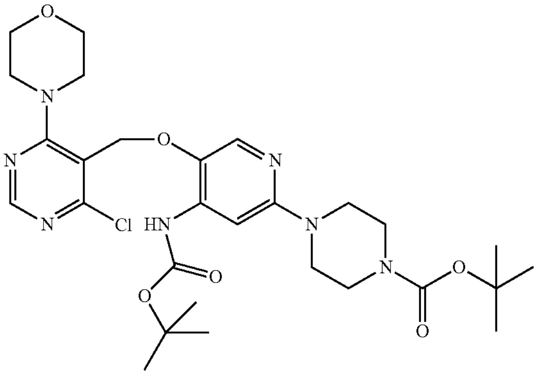 [SMILES: CC(C)(C)OC(=O)Nc1cc(N2CCN(C(=O)OC(C)(C)C)CC2)ncc1OCc1c(Cl)ncnc1N1CCOCC1] from intermediate 149 and intermediate 46 | 1190 | 72 |

Example A70

Preparation of Intermediate 193

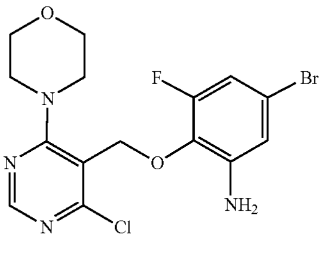 [SMILES: Nc1cc(Br)cc(F)c1OCc1c(Cl)ncnc1N1CCOCC1]

2 equivalent reactions were run in parallel and combined for work-up and purification. A suspension of intermediate 156 (8.2 g, 18.318 mmol) in MeOH (164 mL) and THF (164 mL) was hydrogenated with RaNi (8.2 g, 139.709 mmol) as catalyst at rt under 1 bar of $H_2$ for 5 hours. The two reactions were combined and filtered over Celite®. The filtrate was evaporated until dryness. The residue was purified by column chromatography over silica gel ($SiO_2$; 100% DCM to 98% DCM, 2% MeOH, 0.2% NH4OH). The desired fractions were combined and concentrated under reduced pressure. The solid was washed with MeCN to afford the product (13.6 g; 89%).

Example A71

Preparation of Intermediate 194

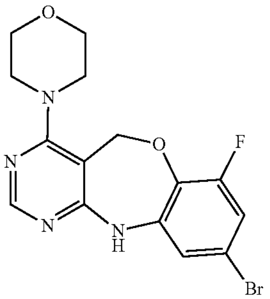 [SMILES: Fc1cc(Br)cc2c1OCc1c(ncnc1N1CCOCC1)N2]

A mixture of intermediate 193 (13.6 g, 32.562 mmol) in tert-amyl-alcohol (141.65 mL, 0.805 g/mL, 1293.574 mmol) in a schlenk tube was stirred at 140° C. for 2 hours. The reaction mixture was cooled down to rt and distilled water was added. The mixture was filtered through a pad of Celite® and the filtrate was extracted with DCM. The organic layer was dried over MgSO4, filtered and evaporated until dryness. The residue was purified by column chromatography over silica gel ($SiO_2$; from 90% Heptane—10% EtOAc to 40% Heptane—60% EtOAc) to afford the product (6.6 g; 53%).

Example A72

Preparation of Intermediate 195

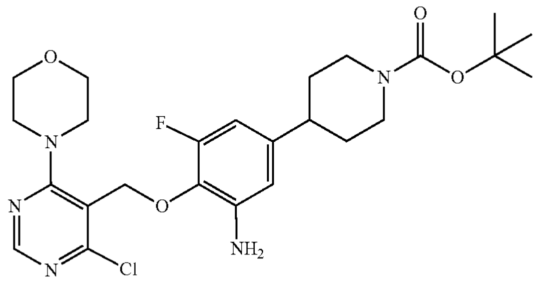

A solution of intermediate 158 (1.6 g, 2.899 mmol), Fe (0.486 g, 8.696 mmol) and $NH_4Cl$ (0.775 g, 14.493 mmol) in THF (10.6 mL), MeOH (10.6 mL) and water, distilled (5.2 mL) was stirred at 80° C. for 3 hours. The reaction was cooled down to rt, diluted with a mixture of DCM:MeOH (9:1) and filtered through a Chromabond PTS. The filtrate was concentrated under reduced pressure to afford the product (1.7 g; quant.) which was used in the next step without further purification.

The intermediates in the Table below were prepared by using an analogous method starting from the respective starting materials.

| compound number | Structure | Mass (mg) | Yield (%) |
|---|---|---|---|
| Intermediate 196 | 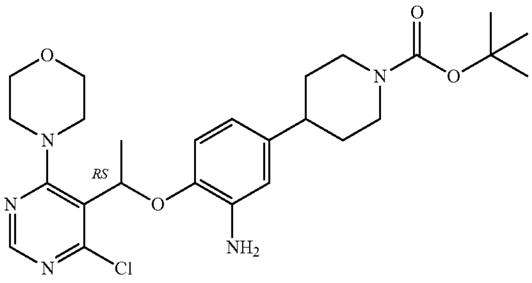 [SMILES: CC(Oc1ccc(C2CCN(C(=O)OC(C)(C)C)CC2)cc1N)c1c(Cl)ncnc1N1CCOCC1] from intermediate 159 | 1650 | quant. |
| Intermediate 197 | 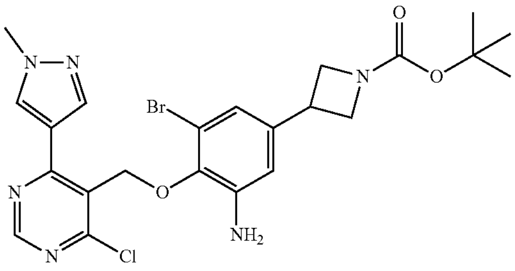 from intermediate 160 | 2600 | 95 |

-continued
| compound number | Structure | Mass (mg) | Yield (%) |
|---|---|---|---|
| Intermediate 198 | 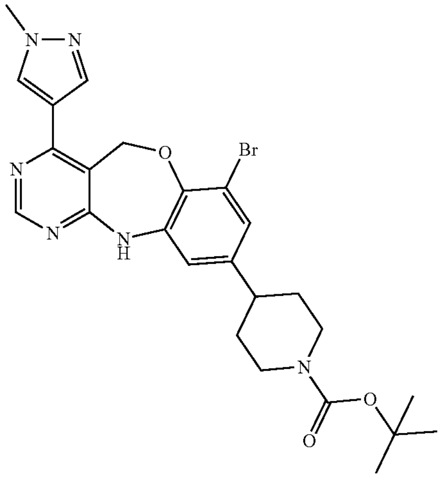 [SMILES: Cn1cc(-c2ncnc3c2COc2c(Br)cc(C4CCN(C(=O)OC(C)(C)C)CC4)cc2N3)cn1] from intermediate 161 - full cyclisation happened during this reduction step | 1610 | 90 |
| Intermediate 199 | 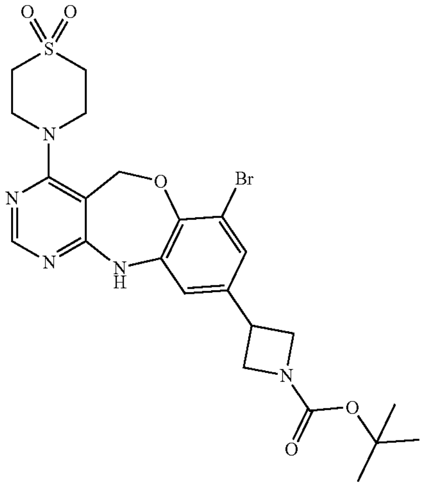 [SMILES: CC(C)(C)OC(=O)N1CC(c2cc(Br)c3c(c2)Nc2ncnc(N4CCS(=O)(=O)CC4)c2CO3)C1] from intermediate 180 - full cyclisation happened during this reduction step | 2300 | 71 |
| Intermediate 200 | 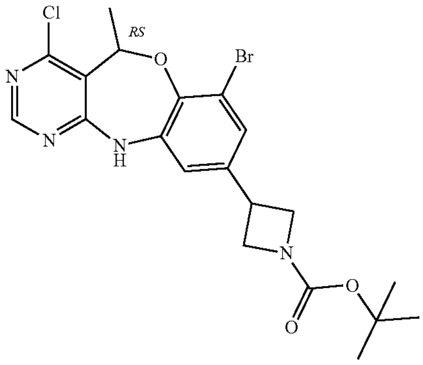 [SMILES: CC1Oc2c(Br)cc(C3CN(C(=O)OC(C)(C)C)C3)cc2Nc2ncnc(Cl)c21] from intermediate 162 - full cyclisation happened during this reduction step | 2000 | 88 |

Example A73

Preparation of Intermediate 201

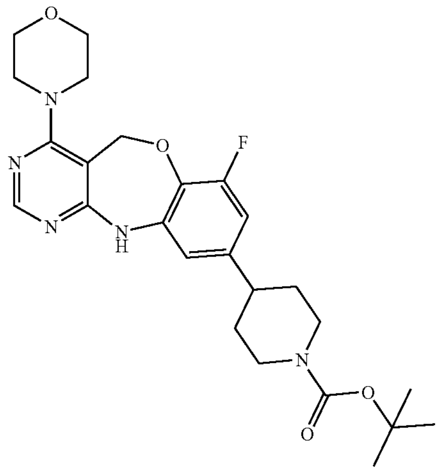 [SMILES: CC(C)(C)OC(=O)N1CCC(c2cc(F)c3c(c2)Nc2ncnc(N4CCOCC4)c2CO3)CC1]

Intermediate 195 (1.7 g, 3.257 mmol) in tert-amyl-alcohol (17.8 mL) was stirred at 140° C. for 4 hours. The volatiles were removed under vacuum and the residue was purified by column chromatography ($SiO_2$; from 100% DCM—0% MeOH to 93% DCM—7% MeOH) to afford the product (1.43 g; 90%).

The intermediates in the Table below were prepared by using an analogous method starting from the respective starting materials.

| compound number | Structure | Mass (mg) | Yield (%) |
|---|---|---|---|
| Intermediate 202 | 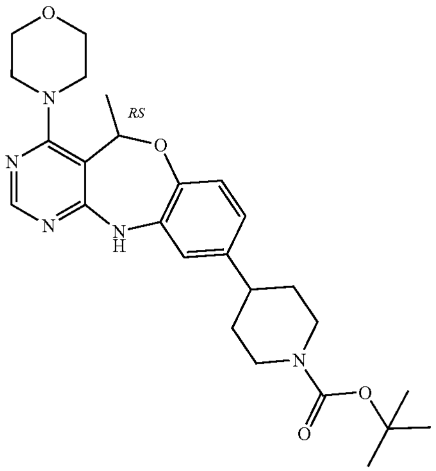 [SMILES: CC1Oc2ccc(C3CCN(C(=O)OC(C)(C)C)CC3)cc2Nc2ncnc(N3CCOCC3)c21] from intermediate 196 | 1210 | 79 |

-continued

| compound number | Structure | Mass (mg) | Yield (%) |
|---|---|---|---|
| Intermediate 203 | 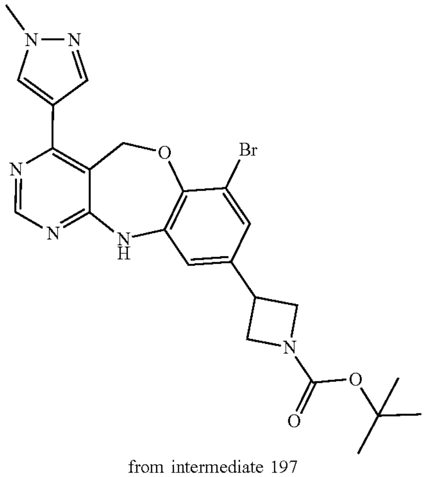 from intermediate 197 | 1790 | 73 |

Example A74

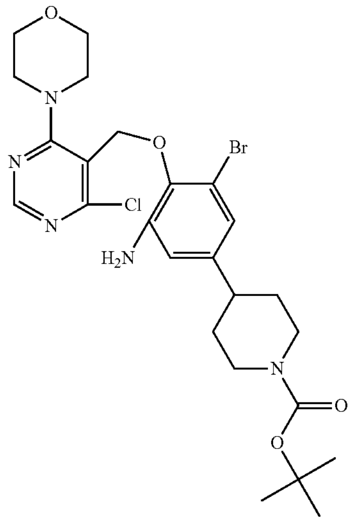 [SMILES: CC(C)(C)OC(=O)N1CCC(c2cc(N)c(OCc3c(Cl)ncnc3N3CCOCC3)c(Br)c2)CC1]

Preparation of Intermediate 204

Iron (1.76 g, 31.5 mmol) was added to a vigorously stirred solution of intermediate 168 in acetic acid (3.6 mL) and MeOH (30 mL) at room temperature. The reaction was stirred for 3 hours. The excess of iron was removed (stirring bar). The mixture was diluted with 1M $Na_2CO_3$ (200 ml) and DCM (200 ml). The organic layer was separated, and aqueous phase extracted once more with DCM (200 ml). The combined organic layers were dried over MgSO4, filtered and concentrated to the crude brownish residue of intermediate 204 (2.36 g, 91%, purity 70%).

Example A75

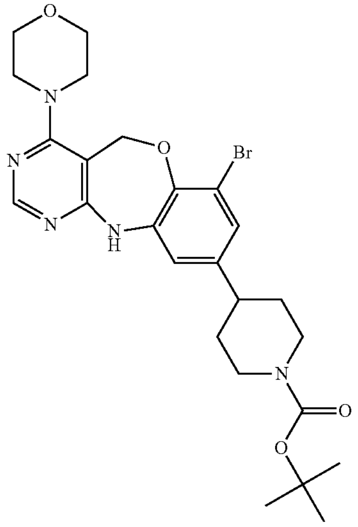 [SMILES: CC(C)(C)OC(=O)N1CCC(c2cc(Br)c3c(c2)Nc2ncnc(N4CCOCC4)c2CO3)CC1]

Preparation of Intermediate 205

Method A: A mixture of intermediate 168 (2 g, 3.26 mmol), iron (0.91 g, 16 mmol) and ammonium chloride (1.76 g, 33 mmol) in THF (13 mL), MeOH (13 mL) and water (6.5 mL) was stirred at 90° C. for 2 hours. After cooling down to rt, the reaction mixture was diluted with DCM and water was added. The organic layer was decanted on Chromabond® and the solvent was evaporated. The crude was purified by preparative LC (Irregular SiOH 15-40 µm 80 g GraceResolv®, mobile phase Gradient from 100% DCM to 95% DCM, 5% MeOH, 0.5% NH4OH). The pure fractions were collected and the solvent was evaporated until dryness to give intermediate 205 (697 mg, 39%) along with intermediate 205' (595 mg, 31%).

Method B: TFA (434 µL, 5.7 mmol) was added to a solution of intermediate 204 in 1,4-Dioxane (45 mL) and heated at 120° C. for 2 hours. The reaction mixture was allowed to cool down to room temperature and diluted with DCM (150 mL). The mixture was washed with 1M $Na_2CO_3$ (50 ml). The organic layer was separated, dried over MgSO4, filtered and concentrated to the crude. Chromatography over silica gel (gradient of EA in heptane from 0 to 100%) afforded intermediate 205 (1.34 g, 85%).

Example A76

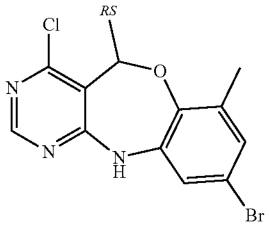 [SMILES: Cc1cc(Br)cc2c1OC(C)c1c(Cl)ncnc1N2]

Preparation of Intermediate 206

2 equivalent reactions were run in parallel and combined for work-up. Intermediate 152 (57.9 g; 142.244 mmol) was dissolved in THF (240 mL), MeOH (240 mL) and $H_2O$ (120 mL). $NH_4Cl$ (15.218 g; 284.488 mmol) and iron powder (23.831 g; 426.732 mmol) were added. The mixture was heated and refluxed at 90° C. for 2 h. A black suspension was observed. The mixture was cooled to 25° C., combined with that from the parallel reaction and filtered off over a pad of celite. The filter cake was rinsed with ethyl acetate/THF (1/1) (3*1 L). The filtrate was concentrated to give a brown solid residue which was treated with ethanol/$H_2O$ (1/1) (150 mL). The mixture was stirred for 5 min and filtered. The filter cake was rinsed with ethanol/$H_2O$ (1/1) (2*100 mL) and dried under high vacuum (50° C., 2 h) to give the product as a brown solid (84 g; 87%, based on two batches).

Alternative preparation of Intermediate 206

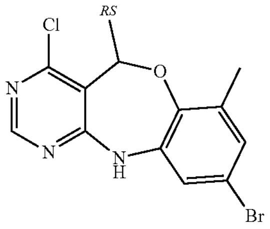 [SMILES: Cc1cc(Br)cc2c1OC(C)c1c(Cl)ncnc1N2]

To a suspension of intermediate 152 (3.2 g; 7.86 mmol) and ammonium chloride (4.205 g; 78.6 mmol) in methanol/THF/water (2/2/1; 55 mL), iron powder (2.195 g; 39.31 mmol) was added and the mixture was heated with stirring to 70° C. for 2 hr. The mixture was allowed to cool to room temperature, diluted with dichloromethane:methanol (9:1) and washed with saturated $NaHCO_3$(aq). The organic layer was dried ($MgSO_4$), filtered and concentrated in vacuo. The resulting crude was dried under high vacuum to give intermediate 206 (1.19 g; 44%). The product was used in the next step without any further purification.

The intermediates in the Table below were prepared by using an analogous method starting from the respective starting materials.

| Intermediate number | Structure | Mass (mg) | Yield (%) |
|---|---|---|---|
| Intermediate 207 | 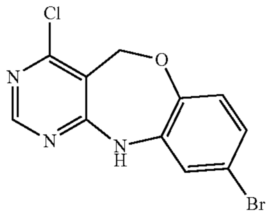 [SMILES: Clc1ncnc2c1COc1ccc(Br)cc1N2] from intermediate 125 | 45000 | 63 |
| Intermediate 208 | 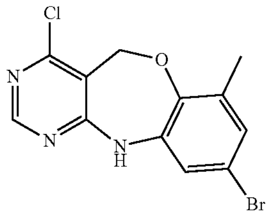 [SMILES: Cc1cc(Br)cc2c1OCc1c(Cl)ncnc1N2] from intermediate 126 | | |
| Intermediate 209 | 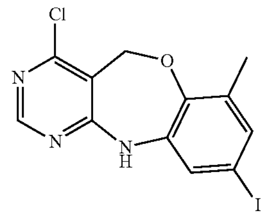 [SMILES: Cc1cc(I)cc2c1OCc1c(Cl)ncnc1N2] from intermediate 128 | 135 | 25 |
| Intermediate 210 | 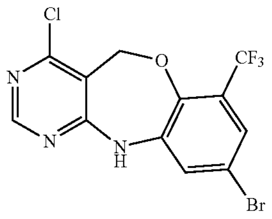 [SMILES: FC(F)(F)c1cc(Br)cc2c1OCc1c(Cl)ncnc1N2] from intermediate 127 | 3620 | 100 |
| Intermediate 211 | 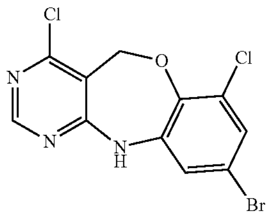 [SMILES: Clc1cc(Br)cc2c1OCc1c(Cl)ncnc1N2] from intermediate 129 | 7100 | 100 |
| Intermediate 212 | 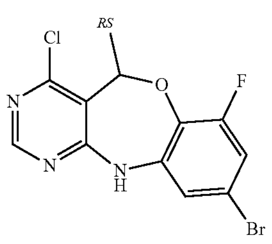 [SMILES: CC1Oc2c(F)cc(Br)cc2Nc2ncnc(Cl)c21] from intermediate 153 | 9200 | 90 |

| Intermediate number | Structure | Mass (mg) | Yield (%) |
|---|---|---|---|
| Intermediate 213 | 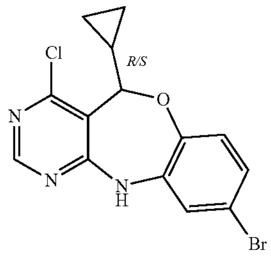 [SMILES: Clc1ncnc2c1C(C1CC1)Oc1ccc(Br)cc1N2] from intermediate 154 | 83 | 72 |
| Intermediate 214 | 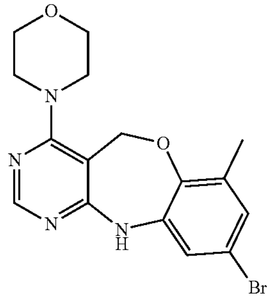 [SMILES: Cc1cc(Br)cc2c1OCc1c(ncnc1N1CCOCC1)N2] from intermediate 155; aqueous $K_2CO_3$ used as base in the work up | 4400 | 52 |
| Intermediate 215 | 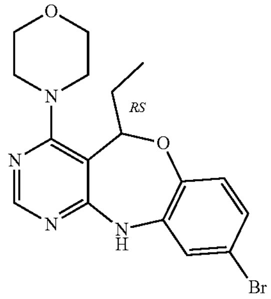 [SMILES: CCC1Oc2ccc(Br)cc2Nc2ncnc(N3CCOCC3)c21] from intermediate 157 | 460 | 69 |
| Intermediate 216 | 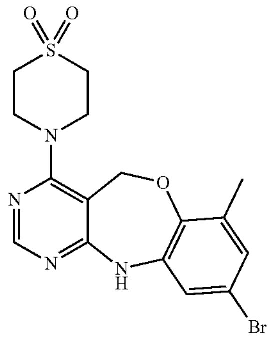 from intermediate 181 | 10700 | 84 |

Preparation of Intermediate 217

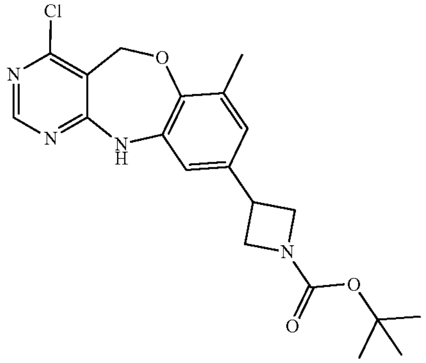 [SMILES: Cc1cc(C2CN(C(=O)OC(C)(C)C)C2)cc2c1OCc1c(Cl)ncnc1N2]

Ammonium chloride (2.11 g, 413.37 mmol) and iron (4.63 g, 620.05 mmol) were added to a solution of intermediate 163 (97 g, 206.68 mmol) in THF/MeOH/H2O (300 mL/300 mL/150 mL). The mixture was heated at 95° C. for 16 h, cooled to 25° C. and filtered off over a pad of celite. The filter cake was washed with ethyl acetate/DMF (1/1) (1500 mL*3). The filtrate was concentrated to give a yellow solid, which was treated with methanol/H2O (1/1) (150 mL). The mixture was stirred for 5 min and filtered. The solid was washed with methanol/H2O (1/1) (2*50 mL) and dried under high vacuum (60° C., 2 h) to give intermediate 217 (63 g, 76%) as an off-white solid.

Example A77

Preparation of Intermediate 218

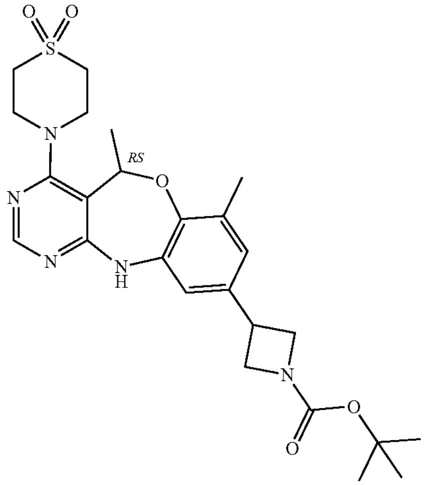 [SMILES: Cc1cc(C2CN(C(=O)OC(C)(C)C)C2)cc2c1OC(C)c1c(ncnc1N1CCS(=O)(=O)CC1)N2]

Three reactions were performed in parallel (6.4 g, 11.5 g and 17 g) and combined for purification. A mixture of intermediate 165 (17 g, 19.568 mmol), iron (5.472 g, 97.977 mmol) and ammonium chloride (10.687 g, 199.79 mmol) in THF (83 mL), MeOH (83 mL) and water (50 mL) was stirred at 85° C. for 24 h. The reaction mixture was diluted in DCM and washed with a saturated aqueous solution of $NaHCO_3$, then filtered on celite. The organic layers were dried over $MgSO_4$ and evaporated in vacuo to give the crude product, which was combined with those from the other two reactions (32.3 g combined) for purification. Purification was performed via preparative LC (Stationary phase: irregular SiOH 35-70 μm 750 g, Mobile phase: gradient from 100% DCM to 95% DCM, 5% MeOH, 0.5% NH4OH). The pure fractions were combined and the solvent was evaporated to give the product as a racemic mixture (13.4 g, yield 58% combined yield).

Preparation of Intermediate 218*R & Intermediate 218*S

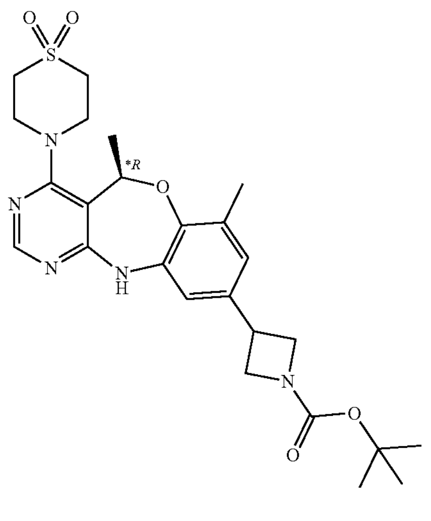

&

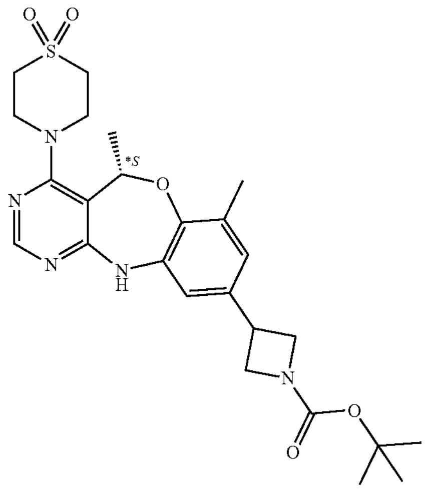

Intermediate 218 was purified via chiral SFC (Stationary phase: CHIRALCEL OD-H 5 μm 250*30 mm, Mobile phase: 60% $CO_2$, 40% EtOH (0.3% $iPrNH_2$)) to afford intermediate 218*R (5.01 g) and intermediate 218*S (5.05 g).

Preparation of Intermediate 219

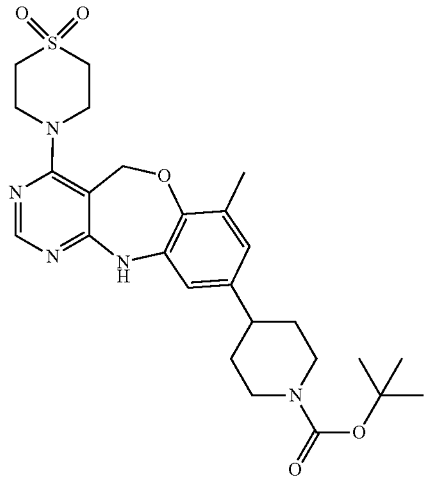 [SMILES: Cc1cc(C2CCN(C(=O)OC(C)(C)C)CC2)cc2c1OCc1c(ncnc1N1CCS(=O)(=O)CC1)N2]

A mixture of intermediate 164 (27.9 g, 46.80 mmol), iron (13.1 g, 234 mmol) and ammonium chloride (25.6 g, 478 mmol) in THF (198 mL), MeOH (198 mL) and water (119 mL) was stirred at 90° C. for 15 hours. After cooling down to rt, the rm was diluted with DCM, filtered over Celite© and the organic layer was dried over MgSO4, filtered and evaporated to give the crude compound (22.7 g). The compound was crystallized from CH3CN, filtered off and washed with Et2O to give the final compound (17.2 g, yield 69%).

The intermediates in the Table below were prepared by using an analogous method starting from the respective starting materials.

| Intermediate number | Structure | Mass (mg) | Yield (%) |
|---|---|---|---|
| Intermediate 221 | 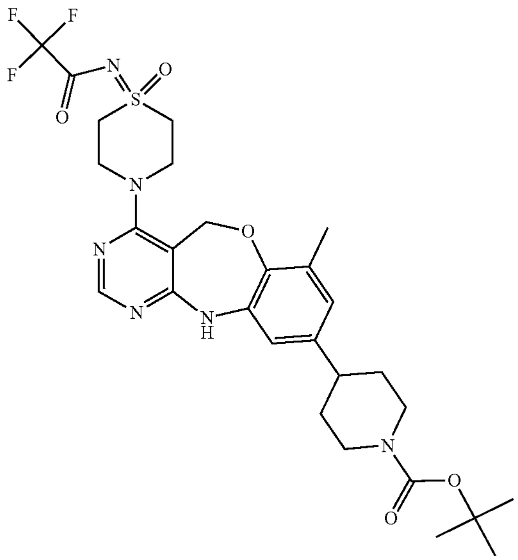 [SMILES: Cc1cc(C2CCN(C(=O)OC(C)(C)C)CC2)cc2c1OCc1c(ncnc1N1CCS(=O)(=NC(=O)C(F)(F)F)CC1)N2] from intermediate 166, 70° C., 2 h | 986 | 37 |
| Intermediate 222 | 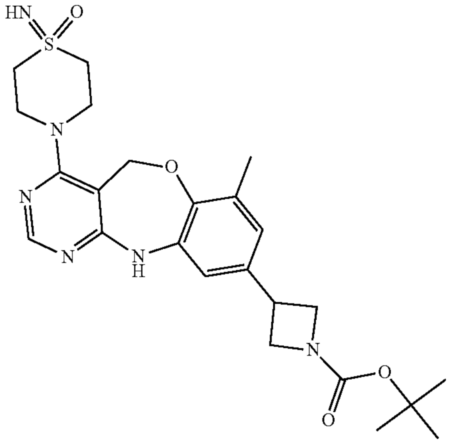 [SMILES: Cc1cc(C2CN(C(=O)OC(C)(C)C)C2)cc2c1OCc1c(ncnc1N1CCS(=N)(=O)CC1)N2] from intermediate 167, 90° C., 2 h | 1860 | 75 |
| Intermediate 223 | 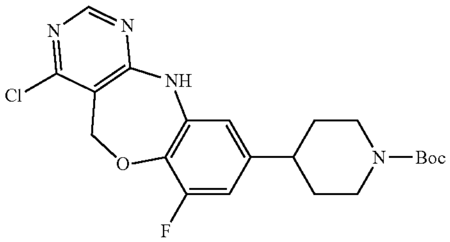 [SMILES: CC(C)(C)OC(=O)N1CCC(c2cc(F)c3c(c2)Nc2ncnc(Cl)c2CO3)CC1] from intermediate 169 | 809 | 88 |

-continued
| Intermediate number | Structure | Mass (mg) | Yield (%) |
|---|---|---|---|
| Intermediate 224 | 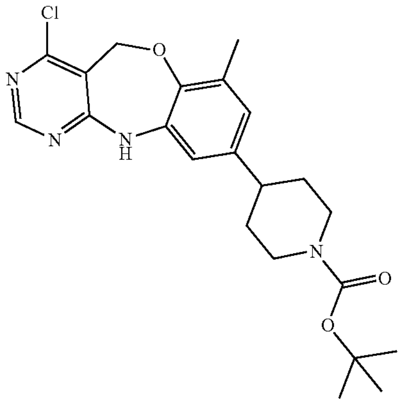 [SMILES: Cc1cc(C2CCN(C(=O)OC(C)(C)C)CC2)cc2c1OCc1c(Cl)ncnc1N2] from intermediate 170, 95° C., 3 h | 70000 | 67 |
| Intermediate 225 | 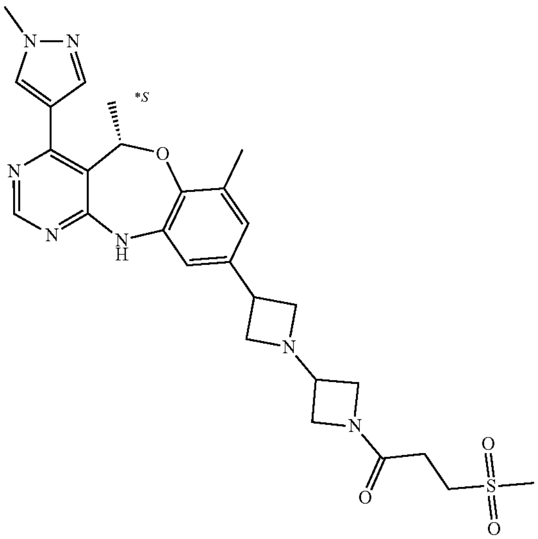 from intermediate 171, 75° C., 2 h | 200 | quant |
| Intermediate 226 | 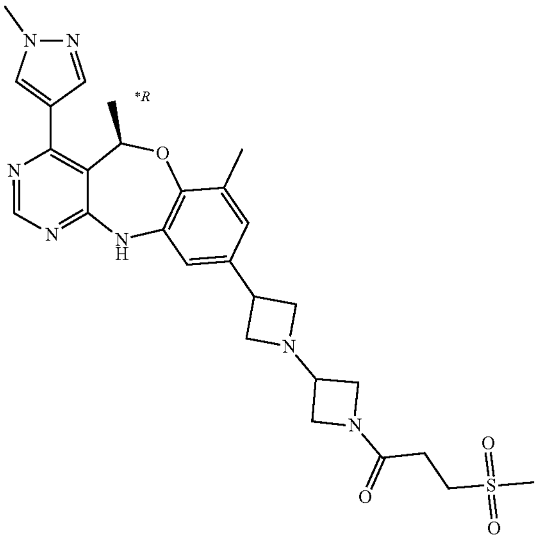 From intermediate 172, 75° C., 2 h | 73 | 85 |

-continued
| Intermediate number | Structure | Mass (mg) | Yield (%) |
| --- | --- | --- | --- |
| Intermediate 227 | 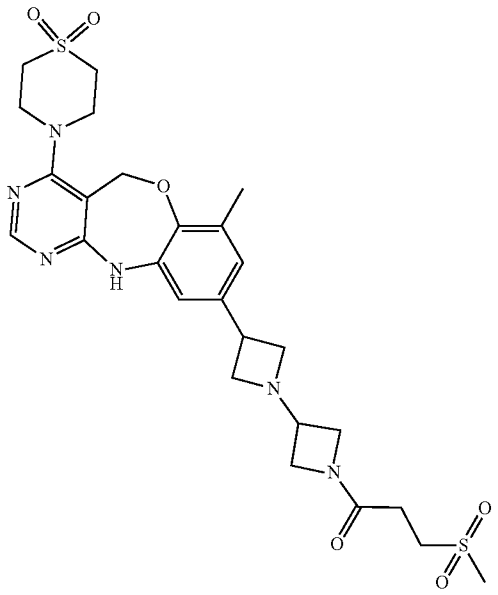 [SMILES: Cc1cc(C2CN(C3CN(C(=O)CCS(C)(=O)=O)C3)C2)cc2c1OCc1c(ncnc1N1CCS(=O)(=O)CC1)N2] From intermediate 173, 85° C., 3 h | 121 | 64 |
| Intermediate 228 | 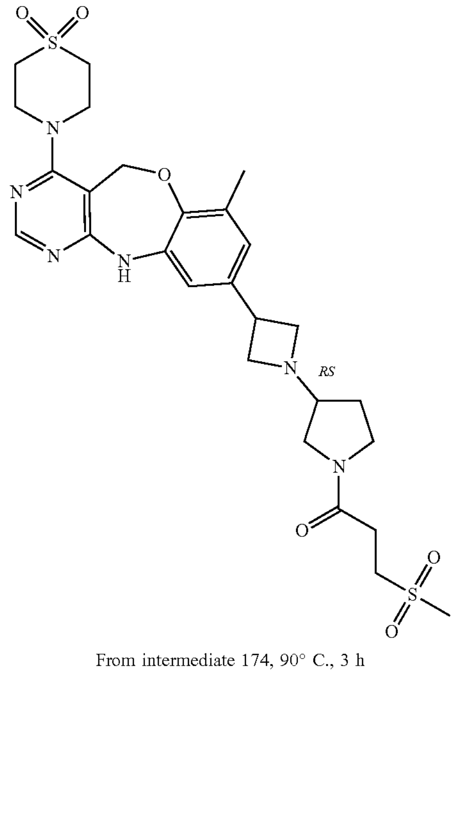 From intermediate 174, 90° C., 3 h | 400 | 26 Purity 94% |

-continued
| Intermediate number | Structure | Mass (mg) | Yield (%) |
| --- | --- | --- | --- |
| Intermediate 229 | 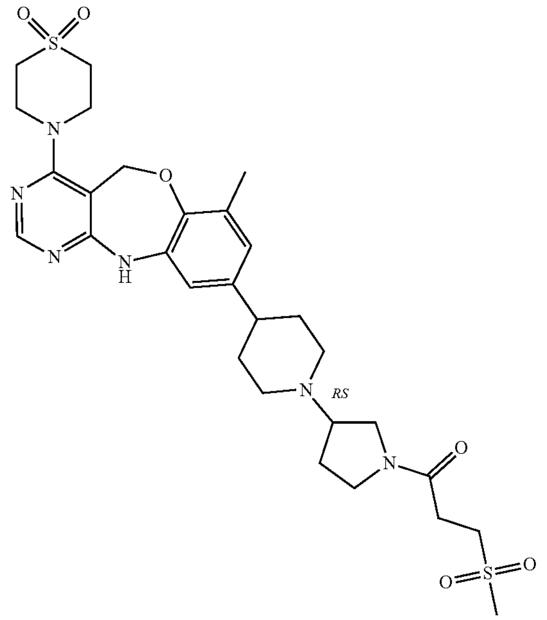 [SMILES: Cc1cc(C2CCN(C3CCN(C(=O)CCS(C)(=O)=O)C3)CC2)cc2c1OCc1c(ncnc1N1CCS(=O)(=O)CC1)N2] From intermediate 175, 90° C., 3 h | 3400 | 80 |
| Intermediate 230 | 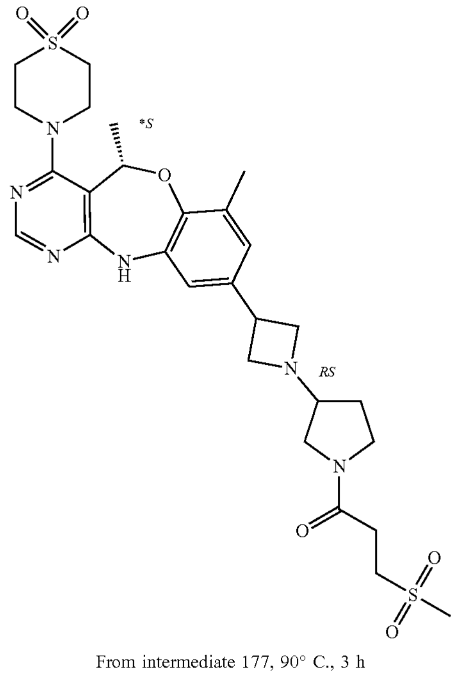 From intermediate 177, 90° C., 3 h | 224 | 68 |

-continued
| Intermediate number | Structure | Mass (mg) | Yield (%) |
|---|---|---|---|
| Intermediate 231 | 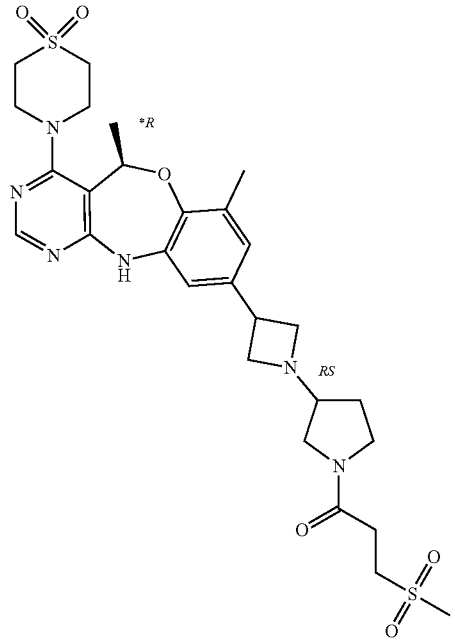 [SMILES: Cc1cc(C2CN(C3CCN(C(=O)CCS(C)(=O)=O)C3)C2)cc2c1O[C@H](C)c1c(ncnc1N1CCS(=O)(=O)CC1)N2] From intermediate 178, 90° C., 3 h | 280 | quant |
| Intermediate 671 | 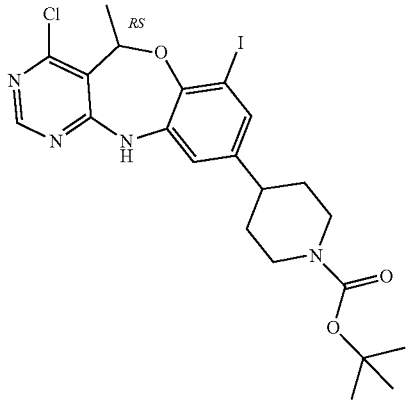 [SMILES: CC1Oc2c(I)cc(C3CCN(C(=O)OC(C)(C)C)CC3)cc2Nc2ncnc(Cl)c21] from intermediate 669, 85° C., 2 h | 8300 | quant |
| Intermediate 672 | 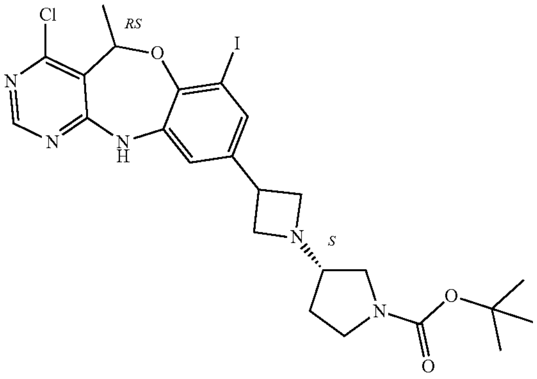 from intermediate 670, 75° C., 1 h | 820 | 94 |

Example A78

Preparation of Intermediate 232

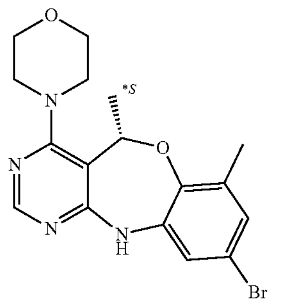 [SMILES: Cc1cc(Br)cc2c1O[C@@H](C)c1c(ncnc1N1CCOCC1)N2]

Intermediate 179 (2.2 g, 4.8 mmol), iron (2684 mg, 48 mmol) and AcOH (5.5 mL, 1.049 g/mL, 96 mmol) in MeOH (78 mL) were stirred at rt for 16 h. Water was added and the reaction mixture was diluted with DCM. The organic layer was separated, dried over MgSO4, filtered and evaporated. A purification was performed via preparative LC (Stationary phase: irregular SiOH 35-70 μm 80 g, Mobile phase: gradient from 100% DCM to 95% DCM, 5% MeOH (2% NNH4OH)). The pure fractions were collected and the solvent was evaporated to give intermediate 232 (1.22 g, yield 65%)

The intermediates in the Table below were prepared by using an analogous method starting from the respective starting materials.

| compound number | Structure | Mass (mg) | Yield (%) |
| --- | --- | --- | --- |
| Intermediate 233 | 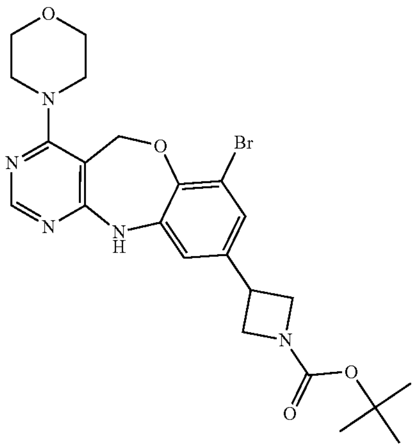 [SMILES: CC(C)(C)OC(=O)N1CC(c2cc(Br)c3c(c2)Nc2ncnc(N4CCOCC4)c2CO3)C1] from intermediate 176 | 503 | 56 |

Example A79

Preparation of Intermediate 234

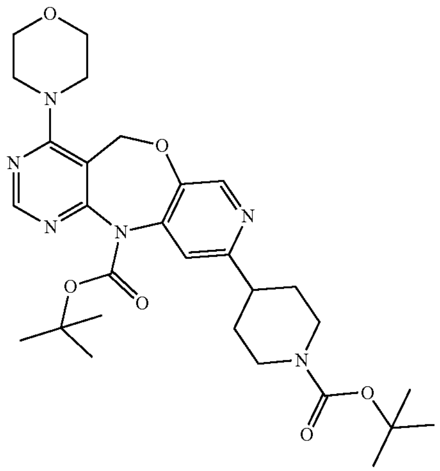 [SMILES: CC(C)(C)OC(=O)N1CCC(c2cc3c(cn2)OCc2c(N4CCOCC4)ncnc2N3C(=O)OC(C)(C)C)CC1]

In a sealed tube, a solution of intermediate 188 (880 mg; 1.43 mmol) and $Cs_2CO_3$ (928.7 mg; 2.85 mmol) in 1,4-dioxane (15 mL) was degassed under $N_2$. Then $Pd_2(dba)_3$ (130.5 mg; 0.143 mmol) and Xantphos (164.9 mg; 0.285 mmol) were added. The reaction mixture was degassed again under N2 and heated at 100° C. overnight. The reaction mixture was partitioned between EtOAc and brine. The organic layer was dried over $MgSO_4$, filtered and concentrated under reduced pressure. The residue was purified by column chromatography ($SiO_2$; Heptane/EtOAc) to afford the product (555 mg; 88%) as a yellow solid.

The intermediates in the Table below were prepared by using an analogous method starting from the respective starting materials.

| compound number | Structure | Mass (mg) | Yield (%) |
|---|---|---|---|
| Intermediate 235 | 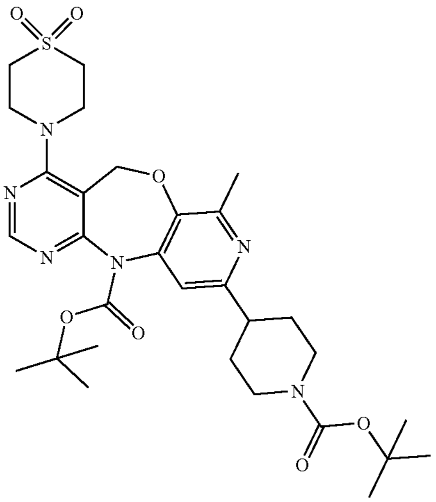 [SMILES: Cc1nc(C2CCN(C(=O)OC(C)(C)C)CC2)cc2c1OCc1c(N3CCS(=O)(=O)CC3)ncnc1N2C(=O)OC(C)(C)C] from intermediate 183 | 2760 | 95 |
| Intermediate 236 | 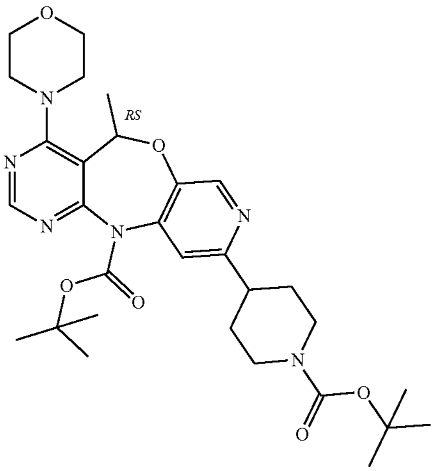 [SMILES: CC1Oc2cnc(C3CCN(C(=O)OC(C)(C)C)CC3)cc2N(C(=O)OC(C)(C)C)c2ncnc(N3CCOCC3)c21] from intermediate 186 | 264 | 80 |
| Intermediate 237 | 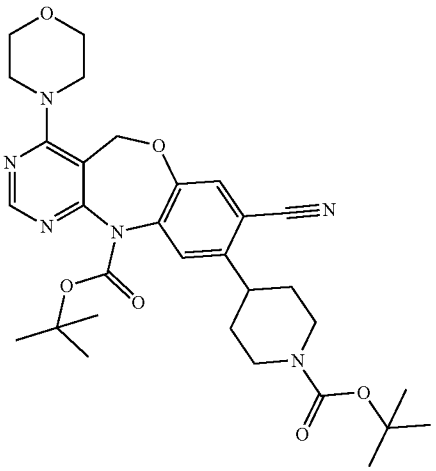 [SMILES: CC(C)(C)OC(=O)N1CCC(c2cc3c(cc2C#N)OCc2c(N4CCOCC4)ncnc2N3C(=O)OC(C)(C)C)CC1] from intermediate 189 | 583 | 64 |

-continued
| compound number | Structure | Mass (mg) | Yield (%) |
|---|---|---|---|
| Intermediate 238 | 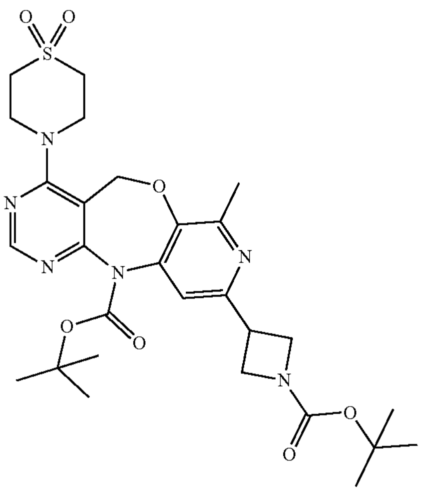 [SMILES: Cc1nc(C2CN(C(=O)OC(C)(C)C)C2)cc2c1OCc1c(N3CCS(=O)(=O)CC3)ncnc1N2C(=O)OC(C)(C)C] from intermediate 190 | 1059 | 41 |
| Intermediate 239 | 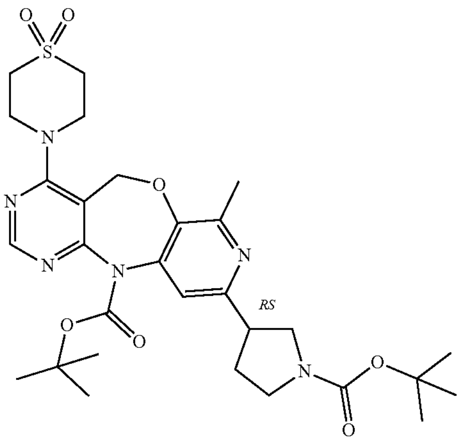 [SMILES: Cc1nc(C2CCN(C(=O)OC(C)(C)C)C2)cc2c1OCc1c(N3CCS(=O)(=O)CC3)ncnc1N2C(=O)OC(C)(C)C] from intermediate 191 | 1110 | 63 |
| Intermediate 240 | 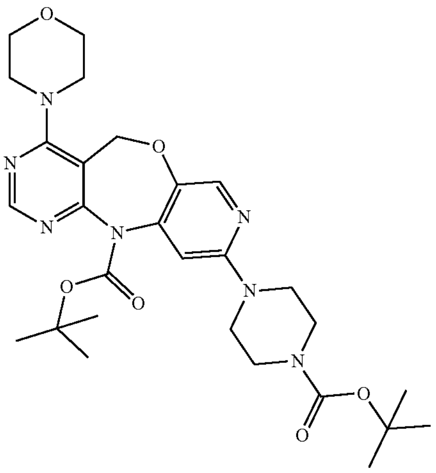 from intermediate 192 | 751 | 64 |

-continued

| compound number | Structure | Mass (mg) | Yield (%) |
|---|---|---|---|
| Intermediate 241 | 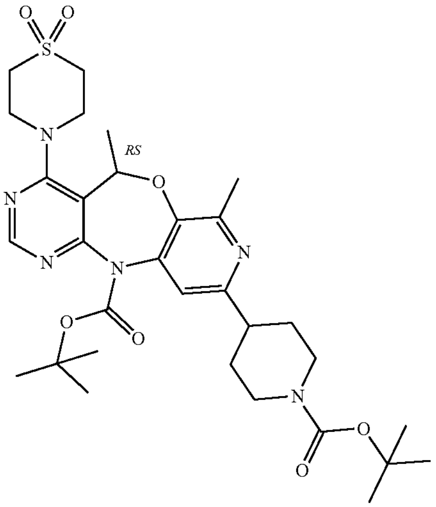 [SMILES: Cc1nc(C2CCN(C(=O)OC(C)(C)C)CC2)cc2c1OC(C)c1c(N3CCS(=O)(=O)CC3)ncnc1N2C(=O)OC(C)(C)C] from intermediate 187 | 421 | 66 |

Example A80

Preparation of Intermediate 242

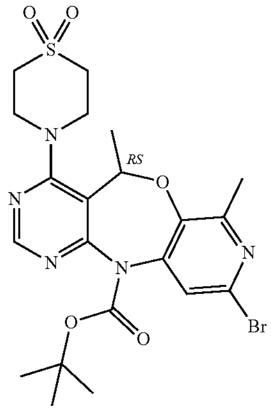 [SMILES: Cc1nc(Br)cc2c1OC(C)c1c(N3CCS(=O)(=O)CC3)ncnc1N2C(=O)OC(C)(C)C]

The reaction was performed on two batches (15.60 mmol and 16.64 mmol), which were combined for purification.

2-Dicyclohexylphosphino-2',6'-dimethoxybiphenyl (1025 mg, 2.50 mmol) and palladium (II) acetate (560 mg, 2.50 mmol) were added to a solution of intermediate 182 (9.60 g, 16.64 mmol) and cesium carbonate (8.13 g, 24.96 mmol) in toluene (300 mL) under nitrogen. The reaction mixture was degassed with nitrogen and heated at 100° C. for 15 h. Brine was added, the aqueous layer was extracted with ethyl acetate, the organic layer was dried over $MgSO_4$, filtered and evaporated to dryness. The crude, combined with the other batch, was purified by flash chromatography (eluting with Heptane/Ethyl Acetate gradient) to afford intermediate 242 (5.36 g, 31%) as a white solid.

Example A81

Method A

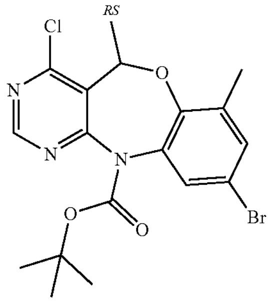 [SMILES: Cc1cc(Br)cc2c1OC(C)c1c(Cl)ncnc1N2C(=O)OC(C)(C)C]

Preparation of Intermediate 243

To a solution of intermediate 206 (14.29 g; 41.96 mmol), DMAP (1.025 g; 8.39 mmol) and triethylamine (11.7 mL; 83.92 mmol) in DCM (200 mL), di-tert-butyl dicarbonate (18.32 g; 83.92 mmol) was added and the mixture was stirred at room temperature for 13 hours. The reaction mixture was concentrated in vacuo and dry-loaded with silica onto a column for purification by flash chromatography ($SiO_2$; Hexane/EtOAc). The desired fractions were combined and concentrated in vacuo to afford the product (11.2 g; 93%).

Alternative preparation of intermediate 243 Method B

Preparation of Intermediate 243

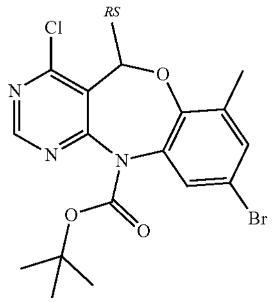

Di-tert-butyl dicarbonate (226.629 g; 986.486 mmol) was added to a suspension of intermediate 206 (84 g; 246.621 mmol) and $Cs_2CO_3$ (136.602 g; 419.256 mmol) in THF (1000 mL) at 25° C. The mixture was stirred and refluxed at 90° C. for 3 h. The mixture was cooled to 20° C. and filtered. The filter cake was rinsed with THF (500 mL) and ethyl acetate (500 mL). The filtrate was concentrated under vacuum to afford an orange oil, which was purified over silica gel on a glass filter (eluent: petroleum ether/ethyl acetate, from 100/0 to 86/14). The desired fractions were collected and the solvent was evaporated to give an orange gum, which was left to stand and solidify overnight. The mixture was treated with petroleum ether (50 mL) and stirred for 5 min. The mixture was filtered. The filter cake was washed with petroleum ether (10 mL) and dried under high vacuum (50° C., 0.5 h) to give the product as a light yellow solid (94.5 g; 87%).

The intermediates in the Table below were prepared by using an analogous method to Method A starting from the respective starting materials.

| Intermediate number | Structure | Mass (mg) | Yield (%) |
|---|---|---|---|
| Intermediate 244 | 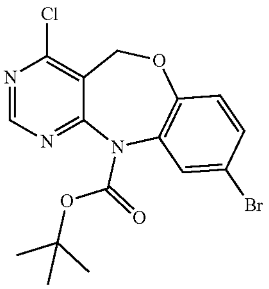 [SMILES: CC(C)(C)OC(=O)N1c2cc(Br)ccc2OCc2c(Cl)ncnc21] from intermediate 207 | 4600 | 67 |
| Intermediate 245 | 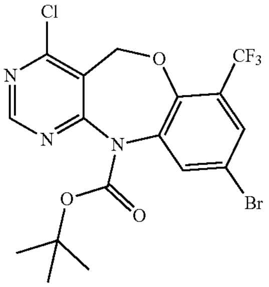 [SMILES: CC(C)(C)OC(=O)N1c2cc(Br)cc(C(F)(F)F)c2OCc2c(Cl)ncnc21] from intermediate 210 | 1170 | 26 |
| Intermediate 246 | 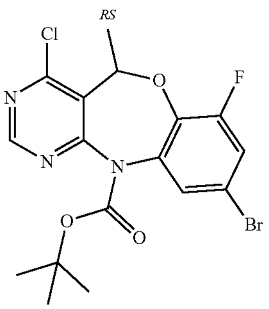 [SMILES: CC1Oc2c(F)cc(Br)cc2N(C(=O)OC(C)(C)C)c2ncnc(Cl)c21] from intermediate 212 | 9600 | 81 |

-continued
| Intermediate number | Structure | Mass (mg) | Yield (%) |
|---|---|---|---|
| Intermediate 247 | 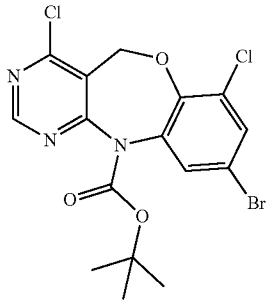 [SMILES: CC(C)(C)OC(=O)N1c2cc(Br)cc(Cl)c2OCc2c(Cl)ncnc21] from intermediate 211 | 4400 | 63 |
| Intermediate 248 | 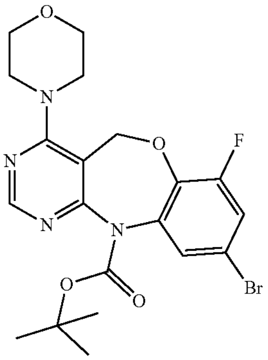 from intermediate 194 | 6500 | 78 |
| Intermediate 249 | 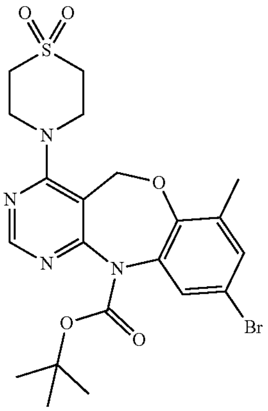 [SMILES: Cc1cc(Br)cc2c1OCc1c(N3CCS(=O)(=O)CC3)ncnc1N2C(=O)OC(C)(C)C] from intermediate 216 | 9110 | 69 |

-continued

| Intermediate number | Structure | Mass (mg) | Yield (%) |
|---|---|---|---|
| Intermediate 673 | 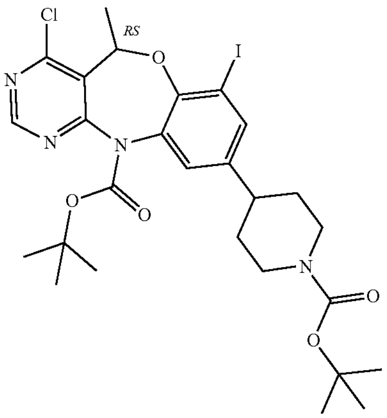 [SMILES: CC1Oc2c(I)cc(C3CCN(C(=O)OC(C)(C)C)CC3)cc2N(C(=O)OC(C)(C)C)c2ncnc(Cl)c21] from intermediate 671 | 6000 | 64 |

Preparation of Intermediate 250

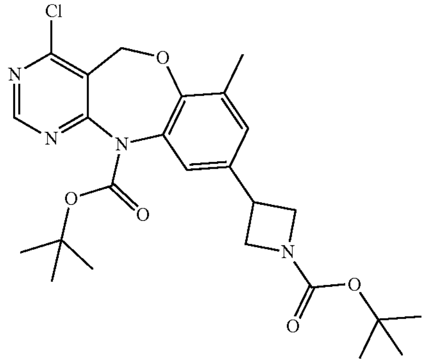 [SMILES: Cc1cc(C2CN(C(=O)OC(C)(C)C)C2)cc2c1OCc1c(Cl)ncnc1N2C(=O)OC(C)(C)C]

Di-tert-butyl dicarbonate (298 mL, 1295.7 mmol) was added to a suspension of intermediate 217 (58 g, 144.0 mmol) and cesium carbonate (79.7 g, 244.7 mmol) in THF (600 mL) at rt. The mixture was stirred at 90° C. for 16 h, then cooled to 20° C., combined with a smaller batch (run on 5 g of intermediate 217) and filtered. The filter cake was washed with THF (300 mL) and ethyl acetate (300 mL). The filtrate was concentrated under vacuum to give an orange oil, which was purified over silica gel (eluent: petroleum ether/ethyl acetate, from 100/0 to 86/14). The desired fractions were collected and the solvent was evaporated to give an orange gum, which was standing overnight. Solid was precipitate. The mixture was treated with methyl t-butyl ether (50 mL) and stirred for 5 min. The mixture was filtered. The filter cake was washed with methyl t-butyl ether (10 mL) and dried under high vacuum (50° C., 0.5 h) to give intermediate 250 (50 g, 63% based on two batches).

Preparation of Intermediate 251

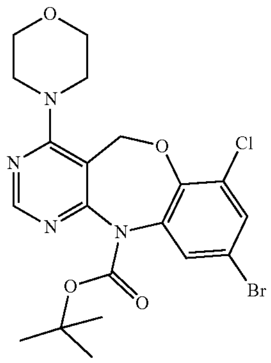 [SMILES: CC(C)(C)OC(=O)N1c2cc(Br)cc(Cl)c2OCc2c(N3CCOCC3)ncnc21]

To a solution of intermediate 263 (2.06 g; 5.18 mmol), DMAP (126.6 mg; 1.04 mmol) and triethylamine (1.44 mL; 10.36 mmol) in DCM (50 mL), di-tert-butyl dicarbonate (2.26 g; 10.36 mmol) was added and the mixture was stirred at room temperature for 15 hours. The reaction mixture was concentrated in vacuo and dry-loaded with silica onto a column for purification by flash chromatography ($SiO_2$; Hexane/EtOAc). The desired fractions were combined and concentrated in vacuo to afford the product (2.05 g; 79%).

The intermediates in the Table below were prepared by using an analogous method starting from the respective starting materials.

| compound number | Structure | Mass (mg) | Yield (%) |
|---|---|---|---|
| Intermediate 252 | 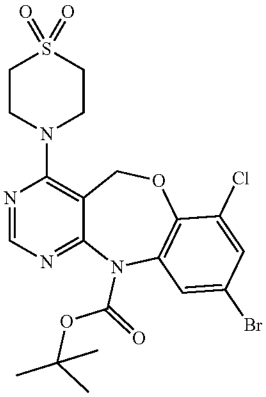 [SMILES: CC(C)(C)OC(=O)N1c2cc(Br)cc(Cl)c2OCc2c(N3CCS(=O)(=O)CC3)ncnc21] from intermediate 264 | 3211 | quant. |
| Intermediate 253 | 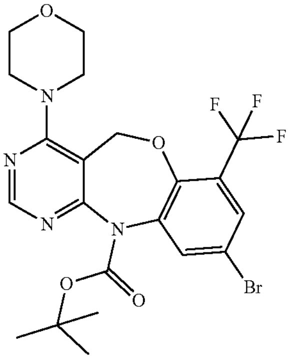 [SMILES: CC(C)(C)OC(=O)N1c2cc(Br)cc(C(F)(F)F)c2OCc2c(N3CCOCC3)ncnc21] from intermediate 265 | 1370 | 38 |

Preparation of Intermediate 254

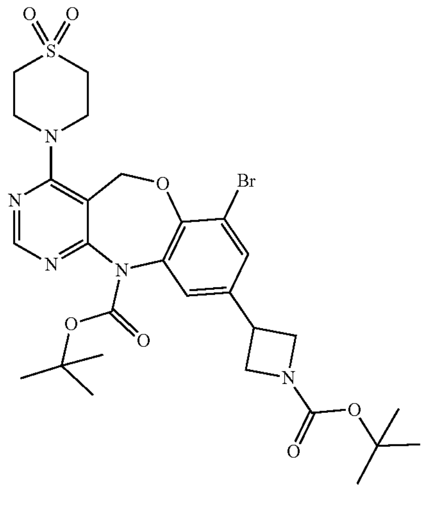 [SMILES: CC(C)(C)OC(=O)N1CC(c2cc(Br)c3c(c2)N(C(=O)OC(C)(C)C)c2ncnc(N4CCS(=O)(=O)CC4)c2CO3)C1]

Following the Method A used for the preparation of intermediate 243 and using intermediate 199 (2.3 g; 4.06 mmol) as starting material, intermediate 254 (1.19 g; 44%) was obtained.

Preparation of Intermediate 255

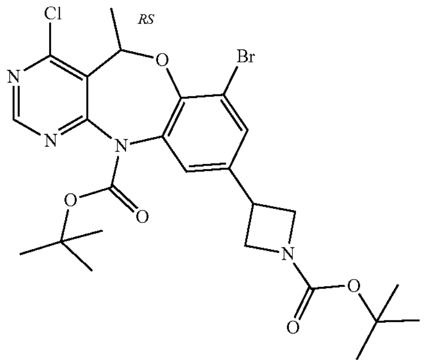 [SMILES: CC1Oc2c(Br)cc(C3CN(C(=O)OC(C)(C)C)C3)cc2N(C(=O)OC(C)(C)C)c2ncnc(Cl)c21]

Following the Method A used for the preparation of intermediate 243 and using intermediate 200 (2.0 g; 4.151 mmol) as starting material, intermediate 255 (1.75 g; 72%) was obtained.

Preparation of Intermediate 256

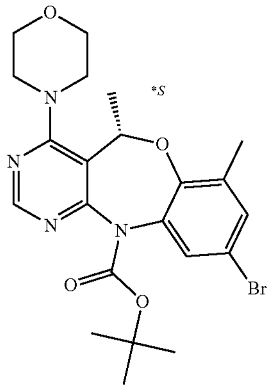 [SMILES: Cc1cc(Br)cc2c1O[C@@H](C)c1c(N3CCOCC3)ncnc1N2C(=O)OC(C)(C)C]

A mixture of intermediate 232 (1.2 g, 3.1 mmol), BOC-anhydride (1.34 g, 6.1 mmol), DMAP (75 mg, 0.61 mmol) and Et3N (0.85 mL, 0.728 g/mL, 6.1 mmol) in DCM (12 mL) was stirred at rt for 24 h. The mixture was diluted with water and extracted with DCM. The organic layer was dried over MgSO4. The solvent was removed under vacuo. The residue was evaporated in vacuo and was purified by chromatography over silica gel (SiO2, Grace, 80 g; eluent: from 90% heptane, 10% AcOEt to 40% heptane, 60% AcOEt). The pure fractions were collected and the solvent was evaporated to give intermediate 256 (1.13 g, 78%, purity 90%)

The intermediates in the Table below were prepared by using an analogous method starting from the respective starting materials.

| compound number | Structure | Mass (mg) | Yield (%) |
| --- | --- | --- | --- |
| Intermediate 257 | 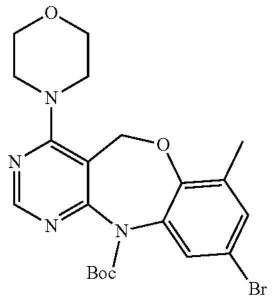 [SMILES: Cc1cc(Br)cc2c1OCc1c(N3CCOCC3)ncnc1N2C(=O)OC(C)(C)C] from intermediate 214 | 5900 | quant |

Example A82

Preparation of Intermediate 258

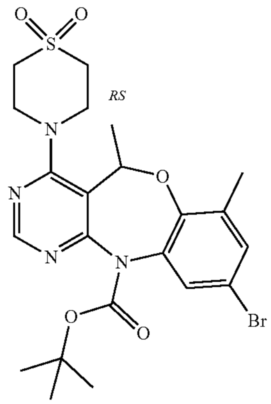 [SMILES: Cc1cc(Br)cc2c1OC(C)c1c(N3CCS(=O)(=O)CC3)ncnc1N2C(=O)OC(C)(C)C]

A light yellow suspension of intermediate 243 (94.5 g; 214.422 mmol), thiomorpholine-1,1-dioxide (28.987 g; 214.422 mmol) and triethylamine (239.09 mL; 0.726 g/mL; 1715.379 mmol) in t-BuOH (1000 mL) was stirred at 100° C. for 16 h to give a yellow solution. The reaction mixture was cooled to RT and concentrated under vacuum. The residue was diluted with ethyl acetate (1 L). The solution was washed with $H_2O$ (300 mL), brine (300 mL), dried over $MgSO_4$, filtered and concentrated under vacuum to give a yellow liquid, which was dissolved in $CH_2Cl_2$ (100 mL) and purified by flash column chromatography on silica gel (eluent: petroleum ether:ethyl acetate from 100:0 to 50:50, gradient). The desired fractions were collected and the solvent was evaporated under vacuum to give the product as a light yellow solid (100.37 g; 86%).

Preparation of Intermediate 258

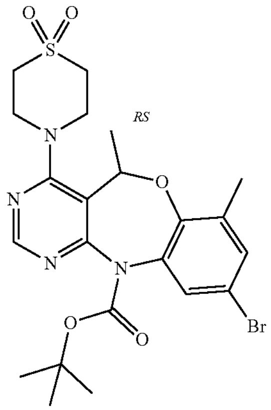 [SMILES: Cc1cc(Br)cc2c1OC(C)c1c(N3CCS(=O)(=O)CC3)ncnc1N2C(=O)OC(C)(C)C]

A suspension of intermediate 243 (57.5 g, 129.9 mmol), thiomorpholine NN-dioxide (70.3 g, 519.7 mmol) and triethylamine (144 mL, 1039.5 mmol) in tert-butanol (600 mL) was stirred at 100° C. for 64 h. The reaction solution was cooled to rt and concentrated under vacuum. The residue was diluted with ethyl acetate (500 mL). The solution was washed with $H_2O$/brine (1/1) (400 mL), brine (600 mL), dried over $MgSO_4$, filtered and concentrated under vacuum. The crude material was purified by column chromatography over silica gel (eluent: petroleum/ethyl acetate=100:0-50:50). The desired fractions were evaporated in vacuum to afford the racemic product as a white solid.

The intermediates in the Table below were prepared by using an analogous method starting from the respective starting materials.

| compound number | Structure | Mass (mg) | Yield (%) |
|---|---|---|---|
| Intermediate 674 | 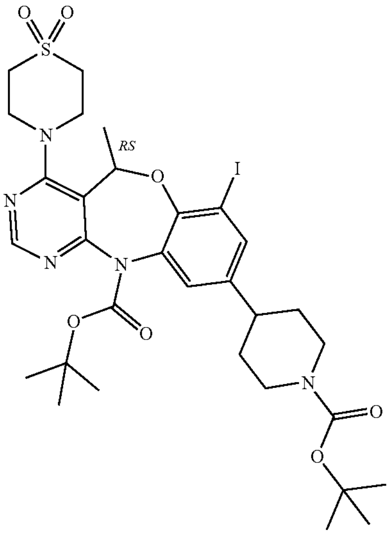 [SMILES: CC1Oc2c(I)cc(C3CCN(C(=O)OC(C)(C)C)CC3)cc2N(C(=O)OC(C)(C)C)c2ncnc(N3CCS(=O)(=O)CC3)c21] from intermediate 673, 16 h | 4000 | 58 |

Example A83

Preparation of Intermediate 259 & Intermediate 260

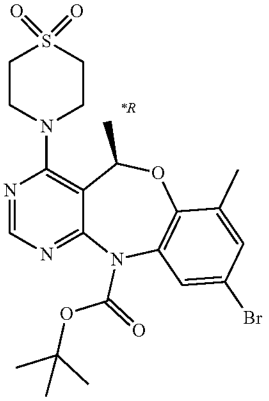

&

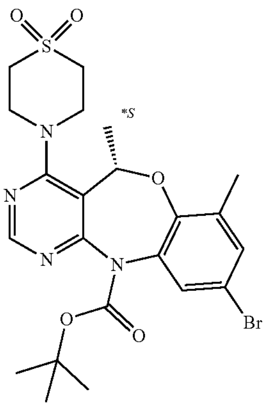

Intermediate 258 (110 g; 203.91 mmol) was purified via chiral SFC (Stationary phase: CHIRALPAK AD-H 5 μm 250*30 mm, Mobile phase: 85% $CO_2$, 15% EtOH). The pure fractions were collected and the solvent was evaporated until dryness to give intermediate 259 (53.5 g; 45%) and intermediate 260 (49.5 g; 41%), together with mixed fractions enriched in intermediate 260 (8.28 g). The mixed fractions were purified via chiral SFC (Stationary phase: CHIRALPAK AD-H 5 μm 250*30 mm, Mobile phase: 85% $CO_2$, 15% EtOH) to afford addition pure intermediate 260 (7.18 g; 6%). (Deprotection of intermediate 259 to give intermediate 667 and correlation with intermediate 664 confirmed the absolute configuration of the stereocentre in intermediate 259 to be R.)

Preparation of Intermediate 259 and Intermediate 260

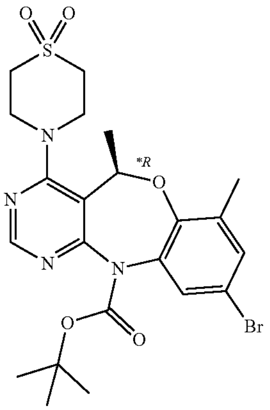

&

-continued

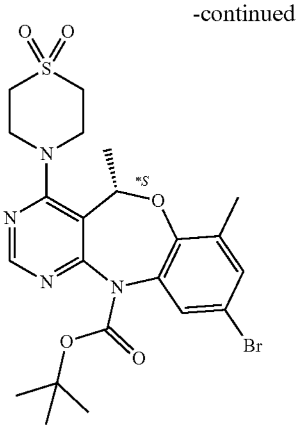

A purification was performed via chiral SFC (Stationary phase: CHIRALPAK AD-H 5 μm 250*30 mm, Mobile phase: 85% CO2, 15% EtOH). The pure fractions were collected and the solvent was evaporated to give intermediate 259 (23.9 g, 34%) and intermediate 260 (22.2 g, 32%). (Deprotection of intermediate 259 to give intermediate 667 and correlation with intermediate 664 confirmed the absolute configuration of the stereocentre in intermediate 259 to be R.)

Example A84

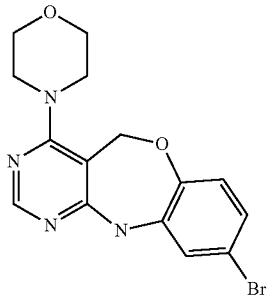 [SMILES: Brc1ccc2c(c1)Nc1ncnc(N3CCOCC3)c1CO2]

Preparation of Intermediate 261

In a sealed vessel, morpholine (6.9 mL; 79.99 mmol) was added to a solution of intermediate 207 (10 g; 32 mmol) and di-isopropylethylamine (14 mL; 79.99 mmol) in MeCN (380 mL) at rt. The reaction mixture was stirred at 100° C. overnight. Then, the mixture was diluted with water and extracted with EtOAc (3×). The combined organic layers were washed with brine, dried over $MgSO_4$, filtered and the solvent was evaporated to give the product as a brown solid that was used without further elaboration (11.77 g; quant.).

The intermediates in the Table below were prepared by using an analogous method starting from the respective starting materials.

| compound number | Structure | Mass (mg) | Yield (%) |
|---|---|---|---|
| Intermediate 262 | 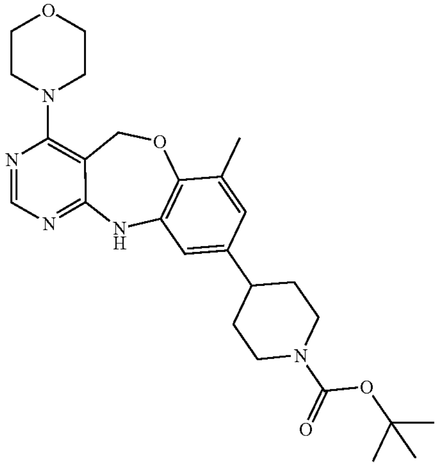 [SMILES: Cc1cc(C2CCN(C(=O)OC(C)(C)C)CC2)cc2c1OCc1c(ncnc1N1CCOCC1)N2] from intermediate 224 and morpholine | 316 | 55 |
| Intermediate 263 | 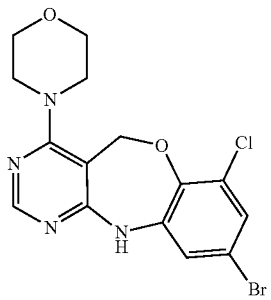 [SMILES: Clc1cc(Br)cc2c1OCc1c(ncnc1N1CCOCC1)N2] from intermediate 211 and morpholine | 2060 | 90 |

-continued
| compound number | Structure | Mass (mg) | Yield (%) |
|---|---|---|---|
| Intermediate 264 | 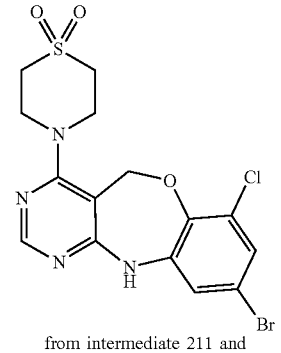 from intermediate 211 and thiomorpholine 1,1-dioxide | 3211 | quant. |
| Intermediate 265 | 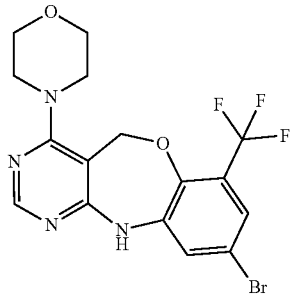 [SMILES: FC(F)(F)c1cc(Br)cc2c1OCc1c(ncnc1N1CCOCC1)N2] from intermediate 210 and morpholine | 2931 | 96 |
| Intermediate 266 | 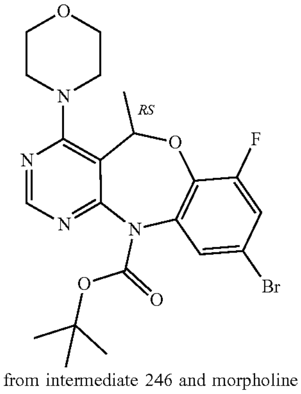 from intermediate 246 and morpholine | 3100 | 80 |
| Intermediate 258 | 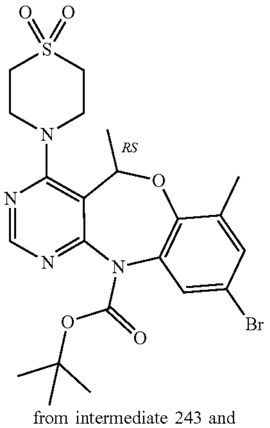 from intermediate 243 and thiomorpholine 1,1-dioxide | 8900 | 68 |

Example A85

Preparation of Intermediate 267

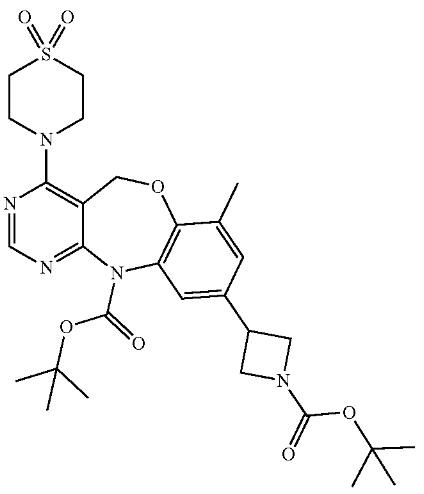 [SMILES: Cc1cc(C2CN(C(=O)OC(C)(C)C)C2)cc2c1OCc1c(N3CCS(=O)(=O)CC3)ncnc1N2C(=O)OC(C)(C)C]

In a sealed tube a mixture of intermediate 250 (500 mg, 0.99 mmol), thiomorpholine-1,1-dioxide (335 mg, 2.48 mmol) and triethylamine (510 μL, 0.728 g/mL, 3.67 mmol) in acetonitrile (12 mL) was heated in a sealed tube was stirred at 150° C. using one single mode microwave (Biotage Initiator EXP 60) with a power output ranging from 0 to 400 W for 10 min [fixed hold time]. The mixture was diluted with water and extracted with DCM. The organic layer was dried over MgSO4. The solvent was removed under vacuo. The residue was evaporated in vacuo and was purified by chromatography over silica gel ($SiO_2$, Grace, 40 g; eluent: from 100% DCM to 95% DCM, 5% MeOH, 0.5% $NH_4OH$). The pure fractions were collected and the solvent was evaporated to give intermediate 267 (227 mg, 38%).

Preparation of Intermediate 268

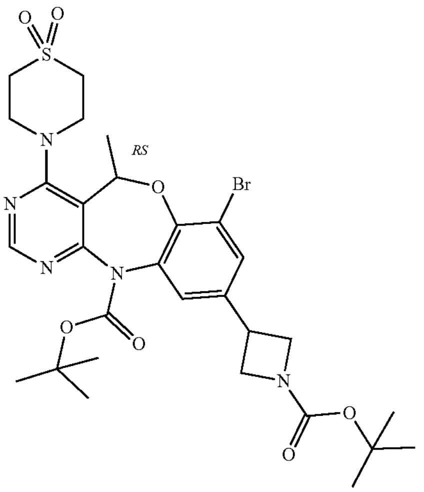 [SMILES: CC1Oc2c(Br)cc(C3CN(C(=O)OC(C)(C)C)C3)cc2N(C(=O)OC(C)(C)C)c2ncnc(N3CCS(=O)(=O)CC3)c21]

Following the protocol used for the preparation of intermediate 261 and using intermediate 255 (1.75 g; 3.007 mmol) and thiomorpholine 1,1-dioxide (0.813 g; 6.015 mmol) as starting materials, intermediate 268 (1.26 g; 62%) was obtained.

Preparation of Intermediate 675

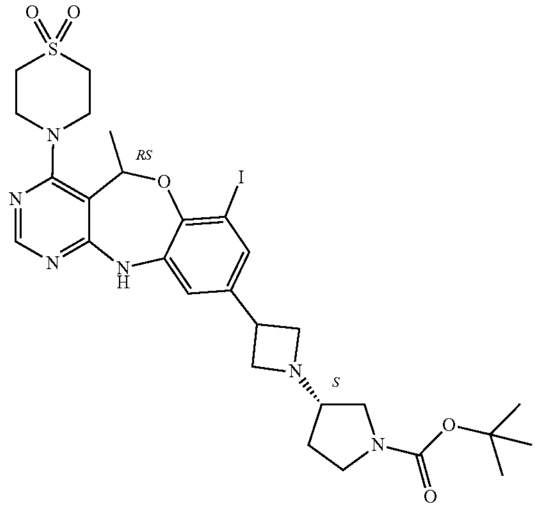

A suspension of intermediate 672 (550 mg, 0.87 mmol), thiomorpholine 1,1-dioxide (702 mg, 5.19 mmol) and DIPEA (0.6 mL, 3.46 mmol) in DMF (2 mL) was stirred at 100° C. for 16 h. The mixture was diluted with water (6 mL), then extracted with ethyl acetate (3*6 mL). The combined organic layers were washed with a solution of $H_2O$/brine 1/1 (10 mL), dried over $MgSO_4$, filtered and concentrated under vacuum. The crude material was purified by flash column chromatography over a 12 g silica gel (eluent: petroleum ether/ethyl acetate from 100/0 to 0/100, then ethyl acetate/methanol from 100/0 to 90/10, gradient). The residue was repurified by prep-TLC (DCM:MeOH=10:1) to give intermediate 675 (284 mg, 47%) as a light yellow solid.

Example A86

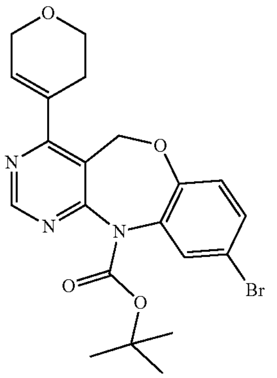 [SMILES: CC(C)(C)OC(=O)N1c2cc(Br)ccc2OCc2c(C3=CCOCC3)ncnc21]

Preparation of Intermediate 269

A solution of intermediate 244 (1.2 g; 2.96 mmol), 3,6-dihydro-2H-pyran-4-boronic acid pinacol ester (747 mg;

3.56 mmol) and $Na_2CO_3$ (5.9 mL; 1 mol/L; 5.93 mmol) in 1,4-dioxane (40 mL) was degassed under $N_2$ for 15 minutes. Bis(triphenylphosphine)palladium(II) dichloride (104 mg; 0.15 mmol) was added and the reaction mixture was heated at 80° C. for 1 hour. The mixture was cooled down to rt, diluted with EtOAc and filtered over Celite®. Filtrate was washed with a 1M $Na_2CO_3$ solution and the organic layer was dried over $MgSO_4$, filtered and concentrated in vacuo. The residue was purified by flash column chromatography ($SiO_2$, from 100% Heptane—0% EtOAc to 50% Heptane—50% EtOAc) to give the product (881 mg; 62%) as a yellow oil.

The intermediates in the Table below were prepared by using an analogous method starting from the respective starting materials.

| compound number | Structure | Mass (mg) | Yield (%) |
|---|---|---|---|
| Intermediate 270 | 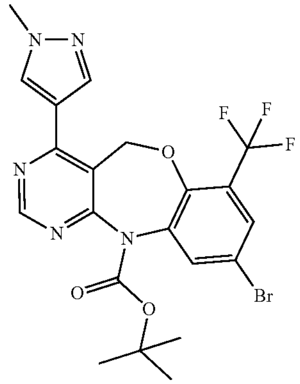 [SMILES: Cn1cc(-c2ncnc3c2COc2c(cc(Br)cc2C(F)(F)F)N3C(=O)OC(C)(C)C)cn1] from intermediate 245 and 1-methylpyrazole-4-boronic acid, pinacol ester | 463 | 40 |
| Intermediate 271 | 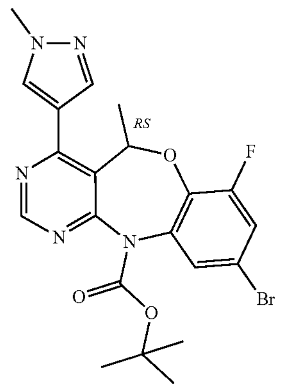 [SMILES: CC1Oc2c(F)cc(Br)cc2N(C(=O)OC(C)(C)C)c2ncnc(-c3cnn(C)c3)c21] from intermediate 246 and 1-methylpyrazole-4-boronic acid, pinacol ester | 811 | 35 |

Example A87

Preparation of Intermediate 272

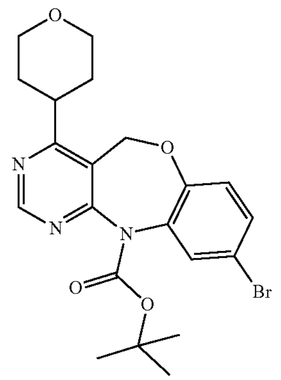 [SMILES: CC(C)(C)OC(=O)N1c2cc(Br)ccc2OCc2c(C3CCOCC3)ncnc21]

To a solution of intermediate 244 (1.55 g; 3.756 mmol), [1,1'-bis(diphenylphosphino)ferrocene]dichloropalladium (II) (153 mg; 0.188 mmol) and CuI (71.5 mg; 0.376 mmol) in DMA (8 mL) under $N_2$ atmosphere was added a solution of intermediate 9 (0.56 mol/L; 4.507 mmol). The resulting solution was stirred at 80° C. for overnight. The reaction mixture was cooled down to rt, diluted with EtOAc and washed with a sat. $NH_4Cl$ solution and with brine. The organic layer was dried over $MgSO_4$, filtered and concentrated in vacuo. The residue was purified by column chromatography over silica gel ($SiO_2$; from 100% Heptane—0% EtOAc to 60% Heptane—40% EtOAc). The desired fractions were collected and evaporated under reduced pressure to afford the product (706 mg; 33%).

The intermediates in the Table below were prepared by using an analogous method starting from the respective starting materials.

| compound number | Structure | Mass (mg) | Yield (%) |
|---|---|---|---|
| Intermediate 273 | 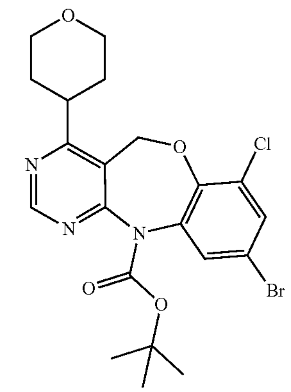 [SMILES: CC(C)(C)OC(=O)N1c2cc(Br)cc(Cl)c2OCc2c(C3CCOCC3)ncnc21] from intermediate 247 and intermediate 9 | 1300 | 37 |
| Intermediate 274 | 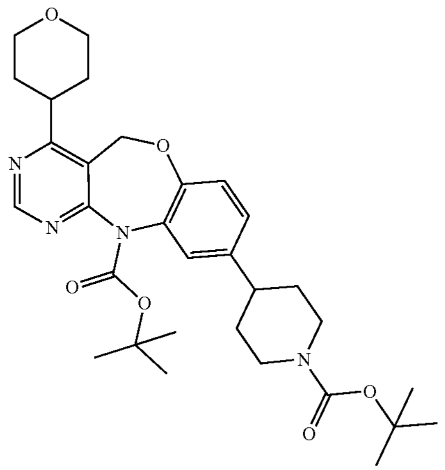 [SMILES: CC(C)(C)OC(=O)N1CCC(c2ccc3c(c2)N(C(=O)OC(C)(C)C)c2ncnc(C4CCOCC4)c2CO3)CC1] from intermediate 10 and intermediate 272 | 401 | 37 |
| Intermediate 275 | 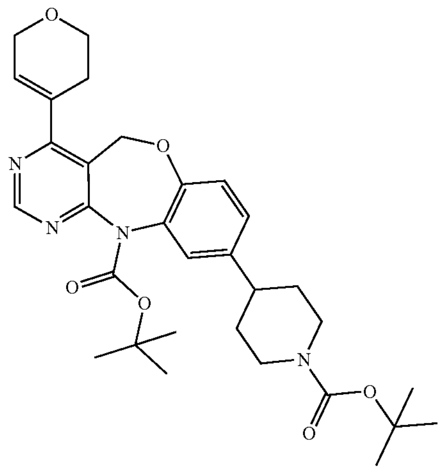 [SMILES: CC(C)(C)OC(=O)N1CCC(c2ccc3c(c2)N(C(=O)OC(C)(C)C)c2ncnc(C4=CCOCC4)c2CO3)CC1] from intermediate 10 and intermediate 269 | 266 | 23 (Purity 84%) |

-continued
| compound number | Structure | Mass (mg) | Yield (%) |
|---|---|---|---|
| Intermediate 276 | 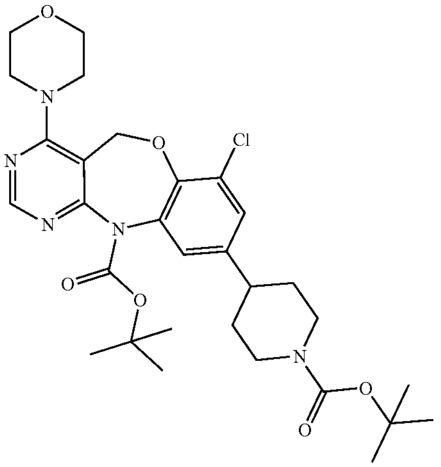 [SMILES: CC(C)(C)OC(=O)N1CCC(c2cc(Cl)c3c(c2)N(C(=O)OC(C)(C)C)c2ncnc(N4CCOCC4)c2CO3)CC1] from intermediate 10 and intermediate 251 | 940 | 56 |
| Intermediate 277 | 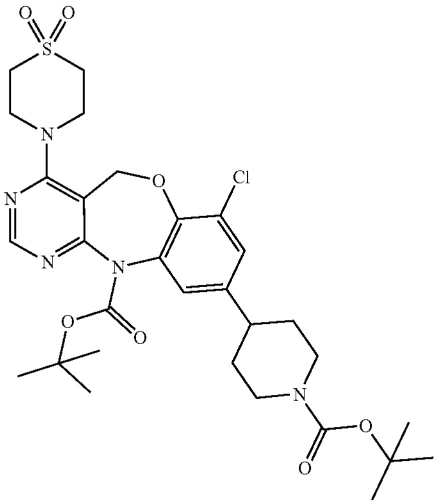 [SMILES: CC(C)(C)OC(=O)N1CCC(c2cc(Cl)c3c(c2)N(C(=O)OC(C)(C)C)c2ncnc(N4CCS(=O)(=O)CC4)c2CO3)CC1] from intermediate 10 and intermediate 252 | 1146 | 62 |
| Intermediate 278 | 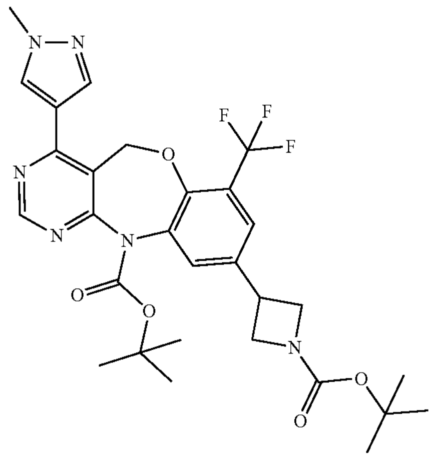 [SMILES: Cn1cc(-c2ncnc3c2COc2c(cc(C4CN(C(=O)OC(C)(C)C)C4)cc2C(F)(F)F)N3C(=O)OC(C)(C)C)cn1] from intermediate 270 and intermediate 11 | 209 | 39 |

-continued
| compound number | Structure | Mass (mg) | Yield (%) |
|---|---|---|---|
| Intermediate 279 | 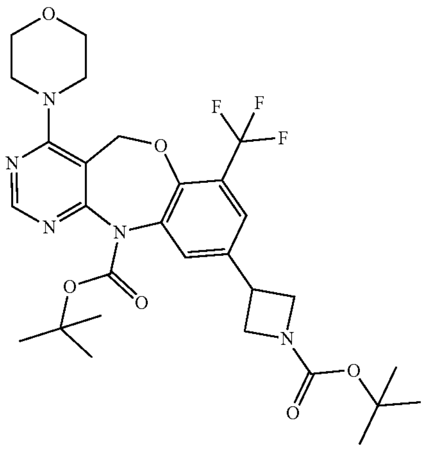 [SMILES: CC(C)(C)OC(=O)N1CC(c2cc3c(c(C(F)(F)F)c2)OCc2c(N4CCOCC4)ncnc2N3C(=O)OC(C)(C)C)C1] from intermediate 11 and intermediate 253 | 319 | 20 |
| Intermediate 280 | 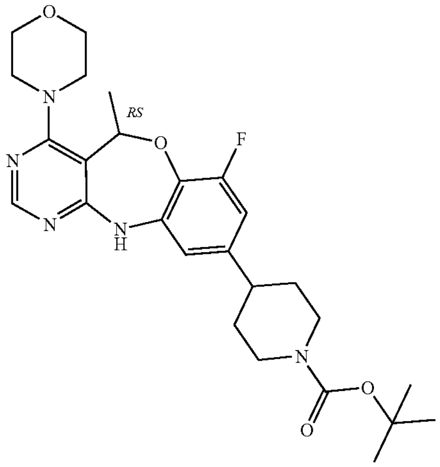 [SMILES: CC1Oc2c(F)cc(C3CCN(C(=O)OC(C)(C)C)CC3)cc2Nc2ncnc(N3CCOCC3)c21] from intermediate 10 and intermediate 266-only compound minus one Boc group was isolated | 679 | 45 |
| Intermediate 281 | 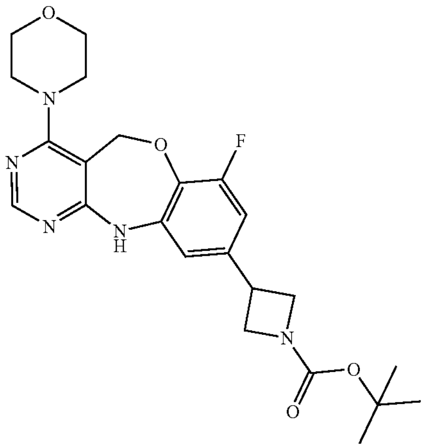 [SMILES: CC(C)(C)OC(=O)N1CC(c2cc(F)c3c(c2)Nc2ncnc(N4CCOCC4)c2CO3)C1] from intermediate 11 and intermediate 248-only compound minus one Boc group was isolated | 3000 | 46 |

-continued
| compound number | Structure | Mass (mg) | Yield (%) |
|---|---|---|---|
| Intermediate 282 | 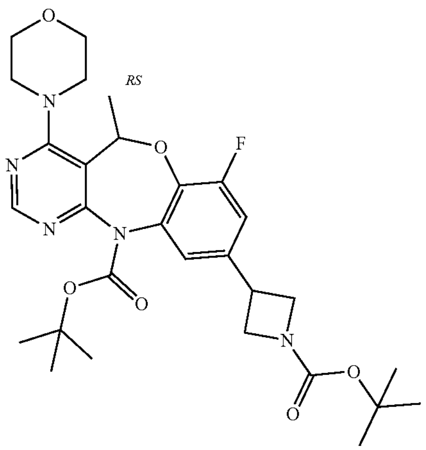 [SMILES: CC1Oc2c(F)cc(C3CN(C(=O)OC(C)(C)C)C3)cc2N(C(=O)OC(C)(C)C)c2ncnc(N3CCOCC3)c21] from intermediate 11 and intermediate 266-also compound minus one Boc group was isolated | 1100 | 64 |
| Intermediate 283 | 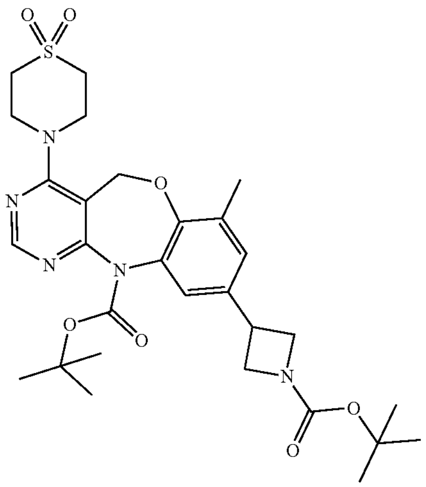 [SMILES: Cc1cc(C2CN(C(=O)OC(C)(C)C)C2)cc2c1OCc1c(N3CCS(=O)(=O)CC3)ncnc1N2C(=O)OC(C)(C)C] from intermediate 11 and intermediate 249 | 785 | 70 |

Example A88

Preparation of Intermediate 284

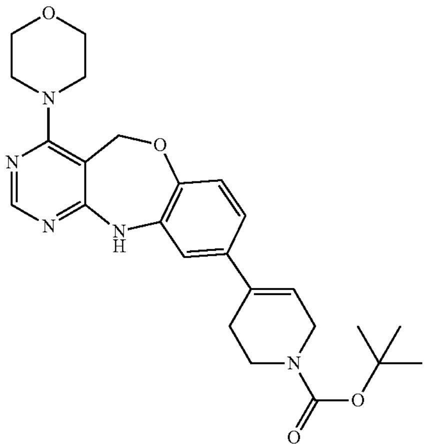 [SMILES: CC(C)(C)OC(=O)N1CC=C(c2ccc3c(c2)Nc2ncnc(N4CCOCC4)c2CO3)CC1]

In a sealed vessel, a solution of intermediate 261 (11.68 g; 32.2 mmol), tert-butyl 4-(4,4,5,5-tetramethyl-1, 3,2-dioxaborolan-2-yl)-3,6-dihydro-2H-pyridine-1-carboxylate (11.9 g; 38.6 mmol) and $K_3PO_4$ (13.65 g; 64.3 mmol) in dioxane (224 mL) and water (32 mL) was degassed under $N_2$. [1,1'-bis(diphenylphosphino)ferrocene]dichloropalladium(II), complex with dichloromethane (2.63 g; 3.22 mmol) was added, the reaction mixture was degassed again under $N_2$ and heated at 80° C. for 4 hours. The reaction mixture was cooled to room temperature, poured into water and extracted with EtOAc. The organic layer was decanted, washed with water then brine, dried over $MgSO_4$, filtered over Celite® and evaporated to dryness. The resultant residue was crystallized from MeCN, filtered and dried to afford the product (12.68 g; 85%).

The intermediates in the Table below were prepared by using an analogous method starting from the respective starting materials.

| compound number | Structure | Mass (mg) | Yield (%) |
|---|---|---|---|
| Intermediate 285 | 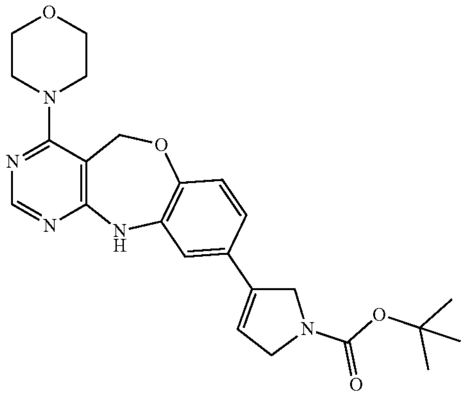 [SMILES: CC(C)(C)OC(=O)N1CC=C(c2ccc3c(c2)Nc2ncnc(N4CCOCC4)c2CO3)C1] from intermediate 261 and 3-(4,4,5,5-tetramethyl-[1,3,2]dioxaborolan-2-yl)-2,5-dihydro-pyrrole-1-carboxylic acid tert-butyl ester, using aqueous $Na_2CO_3$ as base | 1760 | quant |
| Intermediate 286 | 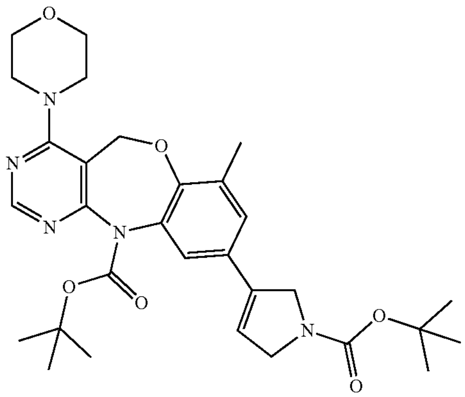 [SMILES: Cc1cc(C2=CCN(C(=O)OC(C)(C)C)C2)cc2c1OCc1c(N3CCOCC3)ncnc1N2C(=O)OC(C)(C)C] from intermediate 257 and 3-(4,4,5,5-tetramethyl-[1,3,2]dioxaborolan-2-yl)-2,5-dihydro-pyrrole-1-carboxylic acid tert-butyl ester, using aqueous $Na_2CO_3$ as base | 2840 | 80 |

-continued
| compound number | Structure | Mass (mg) | Yield (%) |
| --- | --- | --- | --- |
| Intermediate 287 | 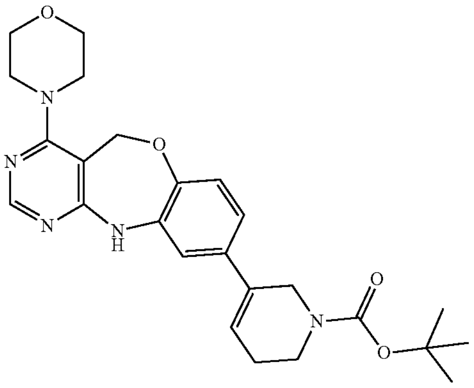 [SMILES: CC(C)(C)OC(=O)N1CCC=C(c2ccc3c(c2)Nc2ncnc(N4CCOCC4)c2CO3)C1] from intermediate 261 and 1-boc-5,6-dihydro-2H-pyridine-3-boronic acid pinacol ester | 732 | 95 |
| Intermediate 288 | 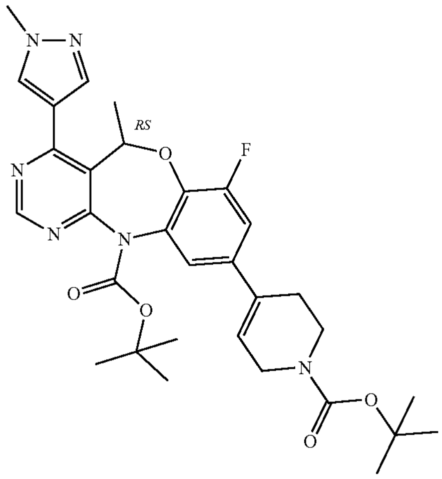 [SMILES: CC1Oc2c(F)cc(C3=CCN(C(=O)OC(C)(C)C)CC3)cc2N(C(=O)OC(C)(C)C)c2ncnc(-c3cnn(C)c3)c21] from intermediate 271 and N-Boc-1,2,3,6-tetrahydropyridine-4-boronic acid pinacol ester | 827 | 84 |
| Intermediate 289 | 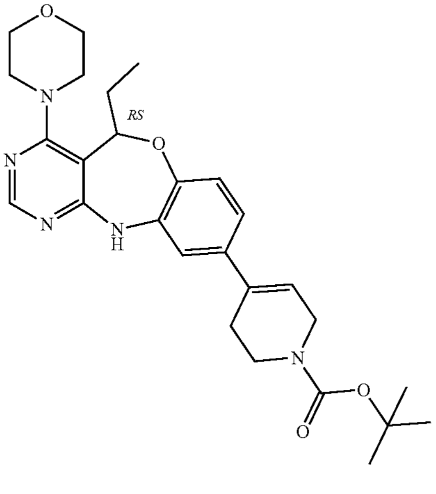 [SMILES: CCC1Oc2ccc(C3=CCN(C(=O)OC(C)(C)C)CC3)cc2Nc2ncnc(N3CCOCC3)c21] from intermediate 215 and N-Boc-1,2,3,6-tetrahydropyridine-4-boronic acid pinacol ester | 534 | 86 |

-continued
| compound number | Structure | Mass (mg) | Yield (%) |
| --- | --- | --- | --- |
| Intermediate 290 | 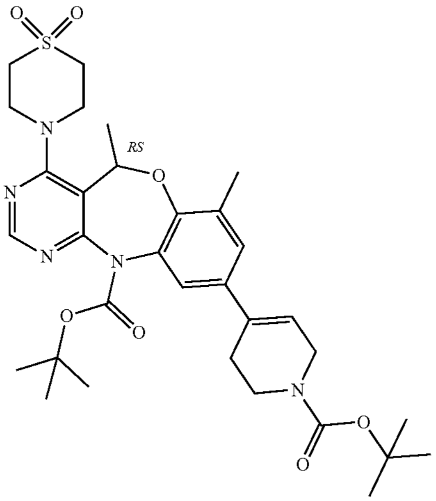 [SMILES: Cc1cc(C2=CCN(C(=O)OC(C)(C)C)CC2)cc2c1OC(C)c1c(N3CCS(=O)(=O)CC3)ncnc1N2C(=O)OC(C)(C)C] from intermediate 258 and N-Boc-1,2,3,6-tetrahydropyridine-4-boronic acid pinacol ester | 1996 | 84 |
| Intermediate 291 | 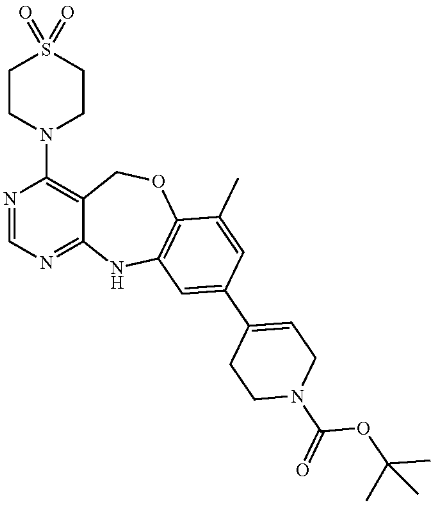 [SMILES: Cc1cc(C2=CCN(C(=O)OC(C)(C)C)CC2)cc2c1OCc1c(ncnc1N1CCS(=O)(=O)CC1)N2] from intermediate 216 | 115 | 33 |

Example A89

Preparation of Intermediate 676: 0

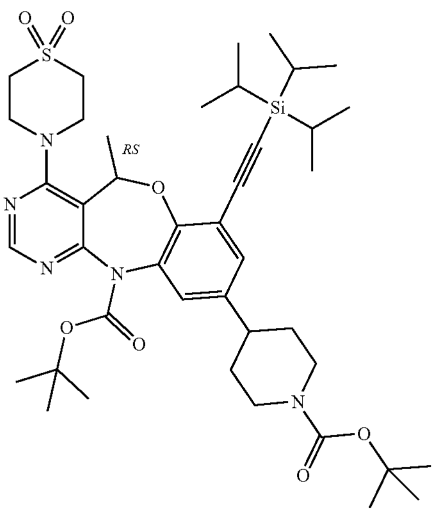 [SMILES: CC1Oc2c(C#C[Si](C(C)C)(C(C)C)C(C)C)cc(C3CCN(C(=O)OC(C)(C)C)CC3)cc2N(C(=O)OC(C)(C)C)c2ncnc(N3CCS(=O)(=O)CC3)c21]

A mixture of intermediate 674 (1100 mg, 1.46 mmol), (2-dicyclohexylphosphino-2',4',6'-triisopropyl-1,1'-biphenyl)[2-(2'-amino-1,1'-biphenyl)]palladium(II) methanesulfonate (123 mg, 0.15 mmol) and cesium carbonate (1233 mg, 3.78 mmol) in toluene (15 mL) was stirred at rt under nitrogen for 1 h. (Triisopropylsilyl)acetylene (0.65 mL, 2.91 mmol) was added dropwise and the mixture was stirred at 80° C. for 3 h. Water (20 mL) was added, the aqueous layer was extracted with EtOAc (2*20 mL), the organic layer was washed with brine (10 mL), dried over anhydrous $Na_2SO_4$ and concentrated. The crude material was purified by flash column chromatography (eluent:petroleumn ether:Ethyl acetate=100:0-0:100) to afford intermediate 676 (1120 mg, 95%) as a light yellow solid.

The intermediates in the Table below were prepared by using an analogous method starting from the respective starting materials.

| compound number | Structure | Mass (mg) | Yield (%) |
| --- | --- | --- | --- |
| Intermediate 677 | 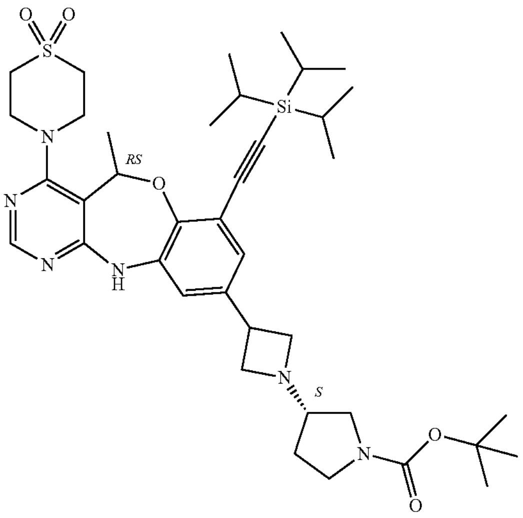 from intermediate 675 | 240 | 67 |

Example A90

Preparation of Intermediate 292

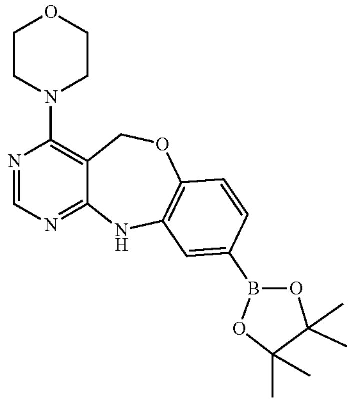 [SMILES: CC1(C)OB(c2ccc3c(c2)Nc2ncnc(N4CCOCC4)c2CO3)OC1(C)C]

[1,1'-bis(diphenylphosphino)ferrocene]dichloropalladium(II), complex with dichloromethane (113 mg; 0.138 mmol) was added to a solution of intermediate 261 (1 g; 2.753 mmol), bis(pinacolato)diboron (839 mg; 3.304 mmol), potassium acetate (540 mg; 5.506 mmol) in 1,4-dioxane (21 mL) under a $N_2$ atmosphere. The reaction mixture was stirred at 80° C. for overnight. The mixture was concentrated under vacuum and purified by flash chromatography ($SiO_2$; Heptane/EtOAc). The desired fractions were combined and concentrated in vacuo to afford the product (1.01 g; 89%).

Example A91

Preparation of Intermediate 293

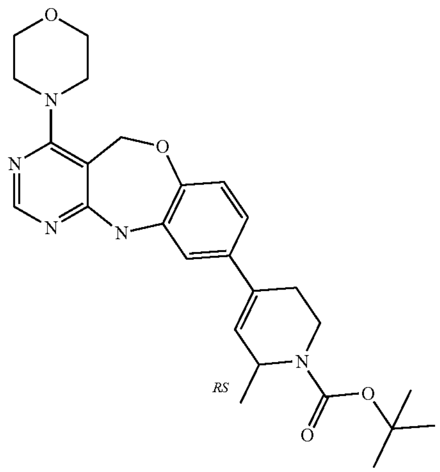

-continued

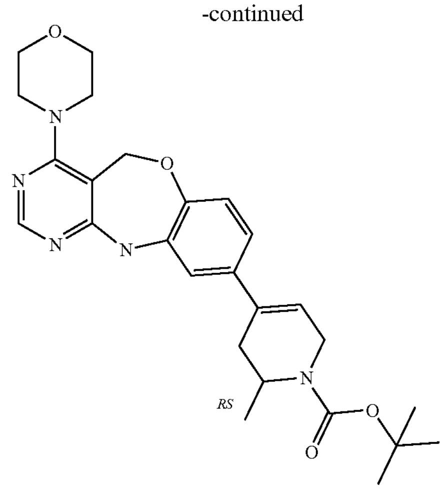

In a sealed vessel, a solution of intermediate 261 (262.19 mg; 0.722 mmol), intermediate 68 (700 mg; 1.083 mmol) and $Na_2CO_3$ (0.722 mL; 2 mol/L; 1.44 mmol) in 1,4-dioxane (4 mL) was degassed under $N_2$. [1,1'-bis(diphenylphosphino)ferrocene]dichloropalladium(II), complex with dichloromethane (23.52 mg; 0.036 mmol) was added, the reaction mixture was degassed again under $N_2$ and heated at 90° C. for 16 hours. The reaction mixture was cooled to room temperature, poured into water and extracted with EtOAc. The organic layer was decanted, washed with water then brine, dried over $MgSO_4$, filtered over Celite® and evaporated to dryness. The resultant residue was purified by column chromatography ($SiO_2$; EtOAc/Heptane). The desired fractions were combined and concentrated in vacuo to afford the product (430 mg; 62%).

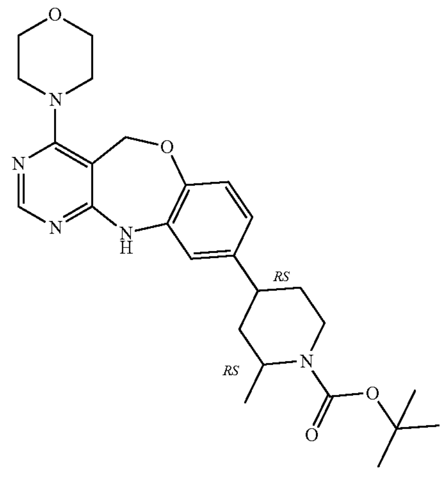 [SMILES: CC1CC(c2ccc3c(c2)Nc2ncnc(N4CCOCC4)c2CO3)CCN1C(=O)OC(C)(C)C]

Preparation of Intermediate 294

A solution of intermediate 293 (856 mg; 0.892 mmol) and Pd/C (10%) (0.6 g) in MeOH (9 mL) and THF (9 mL) was hydrogenated at rt for 12 hours under atmospheric pressure. The reaction mixture was filtered through a pad of Celite® to remove catalyst and the filtrate was evaporated to give the product (330 mg; 77%).

Example A92

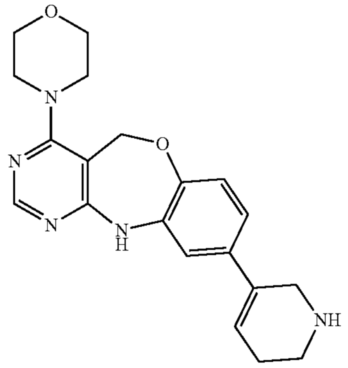 [SMILES: C1=C(c2ccc3c(c2)Nc2ncnc(N4CCOCC4)c2CO3)CNCC1]

Preparation of Intermediate 295

A solution of HCl in dioxane (4M; 7.9 mL; 31.45 mmol) was added to a solution of intermediate 287 (0.73 g; 1.57 mmol) in DCM (79 mL) at rt. The reaction mixture was stirred at rt for the 1 hour. Volatiles were moved under reduced pressure to afford the product (689 mg; 100%) which was used in the next step without further purification.

Preparation of Intermediate 296

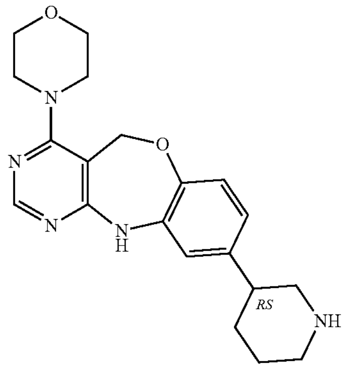 [SMILES: c1nc2c(c(N3CCOCC3)n1)COc1ccc(C3CCCNC3)cc1N2]

A solution of intermediate 295 (689 mg; 1.57 mmol) and Pd/C (10%) (79 mg) in MeOH (31 mL) and THF (31 mL) was hydrogenated at room temperature for 15 hours under atmospheric pressure. The reaction mixture was filtered through a pad of Celite® to remove catalyst and the filtrate was evaporated. The residue was dissolved in DCM and a 10% aqueous solution of $NaHCO_3$ and extracted. The organic phase was dried over $MgSO_4$, filtered and concentrated under reduced pressure to afford the product as a free basis (402 mg; 70%)

Example A93

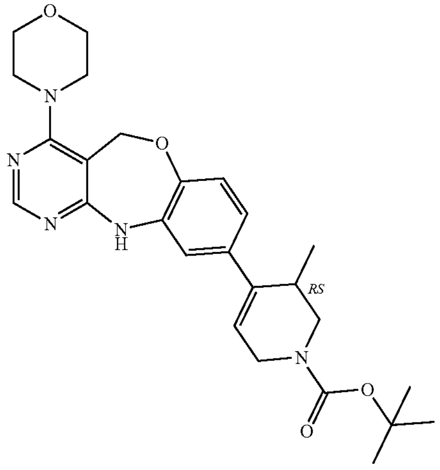 [SMILES: CC1CN(C(=O)OC(C)(C)C)CC=C1c1ccc2c(c1)Nc1ncnc(N3CCOCC3)c1CO2]

Preparation of Intermediate 297

In a sealed tube, a solution of intermediate 292 (600 mg; 1.448 mmol), intermediate 66 (749.97 mg; 2.172 mmol) and $K_3PO_4$ (627.19 mg, 2.896 mmol) in 1,4-dioxane (10.1 mL) and distilled water (1.4 mL) was degassed under N2 for 5 minutes. [1,1'-Bis(diphenylphosphino)ferrocene]dichloropalladium(II), complex with dichloromethane (118.53 mg, 0.145 mmol) was added and the resulting solution was stirred for 2 hours et 80° C. The resulting mixture was partitioned between EtOAc and brine. The organic layer was dried over $MgSO_4$, filtered and concentrated under vacuum. The residue was purified by chromatography over silica gel ($SiO_2$, eluent: from 100% Heptane, 0% EtOAc to 0% Heptane, 100% EtOAc). The pure fractions were combined and concentrated to afford the product (800 mg; 94%) as a yellow solid.

The intermediates in the Table below were prepared by using an analogous method starting from the respective starting materials.

| compound number | Structure | Mass (mg) | Yield (%) |
|---|---|---|---|
| Intermdiate 298 | 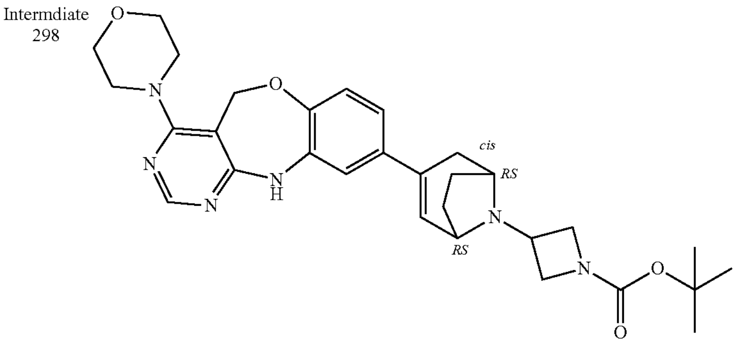 from intermediate 292 and intermediate 67 | 1029 | 73 |

Example A94

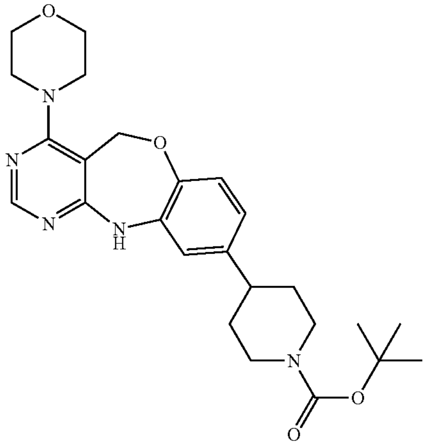 [SMILES: CC(C)(C)OC(=O)N1CCC(c2ccc3c(c2)Nc2ncnc(N4CCOCC4)c2CO3)CC1]

Preparation of Intermediate 299: 0

A solution of intermediate 284 (2.5 g; 5.37 mmol) and Pd/C (10%) (1 g) in MeOH (90 mL) and EtOAc (90 mL) was hydrogenated at room temperature under 3 bars of $H_2$ for 18 hours. The reaction mixture was combined with an analogous reaction (running in parallel on a 500 mg scale) for work up. The combined reactions were filtered through a pad of Celite® to remove catalyst and the filtrate was evaporated to give the product as a brown foam (2.89 g; 96%).

Preparation of Intermediate 300 and Intermediate 301

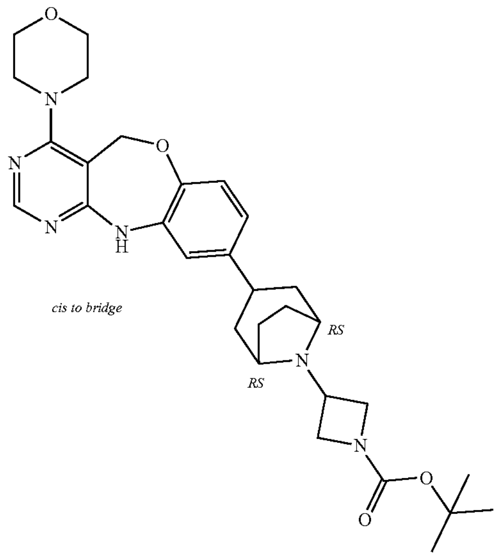

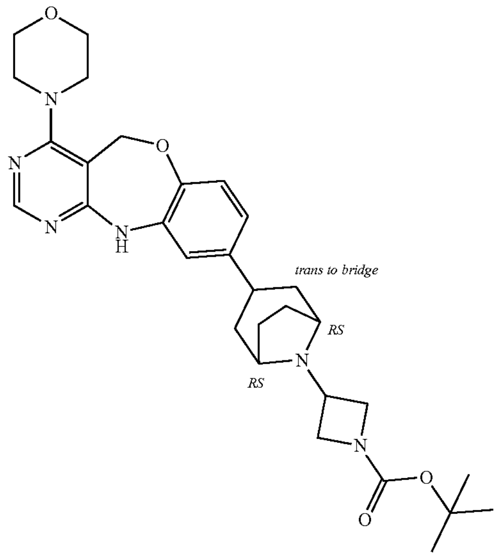

A solution of intermediate 298 (1.03 g; 1.66 mmol) and Pd/C (10%) (83 mg) in MeOH (33 mL) was hydrogenated at rt for 4 days under atmospheric pressure. The reaction mixture was filtered through a pad of Celite® to remove catalyst and the filtrate was evaporated. The residue was purified by reverse phase chromatography to afford the endo product intermediate 300 (76 mg; 8%) and the exo product intermediate 301 (150 mg; 16%).

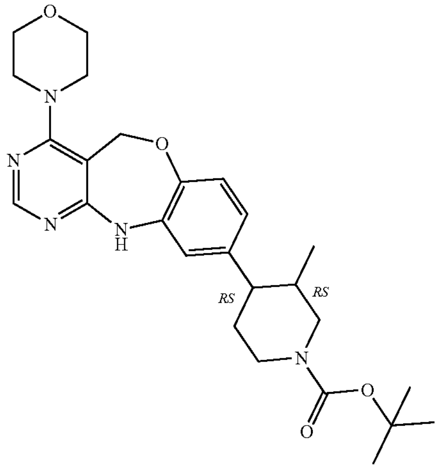 [SMILES: CC1CN(C(=O)OC(C)(C)C)CCC1c1ccc2c(c1)Nc1ncnc(N3CCOCC3)c1CO2]

Preparation of Intermediate 302

A solution of intermediate 297 (800 mg; 1.368 mmol) and Pd/C (10%) (440 mg) in MeOH (20 mL) and THF (20 mL) was hydrogenated at rt for 4 days under atmospheric pressure. The reaction mixture was filtered through a pad of Celite® to remove catalyst and the filtrate was evaporated. The residue was purified by chromatography over silica gel ($SiO_2$, eluent: from 100% Heptane, 0% EtOAc to 0% Heptane, 100% EtOAc) to give the product (414 mg; 47%) as a brown oil.

The intermediates in the Table below were prepared by using an analogous method starting from the respective starting materials.

| compound number | Structure | Mass (mg) | Yield (%) |
|---|---|---|---|
| Intermediate 303 | 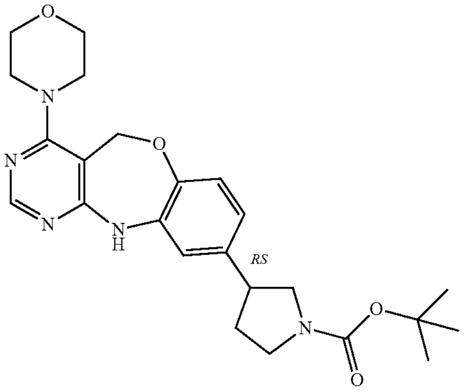 [SMILES: CC(C)(C)OC(=O)N1CCC(c2ccc3c(c2)Nc2ncnc(N4CCOCC4)c2CO3)C1] from intermediate 285; solvent 1:1 MeOH:ethyl acetate | 1080 | 60 |
| Intermediate 304 | 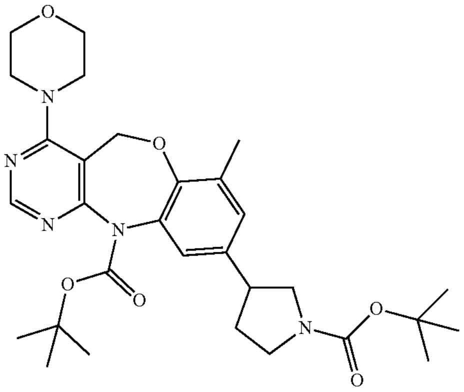 [SMILES: Cc1cc(C2CCN(C(=O)OC(C)(C)C)C2)cc2c1OCc1c(N3CCOCC3)ncnc1N2C(=O)OC(C)(C)C] from intermediate 286; solvent 1:1 MeOH:ethyl acetate | 2730 | 97 |
| Intermediate 305 | 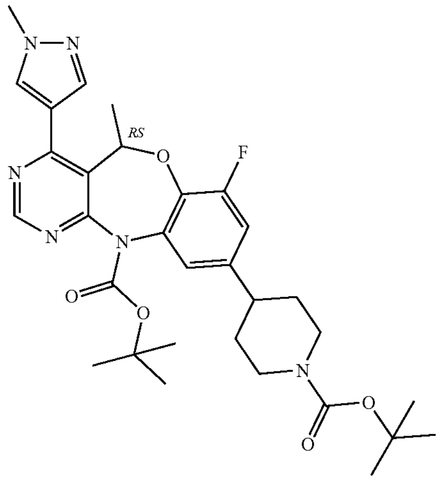 [SMILES: CC1Oc2c(F)cc(C3CCN(C(=O)OC(C)(C)C)CC3)cc2N(C(=O)OC(C)(C)C)c2ncnc(-c3cnn(C)c3)c21] from intermediate 288 | 788 | 95 |

-continued
| compound number | Structure | Mass (mg) | Yield (%) |
|---|---|---|---|
| Intermediate 306 | 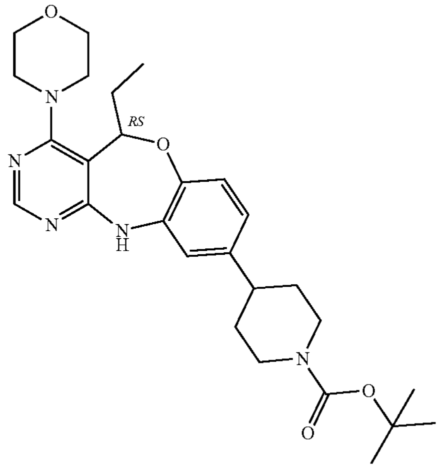 [SMILES: CCC1Oc2ccc(C3CCN(C(=O)OC(C)(C)C)CC3)cc2Nc2ncnc(N3CCOCC3)c21] from intermediate 289 | 470 | 87 |
| Intermediate 307 | 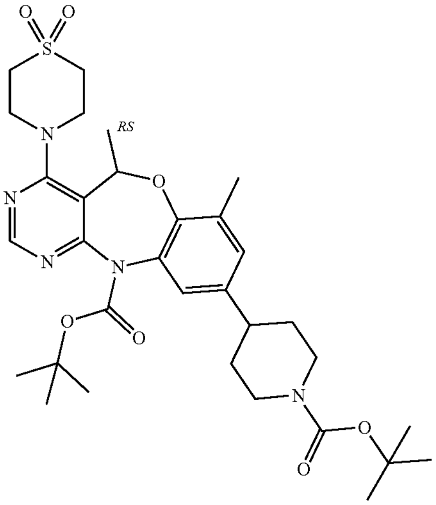 [SMILES: Cc1cc(C2CCN(C(=O)OC(C)(C)C)CC2)cc2c1OC(C)c1c(N3CCS(=O)(=O)CC3)ncnc1N2C(=O)OC(C)(C)C] from intermediate 290 | 2002 | quant. |

Example A95

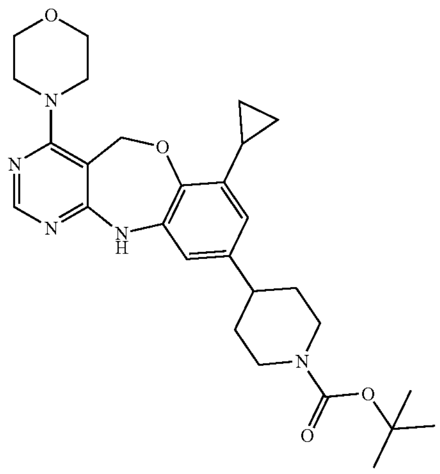 [SMILES: CC(C)(C)OC(=O)N1CCC(c2cc3c(c(C4CC4)c2)OCc2c(ncnc2N2CCOCC2)N3)CC1]

Preparation of Intermediate 308

Intermediate 205 (1.34 g, 2.45 mmol), cyclopropylboronic acid (843 mg, 9.81 mmol), potassium phosphate (2.08 g, 9.81 mmol) and $PdCl_2(dppf)_2$·DCM (200.3 mg, 0.245 mmol) in 1,4-dioxane (20 mL) and distilled water (3 mL) in a sealed tube were stirred at 100° C. for 36 hours. Once the reaction was complete, the reaction mixture was filtered through a pad of Celite© and the filtrate was extracted with EtOAc. Organic layers were combined, washed with brine, dried over $MgSO_4$, filtered and concentrated under reduced pressure. The residue was purified by column chromatography over silica gel ($SiO_2$, from 100% DCM—0% MeOH to 95% DCM—5% MeOH) to afford the product (450 mg; 35%).

Example A96

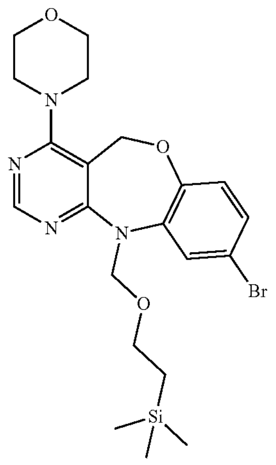 [SMILES: C[Si](C)(C)CCOCN1c2cc(Br)ccc2OCc2c(N3CCOCC3)ncnc21]

Preparation of Intermediate 309

At 5° C. under nitrogen flux, NaH (60% dispersion in mineral oil) (1.01 g, 25.252 mmol) was added to a mixture of intermediate 261 (7.07 g, 19.465 mmol) in DMF (90 mL, 0.944 g/mL, 1162.328 mmol). The reaction was stirred for 20 minutes at 0° C. then 2-(chloromethoxy)ethyltrimethylsilane (4.15 mL, 0.94 g/mL, 23.398 mmol) was added and the reaction was stirred at room temperature for 1 hour. Water was added and the mixture was extracted three times with EtOAc. The organic layer was decanted and the solvent was evaporated until dryness to give the crude product. This crude was purified via preparative LC (Stationary phase: irregular SiOH 15-40 μm 120 g GraceResolv®, Mobile phase: gradient from 100% Heptane to 70% Heptane, 30% EtOAc). The pure fractions were combined and the solvent was evaporated in vacuo to give the desired product (3.11 g; 32%). (Impure fractions were repurified by preparative LC (Stationary phase: irregular SiOH 15-40 μm 120 g Grace, Mobile phase: gradient from 100% Heptane to 70% Heptane, 30% EtOAc) to afford a further 1.81 g (19%) of product.)

Preparation of Intermediate 310

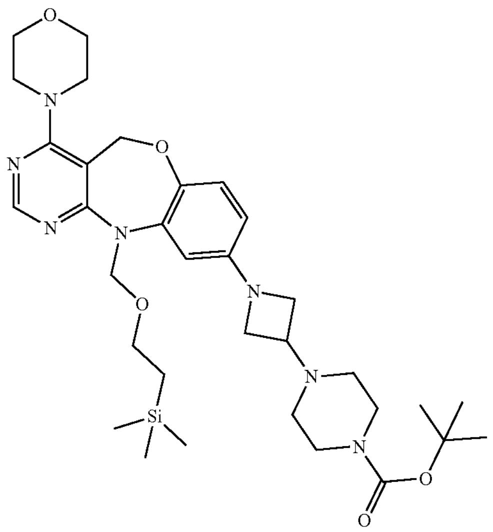 [SMILES: CC(C)(C)OC(=O)N1CCN(C2CN(c3ccc4c(c3)N(COCC[Si](C)(C)C)c3ncnc(N5CCOCC5)c3CO4)C2)CC1]

NaOtBu (2.272 mL, 1 M, 2.272 mmol) was added to a suspension of intermediate 309 (0.701 g, 1.42 mmol), 1-N-BOC-4-azetidin-3-yl-piperazine (514 mg, 2.13 mmol), RuPhos (53.007 mg, 0.114 mmol) and RuPhos precatalyst (46.393 mg, 0.0568 mmol) in 4-methyltetrahydropyran (10.621 mL, 0.857 g/mL, 90.873 mmol) in a sealed tube. The reaction mixture was stirred at 140° C. using one single mode microwave (Anton Paar Monowave300) with a power output ranging from 0 to 850 W for 10 min. (fixed hold time). Water and DCM was added and the whole was evaporated with Celite© in order to perform solid deposite purification. A purification was performed via preparative LC (Stationary phase: irregular SiOH 15-40 μm 80 g Grace, Mobile phase: gradient from 80% Heptane, 20% EtOAc to 40% Heptane, 50% EtOAc, 10% MeOH (5% $NH_4OH$)) to afford the product (778 mg; 84%)

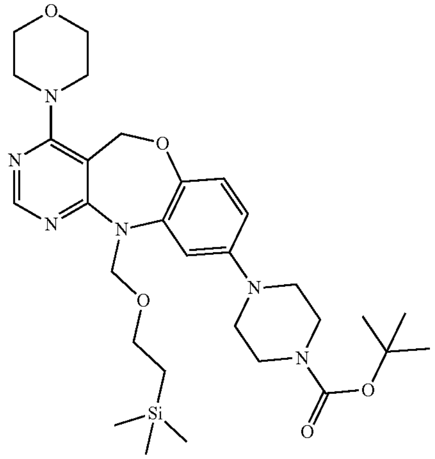 [SMILES: CC(C)(C)OC(=O)N1CCN(c2ccc3c(c2)N(COCC[Si](C)(C)C)c2ncnc(N4CCOCC4)c2CO3)CC1]

Preparation of Intermediate 311

NaOtBu (5.836 mL, 1 M, 5.836 mmol) was added to a suspension of intermediate 309 (1.8 g, 3.648 mmol), N-Boc-piperazine (1.019 g, 5.471 mmol), Ru-Phos (136.17 mg, 0.292 mmol) and RuPhos precatalyst (119.18 mg, 0.146 mmol) in THF (19 mL) in a Schlenk. The reaction mixture was stirred at 105° C. for 10 min. Water was added. The mixture was extracted twice with EtOAc. The combined organic layers were evaporated with Celite© in order to perform solid deposite purification. A purification was performed via preparative LC (Stationary phase: irregular SiOH 15-40 μm 80 g Grace, Mobile phase: gradient from 80% Heptane, 20% EtOAc to 40% Heptane, 60% EtOAc) To afford the product (1.66 g, yield 76%).

Preparation of Intermediate 312

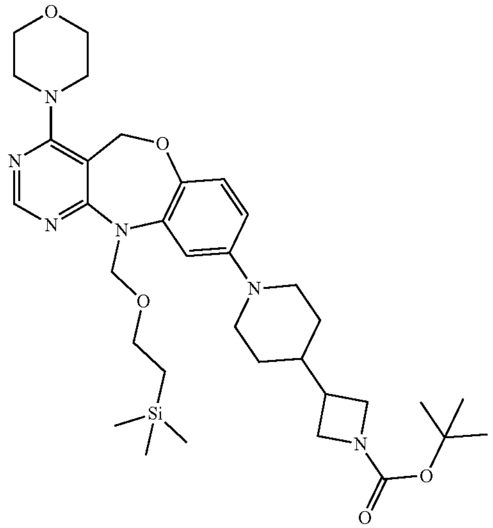 [SMILES: CC(C)(C)OC(=O)N1CC(C2CCN(c3ccc4c(c3)N(COCC[Si](C)(C)C)c3ncnc(N5CCOCC5)c3CO4)CC2)C1]

Intermediate 309 (1231.915 mg, 2.496 mmol), tert-butyl-3-(piperidin-4-yl)azetidine-1-carboxylate (900 mg, 3.745 mmol), Ru-Phos (93.195 mg, 0.2 mmol), NaOtBu (3.994 mL, 1 M, 3.994 mmol) and RuPhos precatalyst (81.567 mg, 0.0999 mmol) in THF (13.00 mL, 0.886 g/mL, 159.77 mmol) in a sealed tube were stirred at 105° C. using one single mode microwave (Biotage Initiator EXP 60) with a power output ranging from 0 to 400 W for 5 min. (fixed hold time). Water was added. The mixture was extracted twice with DCM and Celite© was added to the combined organic layers. The solvent was evaporated. A purification (solid deposit) was performed via preparative LC (Stationary phase: irregular SiOH 15-40 μm 40 g GRACE, Mobile phase: gradient from 90% Heptane, 10% EtOAc to 50% Heptane, 50% EtOAc)) to afford the product (900 mg; 55%).

Example A97

Preparation of Intermediate 313

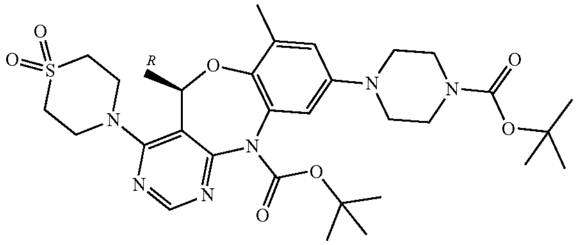

A mixture of intermediate 259 (650 mg, 1.21 mmol), 1-Boc-piperazine (224 mg, 1.21 mmol), $Cs_2CO_3$ (1.18 g, 3.62 mmol) was charged in a sealed tube and purged with $N_2$. 1,4-dioxane (13 mL) was added and the mixture was degassed with $N_2$, then $Pd_2(dba)_3$ (110 mg, 0.120 mmol) and X-Phos (230 mg, 0.482 mmol) were added. The reaction mixture was stirred and heated at 90° C. for 18 h. Water and EtOAc were added to the reaction mixture. The layers were separated. The aqueous layer was extracted twice with EtOAc. The combined organic layers were washed with brine, dried over $MgSO_4$, filtered and evaporated in vacuo to give the crude product as a yellow oil. The crude material was combined with that coming from an analogous reaction on a 50 mg scale and purified by preparative LC (irregular SiOH 40 μm, 40 g Buchi, liquid loading (DCM), mobile phase gradient: from heptane 80%, EtOAc 20% to Heptane 0%, EtOAc 100%). The fractions containing product were combined and evaporated under vacuum to afford the product (707 mg, 84% combined yield).

Example A98

Preparation of Intermediate 314

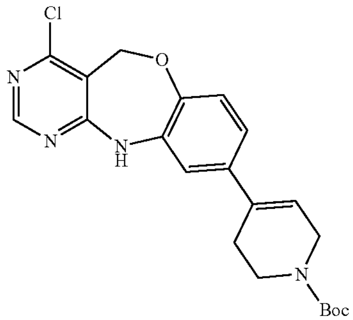 [SMILES: CC(C)(C)OC(=O)N1CC=C(c2ccc3c(c2)Nc2ncnc(Cl)c2CO3)CC1]

Intermediate 207 (5 g, 0.016 mol), tert-butyl 4-(4,4,5,5-tetramethyl-1,3,2-dioxaborolan-2-yl)-5-6-dihydropyridine-1(2H)-carboxylate (4.122 g, 13.331 mmol), $K_3PO_4$ (5.659 g, 26.662 mmol) and [1,1'-Bis(diphenylphosphino)ferrocene] dichloropalladium(II), complex with dichloromethane (0.871 g, 1.066 mmol) in 1,4-dioxane (80 mL), #F #distilled water (12.5 mL) and DMF (10.3 mL) in a Schlenk were stirred at 140° C. for 40 minutes. The reaction mixture was poured out onto water, extracted twice with EtOAc and the organic layers were combined. Celite© was added and the solvent was evaporated. The residue was purified by chromatography over silica gel (SiO2, Grace, 120 g; eluent: from 900% Heptane, 10% EtOAc to 40% Heptane, 50% EtOAc, 10% MeOH (2% $NH_4OH$)). The pure fractions were collected and the solvent was evaporated to afford the product (2 g; 36%).

Example A99

Preparation of Intermediate 315

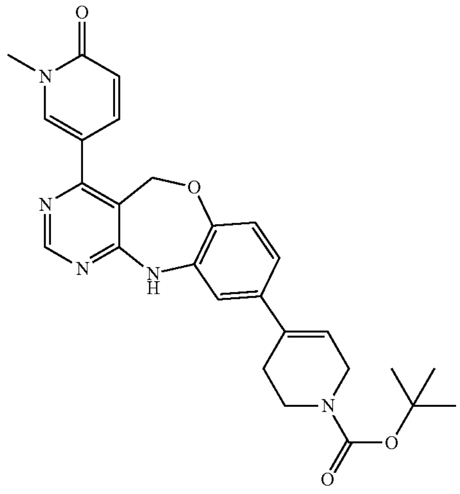 [SMILES: Cn1cc(-c2ncnc3c2COc2ccc(C4=CCN(C(=O)OC(C)(C)C)CC4)cc2N3)ccc1=O]

Intermediate 314 (1 g, 2.41 mmol), 1-methyl-5-(4,4,5,5-tetramethyl-1,3,2-dioxaborolan-2-yl)pyridin-2(1H)-one (679.959 mg, 2.892 mmol), potassium phosphate (1.023 g, 4.821 mmol) and PdCl2(dppf)2·DCM (197.32 mg, 0.241 mmol) in 1,4-dioxane (16.8 mL) and distilled water (2.5 mL) in a sealed tube were stirred at 100° C. using one single mode microwave (Anton Paar) with a power output ranging from 0 to 850 W for 60 min. (fixed hold time). Once the reaction was complete, Celite© was added and the volatiles were evaporated. The crude was purified by solid deposit chromatography. The purification was performed via preparative LC (Stationary phase: irregular SiOH 15-40 μm 80 g Grace, Mobile phase: gradient from 100% DCM to 95% DCM, 5% MeOH (2% $NH_4OH$)) to afford the product (730 mg; 62%).

The intermediates in the Table below were prepared by using an analogous method starting from the respective starting materials.

| Intermediate number | Structure | Mass (mg) | Yield (%) |
|---|---|---|---|
| Intermediate 316 | 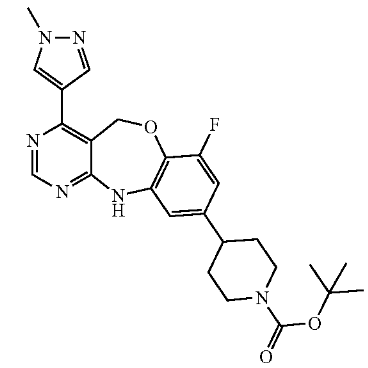 [SMILES: Cn1cc(-c2ncnc3c2COc2c(F)cc(C4CCN(C(=O)OC(C)(C)C)CC4)cc2N3)cn1] from intermediate 223 and 1-methyl-1H-pyrazole-4-boronic acid pinacol ester | 430 | 42 |

Example 100

Preparation of Intermediate 317

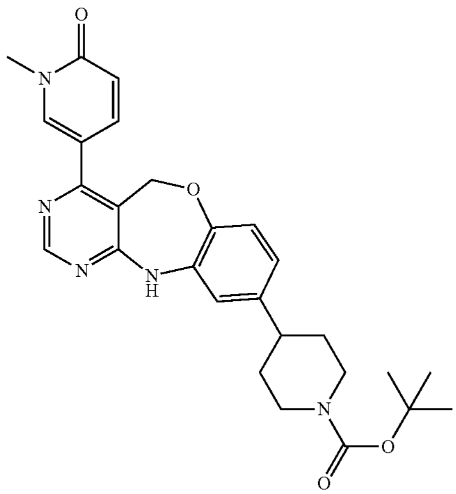 [SMILES: Cn1cc(-c2ncnc3c2COc2ccc(C4CCN(C(=O)OC(C)(C)C)CC4)cc2N3)ccc1=O]

A solution of intermediate 315 (0.73 g, 1.497 mmol) and Pd/C (10%) (0.297 g, 2.789 mmol) in MeOH (25 mL) and EtOAc (25 mL) was hydrogenated at room temperature under 1 bar of $H_2$ for 18 hours. Then the reaction mixture was hydrogenated at room temperature under 2.2 bars of $H_2$ for 5 h. The catalyst was replaced and the reaction mixture hydrogenated at room temperature under 3 bars of $H_2$ for 18 hours. The catalyst was filtered off over Celite©. The filtrate was evaporated affording a solid residue (520 mg). A purification was performed via achiral SFC (Stationary phase: NH2 5 μm 150*30 mm, Mobile phase: 88% $CO_2$, 12% MeOH (0.3% $iPrNH_2$)) to afford the product (360 mg; 49%).

Example 101

Preparation of Intermediate 318

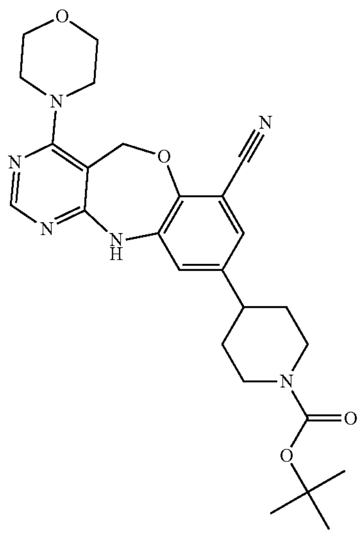 [SMILES: CC(C)(C)OC(=O)N1CCC(c2cc(C#N)c3c(c2)Nc2ncnc(N4CCOCC4)c2CO3)CC1]

A mixture of intermediate 205 (690 mg, 1.26 mmol), zinc cyanide (683 mg, 5.8 mmol, 1,1'-bis(diphenylphosphino) ferrocene (75 mg, 0.135 mmol), tris(dibenzylideneacetone) dipalladium(0) (69 mg, 0.0754 mmol) in DMF (7 mL) was stirred in a sealed tube using one single mode microwave (anton parr monowave) with a power output ranging from 0 to 850 W at 140° C. for 30 minutes.

The reaction was cooled down to room temperature. This reaction was poured into water and this mixture was extracted with EtOAc. The organic layer was decanted and the solvent was evaporated until dryness. The crude was purified (by solid deposit on Celite®) by preparative LC (Irregular SiOH 15-40 μm, 80 g GraceResolv®, mobile phase gradient from 98% DCM, 2% MeOH, 0.2% NH4OH to 95% DCM, 5% MeOH, 0.5% NH4OH). The pure fractions were collected and evaporated until dryness to give 120 mg of intermediate 318;

325 mg of impure fraction which was purified by preparative LC (Irregular SiOH 15-40 μm, 80 g GraceResolv®, mobile phase gradient from 70% Heptane, 30% EtOAc to 40% Heptane, 60% EtOAc) to give 252 mg of intermediate 318. Global yield about 60%.

Preparation of Intermediate 319

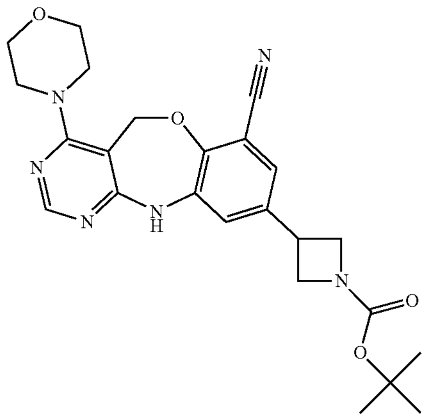 [SMILES: CC(C)(C)OC(=O)N1CC(c2cc(C#N)c3c(c2)Nc2ncnc(N4CCOCC4)c2CO3)C1]

In a sealed tube, a solution of intermediate 233 (399 mg, 0.77 mmol), Potassium hexacyanoferrate(II) trihydrate (0.165 g, 0.39 mmol), (43 mg, 0.44 mmol), XPhos Pd G3 (70 mg, 0.083 mmol), tBu XPhos (38 mg, 0.09 mmol) in 1,4-dioxane (3.6 mL) and water (3.6 mL) was purged with nitrogen flux. Then the reaction was stirred at 100° C. for 5 hours. The reaction was cooled down to room temperature. The reaction was poured onto a saturated solution of NaCl and DCM. The organic layer was decanted on Chromabond® then the solvent was evaporated in vacuo until dryness. This crude was taken up into ACN, dissolved partially and triturated. Few drops of Et2O was added and the precipitate was filtered off and dried to give intermediate 319 (276 mg, 77%)

Preparation of Intermediate 320

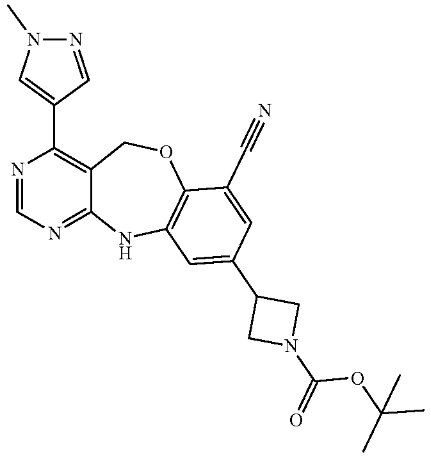 [SMILES: Cn1cc(-c2ncnc3c2COc2c(C#N)cc(C4CN(C(=O)OC(C)(C)C)C4)cc2N3)cn1]

A mixture of zinc cyanide (0.84 g, 7.149 mmol), intermediate 203 (0.8 g, 1.558 mmol), $Pd_2(dab)_3$ (0.088 g, 0.0961 mmol), 1,1'-ferrocenediyl-bis(diphenylphosphine) (0.088 g, 0.159 mmol) in DMF (8.5 mL) was stirred using one single mode microwave (anton parr monowave) with a power output ranging from 0 to 850 W at 140° C. for 40 minutes. The reaction was cooled down to room temperature. This reaction was combined with another bath (scale 200 mg).

The reaction mixture was diluted with DCM and water and filtered over Celite®. The organic layer was concentrated under reduced pressure and the residue was purified by column chromatography over silica gel ($SiO_2$; DCM/MeOH) to afford the product (720 mg; 80%).

The intermediates in the Table below were prepared by using an analogous method starting from the respective starting materials.

| compound number | Structure | Mass (mg) | Yield (%) |
|---|---|---|---|
| Intermediate 321 | 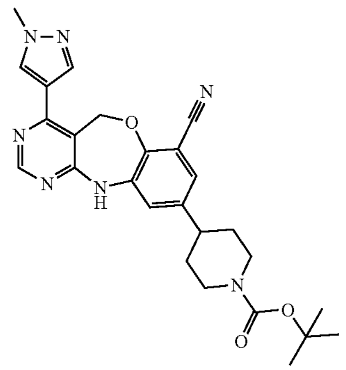 [SMILES: Cn1cc(-c2ncnc3c2COc2c(C#N)cc(C4CCN(C(=O)OC(C)(C)C)CC4)cc2N3)cn1] from intermediate 198 | 690 | 70 |

Example A102

Preparation of Intermediate 322

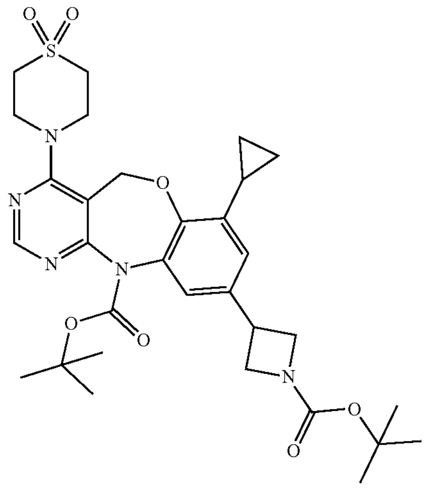 [SMILES: CC(C)(C)OC(=O)N1CC(c2cc(C3CC3)c3c(c2)N(C(=O)OC(C)(C)C)c2ncnc(N4CCS(=O)(=O)CC4)c2CO3)C1]

A solution of intermediate 254 (987.2 mg; 1.481 mmol), cyclopropyl boronic acid 508.9 mg; 5.924 mmol), and $K_3PO_4$ (943.1 mg; 4.443 mmol) in 1,4-dioxane (10.3 mL) and distilled water (1.5 mL) was degassed under N2. Then dichloro[1,1'-bis(diphenylphosphino)ferrocene]palladium (II), complex with dichloromethane (1:1) (121.2 mg; 0.148 mmol) was added. The reaction mixture was degassed again under N2 and heated at 100° C. for 16 hours. The mixture was combined with another batch (0.735 mmol scale). The reaction mixture was partitioned between EtOAc and brine. The combined organic layers were dried over $MgSO_4$, filtered and concentrated under vacuum. The residue was purified by column chromatography over silica gel ($SiO_2$; DCM/MeOH) to afford the product (1.05 g; 75%).

Preparation of Intermediate 323

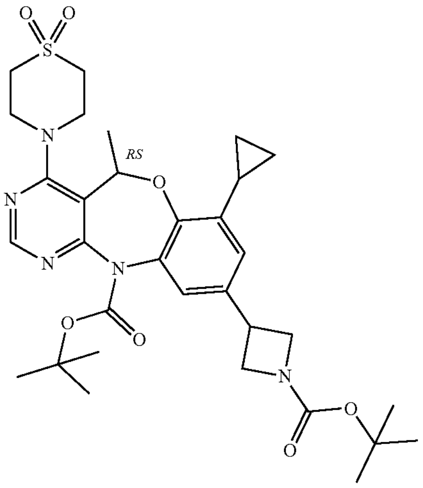 [SMILES: CC1Oc2c(C3CC3)cc(C3CN(C(=O)OC(C)(C)C)C3)cc2N(C(=O)OC(C)(C)C)c2ncnc(N3CCS(=O)(=O)CC3)c21]

Following the protocol used for the preparation of intermediate 322 and using intermediate 268 (1.26 g; 1.851 mmol) as starting material, intermediate 323 (1.09 g; 92%) was obtained.

Example A103

Preparation of Intermediate 324 and Intermediate 325

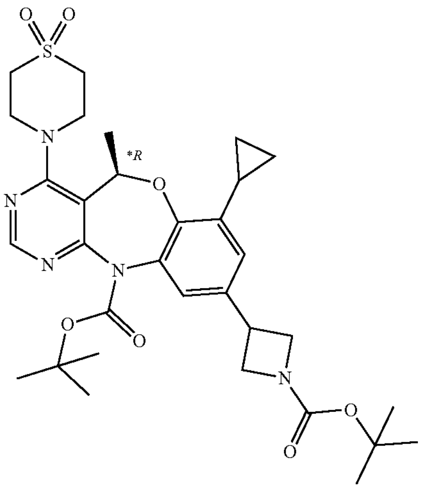

-continued

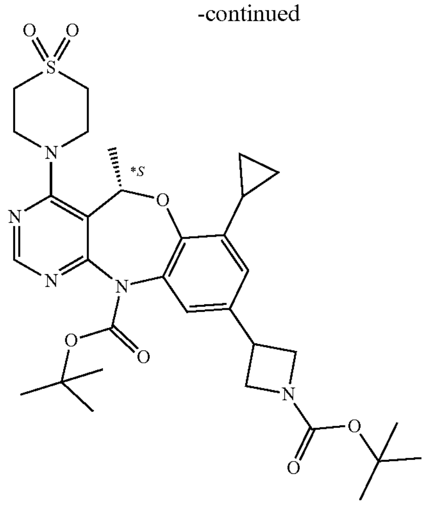

Intermediate 323 (1.09 g; 1.698 mmol) was submitted to chiral separation (Method: Q-M5-Hep-0.1% DEA-(9:1 IPA+0.1% DEA) 300 nm) to afford the intermediate 324 (123 mg; 11%) and the intermediate 325 (244 mg; 22%).

Example A104

Preparation of Intermediate 326

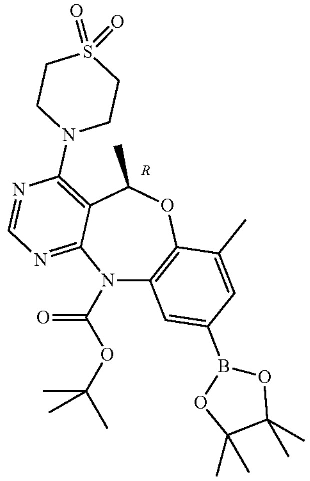

Intermediate 259 (1.0 g, 1.9 mmol), Bis(pinacolato)diboron (706 mg, 2.78 mmol), [1,1'-Bis(diphenylphosphino) ferrocene]palladium(II) Dichloride Dichloromethane Adduct (151 mg, 0.185 mmol) and Potassium Acetate (546 mg, 5.56 mmol) were suspended in 1,4-dioxane (12 mL). The mixture was degassed by bubbling nitrogen for 15 minutes and then heated at 80° C. for 18 hours. The reaction mixture was allowed to cool to room temperature. Water and AcOEt were added. The layers were separated. The organic layer was washed with saturated NaHCO3, dried over MgSO4, filtered and concentrated in vacuo. The crude was purified by preparative LC (irregular SiOH 40 μm, 24 g Buchi, liquid loading (DCM), mobile phase gradient: Heptane/AcOEt from 80/20 to 40/60, 10 CV). The fraction containing product were combined and evaporated to give intermediate 326 (1.09 g, 87%, purity 87%).

Example A105 PGP-663 CI

Preparation of Intermediate 327

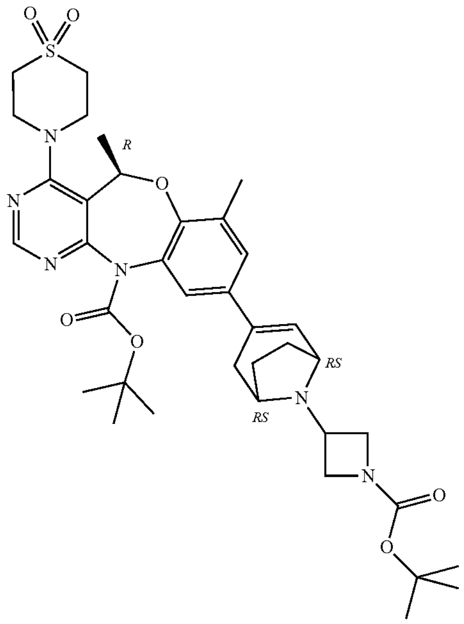

A solution of intermediate 67 (600 mg, 1.46 mmol), intermediate 326 (938 mg, 1.46 mmol) and potassium phosphate (772 mg, 3.64 mmol) in 1,4-dioxane (7.2 mL) and water (3.6 mL) was carefully purged with nitrogen. A catalytic amount of [1,1'-Bis(di-tert-butylphosphino)ferrocene]palladium(II) dichloride (95 mg, 0.145 mmol) was added. The reaction mixture was purged again with nitrogen, sealed and stirred at 70° C. for 17 hours. The reaction mixture was cooled down to rt and combined with another batch starting from 220 mg of intermediate 67.

After dilution in EtOAc, the organic layer was washed with water, then with brine, dried over MgSO4, filtered and evaporated in vacuo to give a residue which was purified by preparative LC (Stationary phase: irregular bare silica 40 g, Mobile phase: Gradient from 5% Heptane, 95% AcOEt to 0% Heptane, 100% AcOEt). The fractions containing the desired product was combined and evaporated in vacuo to give intermediate 327 (930 mg, 66%).

Preparation of Intermediate 328 and Intermediate 329

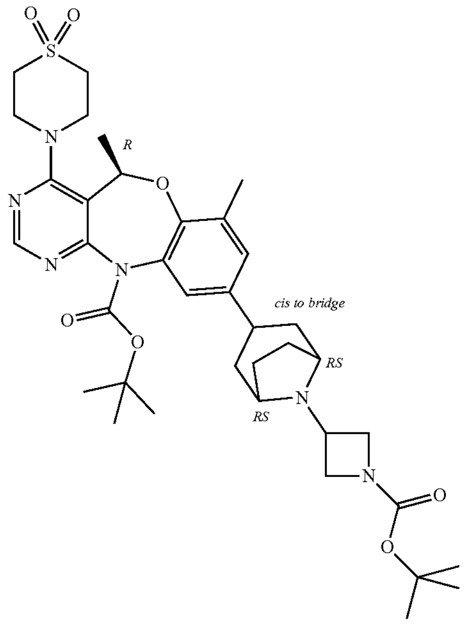

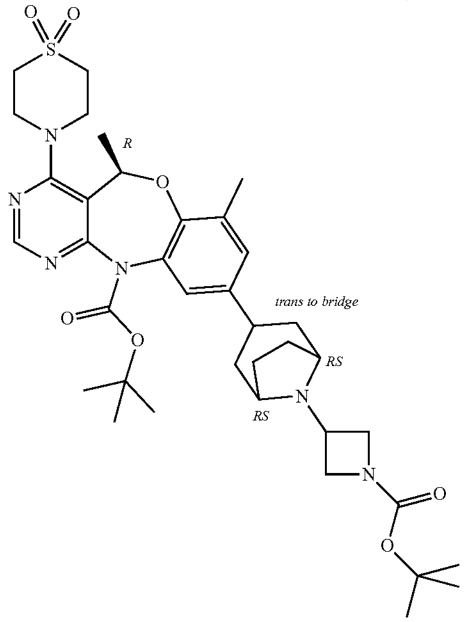

A solution of intermediate 327 (850 mg, 1.2 mmol) in EtOH (10 mL) was warmed at 55° C. Pd/C (5%) (500 mg, 0.235 mmol) was then added, followed by the addition of ammonium formate (741 mg, 11.8 mmol, addition in 2 portions, second portion added 5 minutes after the first one). The flask was capped with a normal plastic cap and the reaction was stirred at 55° C. for 1 h30. The reaction mixture was cooled down to room temperature and filtered through a pug of celite. The filtrate was evaporated in vacuo to afford 645 mg of a grey solid (76%). The crude was purified via chiral SFC (Stationary phase: Whelk-01 (S,S) 5 μm 250*21.2 mm, Mobile phase: 50% CO2, 50% MeOH (0.3% iPrNH2)). Fractions containing desired products were combined to give intermediate 328 (475 mg, 56%) and intermediate 329 (74 mg, 9%).

Example A106

Preparation of Intermediate 330

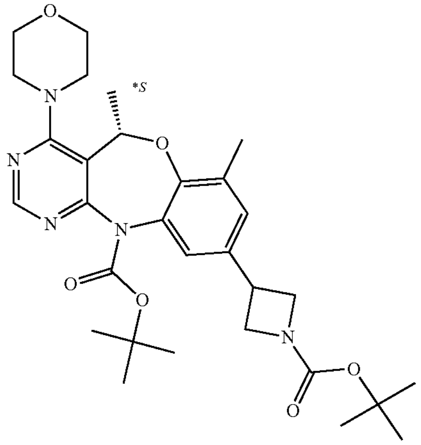 [SMILES: Cc1cc(C2CN(C(=O)OC(C)(C)C)C2)cc2c1O[C@@H](C)c1c(N3CCOCC3)ncnc1N2C(=O)OC(C)(C)C]

Intermediate 256, 1,1'-bis(diphenylphosphino)ferrocene-palladium(ii)dichloride dichloromethane adduct (58.8 mg, 0.071 mmol) and copper(I) iodide (27.1 mg, 0.14 mmol) were added in a sealed tube. The mixture was degassed 3 times. DMA (5.9 mL) was added. The reaction mixture was degassed 3 times. intermediate 11 in DMA (10.175 mL, 0.35 M, 3.561 mmol) was added and the mixture was degassed 3 times. The reaction mixture was stirred at 80° C. using one single mode microwave (Biotage Initiator EXP 60) with a power output ranging from 0 to 400 W for 90 min. [fixed hold time). The reaction mixture was poured out onto water and $NH_4Cl$, extracted twice with DCM, dried over MgSO4, filtered and evaporated.

A purification was performed via preparative LC (Stationary phase: irregular SiOH 35-70 μm 40 g Mobile phase: gradient from 100% Heptane to 40% Heptane, 60% AcOEt). The pure fractions were collected and the solvent was evaporated to give intermediate 330 (439 mg, yield 54%)

The intermediates in the Table below were prepared by using an analogous method starting from the respective starting materials.

| compound number | Structure | Mass (mg) | Yield (%) |
|---|---|---|---|
| Intermediate 331 | 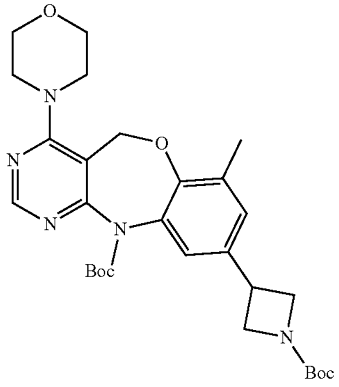 [SMILES: Cc1cc(C2CN(C(=O)OC(C)(C)C)C2)cc2c1OCc1c(N3CCOCC3)ncnc1N2C(=O)OC(C)(C)C] from intermediate 257 | 458 | 39 |
| Intermediate 332 | 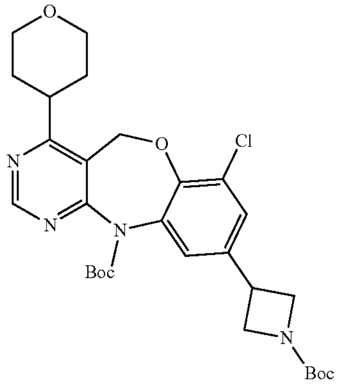 [SMILES: CC(C)(C)OC(=O)N1CC(c2cc(Cl)c3c(c2)N(C(=O)OC(C)(C)C)c2ncnc(C4CCOCC4)c2CO3)C1] from intermediate 273 | 683 | 76 |

Example A107

Preparation of Intermediate 333

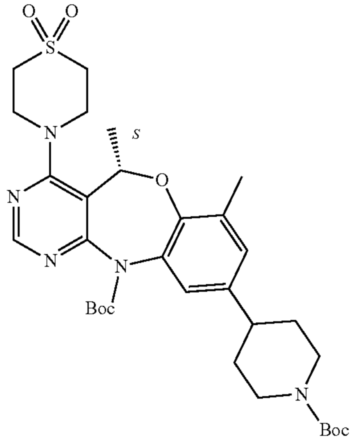

The reaction was performed twice in parallel on a 10.2 g scale of intermediate 260.

Intermediate 260 (10.211 g, 18.928 mmol), nickel (II) iodide (670.765 mg, 2.146 mmol), 4,4'-di-tert-butyl-2,2'-bipyridine (536.604 mg, 1.999 mmol), zinc dust (2.53 g, 38.686 mmol), 1-BOC-4-bromopiperidine (10 g, 37.855 mmol) and magnesium chloride (1.802 g, 18.928 mmol) were placed in a sealed tube. The mixture was degassed 3 times. Pyridine (1.533 mL, 0.982 g/mL, 19.033 mmol) in DMA (134 mL) was added. The reaction mixture was degassed 3 times. The reaction mixture was stirred at rt for 5 hr at rt, before being poured out onto water, extracted twice with DCM and filtered over Celite©. The organic layer was separated, dried over $MgSO_4$, filtered and evaporated. The residue was crystallised from MeCN to afford a first batch of the product (12.9 g; 53%).

The mother liquors were evaporated in vacuo. The residue was purified by preparative LC (Irregular SiOH 15-40 μm 220 g GraceResolv®, mobile phase:100% DCM to 95% DCM, % MeOH (2% $NH_4OH$)). Fractions enriched in the product were combined and the solvent was evaporated. The residue was purified by preparative LC (Irregular SiOH 15-40 μm 80 g GraceResolv®, mobile phase: 90% Heptane, 10% AcOEt to 40% Heptane, 60% AcOEt) to afford a second batch of the product (4.5 g; 18%)

The intermediates in the Table below were prepared by using an analogous method starting from the respective starting materials.

| compound number | Structure | Mass (mg) | Yield (%) |
|---|---|---|---|
| Intermediate 334 | 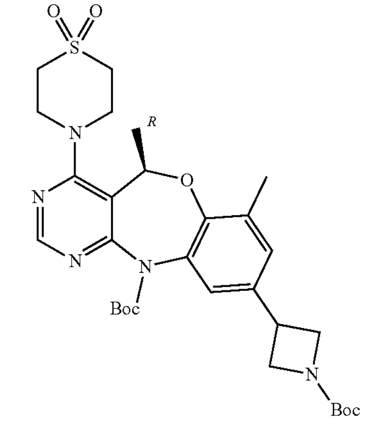 from intermediate 259 and tert-butyl-3-bromoazetidine-1-carboxylate | 510 | 22 |
| Intermediate 335 | 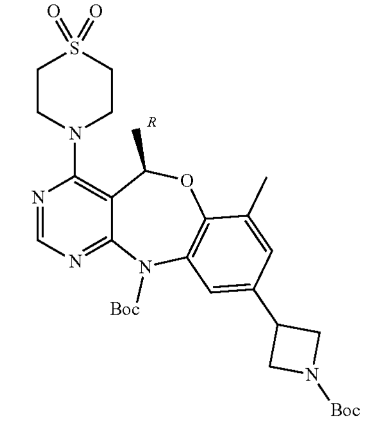 from intermediate 259 and tert-butyl-3-bromoazetidine-1-carboxylate | 1520 | 89 |
| Intermediate 336 | 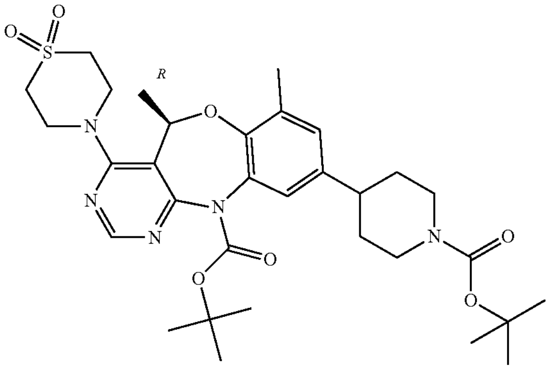 from intermedaite 259 and 1-Boc-4-bromopiperidine | 569 mg (2 batches) | 95 |

-continued
| compound number | Structure | Mass (mg) | Yield (%) |
|---|---|---|---|
| Intermediate 337 | 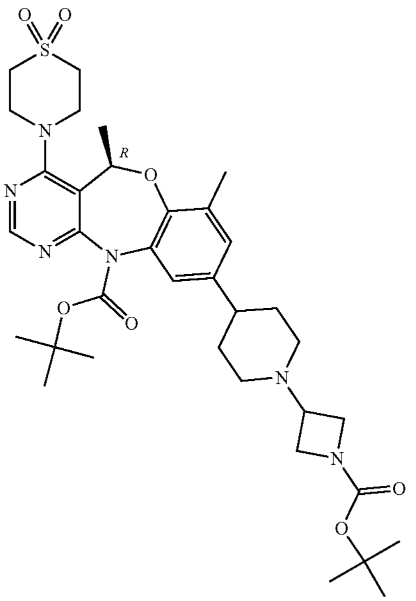<br>from intermediate 259 and intermediate 98 | 1240 | 54% Purity 85% |
| Intermediate 338 | 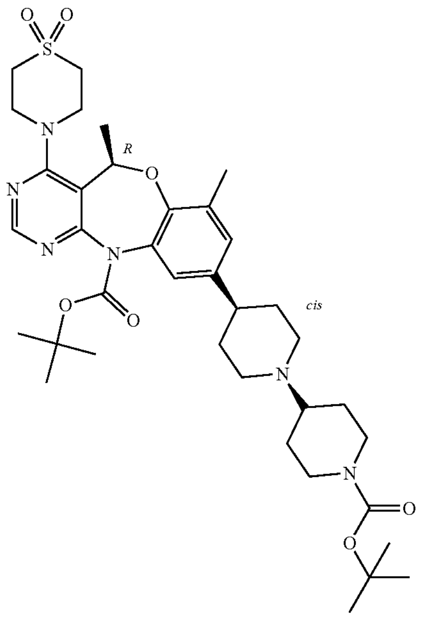<br>from intermediate 259 and intermediate 81. Chiral separation was via SFC (Stationary phase: CHIRALCEL OD-H 5 μm 250*30 mm, Mobile phase: 75% $CO_2$, 25% EtOH(0.3% $iPrNH_2$)) | 77 | 27 |

-continued
| compound number | Structure | Mass (mg) | Yield (%) |
|---|---|---|---|
| Intermediate 339 | 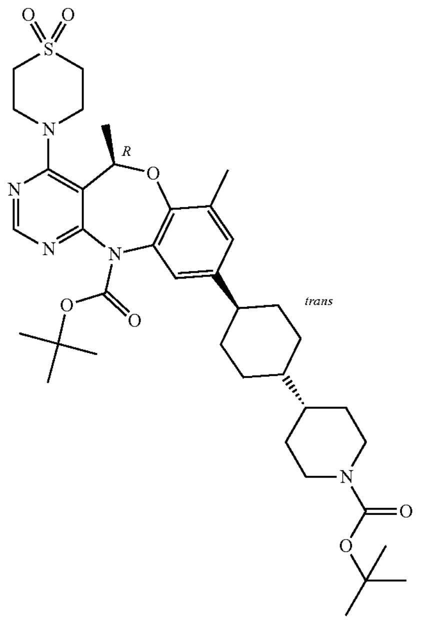<br>from intermediate 259 and intermediate 81. Chiral separation was via SFC (Stationary phase: CHIRALCEL OD-H 5 μm 250*30 mm, Mobile phase: 75% $CO_2$, 25% EtOH(0.3% $iPrNH_2$)) | 153 | 54 |
| Intermediate 340 | 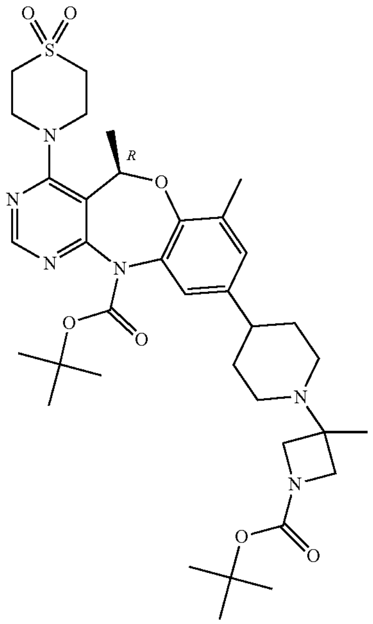<br>from intermediate 259 and intermediate 82 | 2150 | 88 Purity 88% |

-continued
| compound number | Structure | Mass (mg) | Yield (%) |
|---|---|---|---|
| Intermediate 341 | 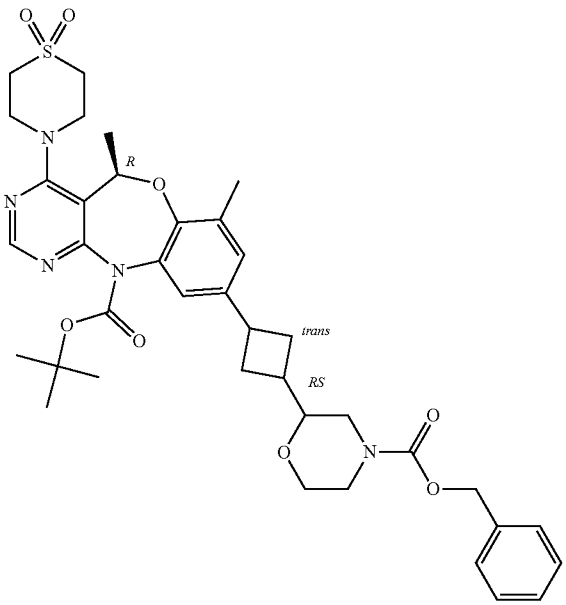 from intermediate 259 and intermediate 83 | 428 | 34 |
| Intermediate 342 | 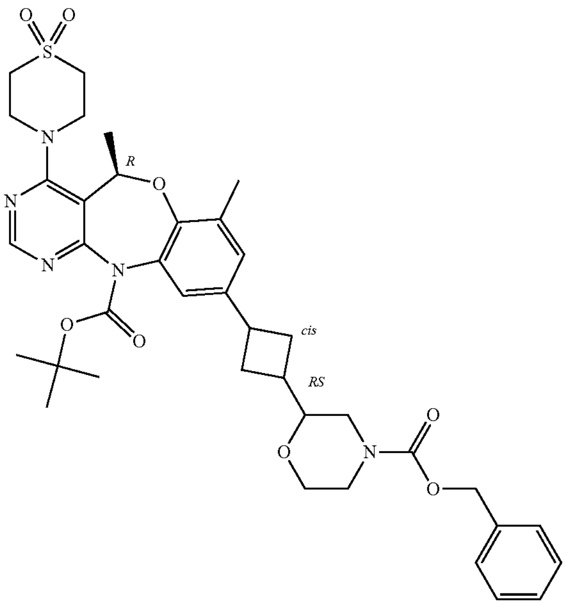 from intermediate 259 and intermediate 83 | 350 | 28 |

Preparation of Intermediate 343

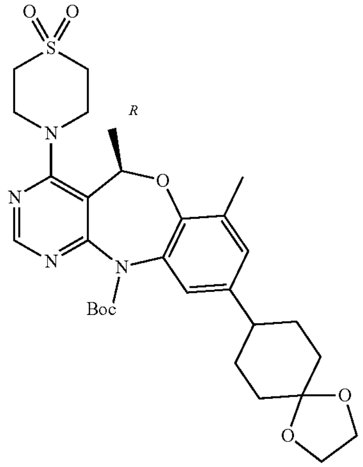

Under $N_2$, a solution of pyridine (60.1 μL, 0.982 g/mL, 0.746 mmol) in DMA (5 mL) was added to a mixture of intermediate 259 (400 mg, 0.741 mmol), intermediate 80 (328 mg, 1.48 mmol), nickel (II) iodide (26.3 mg, 0.0841 mmol), 4,4'-di-tert-butyl-2,2'-bipyridine (21.0 mg, 0.0783 mmol), zinc dust (99.1 mg, 1.52 mmol) and magnesium chloride (70.6 mg, 0.741 mmol). The reaction mixture was purged with $N_2$ (3 times) then stirred at rt for 20 h. The reaction mixture was diluted with DCM then water was added. The aqeuous layer was extracted with DCM. The combined organics layers were washed with water, brine, dried over $MgSO_4$, filtered, evaporated and purified by preparative LC (irregular SiOH 15-40 μm, 40 g Buchi, liquid loading (DCM), mobile phase gradient: from Heptane/EtOAc: 80/20 to 20/80, 15 Column Volumes) to give the product as a colourless oil (423 mg; 80%).

The intermediates in the Table below were prepared by using an analogous method starting from the respective starting materials.

| compound number | Structure | Mass (mg) | Yield (%) |
|---|---|---|---|
| Intermediate 344 | 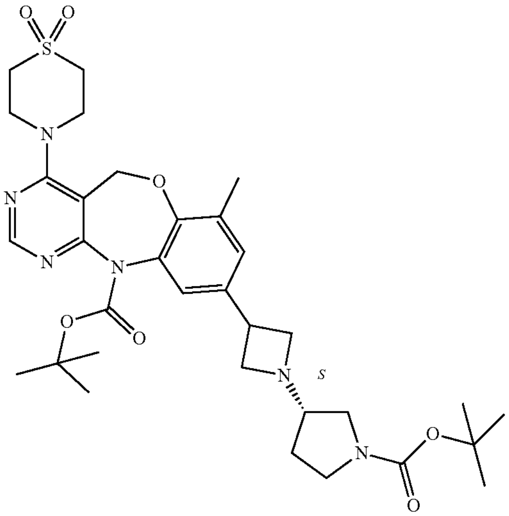 from intermediate 249 and intermediate 101 | 640 | 89 |

-continued

| compound number | Structure | Mass (mg) | Yield (%) |
| --- | --- | --- | --- |
| Intermediate 345 | 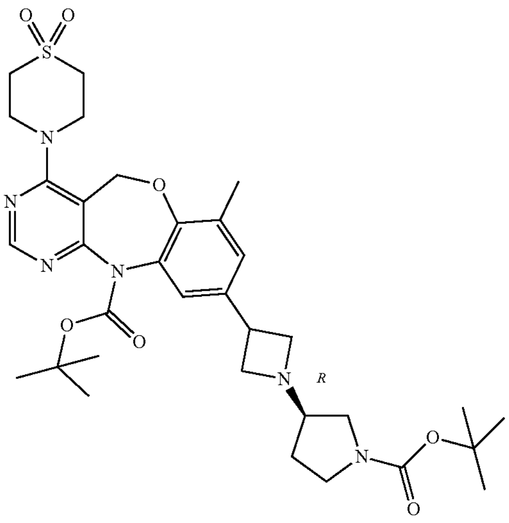 from intermediate 249 and intermediate 102 | 468 | 65 |

Preparation of Intermediate 346 and Intermediate 347

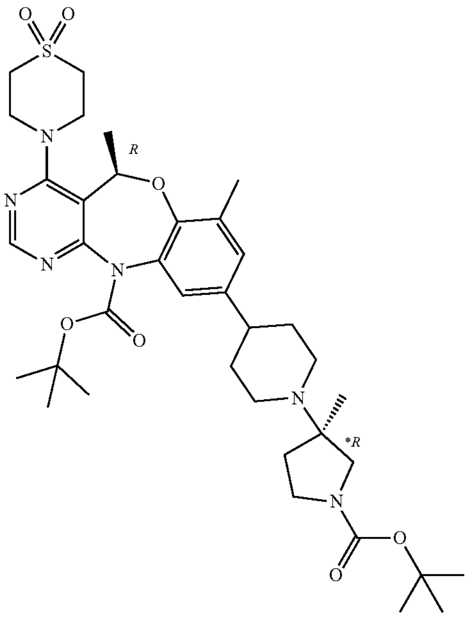

and

-continued

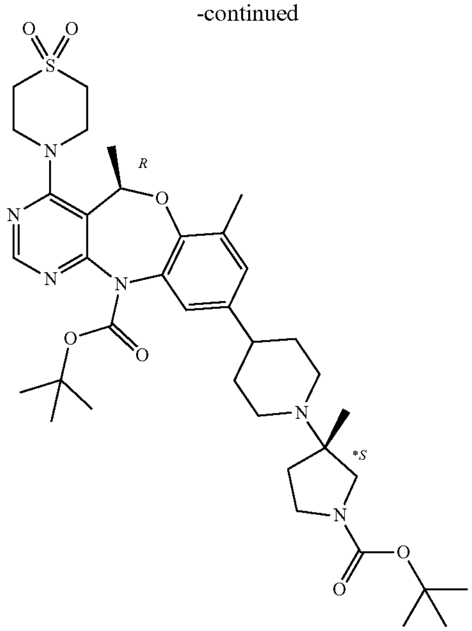

A mixture of intermediate 259 (100 mg, 0.185 mmol), nickel(II) iodide (6.6 mg, 0.021 mmol), 4,4'-di-tert-butyl-2,2'-bipyridine (5.3 mg, 0.020 mmol), zinc dust (24.8 mg, 0.379 mmol) and magnesium chloride (17.7 mg, 0.185 mmol) in a sealed tube was degassed 3 times. Pyridine (15 µL, 0.186 mmol) and intermediate 111 (123 mg, 0.371 mmol) in DMA (1.3 mL) were added. The mixture was degassed 3 times and stirred at rt for 18 h. The reaction was cooled down to rt. Water and EtOAc were added, the mixture was filtered over Celite© and the organic layer was separated. The solvent was evaporated until dryness. A purification was performed via preparative LC (Stationary phase: irregular $SiO_2$ 40 μm 40 g, Mobile phase: from 100% DCM to 93% DCM, 7% MeOH (2% $NH_4OH$)), the fractions were combined and the solvent was evaporated to give the racemic intermediate. A purification was performed via chiral SFC (Stationary phase: Whelk-01 (S,S) 5 μm 250*21.2 mm, Mobile phase: 50% CO2, 50% iPrOH) to give intermediate 346 (70 mg, 28%) and intermediate 347 (65 mg, 26%).

Preparation of Intermediate 348

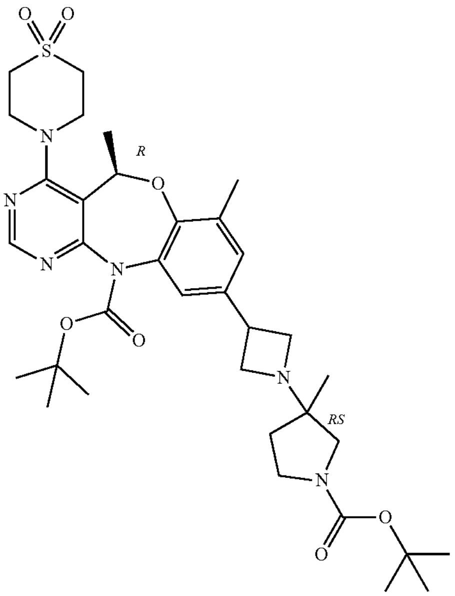

The reaction was performed on two batches (0.78 and 0.26 mmol scale, respectively) which were combined for purification.

Intermediate 259 (422 mg, 0.78 mmol), 4,4'-di-tert-butyl-2,2'-bipyridine (46 mg, 0.17 mmol), nickel(II) iodide (98 mg, 0.31 mmol), zinc dust (102 mg, 1.57 mmol) and magnesium chloride (75 mg, 0.78 mmol) were introduced in an oven-dried tube under nitrogen. A solution of intermediate 113 (300 mg, 0.94 mmol) and pyridine (63 μL, 0.78 mmol) in DMA (3 mL) was added to the mixture, which was stirred at rt for 2 days. Brine was added, the aqueous layer was extracted with ethyl acetate, the organic layer was dried over $MgSO_4$ and concentrated under reduced pressure. The crude was purified by flash chromatography (eluting with DCM-DCM/MeOH). Pure fractions were collected and concentrated to give intermediate 348 (302 mg, 42%).

Preparation of Intermediate 349

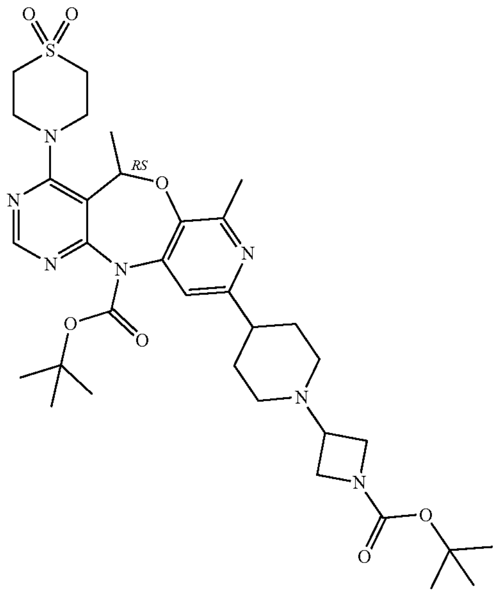

The reaction was performed on two batches (5.55 mmol and 15.73 mmol), which were combined for purification.

Intermediate 242 (8.50 g 15.73 mmol), intermediate 98 (7.53 g, 23.59 mmol), 4,4'-di-tert-butyl-bipyridine (464 mg, 1.73 mmol), nickel(II) iodide (980 mg, 3.15 mmol), zinc dust (2.06 g, 31.46 mmol) and magnesium chloride (1.50 g, 15.73 mmol) were introduced in an oven-dried tube under nitrogen. A solution of pyridine (1.27 mL, 15.73 mmol) in DMA (100 mL) was added, the tube was tightly closed and the mixture was stirred at rt for 16 h. The mixture was diluted with ethyl acetate, washed with brine (5 times) and the organic layer was concentrated. The crude was combined with the other batch and purified by flash chromatography ($SiO_2$, Heptane-Ethyl acetate) to afford intermediate 349 (6.82 g, 62%).

Preparation of Intermediate 350

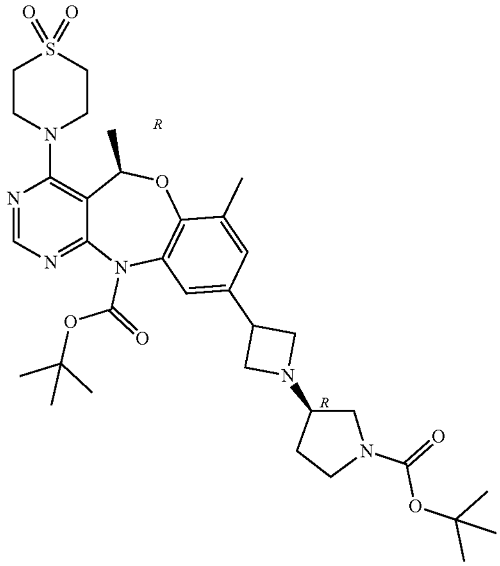

The reaction was performed on two batches (18.54 and 3.71 mmol scale, respectively) which were combined for purification Intermediate 259 (10.00 g, 18.54 mmol), nickel(II) iodide (657 mg, 2.10 mmol), 4,4'-di-tert-butyl-2,2'-bipyridine (526 mg, 1.96 mmol), zinc dust (2.48 g, 37.89 mmol) and magnesium chloride (1.77 g, 18.54 mmol) were introduced in a sealed tube and the mixture was degassed 3 times with nitrogen. Pyridine (1.5 mL, 18.64 mmol) and intermediate 102 (11.32 g, 37.08 mmol) in DMA (130 mL) were added. The mixture was degassed 3 times with nitrogen and stirred at rt for 24 h. The reaction mixture was cooled to rt and combined with the second batch. Water and EtOAc were added, the mixture was filtered over celite and the organic layer was decanted. The solvent was evaporated until dryness. A purification was performed via preparative LC (Stationary phase: irregular $SiO_2$ 40 μm 330 g, Mobile phase: from 100% DCM to 88% DCM, 12% MeOH (2% $NH_4OH$)). A second purification was performed via preparative LC (Stationary phase: irregular $SiO_2$ 40 μm 330 g, Mobile phase: from 80% Heptane, 20% AcOEt to 40% Heptane, 50% AcOEt, 10% MeOH (2% $NH_4OH$)) to give intermediate 350 (9.6 g, 63%).

Preparation of Intermediate 351

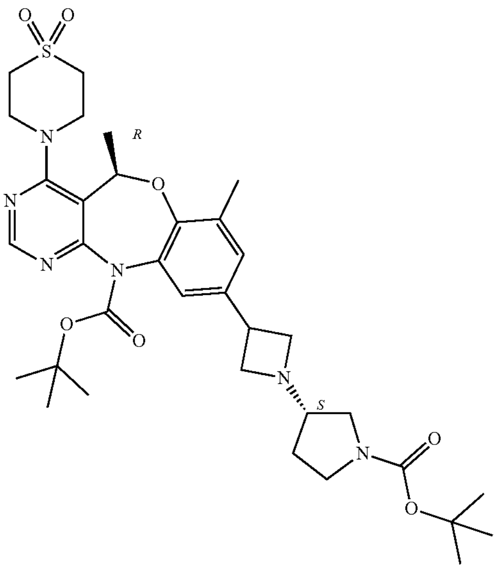

Magnesium chloride (2.43 g, 25.56 mmol) was added to a mixture of intermediate 259 (13.8 g, 25.56 mmol), nickel (II) iodide (918 mg, 2.94 mmol), 4,4'-di-tert-butyl-2,2'-bipyridine (686 mg, 2.56 mmol), zinc dust (3.34 g, 51.11 mmol) and intermediate 101 (15.60 g; 51.11 mmol) in a sealed tube. The mixture was degassed 3 times with nitrogen, then a solution of pyridine (2.06 mL, 25.56 mmol) in DMA (185 mL) was added. The reaction mixture was degassed 3 times with nitrogen and the mixture was stirred at rt for 18 h. The reaction mixture was poured onto water and EtOAc was added. The mixture was filtered through a pad of Celite® and the filtrate was extracted 3 times with EtOAc. The organic layer was washed with brine, dried over $MgSO_4$, filtered and the solvent was evaporated. The crude material was purified by chromatography (irregular $SiO_2$, Buchi®, 330 g; eluent: from 100% DCM to 96% DCM, 4% MeOH, 0.4% $NH_4OH$). The pure fractions were collected and the solvent was evaporated to give intermediate 351 (13.56 g, 77%).

Preparation of Intermediate 352

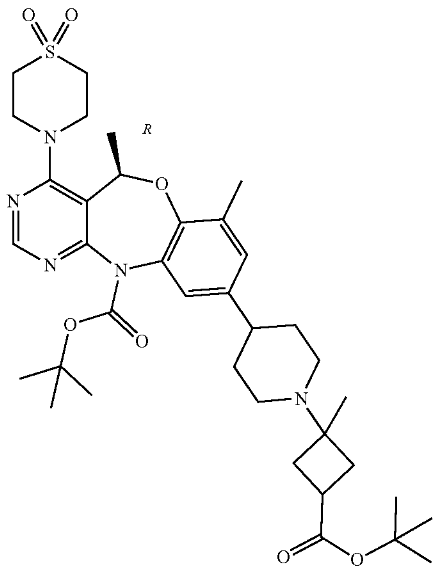

Intermediate 259 (730 mg, 1.36 mmol), nickel(II) iodide (48 mg, 0.15 mmol), 4,4'-di-tert-butyl-2,2'-bipyridine (39 mg, 0.14 mmol), zinc dust (182 mg, 2.78 mmol) and magnesium chloride (130 mg, 1.36 mmol) were introduced in a sealed tube and the mixture was degassed 3 times with nitrogen. Pyridine (110 μL, 1.37 mmol) and intermediate 116 (907 mg, 2.72 mmol) in DMA (10 mL) were added. The mixture was degassed 3 times with nitrogen, then stirred at rt for 18 h. Water and EtOAc were added, the mixture was filtered over celite and the organic layer was decanted. The solvent was evaporated until dryness. A purification was performed via preparative LC (Stationary phase: irregular $SiO_2$ 40 μm 40 g, Mobile phase: from 100% DCM to 93% DCM, 7% MeOH (2% $NH_4OH$)). The fractions were combined and the solvent was evaporated to give intermediate 352 (1060 mg, quant).

Example A108

Preparation of Intermediate 353

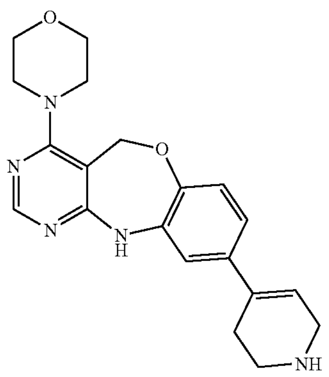 [SMILES: C1=C(c2ccc3c(c2)Nc2ncnc(N4CCOCC4)c2CO3)CCNC1]

TFA (2.165 mL; 1.489 g/mL; 28.27 mmol) was added to a solution of intermediate 284 (329 mg; 0.707 mmol) in DCM (10.6 mL) stirred at 0° C. and 16 h at rt. The reaction mixture was poured into ice water and basified with sat. $NaHCO_3$(aq) and extracted with DCM/MeOH 9:1. The organic phase was dried over $MgSO_4$, filtered and concentrated under reduced pressure to give the product (256 mg; 99%) which was used in the next step without further elaboration.

The intermediates in the Table below were prepared by using an analogous method starting from the respective starting materials.

| Intermediate number | Structure | Mass (mg) | Yield (%) |
|---|---|---|---|
| Intermediate 354 | 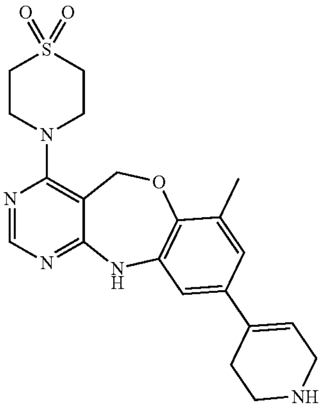 [SMILES: Cc1cc(C2=CCNCC2)cc2c1OCc1c(ncnc1N1CCS(=O)(=O)CC1)N2] from intermediate 291 (work up with $NH_4OH$) | 1960 | 81 |

Preparation of Intermediate 355

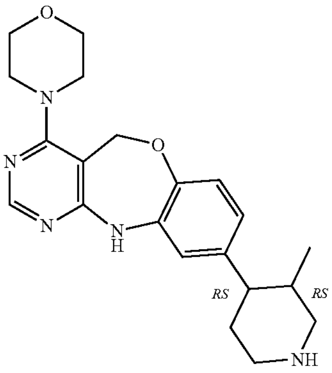 [SMILES: CC1CNCCC1c1ccc2c(c1)Nc1ncnc(N3CCOCC3)c1CO2]

TFA (2.56 mL; 1.489 g/mL; 33.43 mmol) was added to a solution of intermediate 302 (414 mg; 0.636 mmol) in DCM (3.8 mL) and stirred at rt for 6 h. The reaction mixture was concentrated under vacuum. The residue was partitioned between EtOAc and saturated $Na_2CO_3$ solution and the organic layer was dried over $MgSO_4$, filtered and concentrated under reduced pressure to afford the product (240 mg; 79%) which was used in the next step without further purification.

Preparation of Intermediate 356

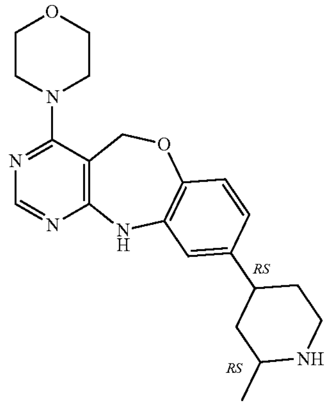 [SMILES: CC1CC(c2ccc3c(c2)Nc2ncnc(N4CCOCC4)c2CO3)CCN1]

TFA (1.04 mL; 1.489 g/mL; 13.58 mmol) was added to a solution of intermediate 294 (327 mg; 0.679 mmol) in DCM (7 mL) and stirred at 0° C. and 2 hours at rt. The reaction mixture was poured into ice water and basified with sat. $Na_2CO_3$(aq) and extracted with DCM/PrOH 9:1. The organic phase was dried over $MgSO_4$, filtered and concentrated under reduced pressure to give the product (200 mg; 77%) which was used in the next step without further elaboration.

Preparation of Intermediate 357

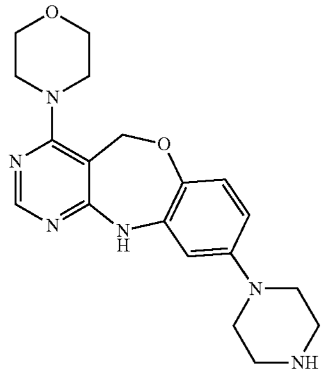 [SMILES: c1nc2c(c(N3CCOCC3)n1)COc1ccc(N3CCNCC3)cc1N2]

Intermediate 311 (1600 mg, 2.672 mmol) in TFA (35.059 mL, 1.49 g/mL, 458.126 mmol) and DCM (67 mL) were stirred at rt for 5 h. The mixture was poured out onto ice. Water and $NH_4OH$ were added until basic pH. The mixture was extracted twice with DCM, dried over $MgSO_4$, filtered and evaporated to afford the product which was used without further elaboration (1070 mg, quant.)

Preparation of Intermediate 358

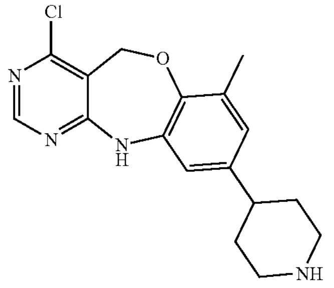 [SMILES: Cc1cc(C2CCNCC2)cc2c1OCc1c(Cl)ncnc1N2]

TFA (18.7 mL, 244 mmol) was added slowly to a solution of intermediate 224 (15 g, 34.8 mmol) in DCM (200 mL) at rt. The mixture was stirred at rt for 12 hours. The mixture was concentrated under vacuum to give the crude compound as yellow solid. Methyl tert-butyl ether (40 mL) was added to the crude compound, stirred for 0.5 hour, filtered. The filter cake dried in vacuum to give intermediate 358 (17 g, 73%) as a white solid.

Preparation of Intermediate 359

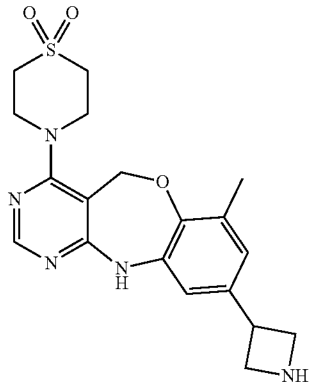 [SMILES: Cc1cc(C2CNC2)cc2c1OCc1c(ncnc1N1CCS(=O)(=O)CC1)N2]

Trifluoroacetic acid (2.89 mL, 1.49 g/mL, 37.725 mmol) was added to a solution of intermediate 267 (227 mg, 0.377 mmol) in DCM (7.5 mL). The reaction mixture was stirred at rt for 12 h. The solvent was evaporated until dryness. This crude was poured out onto ice. Water and $NH_4OH$ were added until basic pH. The mixture was extracted twice with DCM. The organic layer was decanted on Chromabond® and the solvent was evaporated until dryness to give intermediate 359 (144 mg, 95%).

Preparation of Intermediate 360

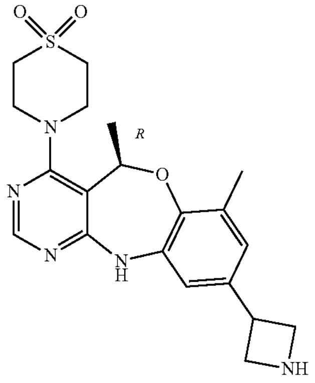

Intermediate 335 (500 mg, 0.81 mmol) was dissolved in DCM (16 mL) and the mixture was cooled to 0° C. then TFA (3.5 mL, 45 mmol) was added slowly. This mixture was stirred at room temperature for 2 h and the mixture was concentrated under reduced pressure to give intermediate 360 (788 mg, quant) as a yellow oil.

The intermediates in the Table below were prepared by using an analogous method starting from the respective starting materials.

| Intermediate number | Structure | Mass (mg) | Yield (%) |
|---|---|---|---|
| Intermediate 361 | 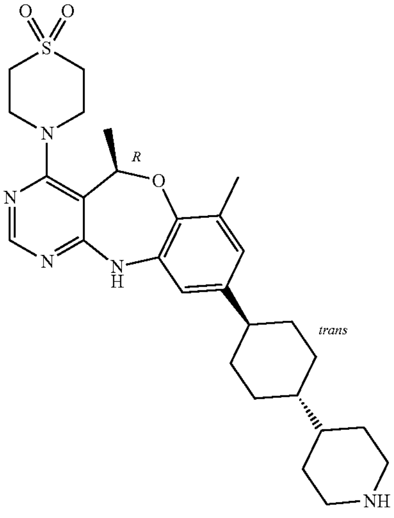 from intermediate 339 | 183 | quant |

-continued

| Intermediate number | Structure | Mass (mg) | Yield (%) |
|---|---|---|---|
| Intermediate 362 | 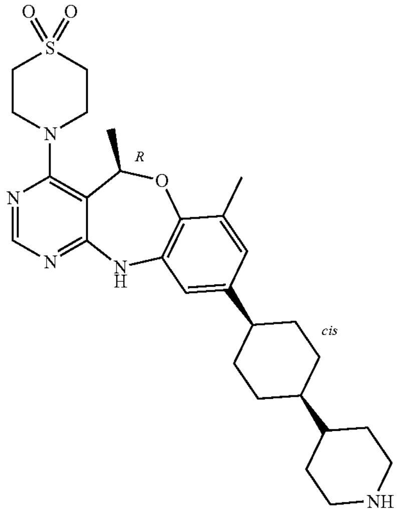 from intermediate 338 | 197 | quant |
| Intermediate 363 | 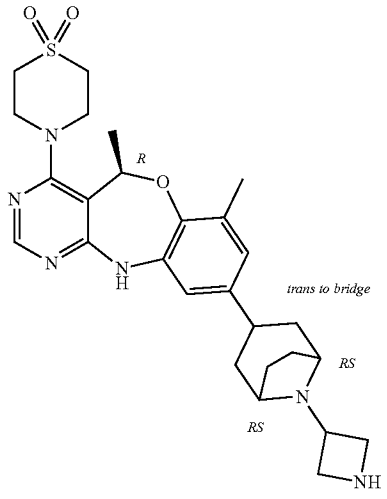 from intermediate 329 | 88 | quant |

-continued

| Intermediate number | Structure | Mass (mg) | Yield (%) |
|---|---|---|---|
| Intermediate 364 | 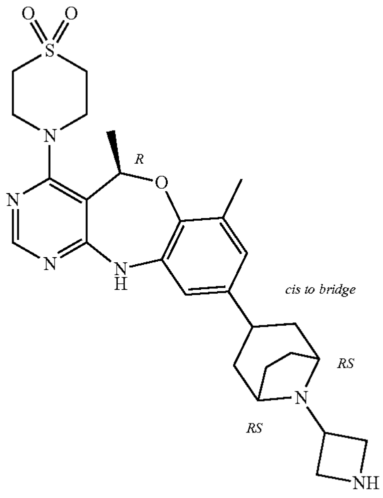 from intermediate 328, TFA salt | 263 | quant |

Example A109

Preparation of Intermediate 365

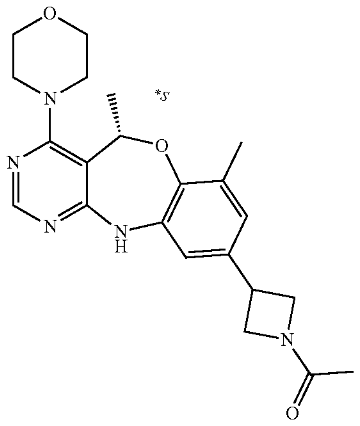

Intermediate 367 (284 mg, 0.77 mmol) and acetic anhydride (0.13 mL, 1.36 mmol) in DCM (5.6 mL) were stirred at rt for 30 minutes. Water and DCM were added. The mixture was made basic with ammoniac. The organic layer was decanted and the solvent was evaporated until dryness. A purification was performed via preparative LC (Stationary phase: irregular SiOH 35-70 μm 40 g, Mobile phase: gradient from 100% DCM to 91% DCM, 9% MeOH (2% $NH_4OH$)). The pure fractions were collected and the solvent was evaporated to give intermediate 365 (231 mg, 73%)

Preparation of Intermediate 366

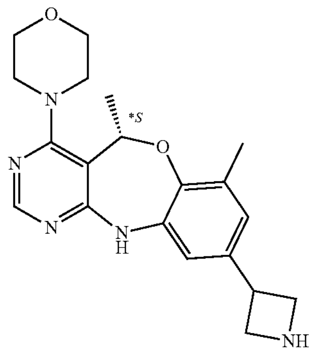 [SMILES: Cc1cc(C2CNC2)cc2c1O[C@@H](C)c1c(ncnc1N1CCOCC1)N2]

A solution of intermediate 365 (226 mg, 0.552 mmol) and NaOH (1M in H2O) (5.5 mL, 1 M, 5.5 mmol) in EtOH (9.5 mL) in a sealed tube was stirred at 140° C. using one single mode microwave (Biotage Initiator EXP 60) with a power output ranging from 0 to 400 W for 15 min. [fixed hold time). The rm was poured out onto water and $NH_4Cl$, extracted twice with DCM, dried over MgSO4, filtered and evaporated to give intermediate 366 (103 mg, 51%).

Preparation of Intermediate 367

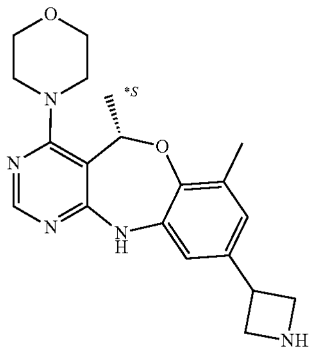 [SMILES: Cc1cc(C2CNC2)cc2c1O[C@@H](C)c1c(ncnc1N1CCOCC1)N2]

TFA (1.7 mL, 1.49 g/mL, 22.4 mmol) was added dropwise to a solution of intermediate 330 (0.439 g, 0.773 mmol) in DCM (3.9 mL) at room temperature. The reaction mixture was stirred for 1 h. The crude was poured out onto ice. Water and NH4OH were added until basic pH. The mixture was extracted twice with DCM. The organic layer was decanted on Chromabond® and the solvent was evaporated until dryness to give intermediate 367 (284 mg, quant)

The intermediates in the Table below were prepared by using an analogous method starting from the respective starting materials.

| compound number | Structure | Mass (mg) | Yield (%) |
|---|---|---|---|
| Intermediate 368 | 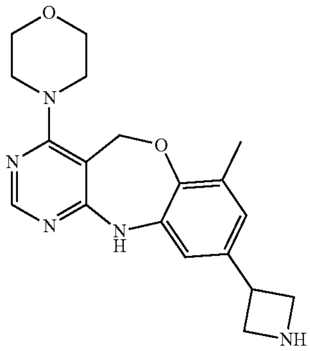 [SMILES: Cc1cc(C2CNC2)cc2c1OCc1c(ncnc1N1CCOCC1)N2] from intermediate 331; rt; aqueous work up with $K_2CO_3$ | 283 | 58 |
| Intermediate 369 | 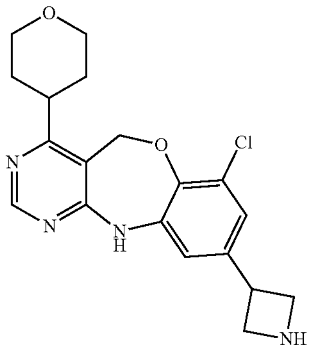 [SMILES: Clc1cc(C2CNC2)cc2c1OCc1c(ncnc1C1CCOCC1)N2] from intermediate 332 | 408 | 92 |

-continued
| compound number | Structure | Mass (mg) | Yield (%) |
|---|---|---|---|
| Intermediate 370 | 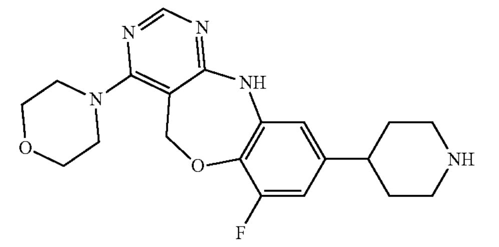 [SMILES: Fc1cc(C2CCNCC2)cc2c1OCc1c(ncnc1N1CCOCC1)N2] from intermediate 201 | 396 | quant |
| Intermediate 371 | 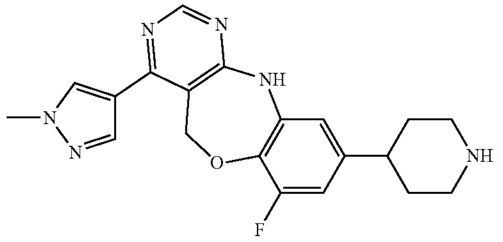 [SMILES: Cn1cc(-c2ncnc3c2COc2c(F)cc(C4CCNCC4)cc2N3)cn1] from intermediate 316 | 270 | 80 |
| Intermediate 372 | 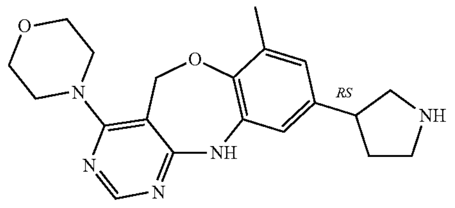 [SMILES: Cc1cc(C2CCNC2)cc2c1OCc1c(ncnc1N1CCOCC1)N2] from intermediate 304; work up with aqueous $K_2CO_3$ | 1600 | 92 |

Preparation of Intermediate 373 and Intermediate 374

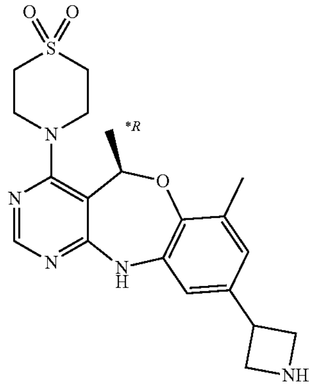

and

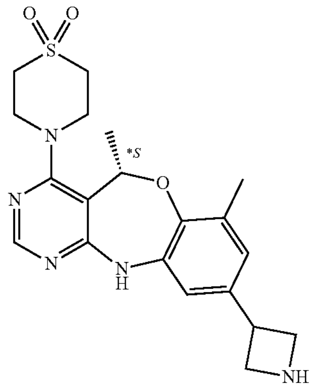

Trifluoroacetic acid (85 mL, 1.49 g/mL, 1105.436 mmol) was added to a solution of intermediate 218 (5.7 g, 11.054 mmol) in DCM (219 mL) at rt. The reaction mixture was stirred at rt for 6 h. The solvent was evaporated until dryness. This crude was poured onto ice. Water and $NH_4OH$ were added until basic pH. The mixture was extracted twice with DCM, the organic layer was decanted on Chromabond® and the solvent was evaporated until dryness to give the racemic intermediate. A purification was performed via preparative LC (Stationary phase: irregular $SiO_2$ 40 μm 200 g, Mobile phase: 0.8% $NH_4OH$, 92% DCM, 8% MeOH). A purification was performed via preparative chiral SFC (Stationary phase: Chiralpak IG, Mobile phase: $CO_2$/MeOH/DCM (+1% $iPrNH_2$) 50/25/25) to give intermediate 373 (1.2 g, 26%) and intermediate 374 (1.2 g, 26%).

Preparation of Intermediate 375

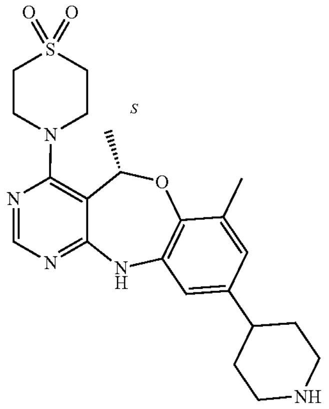

At 0° C. TFA (20.683 mL, 1.49 g/mL, 270.268 mmol) in DCM (87 mL) was added dropwise to a solution of intermediate 333 (5.8 g, 9.009 mmol) in DCM (130 mL). The reaction mixture was allowed to warm to room temperature with stirring and left to stir at room temperature for 48 hrs. The volatiles were evaporated and this crude was taken up into a solution of DCM, water and $NH_4OH$ (aq). The organic layer was decanted and the solvent was evaporated until dryness to give the product (4.8 g, quant).

The intermediates in the Table below were prepared by using an analogous method starting from the respective starting materials.

| compound number | Structure | Mass (mg) | Yield (%) |
| --- | --- | --- | --- |
| Intermediate 376 | 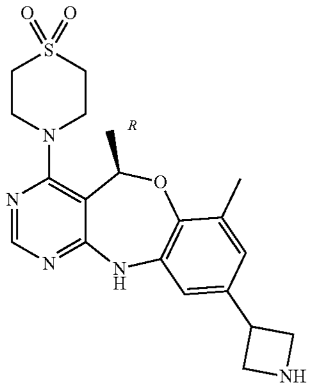 from intermediate 334 | 519 | quant |

-continued
| compound number | Structure | Mass (mg) | Yield (%) |
|---|---|---|---|
| Intermediate 377 | 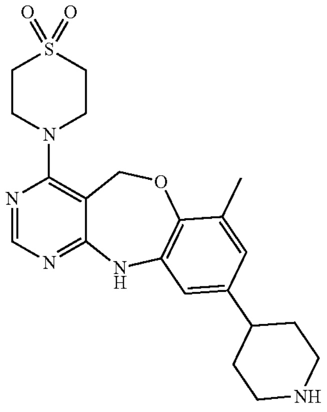 [SMILES: Cc1cc(C2CCNCC2)cc2c1OCc1c(ncnc1N1CCS(=O)(=O)CC1)N2]<br>from intermediate 219 | 6600 | quant |
| Intermediate 220 | 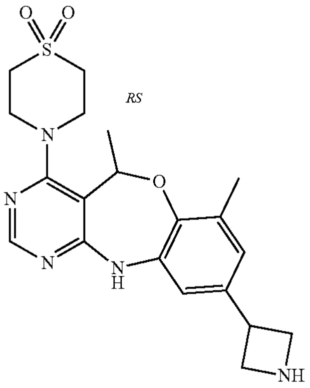<br>From intermediate 218 | 2632 | quant |
| Intermediate 378*R | 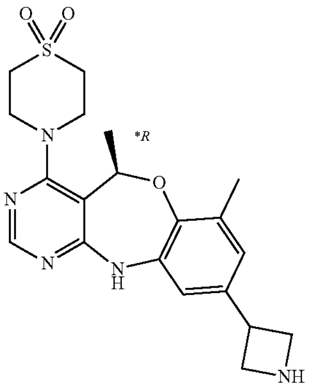<br>From intermediate 218*R | 4440 | quant |

-continued
| compound number | Structure | Mass (mg) | Yield (%) |
|---|---|---|---|
| Intermediate 378*S | 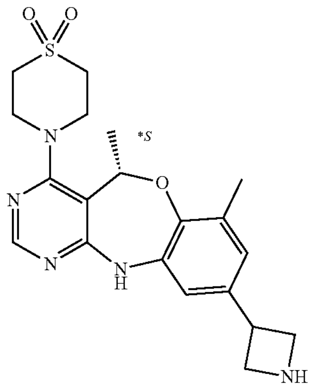 From intermediate 218*S | 4110 | quant |
| Intermediate 379 | 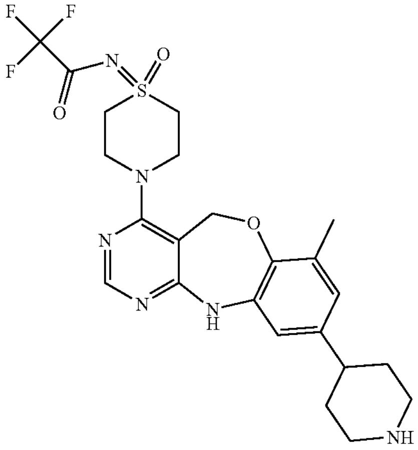 [SMILES: Cc1cc(C2CCNCC2)cc2c1OCc1c(ncnc1N1CCS(=O)(=NC(=O)C(F)(F)F)CC1)N2] From intermediate 221, rt, 2 h | 155 | 74 |
| Intermediate 380 | 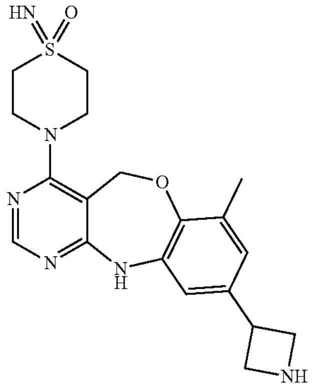 [SMILES: Cc1cc(C2CNC2)cc2c1OCc1c(ncnc1N1CCS(=N)(=O)CC1)N2] From intermediate 222, rt, 5 h | 4000 | Quant Purity 37% |

-continued
| compound number | Structure | Mass (mg) | Yield (%) |
|---|---|---|---|
| Intermediate 381 | 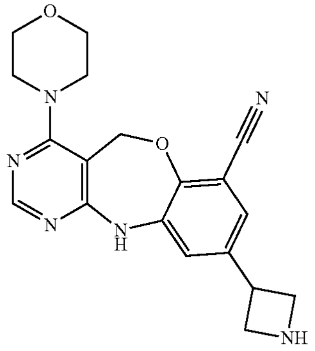 [SMILES: N#Cc1cc(C2CNC2)cc2c1OCc1c(ncnc1N1CCOCC1)N2] From intermediate 319, rt, o.n | 220 | 80 |
| Intermediate 382 | 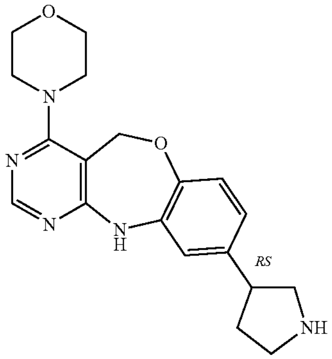 [SMILES: c1nc2c(c(N3CCOCC3)n1)COc1ccc(C3CCNC3)cc1N2] from intermediate 303 | 912 | quant |
| Intermediate 383 | 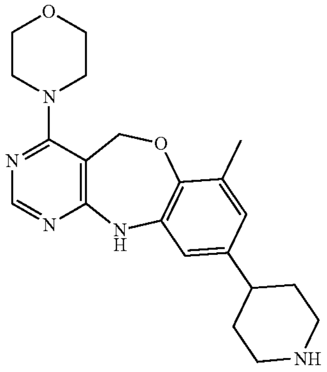 [SMILES: Cc1cc(C2CCNCC2)cc2c1OCc1c(ncnc1N1CCOCC1)N2] from intermediate 262 | 2700 | quant |
| Intermediate 384 | 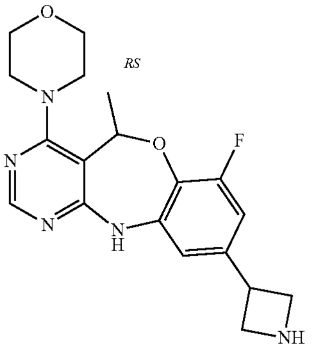 [SMILES: CC1Oc2c(F)cc(C3CNC3)cc2Nc2ncnc(N3CCOCC3)c21] from intermediate 282 | 926 | quant |

-continued
| compound number | Structure | Mass (mg) | Yield (%) |
|---|---|---|---|
| Intermediate 385 | 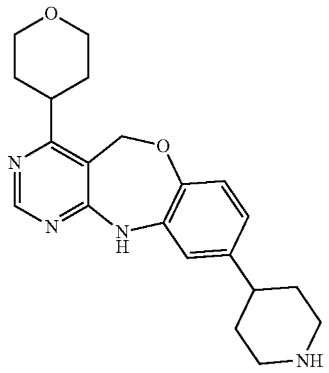 [SMILES: c1nc2c(c(C3CCOCC3)n1)COc1ccc(C3CCNCC3)cc1N2] from intermediate 274 | 214 | 78 |
| Intermediate 386 | 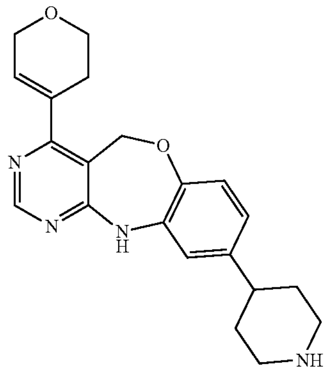 [SMILES: C1=C(c2ncnc3c2COc2ccc(C4CCNCC4)cc2N3)CCOC1] from intermediate 275 | 132 | 46 |
| Intermediate 387 | 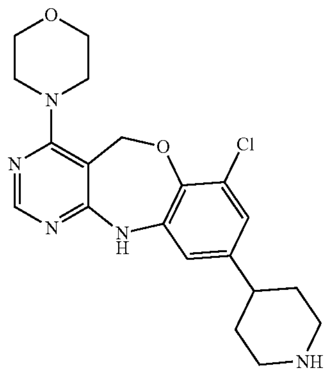 [SMILES: Clc1cc(C2CCNCC2)cc2c1OCc1c(ncnc1N1CCOCC1)N2] from intermediate 276 | 627 | quant. |

-continued
| compound number | Structure | Mass (mg) | Yield (%) |
|---|---|---|---|
| Intermediate 388 | 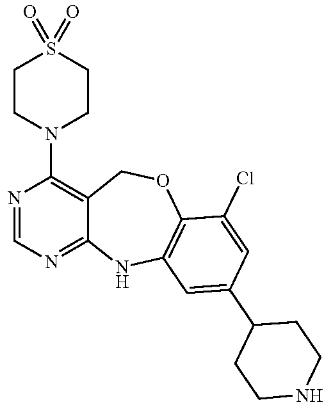 [SMILES: O=S1(=O)CCN(c2ncnc3c2COc2c(Cl)cc(C4CCNCC4)cc2N3)CC1] from intermediate 277 | 793 | quant. |
| Intermediate 389 | 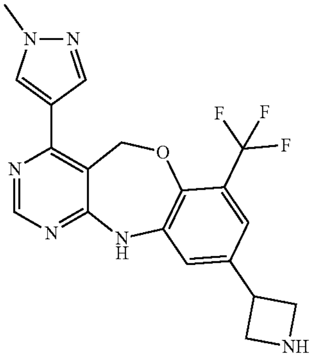 [SMILES: Cn1cc(-c2ncnc3c2COc2c(cc(C4CNC4)cc2C(F)(F)F)N3)cn1] from intermediate 278 | 169 | quant. |
| Intermediate 390 | 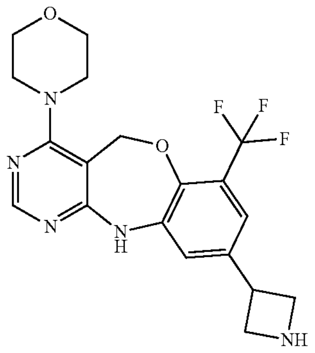 [SMILES: FC(F)(F)c1cc(C2CNC2)cc2c1OCc1c(ncnc1N1CCOCC1)N2] from intermediate 279 | 205 | 96 |

-continued
| compound number | Structure | Mass (mg) | Yield (%) |
|---|---|---|---|
| Intermediate 391 | 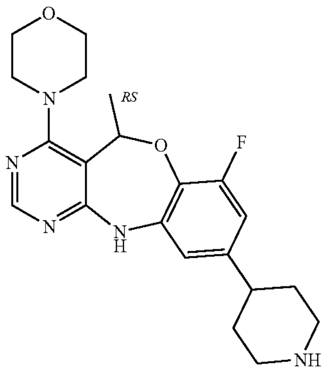 [SMILES: CC1Oc2c(F)cc(C3CCNCC3)cc2Nc2ncnc(N3CCOCC3)c21] from intermediate 280 | 497 | 92 |
| Intermediate 392 | 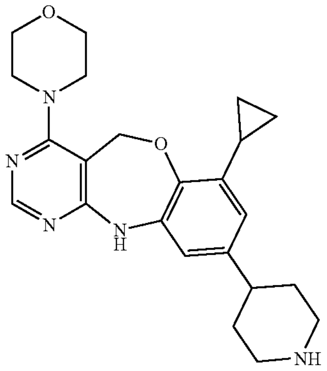 [SMILES: c1nc2c(c(N3CCOCC3)n1)COc1c(cc(C3CCNCC3)cc1C1CC1)N2] from intermediate 308 | 308 | 84 |
| Intermediate 393 | 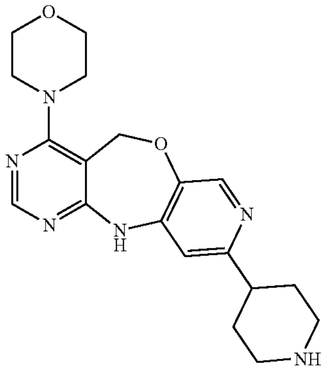 from intermediate 234 | 367 | quant. |

-continued
| compound number | Structure | Mass (mg) | Yield (%) |
|---|---|---|---|
| Intermediate 394 | 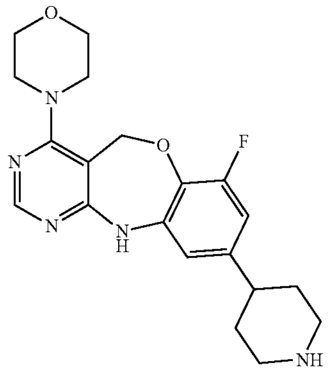 [SMILES: Fc1cc(C2CCNCC2)cc2c1OCc1c(ncnc1N1CCOCC1)N2] from intermediate 201 | 950 | 85 |
| Intermediate 395 | 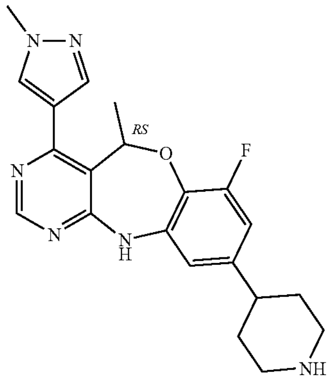 [SMILES: CC1Oc2c(F)cc(C3CCNCC3)cc2Nc2ncnc(-c3cnn(C)c3)c21] from intermediate 305 | 458 | 83 |
| Intermediate 396 | 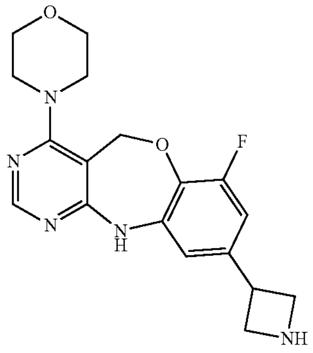 [SMILES: Fc1cc(C2CNC2)cc2c1OCc1c(ncnc1N1CCOCC1)N2] from intermediate 281 - No aqueous work-up only evaporation | 3800 | quant. |

-continued
| compound number | Structure | Mass (mg) | Yield (%) |
|---|---|---|---|
| Intermediate 397 | 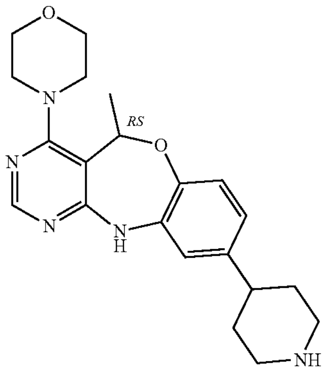 [SMILES: CC1Oc2ccc(C3CCNCC3)cc2Nc2ncnc(N3CCOCC3)c21] from intermediate 202 | 800 | 65 |
| Intermediate 398 | 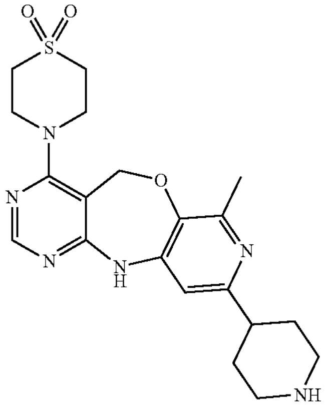 [SMILES: Cc1nc(C2CCNCC2)cc2c1OCc1c(ncnc1N1CCS(=O)(=O)CC1)N2] from intermediate 235 | 1883 | quant. |
| Intermediate 399 | 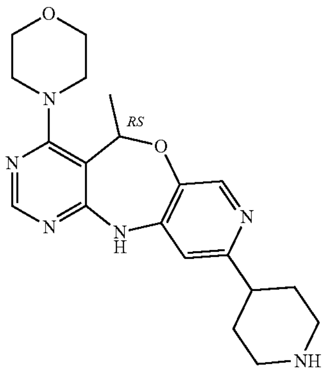 [SMILES: CC1Oc2cnc(C3CCNCC3)cc2Nc2ncnc(N3CCOCC3)c21] from intermediate 236 | 170 | quant. |

-continued
| compound number | Structure | Mass (mg) | Yield (%) |
|---|---|---|---|
| Intermediate 400 | 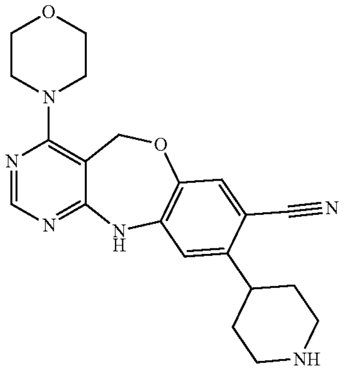 [SMILES: N#Cc1cc2c(cc1C1CCNCC1)Nc1ncnc(N3CCOCC3)c1CO2] from intermediate 237 | 390 | 94 |
| Intermediate 401 | 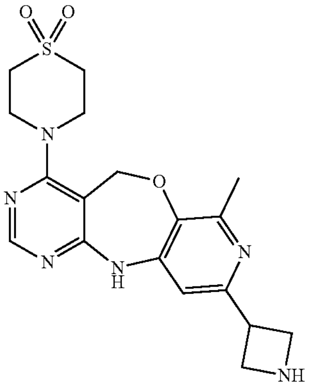 [SMILES: Cc1nc(C2CNC2)cc2c1OCc1c(ncnc1N1CCS(=O)(=O)CC1)N2] from intermediate 238 | 402 | 57 |
| Intermediate 402 | 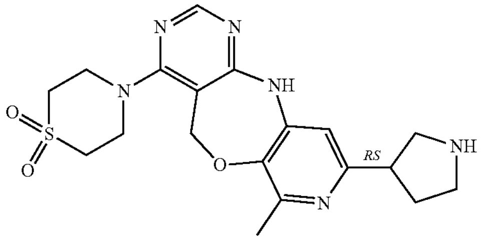 [SMILES: Cc1nc(C2CCNC2)cc2c1OCc1c(ncnc1N1CCS(=O)(=O)CC1)N2] from intermediate 239; work up with aqueous $K_2CO_3$ | 850 | quant |
| Intermediate 403 | 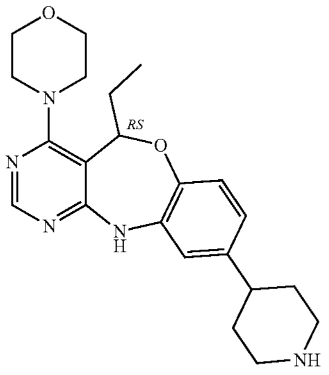 [SMILES: CCC1Oc2ccc(C3CCNCC3)cc2Nc2ncnc(N3CCOCC3)c21] from intermediate 306 | 375 | quant. |

-continued
| compound number | Structure | Mass (mg) | Yield (%) |
|---|---|---|---|
| Intermediate 404 | 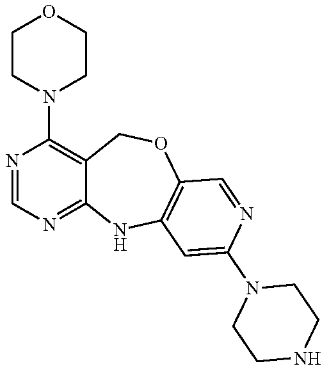 [SMILES: c1nc2c(c(N3CCOCC3)n1)COc1cnc(N3CCNCC3)cc1N2] from intermediate 240 | 455 | 89 |
| Intermediate 405 | 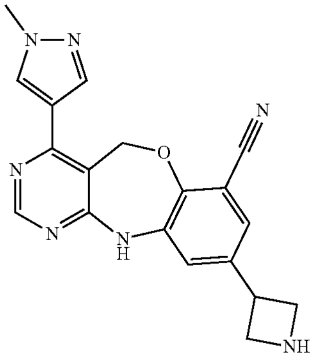 [SMILES: Cn1cc(-c2ncnc3c2COc2c(C#N)cc(C4CNC4)cc2N3)cn1] from intermediate 320 | 600 | 89 |
| Intermediate 406 | 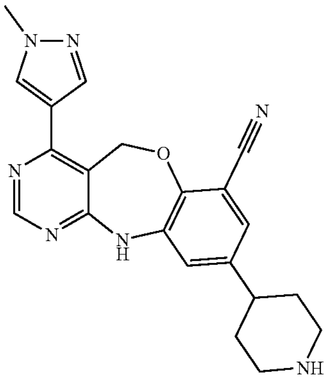 [SMILES: Cn1cc(-c2ncnc3c2COc2c(C#N)cc(C4CCNCC4)cc2N3)cn1] from intermediate 321 | 550 | quant. |

-continued
| compound number | Structure | Mass (mg) | Yield (%) |
|---|---|---|---|
| Intermediate 407 | 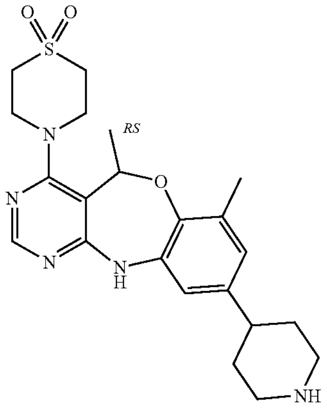 [SMILES: Cc1cc(C2CCNCC2)cc2c1OC(C)c1c(ncnc1N1CCS(=O)(=O)CC1)N2] from intermediate 307 | 1321 | 96 |
| Intermediate 408 | 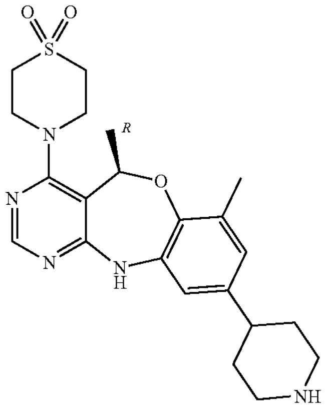 from intermediate 336 | 360 | 92 |
| Intermediate 409 | 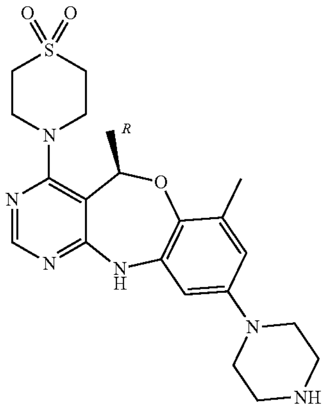 from intermediate 313 | 411 | quant |

-continued
| compound number | Structure | Mass (mg) | Yield (%) |
|---|---|---|---|
| Intermediate 410 | 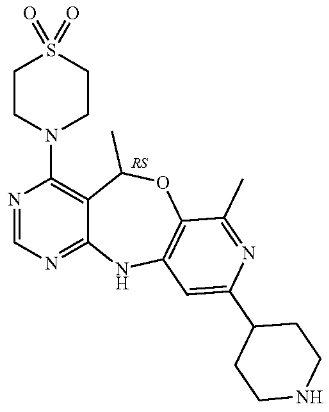<br>from intermediate 241 | 281 | 97 |
| Intermediate 411 | 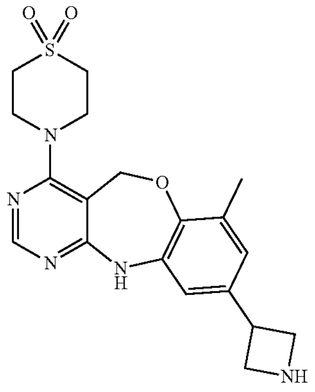 [SMILES: Cc1cc(C2CNC2)cc2c1OCc1c(ncnc1N1CCS(=O)(=O)CC1)N2]<br>from intermediate 283 - No aqueous work-up only evaporation | 1146 | quant. |
| Intermediate 412 | 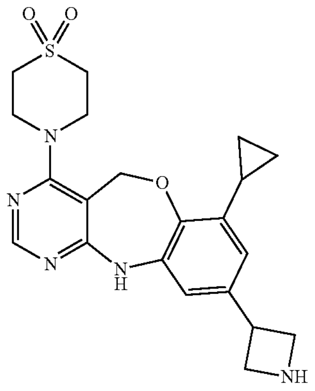 [SMILES: O=S1(=O)CCN(c2ncnc3c2COc2c(cc(C4CNC4)cc2C2CC2)N3)CC1]<br>from intermediate 322 - No aqueous work-up only evaporation | 1490 | quant. |

-continued
| compound number | Structure | Mass (mg) | Yield (%) |
|---|---|---|---|
| Intermediate 413 | 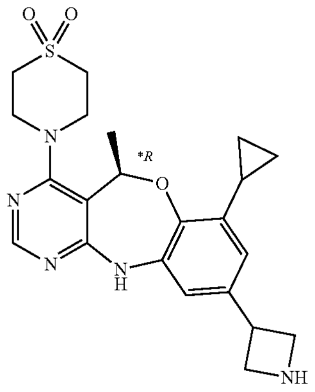 [SMILES: C[C@H]1Oc2c(cc(C3CNC3)cc2C2CC2)Nc2ncnc(N3CCS(=O)(=O)CC3)c21] from intermediate 324 - No aqueous work-up only evaporation | 264 | quant. |
| Intermediate 414 | 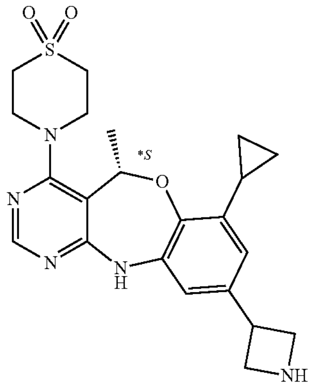 [SMILES: C[C@@H]1Oc2c(cc(C3CNC3)cc2C2CC2)Nc2ncnc(N3CCS(=O)(=O)CC3)c21] from intermediate 325 - No aqueous work-up only evaporation | 364 | quant. |
| Intermediate 358 | 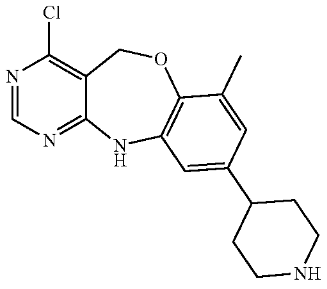 [SMILES: Cc1cc(C2CCNCC2)cc2c1OCc1c(Cl)ncnc1N2] from intermediate 224 (evaporation of the crude, no work up) | 13600 | quant |

Example A110

Preparation of Intermediate 415

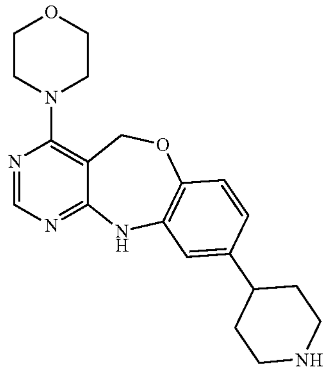

A solution of HCl in dioxane (4M; 5.3 mL; 21.39 mmol) was added to a solution of intermediate 299 (1 g; 2.14 mmol) in DCM (11 mL) at rt. The reaction mixture was stirred at rt for the weekend. A 10% aqueous solution of $K_2CO_3$ and DCM were added. The mixture was stirred at rt for 1 h, then extracted with DCM (3×). The organic layer was dried over $MgSO_4$, filtered and the solvent was evaporated to give 680 mg of brown foam. This crude residue was purified by chromatography over silica gel (SiO2, Grace, 24 g; eluent: from 98% DCM, 2% MeOH, 0.2% $NH_4OH$ to 90% DCM, 10% MeOH, 1% $NH_4OH$). The pure fractions were collected and the solvent was evaporated to give the product as a brown foam (210 mg; 26%).

Preparation of Intermediate 416

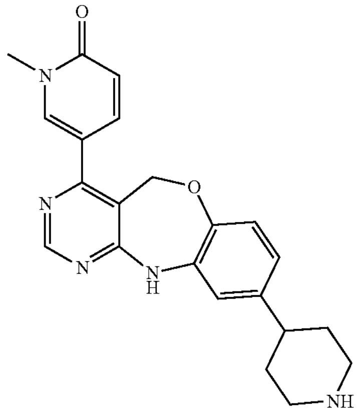 [SMILES: Cn1cc(-c2ncnc3c2COc2ccc(C4CCNCC4)cc2N3)ccc1=O]

HCl (4M in dioxane) (1.762 mL, 4 M, 7.047 mmol) was added to a solution of intermediate 317 (345 mg, 0.705 mmol) in 1,4-dioxane (4.7 mL) and MeOH (2.9 mL) and the mixture was stirred at rt for 12 h. Volatiles were evaporated, and the residue taken up into DCM and re-evaporated to dryness to afford the product (380 mg; quant.) which was used subsequently without further purification.

Preparation of Intermediate 417

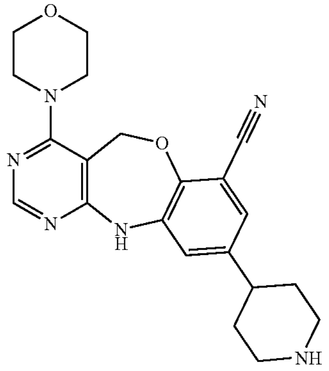 [SMILES: N#Cc1cc(C2CCNCC2)cc2c1OCc1c(ncnc1N1CCOCC1)N2]

At room temperature HCl in dioxane (0.8 mL, 4 M, 3.2 mmol) was added slowly to a mixture of intermediate 318 (120 mg, 0.244 mmol) 1,4-dioxane (2 mL). The reaction mixture was stirred at room temperature for 2 hours and MeOH (0.5 mL, 0.7 g) was added and the mixture was stirred for 1 hour more at room temperature. This reaction was combined with another batch (starting from 300 mg of intermediate 318). The solvent was evaporated until dryness to give intermediate 417 (825 mg, quant)

Preparation of Intermediate 678

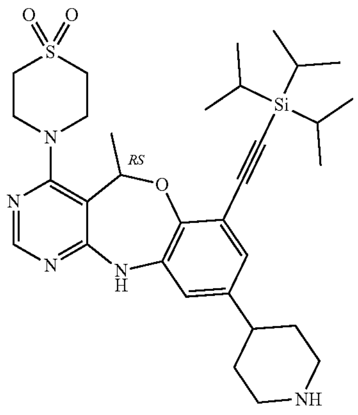 [SMILES: CC1Oc2c(C#C[Si](C(C)C)(C(C)C)C(C)C)cc(C3CCNCC3)cc2Nc2ncnc(N3CCS(=O)(=O)CC3)c21]

HCl in 1,4-dioxane (6.8 mL, 4 M, 27.16 mmol) was added to a solution of intermediate 676 (1100 mg, 1.36 mmol) in DCM (5 mL) at 0° C. The reaction mixture was stirred for 3 h at rt and concentrated in vacuo to give intermediate 678 as HCl salt (1100 mg, 55%).

Example A111

Preparation of Intermediate 418

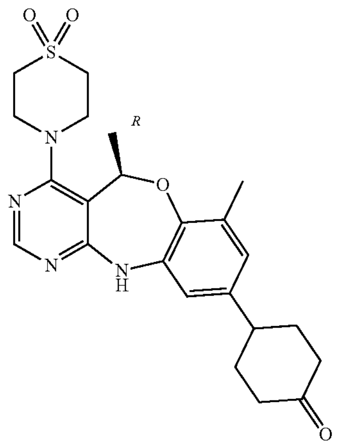

A solution of intermediate 343 (423 mg, 0.591 mmol) in formic acid (7.5 mL) and water (497 μL) was stirred at 50° C. for 2 days. The reaction mixture was cooled down to rt. The mixture was basified with a sat. solution of $NaHCO_3$ (aq) and extracted twice with DCM. The organic layers were combined, dried over $MgSO_4$, filtered, evaporated and purified by preparative LC (irregular SiOH 15-40 μm, 24 g Buchi, liquid loading (DCM), mobile phase gradient: from DCM/(MeOH/$NH_4$OH: 9/1): 100/00 to 95/5, 10 CV). The fractions containing product were evaporated to give the product as a yellow solid (265 mg; 98%).

Example A112

Preparation of Intermediate 419 and Intermediate 420

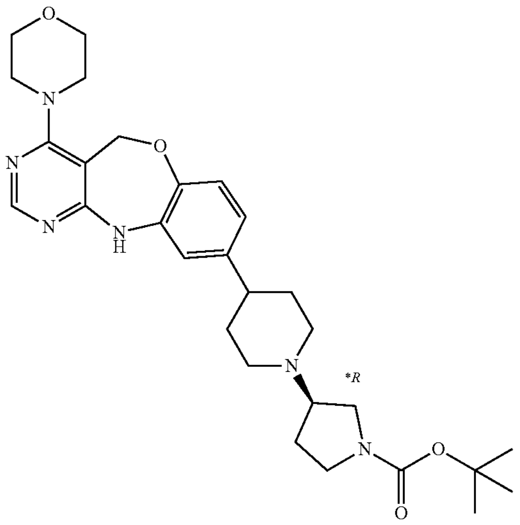

and

-continued

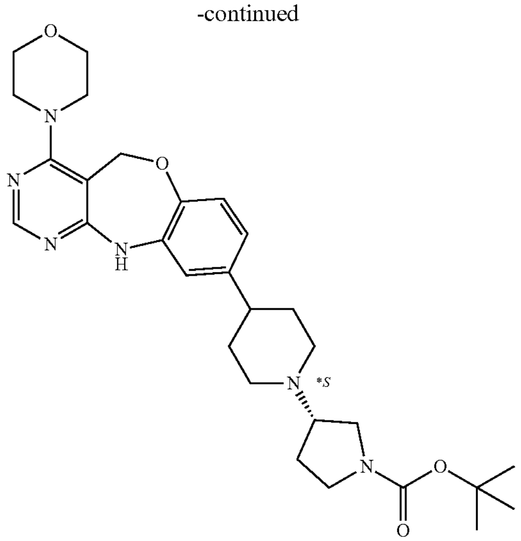

A solution of intermediate 415 (1 g; 2.72 mmol), N-Boc-3-pyrrolidinone (756 mg; 4.08 mmol) and AcOH (281 μL; 4.90 mmol) in dichloroethane (10 mL) was stirred at rt for 15 min, sodium triacetoxyborohydride (1.15 g; 5.44 mmol) was added and the reaction mixture was stirred at rt overnight. The reaction was quenched with a solution of $K_2CO_3$ (aq) 10% and extracted with DCM. The organic layer was washed with water, dried over $MgSO_4$, filtered and the solvent was evaporated to give 1.51 g of a brown residue. The crude was purified by chromatography over silica gel (SiO2; 40 g; Grace; eluent: from 97% DCM, 3% MeOH, 0.3% $NH_4$OH to 90% DCM, 10 MeOH, 1% $NH_4$OH). The pure fractions were collected and the solvent was evaporated to give 2 aliquots of the racemic product as a pale brown foam (613 mg; 42%) and an off-white foam (130 mg; 13%). The pale brown foam was purified via chiral SFC (Stationary phase: CHIRALCEL OJ-H 5 μm 250×20 mm, Mobile phase: 80% $CO_2$, 20% MeOH (0.3% $iPrNH_2$)). The pure fractions were collected and the solvent was evaporated to give as pale brown foams intermediate 419 (287 mg; 20%) and intermediate 420 (287 mg; 20%).

Preparation of Intermediate 421

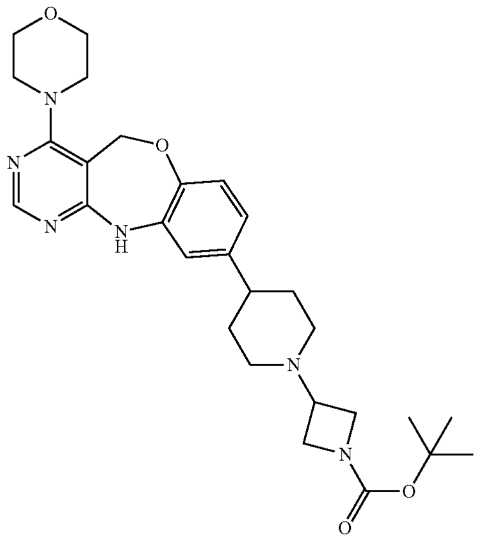 [SMILES: CC(C)(C)OC(=O)N1CC(N2CCC(c3ccc4c(c3)Nc3ncnc(N5CCOCC5)c3CO4)CC2)C1]

A solution of intermediate 415 (210 mg; 0.57 mmol), 1-Boc-azetidinone (147 mg; 0.86 mmol) and AcOH (59 µL; 1.03 mmol) in dichloroethane (2 mL) was stirred at rt for 15 min, sodium triacetoxy borohydride (242 mg; 1.14 mmol) was added and the reaction mixture was stirred at rt overnight. The reaction was quenched with a solution of $K_2CO_3$ (aq) 10% and extracted with EtOAc (3×). The organic layer was washed with brine, dried over $MgSO_4$, filtered and the solvent was evaporated to give 350 mg of the crude product as a pale brown oil. The crude was purified by chromatography over silica gel (SiO2, Grace, 4 g; eluent: from 100% DCM to 97% DCM, 3% MeOH, 0.3% $NH_4OH$). The pure fractions were collected and the solvent was evaporated to give the product as a pale yellow oil (262 mg; 88%).

The intermediates in the Table below were prepared by using an analogous method starting from the respective starting materials.

| compound number | Structure | Mass (mg) | Yield (%) |
|---|---|---|---|
| Intermediate 422 | 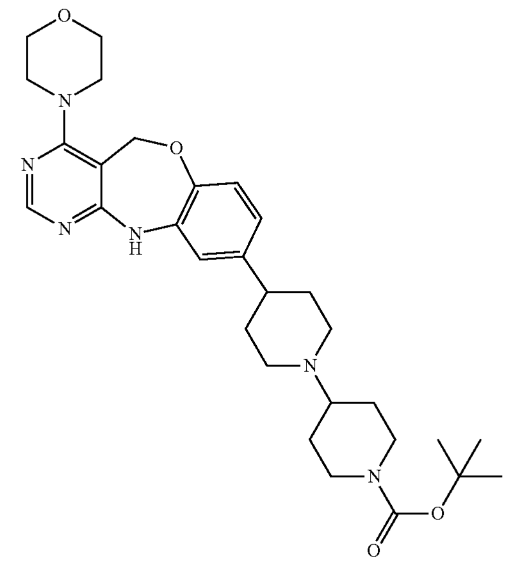 [SMILES: CC(C)(C)OC(=O)N1CCC(N2CCC(c3ccc4c(c3)Nc3ncnc(N5CCOCC5)c3CO4)CC2)CC1] from intermediate 415 and 1-Boc-4-piperidone | 240 | 41 |
| Intermediate 423 | 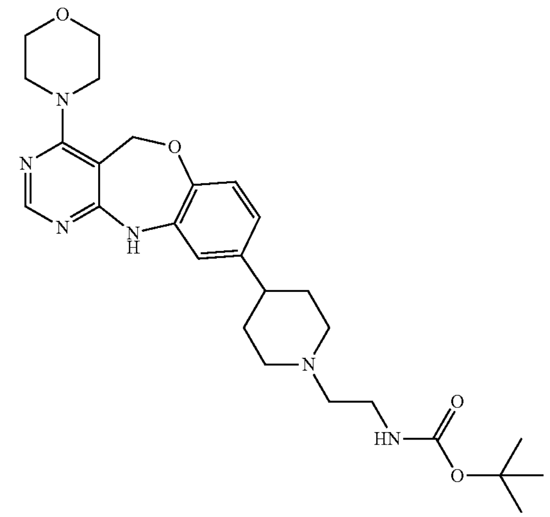 [SMILES: CC(C)(C)OC(=O)NCCN1CCC(c2ccc3c(c2)Nc2ncnc(N4CCOCC4)c2CO3)CC1] from intermediate 415 and N-Boc-2-aminoacetaldehyde | 117 | 24 |

-continued
| compound number | Structure | Mass (mg) | Yield (%) |
|---|---|---|---|
| Intermediate 424 | 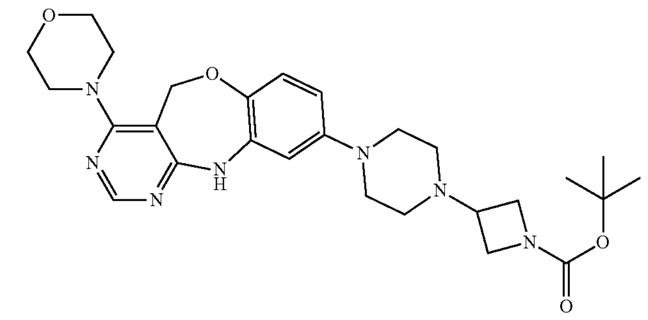 [SMILES: CC(C)(C)OC(=O)N1CC(N2CCN(c3ccc4c(c3)Nc3ncnc(N5CCOCC5)c3CO4)CC2)C1] from intermediate 357 and 1-Boc-azetidinone | 400 | 56 |
| Intermediate 425 | 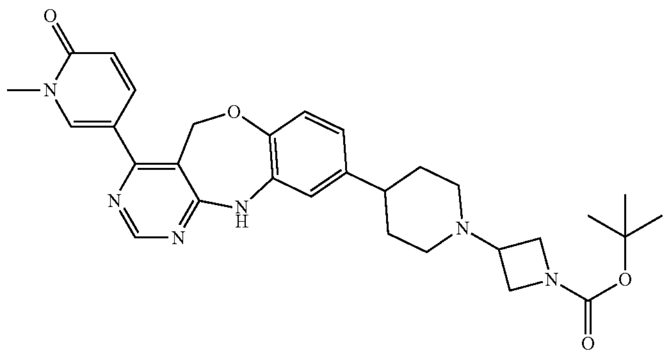 [SMILES: Cn1cc(-c2ncnc3c2COc2ccc(C4CCN(C5CN(C(=O)OC(C)(C)C)C5)CC4)cc2N3)ccc1=O] from intermediate 416 and 1-Boc-azetidinone | 120 | 31 |
| Intermediate 426 | 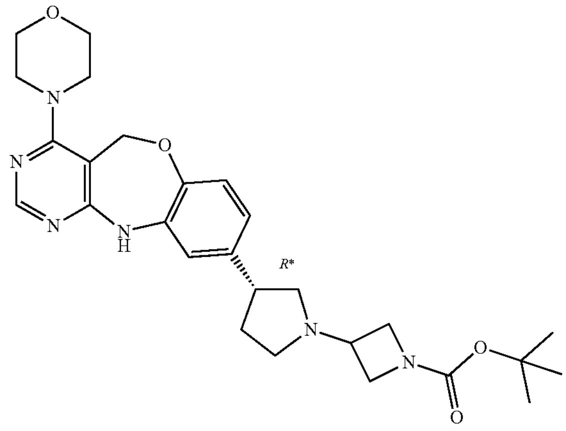 [SMILES: CC(C)(C)OC(=O)N1CC(N2CC[C@H](c3ccc4c(c3)Nc3ncnc(N5CCOCC5)c3CO4)C2)C1] from intermediate 382; solvent 8:1 DCE:MeOH; no AcOH; separation via chiral SFC (Stationary phase: CHIRACEL OJ-H 5 μm 250 * 30 mm, Mobile phase: 80% CO2, 20% iPOH (0.3% iPrNH2)). | 348 | 45 |

-continued
| compound number | Structure | Mass (mg) | Yield (%) |
| --- | --- | --- | --- |
| Intermediate 427 | 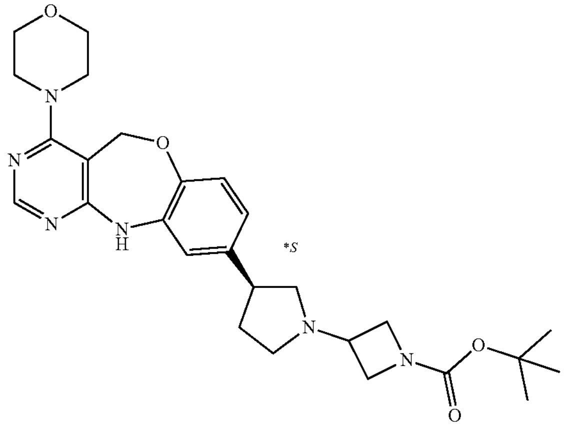 [SMILES: CC(C)(C)OC(=O)N1CC(N2CC[C@@H](c3ccc4c(c3)Nc3ncnc(N5CCOCC5)c3CO4)C2)C1]<br>from intermediate 382; solvent 8:1 DCE:MeOH; no AcOH; separation via chiral SFC (Stationary phase: CHIRACEL OJ-H 5 μm 250 * 30 mm, Mobile phase: 80% CO2, 20% iPOH (0.3% iPrNH2)). | 343 | 44 |
| Intermediate 428 | 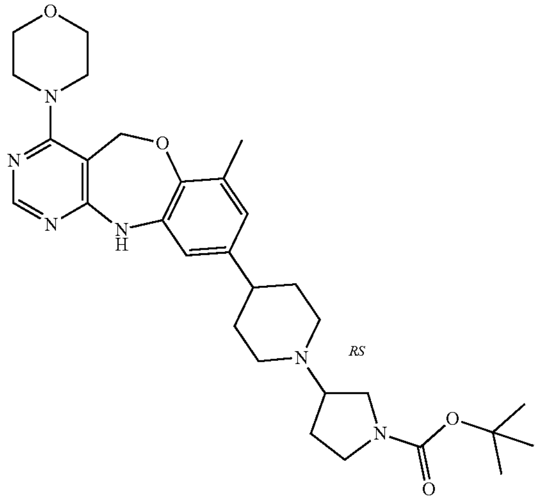 [SMILES: Cc1cc(C2CCN(C3CCN(C(=O)OC(C)(C)C)C3)CC2)cc2c1OCc1c(ncnc1N1CCOCC1)N2]<br>from intermediate 383 and N-Boc-3-pyrrolidinone | 2340 | 60 |

-continued

| compound number | Structure | Mass (mg) | Yield (%) |
|---|---|---|---|
| Intermediate 429 | 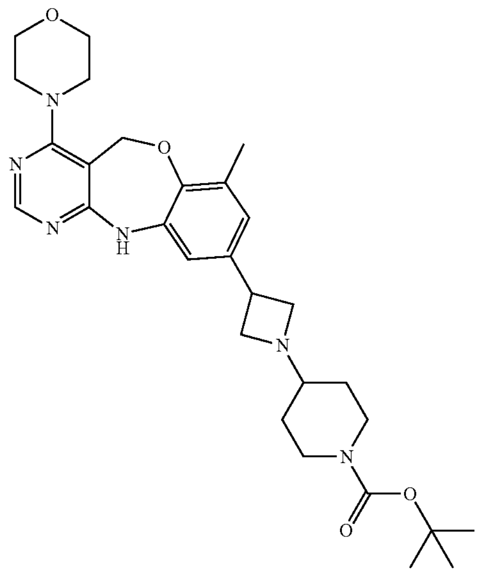 [SMILES: Cc1cc(C2CN(C3CCN(C(=O)OC(C)(C)C)CC3)C2)cc2c1OCc1c(ncnc1N1CCOCC1)N2] from intermediate 368 and 1-Boc-4-piperidone | 275 | 62 |
| Intermediate 430 | 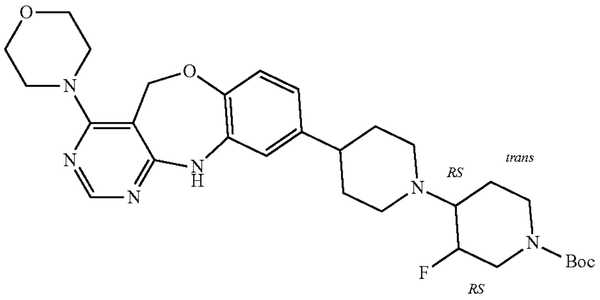 [SMILES: CC(C)(C)OC(=O)N1CCC(N2CCC(c3ccc4c(c3)Nc3ncnc(N5CCOCC5)c3CO4)CC2)C(F)C1] from intermediate 415 and tert-butyl 3-fluoro-4-oxopiperidine-1-carboxylate; purification was performed via Reverse phase (Stationary phase: YMC-DispoPack AT ODS-25: 40 g, Mobile phase: Gradient from 75% NH4HCO3 0.2%, 25% ACN to 45% NH4HCO3 0.2%, 55% ACN) to isolate the trans relative stereochemistry | 130 | 42 |
| Intermediate 431 | 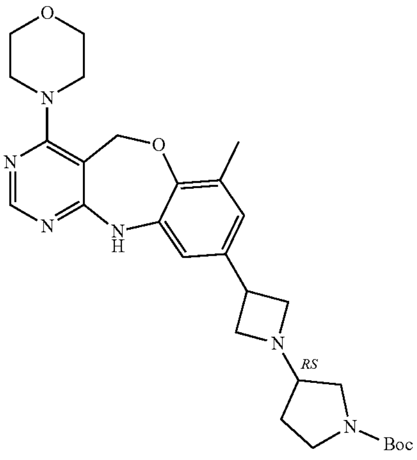 [SMILES: Cc1cc(C2CN(C3CCN(C(=O)OC(C)(C)C)C3)C2)cc2c1OCc1c(ncnc1N1CCOCC1)N2] from intermediate 368 and N-Boc-3-pyrrolidinone | 325 | 78 |

-continued

| compound number | Structure | Mass (mg) | Yield (%) |
|---|---|---|---|
| Intermediate 432 | 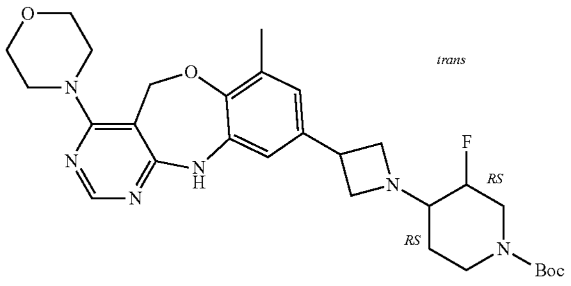 [SMILES: Cc1cc(C2CN(C3CCN(C(=O)OC(C)(C)C)CC3F)C2)cc2c1OCc1c(ncnc1N1CCOCC1)N2] from intermediate 368 and tert-butyl 3-fluoro-4-oxopiperidine-1-carboxylate; purification was performed via preparative LC (Stationary phase: irregular SiOH 15-40 μm 80 g GraceResolv, Mobile phase: gradient from 80% Heptane, 20% AcOEt to 40% Heptane, 50% AcOEt, 10% MeOH (1% NH4OH)). | 110 | 10 |
| Intermediate 433 | 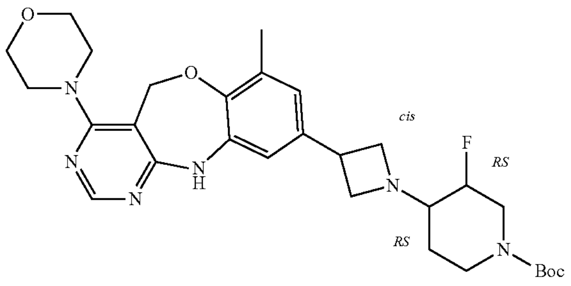 [SMILES: Cc1cc(C2CN(C3CCN(C(=O)OC(C)(C)C)CC3F)C2)cc2c1OCc1c(ncnc1N1CCOCC1)N2] from intermediate 368 and tert-butyl 3-fluoro-4-oxopiperidine-1-carboxylate; purification was performed via preparative LC (Stationary phase: irregular SiOH 15-40 μm 80g GraceResolv, Mobile phase: gradient from 80% Heptane, 20% AcOEt to 40% Heptane, 50% AcOEt, 10% MeOH (1% NH4OH)). | 320 | 28 |
| Intermediate 434 | 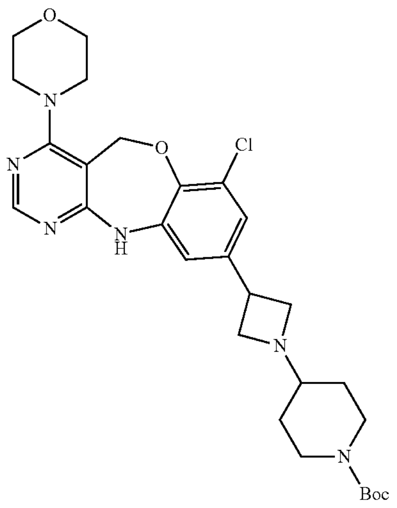 [SMILES: CC(C)(C)OC(=O)N1CCC(N2CC(c3cc(Cl)c4c(c3)Nc3ncnc(N5CCOCC5)c3CO4)C2)CC1] from intermediate 369 and 1-Boc-4-piperidone | 587 | 96 |

-continued

| compound number | Structure | Mass (mg) | Yield (%) |
|---|---|---|---|
| Intermediate 435 | 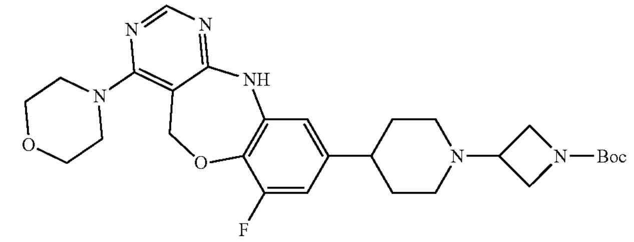 [SMILES: CC(C)(C)OC(=O)N1CC(N2CCC(c3cc(F)c4c(c3)Nc3ncnc(N5CCOCC5)c3CO4)CC2)C1] from intermediate 370 and 1-Boc-azetidinone | 405 | 73 |
| Intermediate 436 | 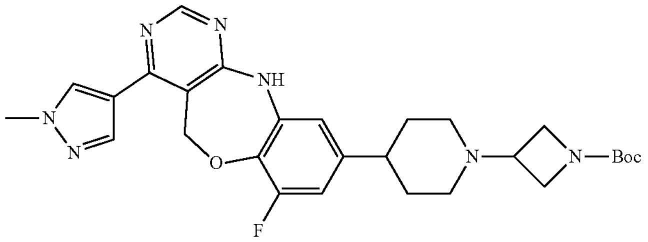 [SMILES: Cn1cc(-c2ncnc3c2COc2c(F)cc(C4CCN(C5CN(C(=O)OC(C)(C)C)C5)CC4)cc2N3)cn1] from intermediate 371 and 1-Boc-azetidinone | 357 | 98 |
| Intermediate 437 | 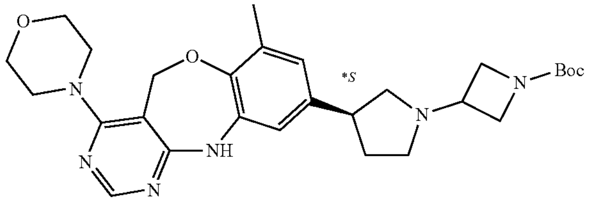 [SMILES: Cc1cc([C@@H]2CCN(C3CN(C(=O)OC(C)(C)C)C3)C2)cc2c1OCc1c(ncnc1N1CCOCC1)N2] from intermediate 372 and 1-Boc-azetidinone; solvent dichloroethane:MeOH (11:2); chiral separation via SFC (Stationary phase: CHIRALCEL OD-H 5 μm 250 * 30 mm, Mobile phase: 65% CO2, 35% iPOH (0.3% iPrNH2)) | 304 | 27 |
| Intermediate 438 | 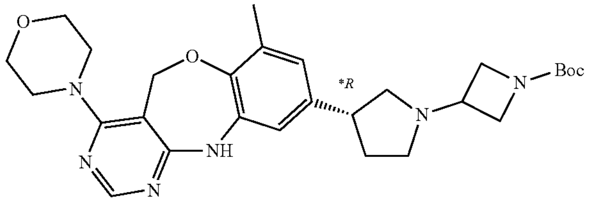 [SMILES: Cc1cc([C@H]2CCN(C3CN(C(=O)OC(C)(C)C)C3)C2)cc2c1OCc1c(ncnc1N1CCOCC1)N2] from intermediate 372 and 1-Boc-azetidinone; solvent dichloroethane:MeOH (11:2); chiral separation via SFC (Stationary phase: CHIRALCEL OD-H 5 μm 250 * 30 mm, Mobile phase: 65% CO2, 35% iPOH (0.3% iPrNH2)) | 295 | 26 |
| Intermediate 439 | 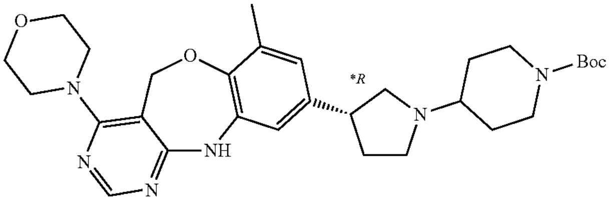 [SMILES: Cc1cc([C@H]2CCN(C3CCN(C(=O)OC(C)(C)C)CC3)C2)cc2c1OCc1c(ncnc1N1CCOCC1)N2] from intermediate 372; and 1-Boc-4-piperidone; solvent dichloroethane:MeOH (6:1); chiral separation via SFC (Stationary phase: Lux-Amylose-2 5 μm 250 * 21.2 mm, Mobile phase: 40% CO2, 60% EtOH (1.0% iPrNH2)) | 382 | 30 |

-continued
| compound number | Structure | Mass (mg) | Yield (%) |
|---|---|---|---|
| Intermediate 440 | 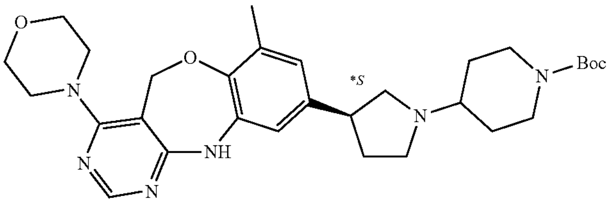 [SMILES: Cc1cc([C@@H]2CCN(C3CCN(C(=O)OC(C)(C)C)CC3)C2)cc2c1OCc1c(ncnc1N1CCOCC1)N2] from intermediate 372; and 1-Boc-4-piperidone; solvent dichloroethane:MeOH (6:1); chiral separation via SFC (Stationary phase: Lux-Amylose-2 5 μm 250 * 21.2 mm, Mobile phase: 40% CO2, 60% EtOH (1.0% iPrNH2)) | 420 | 33 |
| Intermediate 441 | 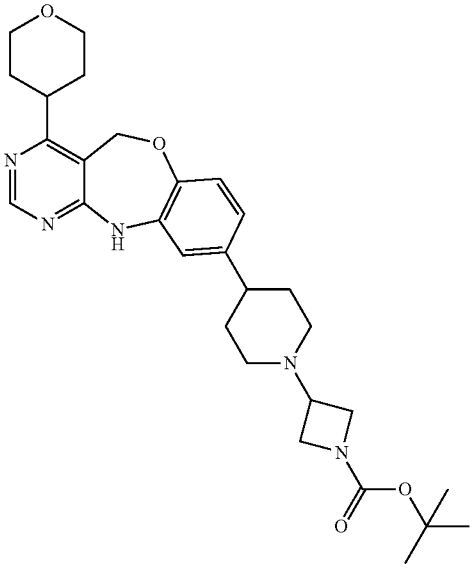 [SMILES: CC(C)(C)OC(=O)N1CC(N2CCC(c3ccc4c(c3)Nc3ncnc(C5CCOCC5)c3CO4)CC2)C1] from intermediate 385 and 1-Boc-azetidinone | 308 | 95 |
| Intermediate 442 | 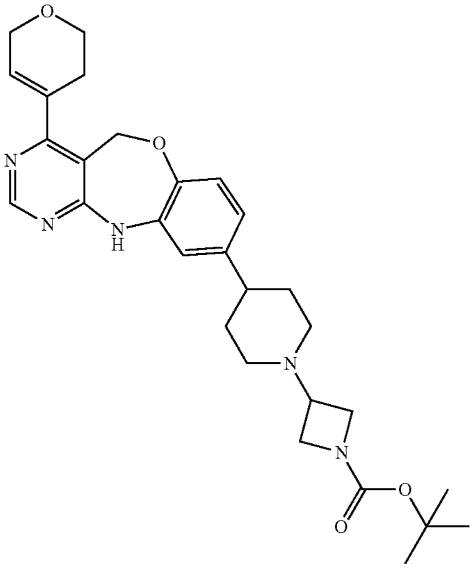 [SMILES: CC(C)(C)OC(=O)N1CC(N2CCC(c3ccc4c(c3)Nc3ncnc(C5=CCOCC5)c3CO4)CC2)C1] from intermediate 386 and 1-Boc-azetidinone | 179 | 88 |

-continued
| compound number | Structure | Mass (mg) | Yield (%) |
|---|---|---|---|
| Intermediate 443 | 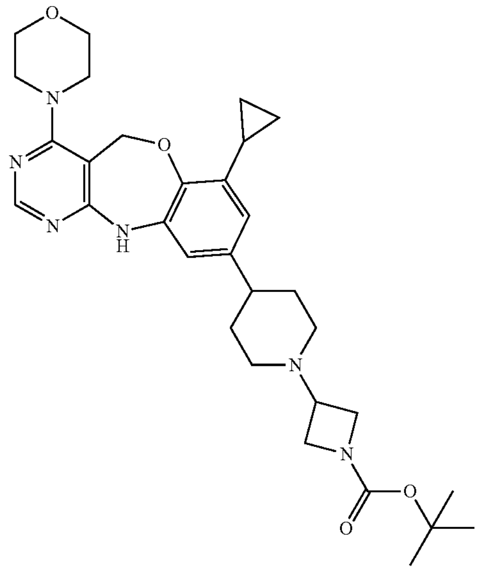 [SMILES: CC(C)(C)OC(=O)N1CC(N2CCC(c3cc4c(c(C5CC5)c3)OCc3c(ncnc3N3CCOCC3)N4)CC2)C1] from intermediate 392 and 1-Boc-azetidinone | 420 | 95 |
| Intermediate 444 | 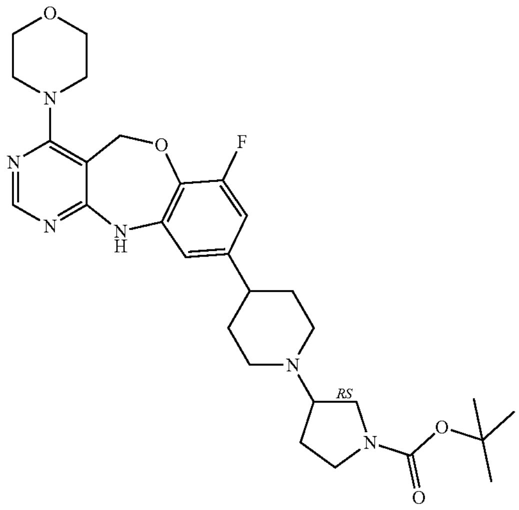 [SMILES: CC(C)(C)OC(=O)N1CCC(N2CCC(c3cc(F)c4c(c3)Nc3ncnc(N5CCOCC5)c3CO4)CC2)C1] from intermediate 394 and N-Boc-3-pyrrolidinone | 960 | 70 |

-continued
| compound number | Structure | Mass (mg) | Yield (%) |
|---|---|---|---|
| Intermediate 445 | 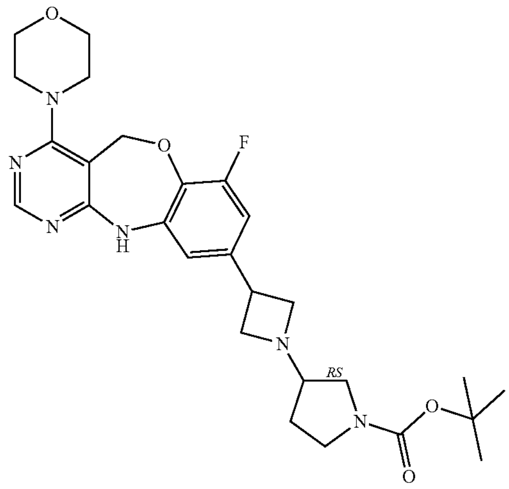 [SMILES: CC(C)(C)OC(=O)N1CCC(N2CC(c3cc(F)c4c(c3)Nc3ncnc(N5CCOCC5)c3CO4)C2)C1] from intermediate 396 and N-Boc-3-pyrrolidinone | 1000 | 59 |
| Intermediate 446 | 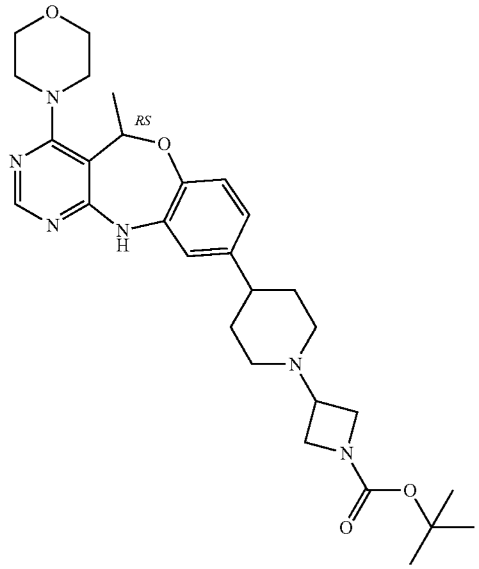 [SMILES: CC1Oc2ccc(C3CCN(C4CN(C(=O)OC(C)(C)C)C4)CC3)cc2Nc2ncnc(N3CCOCC3)c21] from intermediate 397 and 1-Boc-azetidinone | 710 | 81 |

-continued
| compound number | Structure | Mass (mg) | Yield (%) |
|---|---|---|---|
| Intermediate 447 | 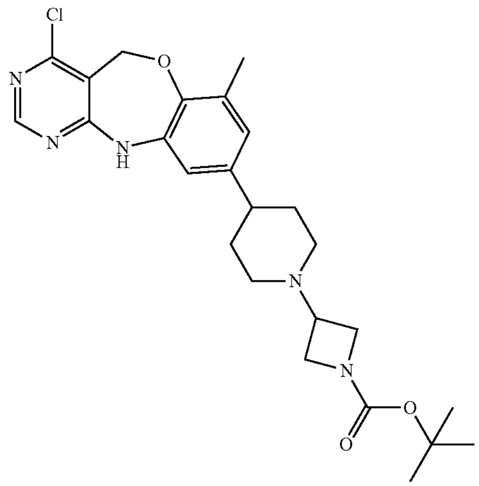 [SMILES: Cc1cc(C2CCN(C3CN(C(=O)OC(C)(C)C)C3)CC2)cc2c1OCc1c(Cl)ncnc1N2] from intermediate 358 and 1-Boc-azetidinone | 7600 | 77 |
| Intermediate 448 | 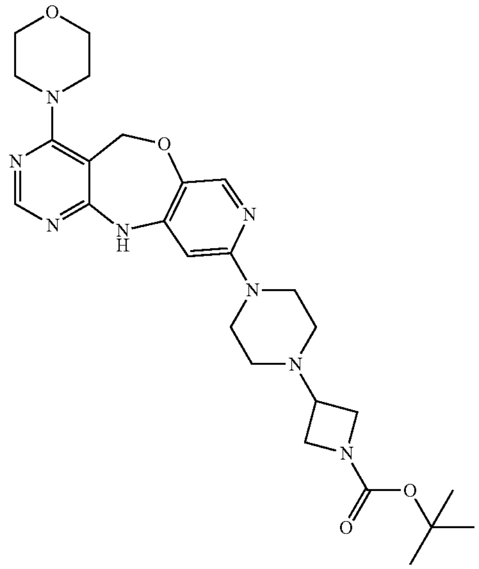 [SMILES: CC(C)(C)OC(=O)N1CC(N2CCN(c3cc4c(cn3)OCc3c(ncnc3N3CCOCC3)N4)CC2)C1] from intermediate 404 and 1-Boc-azetidinone | 640 | quant. |

-continued
| compound number | Structure | Mass (mg) | Yield (%) |
|---|---|---|---|
| Intermediate 449 | 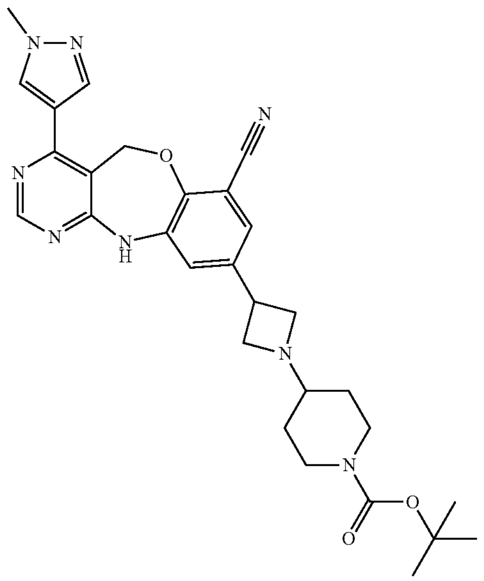 [SMILES: Cn1cc(-c2ncnc3c2COc2c(C#N)cc(C4CN(C5CCN(C(=O)OC(C)(C)C)CC5)C4)cc2N3)cn1] from intermediate 405 and 1-Boc-4-piperidone | 388 | 52 |
| Intermediate 450 | 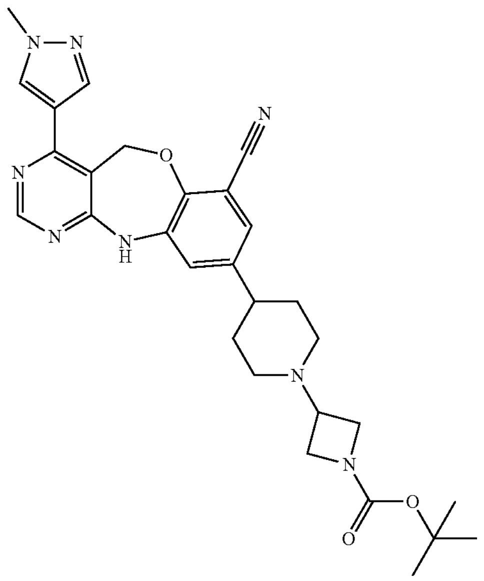 [SMILES: Cn1cc(-c2ncnc3c2COc2c(C#N)cc(C4CCN(C5CN(C(=O)OC(C)(C)C)C5)CC4)cc2N3)cn1] from intermediate 406 and 1-Boc-azetidinone | 355 | 51 |

-continued
| compound number | Structure | Mass (mg) | Yield (%) |
|---|---|---|---|
| Intermediate 451 | 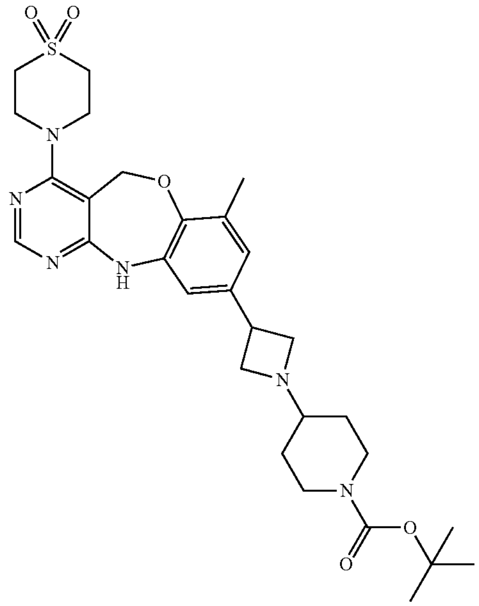 [SMILES: Cc1cc(C2CN(C3CCN(C(=O)OC(C)(C)C)CC3)C2)cc2c1OCc1c(ncnc1N1CCS(=O)(=O)CC1)N2] from intermediate 411 and 1-Boc-4-piperidone | 539 | 65 |
| Intermediate 452 | 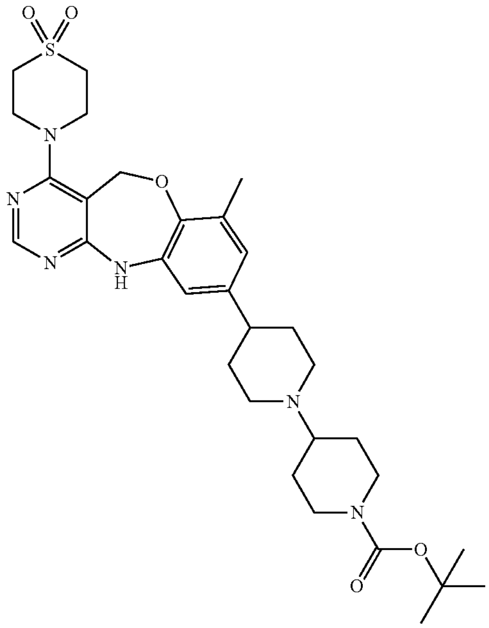 [SMILES: Cc1cc(C2CCN(C3CCN(C(=O)OC(C)(C)C)CC3)CC2)cc2c1OCc1c(ncnc1N1CCS(=O)(=O)CC1)N2] from intermediate 377 and 1-Boc-4-piperidone | 3100 | 54 |

-continued
| compound number | Structure | Mass (mg) | Yield (%) |
|---|---|---|---|
| Intermediate 453 | 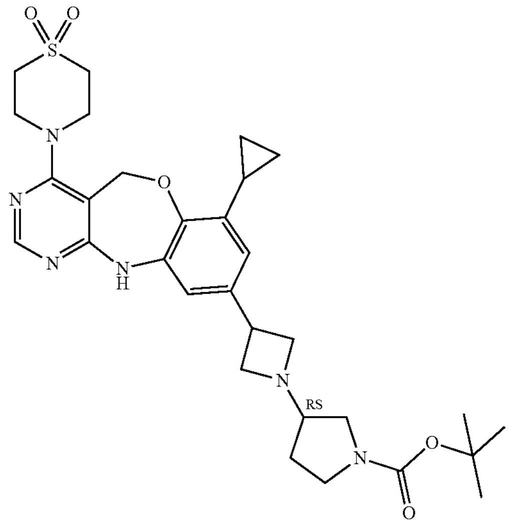 [SMILES: CC(C)(C)OC(=O)N1CCC(N2CC(c3cc4c(c(C5CC5)c3)OCc3c(ncnc3N3CCS(=O)(=O)CC3)N4)C2)C1] from intermediate 412 and N-Boc-3-pyrrolidinone | 681 | 68 |
| Intermediate 456 | 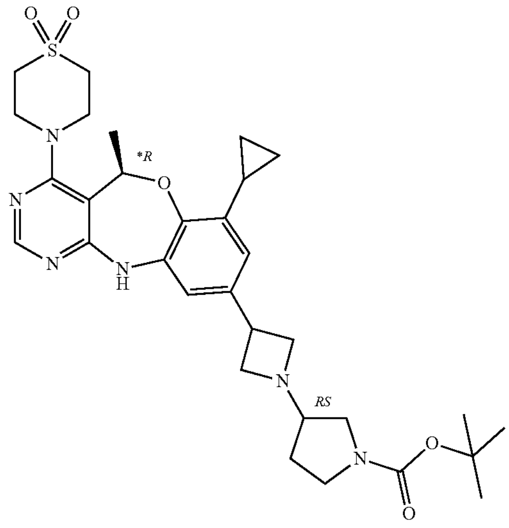 [SMILES: C[C@H]1Oc2c(cc(C3CN(C4CCN(C(=O)OC(C)(C)C)C4)C3)cc2C2CC2)Nc2ncnc(N3CCS(=O)(=O)CC3)c21] from intermediate 413 and N-Boc-3-pyrrolidinone | 170 | 95 |

-continued
| compound number | Structure | Mass (mg) | Yield (%) |
|---|---|---|---|
| Intermediate 459 | 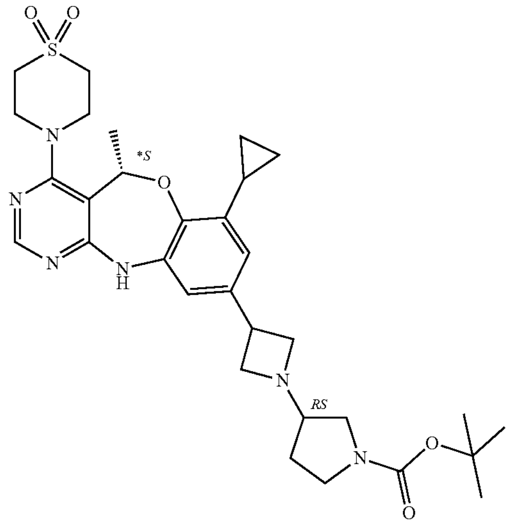 [SMILES: C[C@@H]1Oc2c(cc(C3CN(C4CCN(C(=O)OC(C)(C)C)C4)C3)cc2C2CC2)Nc2ncnc(N3CCS(=O)(=O)CC3)c21] from intermediate 414 and N-Boc-3-pyrrolidinone | 315 | quant. |
| Intermediate 460 | 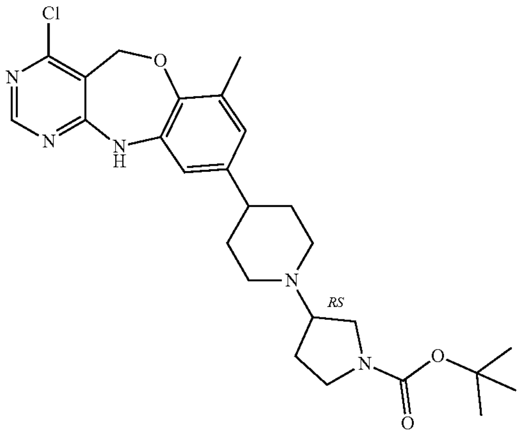 [SMILES: Cc1cc(C2CCN(C3CCN(C(=O)OC(C)(C)C)C3)CC2)cc2c1OCc1c(Cl)ncnc1N2] from intermediate 358 and N-Boc-pyrrolidin-3-one (DCM as solvent, work up with brine) | 3030 | 42 |

-continued

| compound number | Structure | Mass (mg) | Yield (%) |
|---|---|---|---|
| Intermediate 461 | 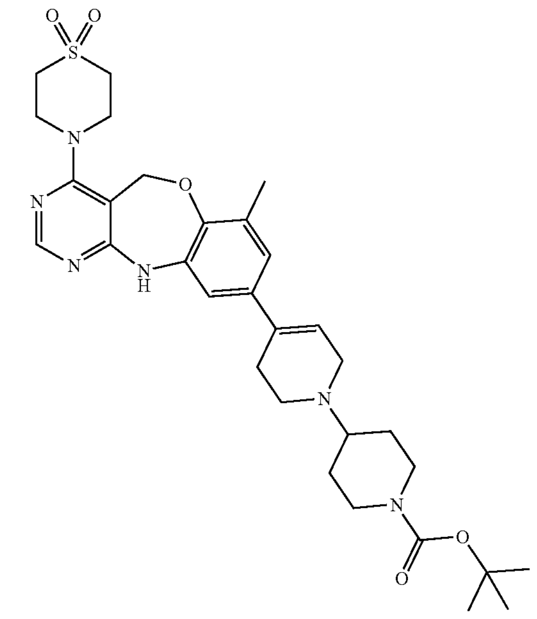 [SMILES: Cc1cc(C2=CCN(C3CCN(C(=O)OC(C)(C)C)CC3)CC2)cc2c1OCc1c(ncnc1N1CCS(=O)(=O)CC1)N2] from intermediate 354 and 1-Boc-piperidone (extraction with DCM) | 2350 | 84 |

Preparation of Intermediate 462

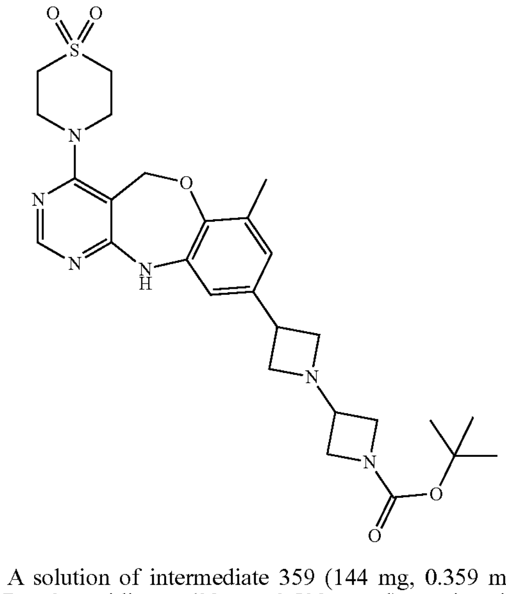

A solution of intermediate 359 (144 mg, 0.359 mmol), 1-Boc-3-azetidinone (92 mg, 0.538 mmol), acetic acid (37 µL, 1.048 g/mL, 0.646 mmol) and sodium triacetoxyborohydride (152 mg, 0.717 mmol) in DCM (1 mL) was stirred at rt for 24 h. The reaction was quenched with an aqueous solution of $K_2CO_3$ 10% and extracted with DCM. The organic layer was washed with brine, dried over $MgSO_4$, filtered and the solvent was evaporated. The residue was purified by chromatography over silica gel ($SiO_2$, Grace 40 g; eluent: from 100% DCM to 95% DCM, 5% MeoH, 0.5% $NH_4OH$). The pure fractions were collected and the solvent was evaporated to give intermediate 462 (127 mg, 64%).

Preparation of Intermediate 463

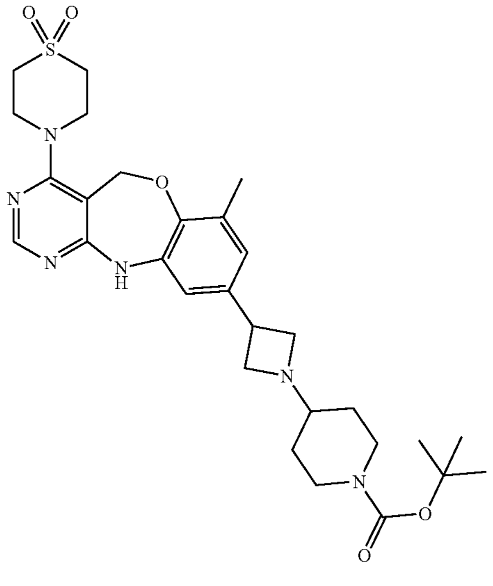 [SMILES: Cc1cc(C2CN(C3CCN(C(=O)OC(C)(C)C)CC3)C2)cc2c1OCc1c(ncnc1N1CCS(=O)(=O)CC1)N2]

tert-Butoxycarbonylpiperidin-4-one (420 mg, 2.11 mmol) was added to a solution of intermediate 359 (1146 mg, 1.06 mmol) and triethylamine (0.88 mL, 6.33 mmol) in 1,2-dichloroethane (15 mL) and the mixture was stirred for 1 h. Sodium triacetoxyborohydride (340 mg) was added and the mixture was stirred at rt for 48 h. Saturated aqueous $NaHCO_3$ was added and the aqueous layer was extracted with DCM. The organic phase was washed with brine, then dried over $MgSO_4$, filtered and evaporated to dryness. The crude was purified by flash column chromatography ($SiO_2$, eluting with heptane-ethyl acetate 50% to 100% to remove some impurities, then with DCM-MeOH 0% to 10% to elute the product) to give intermediate 463 (353 mg, 57%).

The intermediates in the Table below were prepared by using an analogous method starting from the respective starting materials.

| compound number | Structure | Mass (mg) | Yield (%) |
|---|---|---|---|
| Intermediate 679 | 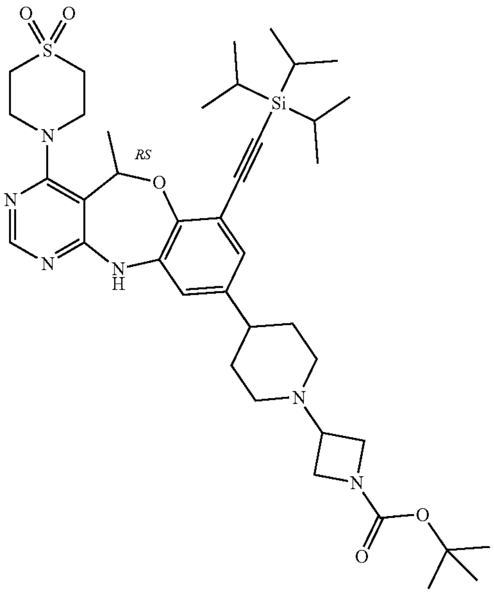 [SMILES: CC1Oc2c(C#C[Si](C(C)C)(C(C)C)C(C)C)cc(C3CCN(C4CN(C(=O)OC(C)(C)C)C4)CC3)cc2Nc2ncnc(N3CCS(=O)(=O)CC3)c21] from intermediate 678 and 1-Boc-azetidinone | 670 | 60 |

Preparation of Intermediate 464

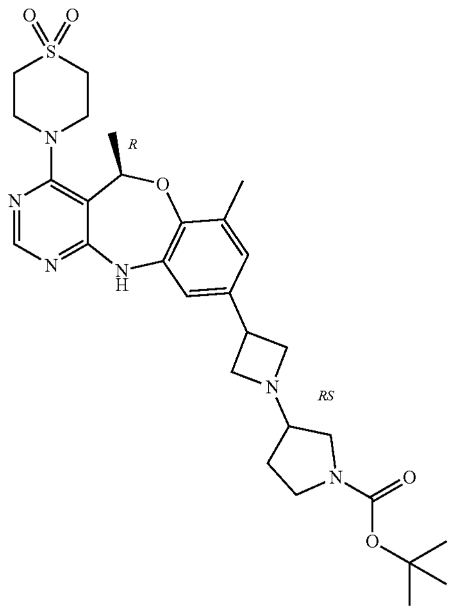

To a solution of intermediate 360 (1.21 g, 1.06 mmol) and TEA (881 μL, 6.34 mmol) in DCE (21 mL), N-Boc-3-pyrrolidinone (391 mg, 2.11 mmol) was added and the reaction mixture was stirred for 4 h. Then sodium triacetoxyborohydride (336 mg, 1.58 mmol) was added and the mixture was stirred at rt for 18 h. DCM and a saturated aqueous solution of $NaHCO_3$ were added and the layers were separated. The aqueous layer was extracted with DCM and the combined organic layers were washed with brine, dried over MgSO4, filtered, concentrated and purified by preparative LC (irregular SiOH 40 μm, 40 g Buchi, liquid injection (CH2Cl2), mobile phase gradient: from CH2Cl2/(MeOH+10% aq. $NH_3$): 98/2 to 90/10, 15 CV). The fractions containing products were evaporated to give intermediate 464 (471 mg, 66%, purity 86%).

Preparation of Intermediate 465

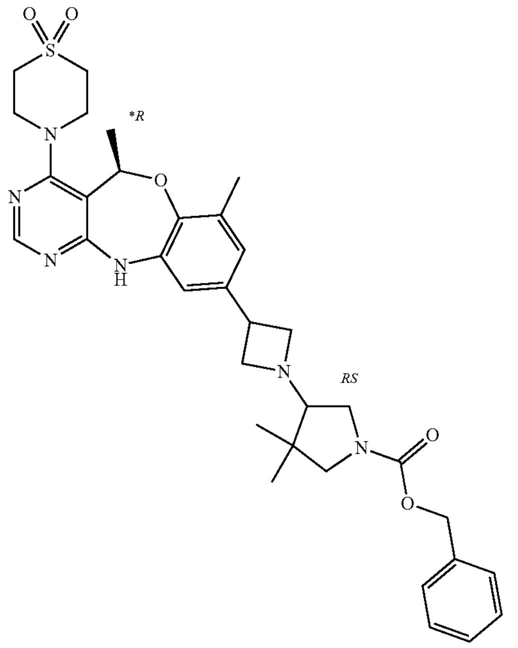

Intermediate 96 (189 mg, 0.765 mmol) was added to a solution of intermediate 378*R (159 mg, 0.383 mmol) in DCE (7.6 mL), and the reaction mixture was stirred ar rt for 1 h. Then, sodium triacetoxyborohydride (122 mg, 0.574 mmol) was added and the mixture was stirred at rt for 70 h. The solvent was removed in vacuo. The crude was purified by preparative LC (irregular SiOH 40 μm, 12 g Buchi, liquid loading (DCM), mobile phase gradient: from DCM/MeOH 100/0 to 90/10). The fractions containing product were evaporated to give 159 mg of a yellow residue. This residue was diluted with a saturated aqueous solution of $NaHCO_3$ and DCM were added. The layers were separated and the aqueous layer was extracted with DCM (twice). The combined organic layers were dried over MgSO4, filtered and the solvent was removed in vacuo to give intermediate 465 (129 mg, 43%, purity 83%).

Example A113

Preparation of Intermediate 466

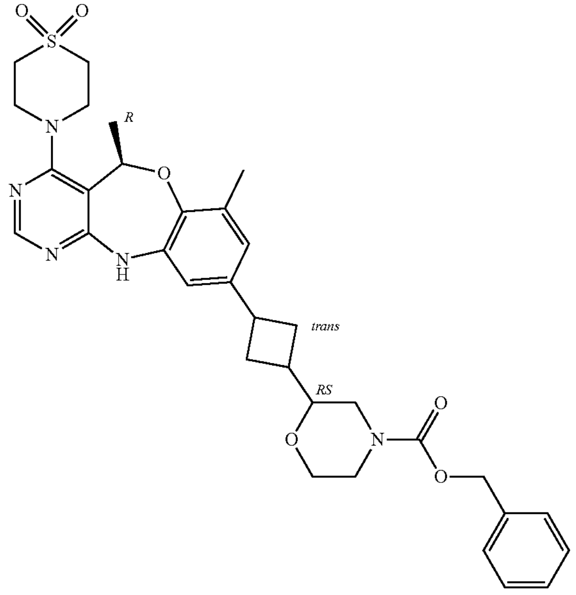

Intermediate 341 (328 mg, 0.447 mmol) was dissolved in DCM (9 mL) and the mixture was cooled to 0° C. then TFA (328 mg, 0.447 mmol) was added slowly. This mixture was stirred at room temperature for 4.5 hours. The reaction mixture concentrated then cooled at 0° C. Water and an aqueous solution of NH4OH 10% were added until pH=10. The aqueous was extracted twice with DCM, The organic layer was washed with brine, dried over MgSO4, filtered and concentrated to give intermediate 466 (311 mg, quant, purity 91%) as a pale yellow solid.

The intermediates in the Table below were prepared by using an analogous method starting from the respective starting materials.

| compound number | Structure | Mass (mg) | Yield (%) |
|---|---|---|---|
| Intermediate 467 | 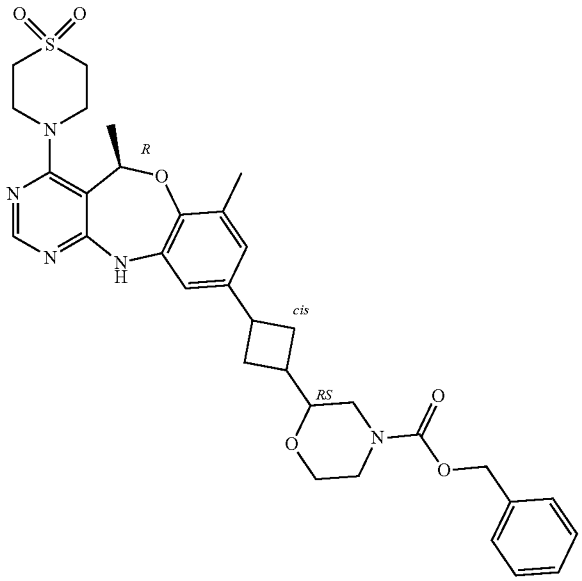 from intermediate 342 | 332 | 71 |

Example A114

Preparation of Intermediate 468

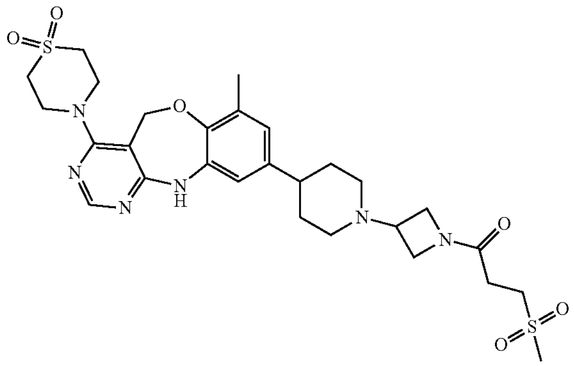 [SMILES: Cc1cc(C2CCN(C3CN(C(=O)CCS(C)(=O)=O)C3)CC2)cc2c1OCc1c(ncnc1N1CCS(=O)(=O)CC1)N2]

A solution of intermediate 377 (6 g; 14 mmol), intermediate 89 (4.3 g; 21 mmol) and AcOH (1.36 mL; 24 mmol) in dichloromethane (138 mL) was stirred at rt for 10 min then sodium triacetoxy borohydride (5.9 g; 28 mmol) was added and the reaction mixture was stirred at rt for 12 h. The reaction mixture was combined with 2 others reaction mixture (starting respectively with 2.3 g and 0.86 g of intermediate 377). The reaction was quenched with a solution of $K_2CO_3$(aq) 10% and extracted with DCM. The organic layer was decanted and the solvent was evaporated to give 9.3 g of the crude product. The crude was purified by chromatography over silica gel (SiO2, Grace, 4 g; eluent: from 100% DCM to 93% DCM, 7% MeOH, 0.7% NH4OH). The pure fractions were collected and the solvent was evaporated to give the product (6.2 g; 47%)

The intermediates in the Table below were prepared by using an analogous method starting from the respective starting materials.

| compound number | Structure | Mass (mg) | Yield (%) |
|---|---|---|---|
| Intermediate 469*R | 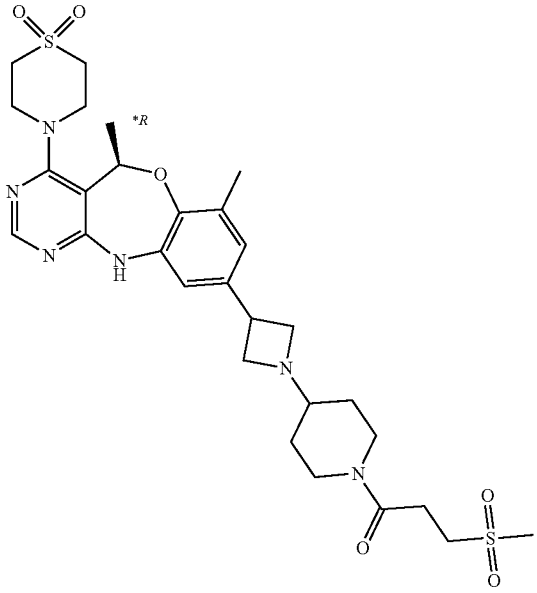 from intermediate 378*R and intermediate 91 | 4910 | 85 |
| Intermediate 470 | 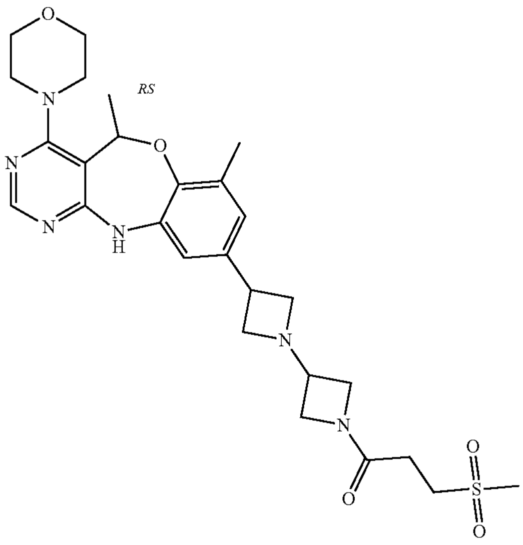 [SMILES: Cc1cc(C2CN(C3CN(C(=O)CCS(C)(=O)=O)C3)C2)cc2c1OC(C)c1c(ncnc1N1CCOCC1)N2] from intermediate 367 and intermediate 89 | 103 | 66 |

-continued
| compound number | Structure | Mass (mg) | Yield (%) |
|---|---|---|---|
| Intermediate 471 and intermediate 472 | 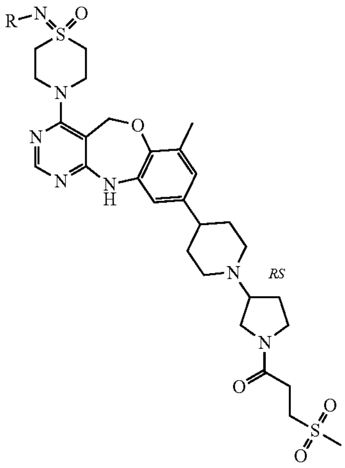 from intermediate 379 and intermediate 90; both R = H and R = $COCF_3$ were obtained | R = H 76 R = COCF3 141 | 40 65 |
| Intermediate 473 | 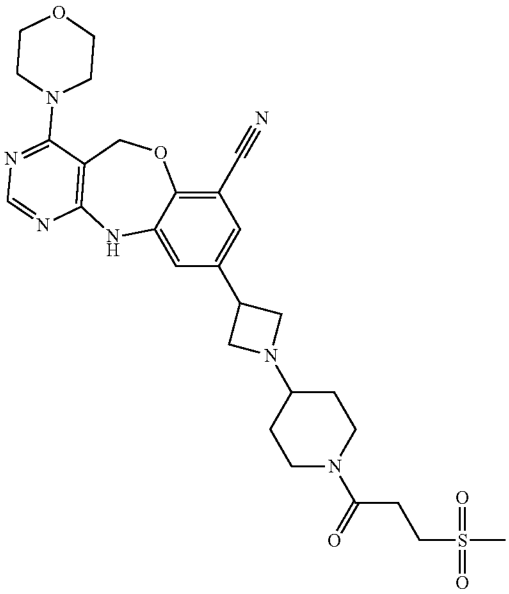 [SMILES: CS(=O)(=O)CCC(=O)N1CCC(N2CC(c3cc(C#N)c4c(c3)Nc3ncnc(N5CCOCC5)c3CO4)C2)CC1] from intermediate 381 and intermediate 91 | 164 | 47 |

-continued

| compound number | Structure | Mass (mg) | Yield (%) |
|---|---|---|---|
| Intermediate 474 | 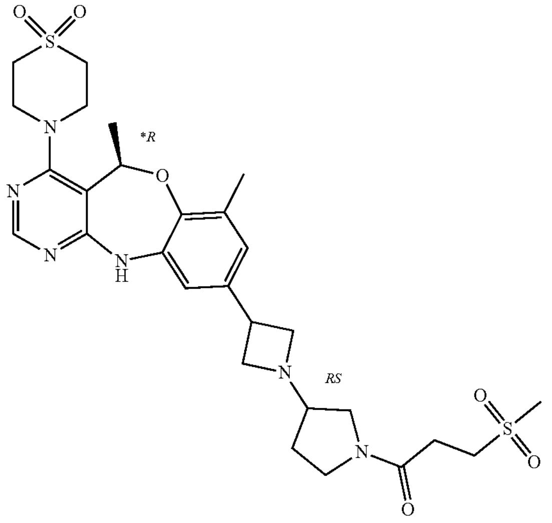 [SMILES: Cc1cc(C2CN(C3CCN(C(=O)CCS(C)(=O)=O)C3)C2)cc2c1O[C@H](C)c1c(ncnc1N1CCS(=O)(=O)CC1)N2] from intermediate 378*R and intermediate 90 | 4900 | 71 |

Preparation of Intermediate 475

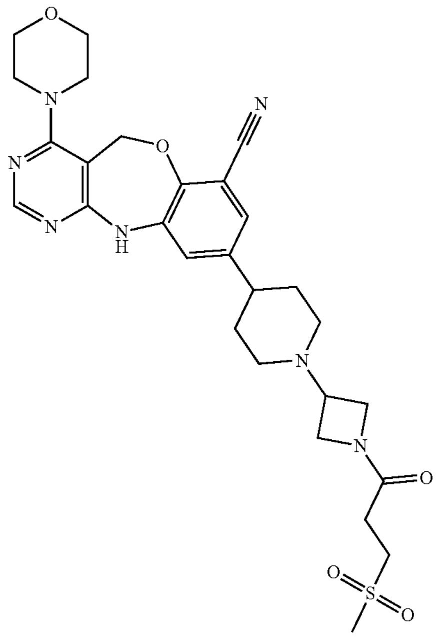 [SMILES: CS(=O)(=O)CCC(=O)N1CC(N2CCC(c3cc(C#N)c4c(c3)Nc3ncnc(N5CCOCC5)c3CO4)CC2)C1]

A mixture of intermediate 417 (339 mg, 0.73 mmol), intermediate 89 (0.224 g, 1.1 mmol), sodium triacetoxy borohydride (0.293 g, 1.38 mmol) in AcOH (0.08 mL, 1.049 g/mL, 1.4 mmol) and DCM (7 mL) was stirred at room temperature overnight then intermediate 89 (70 mg, 0.341 mmol) and sodium triacetoxy borohydride (154 mg, 0.73 mmol) was added and the mixture was stirred at room temperature for 2 days more. Water and an aqueous solution of K2CO3 10% were added. The mixture was extracted twice with EtOAc and once with DCM. The organic layers were combined and the solvent was evaporated until dryness. The crude was purified by preparative LC (Irregular SiOH 15-40 μm 40 g GraceResolv®, mobile phase Gradient from 99% DCM, 1% MeOH, 0.1% NH4OH to 88% DCM, 12% MeOH, 1.2% NH4OH). The pure fractions were collected and the solvent was evaporated until dryness to give intermediate 475 (125 mg, 30%).

Preparation of Intermediate 476 and Intermediate 477

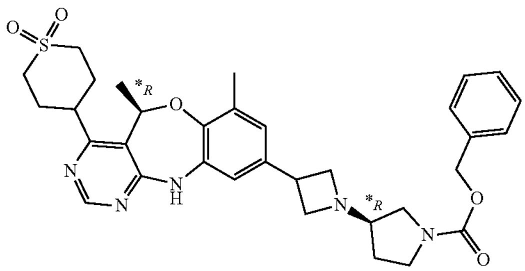

and

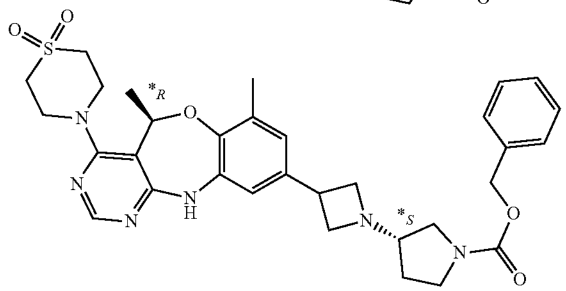

Sodium triacetoxyborohydride (4.386 g, 20.69 mmol) was added to a stirred solution of intermediate 373 (4.3 g, 10.35 mmol), 1-Z-3-pyrrolidinone (3.403 g, 15.52 mmol) and HOAc (1.02 mL, 1.049 g/mL, 17.84 mmol) in DCM (108 mL) at rt. The reaction mixture was stirred at rt for 12 h, diluted in DCM and an aqueous solution of $K_2CO_3$ 10% was added. This mixture was stirred then the organic layer was decanted with Chromabond® and the solvent was evaporated until dryness. This crude was purified by preparative LC (Irregular $SiO_2$ 15-40 μm 120 g GraceResolv®, mobile phase Gradient from: 100% DCM to 94% DCM, 6% MeOH (2% $NH_4OH$)) The pure fractions were collected and the solvent was evaporated until dryness to give the racemic product (6000 mg, 94%). A purification was performed via chiral SFC (Stationary phase: CHIRALPAK AS-H 5 μm 250*20 mm, Mobile phase: 55% CO2, 45% mixture of EtOH/iPrOH 50/50 v/v+10% ACN (+0.3% $iPrNH_2$)) to give intermediate 476 (2.82 g, 44%) and intermediate 477 (2.72 g, 42%).

The intermediates in the Table below were prepared by using an analogous method starting from the respective starting materials.

| compound number | Structure | Mass (mg) | Yield (%) |
|---|---|---|---|
| Intermediate 478 | 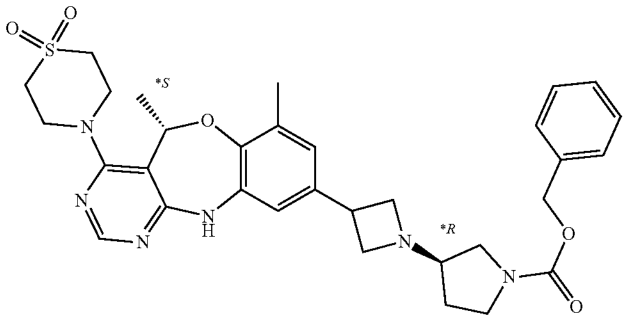 [SMILES: Cc1cc(C2CN([C@@H]3CCN(C(=O)OCc4ccccc4)C3)C2)cc2c1O[C@@H](C)c1c(ncnc1N1CCS(=O)(=O)CC1)N2] from intermediate 374 | 480 | 27 |
| Intermediate 479 | 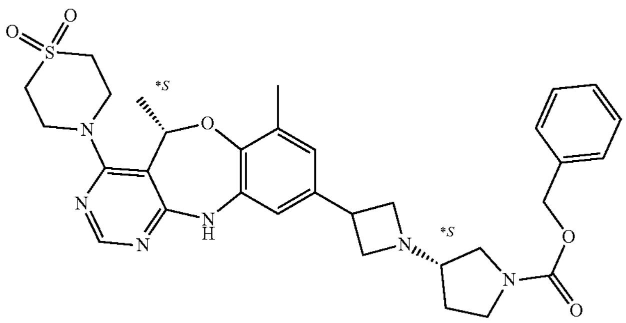 [SMILES: Cc1cc(C2CN([C@H]3CCN(C(=O)OCc4ccccc4)C3)C2)cc2c1O[C@@H](C)c1c(ncnc1N1CCS(=O)(=O)CC1)N2] from intermediate 374 | 580 | 33 |

Example A115

Preparation of Intermediate 480

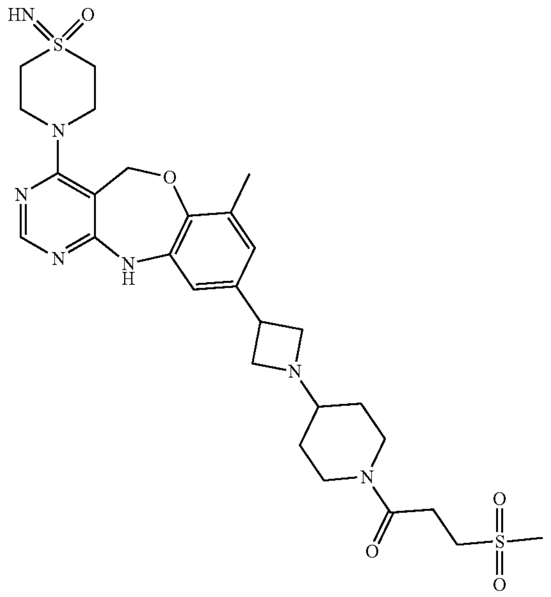 [SMILES: Cc1cc(C2CN(C3CCN(C(=O)CCS(C)(=O)=O)CC3)C2)cc2c1OCc1c(ncnc1N1CCS(=N)(=O)CC1)N2]

Intermediate 380 (1.85 g, 1.71 mmol), intermediate 91 (1.62 g, 6.93 mmol) and AcOH (476 µL, 1.049 g/mL, 8.3 mmol) in EtOH (59 mL) at room temperature. The reaction mixture was stirred for 10 min then sodium cyanoborohydride (785 mg, 9.2 mmol) was added. The reaction mixture was stirred at rt for 12 h. Water was added and EtOH was evaporated.

The aqueous layer was extracted using continuous extraction with DCM to give intermediate 480 (215 mg, 20%).

The intermediates in the Table below were prepared by using an analogous method starting from the respective starting materials.

| compound number | Structure | Mass (mg) | Yield (%) |
|---|---|---|---|
| Intermediate 469*S | 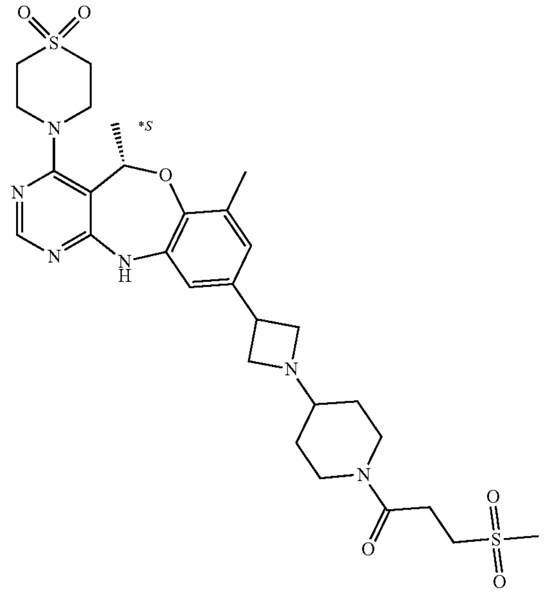 [SMILES: Cc1cc(C2CN(C3CCN(C(=O)CCS(C)(=O)=O)CC3)C2)cc2c1O[C@@H](C)c1c(ncnc1N1CCS(=O)(=O)CC1)N2] from intermediate 378*S and intermediate 91 | 4900 | 92 |

-continued
| compound number | Structure | Mass (mg) | Yield (%) |
|---|---|---|---|
| Intermediate 481 | 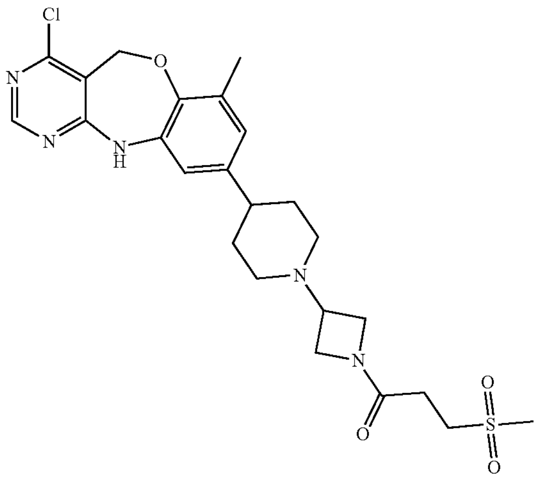 [SMILES: Cc1cc(C2CCN(C3CN(C(=O)CCS(C)(=O)=O)C3)CC2)cc2c1OCc1c(Cl)ncnc1N2] from intermediate 89 and intermediate 358 | 2600 | 28 |
| Intermediate 482 | 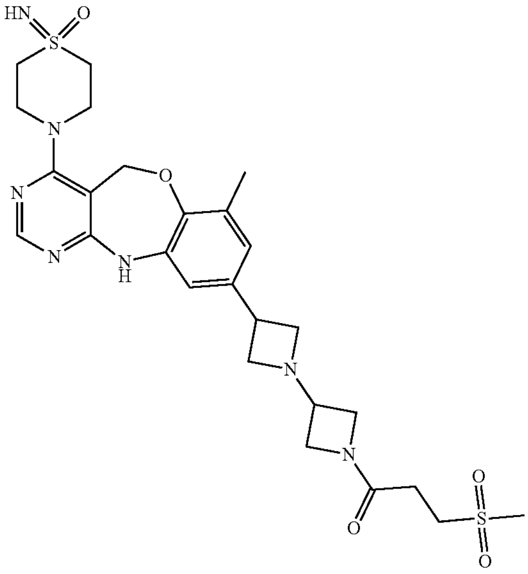 [SMILES: Cc1cc(C2CN(C3CN(C(=O)CCS(C)(=O)=O)C3)C2)cc2c1OCc1c(ncnc1N1CCS(=N)(=O)CC1)N2] from intermediate 380 and intermediate 89 | 230 | 22 82% purity |

Preparation of Intermediate 483

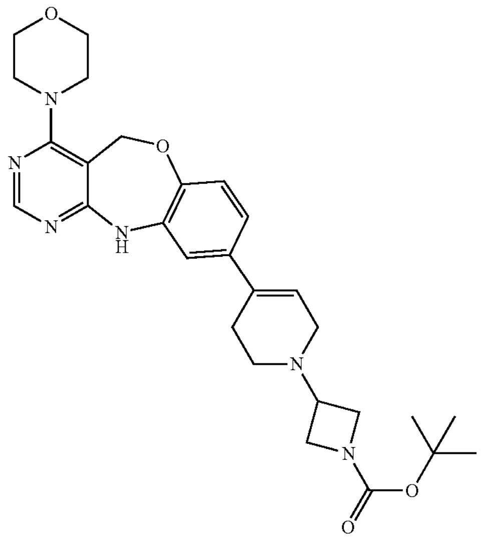 [SMILES: CC(C)(C)OC(=O)N1CC(N2CC=C(c3ccc4c(c3)Nc3ncnc(N5CCOCC5)c3CO4)CC2)C1]

To a solution of intermediate 353 (226 mg; 0.618 mmol) in methanol (5.3 mL) were added 1-Boc-azetidinone (211.8 mg; 1.237 mmol), AcOH (42.4 μl; 1.05 g/mL; 0.742 mmol) and sodium cyanoborohydride (19.4 mg; 0.309 mmol) at room temperature. The mixture was stirred for 16 h. To the reaction mixture was added $NaHCO_3$(aq) and the mixture extracted with ethyl acetate and washed with $NaHCO_3$(aq). The organic phase was dried over $MgSO_4$, filtered and evaporated to dryness. The crude was purified by flash column chromatography eluting with a mixture of DCM/DCM:MeOH 9:1 (40%) to yield the product (228 mg; 71%)

The compounds in the Table below were prepared by using an analogous method starting from the respective starting materials.

| compound number | Structure | Mass (mg) | Yield (%) |
|---|---|---|---|
| Intermediate 653 | 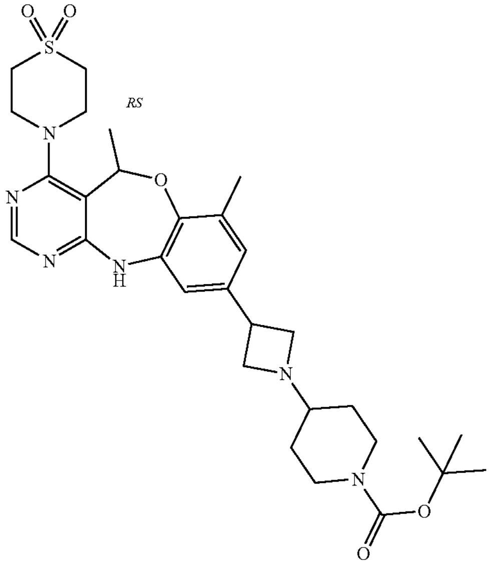 [SMILES: Cc1cc(C2CN(C3CCN(C(=O)OC(C)(C)C)CC3)C2)cc2c1OC(C)c1c(ncnc1N1CCS(=O)(=O)CC1)N2] from intermediate 220 and 1-Boc-4-piperidone | 2300 | 61 |
| Intermediate 484 | 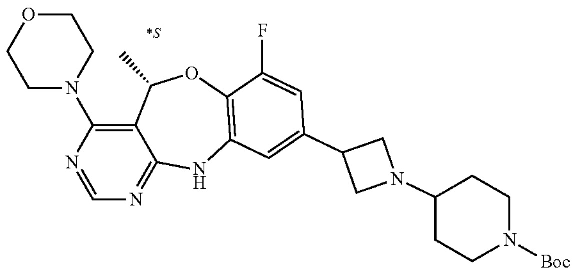 [SMILES: C[C@@H]1Oc2c(F)cc(C3CN(C4CCN(C(=O)OC(C)(C)C)CC4)C3)cc2Nc2ncnc(N3CCOCC3)c21] from intermediate 384 and 1-Boc-4-piperidone; chiral separation via chiral HPLC (Method LUX-CELLULOSE-1, QMG2) | 347 | 35 |

-continued
| compound number | Structure | Mass (mg) | Yield (%) |
|---|---|---|---|
| Intermediate 485 | 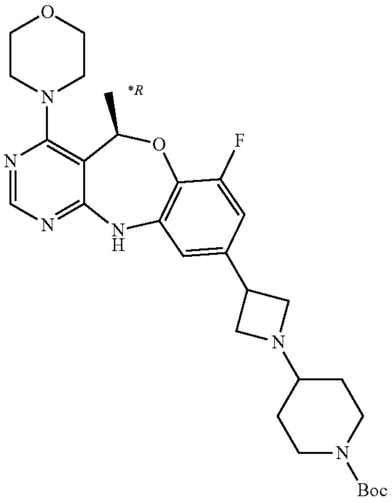 [SMILES: C[C@H]1Oc2c(F)cc(C3CN(C4CCN(C(=O)OC(C)(C)C)CC4)C3)cc2Nc2ncnc(N3CCOCC3)c21] from intermediate 384 and 1-Boc-4-piperidone; chiral separation via chiral HPLC, (Method LUX-CELLULOSE-1, QMG2) | 358 | 36 |
| Intermediate 486 | 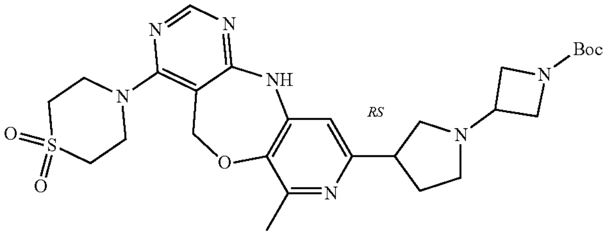 [SMILES: Cc1nc(C2CCN(C3CN(C(=O)OC(C)(C)C)C3)C2)cc2c1OCc1c(ncnc1N1CCS(=O)(=O)CC1)N2] from intermediate 402 and 1-Boc-azetidinone | 354 | 34 |
| Intermediate 483 | 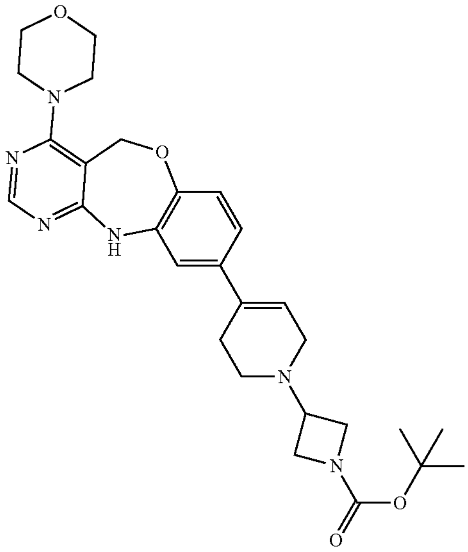 [SMILES: CC(C)(C)OC(=O)N1CC(N2CC=C(c3ccc4c(c3)Nc3ncnc(N5CCOCC5)c3CO4)CC2)C1] from intermediate 353 and 1-Boc-azetidinone | 228 | 71 |

-continued
| compound number | Structure | Mass (mg) | Yield (%) |
|---|---|---|---|
| Intermediate 487 | 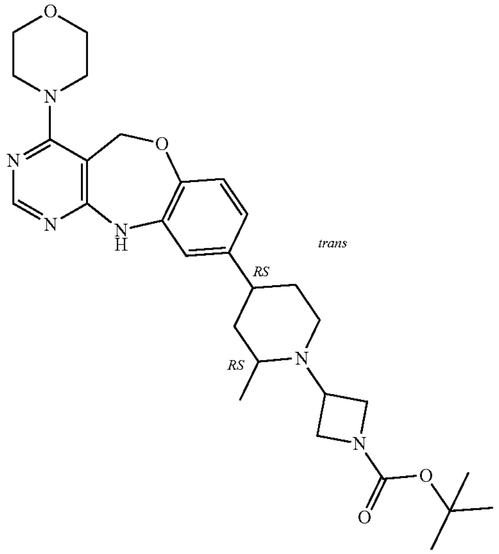 [SMILES: CC1CC(c2ccc3c(c2)Nc2ncnc(N4CCOCC4)c2CO3)CCN1C1CN(C(=O)OC(C)(C)C)C1] from intermediate 356 and 1-Boc-azetidinone—only trans isomer isolated | 300 | 92 |
| Intermediate 488 | 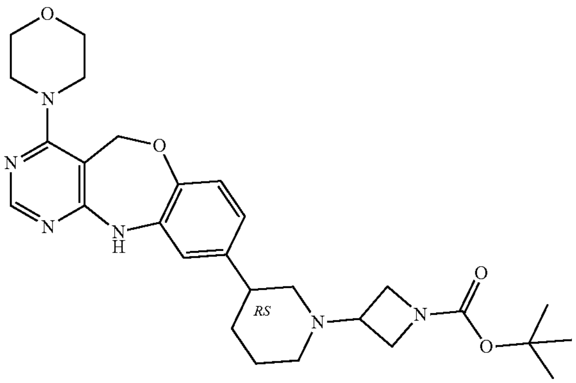 [SMILES: CC(C)(C)OC(=O)N1CC(N2CCCC(c3ccc4c(c3)Nc3ncnc(N5CCOCC5)c3CO4)C2)C1] From intermediate 296 and 1-Boc-azetidinone | 300 | 52 |

-continued
| compound number | Structure | Mass (mg) | Yield (%) |
|---|---|---|---|
| Intermediate 489 | 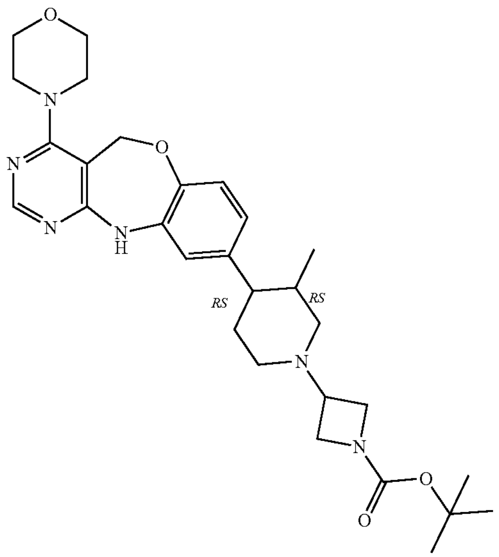 [SMILES: CC1CN(C2CN(C(=O)OC(C)(C)C)C2)CCC1c1ccc2c(c1)Nc1ncnc(N3CCOCC3)c1CO2] from intermediate 355 and 1-Boc-azetidinone | 206 | 72 |
| Intermediate 492 | 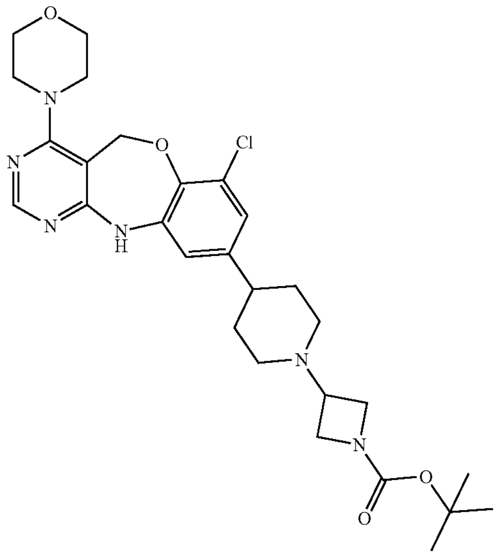 [SMILES: CC(C)(C)OC(=O)N1CC(N2CCC(c3cc(Cl)c4c(c3)Nc3ncnc(N5CCOCC5)c3CO4)CC2)C1] from intermediate 387 and 1-Boc-azetidinone | 1134 | 95 |

-continued
| compound number | Structure | Mass (mg) | Yield (%) |
|---|---|---|---|
| Intermediate 493 | 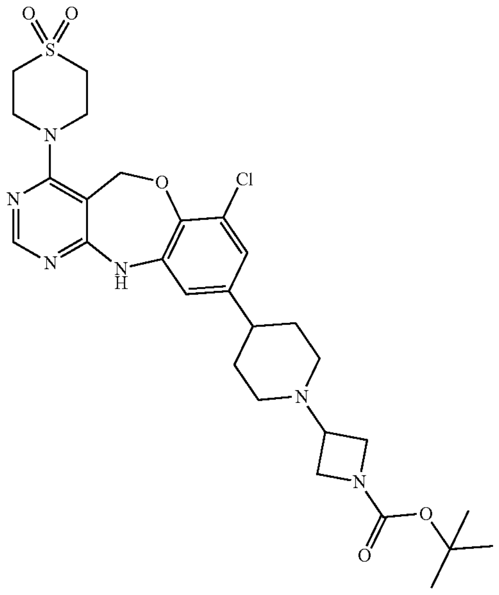 [SMILES: CC(C)(C)OC(=O)N1CC(N2CCC(c3cc(Cl)c4c(c3)Nc3ncnc(N5CCS(=O)(=O)CC5)c3CO4)CC2)C1] from intermediate 388 and 1-Boc-azetidinone | 1040 | 79 |
| Intermediate 494 | 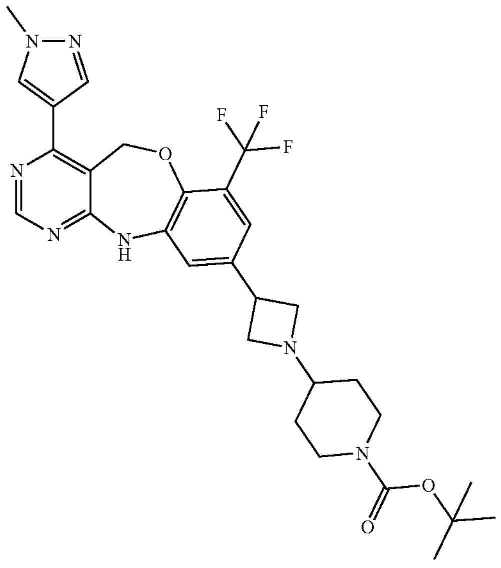 [SMILES: Cn1cc(-c2ncnc3c2COc2c(cc(C4CN(C5CCN(C(=O)OC(C)(C)C)CC5)C4)cc2C(F)(F)F)N3)cn1] from intermediate 389 and 1-Boc-4-piperidone | 154 | 63 |

-continued
| compound number | Structure | Mass (mg) | Yield (%) |
|---|---|---|---|
| Intermediate 495 | 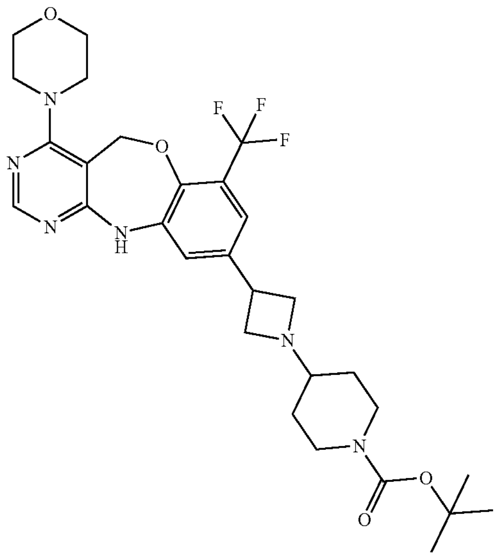 [SMILES: CC(C)(C)OC(=O)N1CCC(N2CC(c3cc4c(c(C(F)(F)F)c3)OCc3c(ncnc3N3CCOCC3)N4)C2)CC1] from intermediate 390 and 1-Boc-4-piperidone | 214 | 72 |
| Intermediate 496 | 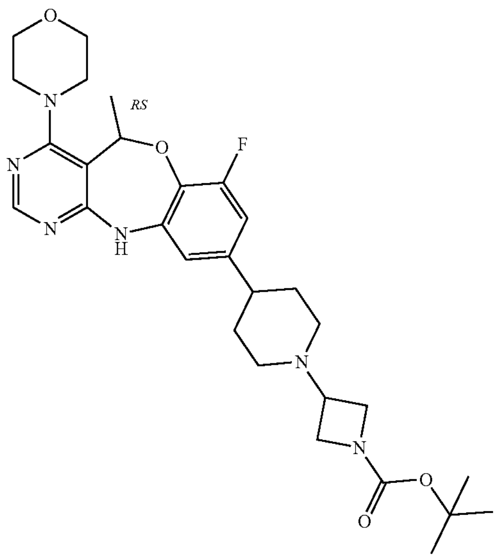 [SMILES: CC1Oc2c(F)cc(C3CCN(C4CN(C(=O)OC(C)(C)C)C4)CC3)cc2Nc2ncnc(N3CCOCC3)c21] from intermediate 391 and 1-Boc-azetidinone | 559 | quant. |

-continued
| compound number | Structure | Mass (mg) | Yield (%) |
|---|---|---|---|
| Intermediate 499 | 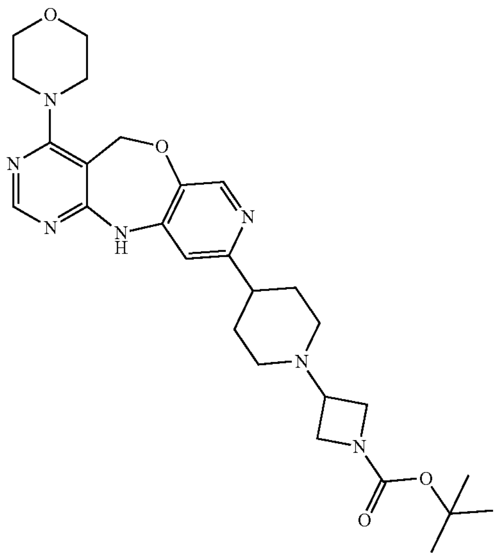 [SMILES: CC(C)(C)OC(=O)N1CC(N2CCC(c3cc4c(cn3)OCc3c(ncnc3N3CCOCC3)N4)CC2)C1] from intermediate 393 and 1-Boc-azetidinone | 395 | 75 |
| Intermediate 500 | 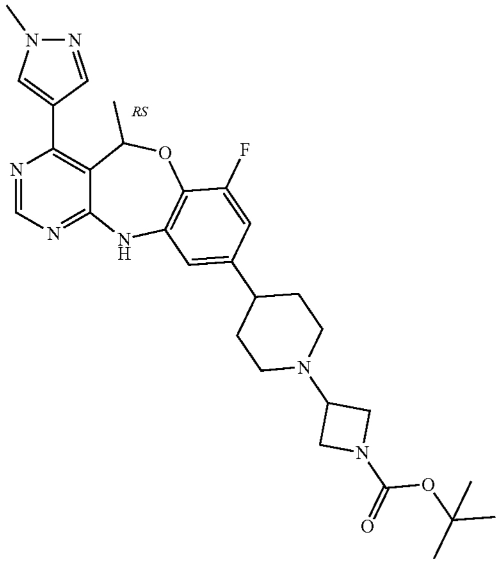 [SMILES: CC1Oc2c(F)cc(C3CCN(C4CN(C(=O)OC(C)(C)C)C4)CC3)cc2Nc2ncnc(-c3cnn(C)c3)c21] from intermediate 395 and 1-Boc-azetidinone | 426 | 67 |

-continued
| compound number | Structure | Mass (mg) | Yield (%) |
|---|---|---|---|
| Intermediate 503 | 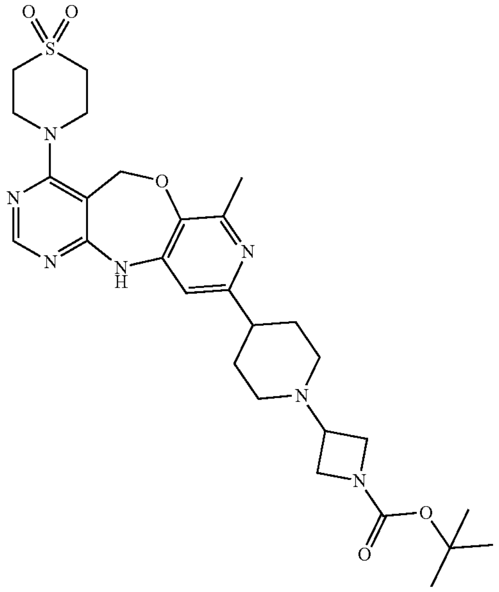 [SMILES: Cc1nc(C2CCN(C3CN(C(=O)OC(C)(C)C)C3)CC2)cc2c1OCc1c(ncnc1N1CCS(=O)(=O)CC1)N2] from intermediate 398 and 1-Boc-azetidinone | 288 | 27 |
| Intermediate 504 | 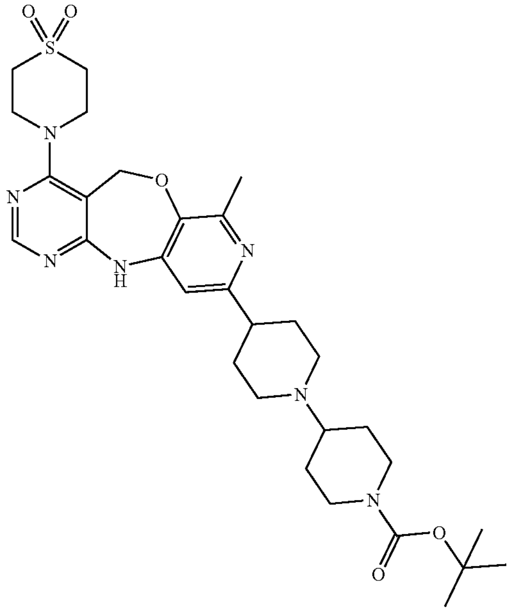 [SMILES: Cc1nc(C2CCN(C3CCN(C(=O)OC(C)(C)C)CC3)CC2)cc2c1OCc1c(ncnc1N1CCS(=O)(=O)CC1)N2] from intermediate 398 and 1-Boc-4-piperidone | 153 | 21 |

-continued
| compound number | Structure | Mass (mg) | Yield (%) |
|---|---|---|---|
| Intermediate 505 | 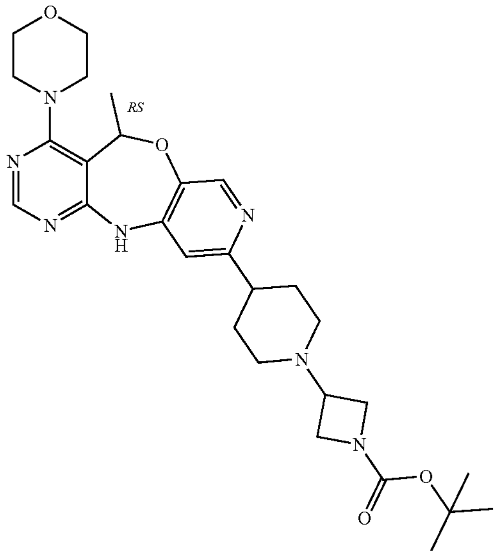 [SMILES: CC1Oc2cnc(C3CCN(C4CN(C(=O)OC(C)(C)C)C4)CC3)cc2Nc2ncnc(N3CCOCC3)c21] from intermediate 399 and 1-Boc-azetidinone | 249 | 42 |
| Intermediate 508 | 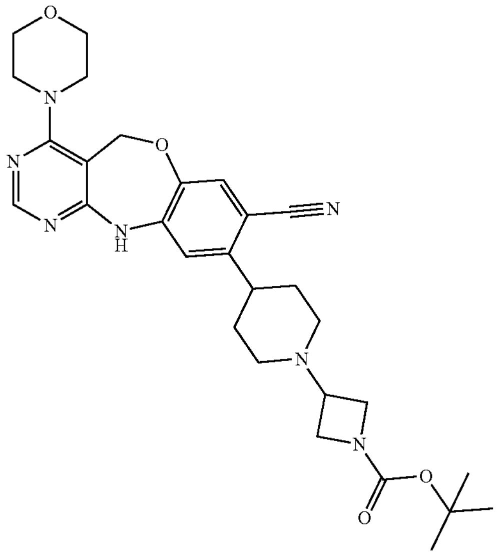 [SMILES: CC(C)(C)OC(=O)N1CC(N2CCC(c3cc4c(cc3C#N)OCc3c(ncnc3N3CCOCC3)N4)CC2)C1] from intermediate 400 and 1-Boc-azetidinone | 442 | 87 |

-continued
| compound number | Structure | Mass (mg) | Yield (%) |
|---|---|---|---|
| Intermediate 509 | 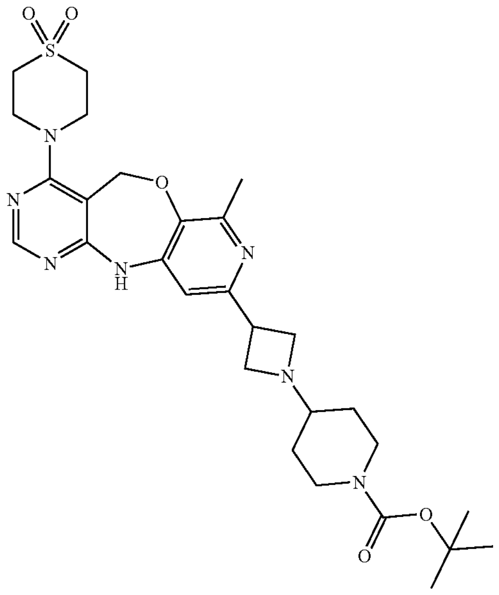 [SMILES: Cc1nc(C2CN(C3CCN(C(=O)OC(C)(C)C)CC3)C2)cc2c1OCc1c(ncnc1N1CCS(=O)(=O)CC1)N2] from intermediate 401 and 1-Boc-4-piperidone | 184 | 31 |
| Intermediate 510 | 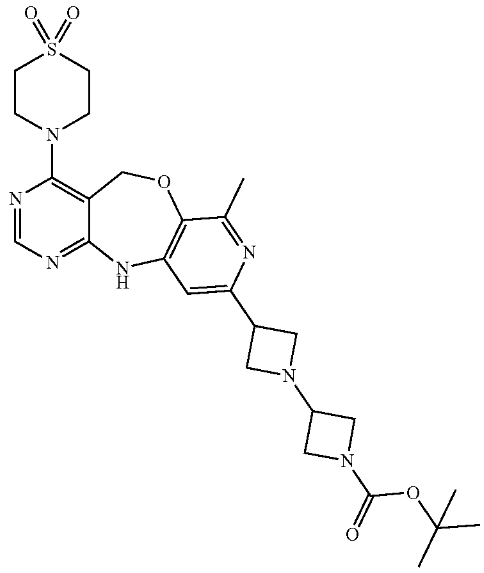 [SMILES: Cc1nc(C2CN(C3CN(C(=O)OC(C)(C)C)C3)C2)cc2c1OCc1c(ncnc1N1CCS(=O)(=O)CC1)N2] from intermediate 401 and 1-Boc-azetidinone | 55 | 50 |

-continued
| compound number | Structure | Mass (mg) | Yield (%) |
|---|---|---|---|
| Intermediate 511 | 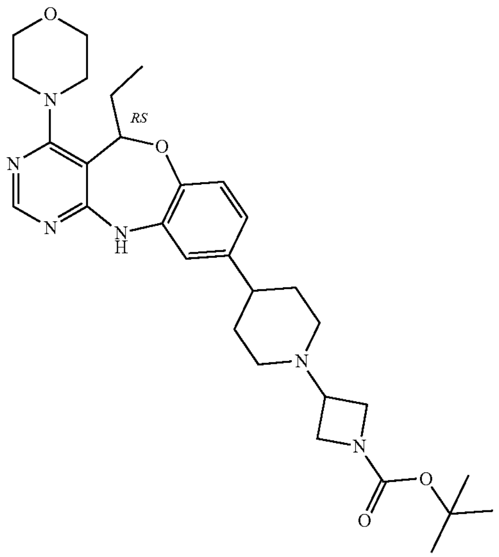 [SMILES: CCC1Oc2ccc(C3CCN(C4CN(C(=O)OC(C)(C)C)C4)CC3)cc2Nc2ncnc(N3CCOCC3)c21] from intermediate 403 and 1-Boc-azetidinone | 1357 | 82 |
| Intermediate 514 | 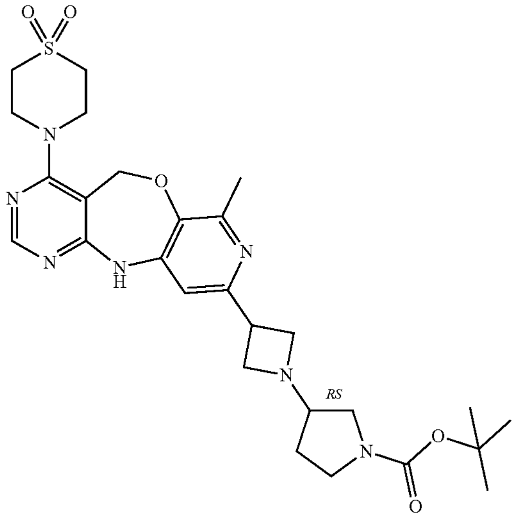 [SMILES: Cc1nc(C2CN(C3CCN(C(=O)OC(C)(C)C)C3)C2)cc2c1OCc1c(ncnc1N1CCS(=O)(=O)CC1)N2] from intermediate 401 and N-Boc-3-pyrrolidinone | 190 | 67 |

-continued
| compound number | Structure | Mass (mg) | Yield (%) |
|---|---|---|---|
| Intermediate 515 | 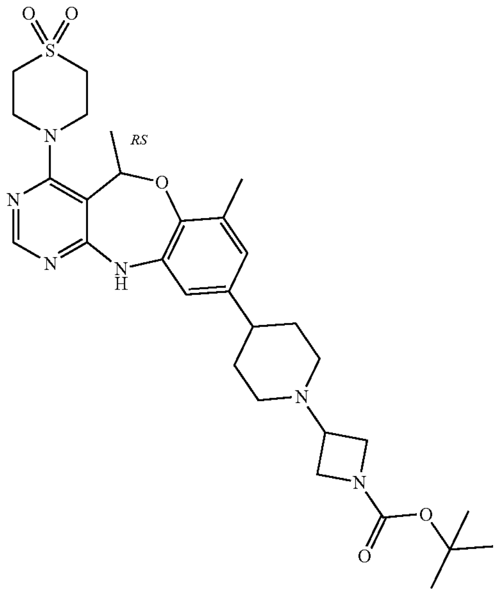 [SMILES: Cc1cc(C2CCN(C3CN(C(=O)OC(C)(C)C)C3)CC2)cc2c1OC(C)c1c(ncnc1N1CCS(=O)(=O)CC1)N2] from intermediate 407 and 1-Boc-azetidinone | 1783 | quant. |
| Intermediate 518 | 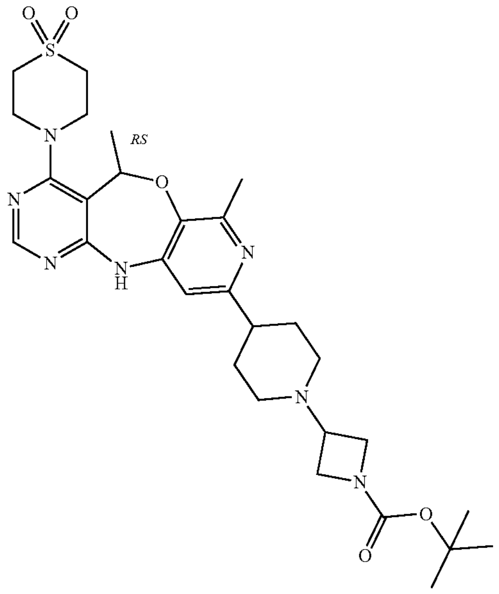 [SMILES: Cc1nc(C2CCN(C3CN(C(=O)OC(C)(C)C)C3)CC2)cc2c1OC(C)c1c(ncnc1N1CCS(=O)(=O)CC1)N2] from intermediate 241 and 1-Boc-azetidinone | 332 | 80 |

Example A116

Preparation of Intermediate 490 and Intermediate 491

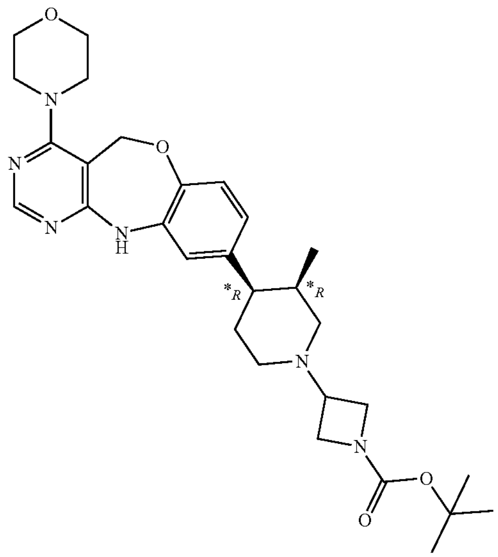

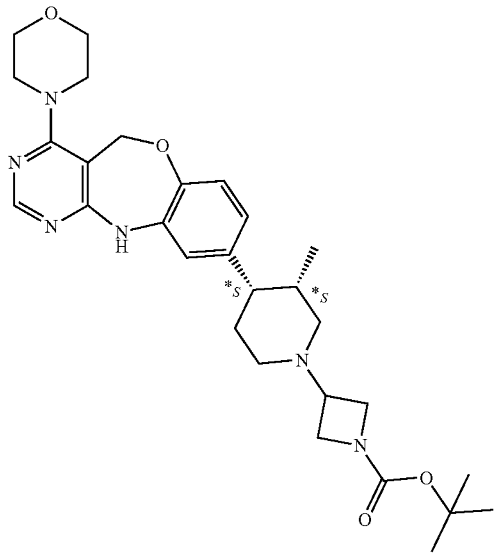

Intermediate 489 (200 mg; 0.354 mmol) was submitted for chiral separation (Start: 59% [n-Heptane+0.1% DEA]—41% [2-Propanol+0.1% DEA]—End: 17% [n-Heptane+0.1% DEA]—83% [2-Propanol+0.1% DEA]) to afford the intermediate 490 (80 mg; 0.148 mmol) and the intermediate 491 (89 mg; 46%).

Preparation of Intermediate 497 and Intermediate 498

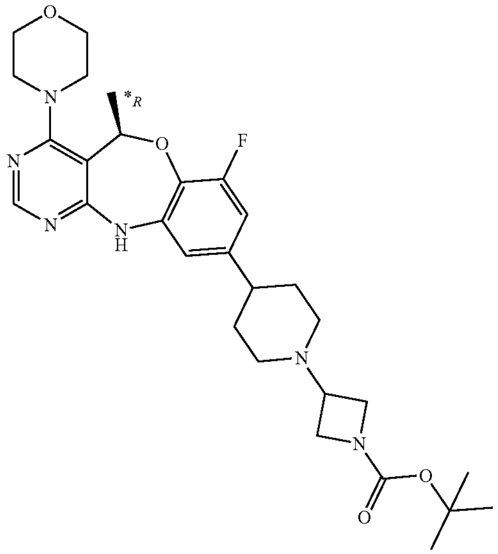

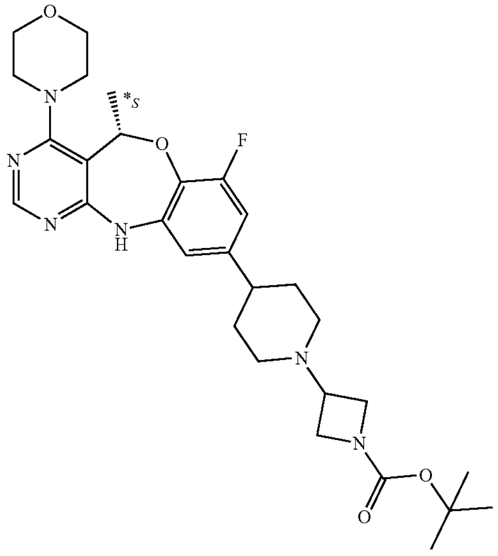

Intermediate 496 (559 mg; 1.01 mmol) was separated by chiral HPLC to afford the pure enantiomers intermediate 497 (213 mg; 38%) and intermediate 498 (189 mg; 34%).

Preparation of Intermediate 501 and Intermediate 502
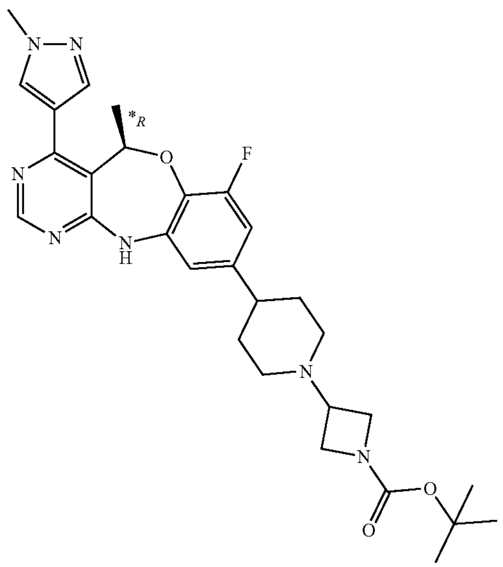
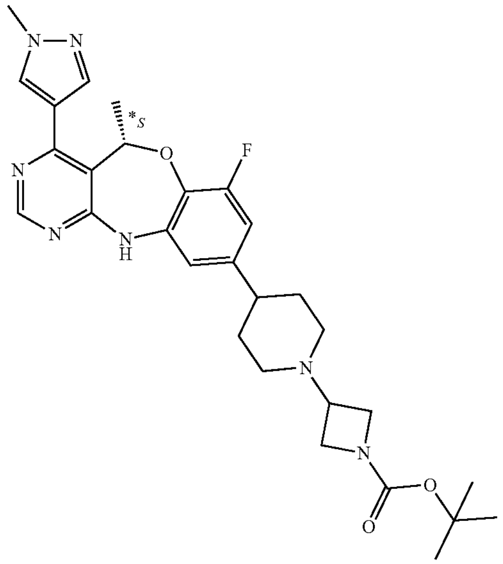
Intermediate 500 (426 mg; 0.775 mmol) was separated by chiral HPLC to afford the pure enantiomers intermediate 501 (194 mg; 46%) and intermediate 502 (200 mg; 47%).
Preparation of Intermediate 506 and Intermediate 507
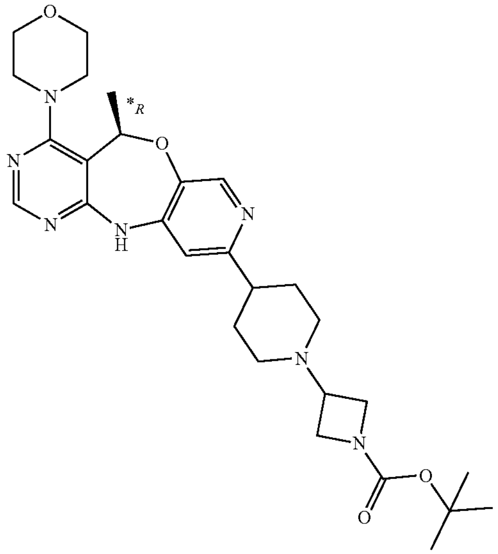
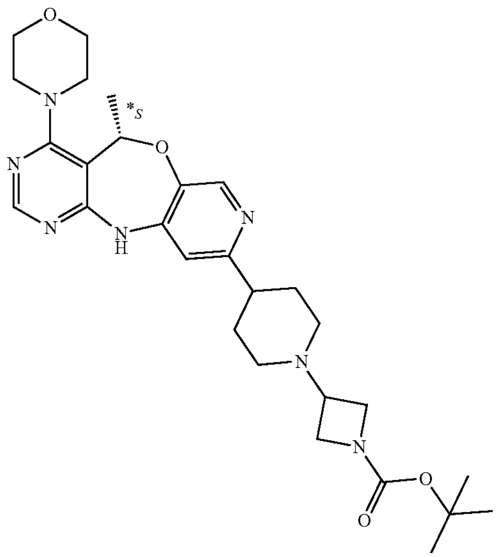
Intermediate 505 (249 mg; 0.463 mmol) was separated by chiral HPLC to afford the pure enantiomers intermediate 506 (97 mg; 39%)) and intermediate 507 (93 mg; 37%).

Preparation of Intermediate 512 and Intermediate 513

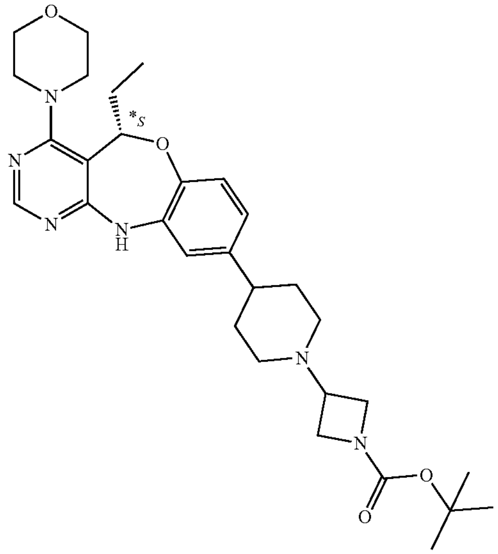

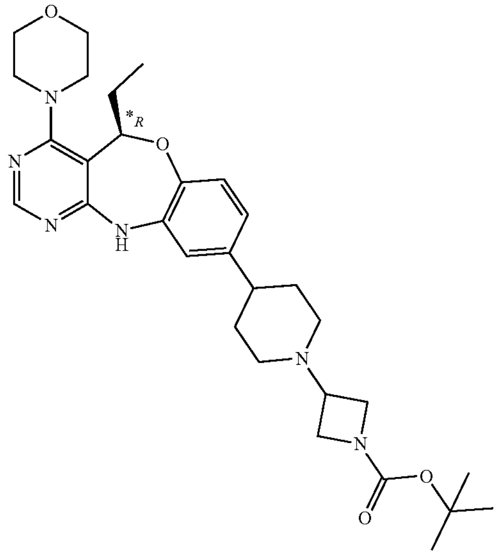

Intermediate 511 (1107 mg; 2.01 mmol) was submitted to chiral separation (Method: CELLULOSE-1 Q_M5 [HEPT-(2-PROP-EtOH 9:1)]+0.1% DEA) to afford the intermediate 512 (392 mg; 35%) and intermediate 513 (445 mg; 40%).

Preparation of Intermediate 516 and Intermediate 517

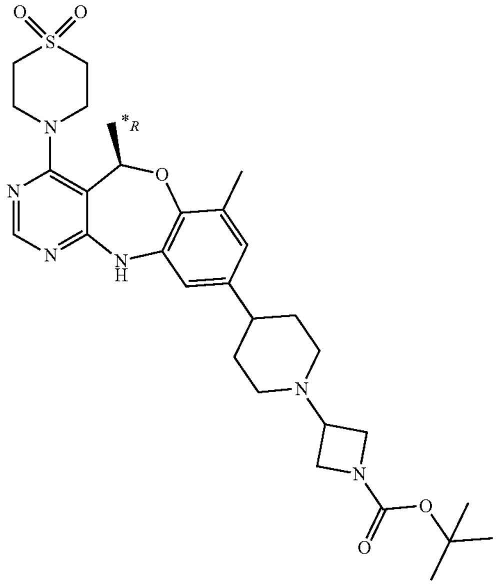

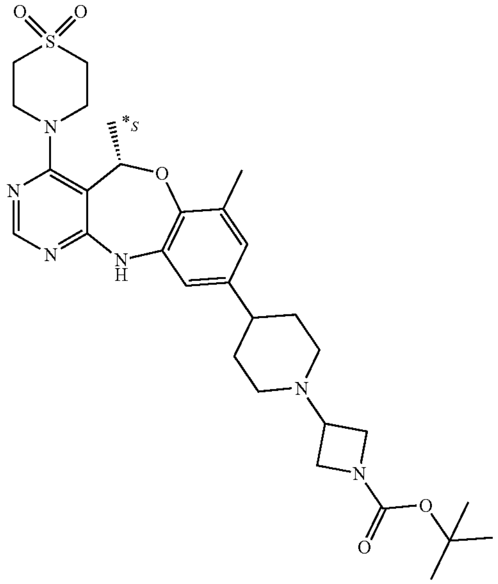

Intermediate 515 (1783; 2.978 mmol) was submitted to chiral separation (Method CELLULOSE-1, Q-MG3 iPrOH-MeOH 9:1+0.1% DEA) to afford the intermediate 516 (656 mg; 37%) and intermediate 517 (637 mg; 36%).

Preparation of Intermediate 519 and Intermediate 520

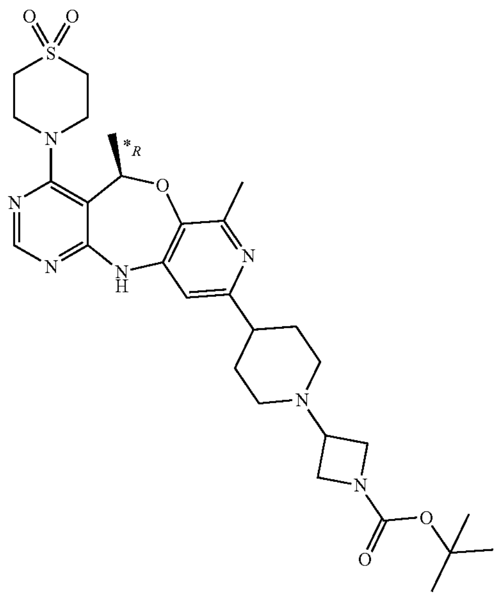

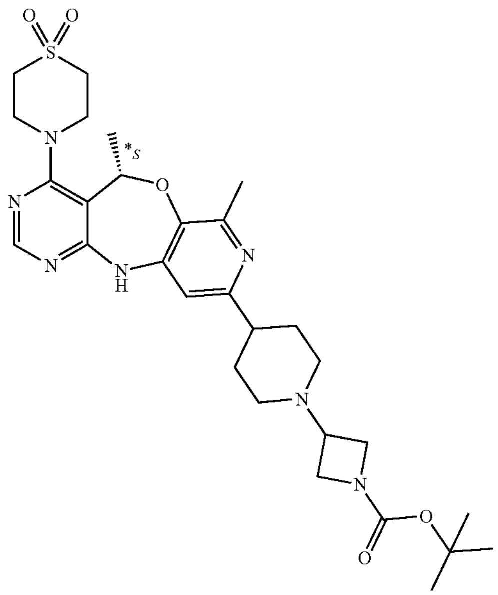

Intermediate 518 (332 mg; 0.554 mmol) was submitted to chiral separation (Method: AMYLOSE_1 Q_MS5[(HEP-T_EtOH 9-1)-(ACN)]+0.1% DEA) to afford the intermediate 519 (133 mg; 40%) and the intermediate 520 (108 mg; 33%).

Preparation of Intermediate 454 and Intermediate 455

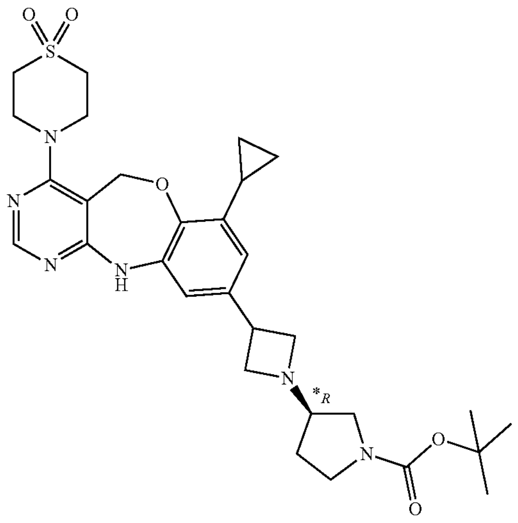

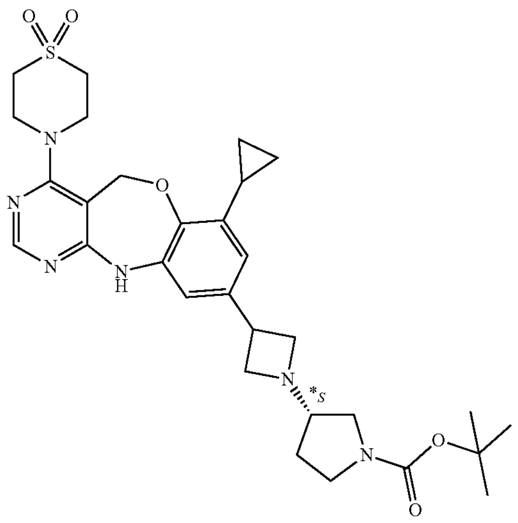

Intermediate 453 (680 mg; 1.14 mmol) was submitted to chiral separation (Method: SFC CELLULOSE-1 ISO 50 MeOH, 234 nm) to afford the intermediate 454 (254 mg; 37%) and the intermediate 455 (154 mg; 23%).

Preparation of Intermediate 457 and Intermediate 458

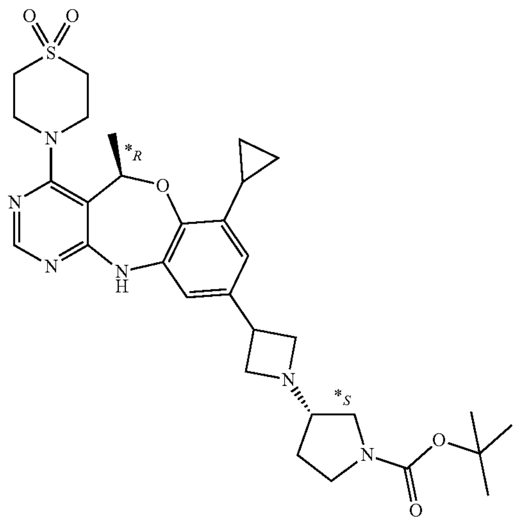

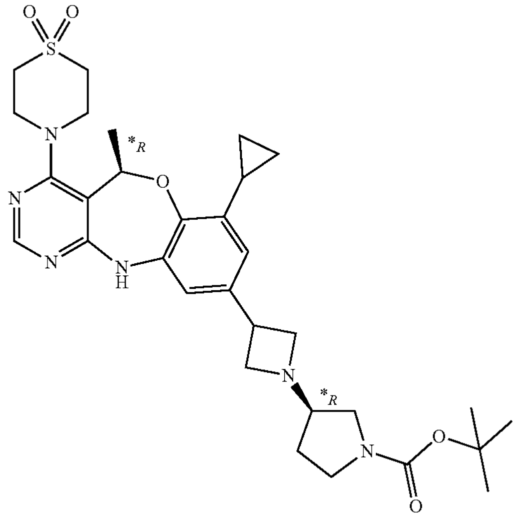

Intermediate 456 (164 mg; 1.14 mmol) was submitted to chiral separation (Method: Stationary phase: CHIRALPAK AD-H 5 μm 250*30 mm, Mobile phase: 60% CO2, 40% iPOH (0.3% iPrNH2))) to afford the intermediate 457 (62 mg; 38%) and the intermediate 458 (60 mg: 37%).

Example A117

Preparation of Intermediate 521 and Intermediate 522

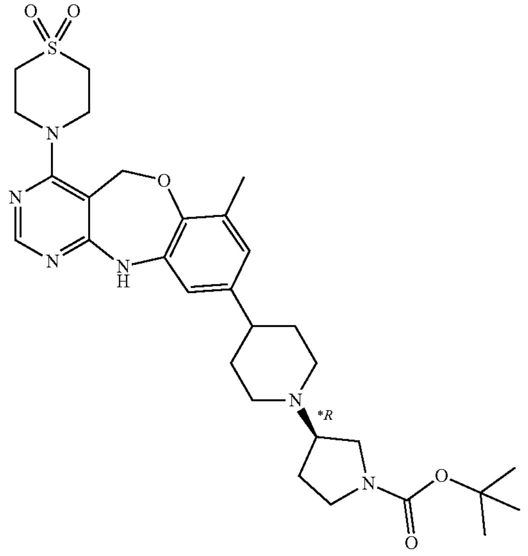

and

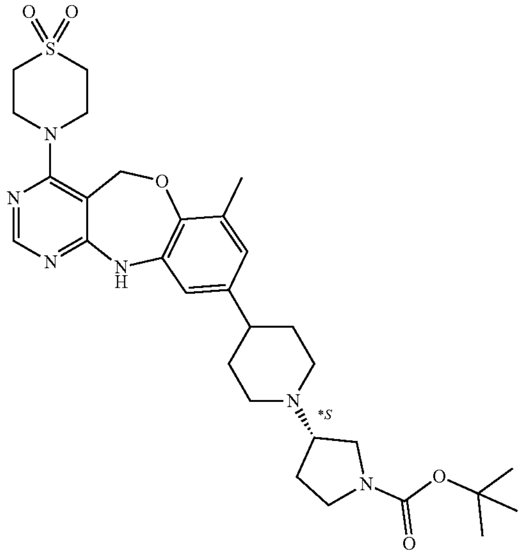

A mixture of intermediate 460 (2.41 g, 4.82 mmol), thiomorpholine-1,1-dioxide (1.303 g, 9.639 mmol), palladium(II) acetate (108 mg, 0.482 mmol), 2,2'-bis(diphenylphosphino)-1,1'-binaphtyl (600 mg, 0.964 mmol), cesium carbonate (3.926 g, 12.049 mmol) in 1,4-dioxane (35 mL) was stirred in a sealed tube at 105° C. for 3 h. The reaction mixture was diluted with DCM and washed with a saturated solution of $NaHCO_3$, then filtered on celite. The organic layer was dried over $MgSO_4$ and evaporated in vacuo. The crude product was purified by preparative LC (irregular $SiO_2$ 15-40 μm, 40 g GraceResolv, mobile phase gradient: from 100% DCM to 95% DCM, 5% MeOH, $NH_4OH$ 0.5%). The pure fractions were collected and solvent evaporated until dryness. The residue was repurified by preparative LC (irregular $SiO_2$ 15-40 μm, 80 g GraceResolv, mobile phase gradient: from 80% Heptane, 20% AcOEt to 40% Heptane, 50% AcOEt, 10% MeOH, $NH_4OH$ 1%). The pure fractions were collected and solvent evaporated until dryness. A purification was performed via Reverse phase (Stationary phase: 120 g, YMC-actus Triart C18 10 μm 30*150 mm, Mobile phase: Gradient from 65% $NH_4HCO_3$ 0.2%, 35% ACN to 25% $NH_4HCO_3$ 0.2%, 75% ACN). The pure fractions were collected and the solvent was evaporated to give the racemic product. A purification was performed via chiral SFC (Stationary phase: CHIRALPAK AD-H 5 μm 250*30 mm, Mobile phase: 50% $CO_2$, 50% iPrOH (0.3% $iPrNH_2$)) to give intermediate 521 (129 mg, 4%) and intermediate 522 (134 mg, 5%).

Example A118

Preparation of Intermediate 523

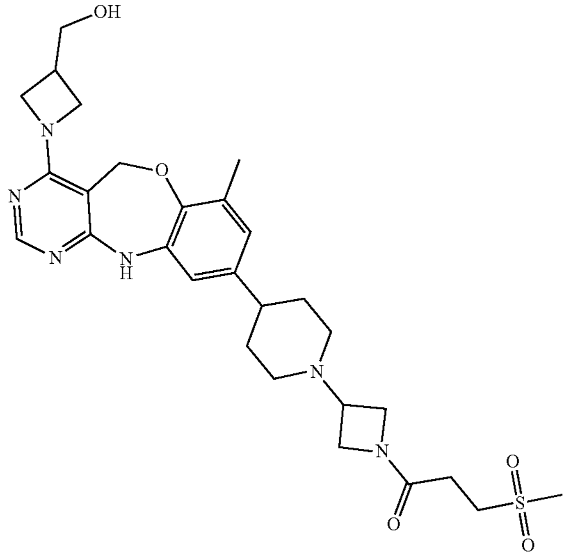 [SMILES: Cc1cc(C2CCN(C3CN(C(=O)CCS(C)(=O)=O)C3)CC2)cc2c1OCc1c(ncnc1N1CC(CO)C1)N2]

A solution of intermediate 481 (250 mg, 0.48 mmol), 3-hydroxymethyl-azetidine [95849-02-8] (106 mg, 0.6 mmol) and DIPEA (331 μL, 0.75 g/mL, 1.9 mmol) in ACN (4.4 mL) in a sealed tube was stirred at 110° C. using one single mode microwave (Biotage Initiator EXP 60) with a power output ranging from 0 to 400 W for 30 min. [fixed hold time]. The reaction was poured onto brine, extracted with DCM.

An insoluble was filtered and dried to give intermediate 523 (45 mg). The organic layer was dried over MgSO4, filtered and evaporated to give 177 mg. The crude was purified via preparative LC (Stationary phase: irregular SiOH 35-70 μm 24 g, Mobile phase: gradient from 100% DCM to 97% DCM, 3% MeOH, 0.3% NH4OH). The pure fractions were collected and the solvent was evaporated until dryness to give intermediate 523 (95 mg).

Overall quantity and yield: 140 mg, 50%

The intermediates in the Table below were prepared by using an analogous method

| compound number | Structure | Mass (mg) | Yield (%) |
|---|---|---|---|
| Intermediate 524 | 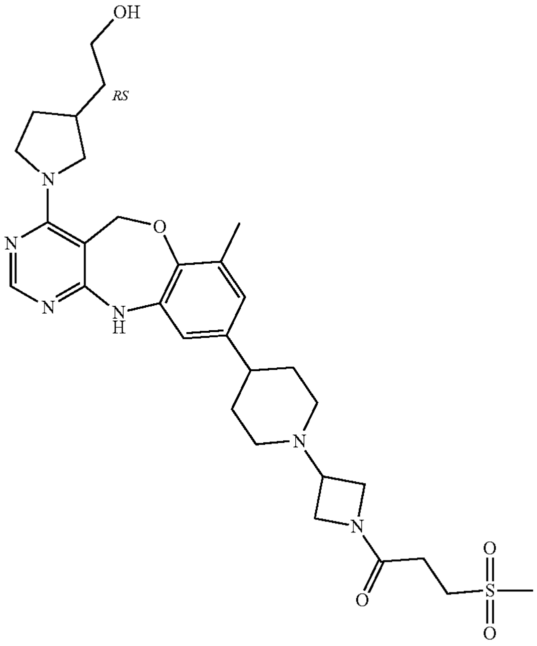 [SMILES: Cc1cc(C2CCN(C3CN(C(=O)CCS(C)(=O)=O)C3)CC2)cc2c1OCc1c(ncnc1N1CCC(CCO)C1)N2] from intermediate 481 and 3-pyrrolidineethanol | 24 | 8 |

Example A119

Preparation of Intermediate 525

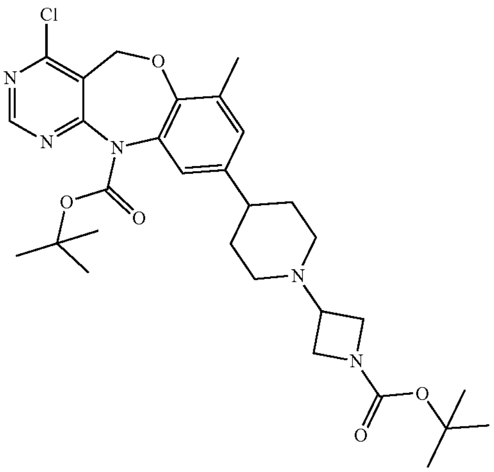 [SMILES: Cc1cc(C2CCN(C3CN(C(=O)OC(C)(C)C)C3)CC2)cc2c1OCc1c(Cl)ncnc1N2C(=O)OC(C)(C)C]

$Boc_2O$ (32.33 mL; 0.95 g/mL; 140.74 mmol) was added to a suspension of intermediate 447 (7.6 g; 15.64 mmol) and Cs2CO3 (5.61 g; 17.20 mmol) in THF (80 mL) at rt. The mixture was refluxed at 85° C. for 16 hours. The mixture was cooled down to rt, filtered and washed with THF (100 mL) and ethyl acetate (100 mL). The filtrate was concentrated under vacuum. The residue was purified by flash chromatography over silica gel (SiO2; petroleum ether/ethyl acetate, from 100/0 to 40/60) to afford the product (7.6 g; 78%) as a light orange solid.

Preparation of Intermediate 526

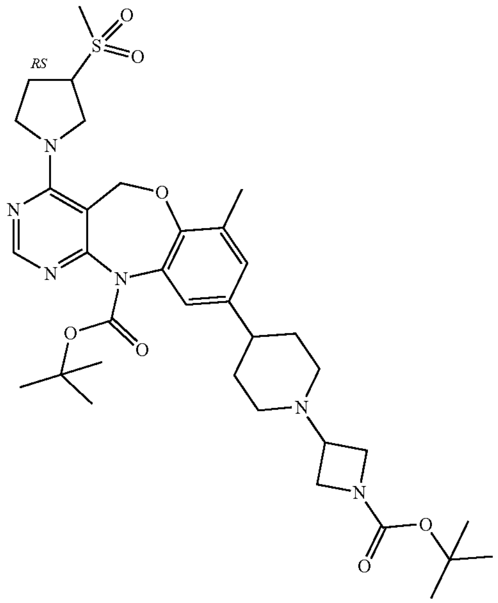 [SMILES: Cc1cc(C2CCN(C3CN(C(=O)OC(C)(C)C)C3)CC2)cc2c1OCc1c(N3CCC(S(C)(=O)=O)C3)ncnc1N2C(=O)OC(C)(C)C]

A solution of intermediate 525 (300 mg, 0.512 mmol), 3-(methylsulfonyl)pyrrolidine (190.931 mg, 1.28 mmol) and DIPEA (352.81 μL, 0.75 g/mL, 2.047 mmol) in MeCN (5.347 mL) in a sealed tube was stirred at 110° C. using one single mode microwave (Biotage Initiator EXP 60) with a power output ranging from 0 to 400 W for 5 minutes. [fixed hold time]. The reaction was poured onto water and NaCl, extracted with DCM, dried over MgSO4, filtered and evaporated. A purification was performed via preparative LC (Stationary phase: irregular SiOH 35-70 μm 24 g, Mobile phase: gradient from 100% DCM to 93% DCM, 7% MeOH (2% NH4OH)) to afford the product (285 mg; 80%).

The compounds in the Table below were prepared by using an analogous method starting from the respective starting materials.

| compound number | Structure | Mass (mg) | Yield (%) |
|---|---|---|---|
| Intermediate 527 | 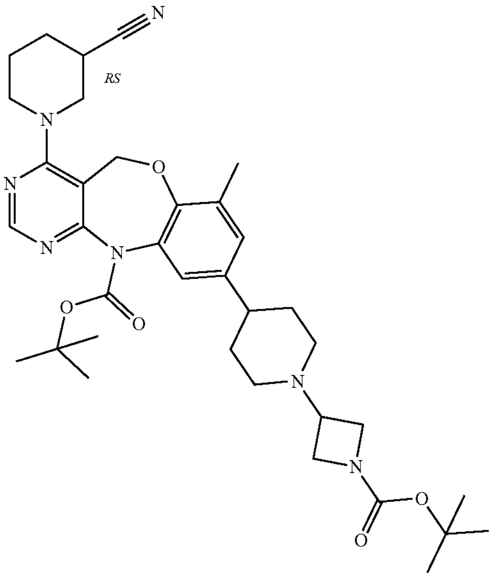 [SMILES: Cc1cc(C2CCN(C3CN(C(=O)OC(C)(C)C)C3)CC2)cc2c1OCc1c(N3CCCC(C#N)C3)ncnc1N2C(=O)OC(C)(C)C]<br>from intermediate 525 and Piperidine-3-carbonitrile | 302 | 89 |
| Intermediate 528 | 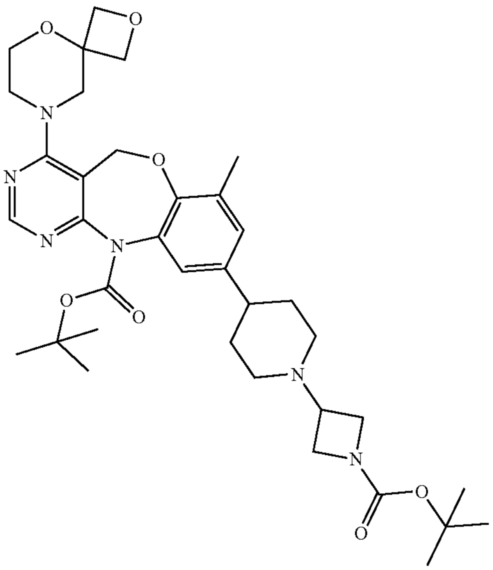 [SMILES: Cc1cc(C2CCN(C3CN(C(=O)OC(C)(C)C)C3)CC2)cc2c1OCc1c(N3CCOC4(COC4)C3)ncnc1N2C(=O)OC(C)(C)C]<br>from intermediate 525 and 2,5-Dioxa-8-azaspiro[3.5]nonane hemioxalate | 300 | 86 |

-continued
| compound number | Structure | Mass (mg) | Yield (%) |
|---|---|---|---|
| Intermediate 529 | 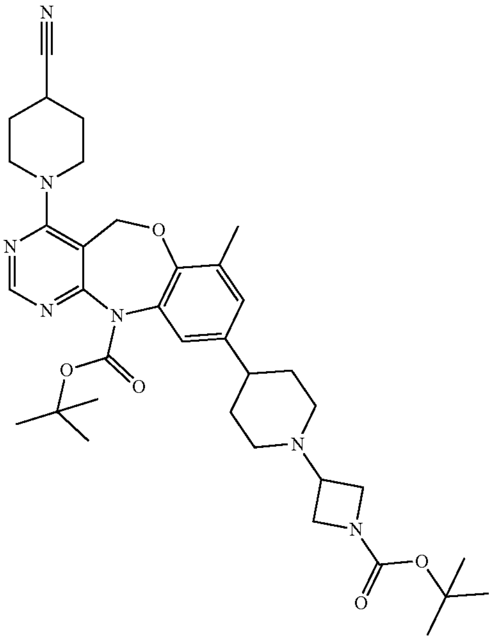 [SMILES: Cc1cc(C2CCN(C3CN(C(=O)OC(C)(C)C)C3)CC2)cc2c1OCc1c(N3CCC(C#N)CC3)ncnc1N2C(=O)OC(C)(C)C] from intermediate 525 and Piperidine-4-carbonitrile | 300 | 92 |
| Intermediate 530 | 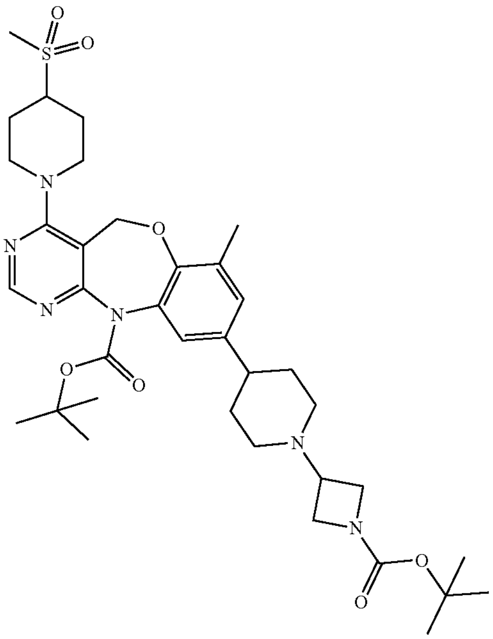 [SMILES: Cc1cc(C2CCN(C3CN(C(=O)OC(C)(C)C)C3)CC2)cc2c1OCc1c(N3CCC(S(C)(=O)=O)CC3)ncnc1N2C(=O)OC(C)(C)C] from intermediate 525 and 4-(Methylsulfonyl)piperidine | 270 | 89 |

-continued

| compound number | Structure | Mass (mg) | Yield (%) |
|---|---|---|---|
| Intermediate 531 | 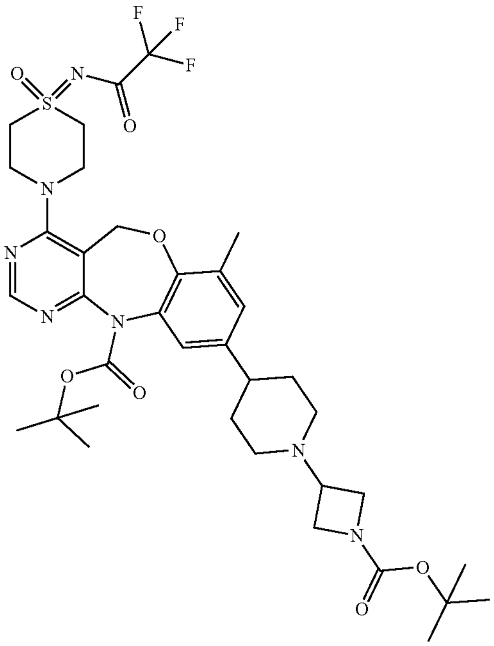 [SMILES: Cc1cc(C2CCN(C3CN(C(=O)OC(C)(C)C)C3)CC2)cc2c1OCc1c(N3CCS(=O)(=NC(=O)C(F)(F)F)CC3)ncnc1N2C(=O)OC(C)(C)C] from intermediate 525 and intermediate 144 | 206 | 22 |

Example A120

Preparation of Intermediate 532

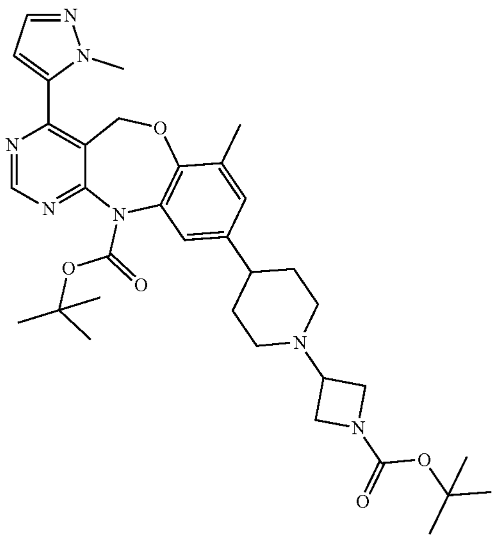 [SMILES: Cc1cc(C2CCN(C3CN(C(=O)OC(C)(C)C)C3)CC2)cc2c1OCc1c(-c3ccnn3C)ncnc1N2C(=O)OC(C)(C)C]

A stirred solution of intermediate 525 (500 mg, 0.853 mmol), 1-methyl-1H-pyrazole-5-boronic acid pinacol ester (204.117 mg, 0.981 mmol) and $K_3PO_4$ (271.611 mg, 1.28 mmol) in 1,4-dioxane (4.765 mL) and water, distilled (2.383 mL) was purged with $N_2$, and [1,1'-Bis(diphenylphosphino) ferrocene]dichloropalladium(II), complex with dichloromethane (34.832 mg, 0.0427 mmol) was added. The reaction mixture was purged again with $N_2$ and stirred at 80° C. for 4 hours. The crude mixture was diluted with EtOAc and water, and the organic layer was washed with brine, dried over MgSO4, filtered and evaporated in vacuo. The residue was purified by preparative LC (Stationary phase: Irregular SiOH 20-45 μm 80 g GRACE), Mobile phase: 99% DCM, 1% MeOH, 0.1% $NH_4OH$ to 90% DCM, 10% MeOH, 1% $NH_4OH$) to afford the product (378 mg; 78%).

The compounds in the Table below were prepared by using an analogous method starting from the respective starting materials.

| compound number | Structure | Mass (mg) | Yield (%) |
|---|---|---|---|
| Intermediate 533 | 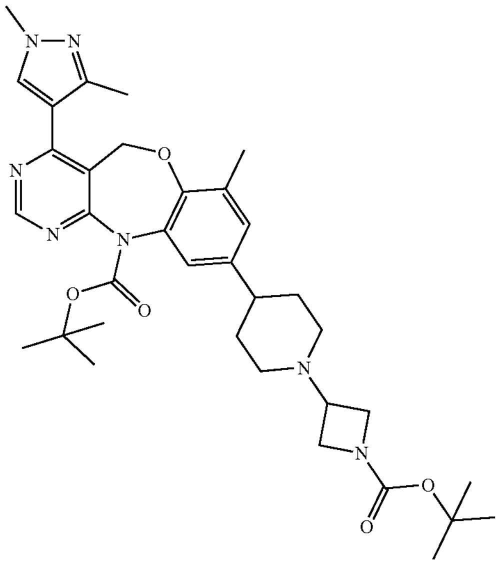 [SMILES: Cc1cc(C2CCN(C3CN(C(=O)OC(C)(C)C)C3)CC2)cc2c1OCc1c(-c3cn(C)nc3C)ncnc1N2C(=O)OC(C)(C)C] from intermediate 525 and 1,3-Dimethylpyrazole-4-boronic acid | 560 | quant. |
| Intermediate 534 | 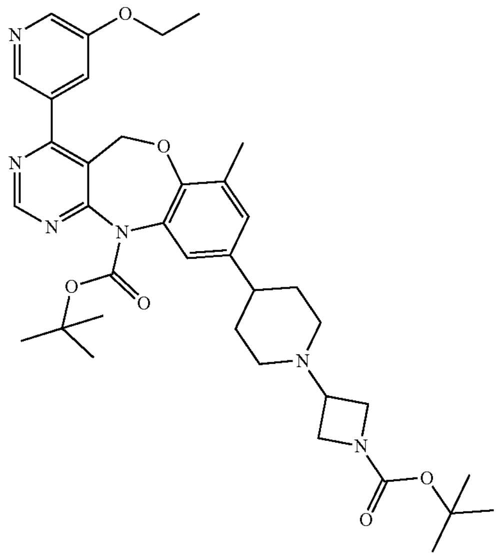 [SMILES: CCOc1cncc(-c2ncnc3c2COc2c(C)cc(C4CCN(C5CN(C(=O)OC(C)(C)C)C5)CC4)cc2N3C(=O)OC(C)(C)C)c1] from intermediate 525 and 5-Ethoxypyridine-3-boronic acid pinacol ester | 490 | 95 |

Example A121

Preparation of Intermediate 535

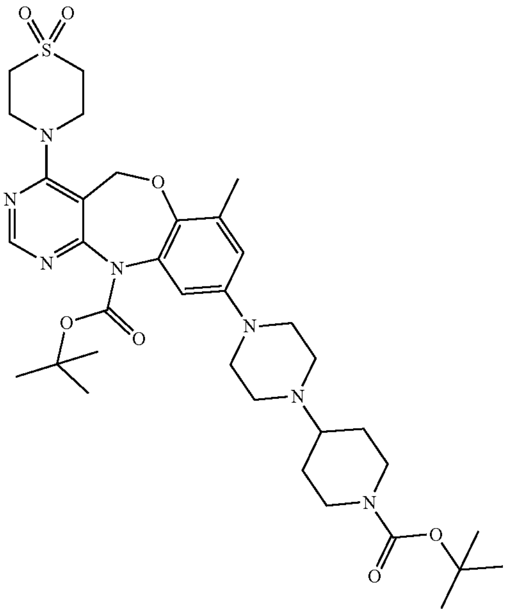 [SMILES: Cc1cc(N2CCN(C3CCN(C(=O)OC(C)(C)C)CC3)CC2)cc2c1OCc1c(N3CCS(=O)(=O)CC3)ncnc1N2C(=O)OC(C)(C)C]

To a solution of intermediate 249 (300 mg; 0.571 mmol), intermediate 105 (308 mg; 1.142 mmol), $Cs_2CO_3$ (372.1 mg; 1.142 mmol) in THF (8 mL) was added DavePhos (44.94 mg; 0.114 mmol) and $Pd_2(dba)_3$ (52.29 mg; 0.057 mmol) under nitrogen. The mixture was heated at 95° C. for 16 hours. The mixture was poured onto water/$NaHCO_3$ and diluted with EtOAc. The organic layer was separated, washed with brine and concentrated under reduced pressure. The residue was purified by flash column chromatography over silica gel ($SiO_2$; Hepthane//Ethyl Acetate and Dichloromethane//Methanol) to afford the product (204 mg; 50%).

The compounds in the Table below were prepared by using an analogous method starting from the respective starting materials.

| compound number | Structure | Mass (mg) | Yield (%) |
|---|---|---|---|
| Intermediate 536 | 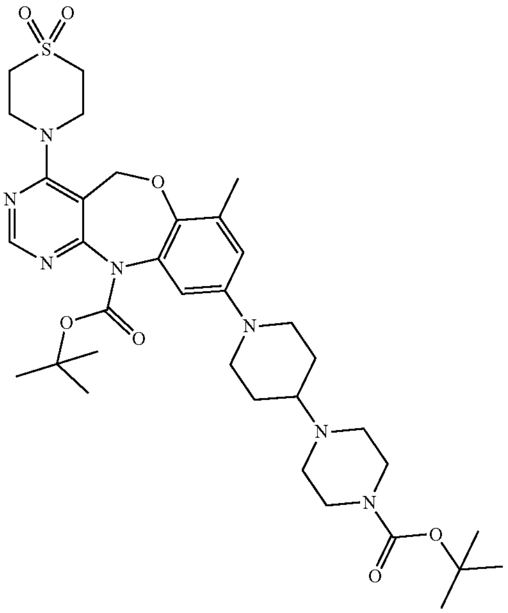 [SMILES: Cc1cc(N2CCC(N3CCN(C(=O)OC(C)(C)C)CC3)CC2)cc2c1OCc1c(N3CCS(=O)(=O)CC3)ncnc1N2C(=O)OC(C)(C)C]<br>from intermediate 249 and intermediate 107 | 254 | 62 |

Example A122

Preparation of Intermediate 537

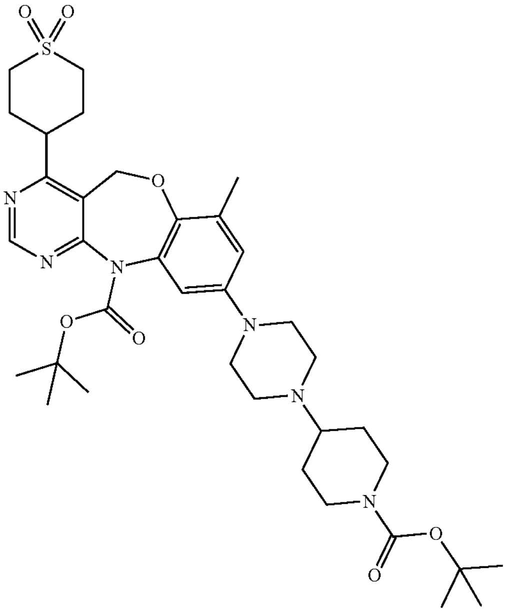 [SMILES: Cc1cc(N2CCN(C3CCN(C(=O)OC(C)(C)C)CC3)CC2)cc2c1OCc1c(C3CCS(=O)(=O)CC3)ncnc1N2C(=O)OC(C)(C)C]

2-Dicyclohexylphosphino-2'-(N,N-dimethylamino)biphenyl (105 mg, 0.27 mmol) and tris(dibenzylideneacetone) dipalladium(0) (122 mg, 0.13 mmol) were added to a solution of intermediate 249 (700 mg, 1.33 mmol), intermediate 105 (718 mg, 2.66 mmol) and cesium carbonate (868 mg, 2.66 mmol) in THF (15 mL) under nitrogen. The mixture was heated at 95° C. for 16 h, then poured onto water/$NaHCO_3$ and diluted with ethyl acetate. The organic layer was separated and washed with brine. The mixture was purified by flash column chromatography (silica; Hepthane/Ethyl Acetate and Dichloromethane/Methanol). The desired fractions were collected and concentrated to afford intermediate 537 (171 mg, 18%).

The intermediates in the Table below were prepared by using an analogous method starting from the respective starting materials.

| Intermediate number | Structure | Mass (mg) | Yield (%) |
|---|---|---|---|
| Intermediate 538 | 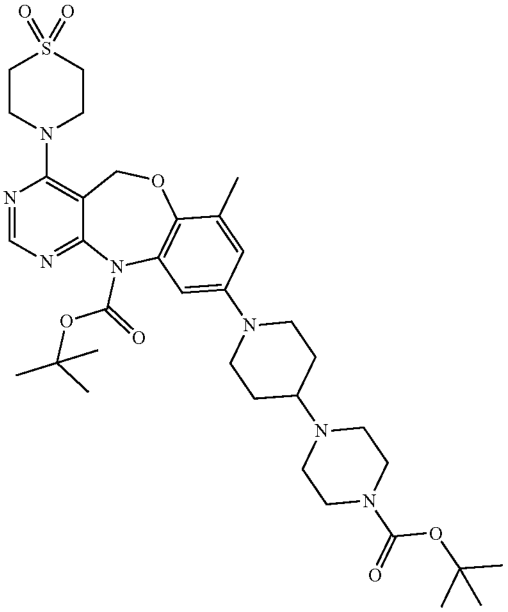 [SMILES: Cc1cc(N2CCC(N3CCN(C(=O)OC(C)(C)C)CC3)CC2)cc2c1OCc1c(N3CCS(=O)(=O)CC3)ncnc1N2C(=O)OC(C)(C)C] from intermediate 249 and intermediate 107 | 115 | 33 |

Preparation of Intermediate 539

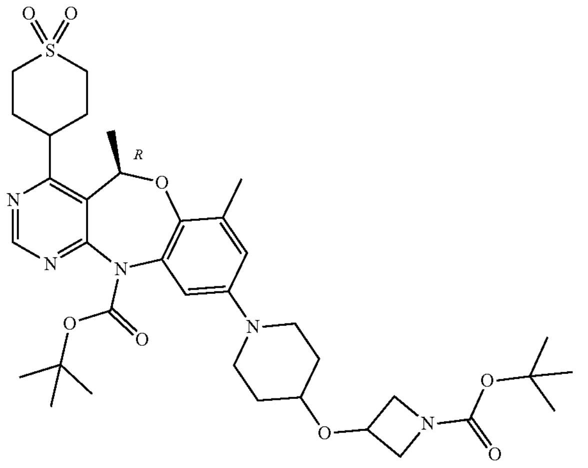

A mixture of intermediate 259 (400 mg, 0.741 mmol), intermediate 104 (190 mg, 0.741 mmol) and cesium carbonate (725 mg, 2.22 mmol) was charged in a sealed tube and purged with $N_2$. 1,4-dioxane (8 mL) was added and the mixture was degassed with $N_2$, then 2-dicyclohexylphosphino-2',4',6'-triisopropylbiphenyl (71 mg, 0.15 mmol) and tris(dibenzylideneacetone)dipalladium(0) (136 mg, 0.148 mmol) were added. The reaction mixture was stirred and heated at 100° C. for 18 h. Water and EtOAc were added to the reaction mixture. The layers were separated. The aqueous layer was extracted twice with EtOAc. The combined organic layers were washed with brine, dried over $MgSO_4$, filtered and evaporated in vacuo. The crude material was purified by preparative LC (irregular $SiO_2$ 40 μm, 40 g Buchi, liquid loading (DCM), mobile phase gradient: from DCM 99%, iPrOH 1% to DCM 90%, iPrOH 10%). The fractions containing product were combined and evaporated under vacuum to give intermediate 539 (320 mg, 60%).

Example A123

Preparation of Intermediate 540

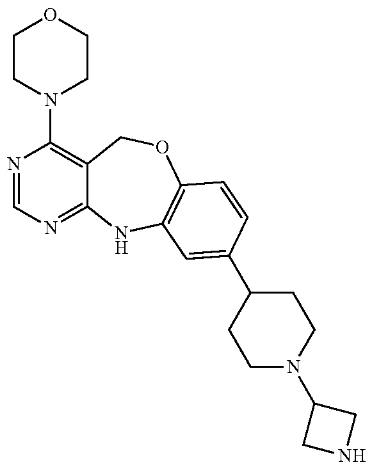 [SMILES: c1nc2c(c(N3CCOCC3)n1)COc1ccc(C3CCN(C4CNC4)CC3)cc1N2]

A solution of HCl in dioxane (4M; 1.244 mL; 4.98 mmol) was added to a solution of intermediate 421 (260 mg; 0.50 mmol) in dioxane (3.3 mL) at rt. The reaction mixture was stirred at rt for 3 h. A 10% aqueous solution of $K_2CO_3$ and DCM were added. The mixture was stirred at rt for 1 h, the suspension was filtered and dried to give 167 mg of white solid (79%).

The compounds in the Table below were prepared by using an analogous method starting from the respective starting materials.

| compound number | Structure | Mass (mg) | Yield (%) |
|---|---|---|---|
| Intermediate 541 | 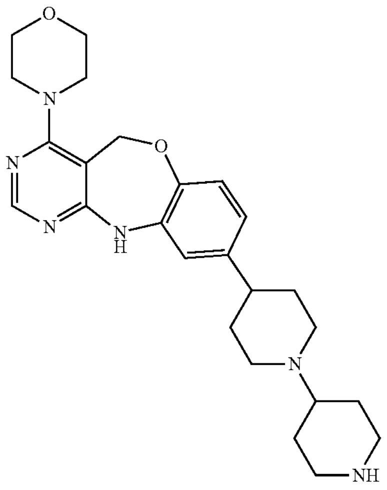 [SMILES: c1nc2c(c(N3CCOCC3)n1)COc1ccc(C3CCN(C4CCNCC4)CC3)cc1N2] from intermediate 422 | 147 | 75 |

-continued
| compound number | Structure | Mass (mg) | Yield (%) |
|---|---|---|---|
| Intermediate 542 | 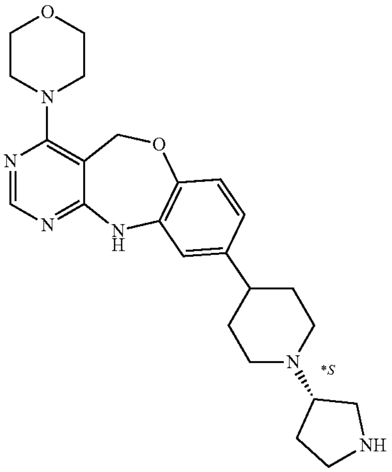 [SMILES: c1nc2c(c(N3CCOCC3)n1)COc1ccc(C3CCN([C@H]4CCNC4)CC3)cc1N2] from intermediate 420 | 140 | 78 |
| Intermediate 543 | 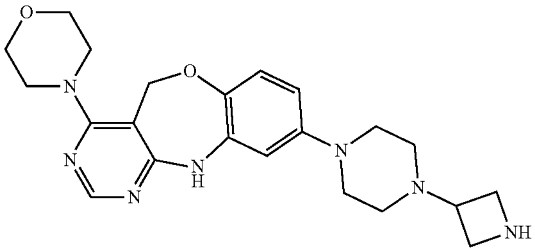 [SMILES: c1nc2c(c(N3CCOCC3)n1)COc1ccc(N3CCN(C4CNC4)CC3)cc1N2] from intermediate 424 | 380 | quant |
| Intermediate 544 | 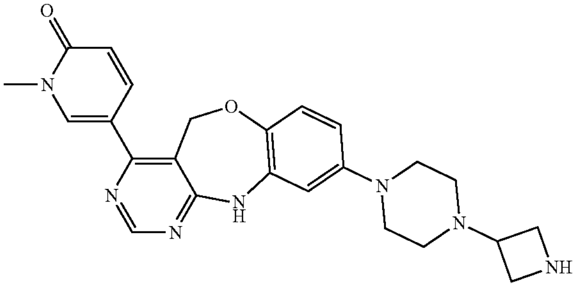 [SMILES: Cn1cc(-c2ncnc3c2COc2ccc(N4CCN(C5CNC5)CC4)cc2N3)ccc1=O] from intermediate 425 | 130 | quant |
| Intermediate 545 | 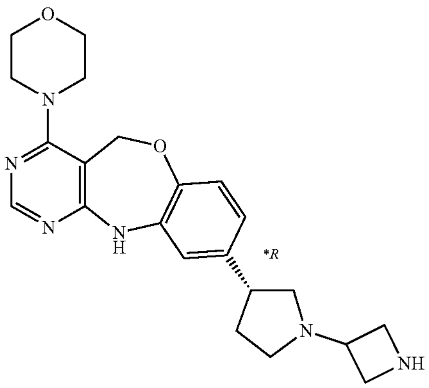 [SMILES: c1nc2c(c(N3CCOCC3)n1)COc1ccc([C@H]3CCN(C4CNC4)C3)cc1N2] from intermediate 426; solvent 3:2 Dioxane:MeOH | 410 | Quant |

-continued
| compound number | Structure | Mass (mg) | Yield (%) |
| --- | --- | --- | --- |
| Intermediate 546 | 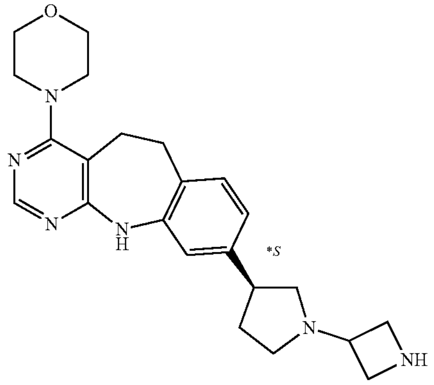 [SMILES: c1nc2c(c(N3CCOCC3)n1)CCc1ccc([C@@H]3CCN(C4CNC4)C3)cc1N2] from intermediate 427; solvent 3:2 Dioxane:MeOH | 440 | Quant |
| Intermediate 547 | 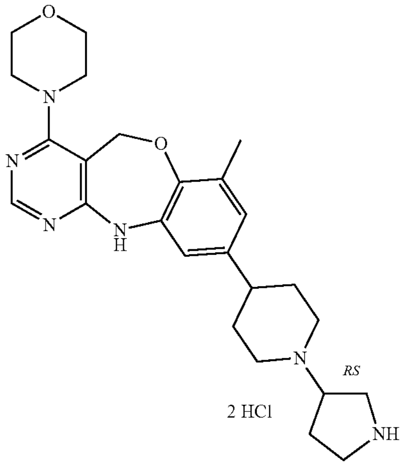 [SMILES: Cc1cc(C2CCN(C3CCNC3)CC2)cc2c1OCc1c(ncnc1N1CCOCC1)N2] from intermediate 428; solvent 3:2 Dioxane:MeOH; No aqueous work-up only evaporation | 2460 | Quant |
| Intermediate 548 | 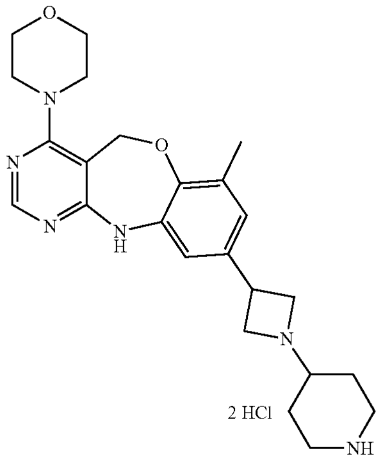 [SMILES: Cc1cc(C2CN(C3CCNCC3)C2)cc2c1OCc1c(ncnc1N1CCOCC1)N2] from intermediate 429; No aqueous work-up only evaporation | 224 | quant |

-continued
| compound number | Structure | Mass (mg) | Yield (%) |
| --- | --- | --- | --- |
| Intermediate 549 | 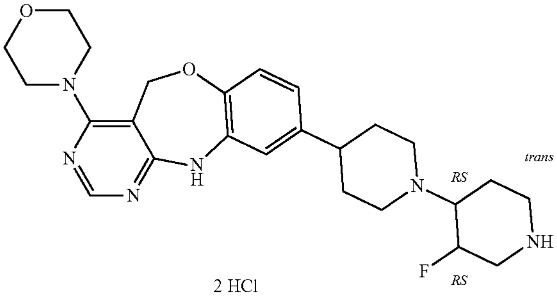 [SMILES: FC1CNCCC1N1CCC(c2ccc3c(c2)Nc2ncnc(N4CCOCC4)c2CO3)CC1] 2 HCl<br>from intermediate 430; No aqueous work-up only evaporation | 124 | quant |
| Intermediate 550 | 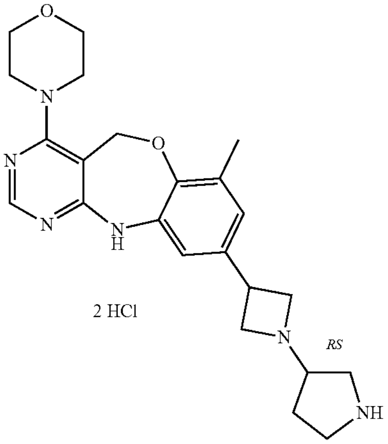 [SMILES: Cc1cc(C2CN(C3CCNC3)C2)cc2c1OCc1c(ncnc1N1CCOCC1)N2] 2 HCl<br>from intermediate 431; No aqueous work-up only evaporation | 285 | quant |
| Intermediate 551 | 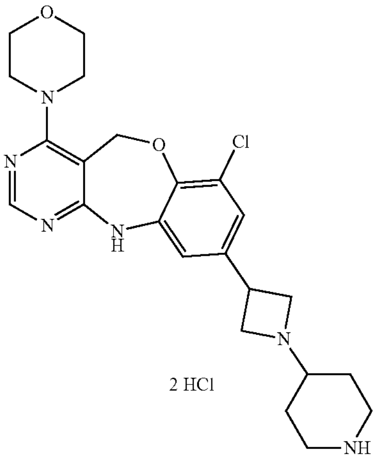 [SMILES: Clc1cc(C2CN(C3CCNCC3)C2)cc2c1OCc1c(ncnc1N1CCOCC1)N2] 2 HCl<br>from intermediate 434; solvent 7:1 Dioxane:EtOH No aqueous work-up only evaporation | 552 | quant |

-continued

| compound number | Structure | Mass (mg) | Yield (%) |
|---|---|---|---|
| Intermediate 552 | 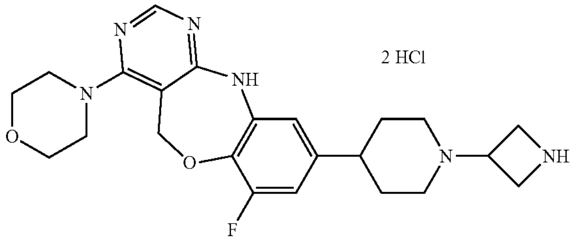 [SMILES: Fc1cc(C2CCN(C3CNC3)CC2)cc2c1OCc1c(ncnc1N1CCOCC1)N2] from intermediate 435; solvent 10:1 Dioxane:MeOH; No aqueous work-up only evaporation | 352 | 92 |
| Intermediate 553 | 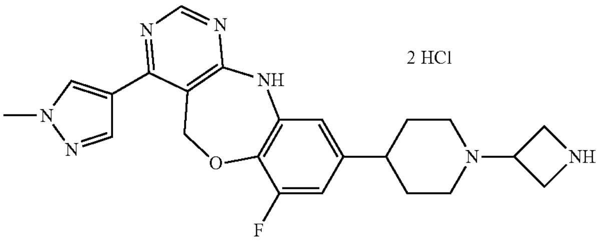 [SMILES: Cn1cc(-c2ncnc3c2COc2c(F)cc(C4CCN(C5CNC5)CC4)cc2N3)cn1] from intermediate 436; solvent 7:1 Dioxane:MeOH; No aqueous work-up only evaporation | 400 | quant |
| Intermediate 554 | 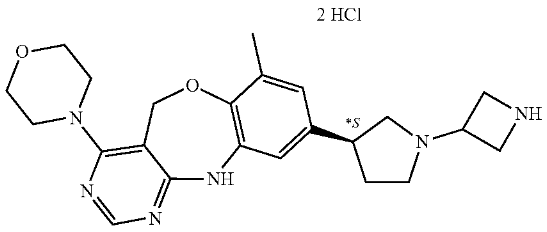 [SMILES: Cc1cc([C@@H]2CCN(C3CNC3)C2)cc2c1OCc1c(ncnc1N1CCOCC1)N2] from intermediate 437; solvent 2:1 Dioxane:MeOH; No aqueous work-up only evaporation | 329 | quant |
| Intermediate 555 | 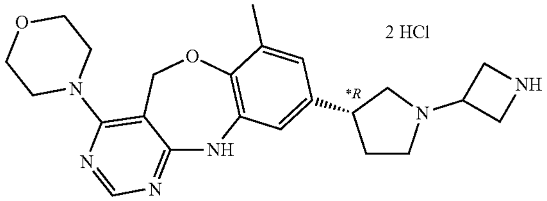 [SMILES: Cc1cc([C@H]2CCN(C3CNC3)C2)cc2c1OCc1c(ncnc1N1CCOCC1)N2] from intermediate 438; solvent 2:1 Dioxane:MeOH; No aqueous work-up only evaporation | 347 | quant |
| Intermediate 556 | 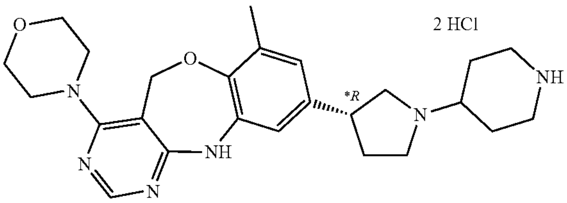 [SMILES: Cc1cc([C@H]2CCN(C3CCNCC3)C2)cc2c1OCc1c(ncnc1N1CCOCC1)N2] from intermediate 439; solvent 2:1 Dioxane:MeOH; No aqueous work-up only evaporation | 450 | quant |

-continued

| compound number | Structure | Mass (mg) | Yield (%) |
|---|---|---|---|
| Intermediate 557 | 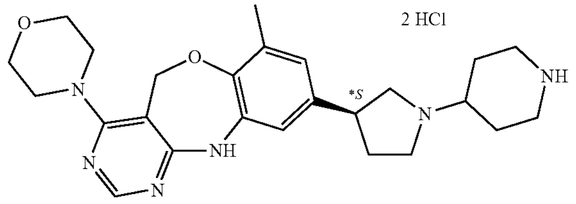 [SMILES: Cc1cc([C@@H]2CCN(C3CCNCC3)C2)cc2c1OCc1c(ncnc1N1CCOCC1)N2] 2 HCl<br>from intermediate 440; solvent 2:1 Dioxane:MeOH; No aqueous work-up only evaporation | 486 | quant |
| Intermediate 558 | 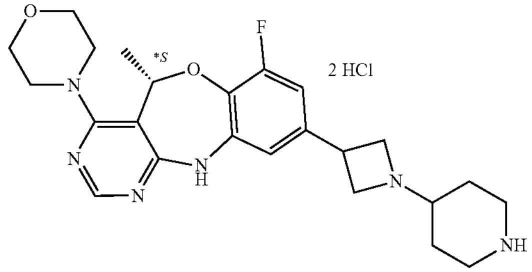 [SMILES: C[C@@H]1Oc2c(F)cc(C3CN(C4CCNCC4)C3)cc2Nc2ncnc(N3CCOCC3)c21] 2 HCl<br>from intermediate 484; solvent 8:1 Dioxane:EtOH; No aqueous work-up only evaporation | 339 | quant |
| Intermediate 559 | 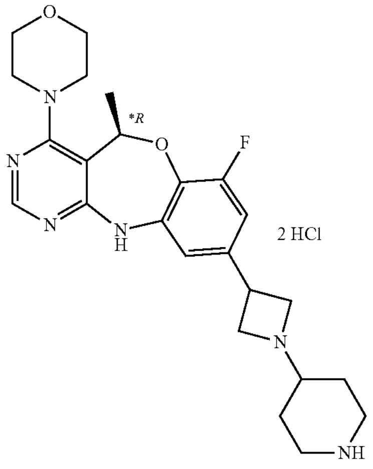 [SMILES: C[C@H]1Oc2c(F)cc(C3CN(C4CCNCC4)C3)cc2Nc2ncnc(N3CCOCC3)c21] 2 HCl<br>from intermediate 485; solvent 8:1 Dioxane:EtOH; No aqueous work-up only evaporation | 307 | 90 |

-continued

| compound number | Structure | Mass (mg) | Yield (%) |
|---|---|---|---|
| Intermediate 560 | 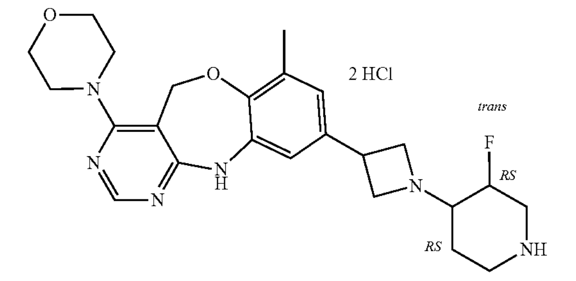 [SMILES: Cc1cc(C2CN(C3CCNCC3F)C2)cc2c1OCc1c(ncnc1N1CCOCC1)N2] from intermediate 432; solvent 8:1 Dioxane:MeOH; No aqeous work-up only evaporation | 113 | quant |
| Intermediate 561 | 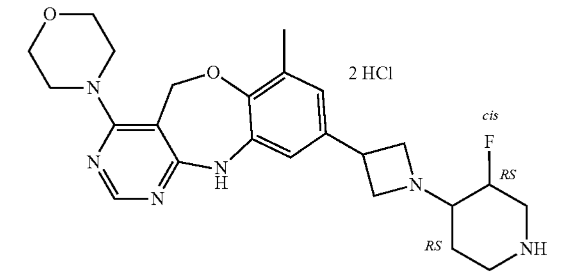 [SMILES: Cc1cc(C2CN(C3CCNCC3F)C2)cc2c1OCc1c(ncnc1N1CCOCC1)N2] from intermediate 433; solvent 8:1 Dioxane:MeOH; No aqueous work-up only evaporation | 372 | quant |
| Intermediate 562 | 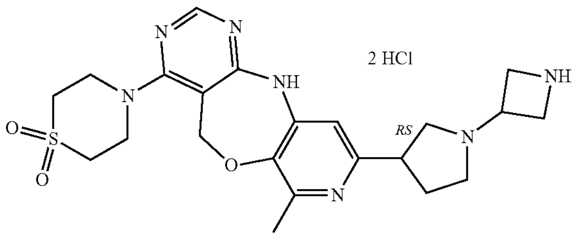 [SMILES: Cc1nc(C2CCN(C3CNC3)C2)cc2c1OCc1c(ncnc1N1CCS(=O)(=O)CC1)N2] from intermediate 486; solvent 5:1 Dioxane:MeOH; No aqueous work-up only evaporation | 256 | quant |
| Intermediate 563 | 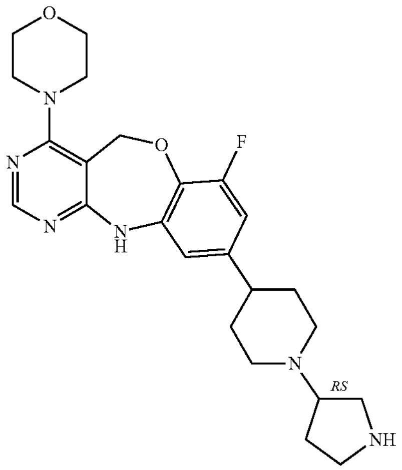 [SMILES: Fc1cc(C2CCN(C3CCNC3)CC2)cc2c1OCc1c(ncnc1N1CCOCC1)N2] from intermediate 444 | 976 | quant. |

-continued
| compound number | Structure | Mass (mg) | Yield (%) |
| --- | --- | --- | --- |
| Intermediate 564 | 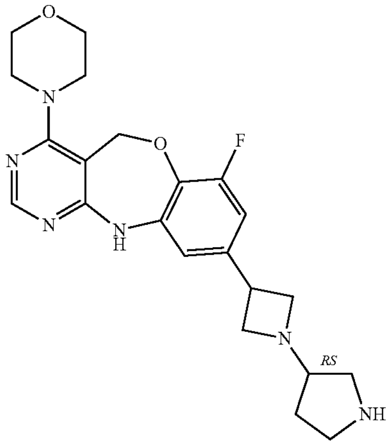 [SMILES: Fc1cc(C2CN(C3CCNC3)C2)cc2c1OCc1c(ncnc1N1CCOCC1)N2] from intermediate 445 - No aqueous work-up only evaporation | 800 | quant. |
| Intermediate 565 | 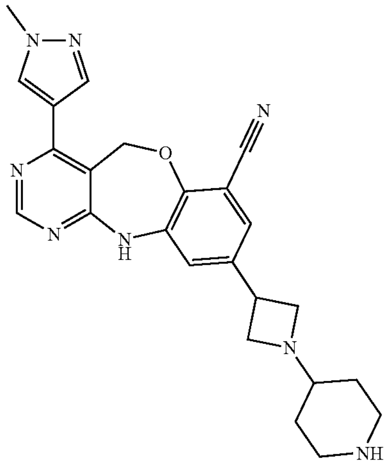 [SMILES: Cn1cc(-c2ncnc3c2COc2c(C#N)cc(C4CN(C5CCNCC5)C4)cc2N3)cn1] from intermediate 449 - No aqueous work-up only evaporation | 396 | quant. |
| Intermediate 566 | 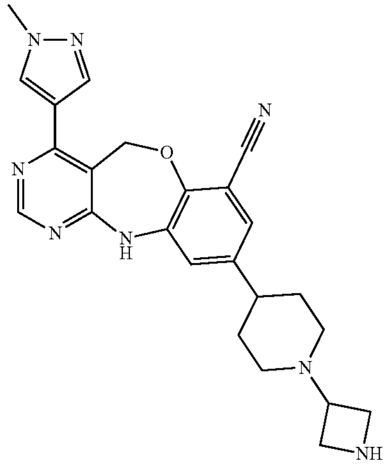 [SMILES: Cn1cc(-c2ncnc3c2COc2c(C#N)cc(C4CCN(C5CNC5)CC4)cc2N3)cn1] from intermediate 450 - No aqueous work-up only evaporation | 305 | 90 |

-continued
| compound number | Structure | Mass (mg) | Yield (%) |
|---|---|---|---|
| Intermediate 567 | 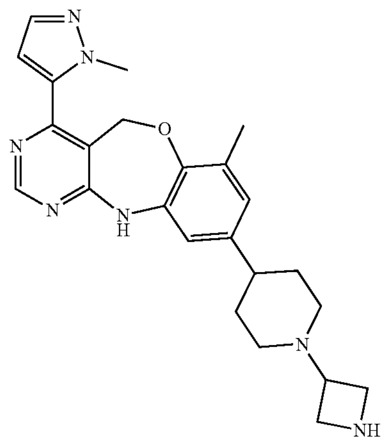 [SMILES: Cc1cc(C2CCN(C3CNC3)CC2)cc2c1OCc1c(ncnc1-c1ccnn1C)N2] from intermediate 532 | 120 | quant. |
| Intermediate 568 | 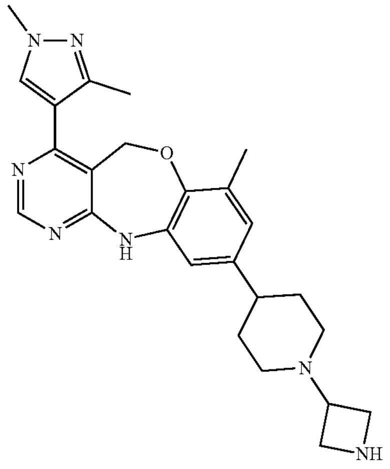 [SMILES: Cc1cc(C2CCN(C3CNC3)CC2)cc2c1OCc1c(ncnc1-c1cn(C)nc1C)N2] from intermediate 533 | 110 | 29 |
| Intermediate 569 | 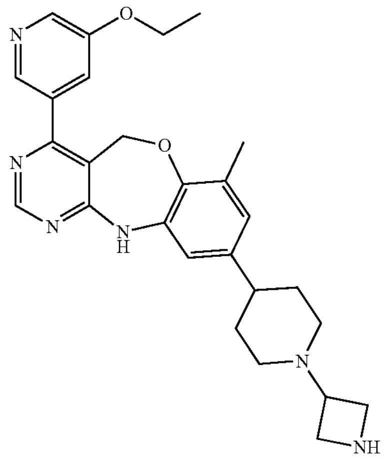 [SMILES: CCOc1cncc(-c2ncnc3c2COc2c(C)cc(C4CCN(C5CNC5)CC4)cc2N3)c1] from intermediate 534 - No aqueous work-up only evaporation | 495 | quant. |

-continued
| compound number | Structure | Mass (mg) | Yield (%) |
|---|---|---|---|
| Intermediate 680 | 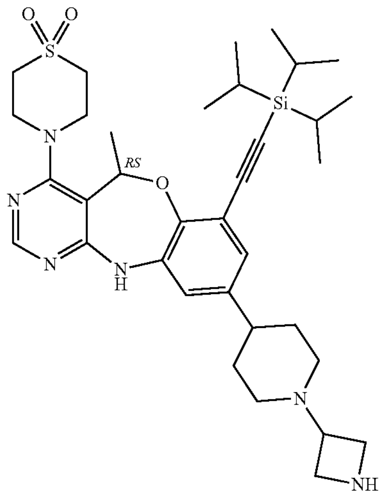 [SMILES: CC1Oc2c(C#C[Si](C(C)C)(C(C)C)C(C)C)cc(C3CCN(C4CNC4)CC3)cc2Nc2ncnc(N3CCS(=O)(=O)CC3)c21] from intermediate 679, solvent DCM, direct evaporation of the crude, obtained as HCl salt | 680 | quant |
| Intermediate 681 | 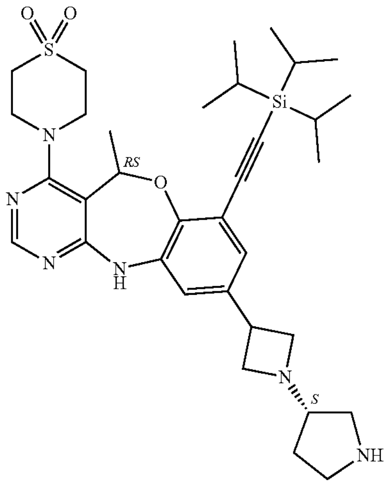 from intermediate 677 using 4 M HCl in MeOH, solvent DCM, direct evaporation of the crude, obtained as HCl salt | 240 | quant |

Preparation of Intermediate 570

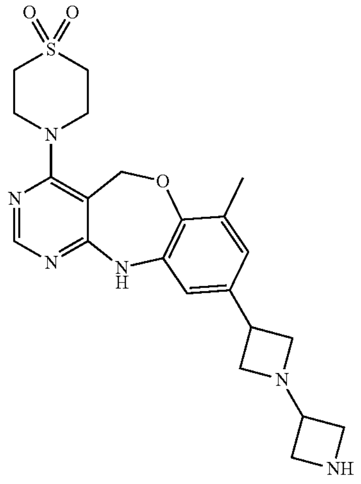 [SMILES: Cc1cc(C2CN(C3CNC3)C2)cc2c1OCc1c(ncnc1N1CCS(=O)(=O)CC1)N2]

At 0° C., a 4 M solution of HCl in 1,4-dioxane (594 L, 2.376 mmol) was added slowly to a solution of intermediate 462 (127 mg, 0.228 mmol) in 1,4-dioxane (3 mL) and MeOH (378 μL). This reaction was stirred for 12 h at rt. The solvent was evaporated until dryness. DCM, water and $NH_4OH$ were added. The organic layer was washed with NaCl, dried over $MgSO_4$, filtered and evaporated to give intermediate 570 (100 mg, 96%).

Example A124

Preparation of Intermediate 571

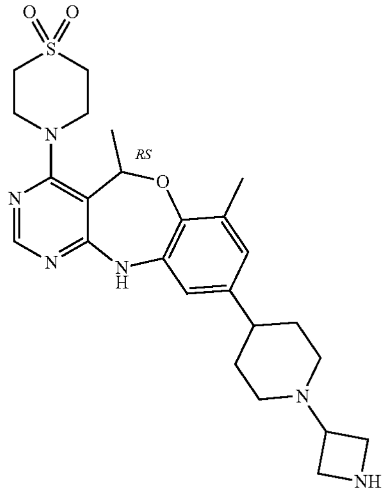 [SMILES: Cc1cc(C2CCN(C3CNC3)CC2)cc2c1OC(C)c1c(ncnc1N1CCS(=O)(=O)CC1)N2]

Intermediate 349 (7.97 g, 11.39 mmol) was dissolved in DCM (30 mL) and trifluoroacetic acid (20 mL) was added. The reaction mixture was stirred at rt for 3 h and evaporated. The resulting crude was dried under high vacuum to give intermediate 571 as TFA salt (5.69 g, quant).

Example A125

Preparation of Intermediate 572

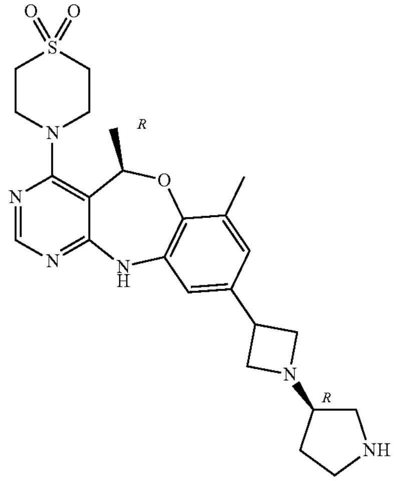

Iodotrimethylsilane (9.9 mL, 69.36 mmol) was added to a solution of intermediate 350 (9.5 g, 13.87 mmol) in acetonitrile (180 mL). The reaction mixture was stirred at rt for 2 h. A 10% aqueous solution of $NaHCO_3$ and EtOAc were added. The mixture was extracted three times with EtOAc. The organic layer was washed with brine, dried over $MgSO_4$, filtered and the solvent was evaporated to give intermediate 572 (7.7 g, quant).

Example A126

Preparation of Intermediate 573

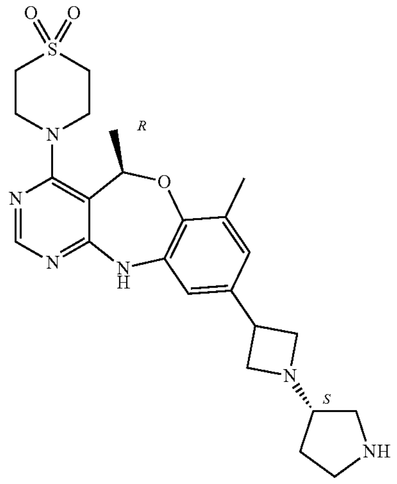

A solution of trifluoroacetic acid (45 mL, 593.99 mmol) in DCM (145 mL) was added dropwise to a solution of intermediate 351 (13.56 g, 19.80 mmol) in DCM (240 mL) at 0° C. The reaction mixture was stirred at rt for 18 h, then diluted with DCM, water and a 30% aqueous solution of $NH_4OH$. The mixture was stirred at rt for 1 h and extracted 3 times with DCM. The organic layer was decanted, dried over $MgSO_4$, filtered and the solvent was evaporated. The crude material was purified by chromatography ($SiO_2$, Buchi, 220 g, eluent: from 95% DCM, 5% MeOH, 0.5% $NH_4OH$ to 85% DCM, 14% MeOH, 1.4% $NH_4OH$). The pure fractions were collected and the solvent was evaporated to give intermediate 573 (8.1 g, 84%).

Preparation of Intermediate 574

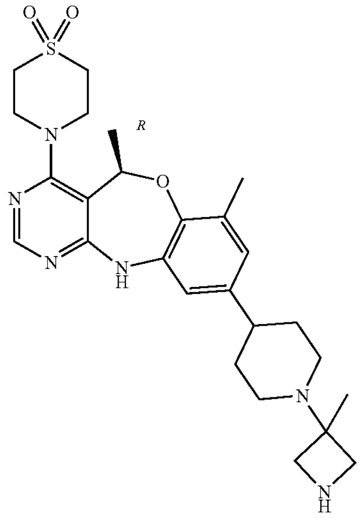

Intermediate 352 (810 mg, 1.14 mmol) was dissolved in DCM (22 mL) and trifluoroacetic acid (4.35 mL, 56.81 mmol) was added dropwise. The mixture was stirred at rt for 20 h. The volatiles were evaporated. The residue was taken up into ice. Water and a 10% aqueous solution of $NH_4OH$ were added until basic pH. The aqueous was extracted twice with EtOAc. The organic layer was dried over $MgSO_4$, filtered and the solvent was evaporated until dryness to give intermediate 574 (536 mg, 92%) as a colourless oil.

Preparation of Intermediate 575

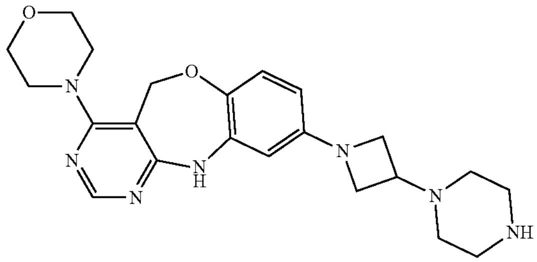 [SMILES: c1nc2c(c(N3CCOCC3)n1)COc1ccc(N3CC(N4CCNCC4)C3)cc1N2]

TFA (14.046 mL, 1.49 g/mL, 183.547 mmol) was added dropwise to a stirred solution of intermediate 310 (700 mg, 1.071 mmol) in DCM (27 mL). The reaction mixture was stirred at rt for 5 h. The mixture was poured out onto ice. Water and $NH_4OH$ were added until basic pH. The mixture was extracted twice with DCM and the combined organics dried over $MgSO_4$, filtered and evaporated in vacuo to afford the product which was used without further elaboration (455 mg; quantitative).

The compounds in the Table below were prepared by using an analogous method starting from the respective starting materials.

| compound number | Structure | Mass (mg) | Yield (%) |
|---|---|---|---|
| Intermediate 576 | 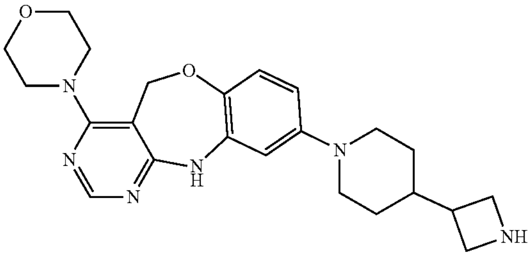 [SMILES: c1nc2c(c(N3CCOCC3)n1)COc1ccc(N3CCC(C4CNC4)CC3)cc1N2] from intermediate 312 | 414 | 75 |

-continued
| compound number | Structure | Mass (mg) | Yield (%) |
|---|---|---|---|
| Intermediate 577 | 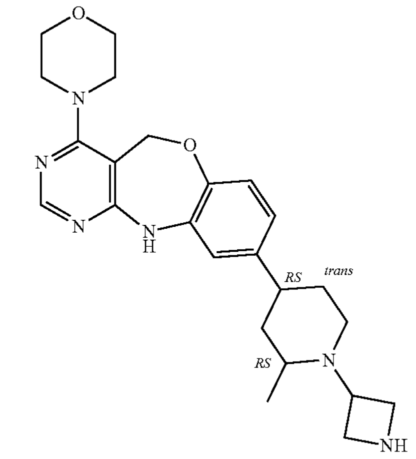 [SMILES: CC1CC(c2ccc3c(c2)Nc2ncnc(N4CCOCC4)c2CO3)CCN1C1CNC1] from intermediate 487 - aqueous work-up with $K_2CO_3$ | 71 | 74 |
| Intermediate 578 | 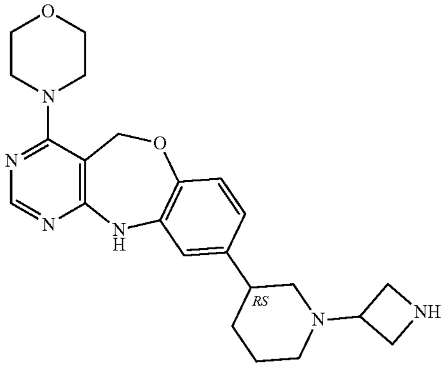 [SMILES: c1nc2c(c(N3CCOCC3)n1)COc1ccc(C3CCCN(C4CNC4)C3)cc1N2] from intermediate 488 - aqueous work-up with $K_2CO_3$ | 243 | 100 |
| Intermediate 579 | 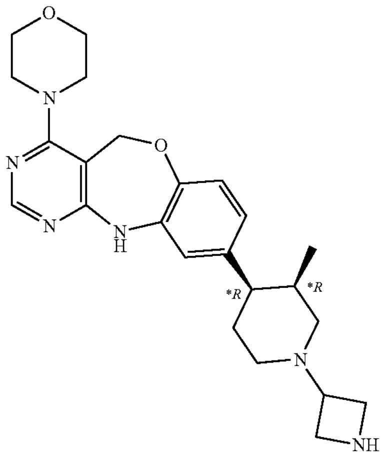 [SMILES: C[C@H]1CN(C2CNC2)CC[C@H]1c1ccc2c(c1)Nc1ncnc(N3CCOCC3)c1CO2] from intermediate 490 - No aqueous work-up only evaporation | 65 | quant. |

-continued
| compound number | Structure | Mass (mg) | Yield (%) |
|---|---|---|---|
| Intermediate 580 | 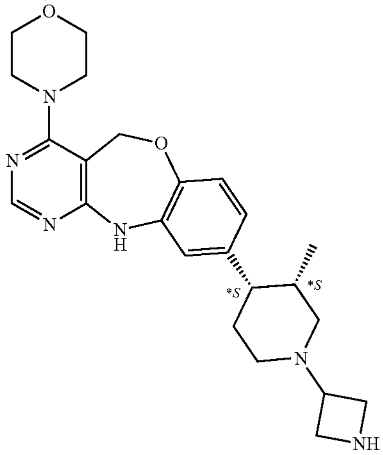 [SMILES: C[C@@H]1CN(C2CNC2)CC[C@@H]1c1ccc2c(c1)Nc1ncnc(N3CCOCC3)c1CO2] from intermediate 491 - No aqueous work-up only evaporation | 72 | quant. |
| Intermediate 581 | 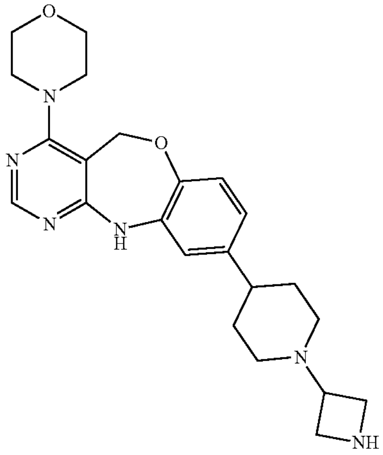 [SMILES: c1nc2c(c(N3CCOCC3)n1)COc1ccc(C3CCN(C4CNC4)CC3)cc1N2] from intermediate 441 | 205 | 79 |
| Intermediate 582 | 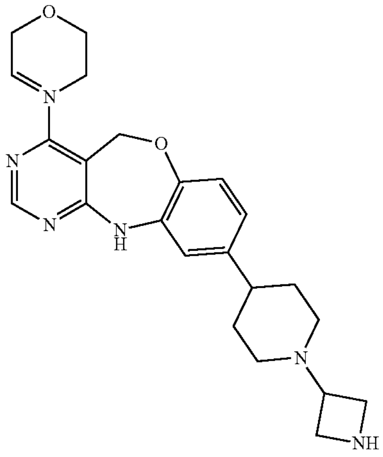 from intermediate 442 | 103 | 66 |

-continued
| compound number | Structure | Mass (mg) | Yield (%) |
|---|---|---|---|
| Intermediate 583 | 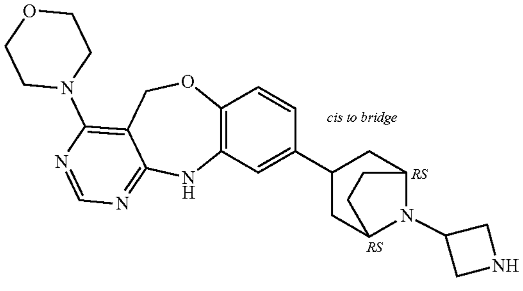 [SMILES: c1nc2c(c(N3CCOCC3)n1)COc1ccc(C3CC4CCC(C3)N4C3CNC3)cc1N2] from intermediate 300 - No aqueous work-up only evaporation | 52 | quant. |
| Intermediate 584 | 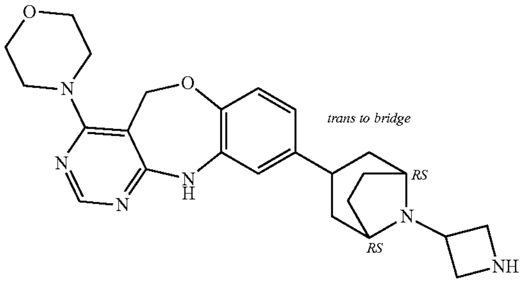 [SMILES: c1nc2c(c(N3CCOCC3)n1)COc1ccc(C3CC4CCC(C3)N4C3CNC3)cc1N2] from intermediate 301- No aqueous work-up only evaporation | 104 | quant. |
| Intermediate 585 | 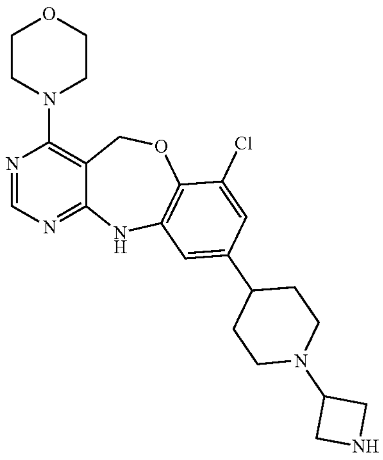 [SMILES: Clc1cc(C2CCN(C3CNC3)CC2)cc2c1OCc1c(ncnc1N1CCOCC1)N2] from intermediate 492 - No aqueous work-up only evaporation | 930 | quant. |

-continued
| compound number | Structure | Mass (mg) | Yield (%) |
|---|---|---|---|
| Intermediate 586 | 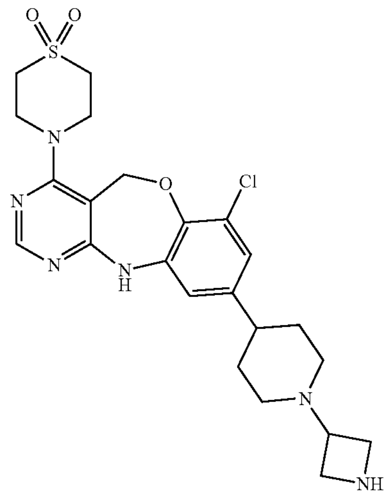 [SMILES: O=S1(=O)CCN(c2ncnc3c2COc2c(Cl)cc(C4CCN(C5CNC5)CC4)cc2N3)CC1] from intermediate 493 - No aqueous work-up only evaporation | 868 | quant. |
| Intermediate 587 | 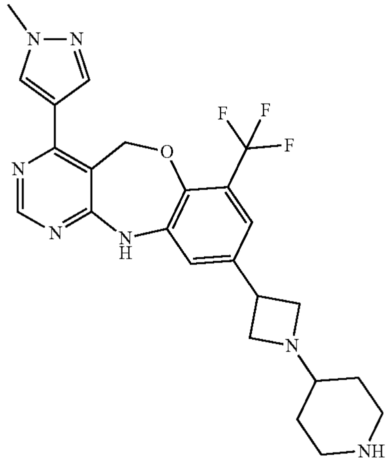 [SMILES: Cn1cc(-c2ncnc3c2COc2c(cc(C4CN(C5CCNCC5)C4)cc2C(F)(F)F)N3)cn1] from intermediate 494 - No aqueous work-up only evaporation | 128 | quant. |
| Intermediate 588 | 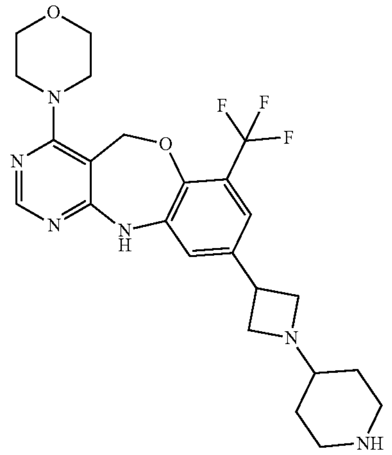 [SMILES: FC(F)(F)c1cc(C2CN(C3CCNCC3)C2)cc2c1OCc1c(ncnc1N1CCOCC1)N2] from intermediate 495 - No aqueous work-up only evaporation | 178 | quant. |

-continued
| compound number | Structure | Mass (mg) | Yield (%) |
| --- | --- | --- | --- |
| Intermediate 589 | 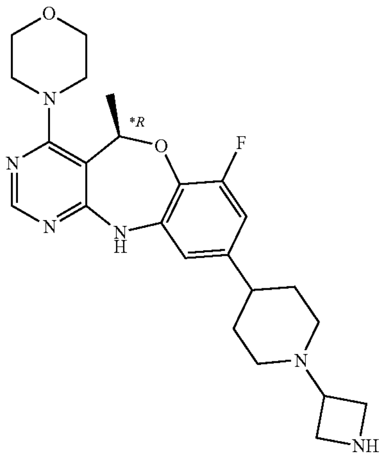 [SMILES: C[C@H]1Oc2c(F)cc(C3CCN(C4CNC4)CC3)cc2Nc2ncnc(N3CCOCC3)c21] from intermediate 497 - No aqueous work-up only evaporation | 175 | quant. |
| Intermediate 590 | 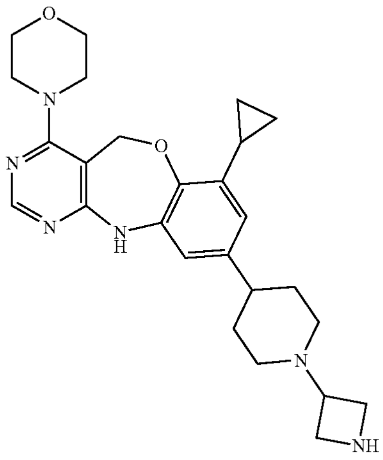 [SMILES: c1nc2c(c(N3CCOCC3)n1)COc1c(cc(C3CCN(C4CNC4)CC3)cc1C1CC1)N2] from intermediate 443 | 293 | 85 |
| Intermediate 591 | 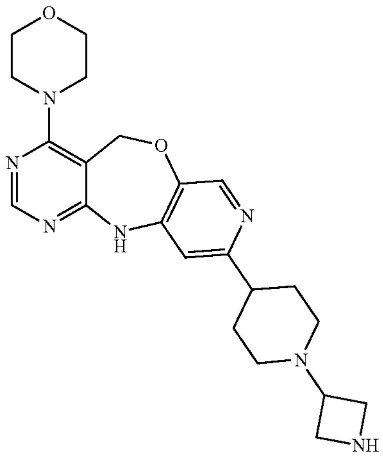 [SMILES: c1nc2c(c(N3CCOCC3)n1)COc1cnc(C3CCN(C4CNC4)CC3)cc1N2] from intermediate 499 - No aqueous work-up only evaporation | 290 | quant. |

-continued
| compound number | Structure | Mass (mg) | Yield (%) |
|---|---|---|---|
| Intermediate 592 | 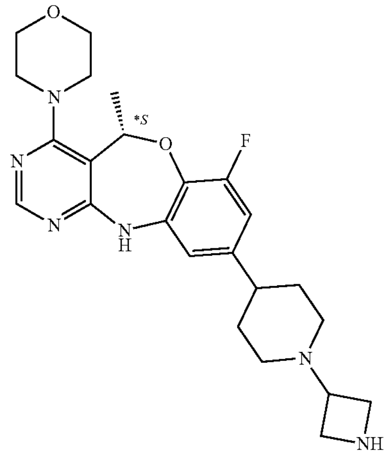 [SMILES: C[C@@H]1Oc2c(F)cc(C3CCN(C4CNC4)CC3)cc2Nc2ncnc(N3CCOCC3)c21] from intermediate 498 - No aqueous work-up only evaporation | 155 | quant. |
| Intermediate 593 | 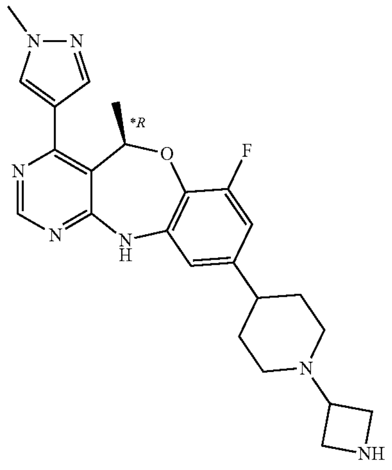 [SMILES: C[C@H]1Oc2c(F)cc(C3CCN(C4CNC4)CC3)cc2Nc2ncnc(-c3cnn(C)c3)c21] from intermediate 501 - No aqueous work-up only evaporation | 159 | quant. |
| Intermediate 594 | 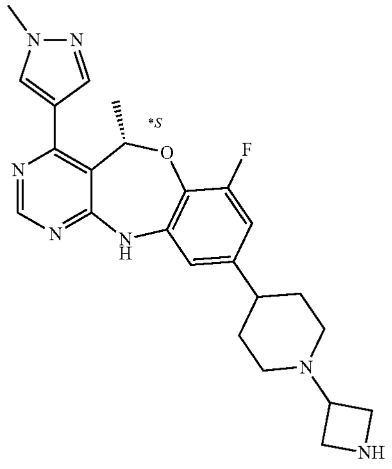 [SMILES: C[C@@H]1Oc2c(F)cc(C3CCN(C4CNC4)CC3)cc2Nc2ncnc(-c3cnn(C)c3)c21] from intermediate 502 - No aqueous work-up only evaporation | 164 | quant. |

-continued
| compound number | Structure | Mass (mg) | Yield (%) |
| --- | --- | --- | --- |
| Intermediate 595 | 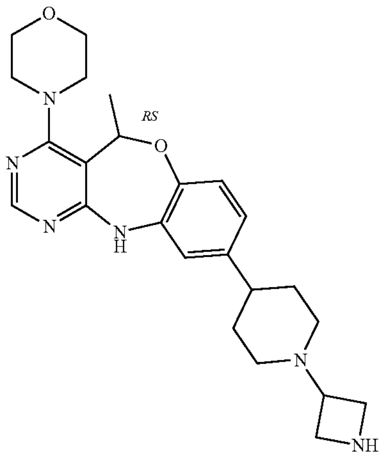 [SMILES: CC1Oc2ccc(C3CCN(C4CNC4)CC3)cc2Nc2ncnc(N3CCOCC3)c21] from intermediate 446 | 960 | quant. |
| Intermediate 596 | 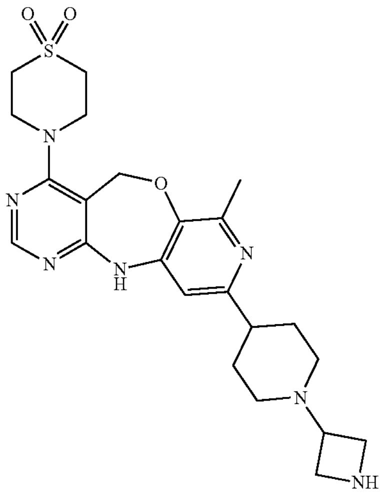 [SMILES: Cc1nc(C2CCN(C3CNC3)CC2)cc2c1OCc1c(ncnc1N1CCS(=O)(=O)CC1)N2] from intermediate 503 - No aqueous work-up only evaporation | 236 | quant. |

-continued
| compound number | Structure | Mass (mg) | Yield (%) |
|---|---|---|---|
| Intermediate 597 | 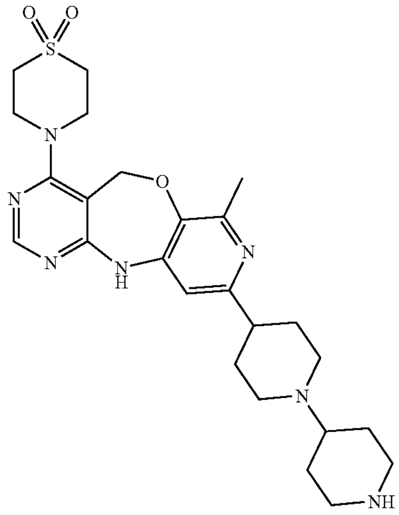 [SMILES: Cc1nc(C2CCN(C3CCNCC3)CC2)cc2c1OCc1c(ncnc1N1CCS(=O)(=O)CC1)N2] from intermediate 504 - No aqueous work-up only evaporation | 118 | quant. |
| Intermediate 598 | 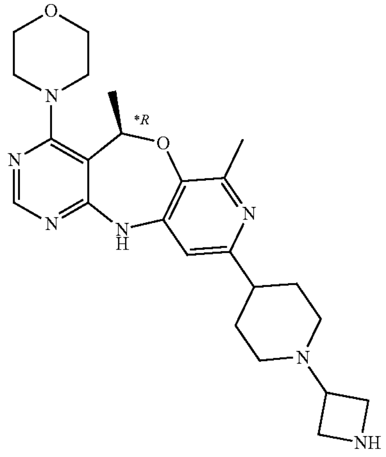 [SMILES: Cc1nc(C2CCN(C3CNC3)CC2)cc2c1O[C@H](C)c1c(ncnc1N1CCOCC1)N2] from intermediate 506 - No aqueous work-up only evaporation | 79 | quant. |

-continued
| compound number | Structure | Mass (mg) | Yield (%) |
|---|---|---|---|
| Intermediate 599 | 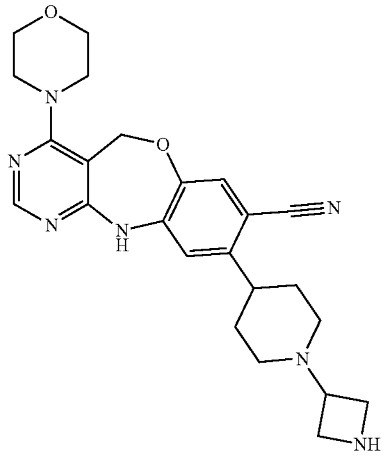 [SMILES: N#Cc1cc2c(cc1C1CCN(C3CNC3)CC1)Nc1ncnc(N3CCOCC3)c1CO2] from intermediate 508 - No aqueous work-up only evaporation | 188 | quant. |
| Intermediate 600 | 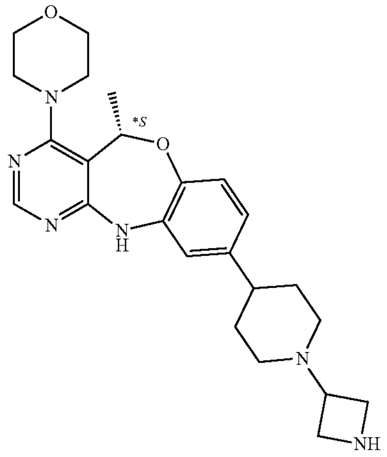 [SMILES: C[C@@H]1Oc2ccc(C3CCN(C4CNC4)CC3)cc2Nc2ncnc(N3CCOCC3)c21] from intermediate 507 - No aqueous work-up only evaporation | 76 | quant. |
| Intermediate 601 | 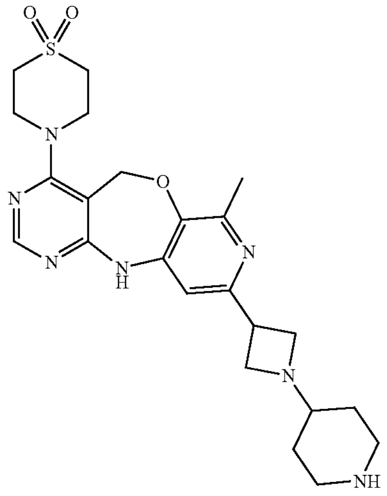 [SMILES: Cc1nc(C2CN(C3CCNCC3)C2)cc2c1OCc1c(ncnc1N1CCS(=O)(=O)CC1)N2] from intermediate 509 - No aqueous work-up only evaporation | 152 | quant. |

-continued
| compound number | Structure | Mass (mg) | Yield (%) |
|---|---|---|---|
| Intermediate 602 | 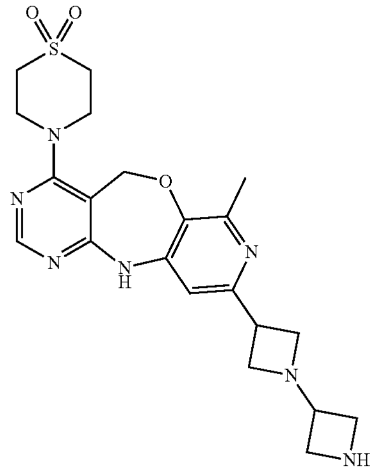 [SMILES: Cc1nc(C2CN(C3CNC3)C2)cc2c1OCc1c(ncnc1N1CCS(=O)(=O)CC1)N2] from intermediate 510 - No aqueous work-up only evaporation | 44 | quant. |
| Intermediate 654 | 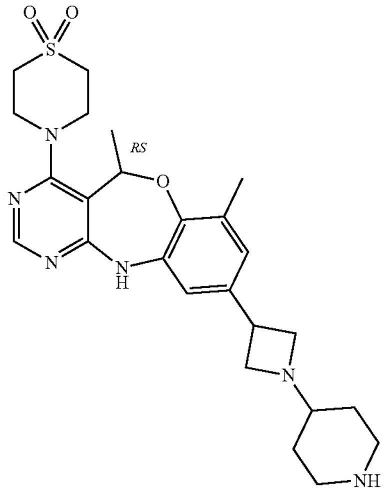 [SMILES: Cc1cc(C2CN(C3CCNCC3)C2)cc2c1OC(C)c1c(ncnc1N1CCS(=O)(=O)CC1)N2] from intermediate 653 - No aqueous work-up only evaporation | 220 | quant |

-continued
| compound number | Structure | Mass (mg) | Yield (%) |
|---|---|---|---|
| Intermediate 603 | 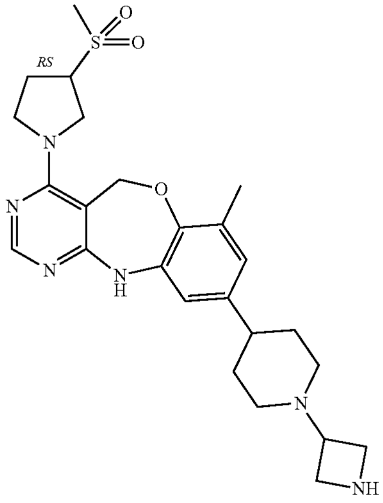 [SMILES: Cc1cc(C2CCN(C3CNC3)CC2)cc2c1OCc1c(ncnc1N1CCC(S(C)(=O)=O)C1)N2] from intermediate 526 | 238 | 80 |
| Intermediate 604 | 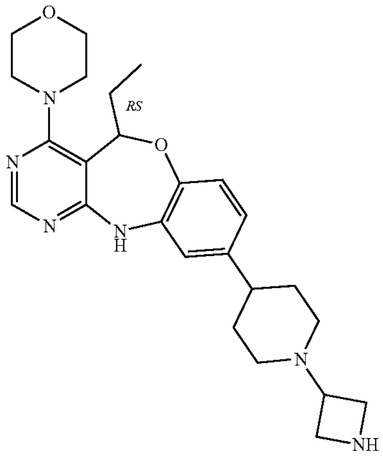 [SMILES: CCC1Oc2ccc(C3CCN(C4CNC4)CC3)cc2Nc2ncnc(N3CCOCC3)c21] from intermediate 511 | 503 | quant. |
| Intermediate 605 | 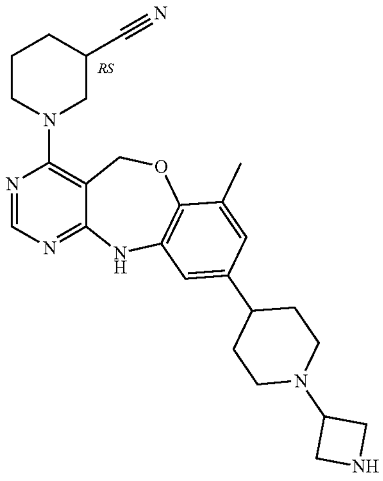 [SMILES: Cc1cc(C2CCN(C3CNC3)CC2)cc2c1OCc1c(ncnc1N1CCCC(C#N)C1)N2] from intermediate 527 | 238 | 76 |

-continued
| compound number | Structure | Mass (mg) | Yield (%) |
|---|---|---|---|
| Intermediate 685 | 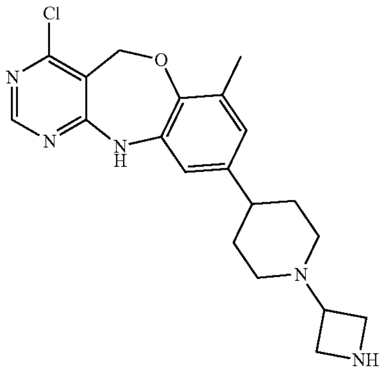 [SMILES: Cc1cc(C2CCN(C3CNC3)CC2)cc2c1OCc1c(Cl)ncnc1N2]<br>from intermediate 525; No aqueous work-up only evaporation to afford TFA salt | 628 | quant. |
| Intermediate 606 | 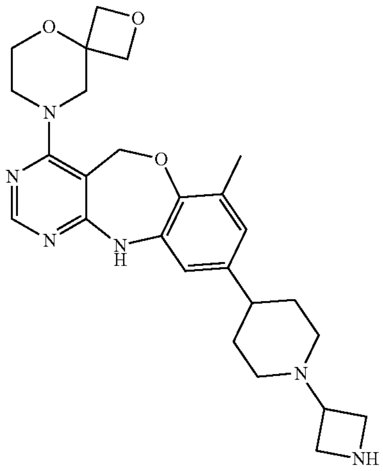 [SMILES: Cc1cc(C2CCN(C3CNC3)CC2)cc2c1OCc1c(ncnc1N1CCOC3(COC3)C1)N2]<br>from intermediate 528 | 258 | quant. |
| Intermediate 607 | 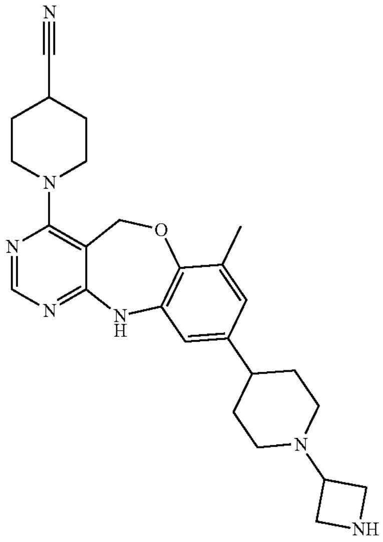 [SMILES: Cc1cc(C2CCN(C3CNC3)CC2)cc2c1OCc1c(ncnc1N1CCC(C#N)CC1)N2]<br>from intermediate 529 | 222 | quant. |

-continued
| compound number | Structure | Mass (mg) | Yield (%) |
|---|---|---|---|
| Intermediate 608 | 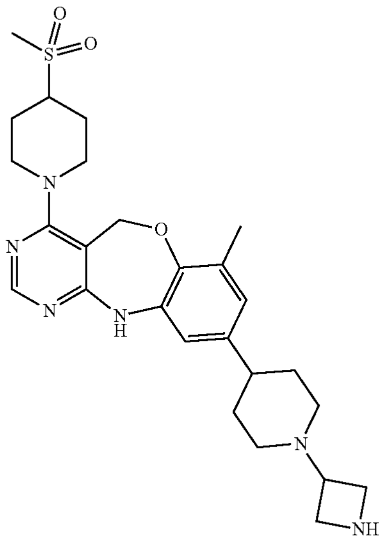 [SMILES: Cc1cc(C2CCN(C3CNC3)CC2)cc2c1OCc1c(ncnc1N1CCC(S(C)(=O)=O)CC1)N2] from intermediate 530 | 266 | 95 |
| Intermediate 609 | 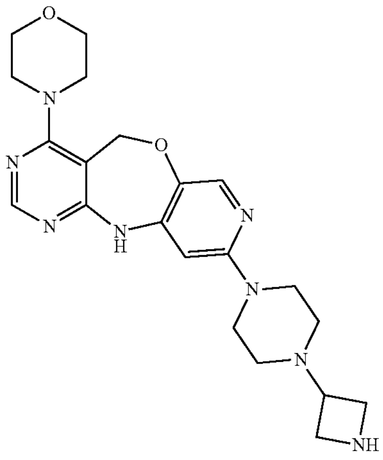 [SMILES: c1nc2c(c(N3CCOCC3)n1)COc1cnc(N3CCN(C4CNC4)CC3)cc1N2] from intermediate 448 | 358 | 68 |

-continued
| compound number | Structure | Mass (mg) | Yield (%) |
|---|---|---|---|
| Intermediate 610 | 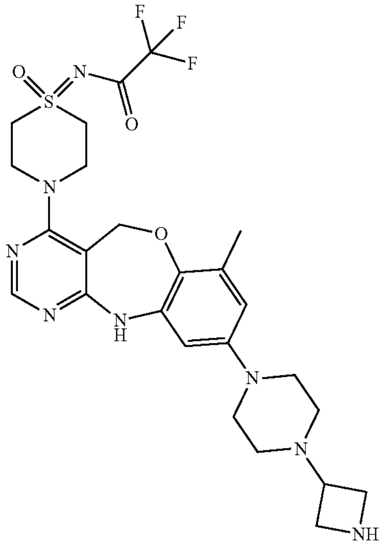 [SMILES: Cc1cc(N2CCN(C3CNC3)CC2)cc2c1OCc1c(ncnc1N1CCS(=O)(=NC(=O)C(F)(F)F)CC1)N2] from intermediate 531 | 155 | quant. |
| Intermediate 611 | 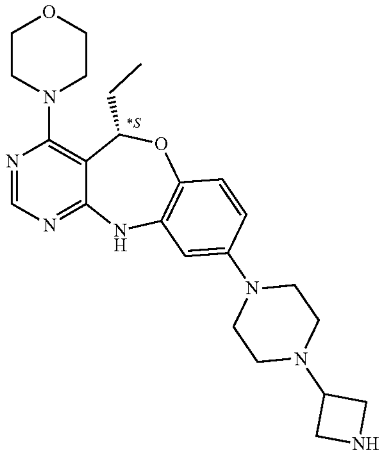 [SMILES: CC[C@@H]1Oc2ccc(N3CCN(C4CNC4)CC3)cc2Nc2ncnc(N3CCOCC3)c21] from intermediate 512 - No aqueous work-up only evaporation | 321 | quant. |

-continued
| compound number | Structure | Mass (mg) | Yield (%) |
|---|---|---|---|
| Intermediate 612 | 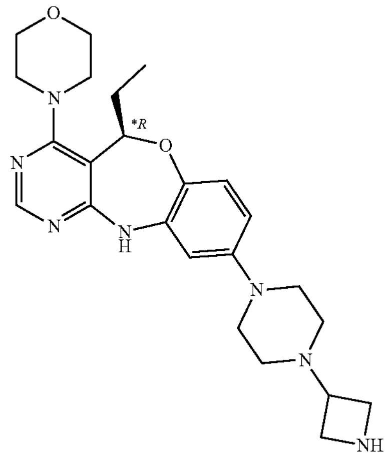 [SMILES: CC[C@H]1Oc2ccc(N3CCN(C4CNC4)CC3)cc2Nc2ncnc(N3CCOCC3)c21] from intermediate 513 - No aqueous work-up only evaporation | 364 | quant. |
| Intermediate 613 | 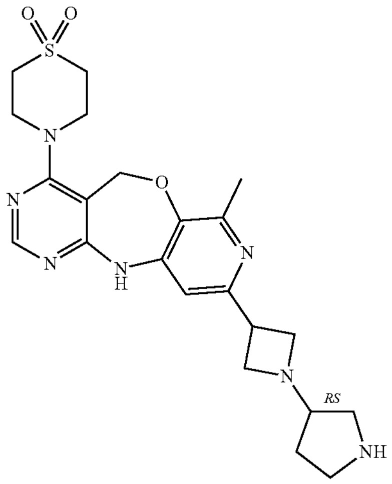 [SMILES: Cc1nc(C2CN(C3CCNC3)C2)cc2c1OCc1c(ncnc1N1CCS(=O)(=O)CC1)N2] from intermediate 514 - No aqueous work-up only evaporation | 165 | quant. |

-continued
| compound number | Structure | Mass (mg) | Yield (%) |
|---|---|---|---|
| Intermediate 614 | 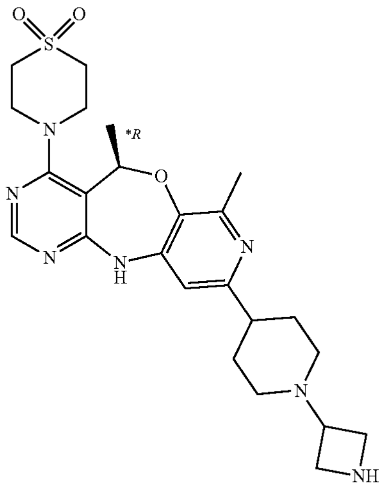 [SMILES: Cc1nc(C2CCN(C3CNC3)CC2)cc2c1O[C@H](C)c1c(ncnc1N1CCS(=O)(=O)CC1)N2] from intermediate 516 - No aqueous work-up only evaporation | 546 | quant. |
| Intermediate 614a | 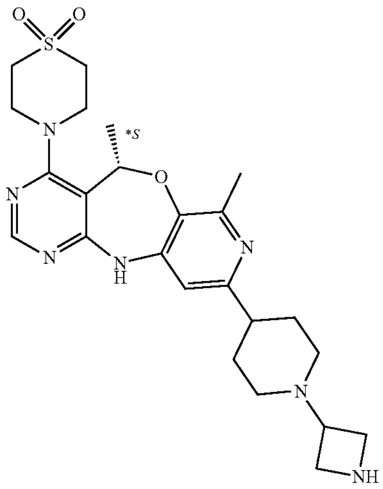 [SMILES: Cc1nc(C2CCN(C3CNC3)CC2)cc2c1O[C@@H](C)c1c(ncnc1N1CCS(=O)(=O)CC1)N2] from intermediate 517 - No aqueous work-up only evaporation | 530 | quant. |

-continued
| compound number | Structure | Mass (mg) | Yield (%) |
|---|---|---|---|
| Intermediate 615 | 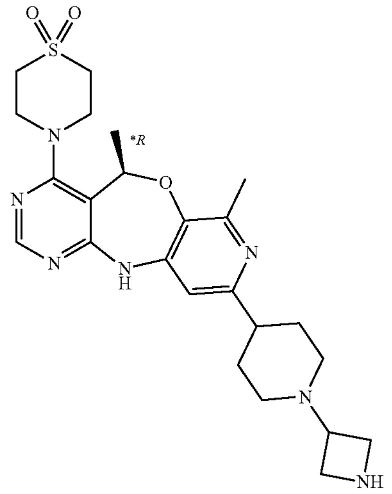 [SMILES: Cc1nc(C2CCN(C3CNC3)CC2)cc2c1O[C@H](C)c1c(ncnc1N1CCS(=O)(=O)CC1)N2] from intermediate 519 - No aqueous work-up only evaporation | 107 | quant. |
| Intermediate 616 | 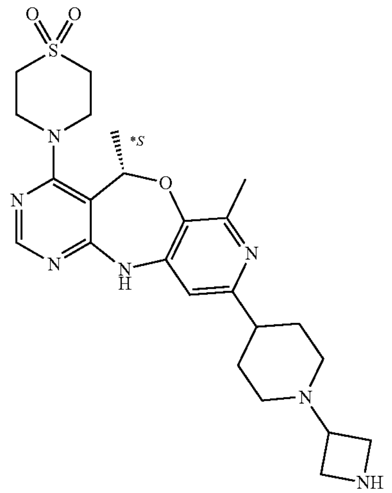 [SMILES: Cc1nc(C2CCN(C3CNC3)CC2)cc2c1O[C@@H](C)c1c(ncnc1N1CCS(=O)(=O)CC1)N2] from intermediate 520 - No aqueous work-up only evaporation | 86 | quant. |

-continued
| compound number | Structure | Mass (mg) | Yield (%) |
|---|---|---|---|
| Intermediate 617 | 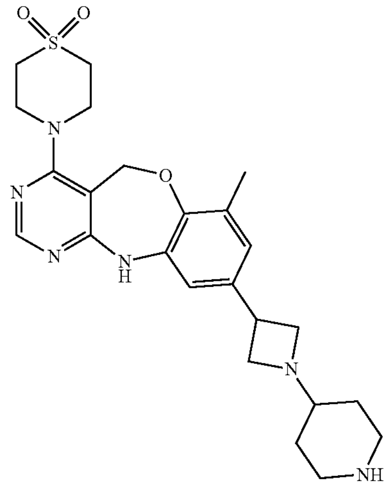 [SMILES: Cc1cc(C2CN(C3CCNCC3)C2)cc2c1OCc1c(ncnc1N1CCS(=O)(=O)CC1)N2] from intermediate 451 - No aqueous work-up only evaporation | 447 | quant. |
| Intermediate 618 | 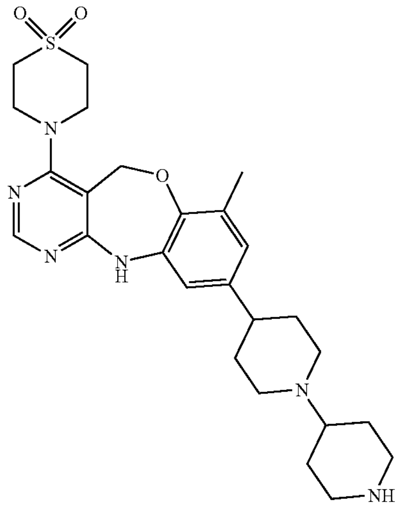 [SMILES: Cc1cc(C2CCN(C3CCNCC3)CC2)cc2c1OCc1c(ncnc1N1CCS(=O)(=O)CC1)N2] from intermediate 452 | 2360 | quant. |

-continued
| compound number | Structure | Mass (mg) | Yield (%) |
|---|---|---|---|
| Intermediate 619 | 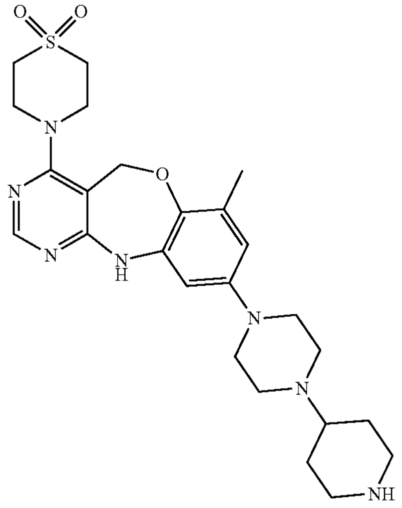 [SMILES: Cc1cc(N2CCN(C3CCNCC3)CC2)cc2c1OCc1c(ncnc1N1CCS(=O)(=O)CC1)N2] from intermediate 535 - No aqueous work-up only evaporation | 145 | quant. |
| Intermediate 620 | 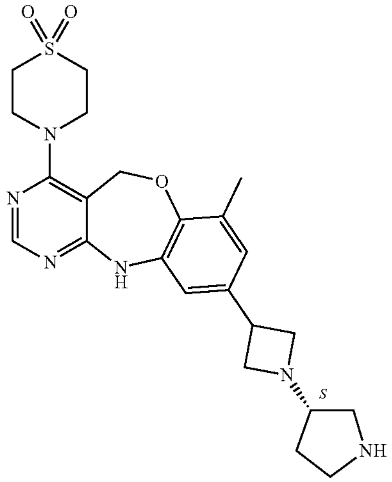 from intermediate 344 - No aqueous work-up only evaporation | 449 | quant. |

-continued
| compound number | Structure | Mass (mg) | Yield (%) |
|---|---|---|---|
| Intermediate 621 | 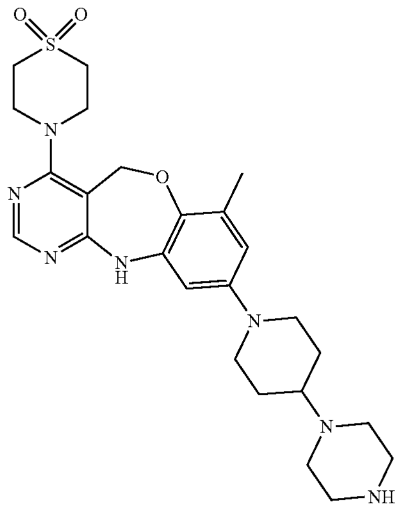 [SMILES: Cc1cc(N2CCC(N3CCNCC3)CC2)cc2c1OCc1c(ncnc1N1CCS(=O)(=O)CC1)N2] from intermediate 536 - No aqueous work-up only evaporation | 183 | quant. |
| Intermediate 622 | 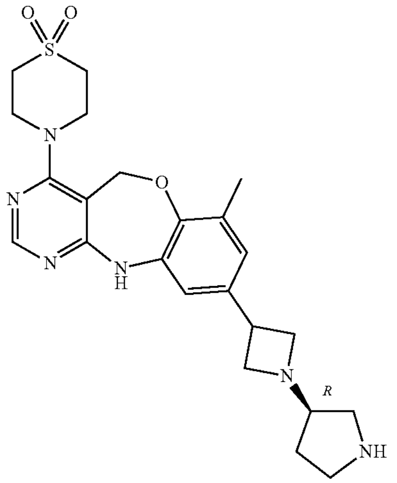 from intermediate 345 - No aqueous work-up only evaporation | 324 | quant. |

-continued
| compound number | Structure | Mass (mg) | Yield (%) |
|---|---|---|---|
| Intermediate 623 | 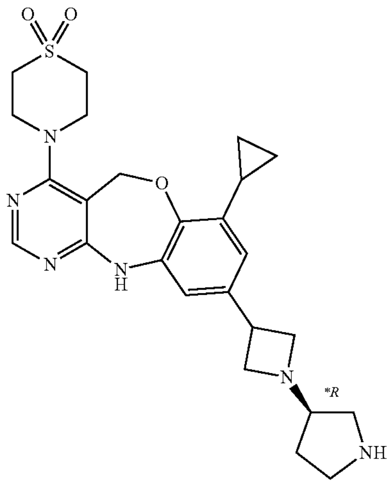 from intermediate 454 - No aqueous work-up only evaporation | 192 | quant. |
| Intermediate 624 | 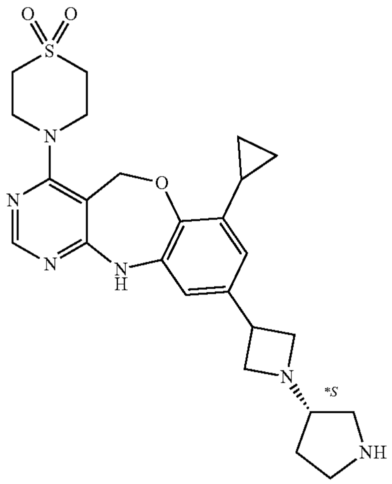 from intermediate 455 - No aqueous work-up only evaporation | 118 | quant. |

-continued
| compound number | Structure | Mass (mg) | Yield (%) |
| --- | --- | --- | --- |
| Intermediate 625 | 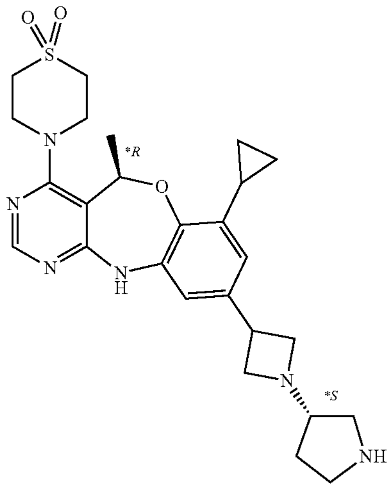 from intermediate 457 - No aqueous work-up only evaporation | 48 | quant. |
| Intermediate 626 | 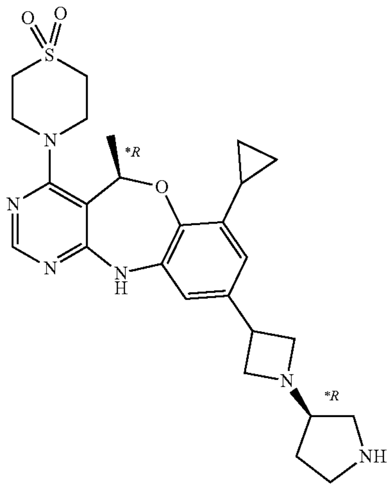 from intermediate 458 - No aqueous work-up only evaporation | 44 | quant. |

-continued

| compound number | Structure | Mass (mg) | Yield (%) |
| --- | --- | --- | --- |
| Intermediate 627 | 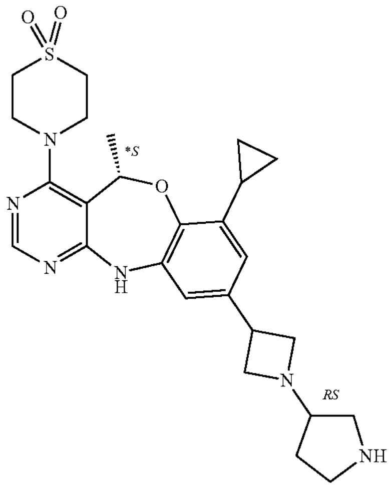 from intermediate 459 - No aqueous work-up only evaporation | 190 | quant. |

Preparation of Intermediate 628

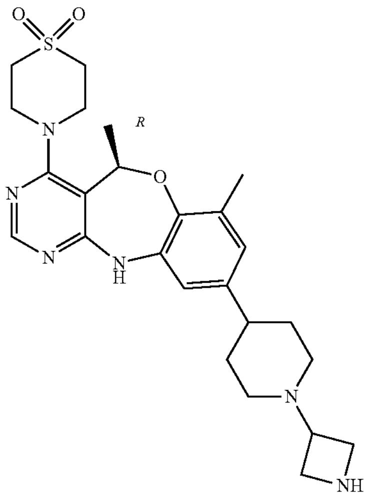

At 0° C., TFA (3 mL, 39.4 mmol) was added dropwise to a stirred solution of intermediate 337 (622 mg, 0.70 mmol) in DCM (14 mL). The reaction mixture was stirred at rt for 18 h. The mixture was poured out onto ice. Water and $NH_4OH$ were added until basic pH. The aqueous layer was extracted twice with DCM and the combined organics washed with brine, dried over $MgSO_4$, filtered and evaporated in vacuo to afford intermediate 628 (373 mg, 95%, purity 89%) as a white solid.

The intermediates in the Table below were prepared by using an analogous method starting from the respective starting materials.

| compound number | Structure | Mass (mg) | Yield (%) |
|---|---|---|---|
| Intermediate 629 | 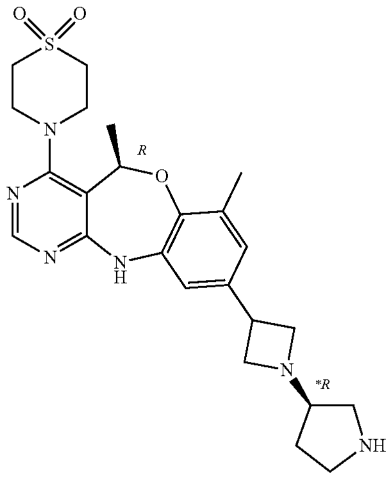 from intermediate 464. Chiral separation was via SFC (Stationary phase: Chiralcel OD-H 5 μm 250 × 21.2 mm, Mobile phase: 50% $CO_2$, 50% MeOH (0.3% $iPrNH_2$)) | 125 | 36 |
| Intermediate 630 | 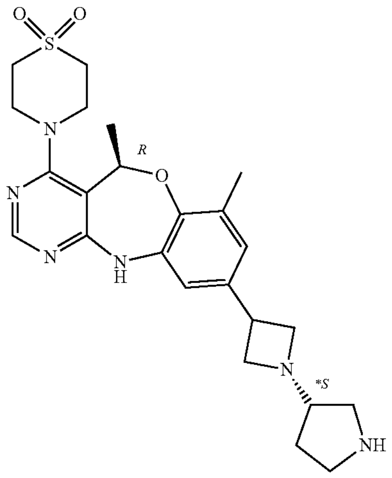 from intermediate 464. Chiral separation was via SFC (Stationary phase: Chiralcel OD-H 5 μm 250 × 21.2 mm, Mobile phase: 50% $CO_2$, 50% MeOH (0.3% $iPrNH_2$)) | 138 | 37 |

-continued

| compound number | Structure | Mass (mg) | Yield (%) |
|---|---|---|---|
| Intermediate 631 | 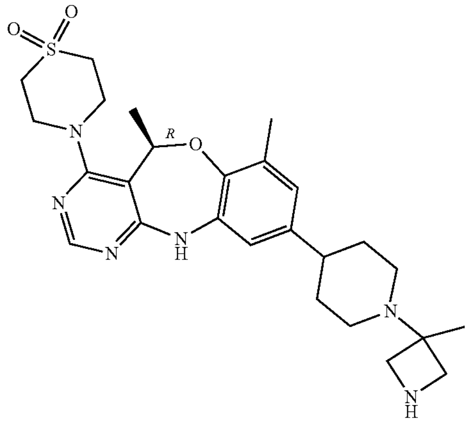 from intermediate 340 | 1550 | Quant purity 89% |

Preparation of Intermediate 632

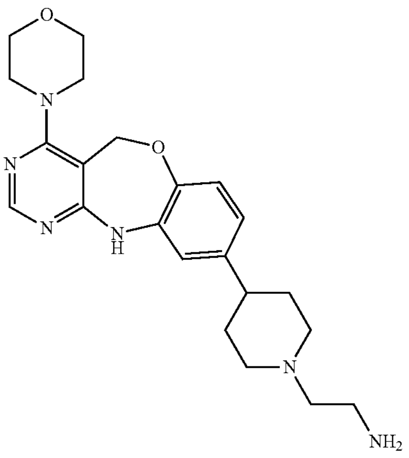 [SMILES: NCCN1CCC(c2ccc3c(c2)Nc2ncnc(N4CCOCC4)c2CO3)CC1]

TFA (500 μL; 6.53 mmol) was added dropwise at 5° C. to a suspension of intermediate 423 (117 mg; 0.23 mmol) in DCM (2 mL) and the reaction mixture was stirred at rt for 6 h. The reaction mixture was diluted with ice-water, a 10% aqueous solution of $K_2CO_3$ and DCM. The reaction mixture was stirred at rt for 1 h, then the mixture was extracted with DCM (3×). The organic layer was dried over $MgSO_4$, filtered and the solvent was evaporated to give the product as a white foam (100 mg; quant.).

| compound number | Structure | Mass (mg) | Yield (%) |
|---|---|---|---|
| Intermediate 633 | 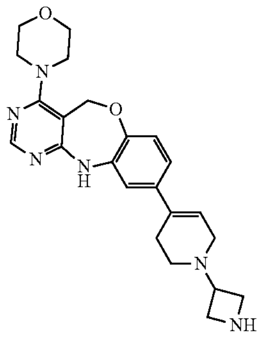 [SMILES: C1=C(c2ccc3c(c2)Nc2ncnc(N4CCOCC4)c2CO3)CCN(C2CNC2)C1] from intermediate 483 | 180 | 98 |
| Intermediate 577 | 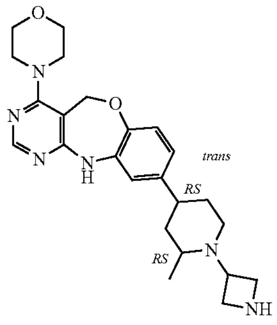 [SMILES: CC1CC(c2ccc3c(c2)Nc2ncnc(N4CCOCC4)c2CO3)CCN1C1CNC1] from intermediate 487—aqueous work-up with $K_2CO_3$ | 71 | 74 |

-continued

| compound number | Structure | Mass (mg) | Yield (%) |
|---|---|---|---|
| Intermediate 634 | 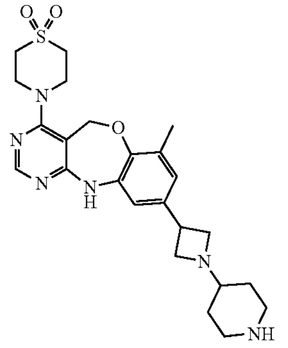 [SMILES: Cc1cc(C2CN(C3CCNCC3)C2)cc2c1OCc1c(ncnc1N1CCS(=O)(=O)CC1)N2] from intermediate 463 (direct evaporation of the crude, obtained as TFA salt) | 447 | quant |
| Intermediate 635 | 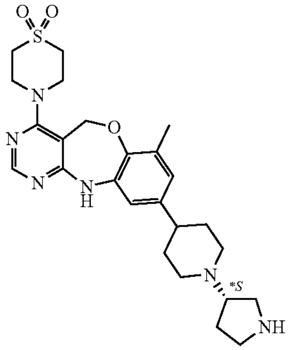 from intermediate 522 (direct evaporation of the crude, obtained as TFA salt) | 162 mg | quant |
| Intermediate 636 | 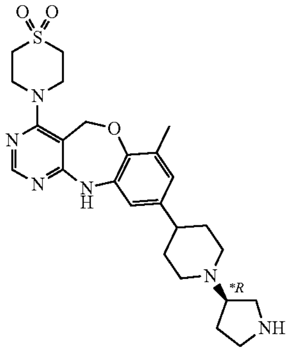 from intermediate 521 (direct evaporation of the crude, obtained as TFA salt) | 157 mg | quant |

-continued

| compound number | Structure | Mass (mg) | Yield (%) |
|---|---|---|---|
| Intermediate 637 | 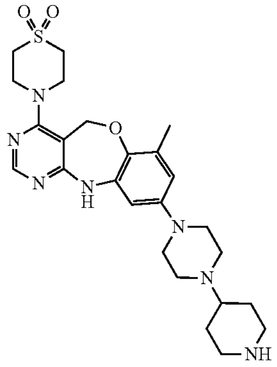 [SMILES: Cc1cc(N2CCC(N3CCNCC3)CC2)cc2c1OCc1c(ncnc1N1CCS(=O)(=O)CC1)N2] from intermediate 537 (direct evaporation of the crude, obtained as TFA salt) | 123 mg | quant |
| Intermediate 638 | 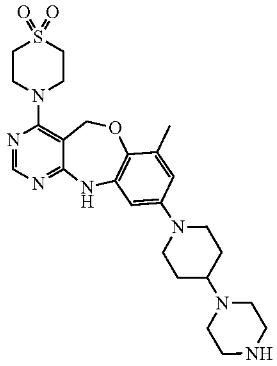 from intermediate 538 (direct evaporation of the crude, obtained as TFA salt) | 183 mg | quant |
| Intermediate 639 | 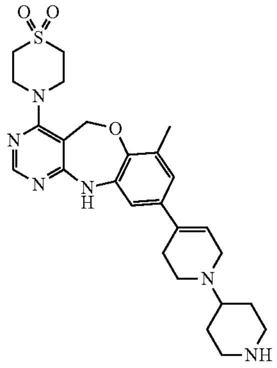 [SMILES: Cc1cc(C2=CCN(C3CCNCC3)CC2)cc2c1OCc1c(ncnc1N1CCS(=O)(=O)CC1)N2] from intermediate 461 (work up with $NH_4OH$) | 1060 | 54 |

-continued

| compound number | Structure | Mass (mg) | Yield (%) |
|---|---|---|---|
| Intermediate 640 | 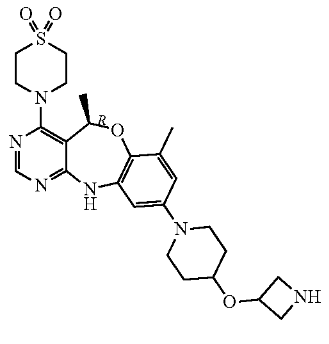 from intermediate 539 (direct evaporation of the crude, obtained as TFA salt) | 383 | quant |
| Intermediate 641 | 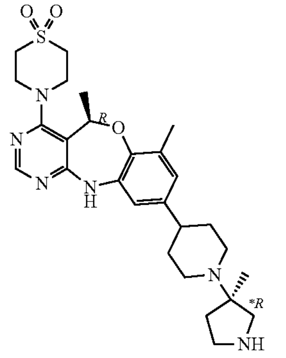 from intermediate 346 (work up with $NH_4OH$) | 51 | 97 |
| Intermediate 642 | 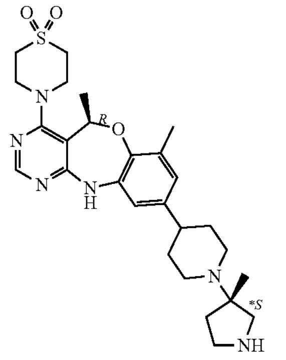 from intermediate 347 (work up with $NH_4OH$) | 47 | quant |
| Intermediate 643 | 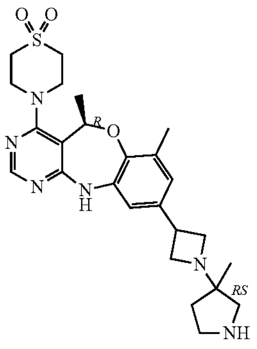 from intermediate 348 (work up with $NaHCO_3$) | 214 | quant |

Example A127

Preparation of Intermediate 644

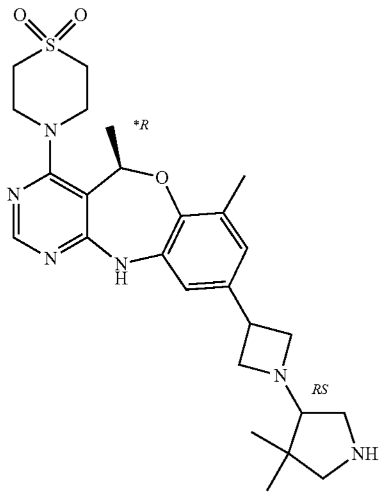

A solution of intermediate 465 (129 mg, 0.166 mmol) in EtOH (5.4 mL) was degassed by N2 bubbling and then warmed at 55° C. (Findenser equipment). Pd/C (5%) (70 mg, 33 μmol) was then added, followed by the addition of ammonium formate (104 mg, 1.66 mmol) and the reaction was stirred at 55° C. for 1 h 30. The reaction mixture was cooled down to rt, diluted with EtOH and the mixture was filtered on a pad of celite. The filtrate was evaporated in vacuo to give intermediate 644 (85 mg, quant)

Preparation of Intermediate 645 and Intermediate 646

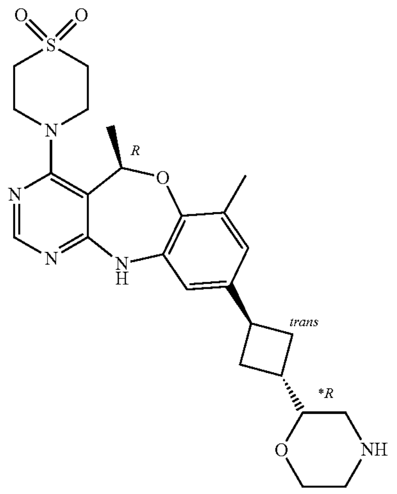

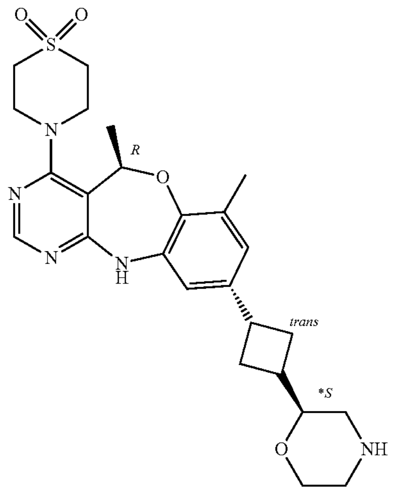

A solution of intermediate 466 (311 mg, 0.45 mmol) in EtOH (4 mL) was warmed at 55° C. Pd/C (5%) (190 mg, 0.089 mmol) was then added, followed by the addition of ammonium formate (282 mg, 4.5 mmol). The flask was capped with a normal plastic cap and the reaction was stirred at 55° C. for 1 h 30. The reaction mixture was filtered, concentrated and purified by preparative LC (spherical C18, 25 μm, 120 g YMC-ODS-25, dry load, mobile phase gradient 0.2% aq. $NH_4$+HCO3-/MeCN from 65:35 to 25:75 in 10 CV). The fractions containing pure product were evaporated to give 113 mg of a white solid. The crude was purified by chiral SFC (Stationary phase: CHIRACEL OJ-H 5 μm 250*30 mm, Mobile phase: 60% CO2, 40% mixture of MeOH/ACN: 80/20 v/v (+0.3% iPrNH2)). The fractions containing pure product were evaporated to give intermediate 645 (54 mg, 24%) and intermediate 646 (47 mg, 21%)

The intermediates in the Table below were prepared by using an analogous method starting from the respective starting materials.

| compound number | Structure | Mass (mg) | Yield (%) |
|---|---|---|---|
| Intermediate 647 | 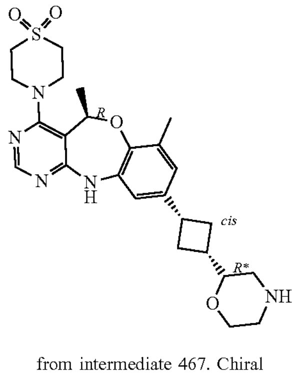 from intermediate 467. Chiral separation was via SFC (Stationary phase: CHIRACEL OJ-H 5 μm 250 * 20 mm, Mobile phase: 50% $CO_2$, 50% MeOH (0.3% $iPrNH_2$)) | 60 | 41 |
| Intermediate 648 | 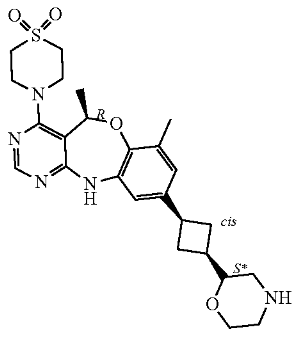 from intermediate 467. Chiral separation via SFC (Stationary phase: CHIRACEL OJ-H 5 μm 250 * 20 mm, Mobile phase: 50% $CO_2$, 50% MeOH (0.3% $iPrNH_2$)) | 59 | 41 |

Example A128

Preparation of Intermediate 649

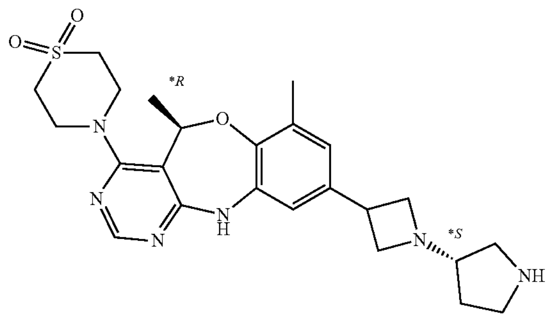

Intermediate 477 (2.7 g, 4.36 mmol) was hydrogenated at rt in MeOH (50 mL) and EtOAc (50 mL) with Pd/C (10%) (546 mg, 0.51 mmol) as a catalyst at atmospheric pressure for 5 h. The catalyst was filtered off on a pad of Celite®. The Celite® was washed twice with a mixture of EtOAc/MeOH (80/20). The solvent was evaporated until dryness to give the product (1.72 g, 81%).

Preparation of Intermediate 650

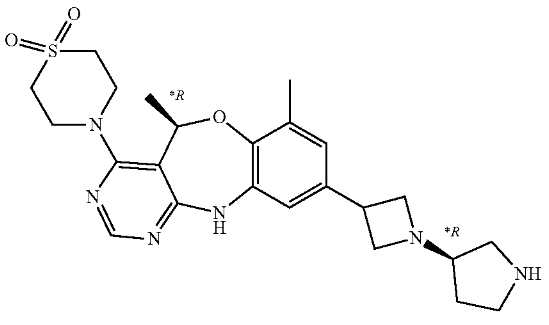

Intermediate 476 (544 mg, 0.879 mmol) was hydrogenated at rt in MeOH (10 mL) and EtOAc (10 mL) with Pd/C (10%) (100 mg, 0.094 mmol) as a catalyst at atmospheric pressure for 5 h. The catalyst was filtered off on a pad of Celite®. The Celite® was washed twice with a mixture of EtOAc/MeOH (80/20). The solvent was evaporated until dryness to give the product (395 mg, 93%).

The intermediates in the Table below were prepared by using an analogous method starting from the respective starting materials.

| compound number | Structure | Mass (mg | Yield (%) |
|---|---|---|---|
| Intermediate 651 | 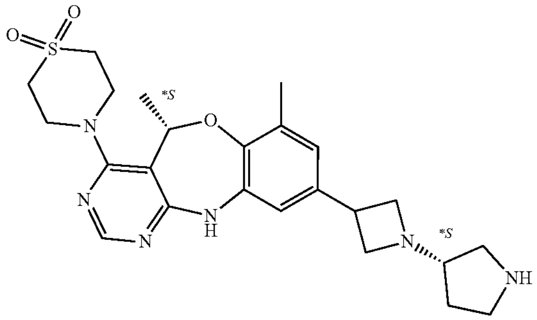 [SMILES: Cc1cc(C2CN([C@H]3CCNC3)C2)cc2c1O[C@@H](C)c1c(ncnc1N1CCS(=O)(=O)CC1)N2] from intermediate 479 | 405 | 89 |
| Intermediate 652 | 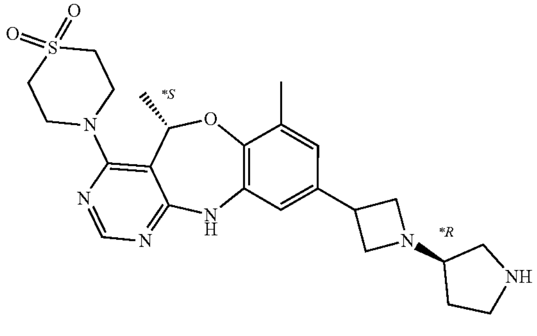 [SMILES: Cc1cc(C2CN([C@@H]3CCNC3)C2)cc2c1O[C@@H](C)c1c(ncnc1N1CCS(=O)(=O)CC1)N2] from intermediate 478 | 291 | 78 |

Example A129

Preparation of Intermediate 682

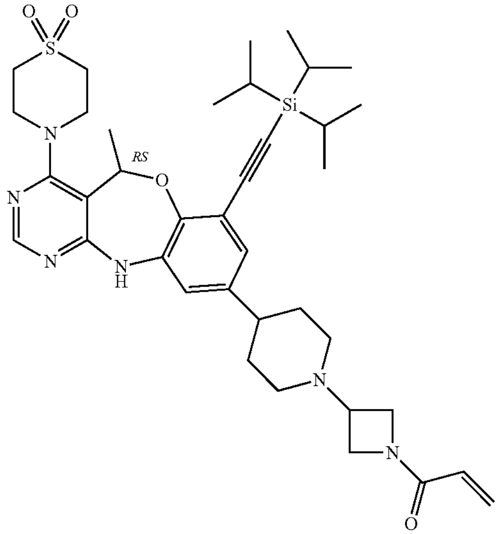

Acryloyl chloride (25 μL, 0.31 mmol) was added to a solution of intermediate 680 (200 mg, 0.29 mmol) and triethylamine (0.2 mL, 1.43 mmol) in DCM (2 mL) at 0° C. The mixture was stirred at 0° C. for 30 min. Water (10 mL) was added, the aqueous layer was extracted with EtOAc (3*10 mL). The combined organic layers were washed with brine (10 mL), dried over $Na_2SO_4$ and concentrated in vacuo. The crude material was purified by silica gel chromatography (petroleum ether/ethyl acetate from 100/0 to 50/50). The product fractions were collected and the solvent was evaporated to give intermediate 682 (180 mg, 88%) as yellow oil.

The intermediates in the Table below were prepared by using an analogous method starting from the respective starting materials.

| compound number | Structure | Mass (mg) | Yield (%) |
|---|---|---|---|
| Intermediate 683 | 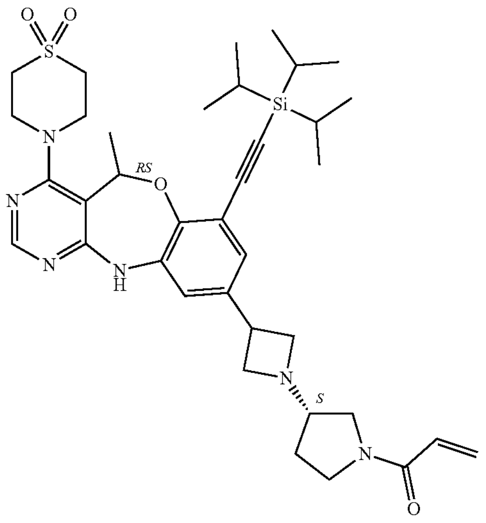 from intermediate 681 | 116 | 63 |

Example A130

Preparation of Intermediate 684

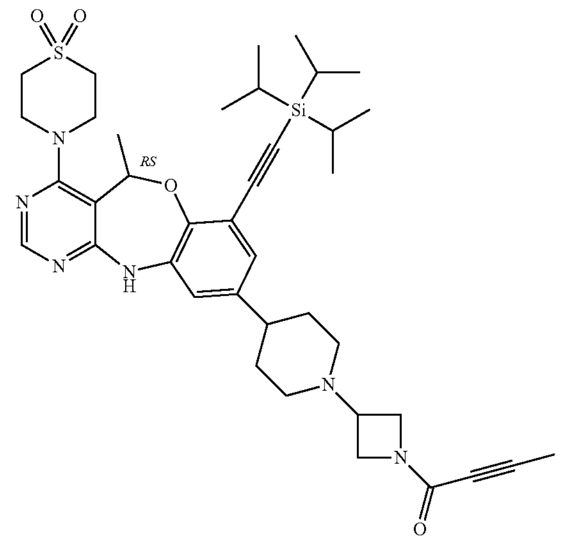

Propylphosphonic anhydride (544 mg, 0.86 mmol) was added to a solution of intermediate 680 (400 mg, 0.57 mmol), 2-butynoic acid (53 mg, 0.63 mmol) and triethylamine (159 μL, 1.14 mmol) in DMF (4 mL) at 0° C. The mixture was stirred at rt overnight. Water (10 mL) was added, the aqueous layer was extracted with EtOAc (3*10 mL). The combined organic layers were washed with brine (10 mL), dried over $Na_2SO_4$ and concentrated in vacuo. The crude material was purified by silica gel chromatography (petroleum ether/ethyl acetate from 100/0 to 50/50). The product fractions were collected and the solvent was evaporated to give intermediate 684 (120 mg, 29%).

Example A131

Preparation of Intermediate 686

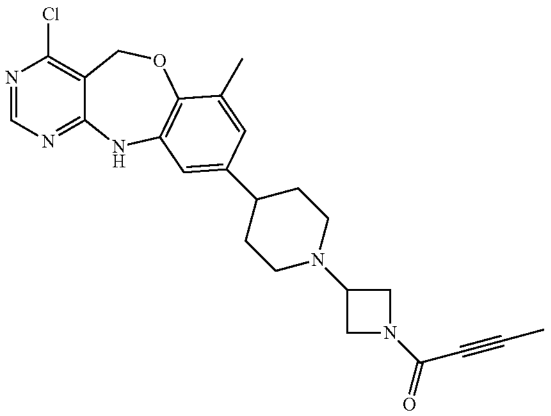 [SMILES: CC#CC(=O)N1CC(N2CCC(c3cc(C)c4c(c3)Nc3ncnc(Cl)c3CO4)CC2)C1]

DIPEA (869.8 μL, 0.76 g/mL, 5.12 mmol) was added to a suspension of butynoic acid (103.2 mg, 1.23 mmol) and O-(1H-benzotriazol-1-yl)-N,N,N',N'-tetramethyluronium hexafluorophosphate (546 mg, 1.43 mmol) in DCM (7.65 mL) at 0-5° C. under nitrogen. The reaction mixture was stirred for 10 minutes. This suspension was added to a solution of intermediate 685 (628 mg, 1.023 mmol) in DCM (22.95 mL) at 0-5° C. and the reaction mixture was stirred for 3 h at room temperature. Water, $NH_4Cl$(aq) and DCM were added. The organic layer was decanted and the solvent was evaporated until dryness. Purification was performed via preparative LC (Stationary phase: irregular SiOH 35-70 μm 40 g, Mobile phase: gradient from 100% DCM to 90% DCM, 10% MeOH, 0.1% $NH_4OH$). The pure fractions were collected and the solvent was evaporated to afford the product (230 mg; 50%).

B. Preparation of the Final Compounds

Example B1

Preparation of Compound 1

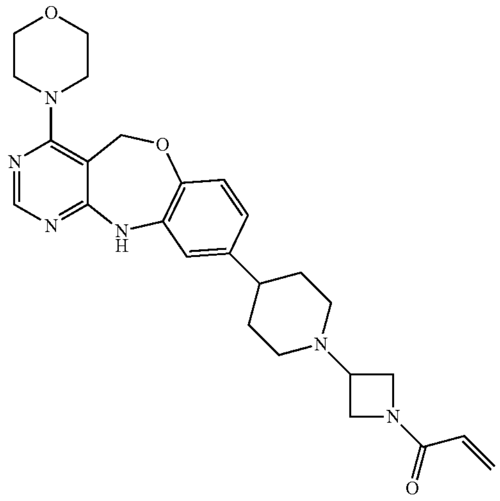 [SMILES: C=CC(=O)N1CC(N2CCC(c3ccc4c(c3)Nc3ncnc(N5CCOCC5)c3CO4)CC2)C1]

A solution of acrylic acid (162 μL; 1.05 g/mL; 2.36 mmol) in DMF (2 mL) was added dropwise to a suspension of intermediate 540 (166 mg; 0.39 mmol), EDCI·HCl (226 mg; 1.18 mmol) and $Et_3N$ (0.75 mL; 0.73 g/mL; 5.41 mmol) in DMF (5.5 mL) and the reaction mixture was stirred at room temperature for 2 h. The reaction mixture was diluted with EtOAc and poured onto water. The mixture was extracted with EtOAc (3×). The organic layer was washed with brine, dried over $MgSO_4$, filtered and the solvent was evaporated to give 152 mg of yellow oil. The oil was purified by chromatography over silica gel ($SiO_2$, Grace, 4 g; eluent: from 97% DCM, 3% MeOH to 95% DCM, 5% MeOH). The pure fractions were collected and the solvent was evaporated to give 60 mg of pale yellow oil. A further purification was performed via Reverse phase chromatography (Stationary phase: YMC-actus Triart-C18 10 m 30*150 mm, Mobile phase: Gradient from 7500 $NH_4HCO_3$ 0.2%, 25% ACN to 35% $NH_4HCO_3$ 0.2%, 65% ACN). The pure fractions were collected and the solvent was evaporated to give the product as a colourless oil (36 mg, 19%).

The compounds in the Table below were prepared by using an analogous method starting from the respective starting materials.

| compound number | Structure | Mass (mg) | Yield (%) |
|---|---|---|---|
| Compound 2 | 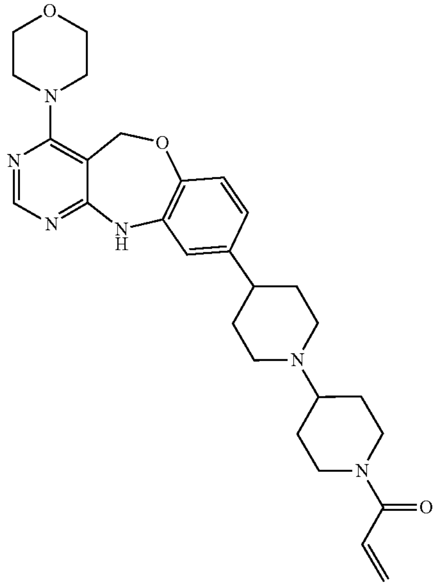 [SMILES: C=CC(=O)N1CCC(N2CCC(c3ccc4c(c3)Nc3ncnc(N5CCOCC5)c3CO4)CC2)CC1] from intermediate 541 | 40 | 25 |

-continued
| compound number | Structure | Mass (mg) | Yield (%) |
|---|---|---|---|
| Compound 3 | 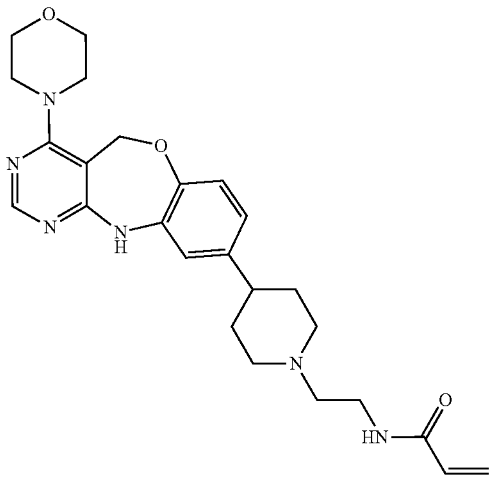 [SMILES: C=CC(=O)NCCN1CCC(c2ccc3c(c2)Nc2ncnc(N4CCOCC4)c2CO3)CC1] from intermediate 632 | 26 | 23 |
| Compound 4 | 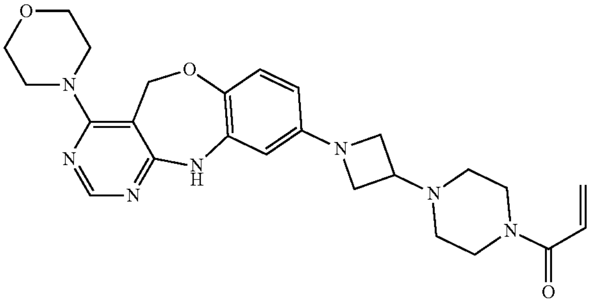 [SMILES: C=CC(=O)N1CCN(C2CN(c3ccc4c(c3)Nc3ncnc(N5CCOCC5)c3CO4)C2)CC1] from intermediate 575 | 130 | 26 |
| Compound 5 | 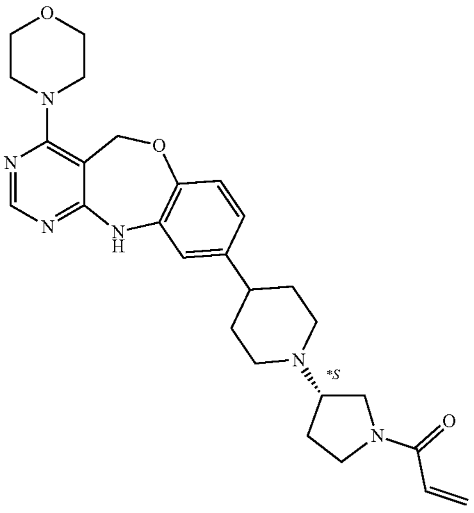 from intermediate 542 | 12 | 10 |

-continued
| compound number | Structure | Mass (mg) | Yield (%) |
|---|---|---|---|
| Compound 6 | 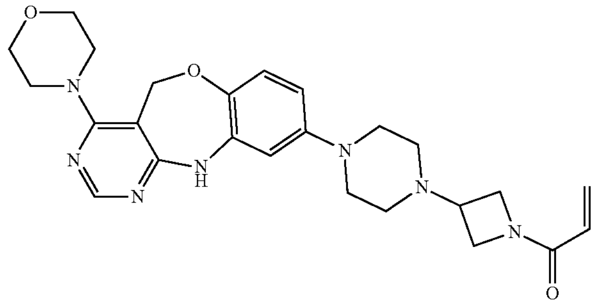 [SMILES: C=CC(=O)N1CC(N2CCN(c3ccc4c(c3)Nc3ncnc(N5CCOCC5)c3CO4)CC2)C1] from intermediate 543 | 96 | 25 |
| Compound 7 | 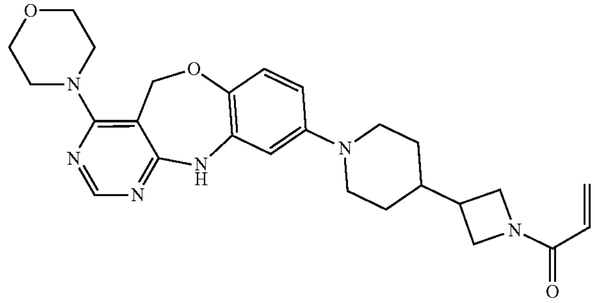 [SMILES: C=CC(=O)N1CC(C2CCN(c3ccc4c(c3)Nc3ncnc(N5CCOCC5)c3CO4)CC2)C1] from intermediate 576 | 156 | 33 |
| Compound 8 | 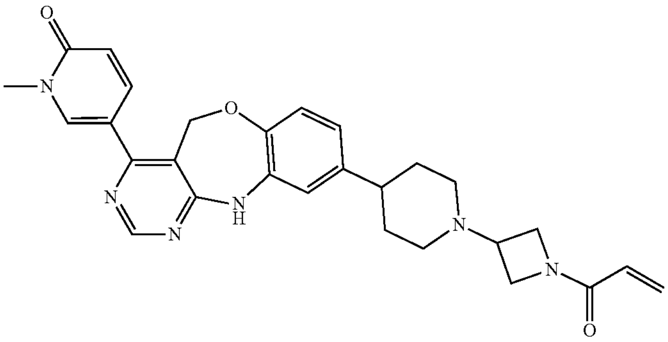 [SMILES: C=CC(=O)N1CC(N2CCC(c3ccc4c(c3)Nc3ncnc(-c5ccc(=O)n(C)c5)c3CO4)CC2)C1] from intermediate 544 | 35 | 36 |
| Compound 9 | 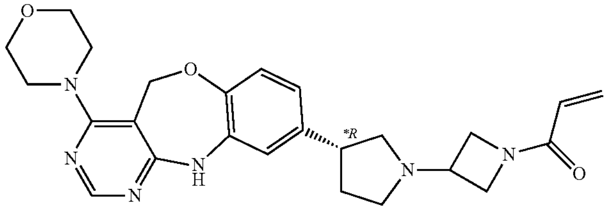 [SMILES: C=CC(=O)N1CC(N2CC[C@H](c3ccc4c(c3)Nc3ncnc(N5CCOCC5)c3CO4)C2)C1] from intermediate 545 | 92 | 30 |
| Compound 10 | 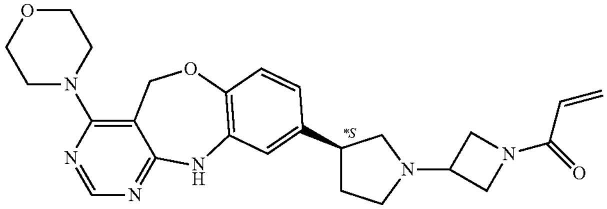 [SMILES: C=CC(=O)N1CC(N2CC[C@@H](c3ccc4c(c3)Nc3ncnc(N5CCOCC5)c3CO4)C2)C1] from intermediate 546 | 49 | 16 |

-continued
| compound number | Structure | Mass (mg) | Yield (%) |
|---|---|---|---|
| Compound 11 | 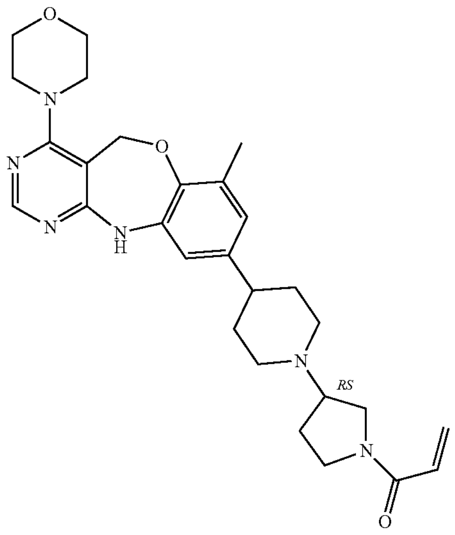 [SMILES: C=CC(=O)N1CCC(N2CCC(c3cc(C)c4c(c3)Nc3ncnc(N5CCOCC5)c3CO4)CC2)C1] from intermediate 547 | 775 | 33 |
| Compound 12 | 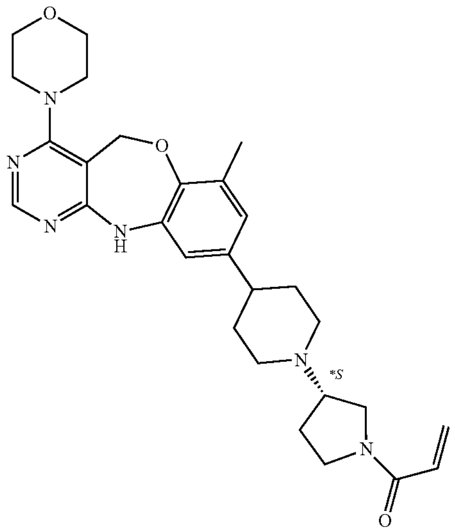 from SFC of an aliquot of compound 11, evaporation and freeze-drying pure fractions (chiral SFC (Stationary phase: Whelk-O1 (S,S) 5 µm 250 * 21.2 mm, Mobile phase: 40% CO2, 60% MeOH (0.3% TEA))) | 69 | 35 |

-continued
| compound number | Structure | Mass (mg) | Yield (%) |
|---|---|---|---|
| Compound 13 | 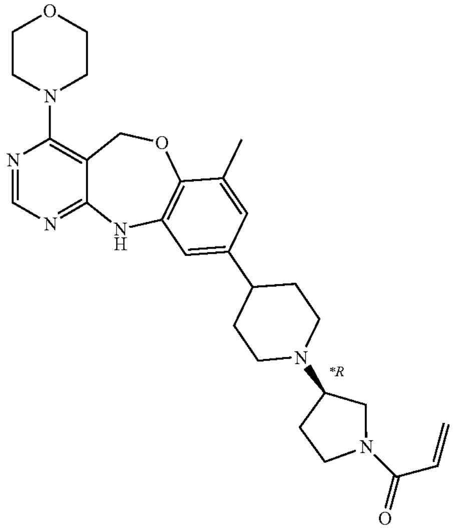 from SFC of an aliquot of compound 11, evaporation and freeze drying pure fractions (chiral SFC (Stationary phase: Whelk-O1 (S,S) 5 μm 250 * 21.2 mm, Mobile phase: 40% CO2, 60% MeOH (0.3% TEA))) | 62 | 31 |
| Compound 14 | 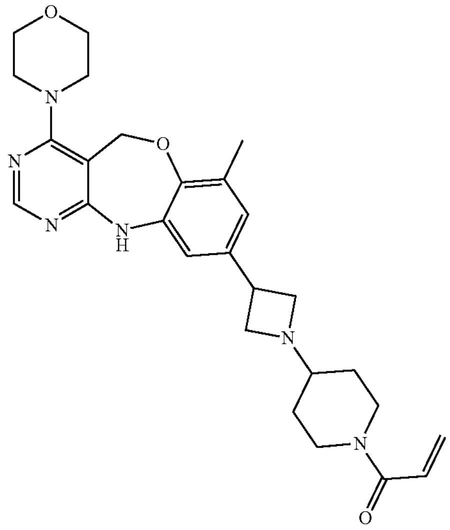 [SMILES: C=CC(=O)N1CCC(N2CC(c3cc(C)c4c(c3)Nc3ncnc(N5CCOCC5)c3CO4)C2)CC1] from intermediate 548 | 80 | 31 |
| Compound 15 | 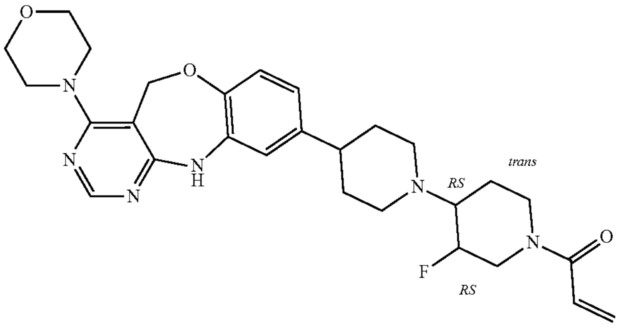 [SMILES: C=CC(=O)N1CCC(N2CCC(c3ccc4c(c3)Nc3ncnc(N5CCOCC5)c3CO4)CC2)C(F)C1] from intermediate 549 | 14 | 12 |

-continued

| compound number | Structure | Mass (mg) | Yield (%) |
|---|---|---|---|
| Compound 16 | 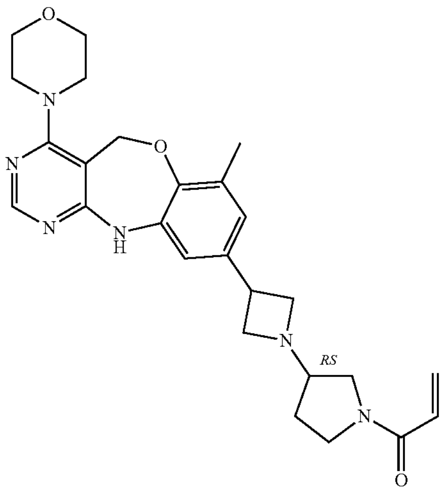 [SMILES: C=CC(=O)N1CCC(N2CC(c3cc(C)c4c(c3)Nc3ncnc(N5CCOCC5)c3CO4)C2)C1] from intermediate 550 | 102 | 34 |
| Compound 17 | 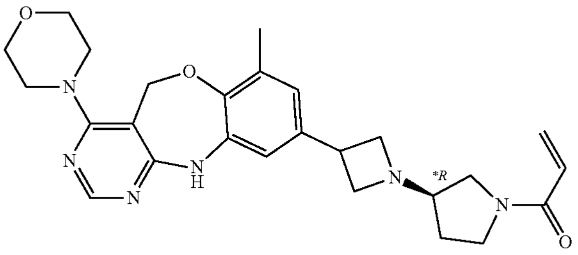 [SMILES: C=CC(=O)N1CC[C@@H](N2CC(c3cc(C)c4c(c3)Nc3ncnc(N5CCOCC5)c3CO4)C2)C1] from SFC of an aliquot of compound 16, evaporation and freeze drying pure fractions (chiral SFC (Stationary phase: Whelk-O1 (S,S) 5 µm 250 * 21.2 mm, Mobile phase: 55% CO2, 45% [MeOH + 10% DCM + (0.6% TEA)])) | 86 | 41 |
| Compound 18 | 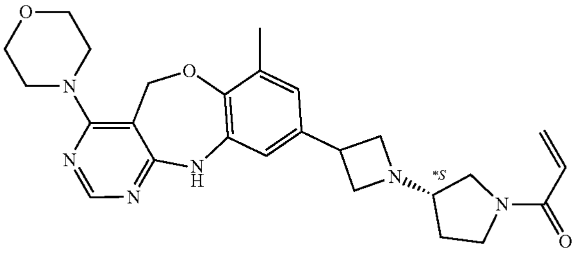 [SMILES: C=CC(=O)N1CC[C@H](N2CC(c3cc(C)c4c(c3)Nc3ncnc(N5CCOCC5)c3CO4)C2)C1] from SFC of an aliquot of compound 16, evaporation and freeze drying pure fractions (chiral SFC (Stationary phase: Whelk-O1 (S,S) 5 µm 250 * 21.2 mm, Mobile phase: 55% CO2, 45% [MeOH + 10% DCM + (0.6% TEA)])) | 95 | 45 |

-continued
| compound number | Structure | Mass (mg) | Yield (%) |
|---|---|---|---|
| Compound 19 | 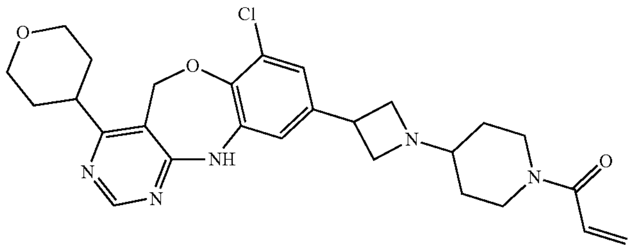 from intermediate 551 | 73 | 14 |
| Compound 20 | 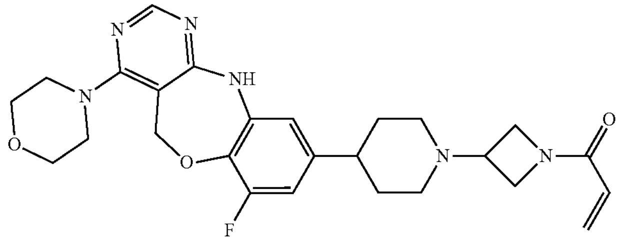 [SMILES: C=CC(=O)N1CC(N2CCC(c3cc(F)c4c(c3)Nc3ncnc(N5CCOCC5)c3CO4)CC2)C1] from intermediate 552 | 43 | 13 |
| Compound 21 | 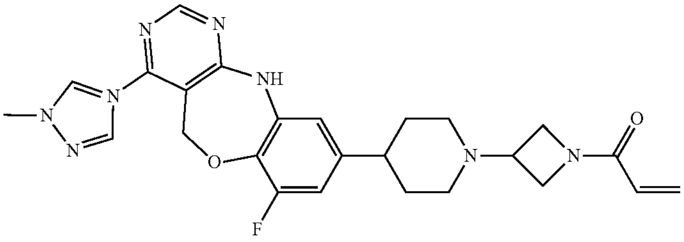 from intermediate 553 | 16 | 5 |
| Compound 22 | 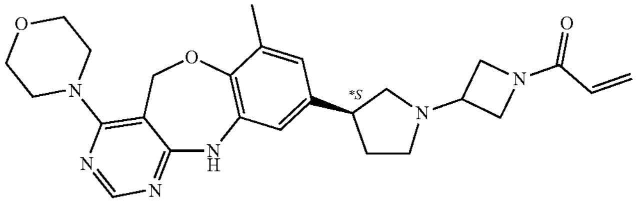 [SMILES: C=CC(=O)N1CC(N2CC[C@@H](c3cc(C)c4c(c3)Nc3ncnc(N5CCOCC5)c3CO4)C2)C1] from intermediate 554 | 32 | 10 |
| Compound 23 | 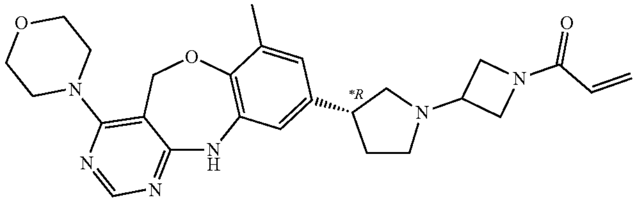 [SMILES: C=CC(=O)N1CC(N2CC[C@H](c3cc(C)c4c(c3)Nc3ncnc(N5CCOCC5)c3CO4)C2)C1] from intermediate 555 | 42 | 14 |

-continued
| compound number | Structure | Mass (mg) | Yield (%) |
|---|---|---|---|
| Compound 24 | 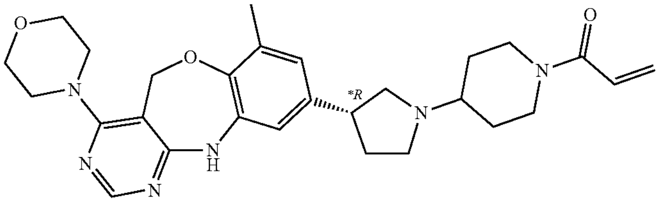 [SMILES: C=CC(=O)N1CCC(N2CC[C@H](c3cc(C)c4c(c3)Nc3ncnc(N5CCOCC5)c3CO4)C2)CC1] from intermediate 556 | 98 | 28 |
| Compound 25 | 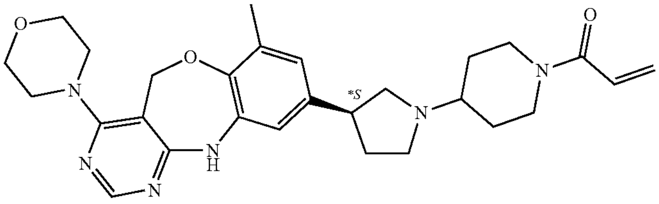 [SMILES: C=CC(=O)N1CCC(N2CC[C@@H](c3cc(C)c4c(c3)Nc3ncnc(N5CCOCC5)c3CO4)C2)CC1] from intermediate 557 | 85 | 22 |
| Compound 26 | 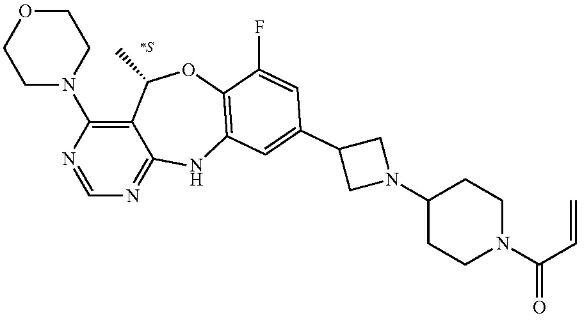 [SMILES: C=CC(=O)N1CCC(N2CC(c3cc(F)c4c(c3)Nc3ncnc(N5CCOCC5)c3[C@H](C)O4)C2)CC1] from intermediate 558 | 66 | 19 |
| Compound 27 | 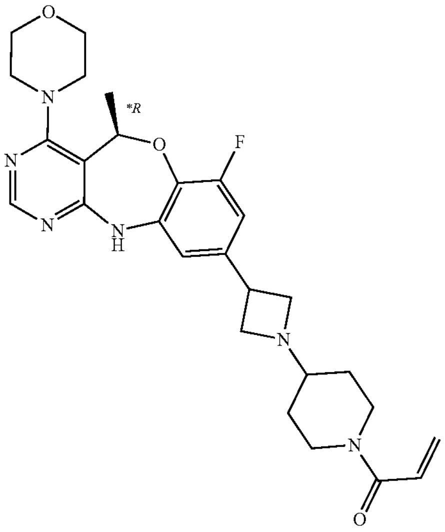 [SMILES: C=CC(=O)N1CCC(N2CC(c3cc(F)c4c(c3)Nc3ncnc(N5CCOCC5)c3[C@@H](C)O4)C2)CC1] from intermediate 559 | 43 | 13 |

-continued
| compound number | Structure | Mass (mg) | Yield (%) |
| --- | --- | --- | --- |
| Compound 28 | 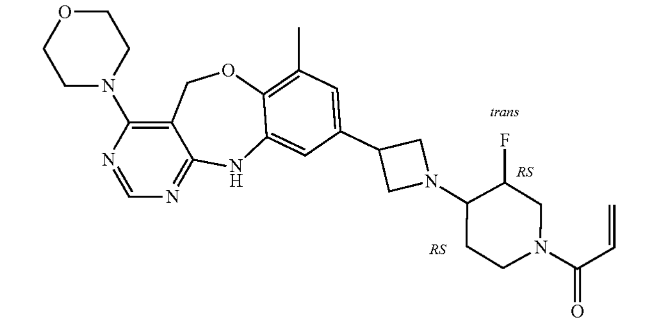 [SMILES: C=CC(=O)N1CCC(N2CC(c3cc(C)c4c(c3)Nc3ncnc(N5CCOCC5)c3CO4)C2)C(F)C1] from intermediate 560 | 15 | 15 |
| Compound 29 | 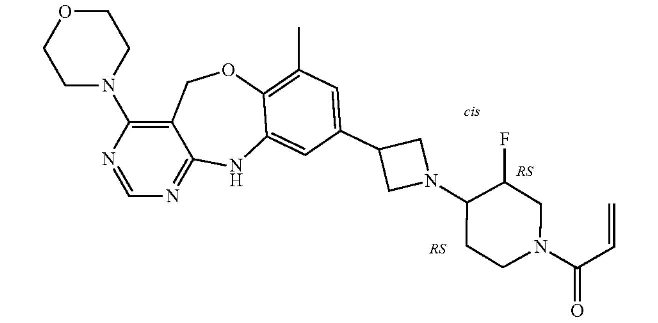 [SMILES: C=CC(=O)N1CCC(N2CC(c3cc(C)c4c(c3)Nc3ncnc(N5CCOCC5)c3CO4)C2)C(F)C1] from intermediate 561 | 75 | 23 |
| Compound 30 | 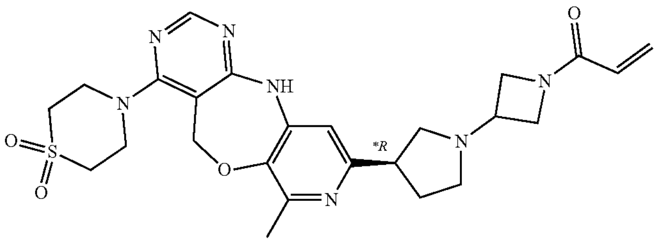 [SMILES: C=CC(=O)N1CC(N2CC[C@@H](c3cc4c(c(C)n3)OCc3c(ncnc3N3CCS(=O)(=O)CC3)N4)C2)C1] from intermediate 562; chiral separation was via SFC (Stationary phase: CHIRALPAK AD-H 5 μm 250 * 30 mm, Mobile phase: 50% CO2, 50% EtOH (1.2% TEA)) | 20 | 8 |
| Compound 31 | 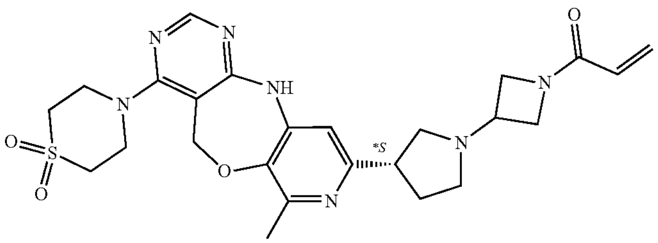 [SMILES: C=CC(=O)N1CC(N2CC[C@H](c3cc4c(c(C)n3)OCc3c(ncnc3N3CCS(=O)(=O)CC3)N4)C2)C1] from intermediate 562; chiral separation was via SFC (Stationary phase: CHIRALPAK AD-H 5 μm 250 * 30 mm, Mobile phase: 50% CO2, 50% EtOH (1.2% TEA)) | 20 | 8 |

Example B2

Preparation of Compound 32

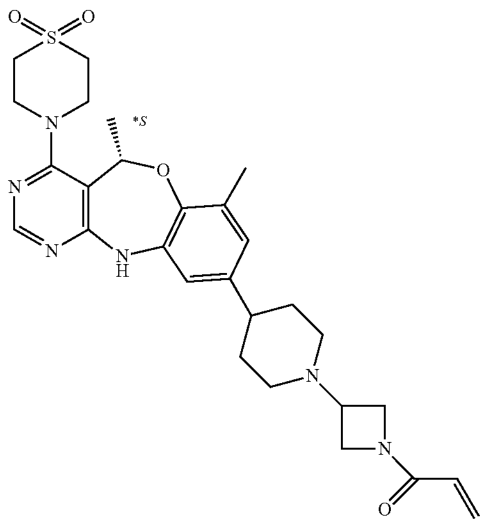

Triethylamine (494.1 μL; 0.726 g/mL; 3.545 mmol) was added to a solution of intermediate 614a (353.54 mg; 0.709 mmol) in DCM (10 mL). The mixture was cooled in an ice bath. Then acryloyl chloride (57.6 μL; 1.114 g/mL; 0.709 mmol) in DCM (2 mL) was added dropwise to the mixture and stirred at room temperature for 3 hours. The reaction mixture was quenched by addition of sat. $NaHCO_3$(aq) and extracted with $CH_2Cl_2$. The organic layer was concentrated under vacuum to leave 368 mg of crude residue, which was purified by reverse phase chromatography to afford the product as a white solid (193 mg; 49%).

The compounds in the Table below were prepared by using an analogous method starting from the respective starting materials.

| compound number | Structure | Mass (mg) | Yield (%) |
|---|---|---|---|
| Compound 33 | 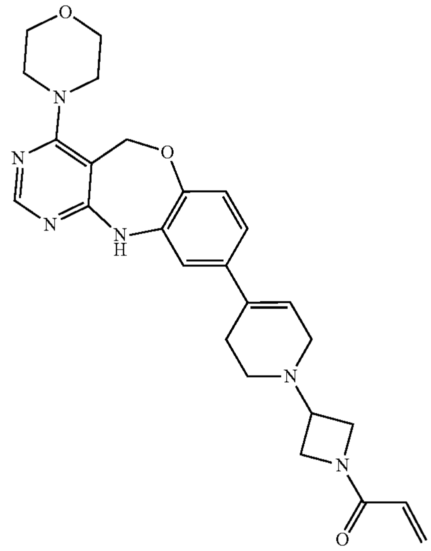 [SMILES: C=CC(=O)N1CC(N2CC=C(c3ccc4c(c3)Nc3ncnc(N5CCOCC5)c3CO4)CC2)C1] from intermediate 633 and Acryloyl chloride | 88 | 43 |

-continued
| compound number | Structure | Mass (mg) | Yield (%) |
|---|---|---|---|
| Compound 34 | 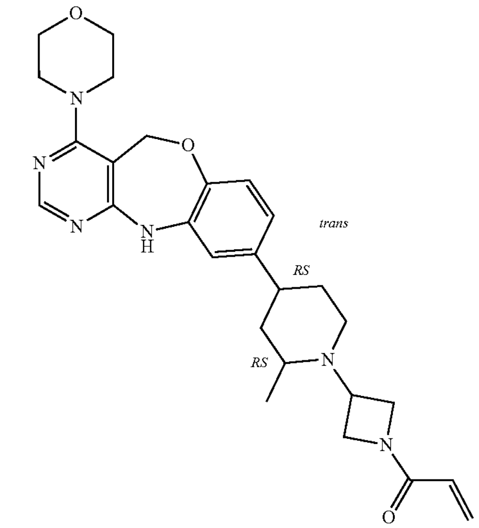 [SMILES: C=CC(=O)N1CC(N2CCC(c3ccc4c(c3)Nc3ncnc(N5CCOCC5)c3CO4)CC2C)C1]<br>from intermediate 577 and Acryloyl chloride | 28 | 35 |
| Compound 35 | 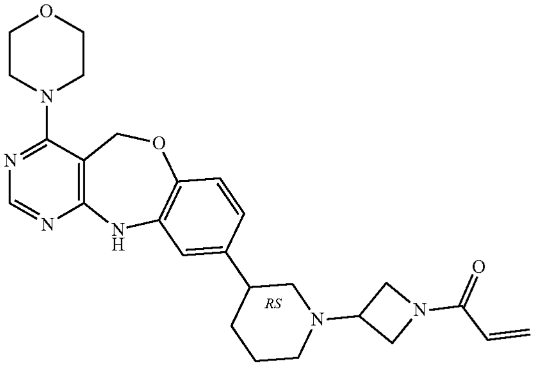 [SMILES: C=CC(=O)N1CC(N2CCCC(c3ccc4c(c3)Nc3ncnc(N5CCOCC5)c3CO4)C2)C1]<br>from intermediate 578 and Acryloyl chloride | 112 | 41 |
| Compound 36 | 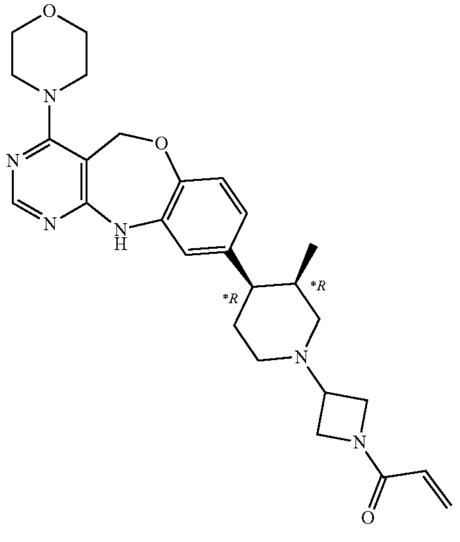<br>from intermediate 579 and Acryloyl chloride | 31 | 73 |

-continued
| compound number | Structure | Mass (mg) | Yield (%) |
|---|---|---|---|
| Compound 37 | 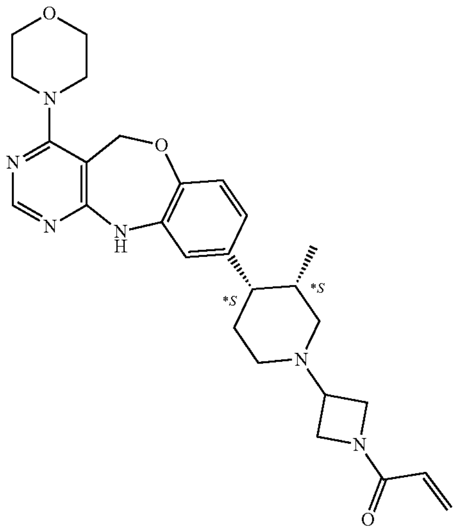 from intermediate 580 and Acryloyl chloride | 23 | 29 |
| Compound 38 | 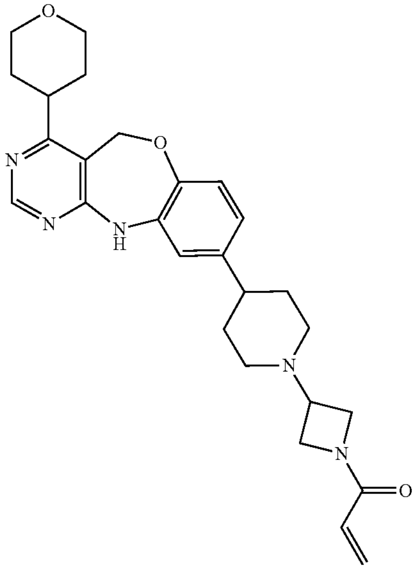 [SMILES: C=CC(=O)N1CC(N2CCC(c3ccc4c(c3)Nc3ncnc(C5CCOCC5)c3CO4)CC2)C1] from intermediate 581 and Acryloyl chloride | 106 | 47 |

-continued
| compound number | Structure | Mass (mg) | Yield (%) |
|---|---|---|---|
| Compound 39 | 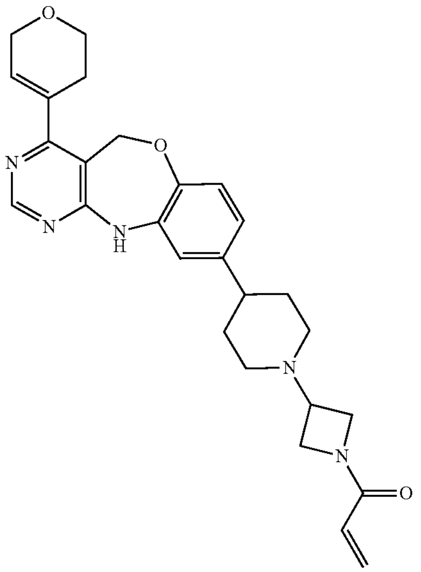 [SMILES: C=CC(=O)N1CC(N2CCC(c3ccc4c(c3)Nc3ncnc(C5=CCOCC5)c3CO4)CC2)C1] from intermediate 582 and Acryloyl chloride | 36 | 32 |
| Compound 40 | 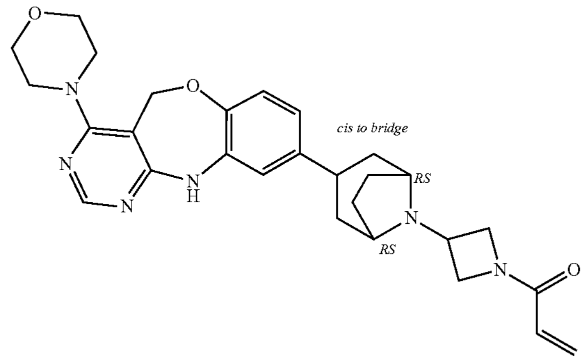 [SMILES: C=CC(=O)N1CC(N2C3CCC2CC(c2ccc4c(c2)Nc2ncnc(N5CCOCC5)c2CO4)C3)C1] from intermediate 583 and Acryloyl chloride | 17 | 29 |
| Compound 41 | 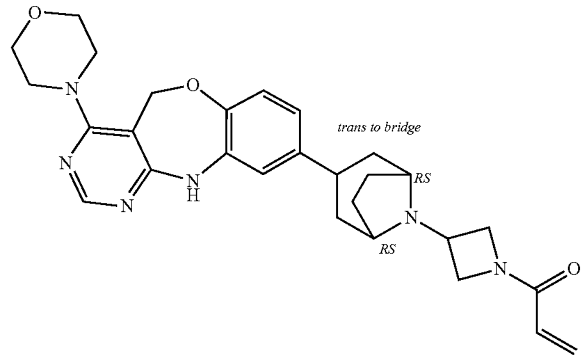 [SMILES: C=CC(=O)N1CC(N2C3CCC2CC(c2ccc4c(c2)Nc2ncnc(N5CCOCC5)c2CO4)C3)C1] from intermediate 584 and Acryloyl chloride | 46 | 40 |

-continued
| compound number | Structure | Mass (mg) | Yield (%) |
|---|---|---|---|
| Compound 42 | 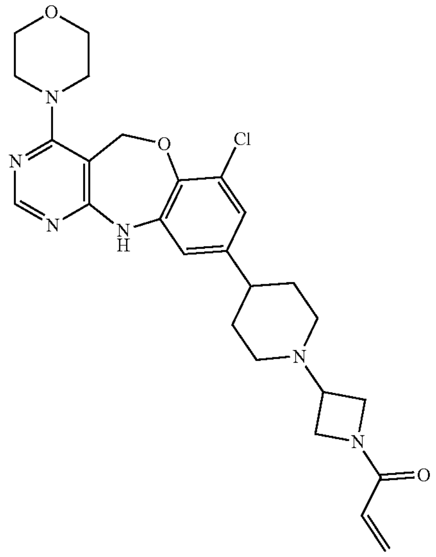 [SMILES: C=CC(=O)N1CC(N2CCC(c3cc(Cl)c4c(c3)Nc3ncnc(N5CCOCC5)c3CO4)CC2)C1] from intermediate 585 and Acryloyl chloride | 460 | 44 |
| Compound 43 | 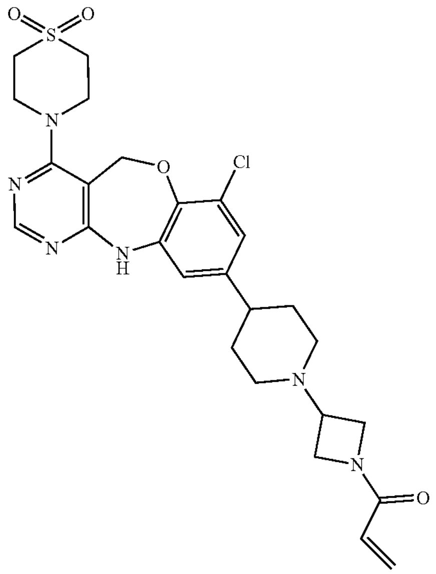 [SMILES: C=CC(=O)N1CC(N2CCC(c3cc(Cl)c4c(c3)Nc3ncnc(N5CCS(=O)(=O)CC5)c3CO4)CC2)C1] from intermediate 586 and Acryloyl chloride | 385 | 40 |

-continued
| compound number | Structure | Mass (mg) | Yield (%) |
|---|---|---|---|
| Compound 44 | 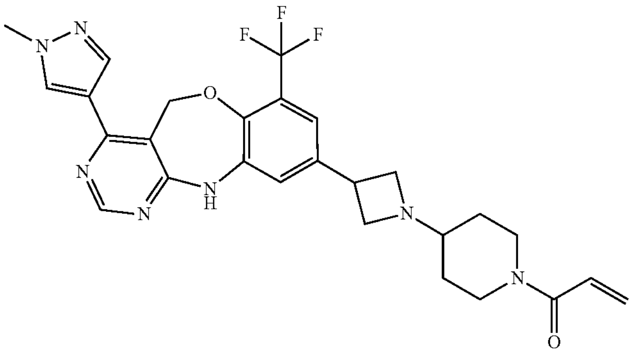 [SMILES: C=CC(=O)N1CCC(N2CC(c3cc4c(c(C(F)(F)F)c3)OCc3c(ncnc3-c3cnn(C)c3)N4)C2)CC1] from intermediate 587 and Acryloyl chloride | 40 | 28 |
| Compound 45 | 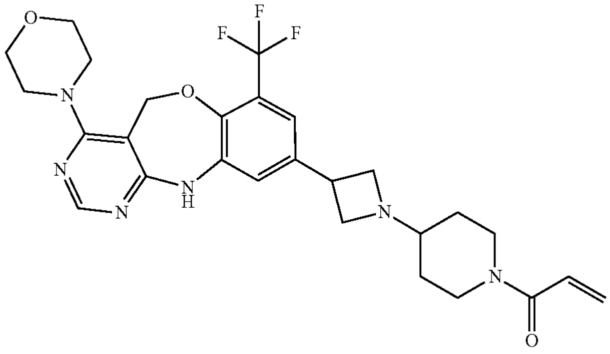 [SMILES: C=CC(=O)N1CCC(N2CC(c3cc4c(c(C(F)(F)F)c3)OCc3c(ncnc3N3CCOCC3)N4)C2)CC1] from intermediate 588 and Acryloyl chloride | 87 | 44 |
| Compound 46 | 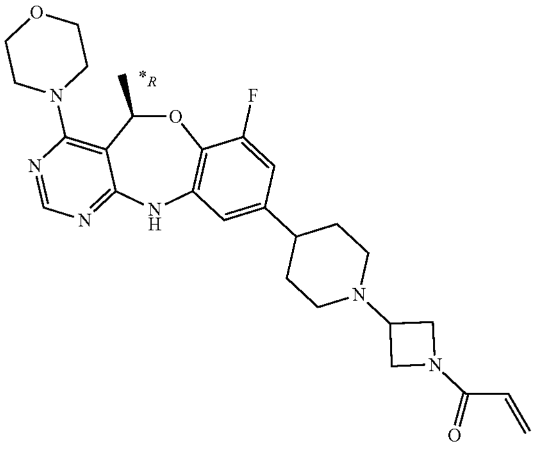 [SMILES: C=CC(=O)N1CC(N2CCC(c3cc(F)c4c(c3)Nc3ncnc(N5CCOCC5)c3[C@@H](C)O4)CC2)C1] from intermediate 589 and Acryloyl chloride | 73 | 37 |

-continued
| compound number | Structure | Mass (mg) | Yield (%) |
|---|---|---|---|
| Compound 47 | 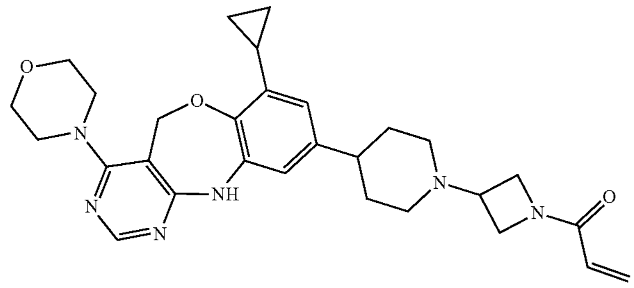 [SMILES: C=CC(=O)N1CC(N2CCC(c3cc4c(c(C5CC5)c3)OCc3c(ncnc3N3CCOCC3)N4)CC2)C1] from intermediate 590 and Acryloyl chloride | 167 | 51 |
| Compound 48 | 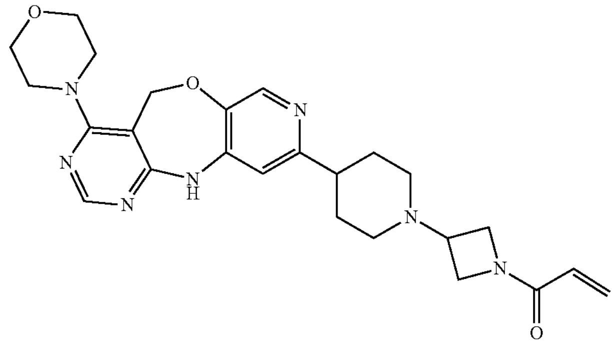 [SMILES: C=CC(=O)N1CC(N2CCC(c3cc4c(cn3)OCc3c(ncnc3N3CCOCC3)N4)CC2)C1] from intermediate 591 and Acryloyl chloride | 145 | 45 |
| Compound 49 | 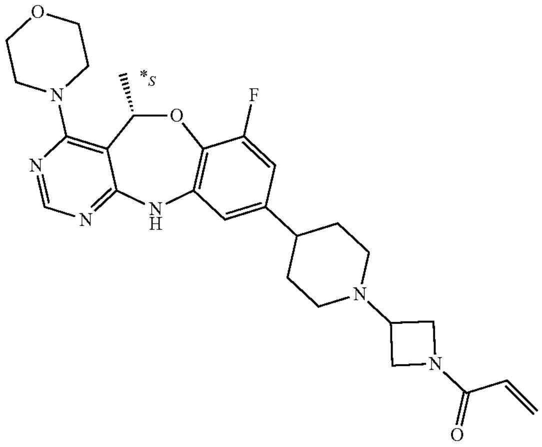 [SMILES: C=CC(=O)N1CC(N2CCC(c3cc(F)c4c(c3)Nc3ncnc(N5CCOCC5)c3[C@H](C)O4)CC2)C1] from intermediate 592 and Acryloyl chloride | 78 | 45 |

-continued

| compound number | Structure | Mass (mg) | Yield (%) |
|---|---|---|---|
| Compound 50 | 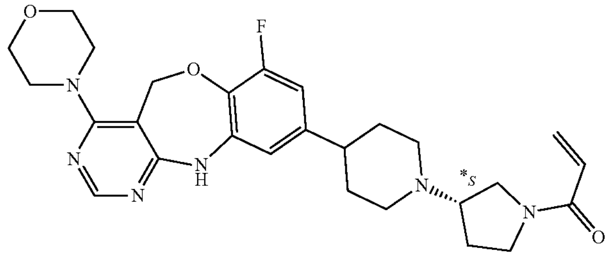 [SMILES: C=CC(=O)N1CC[C@H](N2CCC(c3cc(F)c4c(c3)Nc3ncnc(N5CCOCC5)c3CO4)CC2)C1] from intermediate 563 and Acryloyl chloride followed by SFC separation (Stationary phase: Whelk-O1 (S,S) 5 μm 250*21.2 mm, Mobile phase: 40% $CO_2$, 60% (mixture of MeOH/iPrOH 50/50 v/v(+0.3% TEA) + 10% DCM) | 226 | 26 |
| Compound 51 | 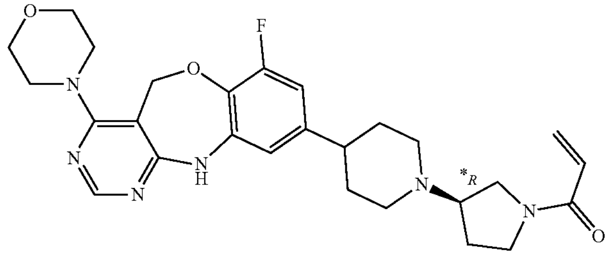 [SMILES: C=CC(=O)N1CC[C@@H](N2CCC(c3cc(F)c4c(c3)Nc3ncnc(N5CCOCC5)c3CO4)CC2)C1] from intermediate 563 and Acryloyl chloride followed by SFC separation (Stationary phase: Whelk-O1 (S,S) 5 μm 250*21.2 mm, Mobile phase: 40% $CO_2$, 60% (mixture of MeOH/iPrOH 50/50 v/v(+0.3% TEA) + 10% DCM) | 225 | 26 |
| Compound 52 | 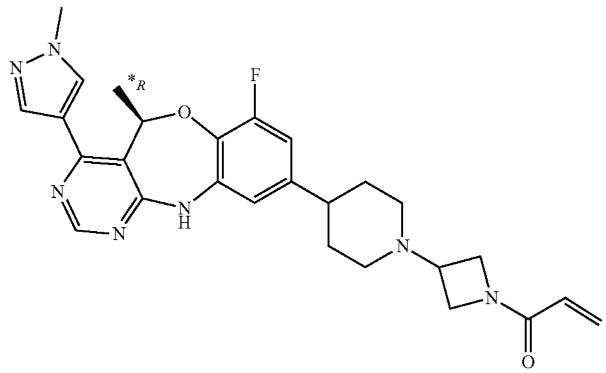 [SMILES: C=CC(=O)N1CC(N2CCC(c3cc(F)c4c(c3)Nc3ncnc(-c5cnn(C)c5)c3[C@@H](C)O4)CC2)C1] from intermediate 593 and Acryloyl chloride | 45 | 25 |

-continued

| compound number | Structure | Mass (mg) | Yield (%) |
|---|---|---|---|
| Compound 53 | 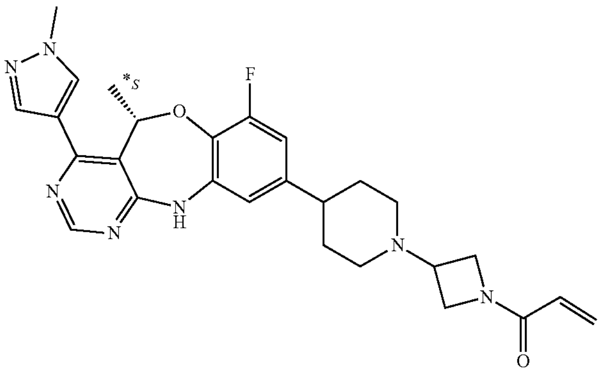 [SMILES: C=CC(=O)N1CC(N2CCC(c3cc(F)c4c(c3)Nc3ncnc(-c5cnn(C)c5)c3[C@H](C)O4)CC2)C1] from intermediate 594 and Acryloyl chloride | 60 | 33 |
| Compound 54 | 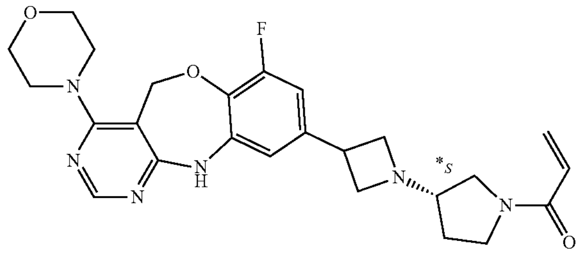 [SMILES: C=CC(=O)N1CC[C@H](N2CC(c3cc(F)c4c(c3)Nc3ncnc(N5CCOCC5)c3CO4)C2)C1] from intermediate 564 and Acryloyl chloride followed by SFC separation (Stationary phase: Whelk-O1 (S,S) 5 μm 250*21.2 mm, Mobile phase: 50% $CO_2$, 50% (MeOH + 10% DCM(0.6% TEA))) | 198 | 21 |
| Compound 55 | 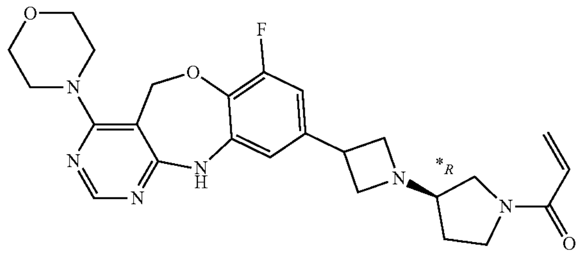 [SMILES: C=CC(=O)N1CC[C@@H](N2CC(c3cc(F)c4c(c3)Nc3ncnc(N5CCOCC5)c3CO4)C2)C1] from intermediate 564 and Acryloyl chloride followed by SFC separation (Stationary phase: Whelk-O1 (S,S) 5 μm 250*21.2 mm, Mobile phase: 50% $CO_2$, 50% (MeOH + 10% DCM(0.6% TEA))) | 184 | 19 |

-continued

| compound number | Structure | Mass (mg) | Yield (%) |
|---|---|---|---|
| Compound 56 | 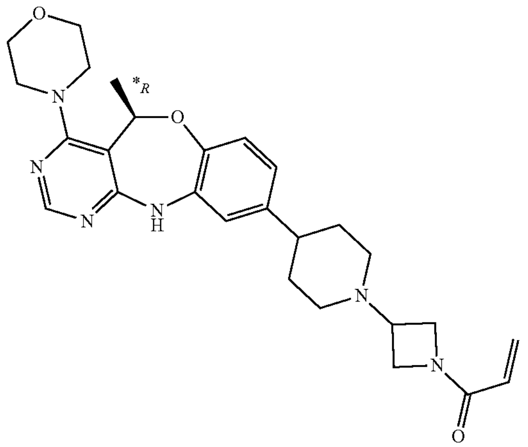 [SMILES: C=CC(=O)N1CC(N2CCC(c3ccc4c(c3)Nc3ncnc(N5CCOCC5)c3[C@@H](C)O4)CC2)C1] from intermediate 595 and Acryloyl chloride followed by SFC separation (Stationary phase: CHIRALPAK IC 5 μm 250*30 mm, Mobile phase: 45% $CO_2$, 55%(EtOH + 10% DCM) + (0.6% TEA)) | 109 | 18 |
| Compound 57 | 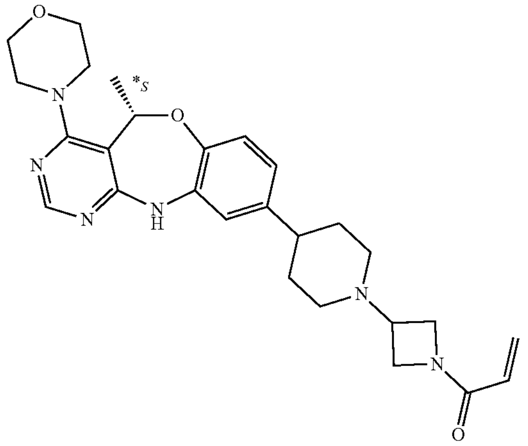 [SMILES: C=CC(=O)N1CC(N2CCC(c3ccc4c(c3)Nc3ncnc(N5CCOCC5)c3[C@H](C)O4)CC2)C1] from intermediate 595 and Acryloyl chloride followed by SFC separation (Stationary phase: CHIRALPAK IC 5 μm 250*30 mm, Mobile phase: 45% $CO_2$, 55%(EtOH + 10% DCM) + (0.6% TEA)) | 116 | 19 |
| Compound 58 | 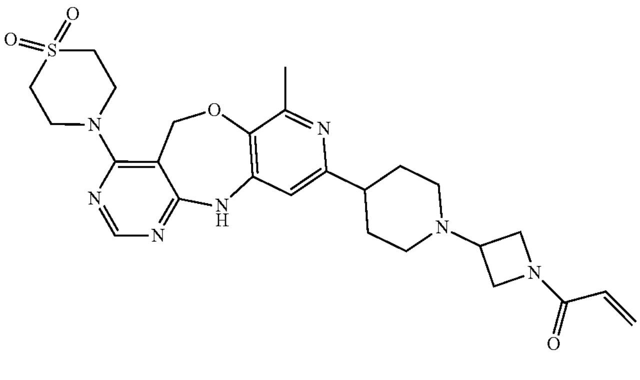 [SMILES: C=CC(=O)N1CC(N2CCC(c3cc4c(c(C)n3)OCc3c(ncnc3N3CCS(=O)(=O)CC3)N4)CC2)C1] from intermediate 596 and Acryloyl chloride | 133 | 51 |

-continued
| compound number | Structure | Mass (mg) | Yield (%) |
|---|---|---|---|
| Compound 59 | 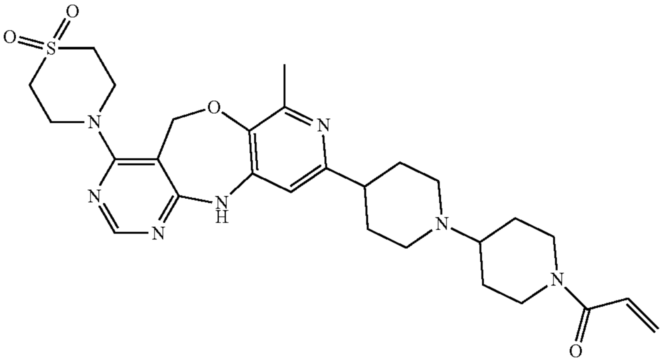 [SMILES: C=CC(=O)N1CCC(N2CCC(c3cc4c(c(C)n3)OCc3c(ncnc3N3CCS(=O)(=O)CC3)N4)CC2)CC1] from intermediate 597 and Acryloyl chloride | 31 | 24 |
| Compound 60 | 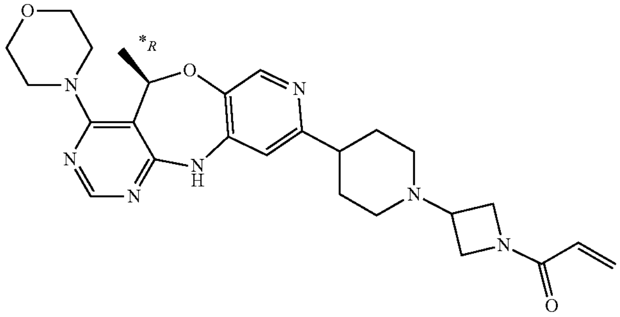 [SMILES: C=CC(=O)N1CC(N2CCC(c3cc4c(cn3)O[C@H](C)c3c(ncnc3N3CCOCC3)N4)CC2)C1] from intermediate 598 and Acryloyl chloride | 23 | 26 |
| Compound 61 | 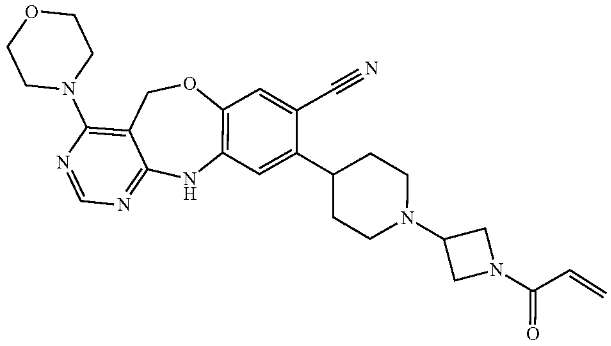 [SMILES: C=CC(=O)N1CC(N2CCC(c3cc4c(cc3C#N)OCc3c(ncnc3N3CCOCC3)N4)CC2)C1] from intermediate 599 and Acryloyl chloride | 71 | 33 |
| Compound 62 | 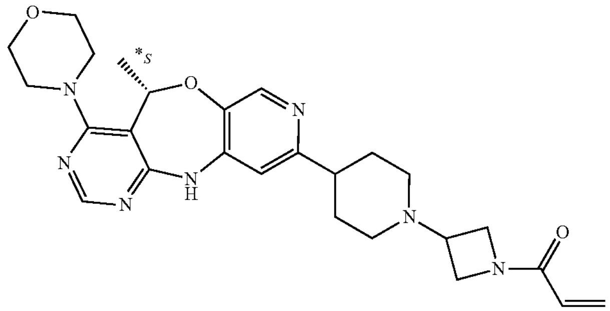 [SMILES: C=CC(=O)N1CC(N2CCC(c3cc4c(cn3)O[C@@H](C)c3c(ncnc3N3CCOCC3)N4)CC2)C1] from intermediate 600 and Acryloyl chloride | 49 | 58 |

-continued
| compound number | Structure | Mass (mg) | Yield (%) |
|---|---|---|---|
| Compound 63 | 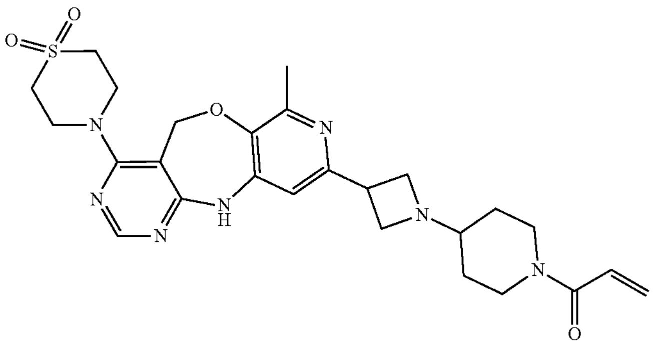 [SMILES: C=CC(=O)N1CCC(N2CC(c3cc4c(c(C)n3)OCc3c(ncnc3N3CCS(=O)(=O)CC3)N4)C2)CC1] from intermediate 601 and Acryloyl chloride | 77 | 45 |
| Compound 64 | 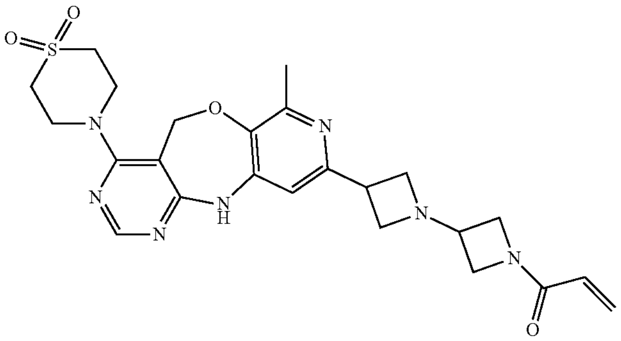 [SMILES: C=CC(=O)N1CC(N2CC(c3cc4c(c(C)n3)OCc3c(ncnc3N3CCS(=O)(=O)CC3)N4)C2)C1] from intermediate 602 and Acryloyl chloride | 27 | 54 |
| Compound 65 | 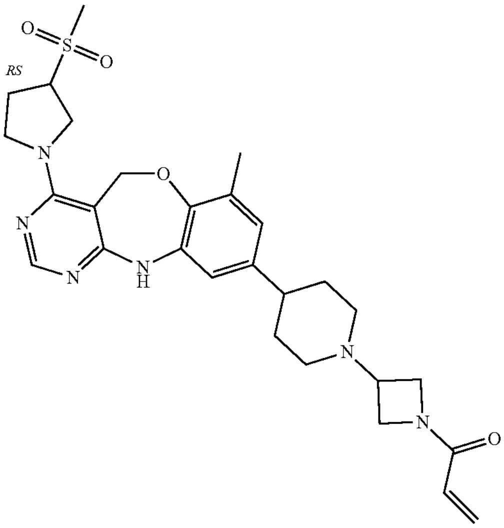 [SMILES: C=CC(=O)N1CC(N2CCC(c3cc(C)c4c(c3)Nc3ncnc(N5CCC(S(C)(=O)=O)C5)c3CO4)CC2)C1] from intermediate 603 and Acryloyl chloride | 91 | 34 |

-continued
| compound number | Structure | Mass (mg) | Yield (%) |
|---|---|---|---|
| Compound 66 | 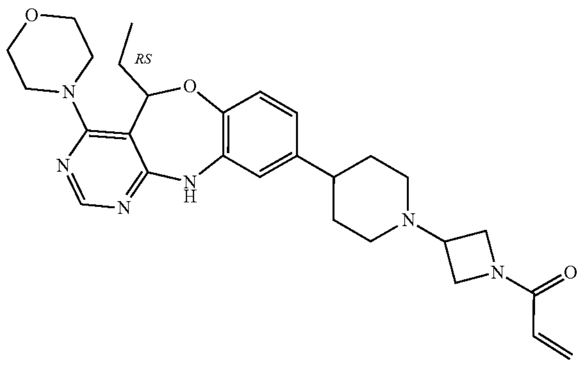 [SMILES: C=CC(=O)N1CC(N2CCC(c3ccc4c(c3)Nc3ncnc(N5CCOCC5)c3C(CC)O4)CC2)C1] from intermediate 604 and Acryloyl chloride | 161 | 29 |
| Compound 67 | 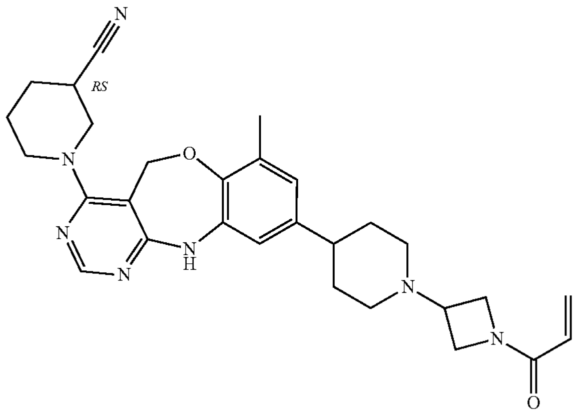 [SMILES: C=CC(=O)N1CC(N2CCC(c3cc(C)c4c(c3)Nc3ncnc(N5CCCC(C#N)C5)c3CO4)CC2)C1] from intermediate 605 and Acryloyl chloride | 86 | 50 |
| Compound 68 | 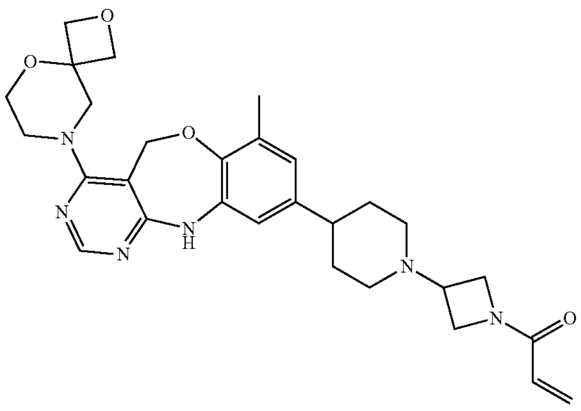 [SMILES: C=CC(=O)N1CC(N2CCC(c3cc(C)c4c(c3)Nc3ncnc(N5CCOC6(COC6)C5)c3CO4)CC2)C1] from intermediate 606 and Acryloyl chloride | 24 | 8 |

-continued
| compound number | Structure | Mass (mg) | Yield (%) |
|---|---|---|---|
| Compound 69 | 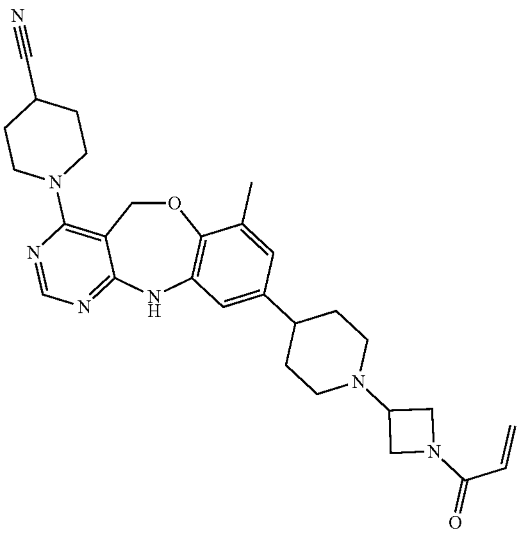 [SMILES: C=CC(=O)N1CC(N2CCC(c3cc(C)c4c(c3)Nc3ncnc(N5CCC(C#N)CC5)c3CO4)CC2)C1] from intermediate 607 and Acryloyl chloride | 88 | 36 |
| Compound 70 | 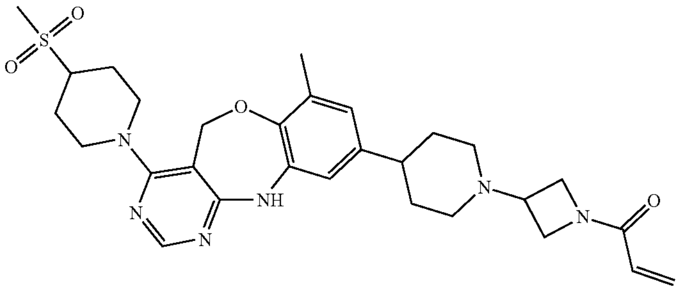 [SMILES: C=CC(=O)N1CC(N2CCC(c3cc(C)c4c(c3)Nc3ncnc(N5CCC(S(C)(=O)=O)CC5)c3CO4)CC2)C1] from intermediate 608 and Acryloyl chloride | 93 | 46 |
| Compound 71 | 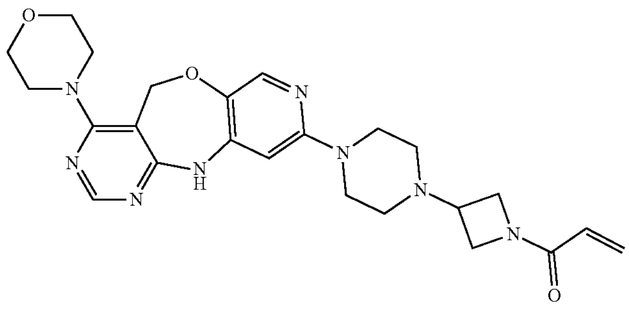 [SMILES: C=CC(=O)N1CC(N2CCN(c3cc4c(cn3)OCc3c(ncnc3N3CCOCC3)N4)CC2)C1] from intermediate 609 and Acryloyl chloride | 297 | 77 |

-continued
| compound number | Structure | Mass (mg) | Yield (%) |
|---|---|---|---|
| Compound 72 | 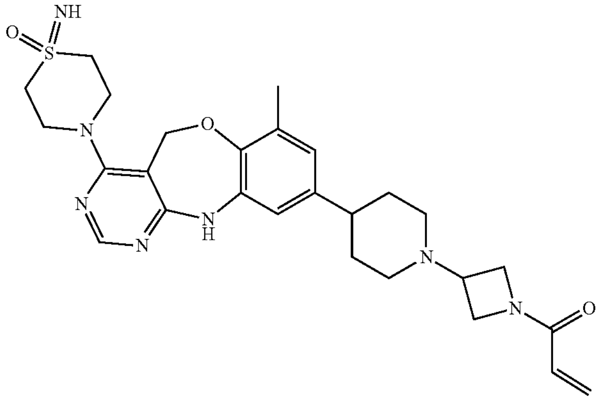 [SMILES: C=CC(=O)N1CC(N2CCC(c3cc(C)c4c(c3)Nc3ncnc(N5CCS(=N)(=O)CC5)c3CO4)CC2)C1] from intermediate 610 and Acryloyl chloride; with concomitant loss of trifluoroaetate moiety | 25 | 17 |
| Compound 73 | 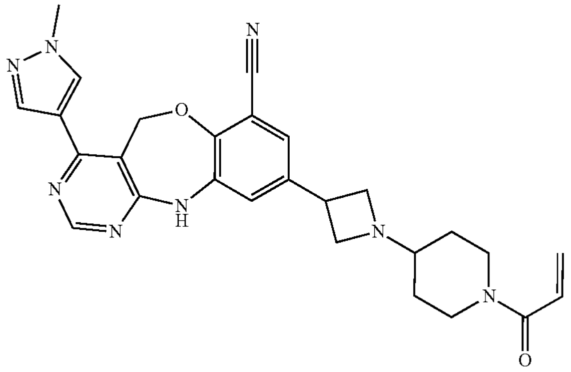 [SMILES: C=CC(=O)N1CCC(N2CC(c3cc(C#N)c4c(c3)Nc3ncnc(-c5cnn(C)c5)c3CO4)C2)CC1] from intermediate 565 and Acryloyl chloride | 99 | 51 |
| Compound 74 | 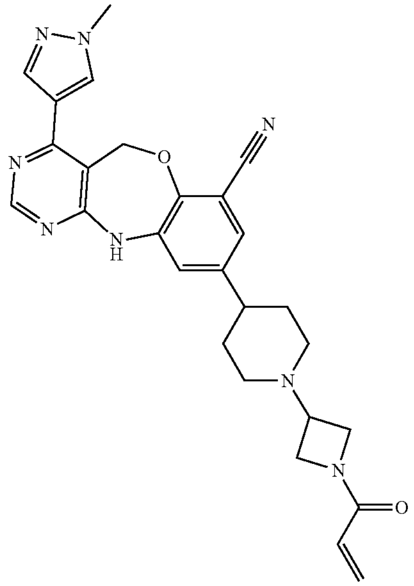 [SMILES: C=CC(=O)N1CC(N2CCC(c3cc(C#N)c4c(c3)Nc3ncnc(-c5cnn(C)c5)c3CO4)CC2)C1] from intermediate 566 and Acryloyl chloride | 61 | 21 |

-continued
| compound number | Structure | Mass (mg) | Yield (%) |
|---|---|---|---|
| Compound 75 | 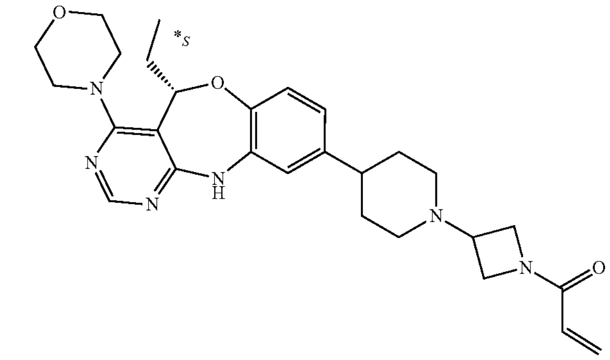 [SMILES: C=CC(=O)N1CC(N2CCC(c3ccc4c(c3)Nc3ncnc(N5CCOCC5)c3[C@H](CC)O4)CC2)C1] from intermediate 611 and Acryloyl chloride | 180 | 50 |
| Compound 76 | 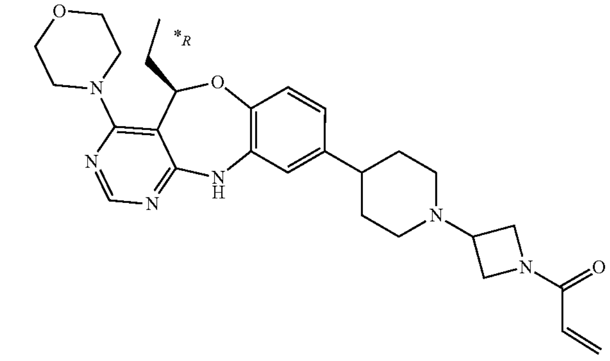 [SMILES: C=CC(=O)N1CC(N2CCC(c3ccc4c(c3)Nc3ncnc(N5CCOCC5)c3[C@@H](CC)O4)CC2)C1] from intermediate 612 and Acryloyl chloride | 143 | 35 |
| Compound 77 | 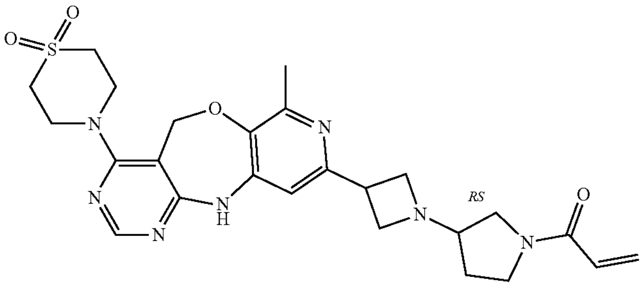 [SMILES: C=CC(=O)N1CCC(N2CC(c3cc4c(c(C)n3)OCc3c(ncnc3N3CCS(=O)(=O)CC3)N4)C2)C1] from intermediate 613 and Acryloyl chloride | 91 | 50 |
| Compound 78 | 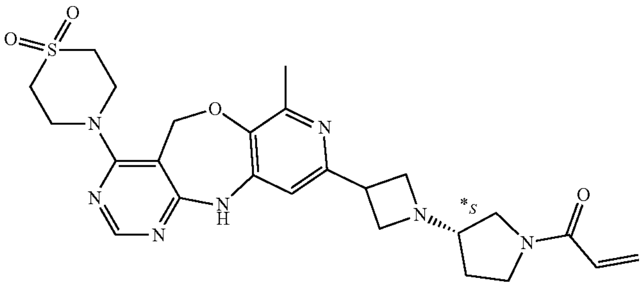 [SMILES: C=CC(=O)N1CC[C@H](N2CC(c3cc4c(c(C)n3)OCc3c(ncnc3N3CCS(=O)(=O)CC3)N4)C2)C1] from intermediate 613 followed by SFC separation (Stationary phase: CHIRALPAK AD-H 5 μm 250*30 mm, Mobile phase: 50% $CO_2$, 50% (mixture of MeOH/ACN 80/20 v/v) +0.6% TEA) | 20 | 36 |

-continued
| compound number | Structure | Mass (mg) | Yield (%) |
|---|---|---|---|
| Compound 79 | 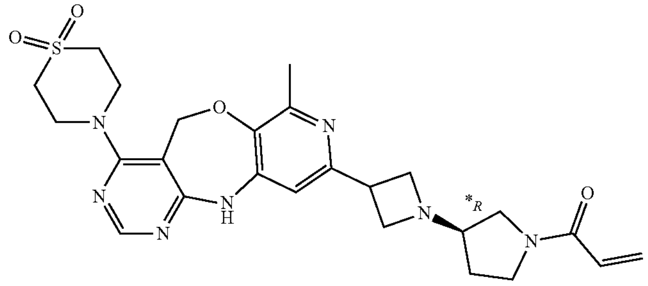 [SMILES: C=CC(=O)N1CC[C@@H](N2CC(c3cc4c(c(C)n3)OCc3c(ncnc3N3CCS(=O)(=O)CC3)N4)C2)C1] from intermediate 613 followed SFC separation (Stationary phase: CHIRALPAK AD-H 5 μm 250*30 mm, Mobile phase: 50% $CO_2$, 50% (mixture of MeOH/ACN 80/20 v/v) +0.6% TEA) | 20 | 36 |
| Compound 80 | 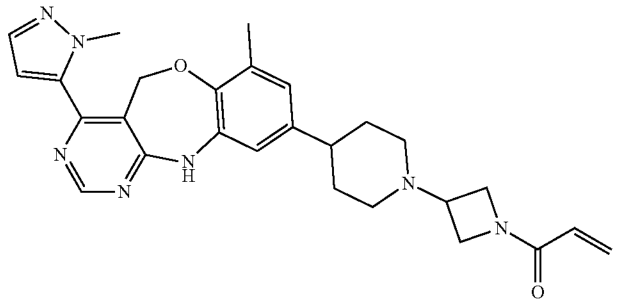 [SMILES: C=CC(=O)N1CC(N2CCC(c3cc(C)c4c(c3)Nc3ncnc(-c5ccnn5C)c3CO4)CC2)C1] from intermediate 567 and Acryloyl chloride | 137 | 66 |
| Compound 81 | 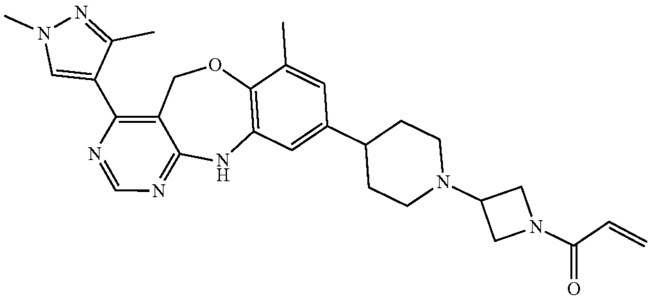 [SMILES: C=CC(=O)N1CC(N2CCC(c3cc(C)c4c(c3)Nc3ncnc(-c5cn(C)nc5C)c3CO4)CC2)C1] from intermediate 568 and Acryloyl chloride | 46 | 41 |
| Compound 82 | 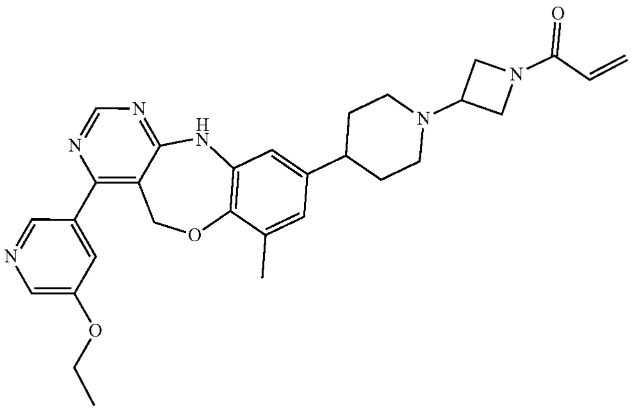 [SMILES: C=CC(=O)N1CC(N2CCC(c3cc(C)c4c(c3)Nc3ncnc(-c5cncc(OCC)c5)c3CO4)CC2)C1] from intermediate 569 and Acryloyl chloride | 157 | 28 |

-continued
| compound number | Structure | Mass (mg) | Yield (%) |
|---|---|---|---|
| Compound 84 | 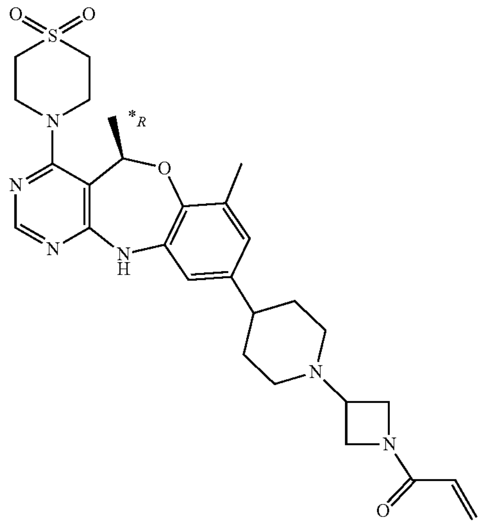 [SMILES: C=CC(=O)N1CC(N2CCC(c3cc(C)c4c(c3)Nc3ncnc(N5CCS(=O)(=O)CC5)c3[C@@H](C)O4)CC2)C1] from intermediate 614 and Acryloyl chloride | 195 | 48 |
| Compound 85 | 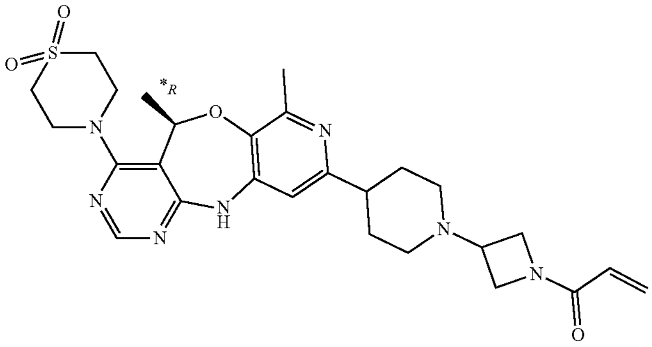 [SMILES: C=CC(=O)N1CC(N2CCC(c3cc4c(c(C)n3)O[C@H](C)c3c(ncnc3N3CCS(=O)(=O)CC3)N4)CC2)C1] from intermediate 615 and Acryloyl chloride | 73 | 62 |
| Compound 86 | 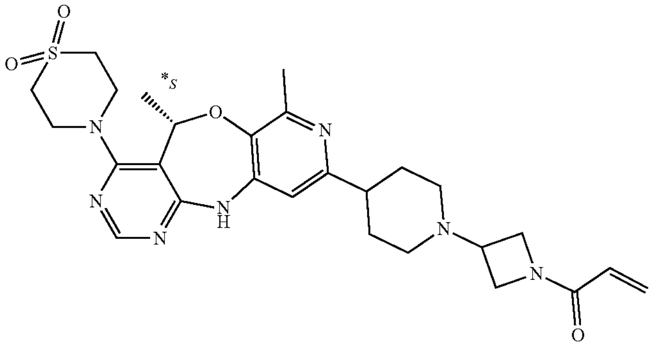 [SMILES: C=CC(=O)N1CC(N2CCC(c3cc4c(c(C)n3)O[C@@H](C)c3c(ncnc3N3CCS(=O)(=O)CC3)N4)CC2)C1] from intermediate 616 and Acryloyl chloride | 52 | 55 |

-continued
| compound number | Structure | Mass (mg) | Yield (%) |
|---|---|---|---|
| Compound 87 | 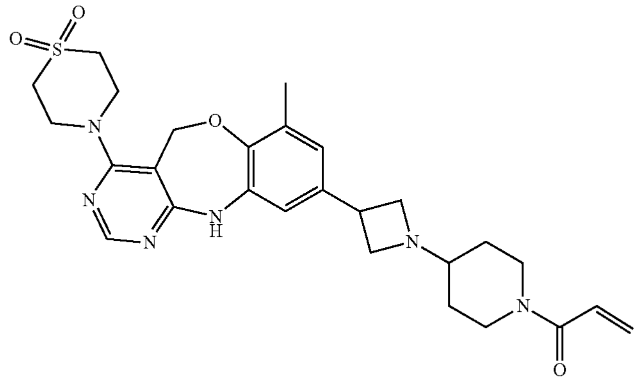 [SMILES: C=CC(=O)N1CCC(N2CC(c3cc(C)c4c(c3)Nc3ncnc(N5CCS(=O)(=O)CC5)c3CO4)C2)CC1] from intermediate 617 and Acryloyl chloride | 165 | 55 |
| Compound 88 | 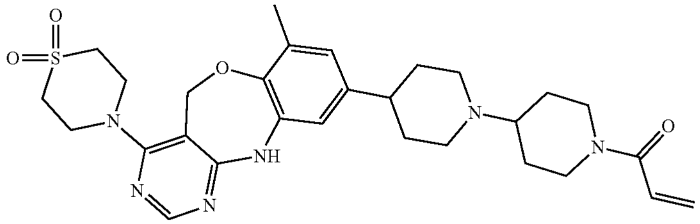 [SMILES: C=CC(=O)N1CCC(N2CCC(c3cc(C)c4c(c3)Nc3ncnc(N5CCS(=O)(=O)CC5)c3CO4)CC2)CC1] from intermediate 618 and Acryloyl chloride | 1240 | 49 |
| Compound 89 | 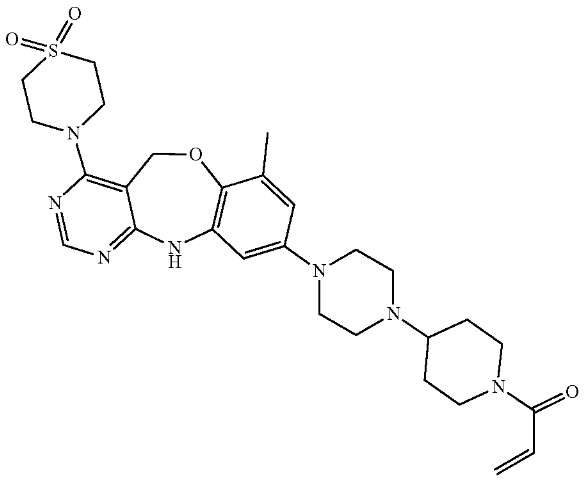 [SMILES: C=CC(=O)N1CCC(N2CCN(c3cc(C)c4c(c3)Nc3ncnc(N5CCS(=O)(=O)CC5)c3CO4)CC2)CC1] from intermediate 619 and Acryloyl chloride | 53 | 33 |
| Compound 90 | 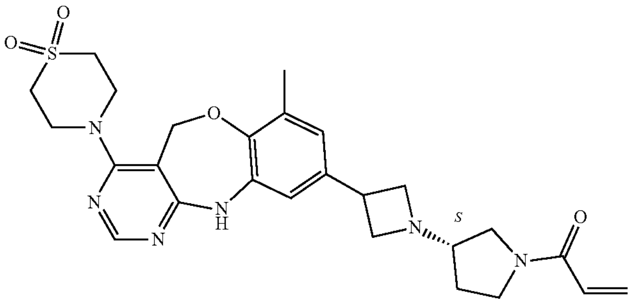 from intermediate 620 and Acryloyl chloride | 315 | 63 |

-continued
| compound number | Structure | Mass (mg) | Yield (%) |
|---|---|---|---|
| Compound 91 | 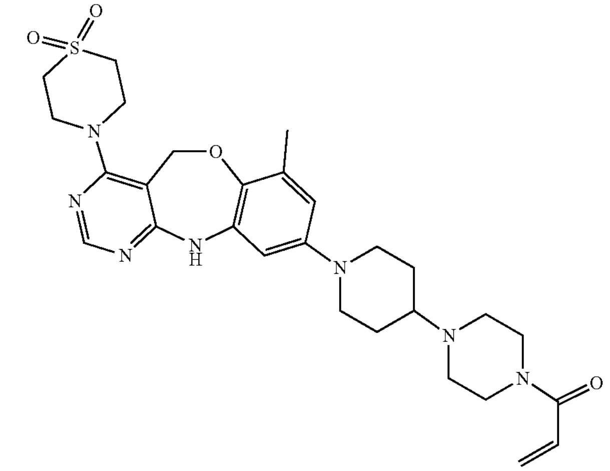 [SMILES: C=CC(=O)N1CCN(C2CCN(c3cc(C)c4c(c3)Nc3ncnc(N5CCS(=O)(=O)CC5)c3CO4)CC2)CC1] from intermediate 621 and Acryloyl chloride | 38 | 42 |
| Compound 92 | 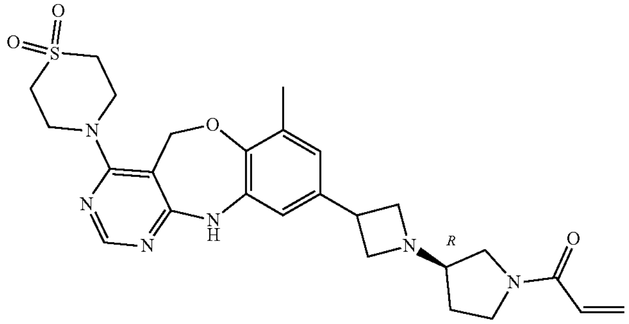 from intermediate 622 and Acryloyl chloride | 252 | 70 |
| Compound 93 | 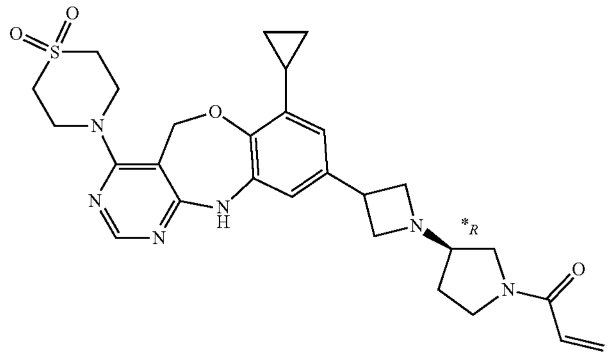 [SMILES: C=CC(=O)N1CC[C@@H](N2CC(c3cc4c(c(C5CC5)c3)OCc3c(ncnc3N3CCS(=O)(=O)CC3)N4)C2)C1] from intermediate 623 and Acryloyl chloride | 94 | 44 |

-continued
| compound number | Structure | Mass (mg) | Yield (%) |
|---|---|---|---|
| Compound 94 | 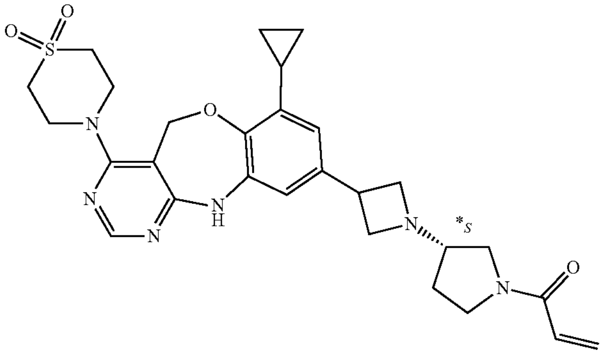 [SMILES: C=CC(=O)N1CC[C@H](N2CC(c3cc4c(c(C5CC5)c3)OCc3c(ncnc3N3CCS(=O)(=O)CC3)N4)C2)C1]<br>from intermediate 624 and Acryloyl chloride | 76 | 58 |
| Compound 95 | 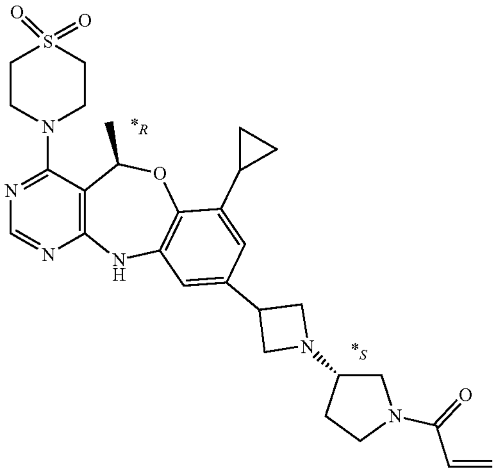 [SMILES: C=CC(=O)N1CC[C@H](N2CC(c3cc4c(c(C5CC5)c3)O[C@H](C)c3c(ncnc3N3CCS(=O)(=O)CC3)N4)C2)C1]<br>from intermediate 625 and Acryloyl chloride | 38 | 72 |
| Compound 96 | 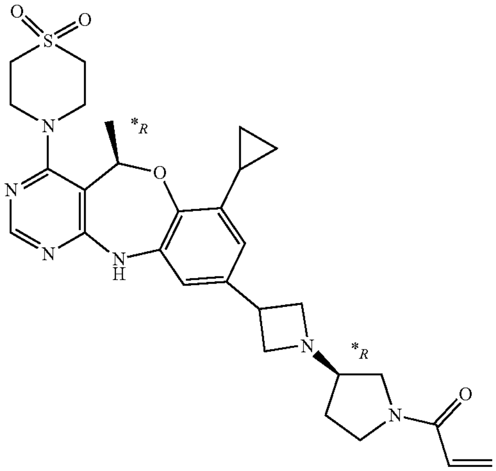 [SMILES: C=CC(=O)N1CC[C@@H](N2CC(c3cc4c(c(C5CC5)c3)O[C@H](C)c3c(ncnc3N3CCS(=O)(=O)CC3)N4)C2)C1]<br>from intermediate 626 and Acryloyl chloride | 34 | 69 |

-continued
| compound number | Structure | Mass (mg) | Yield (%) |
| --- | --- | --- | --- |
| Compound 97 | 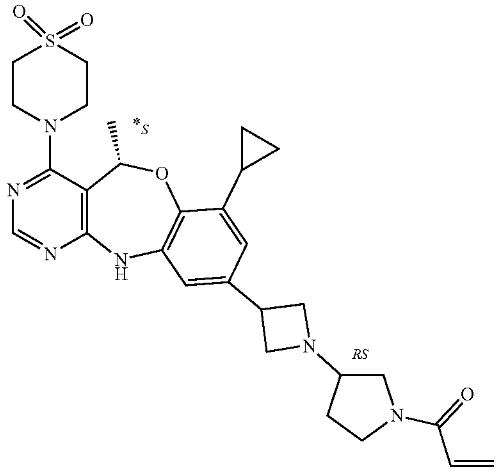 [SMILES: C=CC(=O)N1CCC(N2CC(c3cc4c(c(C5CC5)c3)O[C@@H](C)c3c(ncnc3N3CCS(=O)(=O)CC3)N4)C2)C1] from intermediate 627 and Acryloyl chloride | 108 | 51 |
| Compound 98 | 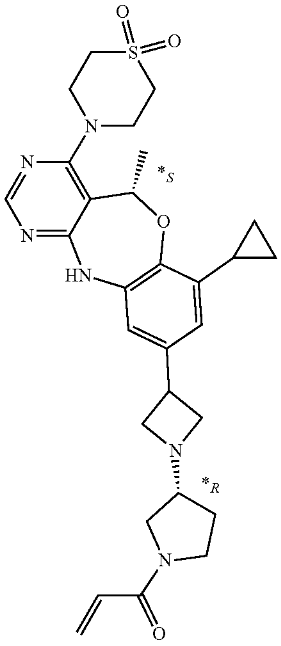 [SMILES: C=CC(=O)N1CC[C@@H](N2CC(c3cc4c(c(C5CC5)c3)O[C@@H](C)c3c(ncnc3N3CCS(=O)(=O)CC3)N4)C2)C1] from intermediate 627 followed by SFC separation (Stationary phase: Whelk-O1 (S,S) 5 μm 250*21.2 mm, Mobile phase: 48% $CO_2$, 52% MeOH(0.6% TEA)) | 30 | 34 |

-continued

| compound number | Structure | Mass (mg) | Yield (%) |
|---|---|---|---|
| Compound 99 | 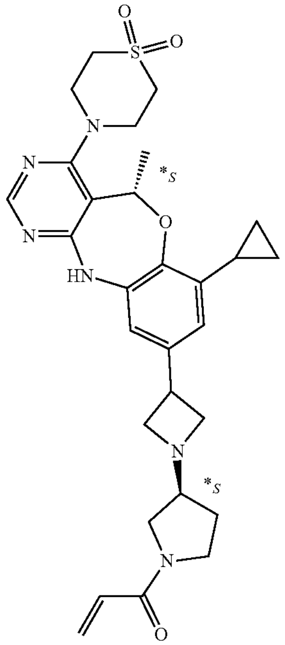 [SMILES: C=CC(=O)N1CC[C@H](N2CC(c3cc4c(c(C5CC5)c3)O[C@@H](C)c3c(ncnc3N3CCS(=O)(=O)CC3)N4)C2)C1] from intermediate 627 followed by SFC separation (Stationary phase: Whelk-O1 (S,S) 5 μm 250*21.2 mm, Mobile phase: 48% $CO_2$, 52% MeOH(0.6% TEA)) | 32 | 36 |

Example B3

Preparation of Compound 100

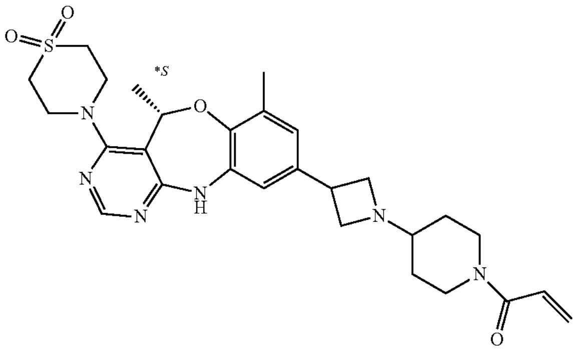

Intermediate 469*S (340 mg, 0.537 mmol) was dissolved in THF (13 mL). The reaction mixture was cooled down to 0° C. under nitrogen. A solution of tBuONa (402.968 μL, 2 M, 0.806 mmol) was added slowly. The reaction mixture was stirred at 0° C. for 20 min, then at rt for 1 h. Water, $NH_4Cl$ and DCM were added. The organic layer was decanted and the solvent was evaporated until dryness. A purification was performed via preparative LC (Stationary phase: irregular SiOH 35-70 μm 40 g, Mobile phase: gradient from 100% DCM to 88% DCM, 12% MeOH, 0.1% $NH_4OH$). The pure fractions were collected and the solvent was evaporated. The resultant residue was crystallized from MeCN to afford the product (148 mg, yield 50%).

The compounds in the Table below were prepared by using an analogous method starting from the respective starting materials.
| compound number | Structure | Mass (mg) | Yield (%) |
| --- | --- | --- | --- |
| Compound 101 | 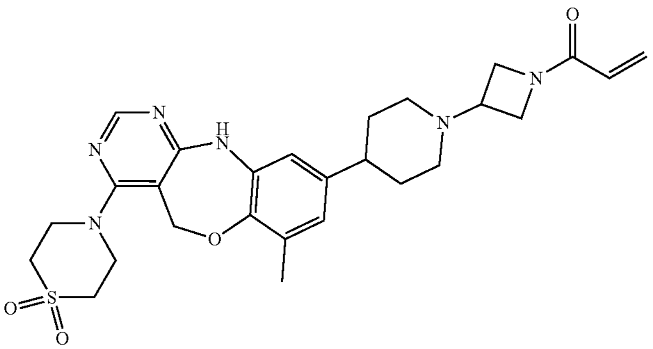 [SMILES: C=CC(=O)N1CC(N2CCC(c3cc(C)c4c(c3)Nc3ncnc(N5CCS(=O)(=O)CC5)c3CO4)CC2)C1] from intermediate 468 | 1940 | 38 |
| Compound 102 | 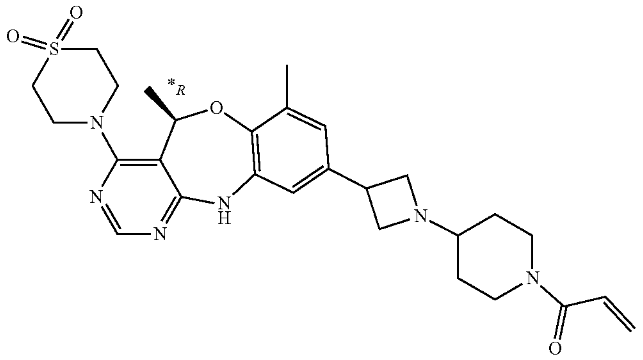 [SMILES: C=CC(=O)N1CCC(N2CC(c3cc(C)c4c(c3)Nc3ncnc(N5CCS(=O)(=O)CC5)c3[C@@H](C)O4)C2)CC1] from intermediate 469*R | 1710 | 40 |
| Compound 103 | 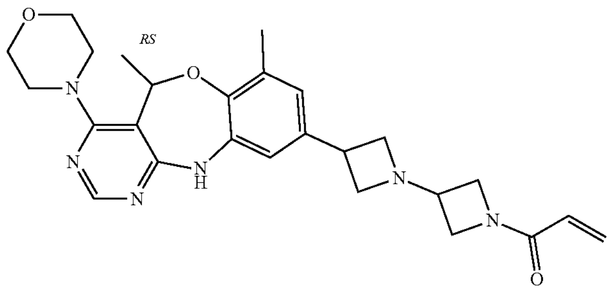 [SMILES: C=CC(=O)N1CC(N2CC(c3cc(C)c4c(c3)Nc3ncnc(N5CCOCC5)c3C(C)O4)C2)C1] from intermediate 470 from −20° C. to rt | 66 | 32 |

-continued
| compound number | Structure | Mass (mg) | Yield (%) |
|---|---|---|---|
| Compound 104 | 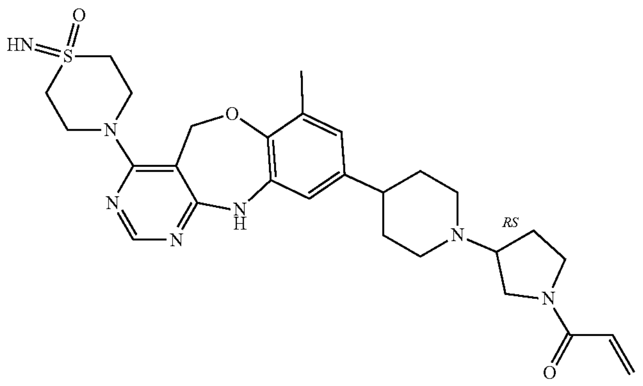 [SMILES: C=CC(=O)N1CCC(N2CCC(c3cc(C)c4c(c3)Nc3ncnc(N5CCS(=N)(=O)CC5)c3CO4)CC2)C1] from intermediate 472 (30 mg; 45%) and intermediate 471 (100 mg; 94%) | 85 | 65 |
| Compound 105 | 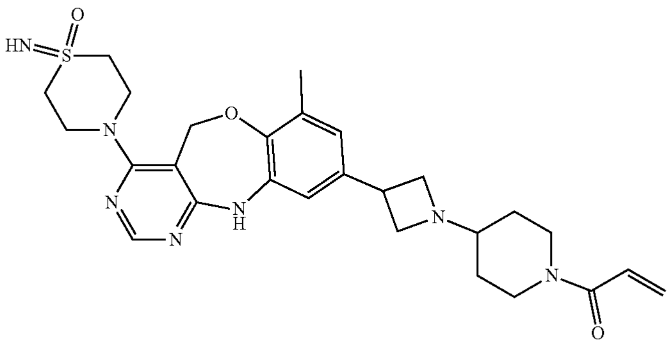 [SMILES: C=CC(=O)N1CCC(N2CC(c3cc(C)c4c(c3)Nc3ncnc(N5CCS(=N)(=O)CC5)c3CO4)C2)CC1] from intermediate 480 | 61 | 33 |
| Compound 106 | 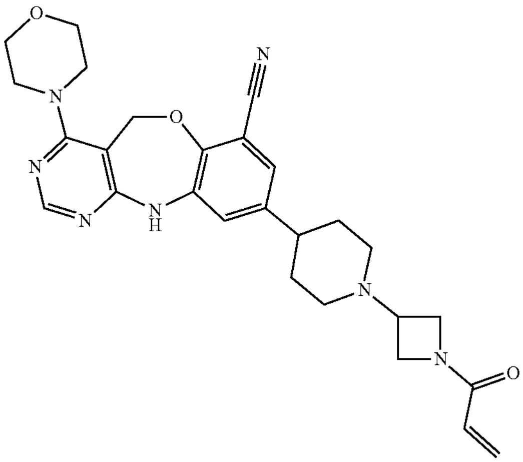 [SMILES: C=CC(=O)N1CC(N2CCC(c3cc(C#N)c4c(c3)Nc3ncnc(N5CCOCC5)c3CO4)CC2)C1] from intermediate 475 | 50 | 46 |

-continued
| compound number | Structure | Mass (mg) | Yield (%) |
|---|---|---|---|
| Compound 107 | 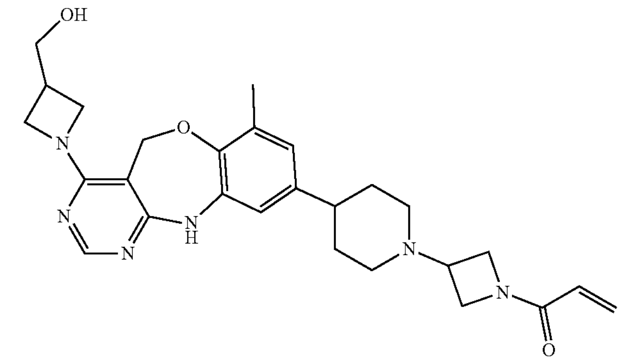 [SMILES: C=CC(=O)N1CC(N2CCC(c3cc(C)c4c(c3)Nc3ncnc(N5CC(CO)C5)c3CO4)CC2)C1] from intermediate intermediate 523 | 56 | 46 |
| Compound 108 | 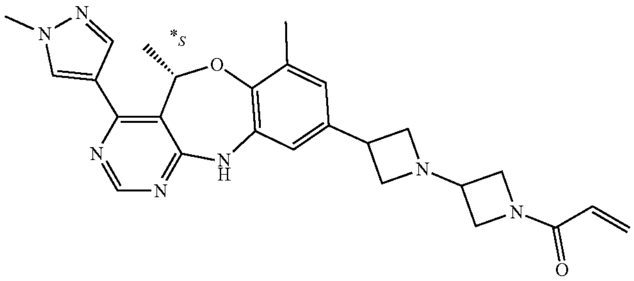 [SMILES: C=CC(=O)N1CC(N2CC(c3cc(C)c4c(c3)Nc3ncnc(-c5cnn(C)c5)c3[C@H](C)O4)C2)C1] from intermediate 225 | 88 | 52 |
| Compound 109 | 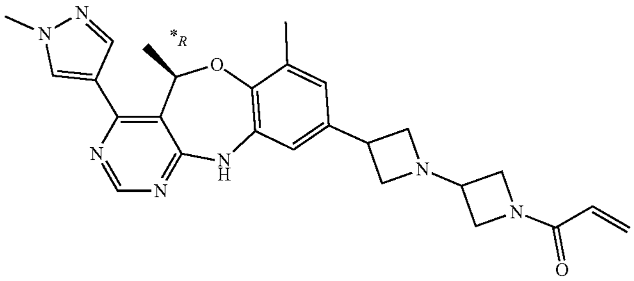 [SMILES: C=CC(=O)N1CC(N2CC(c3cc(C)c4c(c3)Nc3ncnc(-c5cnn(C)c5)c3[C@@H](C)O4)C2)C1] from intermediate 226 | 44 | 71 |
| Compound 110 | 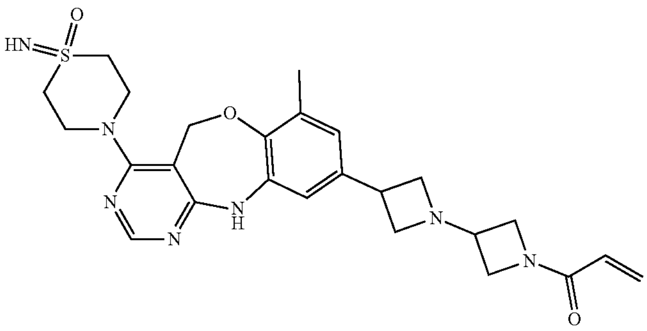 [SMILES: C=CC(=O)N1CC(N2CC(c3cc(C)c4c(c3)Nc3ncnc(N5CCS(=N)(=O)CC5)c3CO4)C2)C1] from intermediate 482 | 29 | 15 |

-continued
| compound number | Structure | Mass (mg) | Yield (%) |
|---|---|---|---|
| Compound 111 | 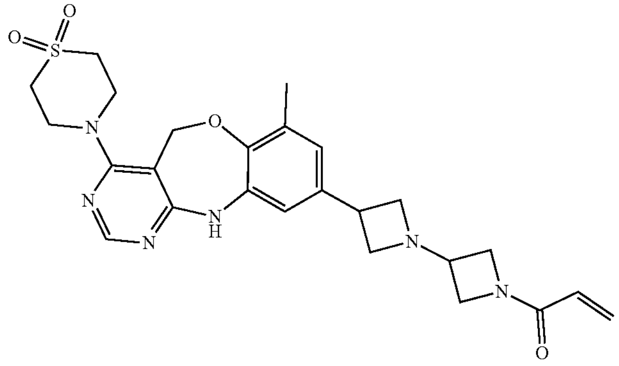 [SMILES: C=CC(=O)N1CC(N2CC(c3cc(C)c4c(c3)Nc3ncnc(N5CCS(=O)(=O)CC5)c3CO4)C2)C1] from intermediate 227 | 53 | 51 |
| Compound 112 | 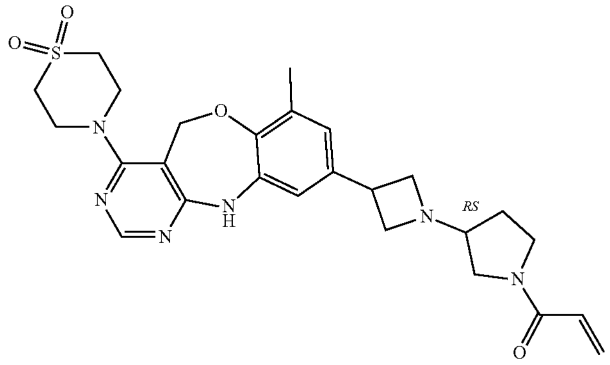 [SMILES: C=CC(=O)N1CCC(N2CC(c3cc(C)c4c(c3)Nc3ncnc(N5CCS(=O)(=O)CC5)c3CO4)C2)C1] from intermediate 228 | 234 | 67 |
| Compound 113 | 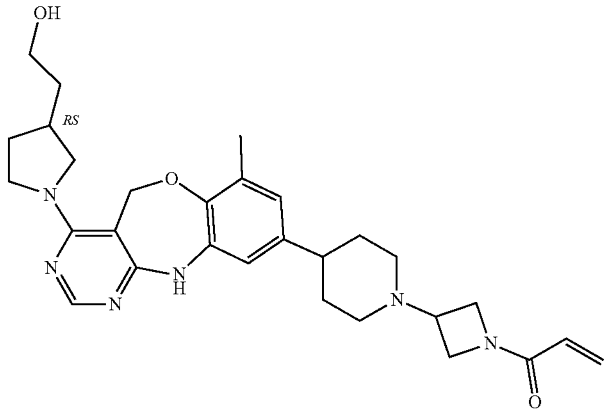 [SMILES: C=CC(=O)N1CC(N2CCC(c3cc(C)c4c(c3)Nc3ncnc(N5CCC(CCO)C5)c3CO4)CC2)C1] from intermediate 524 | 16 | 77 |

-continued

| compound number | Structure | Mass (mg) | Yield (%) |
|---|---|---|---|
| Compound 114 | 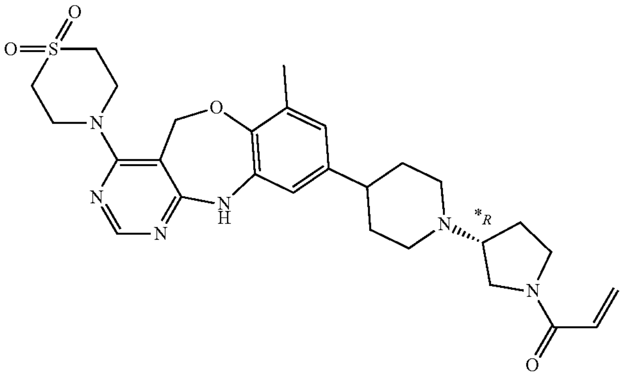 [SMILES: C=CC(=O)N1CC[C@@H](N2CCC(c3cc(C)c4c(c3)Nc3ncnc(N5CCS(=O)(=O)CC5)c3CO4)CC2)C1] from intermediate 229. Chiral separation was via SFC (Stationary phase: Whelk-O1 (S,S) 5 μm 250*21.2 mm, Mobile phase: 50% $CO_2$, 50% MeOH(0.6% TEA)) | 860 | 29 |
| Compound 115 | 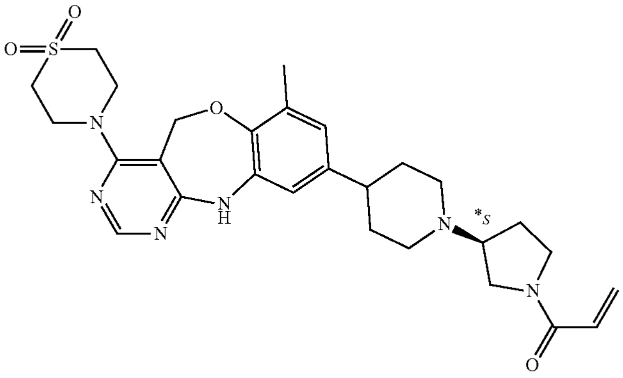 [SMILES: C=CC(=O)N1CC[C@H](N2CCC(c3cc(C)c4c(c3)Nc3ncnc(N5CCS(=O)(=O)CC5)c3CO4)CC2)C1] from intermediate 229. Chiral separation was via SFC (Stationary phase: Whelk-O1 (S,S) 5 μm 250*21.2 mm, Mobile phase: 50% $CO_2$, 50% MeOH(0.6% TEA)). | 700 | 24 |
| Compound 116 | 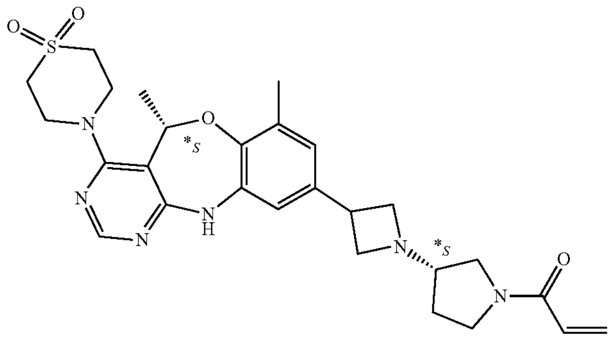 [SMILES: C=CC(=O)N1CC[C@H](N2CC(c3cc(C)c4c(c3)Nc3ncnc(N5CCS(=O)(=O)CC5)c3[C@H](C)O4)C2)C1] from intermediate 230. Chiral separation was via SFC (Stationary phase: Whelk-O1 (S,S) 5 μm 250*21.2 mm, Mobile phase: 60% $CO_2$, 40% MeOH(0.6% TEA)) | 47 | 24 |

-continued

| compound number | Structure | Mass (mg) | Yield (%) |
|---|---|---|---|
| Compound 117 | 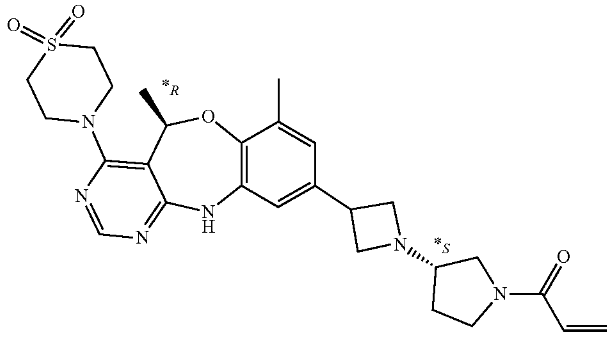 [SMILES: C=CC(=O)N1CC[C@H](N2CC(c3cc(C)c4c(c3)Nc3ncnc(N5CCS(=O)(=O)CC5)c3[C@@H](C)O4)C2)C1] from intermediate 231. Chiral separation was via SFC (Stationary phase: Whelk-O1 (S,S) 5 μm 250*21.2 mm, Mobile phase: 40% $CO_2$, 60% MeOH(0.6% TEA)) | 50 | 21 |
| Compound 118 | 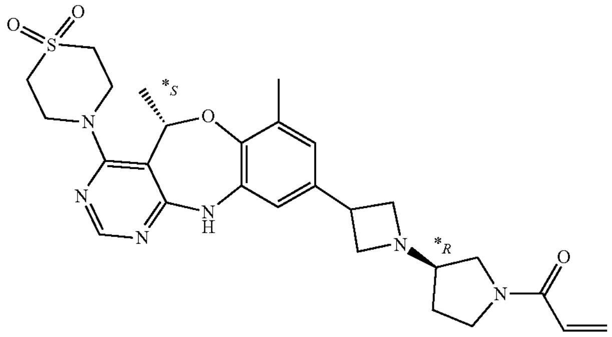 [SMILES: C=CC(=O)N1CC[C@@H](N2CC(c3cc(C)c4c(c3)Nc3ncnc(N5CCS(=O)(=O)CC5)c3[C@H](C)O4)C2)C1] from intermediate 230. Chiral separation was via SFC (Stationary phase: Whelk-O1 (S,S) 5 μm 250*21.2 mm, Mobile phase: 60% $CO_2$, 40% MeOH(0.6% TEA)) | 44 | 23 |
| Compound 119 | 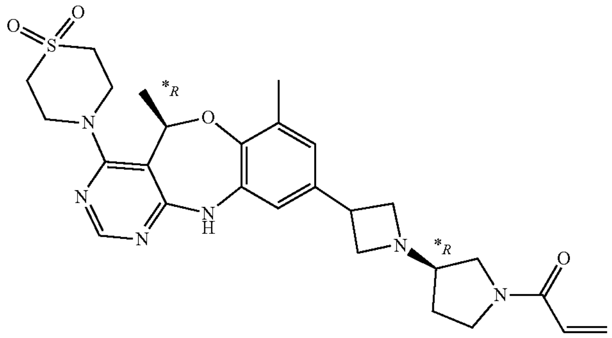 [SMILES: C=CC(=O)N1CC[C@@H](N2CC(c3cc(C)c4c(c3)Nc3ncnc(N5CCS(=O)(=O)CC5)c3[C@@H](C)O4)C2)C1] from intermediate 231. Chiral separation was via SFC (Stationary phase: Whelk-O1 (S,S) 5 μm 250*21.2 mm, Mobile phase: 40% CO2, 60% MeOH(0.6% TEA)) | 60 | 25 |

-continued

| compound number | Structure | Mass (mg) | Yield (%) |
|---|---|---|---|
| Compound 120 | 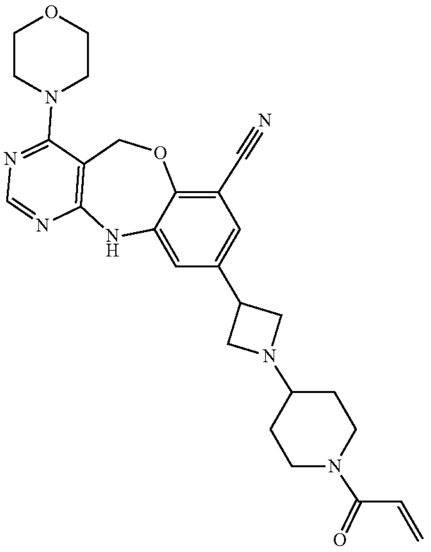 [SMILES: C=CC(=O)N1CCC(N2CC(c3cc(C#N)c4c(c3)Nc3ncnc(N5CCOCC5)c3CO4)C2)CC1] from intermediate 473 | 22 | 16 |
| Compound 121 | 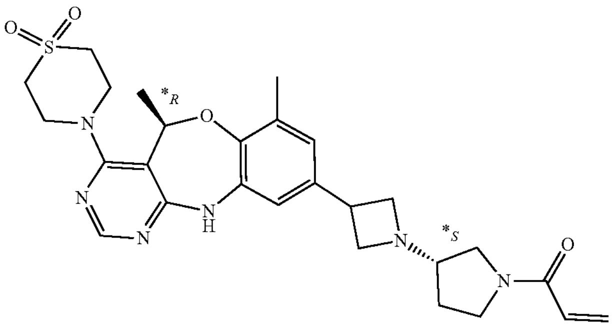 [SMILES: C=CC(=O)N1CC[C@H](N2CC(c3cc(C)c4c(c3)Nc3ncnc(N5CCS(=O)(=O)CC5)c3[C@@H](C)O4)C2)C1] from intermediate 474. Chiral separation was via SFC (Stationary phase: Whelk-O1 (S,S) 5 µm 250*21.2 mm, Mobile phase: 40% CO2, 60% mixture of MeOH/DCM 90/10 v/v +0.6% TEA) | 1376 | 32 |
| Compound 122 | 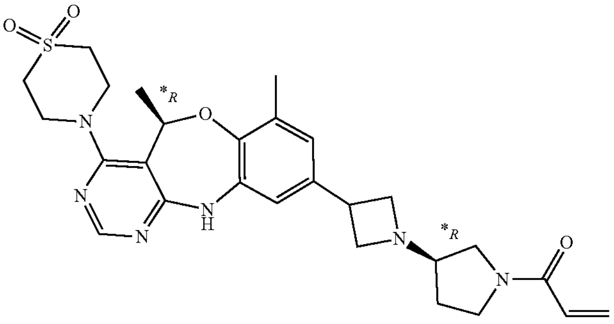 [SMILES: C=CC(=O)N1CC[C@@H](N2CC(c3cc(C)c4c(c3)Nc3ncnc(N5CCS(=O)(=O)CC5)c3[C@@H](C)O4)C2)C1] from intermediate 474. Chiral separation was via SFC (Stationary phase: Whelk-O1 (S,S) 5 µm 250*21.2 mm, Mobile phase: 40% $CO_2$, 60% mixture of MeOH/DCM 90/10 v/v +0.6% TEA) | 1379 | 32 |

Example B4

Preparation of Compound 123

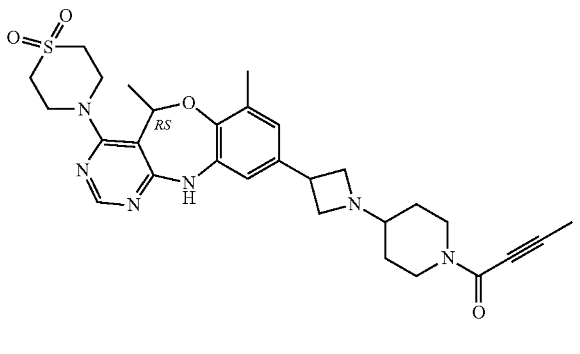 [SMILES: CC#CC(=O)N1CCC(N2CC(c3cc(C)c4c(c3)Nc3ncnc(N5CCS(=O)(=O)CC5)c3C(C)O4)C2)CC1]

HBTU (5.689 g; 15 mmol) was added to a solution of intermediate 654 (4.986 g; 10 mmol), 2-butynoic acid (1.261 g; 15 mmol) and di-isopropylethylamine (8.733 mL; 0.74 g/mL; 50 mmol) in DCM (10 mL), and the mixture was stirred at rt for 2 hours. The reaction mixture was quenched by addition of saturated $NaHCO_3$(aq) and extracted with $CH_2Cl_2$. The organic layer was concentrated under vacuum. Purification was by flash chromatography ($SiO_2$, Methanol-dichloromethane gradient) to afford the product as a racemic mixture (5.4 g; 96%)

Preparation of Compound 124*R and Compound 125*S

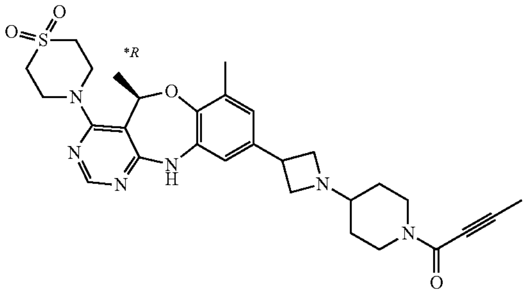

and

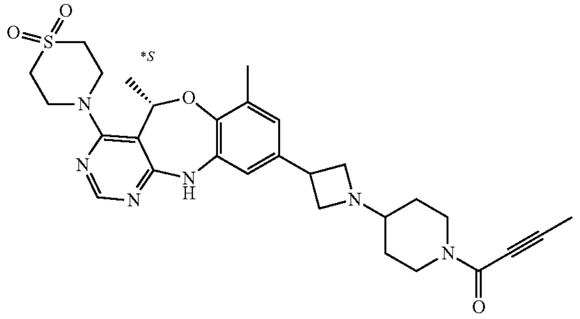

Compound 123 (5.4 g; 9.563 mmol) was purified by separated into the 2 enantiomers compound 124*R and compound 125*S by chiral SFC chromatography, (Method Lux Cellulose_1 SFC isocratic 50% MeOH+0.1DEA) to afford the separated enantiomers. Each separated isomer was purified by flash chromatography (SiO2, Methanol-dichloromethane gradient) to afford compound 124*R (2.485 g; 46%) and compound 125*S (2.260 g; 42%)

Preparation of Compound 126

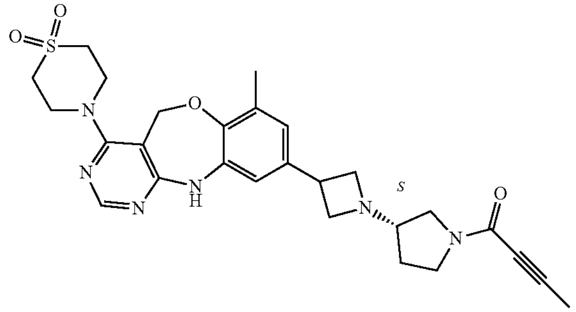

Di-isopropylethylamine (1.8 mL, 0.75 g/mL, 10.445 mmol) was added to a suspension of 2-butynoic acid (0.203 g, 2.415 mmol) and O-(1H-benzotriazol-1-yl)-N,N,N',N'-tetramethyluronium hexafluorophosphate (1 g, 2.623 mmol) in DCM (40 mL) at 0-5° C. under nitrogen. The reaction was stirred for 10 minutes. A solution of intermediate 620 (0.99 g, 2.104 mmol) in DCM (20 mL) was added at 0-5° C. and the reaction was stirred for 45 min at 0° C. then at room temperature for 30 min. Water, an aqueous solution of $NH_4Cl$ and DCM were added. The organic layer was decanted on Chromabond® and the solvent was evaporated until dryness. The crude material was purified via preparative LC (Stationary phase: irregular SiOH 15-40 μm 40 g, Mobile phase: gradient from 98% DCM, 2% MeOH, 0.2% $NH_4OH$ to 90% DCM, 10% MeOH, 0.1% $NH_4OH$). The pure fractions were collected and the solvent was evaporated to give a residue (632 mg) that was taken up into MeCN and was triturated, filtered and dried in vacuo to give the product (588 mg; 52%).

Preparation of Compound 127

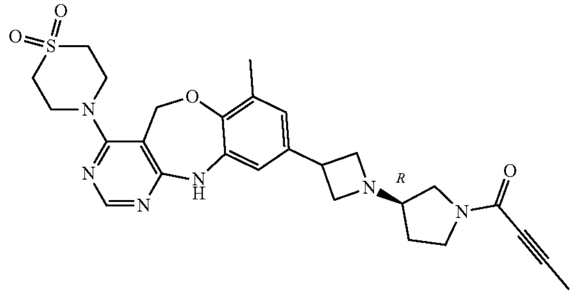

Di-isopropylethylamine (1.66 mL, 0.75 g/mL, 9.635 mmol) was added to a suspension of O-(1H-benzotriazol-1-yl)-N,N,N',N'-tetramethyluronium hexafluorophosphate (0.955 g, 2.505 mmol) and 2-butynoic acid (0.186 g, 2.216 mmol) in DCM (10 mL) at 0-5° C. under nitrogen. The reaction mixture was stirred for 10 minutes. A solution of intermediate 622 (1.346 g, 1.927 mmol) in DCM (55 mL) was added at 0-5° C. and the reaction mixture was stirred for 45 min at 0° C. then rt for 30 min. Water, $NH_4Cl$ (aq) and DCM were added. The organic layer was decanted and the solvent was evaporated until dryness. The resultant crude material was purified via preparative LC (Stationary phase: irregular SiOH 35-70 μm 40 g, Mobile phase: gradient from 100% DCM to 90% DCM, 10% MeOH, 0.1% $NH_4OH$). The pure fractions were collected and the solvent was evaporated to afford the partially pure product (971 mg). A purification was performed via Reverse phase (solid deposit) (Stationary phase: YMC-DispoPack AT ODS-25:40 g, Mobile phase: gradient from 90% $HCCONH_3$ 0.2% in water, 10% MeCN to 50% $HCCONH_3$ 0.2% in water, 50% MeCN). The residue was freeze dried with MeCN and water to afford a solid (666 mg). This fraction was suspended into $Et_2O$, filtered and dried at 70° C. under vacuum for 24 h to afford the product (586 mg, 57%).

Preparation of Compound 128 (corresponds to Compound 142)

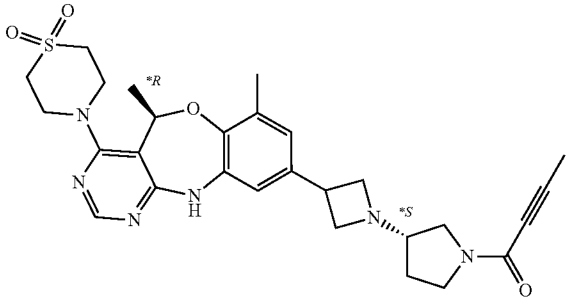

Di-isopropylethylamine (3.08 mL, 0.74 g/mL, 17.63 mmol) was added to a mixture of 2-butynoic acid (361 mg, 4.29 mmol), O-(1H-benzotriazol-1-yl)-N,N,N',N'-tetramethyluronium hexafluorophosphate (2.323 g, 6.12 mmol) in DCM (18 mL) at 0° C. This mixture was stirred for 10 min at 0° C. then a solution of intermediate 649 (1.72 g, 3.55 mmol) in DCM (80 mL) was added. This reaction was stirred at 0° C. for 45 min, an aqueous solution of $NH_4Cl$ 10% was added and this mixture was extracted twice with DCM. The organic layer was decanted on Chromabond® and the solvent was evaporated until dryness. This product was purified by preparative LC (Irregular $SiO_2$ 15-40 μm 320 g GraceResolv®, mobile phase Gradient from: 100% DCM to 93% DCM, 7% MeOH (2% $NH_4OH$). The pure fractions were collected and the solvent was evaporated until dryness. The residue was purified by preparative LC (Irregular $SiO_2$ 15-40 μm 320 g GraceResolv®, mobile phase Gradient from: 100% DCM to 94% DCM, 6% MeOH (2% $NH_4OH$). The pure fractions were collected, celite was added and the solvent was evaporated until dryness. Purification was performed via Reverse phase (solid deposit) (Stationary phase: YMC ODS-25 120 g, Mobile phase: Gradient from 85% $NH_4HCO_3$ 0.2%, 15% ACN to 45% $NH_4HCO_3$ 0.2%, 55% ACN). the pure fractions were collected and the solvent was evaporated until dryness to afford a solid (1.6 g). The fraction was taken up into $Et_2O$, filtered and dried under vacuum at 65° C. for 3 h then for 16 h at 70° C. to afford the product (1.406 g, 72%)

The compounds in the Table below were prepared by using an analogous method starting from the respective starting materials.

| compound number | Structure | Mass (mg) | Yield (%) |
|---|---|---|---|
| Compound 129 | 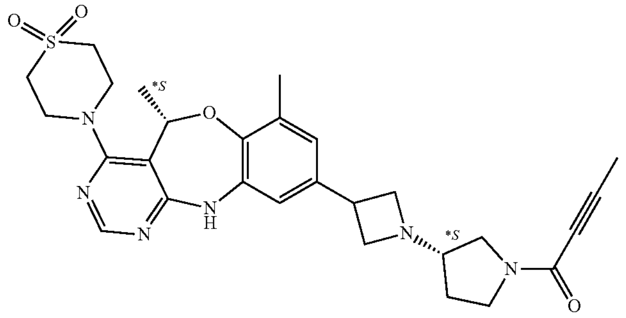 [SMILES: CC#CC(=O)N1CC[C@H](N2CC(c3cc(C)c4c(c3)Nc3ncnc(N5CCS(=O)(=O)CC5)c3[C@H](C)O4)C2)C1] from intermediate 651 | 160 | 35 |
| Compound 130 (corresponds to Compound 141) | 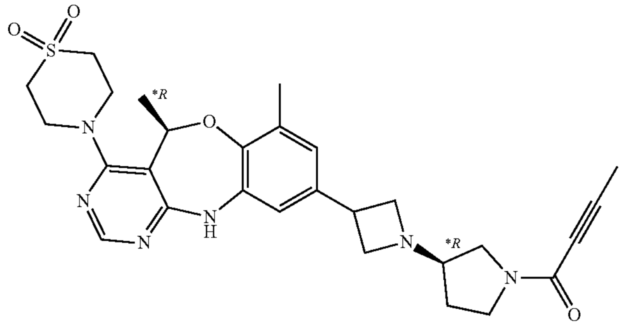 [SMILES: CC#CC(=O)N1CC[C@@H](N2CC(c3cc(C)c4c(c3)Nc3ncnc(N5CCS(=O)(=O)CC5)c3[C@@H](C)O4)C2)C1] N from intermediate 650 | 2701 | 45 |

-continued
| compound number | Structure | Mass (mg) | Yield (%) |
|---|---|---|---|
| Compound 131 | 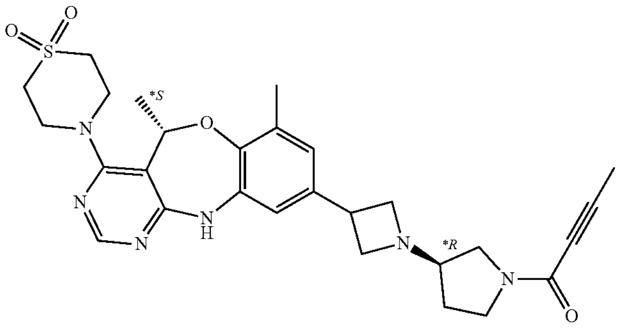 [SMILES: CC#CC(=O)N1CC[C@@H](N2CC(c3cc(C)c4c(c3)Nc3ncnc(N5CCS(=O)(=O)CC5)c3[C@H](C)O4)C2)C1] from intermediate 652 | 139 | 43 |
| Compound 132 | 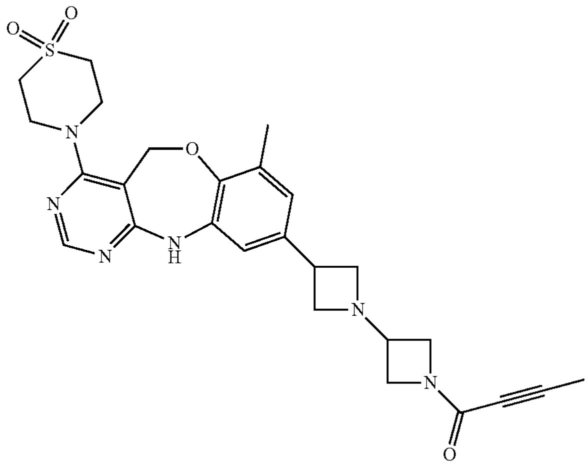 [SMILES: CC#CC(=O)N1CC(N2CC(c3cc(C)c4c(c3)Nc3ncnc(N5CCS(=O)(=O)CC5)c3CO4)C2)C1] from intermediate 570 | 5 | 7 |
| Compound 133 | 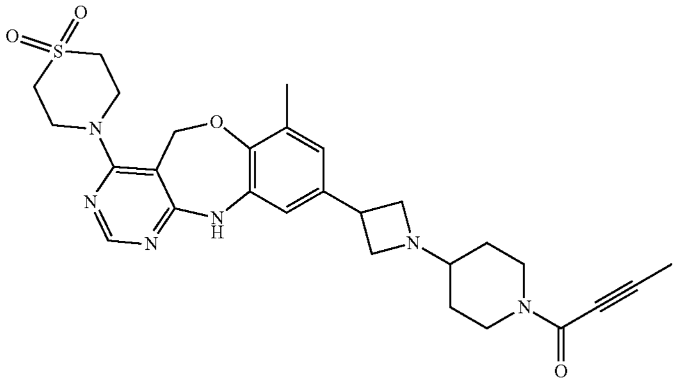 [SMILES: CC#CC(=O)N1CCC(N2CC(c3cc(C)c4c(c3)Nc3ncnc(N5CCS(=O)(=O)CC5)c3CO4)C2)CC1] from intermediate 634 | 125 | 61 |

-continued
| compound number | Structure | Mass (mg) | Yield (%) |
|---|---|---|---|
| Compound 134 | 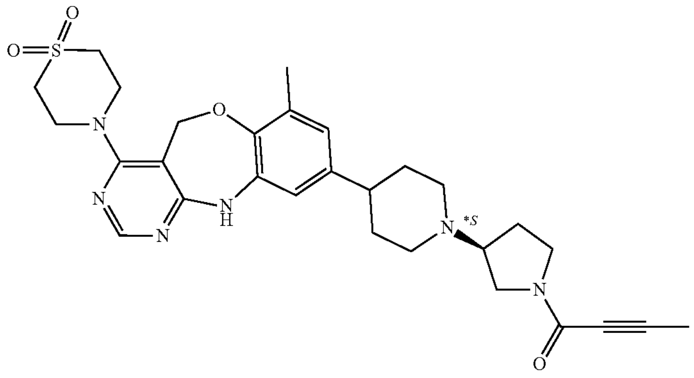 [SMILES: CC#CC(=O)N1CC[C@H](N2CCC(c3cc(C)c4c(c3)Nc3ncnc(N5CCS(=O)(=O)CC5)c3CO4)CC2)C1] from intermediate 635 | 50 | 39 |
| Compound 135 | 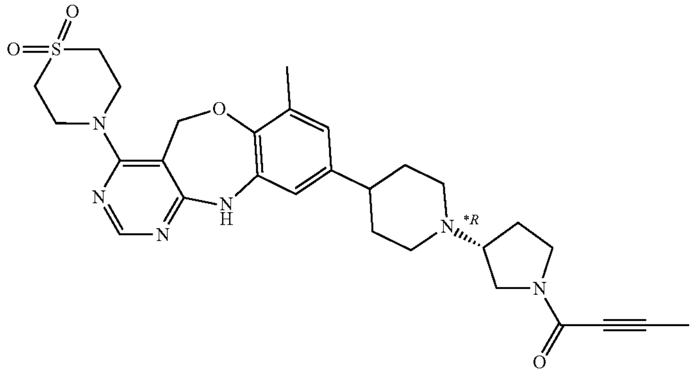 [SMILES: CC#CC(=O)N1CC[C@@H](N2CCC(c3cc(C)c4c(c3)Nc3ncnc(N5CCS(=O)(=O)CC5)c3CO4)CC2)C1] from intermediate 636 | 49 | 40 |
| Compound 136 | 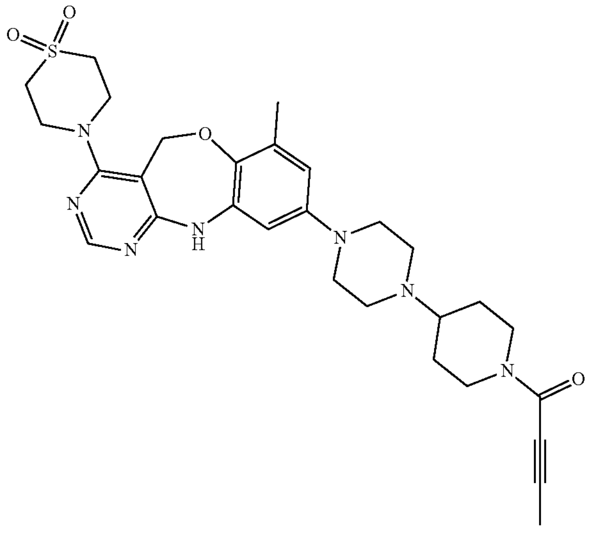 [SMILES: CC#CC(=O)N1CCC(N2CCN(c3cc(C)c4c(c3)Nc3ncnc(N5CCS(=O)(=O)CC5)c3CO4)CC2)CC1] from intermediate 637 | 21 | 15 |

-continued
| compound number | Structure | Mass (mg) | Yield (%) |
|---|---|---|---|
| Compound 137 | 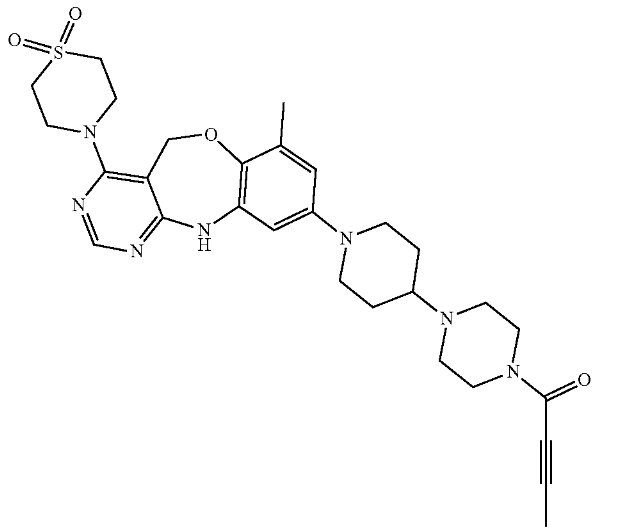 [SMILES: CC#CC(=O)N1CCN(C2CCN(c3cc(C)c4c(c3)Nc3ncnc(N5CCS(=O)(=O)CC5)c3CO4)CC2)CC1] from intermediate 638 | 45 | 36 |
| Compound 138 | 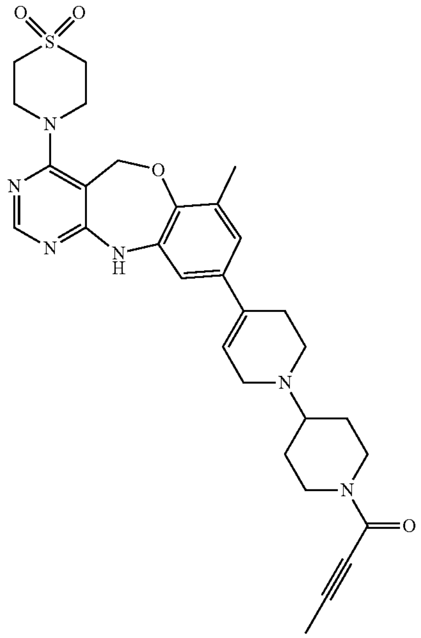 [SMILES: CC#CC(=O)N1CCC(N2CC=C(c3cc(C)c4c(c3)Nc3ncnc(N5CCS(=O)(=O)CC5)c3CO4)CC2)CC1] from intermediate 639 | 52 | 18 |
| Compound 143 | 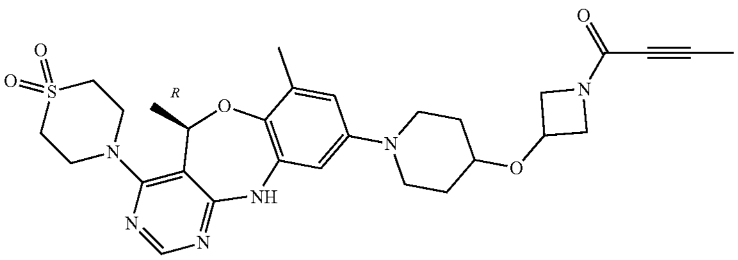 from intermediate 640 | 153 | 66 |

-continued
| compound number | Structure | Mass (mg) | Yield (%) |
|---|---|---|---|
| Compound 145 | 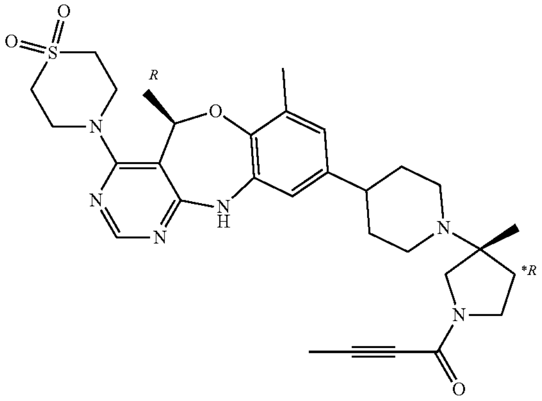 from intermediate 641 | 29 | 53 |
| Compound 146 | 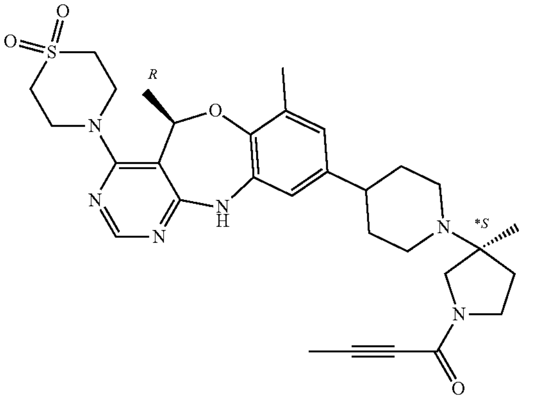 from intermediate 642 | 18 | 32 |
| Compound 147 | 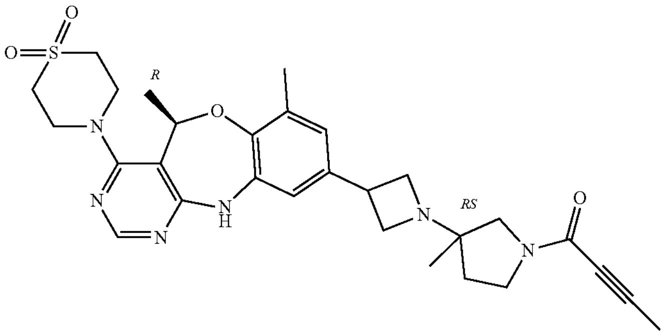 from intermediate 643 | 164 | 67 |

Preparation of Compound 139 and Compound 140

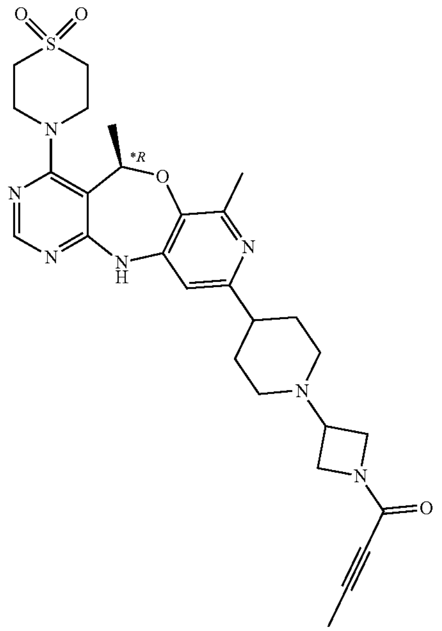

JNJ-

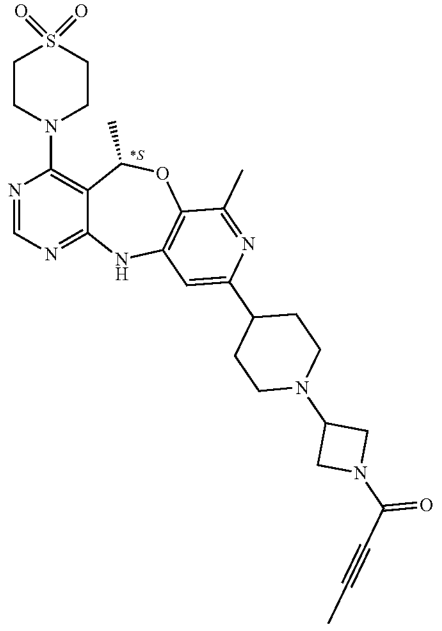

O-(1H-benzotriazol-1-yl)-N,N,N',N'-tetramethyluronium hexafluorophosphate (6.48 g, 17.08 mmol) was added to a solution of intermediate 571 (5.69 g, 11.39 mmol), 2-butynoic acid (1.44 g, 17.08 mmol) and diisopropylethylamine (9.94 mL, 56.94 mmol) in DCM (40 mL). The mixture was stirred at rt for 3 h, then poured onto saturated aqueous $NaHCO_3$ and extracted with dichloromethane. The organic layer was washed with $NaHCO_3$ and brine, then dried over $MgSO_4$ and concentrated. The crude was purified by flash chromatography (eluting with DCM-DCM/MeOH). Pure fractions were collected and concentrated. A purification was performed via chiral SFC (Stationary phase: CHIRACEL OJ-H 5 μm 250*30 mm, Mobile phase: 70% $CO_2$, 30% MeOH (0.6% TEA)). Each fraction was triturated in $Et_2O$, filtered and dried. The resulting solids were respectively dissolved in DCM, washed with 10% aqueous $K_2CO_3$ and water, dried over $MgSO_4$ and concentrated, then triturated in $Et_2O$, filtered and dried at 70° C. for 18 h to give compounds 139 (1210 mg, 19%) and 140 (1270 mg, yield 20%).

Preparation of Compound 141 (Corresponds to Compound 130)

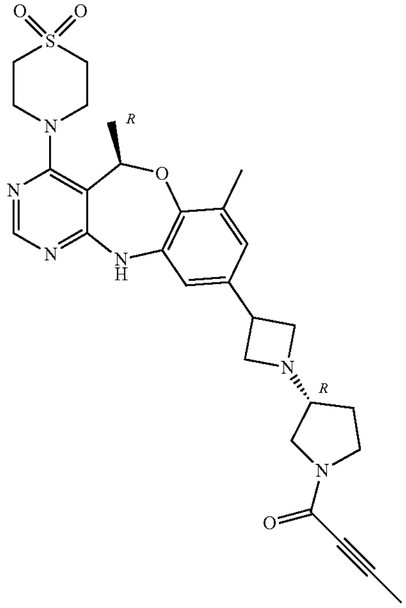

Diisopropylethylamine (13.4 mL, 76.88 mmol) was added to a mixture of 2-butynoic acid (1.57 g, 18.71 mmol) and O-(1H-benzotriazol-1-yl)-N,N,N',N'-tetramethyluronium hexafluorophosphate (10.13 g, 26.71 mmol) in DCM (75 mL) at 0° C. This mixture was stirred for 10 min at 0° C. then a solution of intermediate 572 (7.5 g, 15.48 mmol) in DCM (345 mL) was added. The reaction was stirred at 0° C. for 45 min. A 10% aqueous solution of $NH_4Cl$ was added and this mixture was extracted twice with DCM. The organic layer was decanted on Chromabond® and the solvent was evaporated until dryness. This product was purified by preparative LC (Irregular $SiO_2$ 15-40 μm 320 g GraceResolv®, mobile phase Gradient from: 100% DCM to 88% DCM, 12% MeOH (22% $NH_4OH$). The pure fractions were collected and the solvent was evaporated until dryness. The residue was purified by preparative LC (Irregular $SiO_2$ 15-40 μm 320 g GraceResolv®, mobile phase Gradient from: 60% Heptane, 40% AcOEt to 55% Heptane, 20% AcOEt, 25% MeOH (2% $NH_4OH$). The pure fractions were collected, celite was added and the solvent was evaporated until dryness. A purification was performed via Reverse phase (solid deposit, Stationary phase: YMC ODS-25 300 g, Mobile phase: Gradient from 85% $NH_4HCO_3$ 0.2%, 15% ACN to 45% $NH_4HCO_3$ 0.2%, 55% ACN). The pure fractions were collected and the solvent was evaporated until dryness. A final purification was performed via achiral SFC (Stationary phase: 2-Ethylpyridine 5 μm 150*30 mm, Mobile phase: 87% $CO_2$, 13% MeOH (0.9% $iPrNH_2$)) to give compound 141 (2730 mg, 32%).

Preparation of Compound 142 (Corresponds to Compound 128)

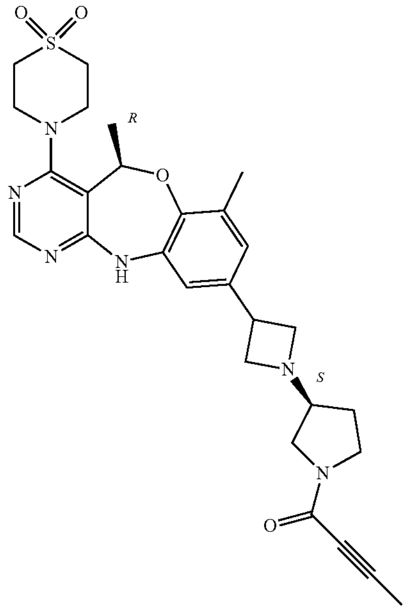

Diisopropylethylamine (13.9 mL, 81.71 mmol) was added to a suspension of 2-butynoic acid (1.65 g, 19.61 mmol) and O-(1H-benzotriazol-1-yl)-N,N,N',N'-tetramethyluronium hexafluorophosphate (8.7 g, 22.88 mmol) in DCM (100 mL) at 0° C. under nitrogen. The reaction mixture was stirred for 10 min. A solution of intermediate 573 (7.92 g, 16.34 mmol) in DCM (350 mL) was added at 0° C. and the reaction mixture was stirred for 45 min at rt. Water, a 10% aqueous solution of $NH_4Cl$ and DCM were added. The mixture was extracted 3 times with DCM. The organic layer was decanted, dried over $MgSO_4$, filtered and the solvent was evaporated. The crude material was purified by chromatography ($SiO_2$, Buchi, 220 g, eluent: from 100% DCM to 93% DCM, 7% MeOH, 0.7% $NH_4OH$). The pure fractions were collected and the solvent was evaporated. The product was purified by reverse phase (YMC, solid deposit (Celite®); 300 g; eluent: from 75% $NH_4HCO_3$ aq (0.2%), 25% ACN to 35% $NH_4HCO_3$ aq (0.2%), 65% ACN). The pure fractions were collected and the solvent was evaporated. DCM and water were added, the mixture was filtered through Chromabond® and the filtrate was evaporated to give compound 142 5.15 g 57%).

Preparation of Compound 144

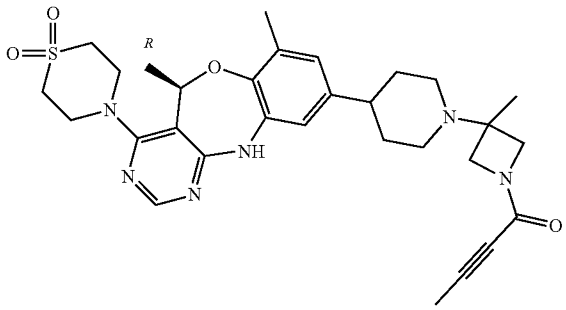

A solution of intermediate 574 (536 mg, 1.05 mmol) and 2-butynoic acid (105 mg, 1.26 mmol) in DCM (23 mL) and diisopropylethylamine (0.907 mL, 5.19 mmol) was cooled down to 0° C. and treated with O-(1H-benzotriazol-1-yl)-N,N,N',N'-tetramethyluronium hexafluorophosphate (595 mg, 1.57 mmol). The reaction mixture was stirred at 0° C. for 1 h, then diluted with a saturated aqueous solution of $NaHCO_3$ and DCM. The organic layer was separated, dried over $MgSO_4$, filtered and evaporated in vacuo. The residue was purified by preparative LC (irregular $SiO_2$ 40 μm, 80 g Buchi, liquid loading (DCM), mobile phase gradient: DCM/MeOH from 100/0 to 90/10, 15 CV). The fraction containing product were combined and evaporated. The product was triturated in $Et_2O$ to afford a solid, which was dried in vacuo to give compound 144 (158 mg, 26%) as a white powder.

Example B5

Preparation of Compound 150

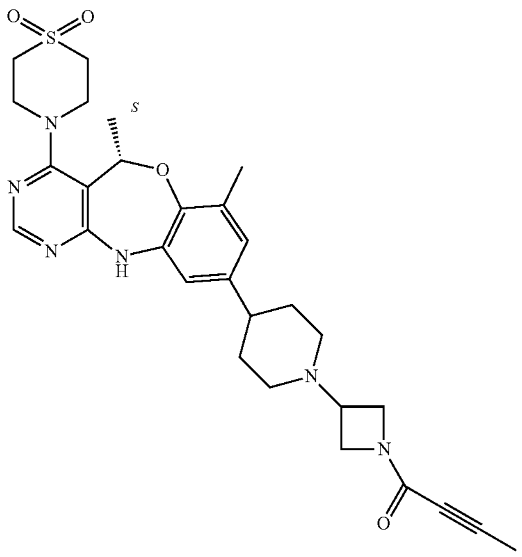

Intermediate 375 (3.992 g, 9 mmol), intermediate 86 (2.461 g, 17.945 mmol), sodium triacetoxyborohydride (3.814 g, 17.997 mmol) and AcOH (939.51 μL, 1.049 g/mL, 16.411 mmol) in anhydrous DCM (113.741 mL) were stirred at rt for 12 h. Water was added and the reaction mixture was extracted twice with DCM. The combined organic layers were washed with brine, dried over $MgSO_4$, filtered and evaporated. The resultant residue was purified via preparative LC (Stationary phase: irregular SiOH 35-70 μm 40 g, Mobile phase: gradient from 100% DCM to 90% DCM, 10% MeOH, 0.1% $NH_4OH$). The pure fractions were collected and the solvent was evaporated to afford a solid (4.8 g) that was further purified via chiral SFC (Stationary phase: CHIRALCEL OD-H 5 μm 250*30 mm, Mobile phase: 50% $CO_2$, 50% EtOH (0.3% $iPrNH_2$)) to afford 3.9 g of product. This material was crystallized from MeCN, dried at 70° C. for 24 h under vacuum to give the final compound (3 g, 59%).

Preparation of Compound 149

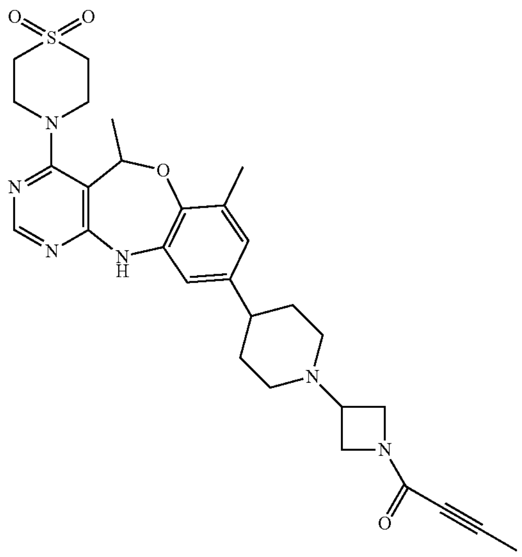 [SMILES: CC#CC(=O)N1CC(N2CCC(c3cc(C)c4c(c3)Nc3ncnc(N5CCS(=O)(=O)CC5)c3C(C)O4)CC2)C1]

Intermediate 407 (2.85 g, 6.425 mmol), intermediate 86 (1.757 g, 12.811 mmol), sodium triacetoxyborohydride (2.723 g, 12.848 mmol) and AcOH (0.671 mL, 1.049 g/mL, 11.716 mmol) in anhydrous DCM (80 mL) were stirred at rt for 2 h. Water was added and the reaction mixture was extracted twice with DCM. The combined organic layers were washed with brine, dried over $MgSO_4$, filtered and evaporated to afford the crude residue. A purification was performed via preparative LC (Stationary phase: irregular SiOH 35-70 μm 80 g, Mobile phase: gradient from 100% DCM to 90% DCM, 10% MeOH, 0.1% $NH_4OH$). The pure fractions were collected and the solvent was evaporated, affording the product as a racemate (3.3 g; 91%).

Preparation of Compound 148 and 150

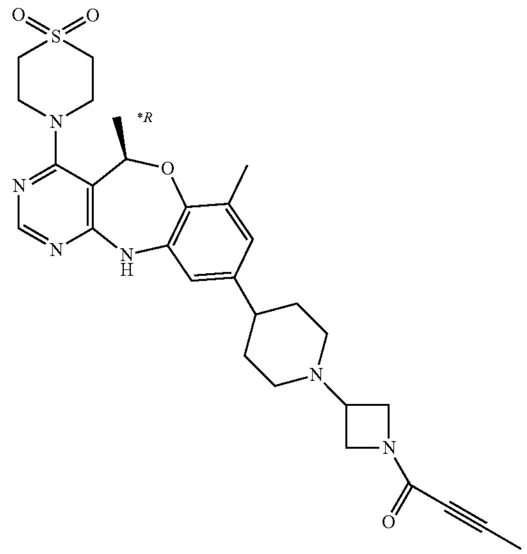

and

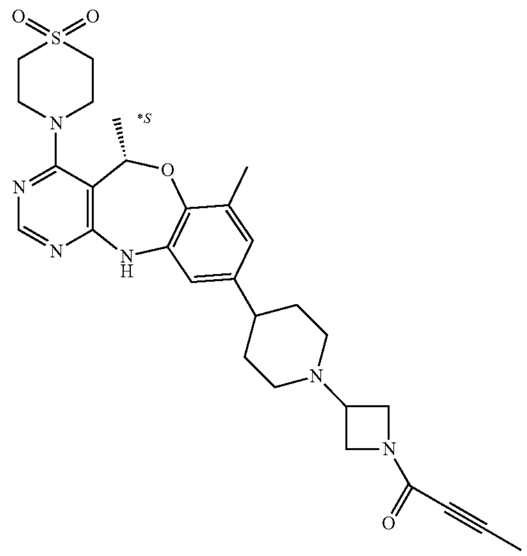

Chiral separation was performed via chiral SFC (Stationary phase: CHIRALCEL OD-H 5 μm 250*30 mm, Mobile phase: 50% $CO_2$, 50% EtOH (0.3% $iPrNH_2$)) to afford a first eluting fraction (1.5 g; 41%) and a second eluting fraction (1.5 g; 41%). The first eluting fraction was crystallized from MeCN and dried under vacuum at 70° C. for 4 h, yielding compound 150 (1.08 g; 30%). The second eluting fraction was crystallized from MeCN and dried under vacuum at 70° C. for 4 h, yielding compound 148 (1.11 g; 31%).

The compounds in the Table below were prepared by using an analogous method starting from the respective starting materials.

| compound number | Structure | Mass (mg) | Yield (%) |
|---|---|---|---|
| Compound 151 | 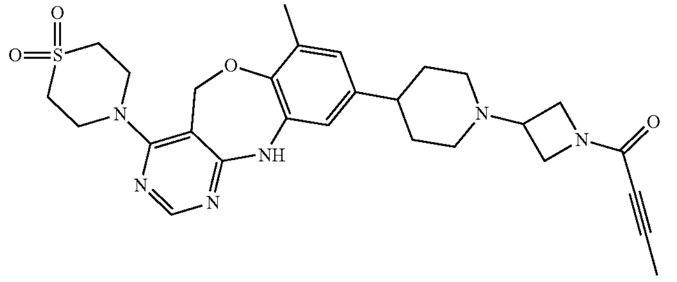 [SMILES: CC#CC(=O)N1CC(N2CCC(c3cc(C)c4c(c3)Nc3ncnc(N5CCS(=O)(=O)CC5)c3CO4)CC2)C1] from intermediate 86 and intermediate 377 | 2950 | 55 |
| Compound 152 | 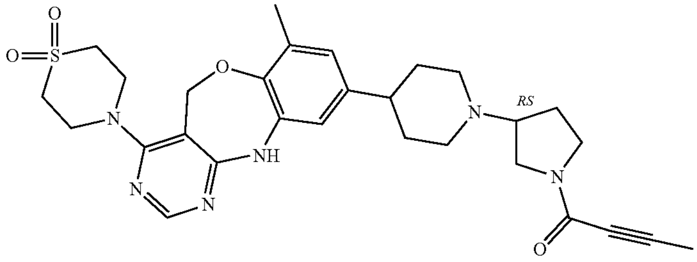 [SMILES: CC#CC(=O)N1CCC(N2CCC(c3cc(C)c4c(c3)Nc3ncnc(N5CCS(=O)(=O)CC5)c3CO4)CC2)C1] from intermediate 377 and intermediate 87 | 2700 | 51 |
| Compound 154 | 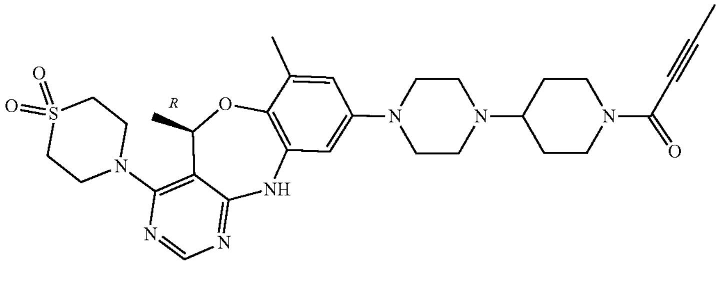 from intermediate 88 & intermediate 409 | 172 | 57 |
| Compound 155 | 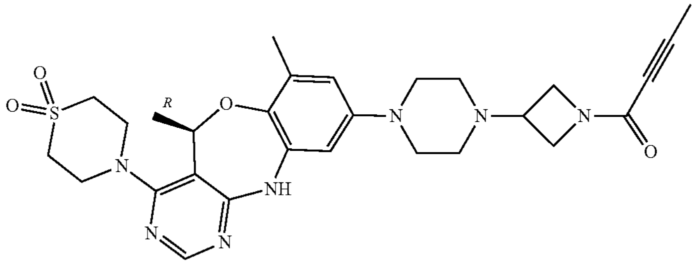 from intermediate 86 & intermediate 409 | 95 | 32 |

-continued

| compound number | Structure | Mass (mg) | Yield (%) |
|---|---|---|---|
| Compound 156 | 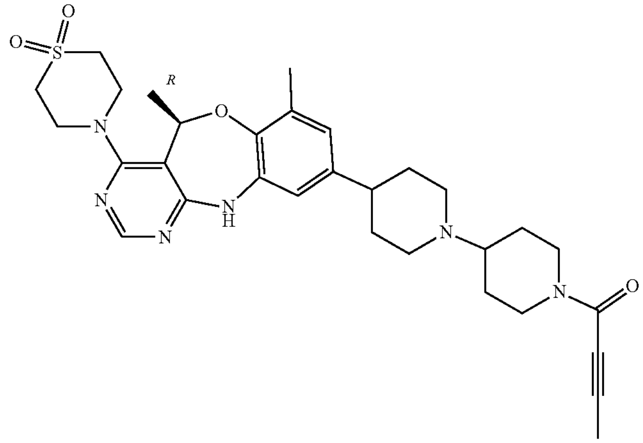 from intermediate 408 and intermediate 88 | 286 | 65 |

Example B6

Preparation of Compound 157 (Compound 148 Citric Acid Salt)

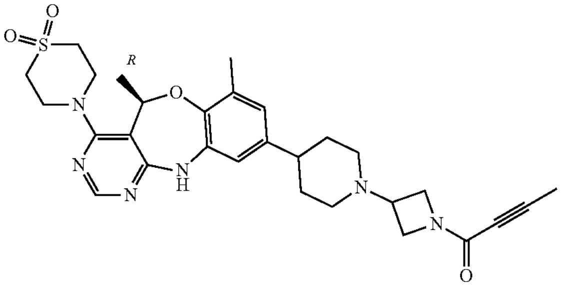

A mixture of compound 148 (125 mg, 0.222 mmol) and citric acid (42.6 mg, 0.222 mmol) in MeOH (3 mL) was stirred at rt for 1 h. The reaction mixture was concentrated in vacuo to give 161 mg of the citric acid salt (96%) as a white solid.

Preparation of Compound 158 (Compound 148 HCl Salt)

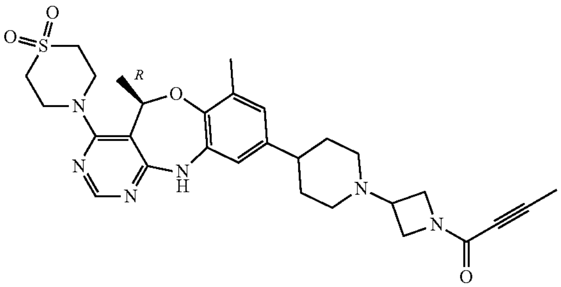

A mixture of compound 148 (114 mg, 0.202 mmol) and HCl solution (4M in dioxane, 101 µL, 0.404 mmol) in MeOH (1.4 mL) was stirred at rt for 1 h. The reaction mixture was concentrated in vacuo to give 112 mg of the HCl salt (87%) as a pale yellow solid.

Example B7

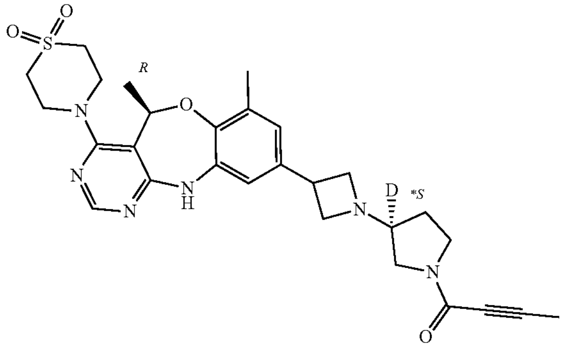

Preparation of Compound 159

Intermediate 376 (260 mg, 0.626 mmol), intermediate 87 (189.18 mg, 1.251 mmol), AcOH (60.9 µL, 1.049 g/mL, 1.064 mmol) and sodium cyanoborodeuteride (82.42 mg, 1.251 mmol) were stirred together in anhydrous DCM (6.2 mL) and MeOH (0.6 mL) at room temperature. The reaction mixture was stirred at room temperature for 12 h. The reaction mixture was diluted with DCM and washed with a saturated solution of $NaHCO_3$(aq). The organics were dried over $MgSO_4$, filtered and evaporated in vacuo to give the crude product. A purification was performed via preparative LC (Stationary phase: irregular SiOH 15-40 µm 40 g Grace, Mobile phase: gradient from 100% DCM to 90% DCM, 10% MeOH, 0.5% $NH_4OH$). The pure fractions were combined and the solvent was evaporated to afford the product as a mixture of diastereoisomers (280 mg; 81%). A separation was performed via chiral SFC (Stationary phase: Whelk-01 (S,S) 5 µm 250*30 mm, Mobile phase: 40% $CO_2$, 60% mixture of MeOH/DCM 90/10 v/v (+0.3% $iPrNH_2$)) affording 168 mg of mixed fractions and a pure fraction of compound 159, that was freeze dried with ACN/water to give the product (53 mg, yield 15%). Common retention time in analytical chiral sfc with compound 128 supports diastereomeric assignment.

The compounds in the Table below were prepared by using an analogous method starting from the respective starting materials.

| compound number | Structure | Mass (mg) | Yield (%) |
|---|---|---|---|
| Compound 160 | 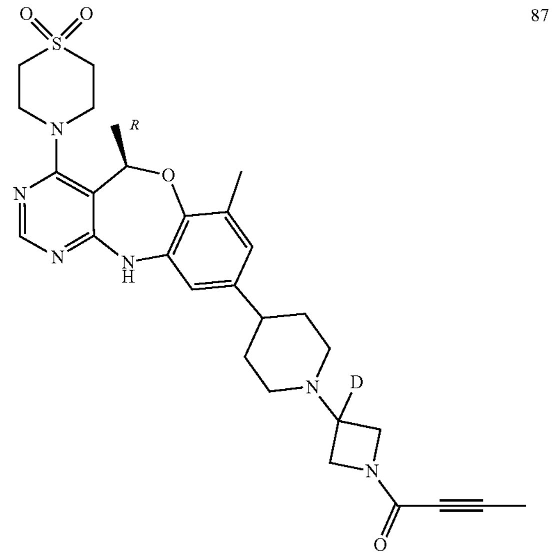 N from intermediate 408 and intermediate 86 | 87 | 34 |

Example B8

Preparation of Compound 161 and 162: Compound 161 and Compound 162

*trans*

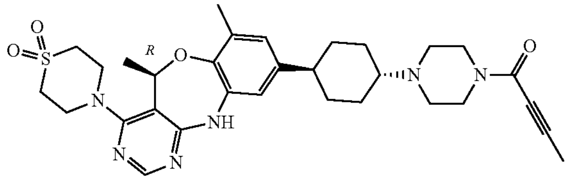

and

*cis*

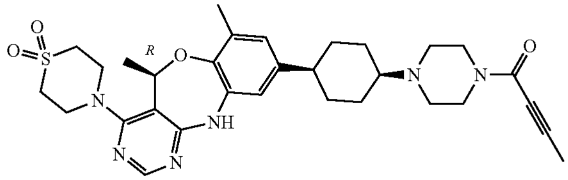

Di-isopropylethylamine (325 µL, 0.75 g/mL, 1.88 mmol) and intermediate 418 (215 mg, 0.471 mmol) were added to a mixture of intermediate 85 (420 mg, 1.01 mmol) in DCM (4.5 mL). The mixture was stirred at rt for 4 h. Sodium triacetoxyborohydride (250 mg, 1.18 mmol) was added and the reaction mixture was stirred at rt for 18 h. Water and DCM were added. The layers were separated and the aqueous layer was extracted with DCM. The combined organic layers were washed with brine, dried over $MgSO_4$, filtered and concentrated to give 353 mg of crude product. The crude material was purified by reverse phase (Stationary phase: YMC-actus Triart C18 10 µm 30*150 mm, Mobile phase gradient: 0.2% aqueous $NH_4HCO_3$/MeCN: from 65/35 to 15/85). The fractions containing product were evaporated to give compound 161 (63 mg; 18%) as a white solid and compound 162 (138 mg; 40%) as a white solid.

Example B9

Preparation of Compound 163

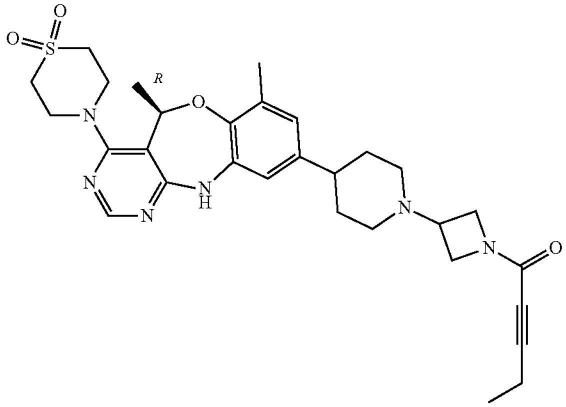

A mixture of intermediate 628 (200 mg, 0.389 mmol), 2-pentynoic acid (45.8 mg, 0.467 mmol) and di-isopropylethylamine (332 µL, 0.75 g/mL, 1.93 mmol) in DCM (4 mL) was stirred at 0° C. 1-Propanephosphonic anhydride (T3P) (582 µL, 1.069 g/mL, 0.977 mmol) was added slowly at 0° C. The mixture was stirred at 0° C. for 10 min and then at rt for 3 h. A sat. aqueous solution of $NaHCO_3$ (aq) and EtOAc were added. The layers were separated. The aqueous layer was extracted with EtOAc. The combined organic layers were washed with brine, dried over $MgSO_4$, filtered, and concentrated in vacuo. The resultant residue was purified by preparative LC (irregular SiOH 15-40 μm, 24 g Buchi, liquid loading (DCM), mobile phase gradient: from DCM/MeOH 99/1 to 95/5, 10 Column Volumes). The fractions containing pure product were combined and evaporated to give the insufficiently pure product (143 mg) as a white solid. The material was further purified by preparative LC (spherical C18, 25 μm, 40 g YMC-ODS-25, liquid loading (MeOH), mobile phase gradient 0.200 aq. $NH_4HCO_3$/MeCN from 75:25 to 35:65 in 10 Column Volumes). The fractions containing pure product were combined and evaporated in vacuo to give the desired product as a white solid (122 mg, 54%).

The compounds in the Table below were prepared by using an analogous method starting from the respective starting materials.

| compound number | Structure | Mass (mg) | Yield (%) |
|---|---|---|---|
| Compound 163 | 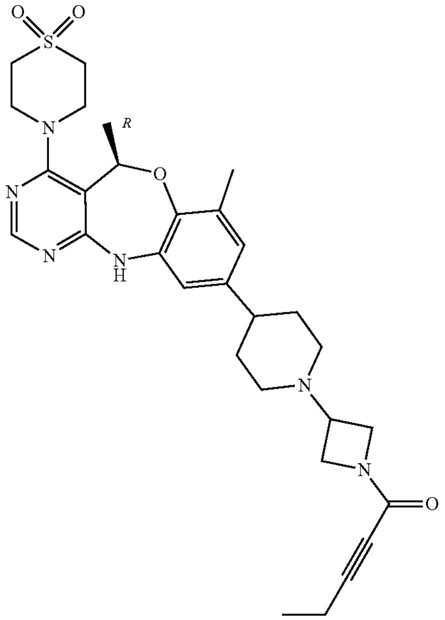 from intermediate 628 and 2-pentynoic acid | 122 | 54 |
| Compound 164 | 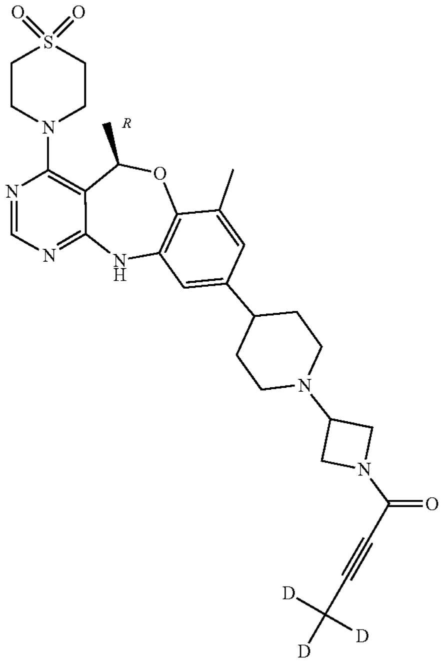 from intermediate 628 and intermediate 119 | 120 | 54 |

-continued
| compound number | Structure | Mass (mg) | Yield (%) |
| --- | --- | --- | --- |
| Compound 165 | 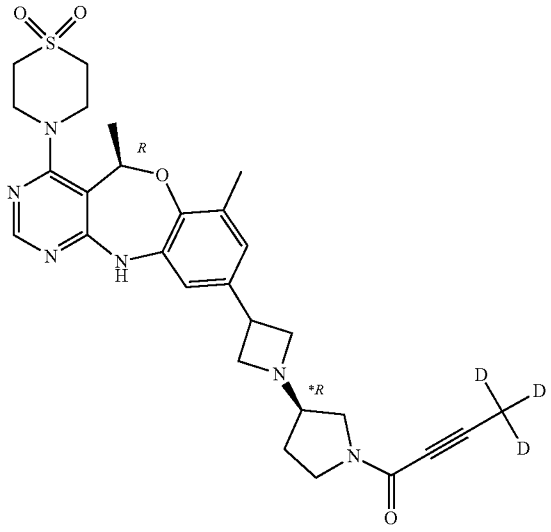 from intermediate 629 and intermediate 119 | 27 | 68 |
| Compound 166 | 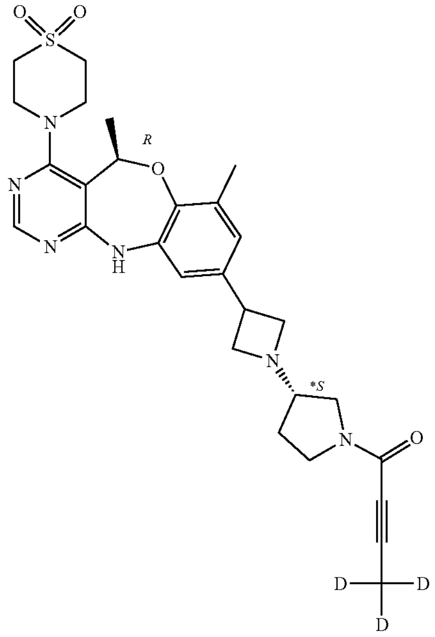 from Intermediate 630 and intermediate 119 | 32 | 72 |

-continued
| compound number | Structure | Mass (mg) | Yield (%) |
|---|---|---|---|
| Compound 167 | 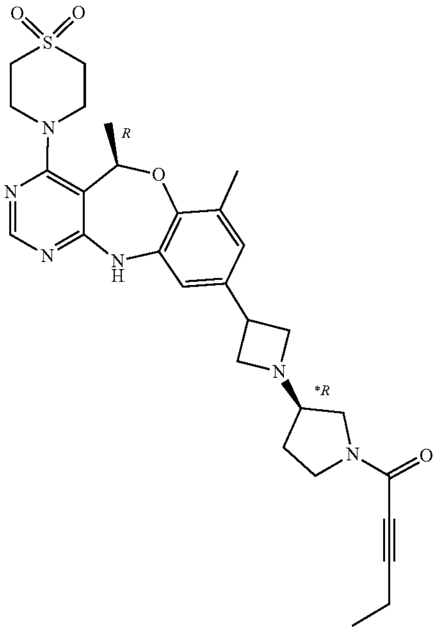 from Intermediate 629 and 2-pentynoic acid | 42 | 82 |
| Compound 168 | 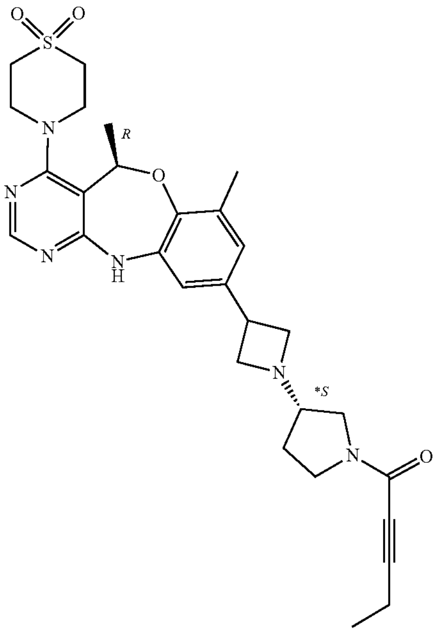 from Intermediate 630 and 2-pentynoic acid | 38 | 91 |

-continued
| compound number | Structure | Mass (mg) | Yield (%) |
|---|---|---|---|
| Compound 169 | 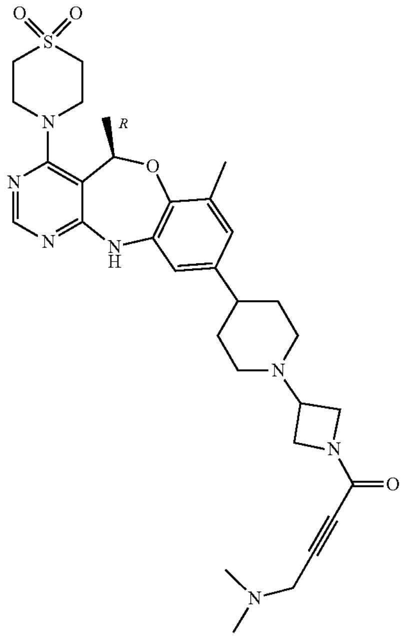 from intermediate 628 and intermediate 120 | 115 | 49 |
| Compound 170 | 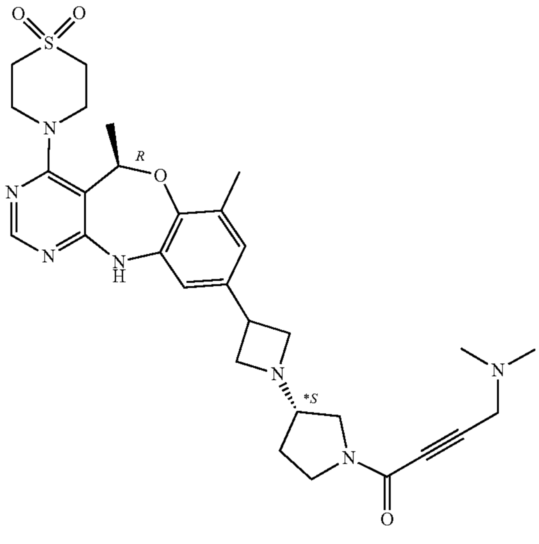 from Intermediate 630 and intermediate 120 | 35 | 62 |

-continued
| compound number | Structure | Mass (mg) | Yield (%) |
| --- | --- | --- | --- |
| Compound 171 | 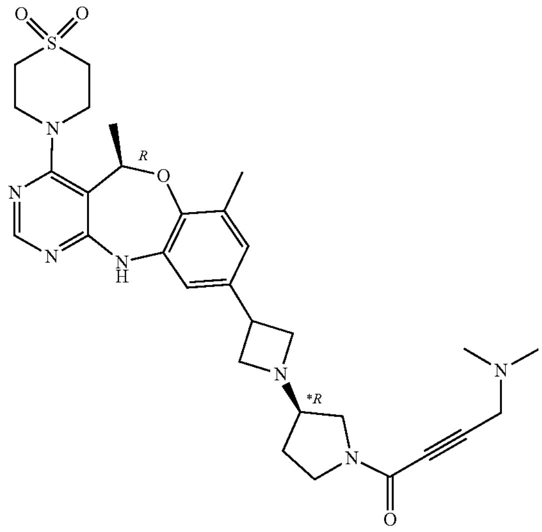 from Intermediate 629 and intermediate 120 | 27 | 57 |
| Compound 172 | 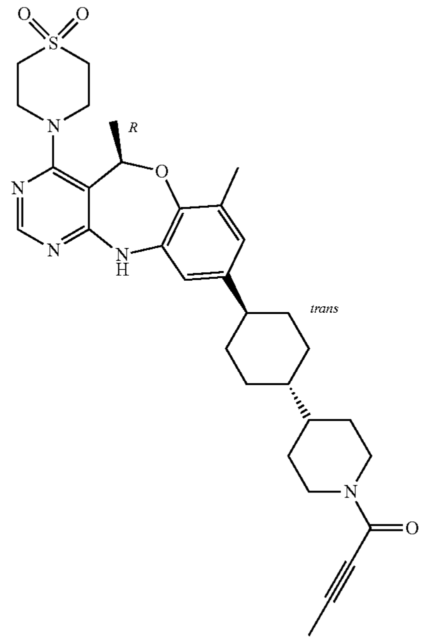 from intermediate 361 and 2-butynoic acid | 145 | 43 |

-continued
| compound number | Structure | Mass (mg) | Yield (%) |
| --- | --- | --- | --- |
| Compound 173 | 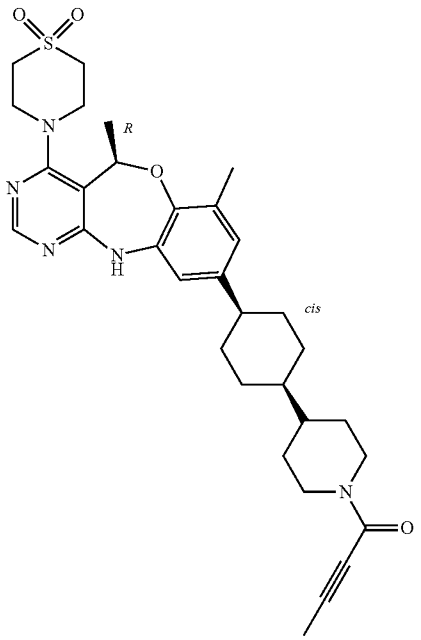 from intermediate 362 and 2-butynoic acid | 115 | 86 |
| Compound 174 | 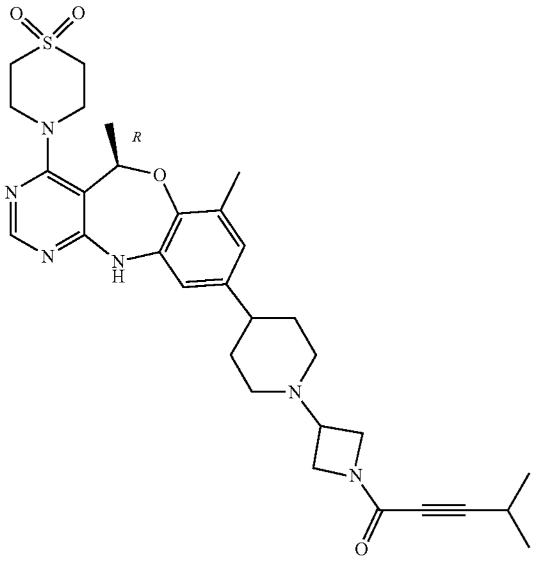 from intermediate 628 and 4-methylpent-2-ynoic acid | 167 | 62 |

-continued
| compound number | Structure | Mass (mg) | Yield (%) |
|---|---|---|---|
| Compound 175 | 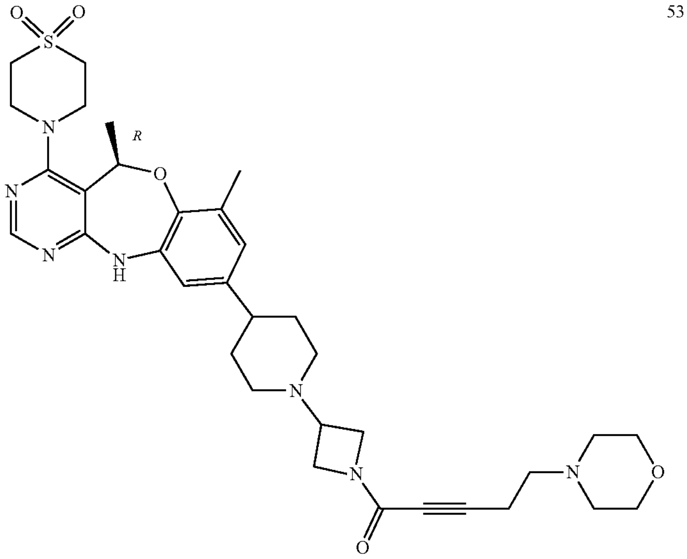 from intermediate 628 and intermediate 121 | 53 | 24 |
| Compound 176 | 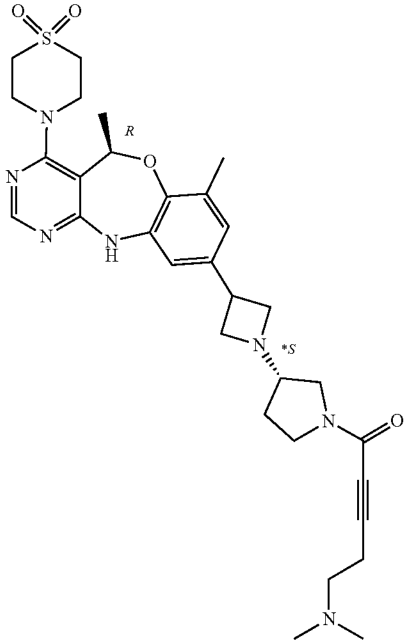 from Intermediate 630 and intermediate 122 | 37 | 59 |

-continued
| compound number | Structure | Mass (mg) | Yield (%) |
|---|---|---|---|
| Compound 177 | 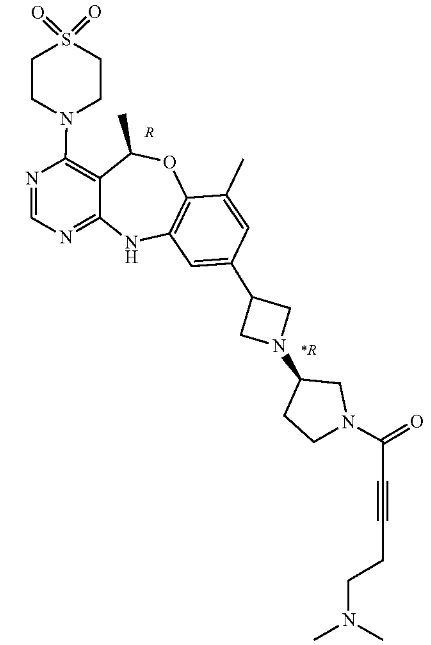 from Intermediate 629 and intermediate 122 | 39 | 62 |
| Compound 178 | 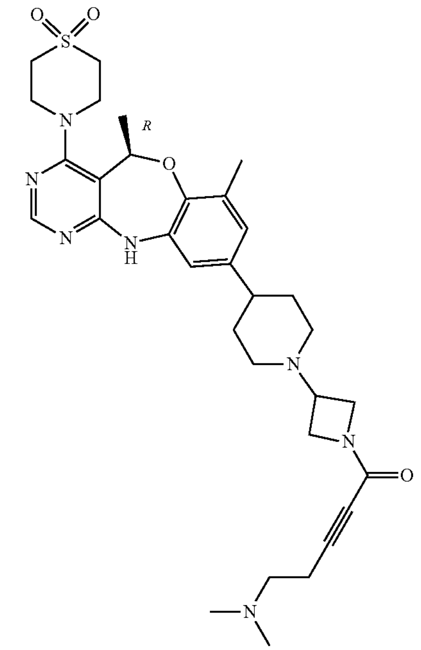 from intermediate 628 and intermediate 122 | 60 | 29 |

-continued
| compound number | Structure | Mass (mg) | Yield (%) |
| --- | --- | --- | --- |
| Compound 179 | 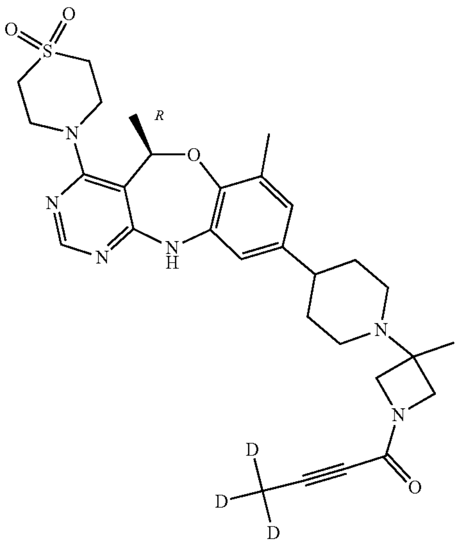 from Intermediate 631 and intermediate 119 | 135 | 51 |
| Compound 180 | 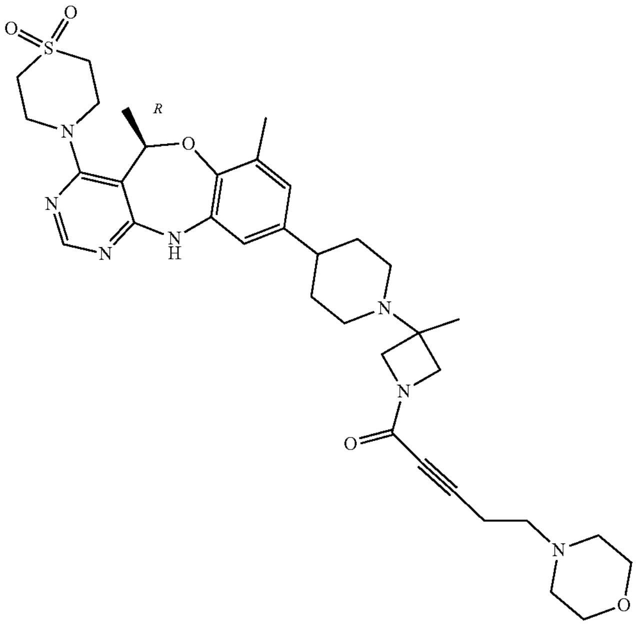 from Intermediate 631 and intermediate 121 | 125 | 58 |

-continued
| compound number | Structure | Mass (mg) | Yield (%) |
|---|---|---|---|
| Compound 181 | 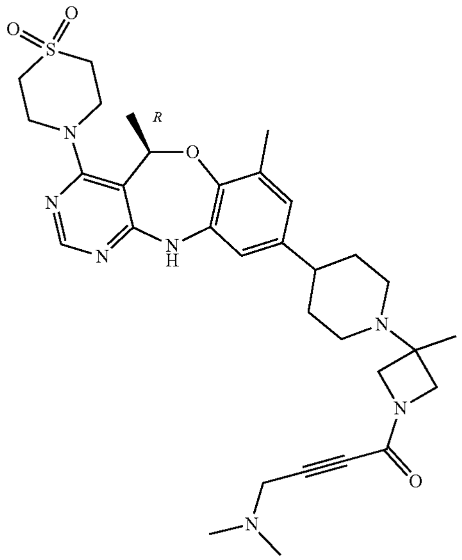 from Intermediate 631 and intermediate 120 | 125 | 58 |
| Compound 182 | 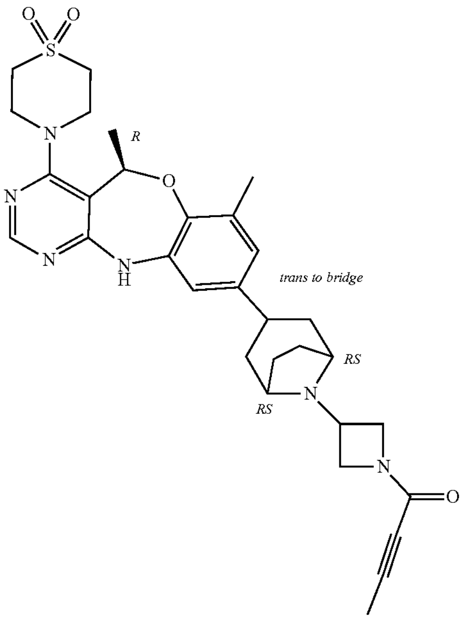 from intermediate 363 and 2-butynoic acid | 28 | 47 |

-continued
| compound number | Structure | Mass (mg) | Yield (%) |
| --- | --- | --- | --- |
| Compound 183 | 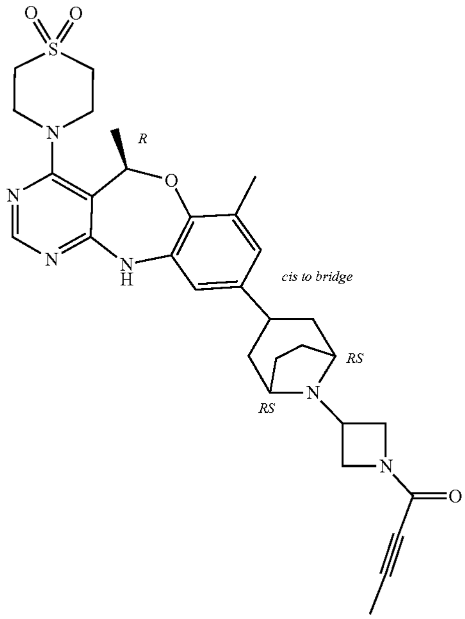 from intermediate 364 and 2-butynoic acid | 111 | 62 |
| Compound 184 | 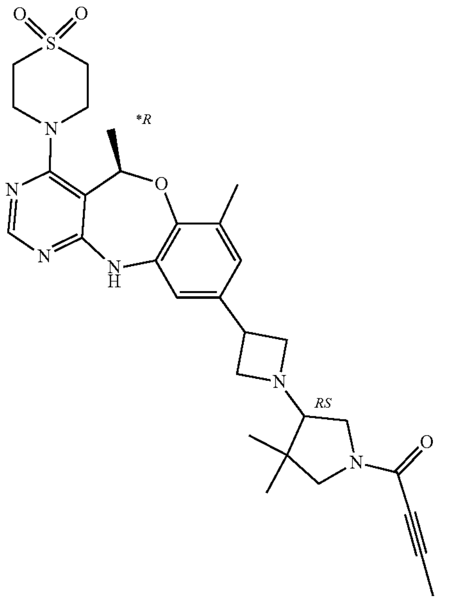 [SMILES: CC#CC(=O)N1CC(N2CC(c3cc(C)c4c(c3)Nc3ncnc(N5CCS(=O)(=O)CC5)c3[C@@H](C)O4)C2)C(C)(C)C1] from intermediate 644 and 2-butynoic acid | 88 | 50 |

-continued
| compound number | Structure | Mass (mg) | Yield (%) |
|---|---|---|---|
| Compound 185 | 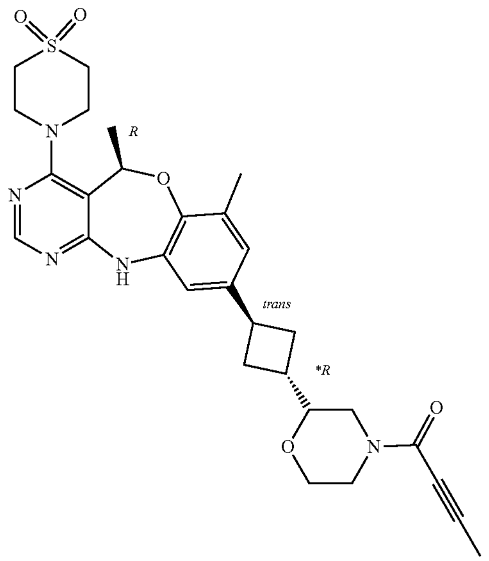 from intermediate 645 and 2-butynoic acid | 25 | 49 |
| Compound 186 | 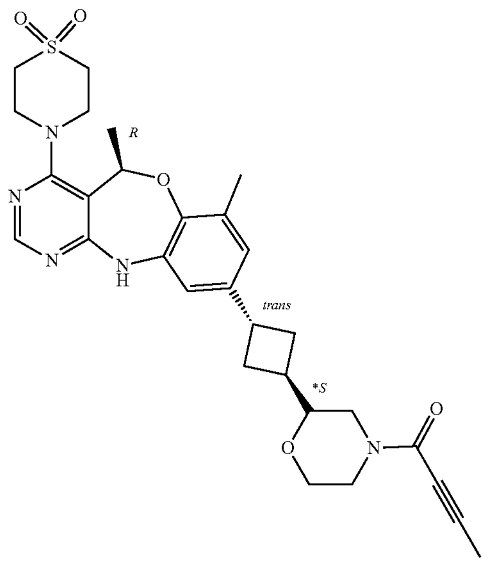 from intermediate 646 and 2-butynoic acid | 22 | 44 |

-continued
| compound number | Structure | Mass (mg) | Yield (%) |
|---|---|---|---|
| Compound 187 | 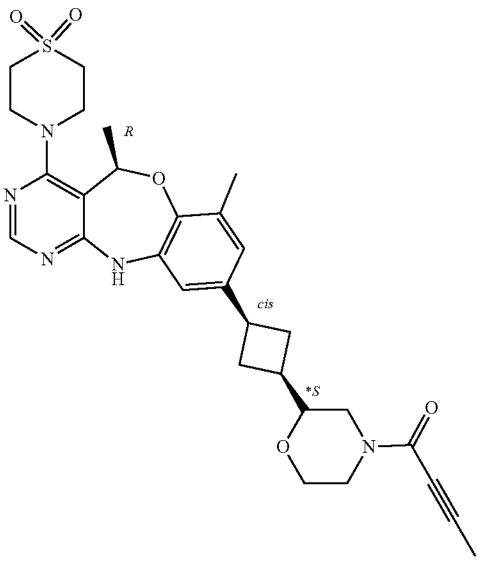 from intermediate 648 and 2-butynoic acid | 40 | 79 |
| Compound 188 | 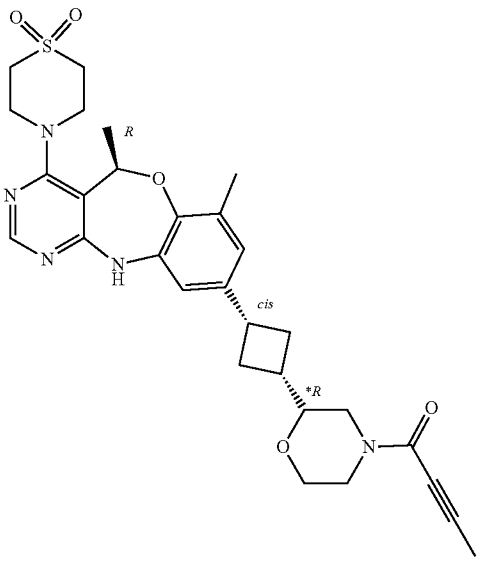 from intermediate 647 and 2-butynoic acid | 39 | 60 |

Example B10

Compound 189 & Compound 190

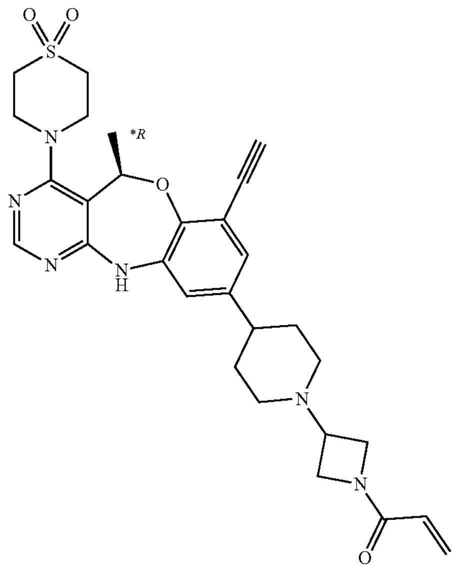

and

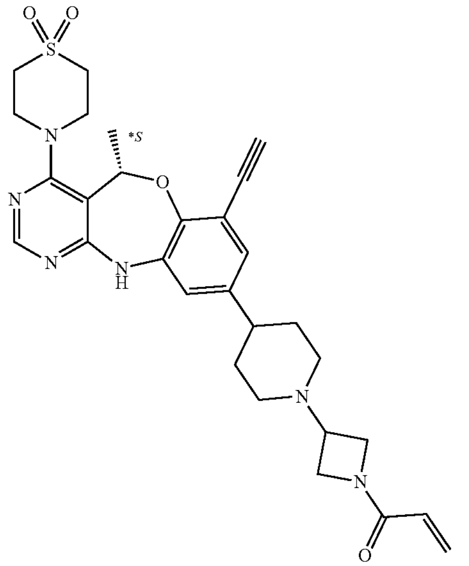

Cesium fluoride (76 mg, 0.50 mmol) was added to a solution of intermediate 682 (180 mg, 0.25 mmol) in DMF (0.5 mL). The mixture was stirred at 70° C. for 2 h. Water (10 mL) was added, the aqueous layer was extracted with dichloromethane/MeOH 10/1 (3*10 mL). The combined organic layers were concentrated in vacuo. The crude material was purified by reverse phase (Xtimate C18 150*25 mm*5 um, water (0.225% $HCOONH_4$)/MeCN 55/45 to 25/75) to give the racemic product (76 mg). The enantiomers were separated via chiral SFC (Stationary phase: CHIRALCEL OD (250 mm*30 mm, 10 um), Mobile phase: 45% $CO_2$, 55% EtOH (0.05% DEA)). The two residues were suspended in water (5 mL) and lyophilized to give compound 189 (19 mg, 14%) and compound 190 (17 mg, 12%).

| compound number | Structure | Mass (mg) | Yield (%) |
|---|---|---|---|
| Compound 189 | 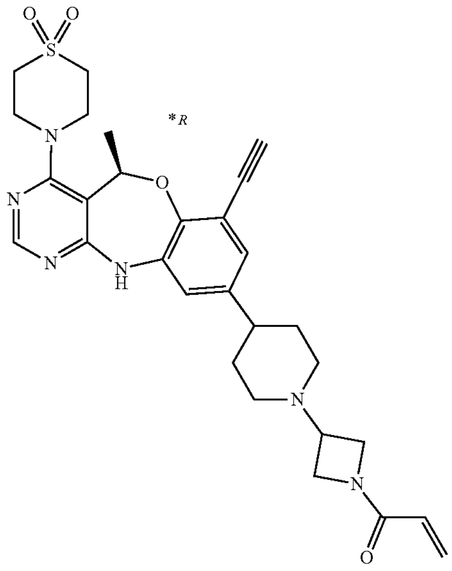 from intermediate 682. Chiral separation was via SFC (Stationary phase: DAICEL CHIRALCEL OD (250 mm*30 mm, 10 um), Mobile phase: 45% $CO_2$, 55% Ethanol (0.05% DEA) | 19 | 14 |
| Compound 190 | 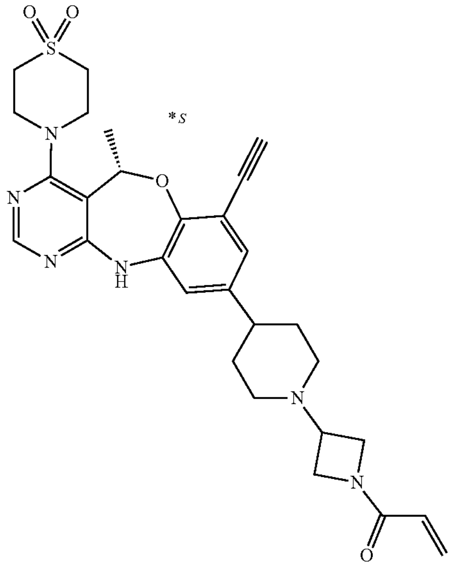 from intermediate 682. Chiral separation was via SFC (Stationary phase: DAICEL CHIRALCEL OD (250 mm*30 mm, 10 um), Mobile phase: 45% $CO_2$, 55% Ethanol (0.05% DEA) | 17 | 12 |

-continued
| compound number | Structure | Mass (mg) | Yield (%) |
| --- | --- | --- | --- |
| Compound 191 | 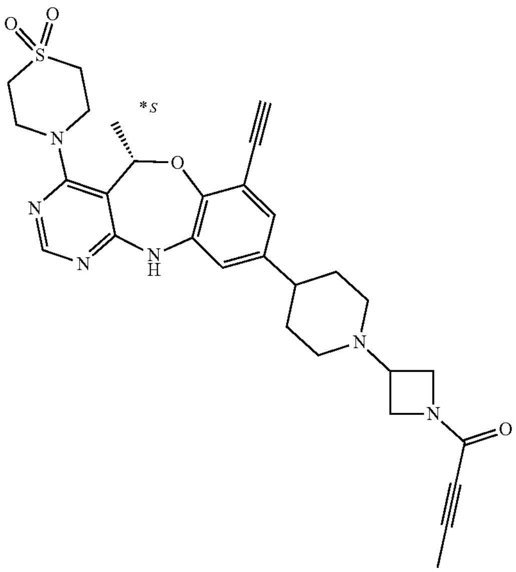 from intermediate 684. Chiral separation was via SFC (Stationary phase: DAICEL CHIRALCEL OD (250 mm*30 mm, 10 um), Mobile phase: 45% $CO_2$, 55% Ethanol (0.1% $NH_3$•$H_2O$). | 17 | 18 |
| Compound 192 | 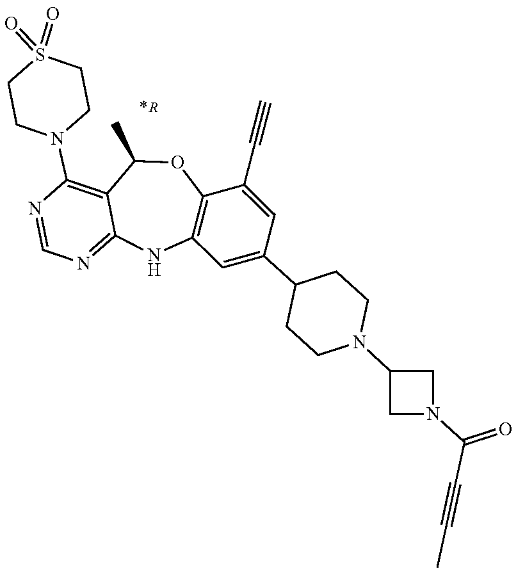 from intermediate 684. Chiral separation was via SFC (Stationary phase: DAICEL CHIRALCEL OD (250 mm*30 mm, 10 um), Mobile phase: 45% $CO_2$, 55% Ethanol (0.1% $NH_3$•$H_2O$). | 17 | 18 |

-continued
| compound number | Structure | Mass (mg) | Yield (%) |
|---|---|---|---|
| Compound 193 | 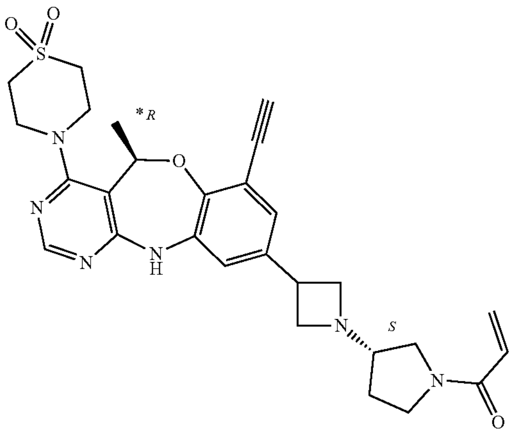 from intermediate 683. Chiral separation was via SFC (Stationary phase: DAICEL CHIRALCEL OD-H (250 mm*30 mm, 5 um), Mobile phase: 60% $CO_2$, 40% Methanol (0.1% $NH_3$•$H_2O$). | 14 | 15 |
| Compound 194 | 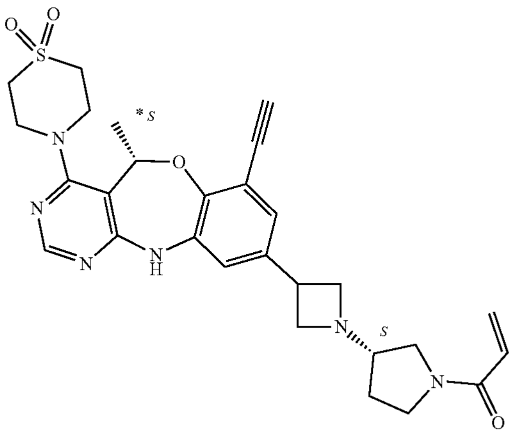 from intermediate 683. Chiral separation was via SFC (Stationary phase: DAICEL CHIRALCEL OD-H (250 mm*30 mm, 5 um), Mobile phase: 60% $CO_2$, 40% Methanol (0.1% $NH_3$•$H_2O$). | 13 | 13 |

Example B11

Preparation of Compound 195

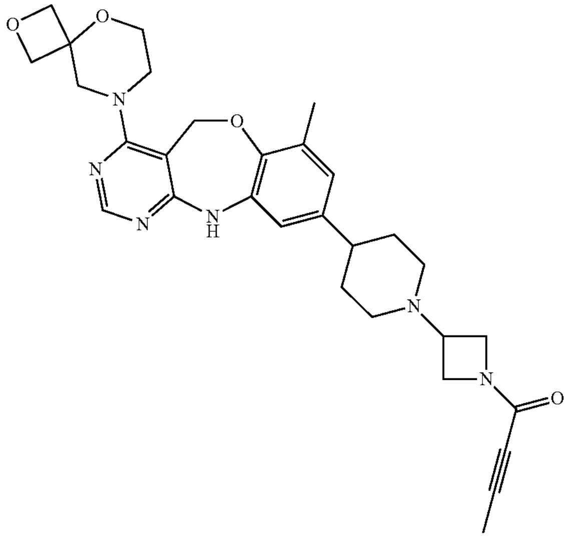 [SMILES: CC#CC(=O)N1CC(N2CCC(c3cc(C)c4c(c3)Nc3ncnc(N5CCOC6(COC6)C5)c3CO4)CC2)C1]

A solution of intermediate 686 (210 mg, 0.465 mmol), 2,5-dioxa-8-azaspiro[3.5]nonane TFA salt (282.5 mg, 1.16 mmol) and DIPEA (400.4 µL, 0.75 g/mL, 2.32 mmol) in ACN (4.85 mL) in a sealed tube was stirred at 140° C. using one single mode microwave (Biotage Initiator EXP 60) with a power output ranging from 0 to 400 W for 40 min. [fixed hold time]. Water was added and the reaction mixture was extracted with DCM, dried over $MgSO_4$, filtered and evaporated. Purification was performed via preparative LC (solid deposit) (Stationary phase: irregular SiOH 35-70 µm 40 g, Mobile phase: gradient from 100% DCM to 88% DCM, 12% MeOH, 0.1% $NH_4OH$). The pure fractions were collected and the solvent was evaporated. A second purification was performed via reverse phase (solid deposit) (Stationary phase: YMC-DispoPack AT ODS-25:40 g, Mobile phase: gradient from 90% $HCCONH_3$ 0.2% in water, 10% ACN to 40% $HCCONH_3$ 0.2% in water, 60% ACN). The pure fractions were collected and the solvent was evaporated. The residue was taken up into DCM, dried over $MgSO_4$, filtered and evaporated. The residue was freeze dried with ACN and water, to afford the product (17 mg, yield 7%).

Analytical Part

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, CL.), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector, "MSD" Mass Selective Detector.

TABLE

LCMS Method codes (Flow expressed in mL/min; column temperature (T) in ° C.; Run time in minutes).

| Method code | Instrument | Column | Mobile phase | gradient | Flow (mL/min) T (° C) | Run time |
|---|---|---|---|---|---|---|
| Method 1 | Waters: Acquity UPLC ® - DAD and Quattro Micro ™ | Waters: BEH C18 (1.7 µm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |
| Method 2 | Waters: Acquity UPLC ® H-Class - DAD and SQD 2 | Waters: BEH C18 (1.7 µm, 2.1 × 100 mm) | A: 95% $CH_3COONH_4$ 7 mM/5% $CH_3CN$, B: $CH_3CN$ | From 84.2% A to 10.5% A in 2.18 min, held for 1.94 min, back to 84.2% A in 0.73 min, held for 0.73 min. | 0.343 40 | 6.1 |
| Method 3 | Waters: Acquity UPLC ® H-Class - DAD and QDa | BEH ® - C18 (1.7 µm, 2.1 × 100 mm) | A: 95% $CH_3COONH_4$ 7 mM/5% $CH_3CN$, B: $CH_3CN$ | 95% A to 5% A in 1 min, held for 1.6 min, back to 95% A in 1.2 min, held for 0.5 min. | 0.5 40 | 3.3 |

TABLE-continued

LCMS Method codes (Flow expressed in mL/min; column temperature (T) in ° C.; Run time in minutes).

| Method code | Instrument | Column | Mobile phase | gradient | Flow (mL/min) T (° C) | Run time |
|---|---|---|---|---|---|---|
| Method 4 | Waters: ZMD quadripole - Waters 1525 LC system with DAD detector or Sedex 85 evaporative light scattering detector | Luna - C18 (3 µm, 30 × 4.6 mm) | A: 95% Water (with 0.1% $CH_3COOH$), B: $CH_3CN$ (with 0.1% $CH_3COOH$) | 95% A held 0.5 min, then from 95% A to 5% A 4.0 min, held for 1.0 min. | 2<br>40 | 5.5 |
| Method 5 | Waters: Micromass ZQ2000 - Waters Acquity UPLC system equipped with PDA detector | Acquity HST - C 18 (1.8 µM, 2.1 × 100 mm) | A: 95% Water (with 0.1% $CH_3COOH$), B: $CH_3CN$ (with 0.1% $CH_3COOH$) | 95% A held 0.4 min, then from 95% A to 5% A 5.2 min, held for 0.8 min. | 0.4<br>40 | 6.4 |
| Method 6 VILLA | Agilent 1100 series DAD LC/MS G1956A | YMC ODS-AQ C18 (50 × 4.6 mm, 3.0 µm) | A: 0.1% HCOOH in $H_2O$ B: $CH_3CN$ | From 95% A to 5% A in 4.8 min, held for 1.0 min, to 90% A in 0.2 min. | 2.6<br>35 | 6.0 |
| Method 7 | Agilent 1260 series equipped with DAD and Agilent G6120B detector | ACE C18 column (3 µM, 3.0 × 50 mm) | A: 100% Water (with 0.05% TFA), B: 100% $CH_3CN$ | 95% A to 0% A in 1.5 min | 2.2 | 2 |
| Method 8 | Agilent 1200 equip with MSD 6110 | Phenomen ex Luna-C18, 50 × 2 mm, 5 µm | A: $H_2O$ (0.1% TFA), B: $CH_3CN$ (0.05% TFA) | 90% A held for 0.8 min then 90% A to 20% A in 3.7 min, held for 2 min, back to 90% A in 2 min, held for 0.5 min. | 0.8<br>50 | 10 |
| Method 9 | Agilent 1200 equip with MSD 6110 | XBridge Shield RP18 (5 µm, 2.1 × 50 mm) | A: $H_2O$ (0.05% $NH_3{\cdot}H_2O$), B: $CH_3CN$ | 100% A held for 1.00 min, then from 100% A to 40% A in 4.00 min, then from 40% A to 5% A in 2.50 min, back to 100% A in 2.00 min. | 0.8<br>40 | 10 |
| Method 10 | Agilent: 1100/1200 - DAD and MSD | Agilent: TC-C18 (5 µm, 2.1 × 50 mm) | A: $CF_3COOH$ 0.1% in water, B: $CF_3COOH$ 0.05% in $CH_3CN$ | 100% A for 1 min, to 40% A in 4 min, to 15% A in 2.5 min, back to 100% A in 2 min. | 0.8<br>50 | 10.5 |
| Method 11 | Agilent 1200 equip with MSD 6110 | Phenomen ex Luna-C18, 50 × 2 mm, 5 µm | A: $H_2O$ (0.1% TFA, B: $CH_3CN$ (0.05% TFA) | 100% A held for 1 mn then 100% A to 40% A in 4 mn then 40% A to 15 % A in 2.5 mn then back to 100% A in 2 mn held for 0.5 min. | 0.8<br>50 | 10 |
| VILLA_2T | Agilent 1260 Infinity DAD TOF-LC/MS G6224A | YMC-pack ODS-AQ C18 (50 × 4.6 mm, 3 µm) | A: 0.1% HCOOH in H2O B: CH3CN | From 95% A to 5% A in 4.8 min, held for 1.0 min, to 95% A in 0.2 min. | 2.6 | 6.8 |
| V6002 V6001 | Waters: Acquity UPLC ® H-Class - DAD and QDa | Waters: BEH C18 (1.7 µm, 2.1 × 100 mm) | A: 95% $CH_3COONH_4$ 7 mM/5% $CH_3CN$, B: $CH_3CN$ | From 85% A to 10% A in 2.1 min, held for 2 min, back to 85% A in 0.8 min, held for 0.7 min. | 0.35<br>40 | 6.1 |

TABLE-continued

| LCMS Method codes (Flow expressed in mL/min; column temperature (T) in ° C.; Run time in minutes). | | | | | | |
|---|---|---|---|---|---|---|
| Method code | Instrument | Column | Mobile phase | gradient | Flow (mL/min) T (° C) | Run time |
| WUXI25 | Agilent: 1100/1200-DAD and MSD | Waters: XB ridge ™ Shield RP18 (5 μm, 2.1 × 50 mm) | A: $NH_4OH$ 0.05% in water, B: $CH_3CN$ | 100% A for 1 min, to 40% A in 4 min, held for 2.5 min, back to 100% A in 2 min. | 0.8 40 | 10.5 |
| WUXI49 | Agilent: 1200-DAD and MSD6110 | Waters: Xbridge-C18, (5 μm, 2.1 × 50 mm) | A: $CF_3COOH$ 0.04% in water, B: $CF_3COOH$ 0.02% in $CH_3CN$ | 100% A for 1 min, to 40% A in 4 min, and then to 15% A in 2.5 min, back to 100% A in 2 min. | 0.8 | 10 |

Melting Point (DSC or K)

For a number of compounds, melting points (MP) were determined with a DSC1 (Mettler-Toledo). Melting points were measured with a temperature gradient of 10° C./minute. Maximum temperature was 350° C. Values are peak values. Indicated in the table as DSC.

For a number of compounds, melting points were obtained with a Kofler hot bench (indicated with (K) in the analytical table), consisting of a heated plate with linear temperature gradient, a sliding pointer and a temperature scale in degrees Celsius.

For a number of compounds, melting points were obtained with an automatic Melting Point Apparatus WRS-2A (indicated with WRS-2A in the analytical table). Melting points were measured with a temperature gradient of 5° C. per minute starting from room temperature to a maximum value of 320° C.

For a number of compounds, melting points were obtained with a Mettler Toledo MP50 apparatus (indicated with MP50 in the analytical table). Melting points were measured with a temperature gradient of 10° C. per minute starting from 50° C. (waiting time 10 second) to a maximum value of 300° C.

For a number of compounds, melting points were obtained with a Mettler Toledo FP72 apparatus (indicated with FP72 in the analytical table). Melting points were measured with a temperature gradient of 10° C. per minute starting from 50° C. (waiting time 10 second) to a maximum value of 300° C.

In the Table below, 'N°' means compound number.

| N° | MP (° C.) | Kofler (K) or DSC or MP50 or FP72 or WRS-2A | Rt | $[M + H]^+$ | LCMS Method |
|---|---|---|---|---|---|
| 1 | 184 | DSC | 2.20 | 477 | 2 |
| 2 | 211 | DSC | 2.14 | 505 | 1 |
| 3 | — | — | 2.10 | 465 | 1 |
| 4 | 151 | DSC | 2.05 | 478 | 2 |
| 5 | — | — | 2.21 | 491 | 2 |
| 6 | — | — | 2.13 | 478 | 1 |
| 7 | 234 | DSC | 2.45 | 477 | 1 |
| 8 | — | — | 2.04 | 499 | 1 |
| 9 | — | — | 2.26 | 463 | 1 |
| 10 | — | — | 2.27 | 463 | 1 |
| 11 | — | — | 2.50 | 505 | 1 |
| 12 | — | — | 2.42 | 505 | 1 |
| 13 | — | — | 2.50 | 505 | 1 |
| 14 | 191 | DSC | 2.26 | 491 | 1 |
| 15 | — | — | 2.41 | 523 | 1 |
| 16 | 151 | DSC | 2.34 | 477 | 1 |
| 17 | — | — | 2.27 | 477 | 1 |
| 18 | — | — | 2.27 | 477 | 1 |
| 19 | — | — | 2.38 | 510 | 1 |
| 20 | — | — | 2.41 | 495 | 1 |
| 21 | — | — | 2.22 | 490 | 1 |
| 22 | | | 2.32 | 477 | 1 |
| 23 | | | 2.32 | 477 | 1 |
| 24 | | | 2.14 | 505 | 1 |
| 25 | | | 2.23 | 505 | 1 |
| 26 | — | — | 2.22 | 509 | 2 |
| 27 | — | — | 2.26 | 509 | 1 |
| 28 | — | — | 2.43 | 509 | 2 |
| 29 | — | — | 2.21 | 509 | 2 |
| 30 | — | — | 1.88 | 526 | 1 |
| 31 | — | — | 1.88 | 526 | 1 |
| 32 | >300° C. | MP50 | 1.83 | 553 | 6 |
| 33 | 193 | MP50 | 1.71 | 475 | 6 |

-continued

| N° | MP (° C.) | Kofler (K) or DSC or MP50 or FP72 or WRS-2A | Rt | [M + H]+ | LCMS Method |
|---|---|---|---|---|---|
| 34 | 213 | MP50 | 1.74 | 491 | 6 |
| 35 | 175 | MP50 | 1.70 | 477 | 6 |
| 36 | 232 | MP50 | 1.86 | 491 | VILLA_2T |
| 37 | 217 | MP50 | 1.74 | 491 | 6 |
| 38 | 151 | Mettler Toledo FP62 | 1.44 | 476 | 6 |
| 39 | 243 | MP50 | 1.58 | 474 | VILLA_2T |
| 40 | 212 | MP50 | 1.86 | 503 | VILLA_2T |
| 41 | 208 | MP50 | 1.85 | 503 | VILLA_2T |
| 42 | >300 | MP50 | 2.02 | 511 | 6 |
| 43 | 296 | MP50 | 1.92 | 559 | 6 |
| 44 | 178 | MP50 | 1.97 | 540 | 6 |
| 45 | 158 | MP50 | 2.20 | 545 | 6 |
| 46 | 175 | MP50 | 1.94 | 509 | 6 |
| 47 | 211 | FP62 | 2.00 | 259 (M + H) +/2 | VILLA_2T |
| 48 | 220 | MP50 | 1.31 | 478 | 6 |
| 49 | 180 | MP50 | 1.93 | 509 | 6 |
| 50 | — | — | 2.36 | 509 | 1 |
| 51 | — | — | 2.36 | 509 | 1 |
| 52 | 245 | MP50 | 1.65 | 504 | 6 |
| 53 | 260 | MP50 | 1.66 | 504 | 6 |
| 54 | — | — | 2.23 | 481 | 1 |
| 55 | — | — | 2.22 | 481 | 1 |
| 56 | — | — | 2.39 | 491 | 1 |
| 57 | — | — | 2.39 | 491 | 1 |
| 58 | 257 | MP50 | 1.28 | 540 | 6 |
| 59 | 259 | MP50 | 1.28 | 568 | 6 |
| 60 | 250 | MP50 | 1.47 | 492 | 6 |
| 61 | >300 | MP50 | 2.03 | 502 | 6 |
| 62 | 253 | MP50 | 1.41 | 492 | 6 |
| 63 | 190 | MP50 | 1.44 | 540 | 6 |
| 64 | >300 | MP50 | 1.41 | 512 | 6 |
| 65 | — | — | 2.23 | 553 | 1 |
| 66 | 118 | MP50 | 1.87 | 505 | 6 |
| 67 | — | — | 2.54 | 514 | 1 |
| 68 | — | — | 2.35 | 533 | 1 |
| 69 | — | — | 2.51 | 514 | 1 |
| 70 | — | — | 2.26 | 567 | 1 |
| 71 | 256 | FP62 | 1.69 | 479 | VILLA_2T |
| 72 | — | — | 2.01 | 538 | 1 |
| 73 | — | — | 1.98 | 497 | 1 |
| 74 | — | — | 2.09 | 497 | 1 |
| 75 | 123 | MP50 | 1.87 | 505 | 6 |
| 76 | 124 | MP50 | 1.86 | 505 | 6 |
| 77 | >300 | MP50 | 1.29 | 526 | 6 |
| 78 | — | — | 1.86 | 526 | 1 |
| 79 | — | — | 1.86 | 526 | 1 |
| 80 | — | — | 2.33 | 486 | 1 |
| 81 | — | — | 2.16 | 500 | 2 |
| 82 | — | — | 2.44 | 527 | 2 |
| 83 | 250 | MP50 | 1.47 | 492 | 6 |
| 84 | >300 | MP50 | 1.83 | 553 | 6 |
| 85 | 240 | MP50 | 1.14 | 554 | 6 |
| 86 | 247 | MP50 | 1.15 | 554 | 6 |
| 87 | 200 | MP50 | 1.77 | 539 | 6 |
| 88 | 241 then 256 | DSC | 2.08 | 568 | 2 |
| 89 | 203 | MP50 | 1.89 | 568 | VILLA_2T |
| 90 | 232 | MP50 | 1.72 | 525 | 6 |
| 91 | 267 | MP50 | 1.74 | 568 | 6 |
| 92 | 241 | MP50 | 1.71 | 525 | 6 |
| 93 | >300 | MP50 | 1.87 | 551 | 6 |
| 94 | 167 | MP50 | 1.89 | 551 | 6 |
| 95 | 193 | MP50 | 2.00 | 565 | 6 |
| 96 | 233 | MP50 | 2.01 | 565 | 6 |
| 97 | 220 | MP50 | 1.97 | 565 | 6 |
| 98 | — | — | 2.35 | 565 | 1 |
| 99 | — | — | 2.35 | 565 | 1 |
| 100 | 226 | DSC | 2.14 | 553 | 1 |
| 101 | 169 | DSC | 2.29 | 539 | 1 |
| 102 | 227 | DSC | 2.16 | 553 | 1 |
| 103 | — | — | 2.31 | 477 | 1 |
| 104 | — | — | 2.03 | 552 | 1 |
| 105 | — | — | 1.80 | 538 | 1 |

-continued

| N° | MP (° C.) | Kofler (K) or DSC or MP50 or FP72 or WRS-2A | Rt | [M + H]+ | LCMS Method |
|---|---|---|---|---|---|
| 106 | — | — | 2.25 | 502 | 1 |
| 107 | 180 | DSC | 2.04 | 491 | 2 |
| 108 | — | — | 2.07 | 472 | 1 |
| 109 | — | — | 1.95 | 472 | 2 |
| 110 | — | — | 1.84 | 5100 | 1 |
| 111 | — | — | 2.09 | 511 | 1 |
| 112 | — | — | 2.02 | 525 | 2 |
| 113 | — | — | 2.18 | 519 | 2 |
| 114 | 251 | DSC | 2.29 | 553 | 1 |
| 115 | — | — | 2.29 | 553 | 1 |
| 116 | — | — | 2.20 | 539 | 1 |
| 117 | — | — | 2.19 | 539 | 1 |
| 118 | — | — | 2.2 | 539 | 1 |
| 119 | — | — | 2.09 | 539 | 2 |
| 120 | — | — | 2.15 | 502 | 1 |
| 121 | | | 2.07 | 539 | 2 |
| 122 | 237 | DSC | 2.06 | 539 | 2 |
| 123 | 218 | MP50 | 2.01 | 565 | VILLA_2T |
| 124 | 292 | MP50 | 1.87 | 565 | 6 |
| 125 | 203 | MP50 | 1.88 | 565 | 6 |
| 126 | — | — | 2.26 | 537 | 1 |
| 127 | — | — | 2.26 | 537 | 1 |
| 128 | 205 | DSC | 2.34 | 551 | 1 |
| 129 | — | — | 2.35 | 551 | 1 |
| 130 | 175 | MP50 | 2.35 | 551 | 1 |
| 131 | — | — | 2.34 | 551 | 1 |
| 132 | — | — | 1.02 | 523 | 3 |
| 133 | 180 | MP50 | 1.86 | 551 | 6 |
| 134 | — | — | 2.40 | 565 | 1 |
| 135 | — | — | 2.41 | 565 | 1 |
| 136 | 240 | MP50 | 1.97 | 580 | VILLA_2T |
| 137 | 267 | MP50 | 1.82 | 580 | 6 |
| 138 | — | — | — | — | 1 |
| 139 | — | — | 2.09 | 566 | 1 |
| 140 | — | — | 2.10 | 566 | 1 |
| 141 | — | — | 2.33 | 551 | 1 |
| 142 | 162 | DSC | 2.34 | 551 | 1 |
| 143 | — | — | 2.38 | 581 | 2 |
| 144 | — | — | 2.71 | 579 | 1 |
| 145 | — | — | 2.55 | 593 | 2 |
| 146 | — | — | 2.55 | 593 | 2 |
| 147 | 244 | MP50 | 1.90 | 565 | 6 |
| 148 | 260 | DSC | 2.50 | 565 | 1 |
| 150 | — | — | 2.47 | 565 | 1 |
| 151 | 189 | DSC | 2.41 | 551 | 1 |
| 152 | — | — | 2.43 | 565 | 1 |
| 154 | — | — | 2.36 | 594 | 1 |
| 155 | — | — | 2.30 | 566 | 1 |
| 156 | — | — | 2.28 | 593 | 1 |
| 157 | — | — | 2.52 | 565 | 1 |
| 158 | — | — | 2.52 | 565 | 1 |
| 159 | — | — | 2.36 | 552 | 1 |
| 160 | — | — | 2.50 | 566 | 1 |
| 161 | — | — | 2.62 | 593 | 1 |
| 162 | — | — | 3.02 | 593 | 1 |
| 163 | — | — | 2.68 | 579 | 1 |
| 164 | | | 2.52 | 568 | 1 |
| 165 | — | — | 2.35 | 554 | 1 |
| 166 | — | — | 2.35 | 554 | 1 |
| 167 | — | — | 2.51 | 565 | 1 |
| 168 | — | — | 2.51 | 565 | 1 |
| 169 | — | — | 2.38 | 608 | 1 |
| 170 | — | — | 2.24 | 594 | 1 |
| 171 | — | — | 2.24 | 594 | 1 |
| 172 | | | 3.15 | 592 | 1 |
| 173 | — | — | 3.24 | 592 | 1 |
| 174 | — | — | 2.84 | 593 | 1 |
| 175 | — | — | 2.41 | 664 | 1 |
| 176 | — | — | 2.13 | 608 | 1 |
| 177 | — | — | 2.13 | 608 | 1 |
| 178 | — | — | 2.29 | 622 | 1 |
| 179 | — | — | 2.70 | 582 | 1 |
| 180 | — | — | 2.56 | 678 | 1 |
| 181 | — | — | 2.56 | 622 | 1 |
| 182 | — | — | 2.64 | 591 | 1 |

-continued

| N° | MP (° C.) | Kofler (K) or DSC or MP50 or FP72 or WRS-2A | Rt | [M + H]+ | LCMS Method |
|---|---|---|---|---|---|
| 183 | — | — | 2.62 | 591 | 1 |
| 184 | — | — | 2.59; 2.68 (2 diastereoisomers) | 579 | 1 |
| 185 | — | — | 2.52 | 566 | V6002V6001 |
| 186 | — | — | 2.52 | 566 | V6002V6001 |
| 187 | — | — | 2.54 | 566 | V6002V6001 |
| 188 | — | — | 2.53 | 566 | V6002V6001 |
| 189 | — | — | 3.28 | 563 | WUXI49 |
| 190 | — | — | 3.26 | 563 | WUXI49 |
| 191 | — | — | 3.26 | 575 | WUXI49 |
| 192 | — | — | 4.13 | 575 | WUXI25 |
| 193 | — | — | 3.74 | 549 | WUXI49 |
| 194 | — | — | 3.24 | 549 | WUXI49 |
| 195 | — | — | 2.49 | 545 | 1 |

NMR

The NMR experiments were carried out using a Bruker Avance 500 III using internal deuterium lock and equipped with reverse triple-resonance ($^{1}H$, $^{13}C$, $^{15}N$ TXI) probe head or using a Bruker Avance DRX 400 spectrometer at ambient temperature, using internal deuterium lock and equipped with reverse double-resonance ($^{1}H$, $^{13}C$, SEI) probe head with z gradients and operating at 400 MHz for the proton and 100 MHz for carbon. Chemical shifts (6) are reported in parts per million (ppm). J values are expressed in Hz.

Compound 1

$^{1}H$ NMR (500 MHz, DMSO-$d_6$) δ ppm 9.55 (s, 1H), 8.21 (s, 1H), 7.13 (d, J=1.9 Hz, 1H), 6.89 (d, J=8.2 Hz, 1H), 6.73 (dd, J=8.2, 2.2 Hz, 1H), 6.31 (dd, J=16.9, 10.2 Hz, 1H), 6.10 (dd, J=17.0, 2.2 Hz, 1H), 5.67 (dd, J=10.4, 2.2 Hz, 1H), 4.90 (s, 2H), 4.24 (t, J=8.0 Hz, 1H), 4.03 (dd, J=8.8, 5.0 Hz, 1H), 3.94 (dd, J=10.2, 7.4 Hz, 1H), 3.74 (dd, J=10.4, 5.0 Hz, 1H), 3.69 (t, J=4.4 Hz, 4H), 3.16 (t, J=4.4 Hz, 4H), 3.14-3.10 (m, 1H), 2.96-2.81 (m, 2H), 2.44-2.38 (m, 1H), 1.95-1.84 (m, 2H), 1.78-1.69 (m, 2H), 1.63-1.51 (m, 2H)

Compound 32

$^{1}H$ NMR (300 MHz, Chloroform-d) δ ppm 8.25 (s, 1H), 6.71 (s, 1H), 6.53 (s, 1H), 6.38-6.29 (m, 1H), 6.19 (dd, J=16.9, 10.2 Hz, 1H), 5.71-5.56 (m, 2H), 4.34-3.97 (m, 5H), 3.97-3.74 (m, 5H), 3.41-3.22 (m, 3H), 3.22-2.91 (m, 5H), 2.58-2.38 (m, 1H), 2.22 (s, 3H), 2.17-2.01 (m, 2H), 1.93-1.79 (m, 2H), 1.30 (d, J=6.7 Hz, 3H).

Compound 100:

$^{1}H$ NMR (300 MHz, Chloroform-d) δ ppm 8.25 (s, 1H), 7.29 (s, 1H), 6.75 (s, 1H), 6.64 (s, 1H), 6.58 (dd, J=17.0, 10.7 Hz, 1H), 6.26 (dd, J=16.9, 2.0 Hz, 1H), 5.68 (s, 1H), 5.64 (q, J=6.8 Hz, 1H), 4.43-4.26 (m, 1H), 4.00-3.86 (m, 3H), 3.87-3.73 (m, 4H), 3.71-3.59 (m, 1H), 3.41-3.27 (m, 2H), 3.27-2.98 (m, 6H), 2.53-2.38 (m, 1H), 2.24 (s, 3H), 1.86-1.71 (m, 3H), 1.47-1.34 (m, 3H), 1.29 (d, J=6.8 Hz, 3H).

Compound 123

$^{1}H$ NMR (300 MHz, Chloroform-d) δ ppm 8.25 (s, 1H), 7.41 (s, 1H), 6.74 (s, 2H), 5.63 (q, J=6.8 Hz, 1H), 4.40 (s, 2H), 4.12 (s, 2H), 4.04-3.70 (m, 4H), 3.57 (s, 1H), 3.42-3.04 (m, 5H), 2.91 (s, 2H), 2.24 (s, 3H), 2.01 (s, 3H), 1.91 (s, 2H), 1.73-1.41 (m, 4H), d 1.29 (d, J=6.7 Hz, 3H).

Compound 124

$^{1}H$ NMR (300 MHz, Chloroform-d) δ ppm 8.24 (s, 1H), 7.48 (s, 1H), 6.76 (s, 1H), 6.66 (t, J=2.7 Hz, 1H), 5.62 (q, J=6.8 Hz, 1H), 4.32-4.10 (m, 2H), 4.03-3.70 (m, 6H), 3.63 (q, J=7.5 Hz, 1H), 3.42-3.25 (m, 3H), 3.24-2.94 (m, 5H), 2.41 (d, J=10.0 Hz, 1H), 2.23 (s, 3H), 2.01 (s, 3H), 1.84-1.62 (m, 2H), 1.49-1.21 (m, 5H).

Compound 125

$^{1}H$ NMR (300 MHz, Chloroform-d) δ ppm 8.23 (s, 1H), 7.72 (s, 1H), 6.75 (s, 1H), 6.68 (s, 1H), 5.61 (q, J=6.8 Hz, 1H), 4.19 (dd, J=13.4, 5.7 Hz, 2H), 4.01-3.68 (m, 6H), 3.61 (p, J=7.4 Hz, 1H), 3.32 (tt, J=9.4, 3.9 Hz, 3H), 3.11 (dt, J=23.2, 8.3 Hz, 5H), 2.45-2.32 (m, 1H), 2.23 (s, 3H), 2.00 (s, 3H), 1.83-1.64 (m, 2H), 1.47-1.15 (m, 5H).

Compound 126

$^{1}H$ NMR (500 MHz, DMSO-$d_6$) δ ppm 9.59 (d, J=2.5 Hz, 1H), 8.23 (s, 1H), 7.05 (s, 1H), 6.75 (s, 1H), 4.96 (s, 2H), 3.65-3.40 (m, 9H), 3.30-3.12 (m, 6H), 3.06-2.96 (m, 3H), 2.21 (s, 3H), 2.00 (d, J=1.6 Hz, 3H), 1.90-1.64 (m, 2H)

Compound 127

$^{1}H$ NMR (500 MHz, DMSO-$d_6$) δ ppm 9.59 (d, J=2.8 Hz, 1H), 8.23 (s, 1H), 7.05 (s, 1H), 6.75 (s, 1H), 4.96 (s, 2H), 3.62-3.32 (m, 10H, partially obscured by solvent peak), 3.27-3.11 (m, 5H), 3.06-2.95 (m, 3H), 2.21 (s, 3H), 2.00 (d, J=2.2 Hz, 3H), 1.88-1.65 (m, 2H)

Compound 128

$^{1}H$ NMR (500 MHz, DMSO-$d_6$) δ ppm 9.76 (s, 1H), 8.27 (s, 1H), 7.11 (s, 1H), 6.74 (s, 1H), 5.68 (q, J=6.7 Hz, 1H), 3.68-3.53 (m, 7H), 3.52-3.30 (m, 7H, partially obscured by solvent peak), 3.24-3.11 (m, 1H), 3.08-2.97 (m, 3H), 2.17 (s, 3H), 2.00 (d, J=1.6 Hz, 3H), 1.90-1.68 (m, 2H), 1.18 (d, J=6.6 Hz, 3H)

Compound 129

$^{1}H$ NMR (400 MHz, DMSO-$d_6$) δ ppm 9.80 (s, 1H), 8.28 (s, 1H), 7.11 (s, 1H), 6.75 (s, 1H), 5.68 (q, J=6.4 Hz, 1H), 3.59 (br s, 7H), 3.52-3.33 (m, 5H, partially obscured by solvent peak), 3.30-3.25 (m, 2H, partially obscured by solvent peak), 3.25-3.11 (m, 1H), 3.01 (br t, J=6.8 Hz, 3H), 2.17 (s, 3H), 2.01 (s, 3H), 1.91-1.65 (m, 2H), 1.18 (br d, J=6.6 Hz, 3H)

Compound 130

$^{1}H$ NMR (500 MHz, DMSO-$d_6$) δ ppm 9.76 (s, 1H), 8.27 (s, 1H), 7.11 (s, 1H), 6.74 (br s, 1H), 5.68 (q, J=6.6 Hz, 1H), 3.67-3.53 (m, 7H), 3.52-3.30 (m, 7H, partially obscured by solvent peak), 3.24-3.12 (m, 1H), 3.08-2.95 (m, 3H), 2.17 (s, 3H), 2.00 (d, J=1.3 Hz, 3H), 1.90-1.66 (m, 2H), 1.18 (d, J=6.6 Hz, 3H)

Compound 131

$^{1}H$ NMR (400 MHz, DMSO-$d_6$) δ ppm 9.80 (s, 1H), 8.28 (s, 1H), 7.11 (s, 1H), 6.74 (s, 1H), 5.68 (q, J=6.3 Hz, 1H), 3.68-3.54 (m, 7H), 3.53-3.33 (m, 5H, partially obscured by solvent peak), 3.30-3.11 (m, 3H, partially obscured by solvent peak), 3.09-2.96 (m, 3H), 2.17 (s, 3H), 2.01 (s, 3H), 1.66-1.66 (m, 2H), 1.17 (br d, J=6.7 Hz, 3H)

Compound 139

$^1$H NMR (500 MHz, DMSO-$d_6$) δ ppm 10.05 (br s, 1H), 8.28 (s, 1H), 6.90 (s, 1H), 5.64 (q, J=6.4 Hz, 1H), 4.08 (br t, J=7.7 Hz, 1H), 3.90-3.82 (m, 2H), 3.68-3.51 (m, 5H), 3.35-3.24 (m, 5H, partially obscured by solvent peak), 3.12-3.06 (m, 1H), 2.81 (br d, J=10.1 Hz, 2H), 2.26 (s, 3H), 1.93 (s, 3H), 1.84 (br t, J=10.9 Hz, 2H), 1.74 (br d, J=12.0 Hz, 2H), 1.62-1.51 (m, 2H), 1.14 (br d, J=6.3 Hz, 3H)

Compound 140

$^1$H NMR (500 MHz, DMSO-$d_6$) δ ppm 10.19-9.89 (m, 1H), 8.28 (s, 1H), 6.90 (s, 1H), 5.64 (q, J=6.4 Hz, 1H), 4.12-4.03 (m, 1H), 3.90-3.80 (m, 2H), 3.68-3.50 (m, 6H), 3.33-3.24 (m, 4H), 3.09 (quin, J=6.0 Hz, 1H), 2.81 (br d, J=10.4 Hz, 2H), 2.26 (s, 3H), 1.93 (s, 3H), 1.84 (br t, J=11.3 Hz, 2H), 1.74 (br d, J=11.0 Hz, 2H), 1.62-1.52 (m, 2H), 1.14 (br d, J=6.9 Hz, 3H)

Compound 141 (corresponds to Compound 130)

$^1$H NMR (500 MHz, DMSO-$d_6$) δ ppm 9.76 (s, 1H), 8.27 (s, 1H), 7.11 (br s, 1H), 6.75 (br s, 1H), 5.68 (q, J=6.6 Hz, 1H), 3.70-3.52 (m, 7H), 3.52-3.29 (m, 7H, partially obscured by solvent peak), 3.25-3.12 (m, 1H), 3.08-2.96 (m, 3H), 2.17 (s, 3H), 2.00 (s, 3H), 1.91-1.66 (m, 2H), 1.18 (br d, J=6.6 Hz, 3H)

Compound 142 (corresponds to Compound 128)

$^1$H NMR (500 MHz, DMSO-$d_6$) δ ppm 9.81 (d, J=2.2 Hz, 1H), 8.28 (s, 1H), 7.13-7.10 (m, 1H), 6.75 (s, 1H), 5.68 (q, J=6.6 Hz, 1H), 3.69-3.52 (m, 7H), 3.52-3.33 (m, 5H, partially obscured by solvent peak), 3.32-3.25 (m, 2H, partially obscured by solvent peak), 3.24-3.11 (m, 1H), 3.08-2.96 (m, 3H), 2.17 (s, 3H), 2.01 (d, J=1.9 Hz, 3H), 1.90-1.66 (m, 2H), 1.17 (d, J=6.6 Hz, 3H)

Compound 144

$^1$H NMR (500 MHz, DMSO-$d_6$) δ ppm 9.76 (s, 1H), 8.27 (s, 1H), 7.00 (s, 1H), 6.69 (s, 1H), 5.67 (q, J=6.7 Hz, 1H), 3.89 (d, J=8.7 Hz, 1H), 3.76 (d, J=8.5 Hz, 1H), 3.68-3.51 (m, 6H), 3.39-3.24 (m, 4H), 2.75-2.67 (m, 2H), 2.39-2.29 (m, 1H), 2.21-2.10 (m, 5H), 2.00 (s, 3H), 1.74 (d, J=11.4 Hz, 2H), 1.63-1.49 (m, 2H), 1.22 (s, 3H), 1.17 (d, J=6.7 Hz, 3H).

Compound 148

$^1$H NMR (500 MHz, DMSO-$d_6$) δ ppm 9.77 (s, 1H), 8.27 (s, 1H), 7.00 (s, 1H), 6.69 (s, 1H), 5.67 (q, J=6.6 Hz, 1H), 4.15 (t, J=8.0 Hz, 1H), 3.98-3.87 (m, 2H), 3.70 (dd, J=10.2, 5.2 Hz, 1H), 3.65-3.53 (m, 4H), 3.39-3.25 (m, 4H), 3.24-3.11 (m, 1H), 2.91-2.84 (m, 2H), 2.41-2.31 (m, 1H), 2.16 (s, 3H), 2.00 (s, 3H), 1.94-1.84 (m, 2H), 1.79-1.69 (m, 2H), 1.64-1.52 (m, 2H), 1.18 (d, J=6.9 Hz, 3H).

Compound 150

$^1$H NMR (400 MHz, DMSO-$d_6$) δ

9.77 (s, 1H), 8.27 (s, 1H), 7.00 (s, 1H), 6.69 (s, 1H), 5.67 (q, J=6.6 Hz, 1H), 4.15 (t, J=8.0 Hz, 1H), 4.00-3.84 (m, 2H), 3.70 (dd, J=10.1, 4.8 Hz, 1H), 3.66-3.51 (m, 4H), 3.42-3.24 (m, 4H), 3.21-3.09 (m, 1H), 2.94-2.82 (m, 2H), 2.41-2.29 (m, 1H), 2.16 (s, 3H), 2.00 (s, 3H), 1.94-1.79 (m, 2H), 1.79-1.66 (m, 2H), 1.66-1.48 (m, 2H), 1.18 (d, J=6.6 Hz, 3H).

Compound 159

$^1$H NMR (500 MHz, DMSO-$d_6$) δ ppm 9.81 (br d, J=1.3 Hz, 1H), 8.28 (s, 1H), 7.12 (s, 1H), 6.75 (s, 1H), 5.68 (q, J=6.5 Hz, 1H), 3.69-3.52 (m, 7H), 3.51-3.36 (m, 3H, partially obscured by solvent peak), 3.31-3.24 (m, 2H, partially obscured by solvent peak), 3.24-3.11 (m, 1H), 3.09-2.97 (m, 2H), 2.17 (s, 3H), 2.01 (d, J=1.6 Hz, 3H), 1.89-1.65 (m, 2H), 1.18 (br d, J=6.6 Hz, 3H)

Compound 161

$^1$H NMR (500 MHz, DMSO-d6) δ ppm 9.44 (s, 1H), 8.26 (s, 1H), 7.00 (d, J=2.0 Hz, 1H), 6.67 (d, J=1.8 Hz, 1H), 5.67 (q, J=6.7 Hz, 1H), 3.67-3.55 (m, 6H), 3.47 (br s, 2H), 3.33-3.21 (m, 4H), 2.55 (br s, 2H), 2.40-2.28 (m, 2H), 2.16 (s, 3H), 2.00 (s, 3H), 1.92-1.83 (m, 4H), 1.47-1.30 (m, 4H), 1.20 (d, J=6.7 Hz, 3H)

Compound 162

$^1$H NMR (400 MHz, DMSO-d6) δ ppm 9.80 (s, 1H), 8.27 (s, 1H), 7.05 (d, J=1.8 Hz, 1H), 6.66 (d, J=1.6 Hz, 1H), 5.67 (q, J=6.9 Hz, 1H), 3.73-3.46 (m, 8H), 3.36 (br s, 1H), 3.27 (br s, 1H), 2.44 (br s, 2H), 2.38 (br s, 2H), 2.22 (br s, 1H), 2.16 (s, 3H), 2.02 (s, 3H), 1.98-1.87 (m, 2H), 1.86-1.74 (m, 2H), 1.57-1.43 (m, 4H), 1.18 (d, J=6.7 Hz, 3H)

Compound 163

$^1$H NMR (xxx MHz, Chloroform-d) δ ppm 9.78 (s, 1H), 8.27 (s, 1H), 7.00 (d, J=0.7 Hz, 1H), 6.69 (s, 1H), 5.67 (q, J=6.7 Hz, 1H), 4.15 (t, J=8.3 Hz, 1H), 3.98-3.86 (m, 2H), 3.76-3.66 (m, 1H), 3.66-3.53 (m, 4H), 3.38-3.25 (m, 4H), 3.19-3.09 (m, 1H), 2.93-2.81 (m, 2H), 2.37 (q, J=7.3 Hz, 3H), 2.16 (s, 3H), 1.95-1.84 (m, 2H), 1.79-1.68 (m, 2H), 1.66-1.50 (m, 2H), 1.18 (d, J=6.6 Hz, 3H), 1.12 (t, J=7.5 Hz, 3H).

Compound 189:

$^1$H NMR (400 MHz, METHANOL-d4) δ

8.25 (s, 1H), 7.05 (d, J=2.0 Hz, 1H), 6.98 (d, J=2.2 Hz, 1H), 6.43-6.21 (m, 2H), 5.81-5.73 (m, 2H), 4.37 (t, J=8.2 Hz, 1H), 4.20-4.10 (m, 2H), 3.93 (dd, J=5.4, 10.8 Hz, 1H), 3.85-3.67 (m, 4H), 3.64 (s, 1H), 3.41-3.33 (m, 2H), 3.28-3.20 (m, 1H), 3.28-3.20 (m, 2H), 3.01 (br t, J=12.2 Hz, 2H), 2.57-2.48 (m, 1H), 2.04 (br t, J=11.6 Hz, 2H), 1.88 (br d, J=13.7 Hz, 2H), 1.79-1.69 (m, 2H), 1.30 (d, J=6.8 Hz, 3H)

Compound 190

$^1$H NMR (400 MHz, METHANOL-d4) δ

8.26 (s, 1H), 7.05 (d, J=2.0 Hz, 1H), 7.00-6.97 (m, 1H), 6.99 (d, J=2.0 Hz, 1H), 6.42-6.20 (m, 2H), 5.81-5.73 (m, 2H), 4.38 (t, J=8.1 Hz, 1H), 4.20-4.10 (m, 2H), 3.94 (dd, J=5.0, 10.4 Hz, 1H), 3.87-3.70 (m, 4H), 3.63 (s, 1H), 3.36 (br s, 3H), 3.28-3.20 (m, 2H), 3.02 (br t, J=12.7 Hz, 2H), 2.54 (br t, J=12.1 Hz, 1H), 2.05 (br t, J=11.4 Hz, 2H), 1.89 (br d, J=10.3 Hz, 2H), 1.81-1.70 (m, 2H), 1.31 (d, J=6.8 Hz, 3H)

Compound 195

$^1$H NMR (500 MHz, DMSO-d6) δ ppm 9.49 (s, 1H), 8.22 (s, 1H), 6.94 (d, J=1.9 Hz, 1H), 6.68 (d, J=1.6 Hz, 1H), 4.94 (s, 2H), 4.45 (d, J=6.9 Hz, 1H), 4.43 (d, J=6.9 Hz, 1H), 4.18-4.11 (m, 1H), 3.96-3.86 (m, 2H), 3.74-3.66 (m, 3H), 3.40 (s, 2H), 3.17-3.12 (m, 1H), 3.05-3.01 (m, 2H), 2.88 (br d, J=11.0 Hz, 2H), 2.41-2.31 (m, 2H), 2.20 (s, 3H), 2.00 (s, 3H), 1.94-1.85 (m, 2H), 1.72 (br d, J=11.0 Hz, 2H), 1.63-1.51 (m, 2H)

OR

Optical Rotation is measured with a polarimeter 341 Perkin Elmer. The polarized light is passed through a sample with a path length of 1 decimeter and a sample concentration of 0.2 to 0.4 gram per 100 milliliters. 2 to 4 mg of the product in vial are weight, then dissolved with 1 to 1.2 ml of spectroscopy solvent (DMF for example). The cell is filled with the solution and put into the polarimeter at a temperature of 20° C. The OR is read with 0.004° of precision.

Calculation of the concentration: weight in gram×100/volume in ml $$[\alpha]_d^{20}:(\text{read rotation}\times 100)/(1.000\ \text{dm}\times\text{concentration}).$$

$^d$ is sodium D line (589 nanometer).

Table: Co. No. means compound number; Retention time ($R_t$) in min; MP means melting point (° C.); dec means decomposition; n.d. means not determined.

OR data: Solvent: DMF; temperature: 20° C.; wavelength: 589 nm; 'N°' means compound number

| N° | OR (°) | Concentration (g/100 mL) |
|---|---|---|
| 9 | −38.5 | 0.27 |
| 10 | +30.9 | 0.21 |
| 12 | −11.4 | 0.21 |
| 13 | +45.7 | 0.23 |
| 17 | −22.2 | 0.27 |
| 18 | −4.7 | 0.3 |
| 22 | +45.9 | 0.17 |
| 23 | −42.2 | 0.18 |
| 24 | +44.3 | 0.21 |
| 25 | −48 | 0.2 |
| 26 | −47.8 | 0.23 |
| 27 | +46.2 | 0.21 |
| 50 | +44.1 | 0.25 |
| 51 | −9.3 | 0.27 |
| 54 | −16.7 | 0.12 |
| 55 | +18.1 | 0.13 |
| 56 | +37.2 | 0.23 |
| 57 | −39.6 | 0.21 |
| 78 | −24.8 | 0.21 |
| 79 | +30.0 | 0.19 |
| 98 | −40.5 | 0.19 |
| 99 | −41.0 | 0.20 |
| 114 | +61.2 | 0.17 |
| 115 | −69.4 | 0.18 |
| 116 | +13.4 | 0.16 |
| 117 | −53.7 | 0.19 |
| 118 | +55.3 | 0.18 |
| 119 | −38.4 | 0.31 |
| 121 | −127.4 | 0.27 |
| 122 | −115.2 | 0.33 |
| 126 | +25.2 | 0.25 |
| 127 | −5.3 | 0.25 |
| 128 | −33.1 | 0.14 |
| 129 | +35.4 | 0.24 |
| 130 | −38.5 | 0.15 |
| 131 | +60.1 | 0.28 |
| 134 | −37.0 | 0.21 |
| 135 | +34.6 | 0.21 |
| 139 | −47.5 | 0.20 |
| 140 | +42 | 0.20 |
| 143 | −56.6 | 0.29 |
| 144 | −48.9 | 0.27 |
| 148 | −53.3 | 0.28 |
| 150 | +45.0 | 0.20 |
| 154 | −53.3 | 0.27 |
| 155 | −53.6 | 0.25 |

-continued

| N° | OR (°) | Concentration (g/100 mL) |
|---|---|---|
| 156 | −54.6 | 0.33 |
| 157 | −44.6 | 0.26 |
| 158 | −87.0 | 0.27 |
| 161 | −48.8 | 0.25 |
| 162 | −51.2 | 0.25 |
| 163 | −53.6 | 0.25 |
| 164 | −55.9 | 0.29 |
| 165 | −58.3 | 0.18 |
| 166 | −50.4 | 0.24 |
| 167 | −49.0 | 0.30 |
| 168 | −52.7 | 0.26 |
| 169 | −54.8 | 0.29 |
| 170 | −42.3 | 0.26 |
| 171 | −52.0 | 0.25 |
| 172 | −51.8 | 0.28 |
| 173 | −55.0 | 0.28 |
| 174 | −49.4 | 0.32 |
| 176 | −44.8 | 0.23 |
| 177 | −59.2 | 0.24 |
| 178 | −54.4 | 0.25 |
| 179 | −61.4 | 0.28 |
| 180 | −50.8 | 0.25 |
| 181 | −54.4 | 0.25 |
| 182 | −47.2 | 0.29 |
| 183 | −56.4 | 0.28 |
| 185 | −82.2 | 0.23 |
| 186 | −21.3 | 0.23 |
| 187 | −51.7 | 0.23 |
| 188 | −57.1 | 0.28 |

SFC-MS Method

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

TABLE

Analytical SFC-MS Methods (flow expressed in mL/min; colμmn temperature (T) expressed in ° C.; run time expressed in minutes, backpressure (BPR) expressed in bars).

| Method | colμmn | mobile phase | gradient | Flow<br>*Col T* | Run Time<br>*BPR* |
|---|---|---|---|---|---|
| Method 1<br>2_ASS3_IPOHB1_30_FTP2 | Chiralpak ® AS-3 column (3 μm, 100 × 4.6 mm) | A: $CO_2$<br>B: iPrOH (0.3% $iPrNH_2$) | 30% B hold 3 min, | 3.5<br>35 | 3<br>103 |
| Method 2<br>UPCC_AD3_ETOH_50_6MIN | Chiralpak ® AD-3 column (3 μm, 100 × 4.6 mm) | A: CO2<br>B: EtOH (0.3% iPrNH2) | 50% B hold 6 min, | 3.5<br>35 | 6<br>103 |
| Method 3<br>UPCC_AS3_MEOH_30_3MIN | Chiralpak ® AS-3 column (3 μm, 100 × 4.6 mm) | A: CO2<br>B: MeOH (0.3% iPrNH2) | 30% B hold 3 min, | 3.5<br>35 | 3<br>103 |
| Method 4<br>UPCC_AS3_MEOH_35_3MIN | Chiralpak ® AS-3 column (3 μm, 100 × 4.6 mm) | A: CO2<br>B: MeOH (0.3% iPrNH2) | 35% B hold 3 min, | 3.5<br>35 | 3<br>103 |
| Method 5<br>UPCC_WHELK_MEOH_55_6MIN | (S,S)-Whelk-O 1 column (3 μm, 100 × 4.6 mm) | A: CO2<br>B: MeOH (0.3% iPrNH2) | 55% B hold 6 min, | 3.5<br>35 | 6<br>103 |

TABLE-continued

Analytical SFC-MS Methods (flow expressed in mL/min; column temperature (T) expressed in ° C.; run time expressed in minutes, backpressure (BPR) expressed in bars).

| Method | column | mobile phase | gradient | Flow / *Col T* | Run Time / *BPR* |
|---|---|---|---|---|---|
| Method 6 UPCC_WHELK_MEOH_60_6MIN | (S,S)-Whelk-O 1 column (3 μm, 100 × 4.6 mm) | A: CO2 B: MeOH (0.3% iPrNH2) | 60% B hold 6 min, | 3.5 35 | 6 103 |
| Method 7 UPCC_WHELK_MEOH_50_6MIN | (S,S)-Whelk-O 1 column (3 μm, 100 × 4.6 mm) | A: CO2 B: MeOH (0.3% iPrNH2) | 50% B hold 6 min, | 3.5 35 | 6 103 |
| Method 8 UPCC_OJ3_MEOH_30_3min | Chiralcel ® OJ-3 column (3 μm, 100 × 4.6 mm) | A: CO2 B: MeOH (0.3% iPrNH2) | 30% B hold 3 min, | 3.5 35 | 3 103 |
| Method 9 UPCC_OD3_MEOH_50_10MIN | Chiralcel ® OD-3 column (3 μm, 100 × 4.6 mm) | A: CO2 B: MeOH (0.3% iPrNH2) | 50% B hold 10 min, | 3.5 35 | 10 103 |
| Method 10 UPCC_OD3_ETOH_50_3MIN | Chiralcel ® OD-3 column (3 μm, 100 × 4.6 mm) | A: CO2 B: EtOH (0.3% iPrNH2) | 50% B hold 3 min, | 3.5 35 | 3 103 |
| Method 11 UPCC_OD3_MEOH_50_6MIN | Chiralcel ® OD-3 column (3 μm, 100 × 4.6 mm) | A: CO2 B: MeOH (0.3% iPrNH2) | 50% B hold 6 min, | 3.5 35 | 6 103 |
| Method 12 UPCC_WHELK_MEOH_50_10MIN | (S,S)-Whelk-O 1 column (3 μm, 100 × 4.6 mm) | A: CO2 B: MeOH (0.3% iPrNH2) | 50% B hold 10 min, | 3.5 35 | 10 103 |
| Method 13 UPCC_OJ3_MEOH_40_3min | Chiralcel ® OJ-3 column (3 μm, 100 × 4.6 mm) | A: CO2 B: MeOH (0.3% iPrNH2) | 40% B hold 3 min, | 3.5 35 | 3 103 |
| Method 14 UPCC_OD3_ETOH_50_6MIN | Chiralcel ® OD-3 column (3 μm, 100 × 4.6 mm) | A: CO2 B: EtOH (0.3% iPrNH2) | 50% B hold 6 min, | 3.5 35 | 6 103 |
| Method 15 UPCC_AS3_MEOH_40_3MIN | Chiralpak ® AS-3 column (3 μm, 100 × 4.6 mm) | A: CO2 B: MeOH (0.3% iPrNH2) | 40% B hold 3 min, | 3.5 35 | 3 103 |
| Method 16 UPCC_OJ3_MEOH_50_6min | Chiralcel ® OJ-3 column (3 μm, 100 × 4.6 mm) | A: CO2 B: MeOH (0.3% iPrNH2) | 50% B hold 6 min, | 3.5 35 | 6 103 |
| Method 17 OD_ETOH_DEA_40_4ML_5CM | OD-5 cm column | A: CO2 B: EtOH (0.3% iEt2NH) | | 4.0 35 | 103 |

TABLE

Analytical SFC data ($R_t$ means retention time (in minutes), $[M + H]^+$ means the protonated mass of the compound, method refers to the method used for SFC-MS analysis of enantiomerically pure compounds).

| Compound number | Rt | $[M + H]^+$ | Chiral purity UV Area % | Method |
|---|---|---|---|---|
| 11 | 2.44/ 2.94 | 505 | 49.94, 50.06 | 5 |
| 12 | 2.92 | 505 | 99.39 | 5 |
| 13 | 2.42 | 505 | 100 | 5 |
| 30 | 3.07 | 526 | 100 | 2 |
| 31 | 3.72 | 526 | 100 | 2 |
| 78 | 4.07 | 526 | 99.30 | 2 |
| 79 | 2.53 | 526 | 100 | 2 |
| 100 | 1.34 | 553 | 100 | 3 |
| 108 | 0.89 | 472 | 99.53 | 4 |
| 112 | 3.12/ | 525 | 50.36, | 5 |

TABLE-continued

Analytical SFC data ($R_t$ means retention time (in minutes), $[M + H]^+$ means the protonated mass of the compound, method refers to the method used for SFC-MS analysis of enantiomerically pure compounds).

| Compound number | Rt | $[M + H]^+$ | Chiral purity UV Area % | Method |
|---|---|---|---|---|
| racemate | 3.64 | | 49.64 | |
| 114 | 2.80 | 553 | 100 | 6 |
| 115 | 3.40 | 553 | 99.68 | 6 |
| 116 | 2.94 | 539 | 100 | 7 |
| 118 | 3.49 | 539 | 99.80 | 7 |
| 119 | 2.57 | 539 | 99.75 | 6 |
| 128 | 2.65 | 551 | 100 | 6 |
| 129 | 2.46 | 551 | 100 | 6 |
| 130 | 2.99 | 551 | 100 | 6 |
| 131 | 2.77 | 551 | 100 | 6 |
| 134 | 3.99 | 565 | 100 | 6 |

TABLE-continued

Analytical SFC data ($R_t$ means retention time (in minutes), $[M + H]^+$ means the protonated mass of the compound, method refers to the method used for SFC-MS analysis of enantiomerically pure compounds).

| Compound number | Rt | $[M + H]^+$ | Chiral purity UV Area % | Method |
|---|---|---|---|---|
| 135 | 3.39 | 565 | 100 | 6 |
| 139 | 1.29 | 566 | 98 | 8 |
| 140 | 1.01 | 566 | 100 | 8 |
| 141 | 3.00 | 551 | 100 | 6 |
| 142 | 2.58 | 551 | 100 | 6 |
| 143 | 3.73 | 581 | 98.24 | 9 |
| 144 | 2.23 | 579 | 98.03 | 9 |
| 145 | 2.56 | 593 | 98.65 | 9 |
| 146 | 2.26 | 593 | 98.95 | 9 |
| 148 | 1.88 | 565 | 99.74 | 10 |
| 150 | 1.14 | 565 | 100 | 10 |
| 154 | 7.29 | 594 | 98.66 | 9 |
| 155 | 5.25 | 566 | 98.68 | 9 |
| 156 | 2.00 | 593 | 99.32 | 9 |
| 157 | 2.14 | 565 | 99.27 | 11 |
| 158 | 2.15 | 565 | 98.63 | 11 |
| 159 | 2.60 | 552 | 100 | 6 |
| 160 | 1.89 | 566 | 97.83 | 10 |
| 161 | 2.89 | 593 | 93.43 | 9 |
| 162 | 2.32 | 593 | 94.92 | 9 |
| 163 | 2.14 | 579 | 98.36 | 9 |
| 164 | 2.22 | 568 | 98.82 | 9 |
| 165 | 3.90 | 554 | 100 | 7 |
| 166 | 4.39 | 554 | 100 | 7 |
| 167 | 3.80 | 565 | 99.63 | 7 |
| 168 | 4.32 | 565 | 100 | 7 |
| 169 | 1.92 | 608 | 98.77 | 9 |
| 170 | 5.46 | 594 | 100 | 12 |
| 171 | 4.76 | 594 | 100 | 12 |
| 172 | 1.88 | 592 | 100 | 13 |
| 173 | 1.43 | 592 | 100 | 13 |
| 174 | 1.37 | 593 | 98.75 | 14 |
| 175 | 3.21 | 664 | 98.21 | 11 |
| 176 | 4.26 | 608 | 100 | 6 |
| 177 | 3.74 | 608 | 100 | 6 |
| 178 | 1.79 | 622 | 98.47 | 11 |
| 179 | 4.24 | 582 | 99.14 | 7 |
| 181 | 1.49 | 622 | 99.50 | 10 |
| 182 | 1.78 | 591 | 100 | 11 |
| 183 | 2.71 | 591 | 100 | 11 |
| 184 | 1.52 | 579 | 98.28 | 11 |
| 185 | 1.31 | 566 | 99.39 | 15 |
| 186 | 1.15 | 566 | 98.72 | 15 |
| 187 | 2.49 | 566 | 99.22 | 16 |
| 188 | 1.45 | 566 | 100 | 16 |
| 189 | 0.93 | 563 | 99.82 | 17 |
| 190 | 1.54 | 563 | 99.79 | 17 |
| 191 | 1.62 | 575 | 99.95 | 17 |
| 192 | 0.89 | 575 | 98.65 | 17 |
| 193 | 0.85 | 549 | 100 | 17 |
| 194 | 1.20 | 549 | 99.57 | 17 |

Example C: PHARMACOLOGICAL ASSAYS

Expression and Purification of a Trimeric Complex of CDK7, Cyclin H, and MAT1

Human CDK7 (amino acids 1-346) containing an N-terminal $His_6$-tag followed by a tobacco etch virus (TEV) protease cleavage site, human MAT1 (amino acids 1-309) and human cyclin H (amino acids 1-323) were co-expressed in the baculovirus-SF9 insect cell expression system to generate a trimeric complex. Cell pellets were collected 72 h post-infection and were resuspended by Dounce homogenization in 20 mM Hepes-NaOH (pH 8.0), 300 mM NaCl, 10% glycerol, 2 mM dithiothreitol DTT), and 20 mM Imidazole supplemented with cOmplete™ Protease Inhibitor Cocktail (Roche) and 25 U/mL Benzonase® Nuclease HC according to the manufacturer's instructions. Cells were lysed by passing through a Microfluidics M110Y Microfluidizer 3 times at 600 kPa followed by centrifugation at 38,000×g at 4° C. for 1 hour. The supernatant was loaded onto a pre-equilibrated HisTrap HP column and eluted in 20 mM Hepes-NaOH (pH 8.0), 50 mM NaCl, 10% glycerol, 2 mM DTT, and 400 mM Imidazole. The eluate was further purified by gel filtration on a Superdex S200 16/60 column and eluted with 20 mM Hepes-NaOH (pH 7.5), 50 mM NaCl, 10% Glycerol, 2 mM DTT. Fractions containing a trimeric complex of CDK7, cyclin H, and MAT1 in a 1:1:1 ratio were pooled and concentrated to 3 mg/mL in a 10 kDa MWCO concentrator, and diluted to a final concentration of 1.6 mg/mL in 11.1 mM Hepes-NaOH (pH 8.0), 27.8 mM NaCl, 1.1 mM DTT and 50% glycerol.

Materials

ATP, phosphoenolpyruvate (PEP), NADH, $MgCl_2$, Triton X-100 (10% solution), pyruvate, kinase/lactate dehydrogenase, 384-well assay plates (Greiner UV-Star Clear), and 384-well compound dilution plates (Greiner bio-one) were purchased from Sigma-Aldrich (St. Louis, MO). 1M Tris-HCl (pH 7.4) and CDK7/9 tide were obtained from Teknova (Hillister, CA) and Anaspec (Freemont, CA), respectively.

In Vitro CDK7 Assay and Determination of Potency for Irreversible Covalent Inhibitors CDK7 activity is measured by following the production of ADP generated from ATP-dependent phosphorylation of the peptide substrate derived from RNA Pol II (CDK7/9 tide) by CDK7. Pyruvate kinase converts ADP and phosphoenolpyruvate (PEP) to ATP and pyruvate. Lactase dehydrogenase catalyzes pyruvate to lactate with a concomitant conversion of NADH to oxidized form $NAD^+$, which is spectrophotometrically measured at 340 nm. The CDK7 assay was performed in 384-well microplates with a final volume of 100 μL. Inhibitor serial dilutions and liquid handing for the assay were performed by using Janus from PerkinElmer (Downers Grove, IL) and Tempest from Formulatrix (Bedford, MA), respectively. To determine inhibitor potency of irreversible covalent inhibitors ($k_{inact}/K_I$ ratios), 500 nL of inhibitor in DMSO (or DMSO for controls) was added to the assay plate using Echo 555 from Labcyte (San Jose, CA) followed by 50 μL of assay mixture consisting of 600 μM peptide substrate (CDK7/9 tide, YSPTSPSYSPTSPSYSPTSPSKKKK), 1 mM ATP, 1 mM PEP, 200 μM NADH, 1.2-2 units of PK, 1.8-2.8 units of LDH, 20 mM Tris-HCl (pH 7.4), 10 mM $MgCl_2$, and 0.004% Triton X-100. Reactions were initiated by the addition of 50 μL of 40 nM CDK7/cyclinH/MAT1 trimeric complex in 20 mM Tri-HCl (pH 7.4), 10 mM $MgCl_2$, and 0.004% Triton X-100. The assay plates were centrifuged at 3220 g for 5 min using Centrifuge 5810 from Eppendorf (Hauppauge, NY) and then the absorbance changes were read at 340 nm at room temperature using Infinite M1000 from Tecan (Mannedorf, Switzerland) every 2 min for 8 hours.

For data analysis to determine potency ($k_{inact}/K_I$ ratios), the reaction progress curves corresponding to the linear range of the DMSO control were fit to equation 1, where $V_o$ is the initial rate in Abs/sec and t is time in seconds, yielding the first order rate constant for enzyme inactivation ($k_{obs}$) at each inhibitor concentration. The $k_{obs}$ values were then plotted versus inhibitor concentration ([I]) and fit to equation 2 where $k_{inact}$ is the maximal rate of inactivation that is achieved at infinite concentration of inhibitor and $K_I$ is the inhibitor concentration that yields half the rate of maximal inactivation. When [I]$K_I$, equation 2 is simplified to equation 3. Thus, at inhibitor concentrations of well below $K_I$, a plot of $k_{obs}$ versus inhibitor concentration ([I]) is linear, and the slope of the line is equal to $k_{inact}/K_I$.

$$\text{Product} = \frac{V_0}{k_{obs}}[1 - \exp(-k_{obs}t)] \quad (1)$$

$$k_{obs} = \frac{k_{inact}[I]}{K_I + [I]} \quad (2)$$

$$k_{obs} = \frac{k_{inact}}{K_I}[I] \quad (3)$$

Imaging-Based Cellular RNA PolII Ser5 Phosphorylation Assay

To evaluate inhibition of CDK7 kinase activity, a 384-well automated imaging assay was used. This assay detects Serine 5 phosphorylation on a unique heptapeptide sequence in the C-terminal domain of Rpbl subunit of RNA polymerase II, the downstream substrate of CDK7. This heptapeptide sequence is repeated up to 52 times in the CTD of Rpbl.

Materials

A549 adenocarcinoma human alveolar basal epithelial cells (ATCC, CCL-185), rabbit Phospho-Rpbl CTD (Ser5) antibody (D9N51 (Cell Signaling Technology)), DMEM (Sigma), Fetal Bovine Serum (Biowest), L-glutamine (Sigma), Penicillin/Streptomycin (Life Technologies), Sodium Pyruvate (Sigma), Hepes (Sigma), poly-D-lysine coated µclear 384 black plates (Greiner), formaldehyde (PolySciences), D-PBS (Sigma), Methanol (Sigma), Alexa Fluor 488 goat anti rabbit IgG secondary antibody (Life Technologies), HCS CellMask™ Deep Red stain (Life Technologies), Hoechst 33258 (Invitrogen).

RNA Polymerase II Serine 5 phosphorylation was detected using a specific rabbit Phospho-Rpbl CTD (Ser5) antibody. A549 adenocarcinoma human alveolar basal epithelial cells were seeded in 20 µl medium (DMEM supplemented with 1% Fetal Bovine Serum (heat inactivated 30' 56° C.), 2 mM L-glutamine, 50 U/ml penicillin 50 µg/ml streptomycin, 1 mM sodium pyruvate and 50 mM hepes) at 1000 cells/well and cultured in poly-D-lysine coated µclear 384 black plates for 20 hours at 37° C. and 5% $CO_2$.

After incubation cells were challenged with compound for 3 hours at 37° C. and 5% $CO_2$. DMSO was used as high control and as low control 10 µM of the following reference compound was used:

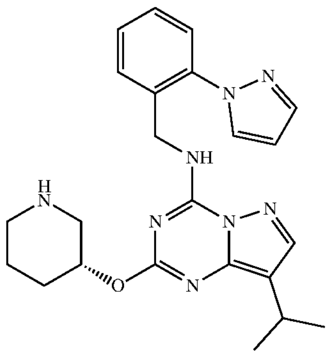 [SMILES: CC(C)c1cnn2c(NCc3ccccc3-n3cccn3)nc(O[C@@H]3CCCNC3)nc12]

40 nl of test compounds and controls were spotted in cell plates using Echo Liquid Handler (Echo 550, Labcyte). Incubation was followed by 20 minutes fixation with 20 µl 10% formaldehyde at room temperature. Medium/formaldehyde solution was removed, plates were washed 3 times with 30 µl D-PBS (w/o $Ca^{2+}$ and $Ma^{2+}$) and permeabilization was done by adding 20 µl ice cold methanol for 20 minutes. Cells were washed again 3 times with 30 µl D-PBS and 20 µl blocking buffer (25 ml fetal bovine serum in 500 ml D-PBS) was added for 1 hour.

After removing blocking buffer 20 µl 1/1000 primary antibody rabbit Phospho-Rpbl CTD (Ser5) antibody was added which binds to the phosphorylated Serine5 of the heptapeptide sequences in the CTD of Rpbl. Primary antibody was removed, and plates were washed 3 times with 30 µl D-PBS followed by addition of 20 µl 1/2000 Alexa Fluor 488 goat anti rabbit IgG secondary antibody for final detection of Phospho-Rpbl CTD (Ser5) together with 1/5000 HCS CellMask™ Deep Red stain for membrane staining and 1/5000 Hoechst 33258 for nucleus staining. Last, plates were washed 2 times with 30 µl D-PBS and wells were filled with 40 µL D-PBS, plates were sealed (Thermowell sealing tape) and stored at 4° C. until reading. Plates were read with Opera Phenix (Perkin Elmer) with 10× air objective. Data were calculated and analyzed in Phaedra.

$IC_{50}$ values were calculated using the following formula $$LC = \text{Average of low control values}$$
$$= \text{Cells treated with } 10\,\mu M \text{ of } LDC4297\ (JNJS64085047\text{-}AAA)$$
$$HC = \text{Average of the high control values}$$
$$= \text{Cells treated with } 0.2\%\ DMSO$$

Average value of all HC's and all LC's are used for normalizations.

$$\%\ \text{Effect} = 100 - (\text{sample} - LC)/(HC - LC) \times 100$$
$$\%\ \text{Control} = (\text{sample}/HC) \times 100$$

A best-fit curve is fitted by a minimum sum of squares method to the plot of % Control vs. compound concentration. From this an IC50 value can be obtained. An estimate of the slope of the plot in terms of the Hill coefficient is also obtained.

In parallel this assay was performed in A549 cells overexpressing CDK7-mutant (C312S) to evaluate the effect of the covalent bond on potency and to screen for potential off-target effects. Mutation of Cysteine to Serine (C312S), a less nucleophilic amino acid, prevents CDK7 inhibitors from covalently binding to CDK7 and from inhibiting CDK7 activity in an irreversible manner. A stably transduced A549 cell pool was generated that overexpresses CDK7 mutant (C312S), but also expresses endogenous CDK7-WT. Covalent binders targeting the cysteine at position 312 will show a shift in potency in A549 cells overexpressing mutant C312S CDK7.

Proliferation Assay Using OCI-AML3 Cells Overexpressing WT or C312S Mutant CDK7

Materials

OCI-AML-3 acute myeloid leukemia cells (DSMZ ACC 582), alpha-MEM (Sigma M4526), fetal bovine serum (Bio- West S1810-500), L-glutamine (Sigma G7513), Gentamycin (Life Technologies 15750-037), 96-well plates (Costar, catalogue number 3904), CellTiterGLO reagent (Promega G7573).

To assess anti-proliferative effects, CDK7 inhibitor test compounds were tested in 4-day proliferation assays using two different AML cell lines. The parental OCI-AML-3 cell line was used to generate two OCI-AML-3 cell lines overexpressing either CDK7 WT or CDK7 C312S mutant. Mutation of Cysteine to Serine (C312S), a less nucleophilic amino acid, prevents CDK7 inhibitors from covalently binding to CDK7 and from inhibiting CDK7 activity in an irreversible manner.

OCI-AML-3 cells were propagated in alpha-MEM supplemented with 20% heat inactivated fetal bovine serum, 2 mM L-glutamine and 50 μg/ml Gentamycin. Cells were kept between 0.5-2.5 million cells per mL during culturing. Cell passage numbers were not exceeding 30. To assess anti-proliferative effects, 3000 cells were seeded in 135 μL medium per well of a 96-well plate. Compounds were diluted in DMSO at 500× of the desired final concentrations. A pre-dilution of 1/50 of the compounds was prepared in culture medium. 15 μL of these pre-diluted compounds was added per well of 96-well plates. Cells were incubated for 4 days at 37° C. and 5% $CO_2$. Cell plating numbers were chosen based on growth curves to ensure linear cell growth. After 4 days of incubation 75 μL CellTiterGLO reagent was added to each well. After 10 min of incubation with shaking at 500 rpm at room temperature, luminescence was measured on the Envision multimode plate reader (Perkin Elmer). Covalent binders targeting the cysteine at position 312 will show a shift in potency in OCI-AML3 cells overexpressing mutant C312S CDK7.

$IC_{50}$ values were calculated using the following formula (Z prime should be >0.5)

$$LC = \text{median of low control values}$$
$$= \text{Low control: Reaction without cells}$$
$$HC = \text{Median of the High control values}$$
$$= \text{High control: Reaction with cells without compound}$$

$$\%\ \text{Effect} = 100 - (\text{sample} - LC)/(HC - LC) \times 100$$
$$\%\ \text{Control} = (\text{sample}/HC) \times 100$$
$$\%\ \text{Controlmin} = (\text{sample} - LC)/(HC - LC) \times 100$$

A best-fit curve was fitted by a minimum sum of squares method to the plot of % Control vs. compound concentration. From this an $IC_{50}$ value (inhibitory concentration causing 50% cytotoxicity) can be obtained. An estimate of the slope of the plot in terms of the Hill coefficient was also obtained.

Data for the compounds of the invention in the above assays are provided in Tables A, B, and C (the values in Table are averaged values over all measurements on all batches of a compound; 'n.c.' means not calculated).

TABLE A

Cellular assays results with the compounds of the present disclosure

| Compound # | CDK7_A549 Wild-type CDK7 (pIC50) | CDK7_ A549 mutant hCDK7(pIC50) |
|---|---|---|
| 1 | 6.1 | <5 |
| 1 | 6.18 | <5 |
| 1 | 5.66 | <5 |
| 1 | 6.06 | <5 |
| 1 | 6.03 | <5 |
| 2 | 6.48 | <5 |
| 2 | 6.49 | <5 |
| 3 | 6.04 | <5 |
| 4 | <5 | <5 |
| 5 | 6.05 | ~5.05 |
| 6 | 5.42 | <5 |
| 7 | 5.17 | <5 |
| 8 | 5.26 | <5 |
| 9 | 5.68 | <5 |
| 10 | 5.74 | <5 |
| 11 | 6.54 | 5.05 |
| 12 | 6.34 | <5 |
| 12 | 6.55 | <5 |
| 13 | 6.56 | <5 |
| 13 | 6.63 | <5 |
| 14 | 6.33 | <5 |
| 15 | 6.02 | <5 |
| 16 | 6.34 | <5 |
| 17 | 6.42 | <5 |
| 18 | 6.42 | <5 |
| 19 | 6.06 | <5 |
| 20 | 6.19 | <5 |
| 21 | 6.08 | <5 |
| 22 | ~6.21 | <5 |
| 23 | 6.22 | <5 |
| 24 | 6.19 | <5 |
| 25 | 6.13 | <5 |
| 26 | 6.54 | <5 |
| 27 | 5.32 | <5 |
| 28 | 6.12 | <5 |
| 29 | 5.95 | <5 |
| 30 | 5.82 | <5 |
| 31 | 5.56 | <5 |
| 32 | ~7.9 | <5 |
| 33 | 5.63 | <5 |
| 34 | 6 | <5 |
| 35 | ~5.1 | <5 |
| 36 | 6.13 | <5 |
| 36 | 6.32 | <5 |
| 37 | 6.04 | <5 |
| 37 | 6.17 | <5 |
| 38 | 5.94 | <5 |
| 39 | 5.65 | <5 |
| 40 | 6.36 | <5 |
| 41 | 5.92 | <5 |
| 41 | 5.88 | <5 |
| 42 | 6.43 | <5 |
| 43 | 6.88 | <5 |
| 44 | 5.93 | <5 |
| 45 | 6.37 | <5 |
| 46 | 6.68 | <5 |
| 47 | 6.61 | <5 |
| 48 | 6.11 | <5 |
| 49 | 6.75 | <5 |
| 50 | 6.7 | <5 |
| 51 | 6.49 | <5 |
| 52 | 6.91 | <5 |
| 53 | <5 | <5 |
| 54 | 5.98 | <5 |
| 55 | 6.03 | <5 |
| 56 | 5.49 | <5 |
| 57 | 6.58 | <5 |
| 58 | 6.54 | <5 |
| 59 | 6.82 | <5 |
| 60 | 6.59 | <5 |
| 61 | 5.7 | <5 |
| 62 | 6.52 | <5.4 |
| 62 | 5.9 | <5.4 |

TABLE A-continued

Cellular assays results with the compounds of the present disclosure

| Compound # | CDK7_A549 Wild-type CDK7 (pIC50) | CDK7_ A549 mutant hCDK7(pIC50) |
|---|---|---|
| 63 | 5.77 | <5 |
| 64 | 5.14 | <5 |
| 65 | 5.19 | <5 |
| 66 | 6.03 | <5 |
| 67 | 5.88 | <5 |
| 68 | 7.06 | <5 |
| 69 | 5.8 | <5 |
| 70 | <5 | <5 |
| 71 | 5.87 | <5 |
| 72 | 6.86 | 6.08 |
| 73 | 5.78 | <5 |
| 74 | 5.93 | <5 |
| 75 | 6.19 | <5 |
| 76 | 5.78 | <5 |
| 77 | 5.39 | <5 |
| 78 | 5.27 | <5 |
| 79 | 5.34 | <5 |
| 80 | 6.66 | <5 |
| 81 | 6.44 | <5 |
| 82 | 5.9 | <5 |
| 83 | 6.86 | <5.4 |
| 84 | 6.95 | <5 |
| 85 | 7.17 | <5 |
| 86 | 6.28 | <5 |
| 87 | 7.09 | 5.11 |
| 88 | 7.46 | 5.09 |
| 89 | 6.02 | <5 |
| 90 | 6.6 | ~5 |
| 91 | 6.96 | <5 |
| 92 | 6.37 | <5 |
| 93 | 6.37 | <5 |
| 94 | 6.27 | <5 |
| 95 | ~6.02 | <5 |
| 96 | 6.28 | <5 |
| 97 | 6.63 | <5 |
| 98 | 6.46 | <5 |
| 99 | ~6.1 | <5 |
| 100 | 7.8 | ~5.18 |
| 100 | ~7.89 | 5.25 |
| 100 | ~7.86 | 5.24 |
| 100 | ~7.69 | 5.25 |
| 100 | >8.01 | 5.16 |
| 101 | 7.42 | <5 |
| 101 | 7.23 | <5 |
| 101 | 7.16 | <5 |
| 101 | 6.87 | <5 |
| 102 | 6.73 | <5 |
| 102 | 6.76 | <5 |
| 102 | 6.82 | <5 |
| 102 | 6.83 | <5 |
| 103 | ~5.99 | <5 |
| 104 | 7.3 | <5 |
| 105 | 6.55 | <5 |
| 106 | 6.61 | <5 |
| 107 | 5.41 | <5 |
| 108 | <5 | <5 |
| 109 | 6.44 | <5 |
| 110 | 6.09 | <5 |
| 111 | 6.54 | <5 |
| 112 | 6.69 | <5 |
| 113 | 5.04 | <5 |
| 114 | 7.29 | ~5 |
| 114 | 7.55 | <5 |
| 115 | 7.42 | <5 |
| 115 | 7.76 | <5 |
| 116 | 6.72 | <5 |
| 116 | 6.57 | <5 |
| 117 | ~7.09 | <5 |
| 117 | ~7.62 | <5 |
| 117 | ~7.65 | <5 |
| 118 | 6.69 | <5 |
| 118 | 6.47 | <5 |
| 119 | 7.51 | <5 |
| 119 | 7.25 | 4.95 |
| 119 | ~7.14 | <5 |
| 120 | 6.28 | <5 |
| 121 | 7.55 | <5 |
| 121 | ~7.5 | <5 |
| 121 | | |
| 122 | 7.09 | <5 |
| 122 | 7.1 | <5 |
| 122 | 7.21 | <5 |
| 123 | 7.3 | 5.08 |
| 124 | 6.6 | <5 |
| 124 | 6.86 | <5 |
| 125 | ~7.75 | 5.17 |
| 125 | ~7.57 | 5.26 |
| 126 | 6.29 | <5 |
| 127 | 6.29 | <5 |
| 128 | 7.32 | <5 |
| 128 | 6.83 | <5 |
| 128 | 7.01 | <5 |
| 128 | 7.11 | <5 |
| 128 | 6.69 | <5 |
| 129 | 6.54 | <5 |
| 129 | 6.02 | <5 |
| 130 | 7.37 | <5 |
| 130 | 6.56 | <5 |
| 130 | 6.9 | <5 |
| 130 | 6.63 | <5 |
| 131 | 6.46 | <5 |
| 131 | 6.04 | <5 |
| 132 | 6.09 | <5 |
| 133 | 7.04 | 5.07 |
| 134 | 7.08 | <5 |
| 135 | ~7.3 | <5 |
| 136 | 6.59 | <5 |
| 137 | 6.78 | <5 |
| 138 | 7.33 | <5 |
| 139 | 7.14 | <5 |
| 139 | 6.2 | <5 |
| 140 | 5.5 | <5 |
| 141 | 6.79 | <5 |
| 142 | | |
| 142 | 6.45 | <5 |
| 143 | 6.04 | <5 |
| 144 | ~7.33 | <5 |
| 145 | ~7.84 | 5.34 |
| 146 | >8.61 | 5.36 |
| 147 | 6.51 | <5 |
| 148 | 7.37 | <5 |
| 148 | 7.22 | <5 |
| 148 | 7.12 | <5 |
| 148 | 7.2 | <5 |
| 148 | | |
| 148 | ~7.21 | <5 |
| 150 | 6.5 | <5 |
| 150 | 6.34 | <5 |
| 151 | 6.94 | <5 |
| 152 | 7.19 | ~5.08 |
| 154 | ~7.27 | <5 |
| 155 | 6.67 | <5 |
| 156 | >8.61 | 5.71 |
| 157 | 7.12 | 5.12 |
| 158 | 7.13 | ~5.22 |
| 159 | 6.75 | <5 |
| 160 | 6.94 | <5 |
| 161 | >8.01 | <5 |
| 162 | 6.68 | <5 |
| 163 | ~7.5 | <5 |
| 164 | 7.27 | <5 |
| 165 | 6.98 | <5 |
| 166 | 6.85 | <5 |
| 167 | 7.26 | <5 |
| 168 | 6.88 | <5 |
| 169 | >8.61 | 5.38 |

TABLE A-continued

Cellular assays results with the compounds of the present disclosure

| Compound # | CDK7_A549 Wild-type CDK7 (pIC50) | CDK7_ A549 mutant hCDK7(pIC50) |
|---|---|---|
| 170 | >8.01 | 5.14 |
| 171 | >8.01 | 5.07 |
| 172 | 6.45 | <5 |
| 173 | <5 | <5 |
| 174 | 7.23 | 5.11 |
| 175 | ~7.58 | ~5 |
| 176 | >8.01 | 5.04 |
| 177 | ~7.89 | 5.14 |
| 178 | >8.01 | 5.24 |
| 179 | ~7.25 | <5 |
| 180 | >8.01 | <5 |
| 181 | 7.38 | 5.63 |
| 182 | ~7.14 | 5.22 |
| 183 | 6.46 | <5 |
| 184 | 6.73 | <5 |
| 185 | ~6.42 | <5 |
| 186 | 6.57 | <5 |
| 187 | 5.21 | <5 |
| 188 | 6.41 | <5 |
| 189 | 6.71 | <5 |
| 189 | 6.7 | <5 |
| 190 | ~7.3 | <5 |
| 190 | ~7.39 | <5 |
| 191 | 6.72 | <5 |
| 192 | 6.34 | <5 |
| 193 | 6.29 | <5 |
| 194 | 6.8 | <5 |
| 195 | 6.99 | <5 |

TABLE B

Biochemical and enzymatic assay results with the compounds of the present disclosure

| compound # | CDK7 (KI(μM)) | CDK7 (kinact, $s^{-1}$) | CDK7 (kinact/ KI, $M^{-1}*s^{-1}$) |
|---|---|---|---|
| 1 | 0.1666 | 0.0001724 | 1034.81 |
| 1 | 0.60805 | 0.0004883 | 810.935 |
| 1 | 0.28485 | 0.00018825 | 629.351 |
| 1 | 0.59795 | 0.00025415 | 476.777 |
| 2 | 0.3654 | 0.0001984 | 543 |
| 3 | 1.029 | 0.0001661 | 161.419 |
| 5 | 0.5954 | 0.000243 | 408.129 |
| 6 | 2.731 | 0.000504 | 184.548 |
| 7 | 1.792 | 0.0001783 | 99.4978 |
| 8 | 0.2511 | 0.0001881 | 749.104 |
| 9 | 0.72015 | 0.0002155 | 305.814 |
| 10 | 0.3796 | 0.0001554 | 409.378 |
| 34 | 0.2581 | 0.0001861 | 721.038 |
| 35 | 2.046 | 8.56E−05 | 41.81 |
| 36 | 0.0802678 | 8.19E−05 | 1019.9 |
| 36 | 0.232715 | 0.00012562 | 539.8 |
| 37 | 0.164221 | 0.000136592 | 831.757 |
| 37 | 0.152279 | 7.29E−05 | 478.485 |
| 38 | 0.251404 | 9.70E−05 | 385.934 |

TABLE C

Biochemical and enzymatic assay results with the compounds of the present disclosure

| compound # | CDK7 (20 nM enz.) (KI, μM) | CDK7 (20 nM enz.) (kinact, $s^{-1}$) | CDK7 (20 nM enz.) (kinact/ KI, $M^{-1}*s^{-1}$) | CDK7 (20 nM enz.) (kobs/[I], $M^{-1}*s^{-1}$) |
|---|---|---|---|---|
| 1 | 0.389298 | 9.10E−05 | 233.643 | |
| 2 | 0.75448 | 6.34E−05 | 98.6955 | |
| 11 | 0.0411186 | 3.59E−05 | 874.224 | |
| 12 | 0.191211 | 7.04E−05 | 367.993 | |
| 12 | 0.497835 | 0.000127537 | 256.184 | |
| 13 | 0.078084 | 5.64E−05 | 721.717 | |
| 13 | 0.315115 | 8.30E−05 | 263.296 | |
| 14 | 0.182956 | 3.46E−05 | 189.253 | |
| 15 | 0.632481 | 5.72E−05 | 90.4603 | |
| 16 | 0.191848 | 5.05E−05 | 263.271 | |
| 17 | 0.71558 | 6.70E−05 | 93.6507 | |
| 18 | 0.528525 | 8.20E−05 | 155.226 | |
| 19 | 0.541966 | 8.14E−05 | 150.207 | |
| 20 | 0.0692994 | 4.85E−05 | 699.356 | |
| 21 | 0.407831 | 5.42E−05 | 132.871 | |
| 22 | 0.208222 | 6.38E−05 | 306.61 | |
| 23 | 0.254683 | 5.86E−05 | 230.004 | |
| 24 | 0.533314 | 4.78E−05 | 89.5966 | |
| 25 | 1.21774 | 6.34E−05 | 52.0911 | |
| 26 | 0.336299 | 4.84E−05 | 202.693 | |
| 27 | 5.21038 | 4.89E−05 | 9.39182 | |
| 28 | 0.686447 | 8.88E−05 | 129.424 | |
| 29 | 0.780108 | 7.30E−05 | 93.6387 | |
| 30 | 0.175255 | 5.79E−05 | 330.171 | |
| 31 | 0.225611 | 5.87E−05 | 260.04 | |
| 32 | 0.0249275 | 4.14E−05 | 1659.41 | 1282.92 |
| 39 | 0.6101 | 5.09E−05 | 83.4 | |
| 40 | 0.1603 | 5.56E−05 | 347 | |
| 41 | 0.9905 | 5.55E−05 | 56 | |
| 41 | 0.8977 | 5.25E−05 | 58.5 | |
| 42 | 0.0282498 | 4.14E−05 | 1464.67 | |
| 43 | | | | 1487.97 |

TABLE C-continued

Biochemical and enzymatic assay results with the compounds of the present disclosure

| compound # | CDK7 (20 nM enz.) (KI, μM) | CDK7 (20 nM enz.) (kinact, $s^{-1}$) | CDK7 (20 nM enz.) (kinact/ KI, $M^{-1}*s^{-1}$) | CDK7 (20 nM enz.) (kobs/[I], $M^{-1}*s^{-1}$) |
|---|---|---|---|---|
| 44 | 0.670298 | 4.31E−05 | 64.3521 | |
| 45 | 0.218764 | 4.44E−05 | 202.765 | |
| 46 | 0.094027 | 5.18E−05 | 666.886 | |
| 47 | 0.174938 | 7.35E−05 | 420.065 | |
| 48 | 0.23241 | 5.90E−05 | 253.785 | |
| 49 | 0.118276 | 5.65E−05 | 477.968 | |
| 50 | 0.302002 | 7.72E−05 | 255.699 | |
| 51 | 0.642893 | 8.79E−05 | 136.718 | |
| 52 | 0.0825436 | 5.90E−05 | 714.303 | |
| 53 | | | | 3.8 |
| 54 | 1.35758 | 7.77E−05 | 57.2457 | |
| 55 | 1.03939 | 6.83E−05 | 65.6712 | |
| 56 | 4.20266 | 8.48E−05 | 20.1716 | |
| 57 | 0.0876309 | 7.70E−05 | 878.743 | |
| 58 | 0.0450646 | 5.57E−05 | 1235.61 | |
| 59 | 0.0714931 | 5.06E−05 | 708.163 | |
| 60 | 0.282886 | 5.21E−05 | 184.255 | |
| 61 | 0.830289 | 5.10E−05 | 61.3807 | |
| 62 | 0.503645 | 5.74E−05 | 113.998 | |
| 62 | 2.0543 | 4.79E−05 | 23.3334 | |
| 63 | 0.173664 | 3.22E−05 | 185.5 | |
| 64 | 0.426532 | 4.81E−05 | 112.821 | |
| 65 | 4.12181 | 0.000100289 | 24.3314 | |
| 66 | 0.528374 | 4.52E−05 | 85.5337 | |
| 67 | 1.19858 | 0.000102852 | 85.8121 | |
| 68 | 0.0415685 | 8.54E−05 | 2055.37 | |
| 69 | 1.10062 | 6.30E−05 | 57.232 | |
| 70 | 52.977 | 0.000280817 | 5.30073 | |
| 71 | 3.2036 | 7.12E−05 | 22.2172 | |
| 72 | | | | 1086.41 |
| 73 | 1.2414 | 3.75E−05 | 30.2225 | |
| 74 | 0.131702 | 5.42E−05 | 411.756 | |
| 75 | 0.264655 | 3.84E−05 | 145.098 | |
| 76 | 0.457247 | 3.90E−05 | 85.2769 | |
| 77 | 0.172001 | 3.83E−05 | 222.617 | |
| 78 | 0.167723 | 3.85E−05 | 229.287 | |
| 79 | 0.188553 | 3.93E−05 | 208.559 | |
| 80 | 0.32001 | 4.18E−05 | 130.568 | |
| 81 | 0.309885 | 4.82E−05 | 155.591 | |
| 82 | 1.27604 | 4.27E−05 | 33.4495 | |
| 83 | 0.0589919 | 2.22E−05 | 376.933 | |
| 84 | 0.148039 | 8.33E−05 | 562.538 | |
| 85 | | | | 724.782 |
| 86 | 0.117119 | 6.46E−05 | 551.445 | |
| 87 | 0.233607 | 4.30E−05 | 184.075 | |
| 88 | 0.0485276 | 4.48E−05 | 923.478 | |
| 89 | 0.128417 | 5.45E−05 | 424.559 | |
| 90 | 0.109613 | 8.04E−05 | 733.484 | |
| 91 | 0.0405727 | 5.75E−05 | 1416.1 | |
| 92 | 0.100394 | 6.11E−05 | 608.866 | |
| 93 | 0.277466 | 6.26E−05 | 225.54 | |
| 94 | 0.498114 | 8.53E−05 | 171.226 | |
| 95 | 0.07076 | 2.35E−05 | 332.2 | |
| 96 | 0.0324 | 2.16E−05 | 665.4 | |
| 97 | 0.0068 | 2.76E−05 | 4031 | |
| 100 | 0.0811719 | 2.96E−05 | 364.853 | 976.446 |
| 100 | 0.0337977 | 3.21E−05 | 948.498 | |
| 100 | 0.020592 | 4.36E−05 | 2118.57 | |
| 100 | 0.0373664 | 4.41E−05 | 1181.41 | |
| 100 | 0.0291524 | 3.97E−05 | 1361.67 | |
| 101 | | | | 1463.39 |
| 101 | | | | 1455 |
| 101 | 0.077029 | 5.87E−05 | 761.724 | |
| 101 | 0.0323393 | 8.74E−05 | 2704.04 | |
| 102 | 0.531634 | 4.39E−05 | 82.6598 | |
| 102 | 1.289 | 6.34E−05 | 49.2129 | |
| 102 | 0.515657 | 5.62E−05 | 108.953 | |
| 102 | 0.50391 | 6.76E−05 | 134.098 | |
| 103 | 0.32035 | 5.08E−05 | 158.71 | |
| 104 | | | | 1140 |
| 105 | 0.120835 | 3.13E−05 | 258.754 | |
| 106 | 0.0858289 | 6.75E−05 | 785.928 | |
| 107 | 0.960402 | 5.21E−05 | 54.2934 | |

TABLE C-continued

Biochemical and enzymatic assay results with the compounds of the present disclosure

| compound # | CDK7 (20 nM enz.) (KI, μM) | CDK7 (20 nM enz.) (kinact, $s^{-1}$) | CDK7 (20 nM enz.) (kinact/ KI, $M^{-1}*s^{-1}$) | CDK7 (20 nM enz.) (kobs/[I], $M^{-1}*s^{-1}$) |
|---|---|---|---|---|
| 109 | 0.130242 | 4.50E−05 | 345.373 | |
| 110 | 0.0322397 | 4.30E−05 | 1332.21 | |
| 111 | 0.112286 | 0.000116093 | 1033.9 | |
| 112 | 0.0566599 | 2.73E−05 | 482.432 | |
| 113 | | 3.36E−06 | | |
| 114 | 0.0288364 | 4.67E−05 | 1619.41 | |
| 114 | 0.067826 | 8.94E−05 | 1318 | |
| 115 | 0.0594702 | 7.64E−05 | 1284.26 | |
| 115 | 0.0434165 | 5.98E−05 | 1377.97 | |
| 116 | 0.300237 | 4.57E−05 | 152.193 | |
| 116 | 0.188595 | 3.89E−05 | 206.471 | |
| 117 | 0.0339779 | 5.26E−05 | 1546.72 | |
| 117 | 0.029012 | 8.40E−05 | 2895.79 | |
| 117 | 0.0215166 | 4.63E−05 | 2153.89 | 800 |
| 118 | 0.27985 | 4.20E−05 | 149.971 | |
| 118 | 0.280596 | 5.02E−05 | 179.017 | |
| 119 | 0.024906 | 4.79E−05 | 1923.49 | |
| 119 | 0.042568 | 6.10E−05 | 1433.61 | |
| 119 | 0.0226763 | 4.27E−05 | 1881.64 | |
| 120 | 0.294975 | 3.80E−05 | 128.984 | |
| 121 | | | | 1089.23 |
| 121 | | | 611.255 | |
| 122 | 0.0292187 | 4.85E−05 | 1658.55 | |
| 122 | | | 891.412 | |
| 123 | 0.192824 | 4.09E−05 | 212.256 | |
| 124 | 0.42978 | 3.92E−05 | 91.1296 | |
| 124 | 0.381248 | 4.85E−05 | 127.249 | |
| 125 | 0.0395847 | 3.28E−05 | 828.7 | |
| 125 | 0.0196535 | 4.27E−05 | 2172.44 | |
| 126 | 0.108299 | 3.41E−05 | 315.029 | |
| 127 | 0.0921756 | 3.51E−05 | 380.793 | |
| 128 | 0.0368567 | 2.78E−05 | 754.645 | |
| 128 | 0.045144 | 4.46E−05 | 987.775 | |
| 128 | 0.0820916 | 4.01E−05 | 488.393 | |
| 128 | 0.00297 | 3.61E−05 | 12160 | |
| 129 | 0.577069 | 3.75E−05 | 65.0047 | |
| 129 | 1.10948 | 4.33E−05 | 39.0113 | |
| 130 | 0.0574052 | 2.71E−05 | 472.899 | |
| 130 | 0.0455582 | 3.30E−05 | 724.174 | |
| 130 | 0.1166 | 0.00012 | 1022 | |
| 131 | 1.079 | 7.92E−05 | 73.3914 | |
| 131 | 2.04634 | 3.69E−05 | 18.0417 | |
| 133 | 0.172976 | 2.65E−05 | 153.039 | |
| 134 | 0.058922 | 4.45E−05 | 755.681 | |
| 135 | 0.0344169 | 4.90E−05 | 1422.45 | |
| 136 | 0.0874213 | 5.36E−05 | 613.106 | |
| 137 | 0.253675 | 9.43E−05 | 371.696 | |
| 138 | 0.0907833 | 7.15E−05 | 787.61 | |
| 139 | 0.13464 | 5.63E−05 | 418.277 | |
| 139 | 0.0466 | 6.20E−05 | 1326 | |
| 140 | 2.57378 | 8.10E−05 | 31.4893 | |
| 142 | 0.007508 | 3.76E−05 | 5001 | |
| 144 | 0.00389 | 4.73E−05 | 12150 | |
| 148 | 0.0217548 | 4.04E−05 | 1856.36 | |
| 148 | | | | 952.381 |
| 148 | 0.0472962 | 6.08E−05 | 1029.7 | 1230.83 |
| 148 | 0.0348229 | 5.32E−05 | 1527.22 | |
| 148 | 0.00601 | 4.30E−05 | 7159 | |
| 150 | 0.283192 | 6.55E−05 | 231.324 | |
| 150 | 0.179643 | 4.70E−05 | 261.659 | |
| 151 | 0.15954 | 5.91E−05 | 370.265 | |
| 152 | 0.029364 | 3.94E−05 | 1342.29 | |
| 154 | 0.00416 | 5.87E−05 | 14110 | |
| 155 | 0.00172 | 2.06E−05 | 12170 | |
| 159 | 0.009 | 5.04E−05 | 5602 | |
| 160 | 0.01348 | 9.88E−05 | 7336 | |
| 189 | 0.0806302 | 8.10E−05 | 878.671 | |
| 190 | | | | 838.816 |
| 191 | 0.100466 | 8.29E−05 | 809.36 | |
| 192 | 0.856383 | 8.38E−05 | 102.591 | |
| 193 | 0.156092 | 2.62E−05 | 167.607 | |

TABLE C-continued

Biochemical and enzymatic assay results with the compounds of the present disclosure

| compound # | CDK7 (20 nM enz.) (KI, μM) | CDK7 (20 nM enz.) (kinact, $s^{-1}$) | CDK7 (20 nM enz.) (kinact/ KI, $M^{-1}*s^{-1}$) | CDK7 (20 nM enz.) (kobs/[I], $M^{-1}*s^{-1}$) |
|---|---|---|---|---|
| 194 | 0.0176756 | 2.42E−05 | 1370.86 | |
| 195 | 0.10754 | 5.21E−05 | 484.552 | |

Example D: Prophetic Formulations

"Active ingredient" (a.i.) as used throughout these examples relates to a compound of Formula (I), including any tautomer or stereoisomeric form thereof, or a pharmaceutically acceptable addition salt, or a solvate thereof, in particular to any one of the exemplified compounds.

Typical examples of recipes for the formulation of the invention are as follows

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of formula (I), including any tautomeric and stereochemically isomeric form, isotopically labeled derivative, or a pharmaceutically acceptable salt or solvate thereof:

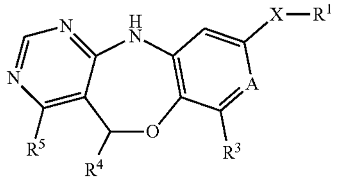

(I)

wherein,

X is a 4-7 membered non-aromatic heterocycle, a 4-10 membered non-aromatic bridged heterocycle, $C_{3-7}$cycloalkyl, $C_{5-7}$cycloalkenyl; wherein each of the cycles, independently, may be optionally substituted with —$C_{1-3}$alkyl;

$R^1$ is a 4-7 membered non-aromatic heterocycle having at least one nitrogen atom, wherein the at least one nitrogen atom is substituted with —C(═O)—CH═CH—$R^6$, or —C(═O)—CH≡CH—$R^7$, and wherein the 4-7 membered non-aromatic heterocycle is optionally substituted with $C_{1-3}$alkyl, halo, or D; or $R^1$ is $C_{1-3}$alkyl substituted with —NH—C(═O)—CH═CH—$R^6$ or —NH—C(═O)—CH═CH—$R^7$;

A is a $CR^2$ or N;

$R^2$ is H, $C_{1-3}$alkyl, cyano, halo, or $C_{2-3}$alkynyl;

$R^3$ is $C_{1-3}$alkyl, H, halogen, $C_{2-3}$alkenyl, $C_{2-3}$alkynyl, cyano, $C_{3-7}$cycloalkyl; $C_{1-3}$alkyl substituted with one, two, or three halo, hydroxy, carboxyl, amino, mono- or di($C_{1-6}$alkyl)amino; 1-imidazolyl, 2-imidazolyl, or 4-imidazolyl;

$R^4$ is $C_{1-3}$alkyl; $C_{1-3}$alkyl substituted with one, two, or three halo; H;

$R^5$ is a 4-7 membered saturated or partially unsaturated heterocycle, a 5-6 membered heteroaryl, or a 6-12 membered spiro-bicyclic heterocycle; wherein each of the cycles have one, two, or three heteroatoms selected from sulphur, nitrogen, and oxygen; and wherein, said sulphur, if present, is substituted with dioxo, or with oxo and imino;

said one, two, or three nitrogens, if present, may, each independently, be optionally substituted with $C_{1-3}$alkyl;

any one of the carbon atoms of the cycles may be optionally substituted with $C_{1-3}$alkyl, hydroxy$C_{1-3}$alkyl, $C_{1-3}$alkoxy, oxo, $C_{1-3}$alkylsulfonyl, cyano, hydroxy, halo, carboxyl, mono- or di($C_{1-6}$alkyl)amino, polyhalo$C_{1-3}$alkyl, polyhalo$C_{1-3}$alkoxy, $C_{2-3}$alkenyl, and $C_{2-3}$alkynyl;

$R^6$ is H; —$C_{1-3}$alkyl optionally substituted with one, two, or three substituents selected from halo, D, and —$NR^{7a}R^{7b}$, wherein each of $R^{7a}$ and $R^{7b}$ is, independently, $C_{1-3}$alkyl; or $R^{7a}$ and $R^{7b}$ taken together form a heterocycle; and $R^7$ is —$C_{1-3}$alkyl optionally substituted with one, two, or three substituents selected from halo, D, and —$NR^{7a}R^{7b}$, wherein each of $R^{7a}$ and $R^{7b}$ is, independently, $C_{1-3}$alkyl, or $R^{7a}$ and $R^{7b}$ taken together form a heterocycle.

2. The compound according to claim 1, including any tautomeric and stereochemically isomeric form, isotopically labeled derivative, or a pharmaceutically acceptable salt or solvate thereof, wherein, X is a 4-7 membered non-aromatic heterocycle, a 4-10 membered non-aromatic bridged heterocycle, $C_{4-7}$cycloalkyl, $C_{5-7}$cycloalkenyl; wherein each of the cycles, independently, may be optionally substituted with —$C_{1-3}$alkyl;

$R^1$ is a 4-7 membered non-aromatic heterocycle having at least one nitrogen atom, wherein the at least one nitrogen atom is substituted with —C(═O)—CH═CH—$R^6$, or —C(═O)—CH═CH—$R^7$, and wherein the 4-7 membered non-aromatic heterocycle is optionally substituted with $C_{1-3}$alkyl, halo, or D; or $R^1$ is $C_{1-3}$alkyl substituted with —NH—C(═O)—CH—CH—$R^6$ or —NH—C(═O)—CH═CH—$R^7$;

A is a $CR^2$ or N;

$R^2$ is H, $C_{1-3}$alkyl, or cyano;

$R^3$ is $C_{1-3}$alkyl, H, halogen, cyano, $C_{3-7}$cycloalkyl; or $C_{1-3}$alkyl substituted with one, two, or three halo;

$R^4$ is methyl or H;

$R^5$ a 4-7 membered saturated or partially unsaturated heterocycle, a 5-6 membered heteroaryl, or a 6-12 membered spiro-bicyclic heterocycle; wherein each of the cycles have one, two, or three heteroatoms selected from sulphur, nitrogen, and oxygen; and wherein, said sulphur, if present, is substituted with dioxo, or with oxo and imino;

said one, two, or three nitrogens, if present, may, each independently, be optionally substituted with $C_{1-3}$alkyl;

any one of the carbon atoms of the cycles may be optionally substituted with $C_{1-3}$alkyl, hydroxy$C_{1-3}$alkyl, $C_{1-3}$alkoxy, oxo, $C_{1-3}$alkylsulfonyl, cyano, hydroxy, halo, carboxyl, mono- or di($C_{1-6}$alkyl)amino, polyhalo$C_{1-3}$alkyl, polyhalo$C_{1-3}$alkoxy, $C_{2-3}$alkenyl, and $C_{2-3}$alkynyl;

$R^6$ is H; —$C_{1-3}$alkyl optionally substituted with one, two, or three substituents selected from halo, D, and —$NR^{7a}R^{7b}$, wherein each of $R^{7a}$ and $R^{7b}$ is, independently, $C_{1-3}$alkyl; or $R^{7a}$ and $R^{7b}$ taken together form a heterocycle; and $R^7$ is —$C_{1-3}$alkyl optionally substituted with one, two, or three substituents selected from halo, D, and —$NR^{7a}R^{7b}$, wherein each of $R^{7a}$ and $R^{7b}$ is, independently, $C_{1-3}$alkyl; or $R^{7a}$ and $R^{7b}$ taken together form a heterocycle.

3. The compound according to claim 1, wherein the compound is of formula (II), including any tautomeric and stereochemically isomeric form, isotopically labeled derivative, or a pharmaceutically acceptable salt or solvate thereof, (II)

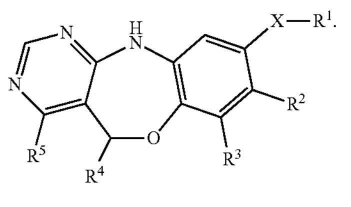

4. The compound according to claim 1, wherein the compound is of formula (IIa), (IIb), (IIc), (IId), (IIe), or (IIf), including any tautomeric and stereochemically isomeric form, isotopically labeled derivative, or a pharmaceutically acceptable salt or solvate thereof:

(IIa)

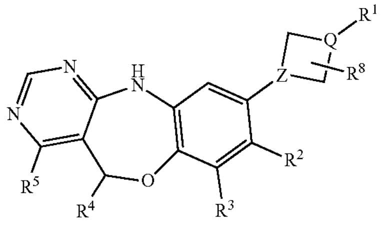

(IIb)

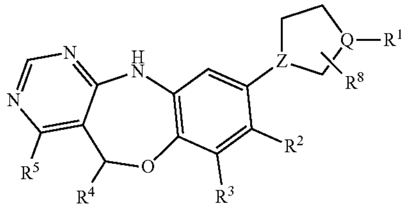

(IIc)

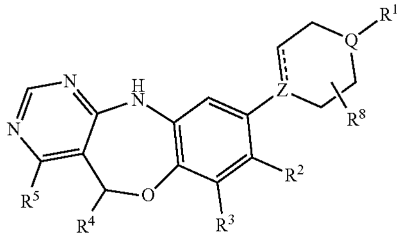

(IId)

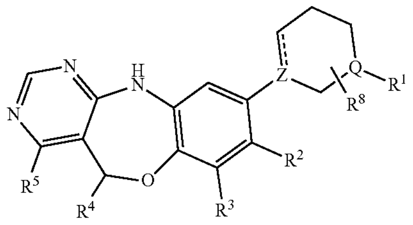

(IIe)

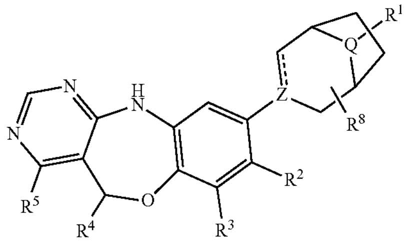

(IIf)

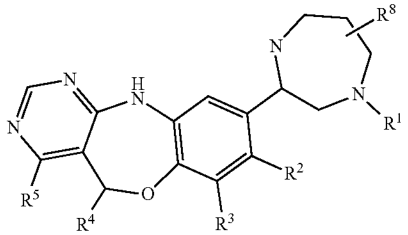

wherein in each of the compounds of formula (IIa), (IIb), (Ic), (IId), (IIe), or (IIf), each Q is, independently, CH or N;

each Z is, independently, CH or N;

each $R^8$ is, independently, H or —$C_{1-3}$alkyl; and said $R^8$ may be bound to any carbon or nitrogen atom of the cycle; and each dashed bond is, independently, an optional double bond.

5. The compound according to claim 1, wherein $R^1$ is selected from

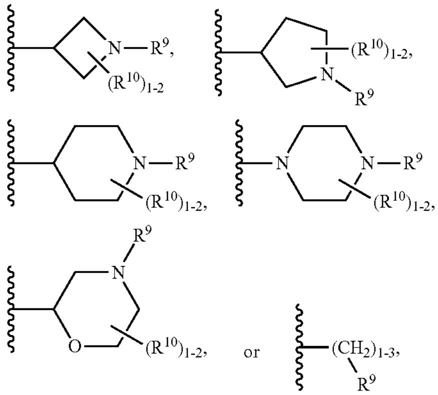

wherein each $R^9$ is, independently, —C(═O)—CH═CH—$R^6$, or —C(═O)—CH═CH—$R^7$;

each $R^{10}$ is, independently, H, —$C_{1-3}$alkyl, halo, or D; and said $R^{10}$ may be bound to any carbon atom of the cycle; and $R^5$ is selected from

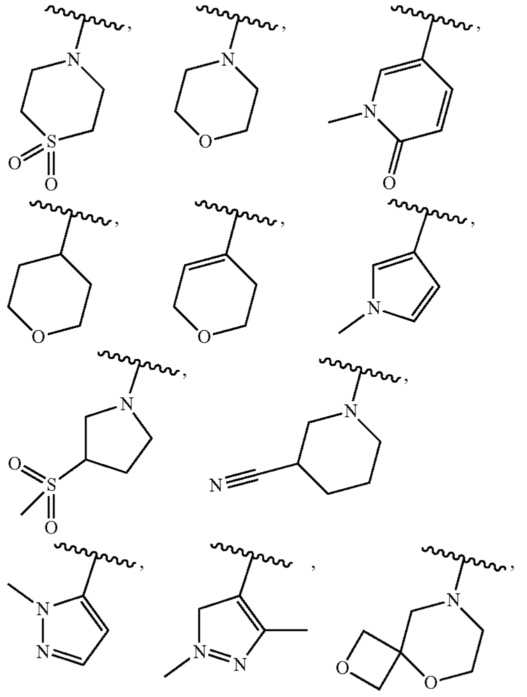

-continued

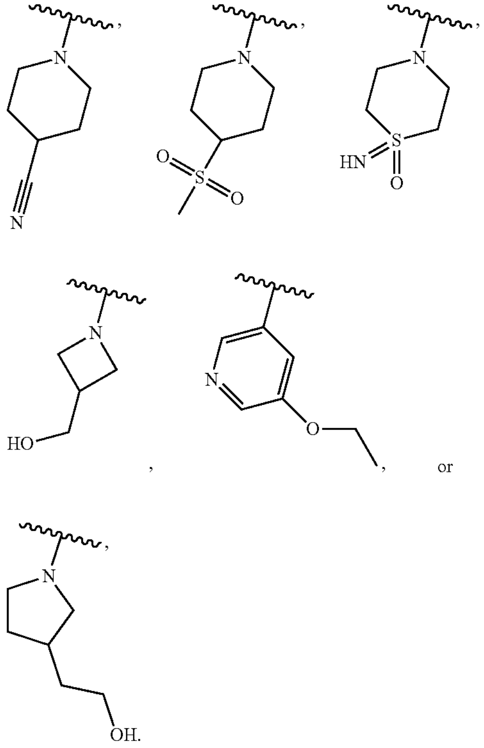

6. The compound according to claim 1, wherein the compound is of formula (IIIa), (IIIb), (IIIc), (IIId), (IIIe), or (IIIf), including any tautomeric and stereochemically isomeric form, isotopically labeled derivative, or a pharmaceutically acceptable salt or solvate thereof:

(IIIa)

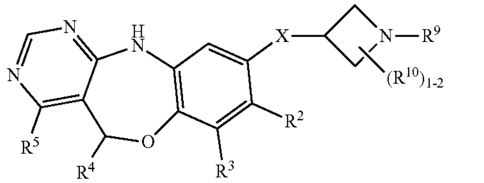

(IIIb)

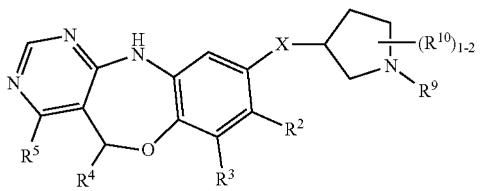

(IIIc)

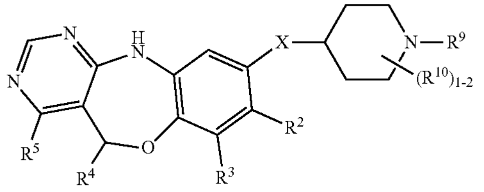

-continued (IIId)

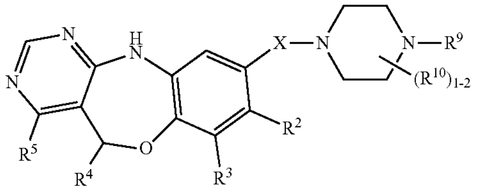

(IIIe)

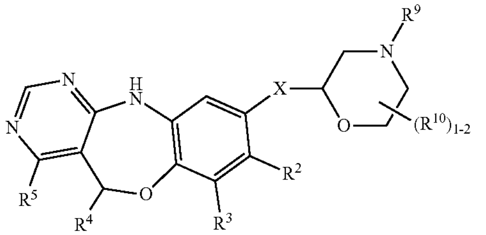

(IIIf)

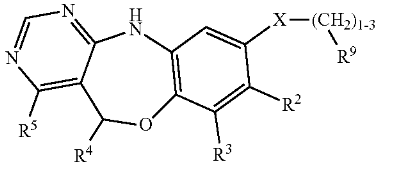

wherein each $R^9$ is, independently, —C(═O)—CH═CH—$R^6$, or —C(═O)—CH═CH—$R^7$;

each $R^{10}$ is, independently, H, —$C_{1-3}$alkyl, halo, or D; and said $R^{10}$ may be bound to any carbon atom of the cycle.

7. The compound according to claim 1, wherein the compound is of formula (IVa), (IVb), (IVc), (IVd), (IVe), (IVf), (IVg), (IVh), (IVi), (IVj), (IVk), (IVl), (IVm), (IVn), (Ivo), (IVp), or (IVq), including any tautomeric and stereochemically isomeric form, isotopically labeled derivative, or a pharmaceutically acceptable salt or solvate thereof:

(IVa)

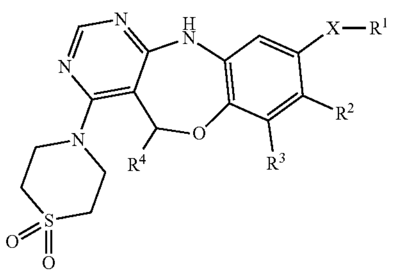

(IVb)

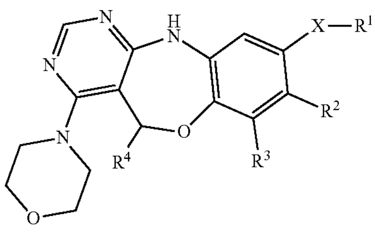

-continued (IVc)

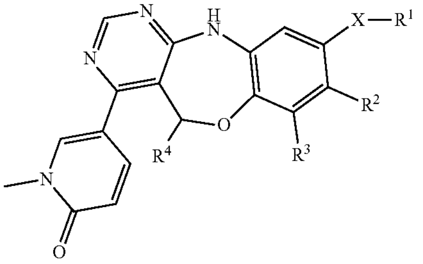

(IVd)

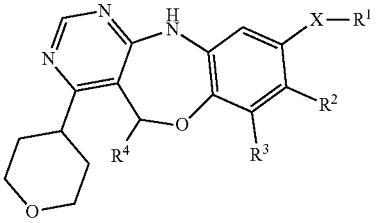

(IVe)

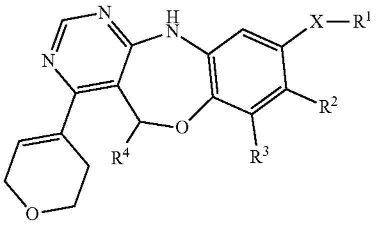

(IVf)

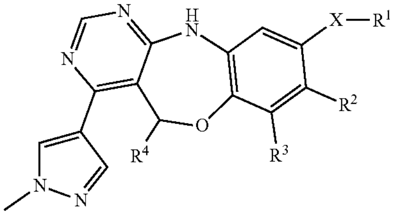

(IVg)

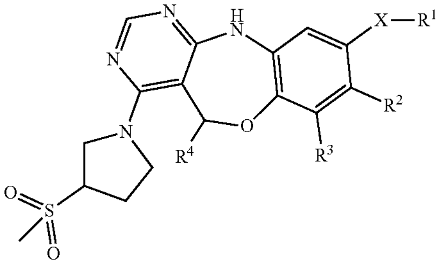

(IVh)

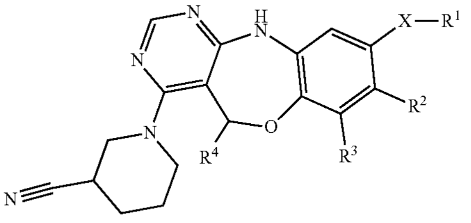

-continued (IVi)

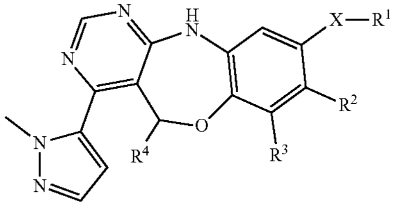

(IVj)

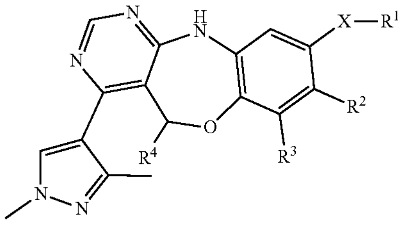

(IVk)

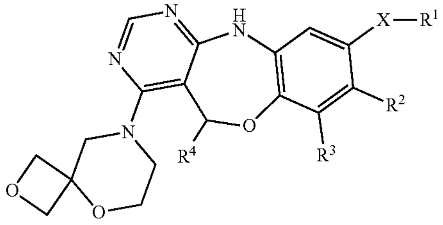

(IVl)

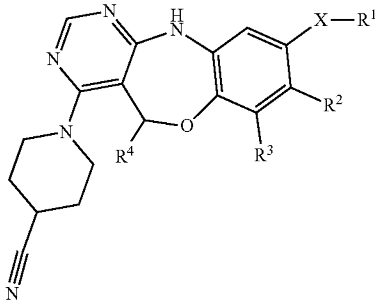

(IVm)

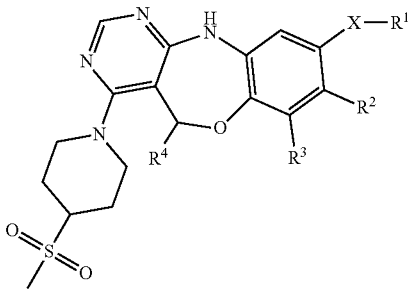

(IVn)

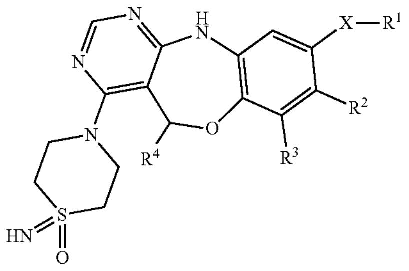

-continued (IVo)

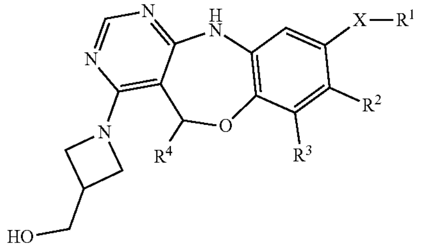

(IVp)

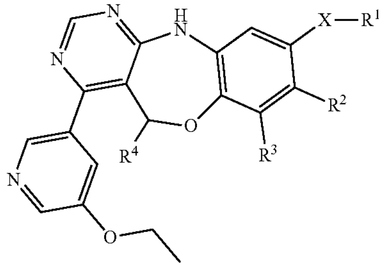

(IVq)

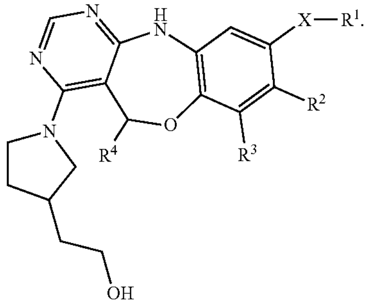

8. The compound according to claim 1, wherein the compound is of formula (Va) or (Vb), including any tautomeric and stereochemically isomeric form, isotopically labeled derivative, or a pharmaceutically acceptable salt or solvate thereof:

(Va)

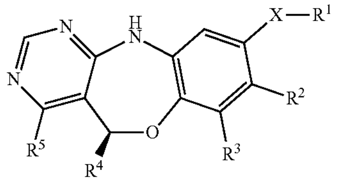

(Vb)

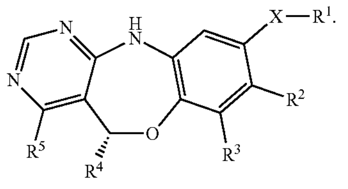

9. The compound according to claim 1, wherein the compound is of formula (VI), including any tautomeric and stereochemically isomeric form, isotopically labeled derivative, or a pharmaceutically acceptable salt or solvate thereof, (VI)

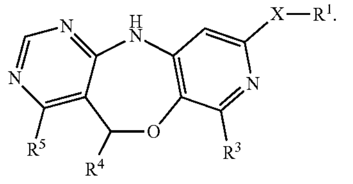

10. The compound according to claim 9, including any tautomeric and stereochemically isomeric form, isotopically labeled derivative, or a pharmaceutically acceptable salt or solvate thereof, wherein, X is a 4-7 membered non-aromatic heterocycle;

$R^1$ is a 4-7 membered non-aromatic heterocycle having at least one nitrogen atom, wherein the at least one nitrogen atom is substituted with —C(=O)—CH=CH—$R^6$, or —C(=O)—CH=CH—$R^7$;

$R^3$ is $C_{1-3}$alkyl, H, halogen, cyano, $C_{3-7}$cycloalkyl; or $C_{1-3}$alkyl substituted with one, two, or three halo;

$R^4$ is methyl or H;

$R^5$ is a 4-7 membered saturated or partially unsaturated heterocycle, a 5-6 membered heteroaryl, or a 6-12 membered spiro-bicyclic heterocycle; wherein each of the cycles have one, two, or three heteroatoms selected from sulphur, nitrogen, and oxygen; and wherein, said sulphur, if present, is substituted with dioxo, or with oxo and imino;

said one, two, or three nitrogens, if present, may, each independently, be optionally substituted with $C_{1-3}$alkyl;

any one of the carbon atoms of the cycles may be optionally substituted with $C_{1-3}$alkyl, hydroxy$C_{1-3}$alkyl, $C_{1-3}$alkoxy, oxo, $C_{1-3}$alkylsulfonyl, cyano, hydroxy, halo, carboxyl, mono- or di($C_{1-6}$alkyl)amino, polyhalo$C_{1-3}$alkyl, polyhalo$C_{1-3}$alkoxy, $C_{2-3}$alkenyl, and $C_{2-3}$alkynyl;

$R^6$ is H; —$C_{1-3}$alkyl optionally substituted with one, two, or three substituents selected from halo, D, and —$NR^{7a}R^{7b}$, wherein each of $R^{7a}$ and $R^{7b}$ is, independently, $C_{1-3}$alkyl; or $R^{7a}$ and $R^{7b}$ taken together form a heterocycle; and $R^7$ is —$C_{1-3}$alkyl optionally substituted with one, two, or three substituents selected from halo, D, and —$NR^{7a}R^{7b}$, wherein each of $R^{7a}$ and $R^{7b}$ is, independently, $C_{1-3}$alkyl; or $R^{7a}$ and $R^{7b}$ taken together form a heterocycle.

11. The compound according to claim 9, wherein the compound is of formula (VIIa), (VIIb), (VIIc), (VIId), (VIIe), or (VIIf), including any tautomeric and stereochemically isomeric form, isotopically labeled derivative, or a pharmaceutically acceptable salt or solvate thereof:

(VIIa)

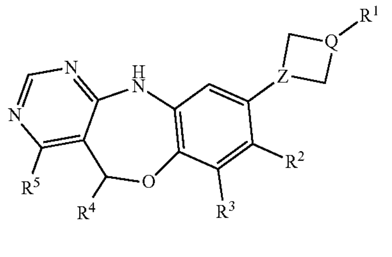

-continued (VIIb)

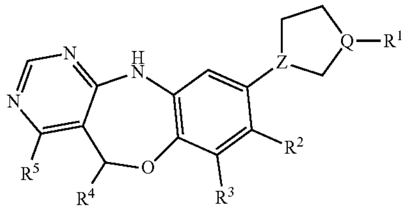

(VIIc)

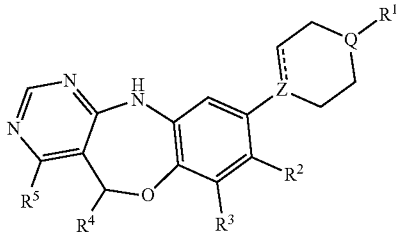

(VIId)

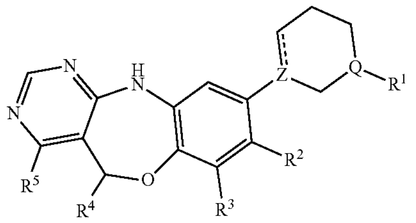

(VIIe)

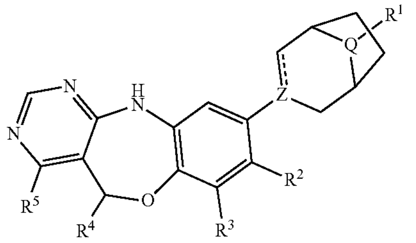

(VIIf)

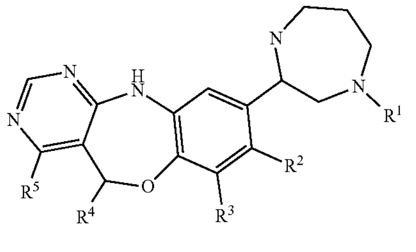

wherein, each Q is, independently, CH or N;

each Z is, independently, CH or N.

12. The compound according to claim 9, wherein the compound is of formula (VIIIa), (VIIIb), (VIIIc), (VIIId), (VIIIe), or (VIIIf) including any tautomeric and stereochemically isomeric form, isotopically labeled derivative, or a pharmaceutically acceptable salt or solvate thereof:

(VIIIa)

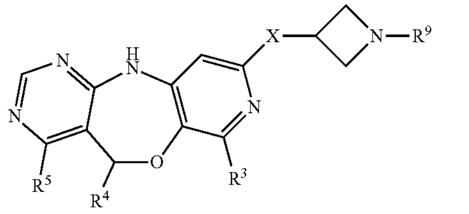

(VIIIb)

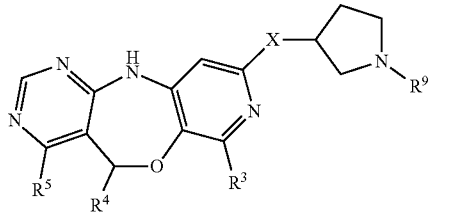

(VIIIc)

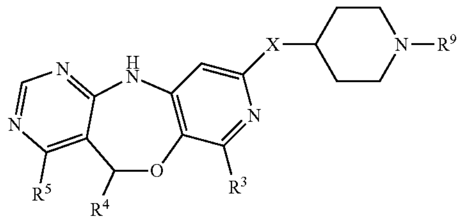

(VIIId)

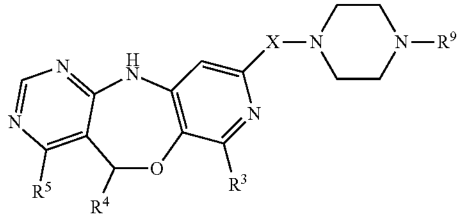

(VIIIe)

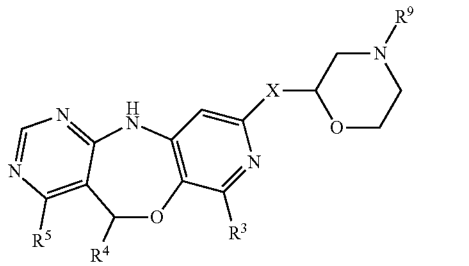

(VIIIf)

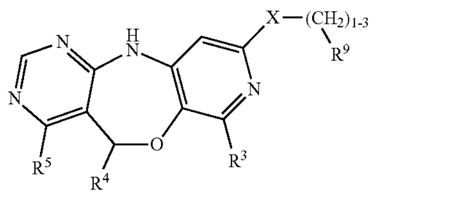

wherein $R^9$ is —C(=O)—CH=CH—$R^6$, or —C(=O)—CH=CH—$R^7$.

13. The compound according to claim 9, wherein the compound is of formula (IXa), (IXb), (IXc), (IXd), (IXe), (IXf), (IXg), (IXh), (IXi), (IXj), (IXk), (IXl), (IXm), (IXn), (IXo), (IXp), or (IXq), including any tautomeric and stereochemically isomeric form, isotopically labeled derivative, or a pharmaceutically acceptable salt or solvate thereof:

(IXa)

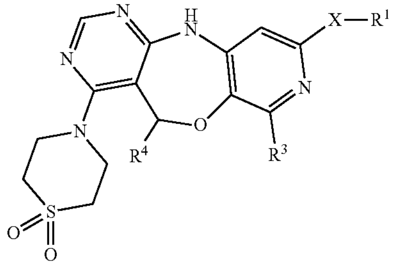

(IXb)

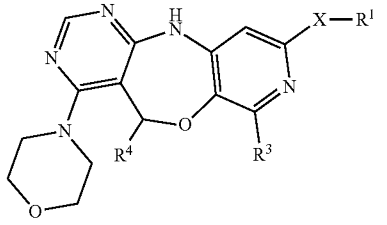

(IXc)

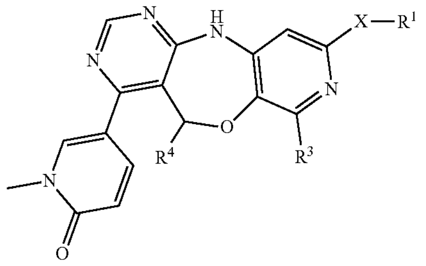

(IXd)

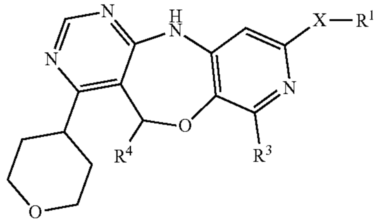

(IXe)

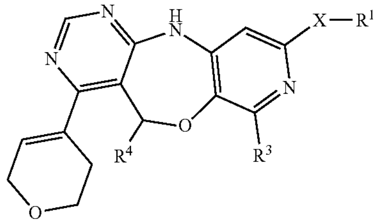

(IXf)

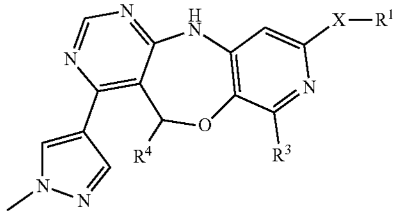

(IXg)
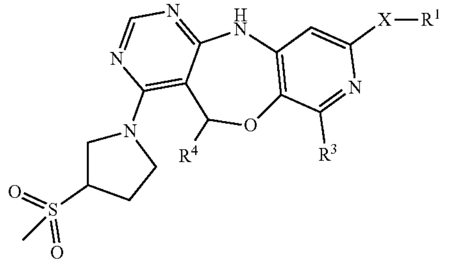
(IXh)
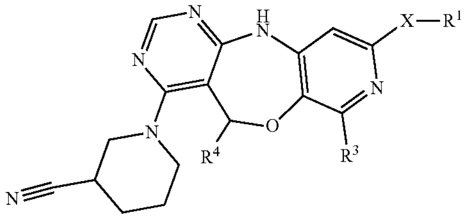
(IXi)
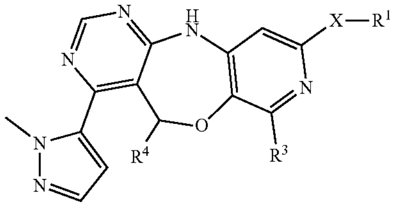
(IXj)
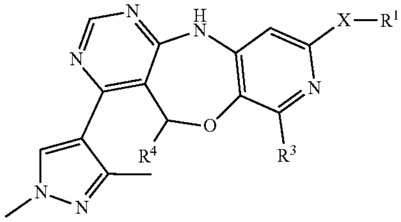
(IXk)
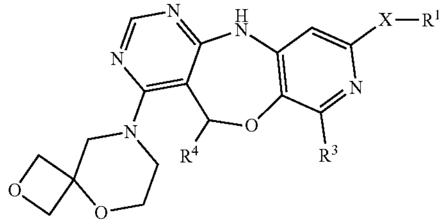
(IXl)
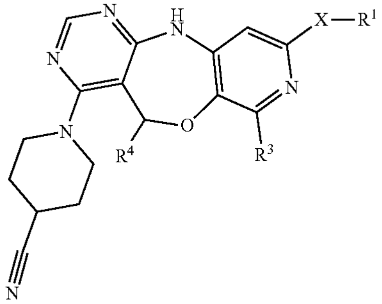
(IXm)
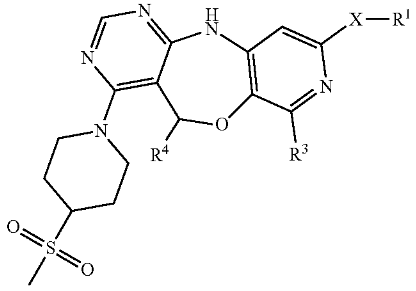
(IXn)
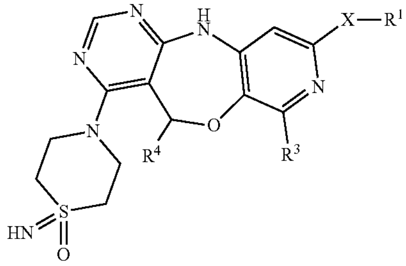
(IXo)
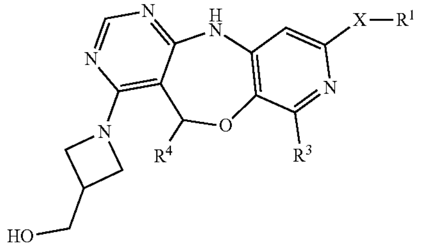
(IXp)
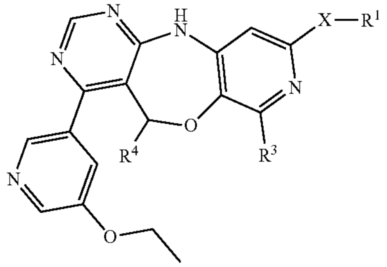
(IXq)
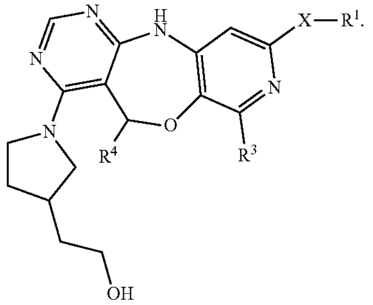

14. The compound according to claim 9, including any tautomeric and stereochemically isomeric form, isotopically labeled derivative, or a pharmaceutically acceptable salt or solvate thereof: wherein, $R^5$ is

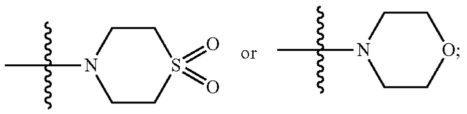 [SMILES: *N1CCS(=O)(=O)CC1 ; *N1CCOCC1]

15. The compound according to claim 9, wherein the compound is of formula (Xa) or (Xb), including any tautomeric and stereochemically isomeric form, isotopically labeled derivative, or a pharmaceutically acceptable salt or solvate thereof:

(Xa)

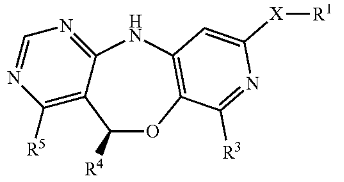

(Xb)

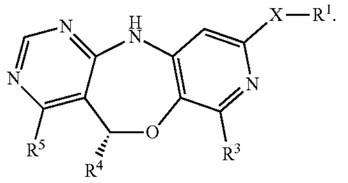

16. The compound according to claim 1, including any tautomeric and stereochemically isomeric form, isotopically labeled derivative, or a pharmaceutically acceptable salt or solvate thereof, wherein the compound is selected from:

| Cpd # | Structure | Cpd # | Structure |
|---|---|---|---|
| 1 | 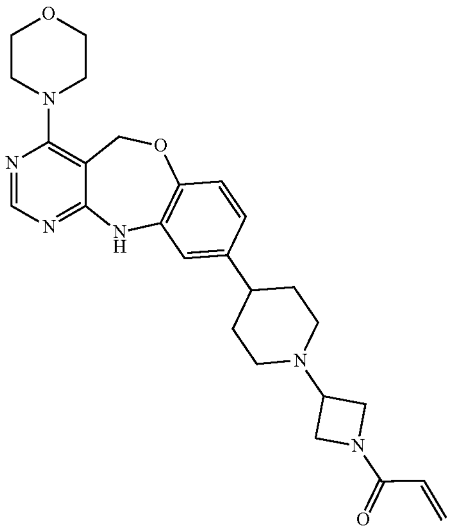 [SMILES: C=CC(=O)N1CC(N2CCC(c3ccc4c(c3)Nc3ncnc(N5CCOCC5)c3CO4)CC2)C1] | 4 | 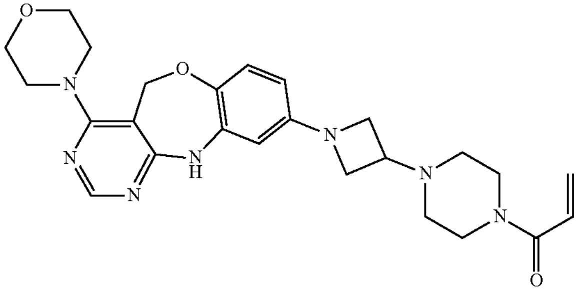 [SMILES: C=CC(=O)N1CCN(C2CN(c3ccc4c(c3)Nc3ncnc(N5CCOCC5)c3CO4)C2)CC1] |

-continued
| Cpd # | Structure | Cpd # | Structure |
|---|---|---|---|
| 2 | 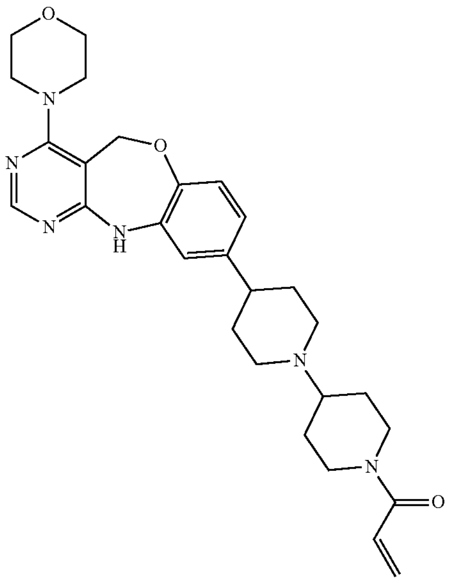 [SMILES: C=CC(=O)N1CCC(N2CCC(c3ccc4c(c3)Nc3ncnc(N5CCOCC5)c3CO4)CC2)CC1] | 5 | 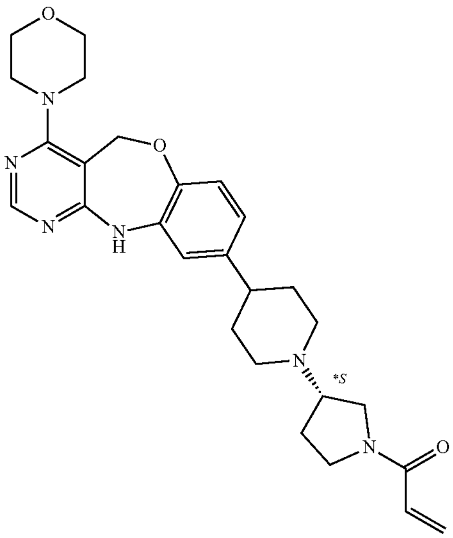 [SMILES: C=CC(=O)N1CC[C@H](N2CCC(c3ccc4c(c3)Nc3ncnc(N5CCOCC5)c3CO4)CC2)C1] |

-continued
| Cpd # | Structure | Cpd # | Structure |
| --- | --- | --- | --- |
| 3 | 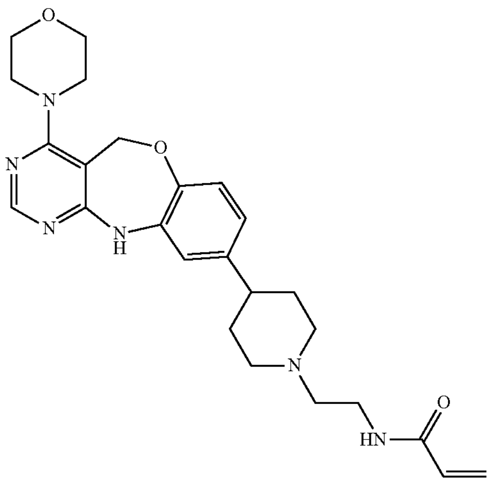 [SMILES: C=CC(=O)NCCN1CCC(c2ccc3c(c2)Nc2ncnc(N4CCOCC4)c2CO3)CC1] | 6 | 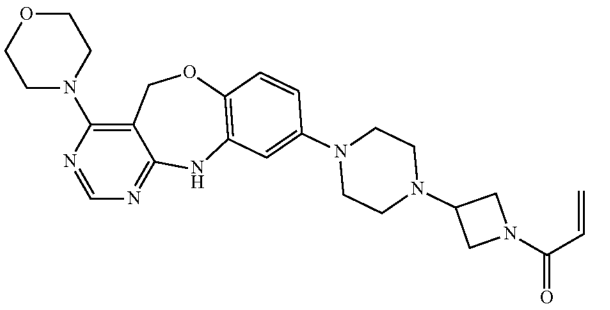 |
| 7 | 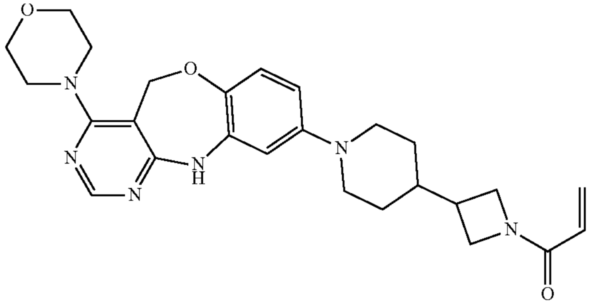 | 10 | 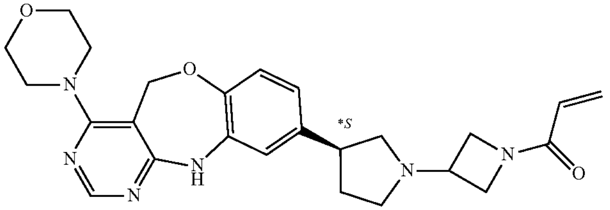 [SMILES: C=CC(=O)N1CC(N2CC[C@@H](c3ccc4c(c3)Nc3ncnc(N5CCOCC5)c3CO4)C2)C1] |

-continued
| Cpd # | Structure | Cpd # | Structure |
|---|---|---|---|
| 8 | 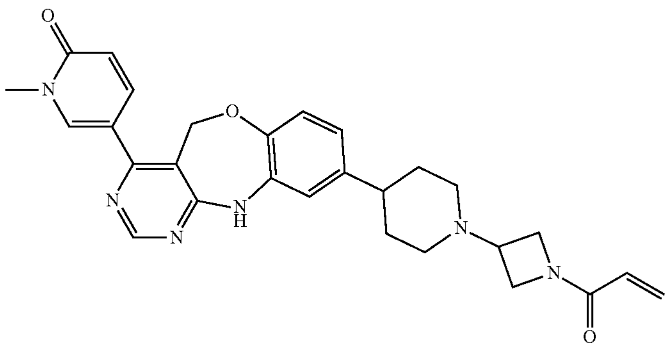 [SMILES: C=CC(=O)N1CC(N2CCC(c3ccc4c(c3)Nc3ncnc(-c5ccc(=O)n(C)c5)c3CO4)CC2)C1] | 11 | 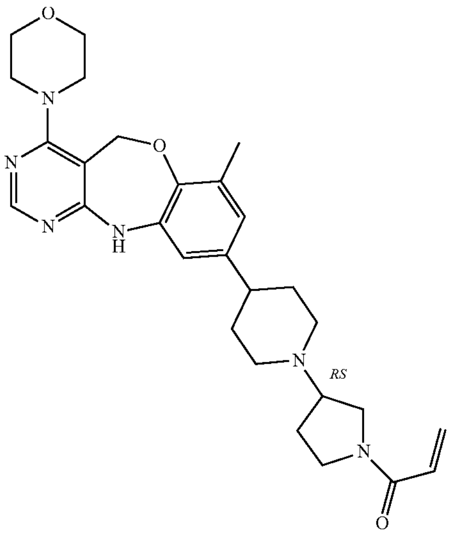RS |

-continued
| Cpd # | Structure | Cpd # | Structure |
|---|---|---|---|
| 9 | 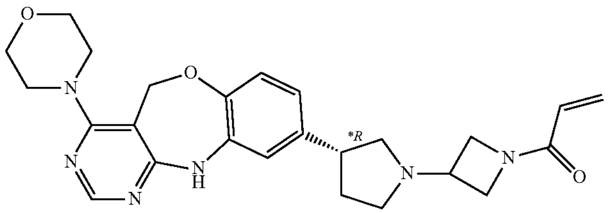 [SMILES: C=CC(=O)N1CC(N2CC[C@H](c3ccc4c(c3)Nc3ncnc(N5CCOCC5)c3CO4)C2)C1] | 12 | 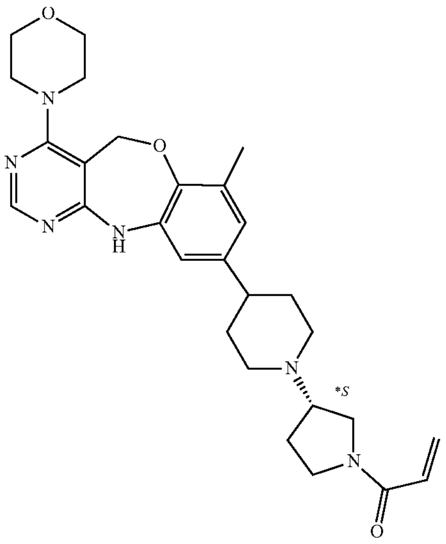 |

-continued
| Cpd # | Structure | Cpd # | Structure |
|---|---|---|---|
| 13 | 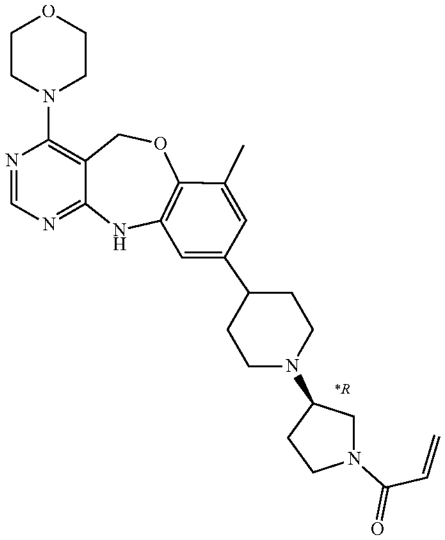 | 16 | 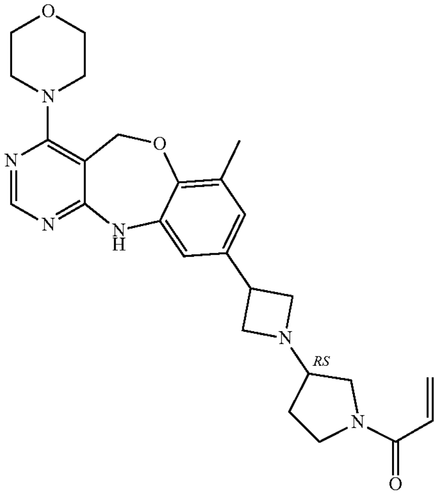 [SMILES: C=CC(=O)N1CCC(N2CC(c3cc(C)c4c(c3)Nc3ncnc(N5CCOCC5)c3CO4)C2)C1] |

-continued
| Cpd # | Structure | Cpd # | Structure |
|---|---|---|---|
| 14 | 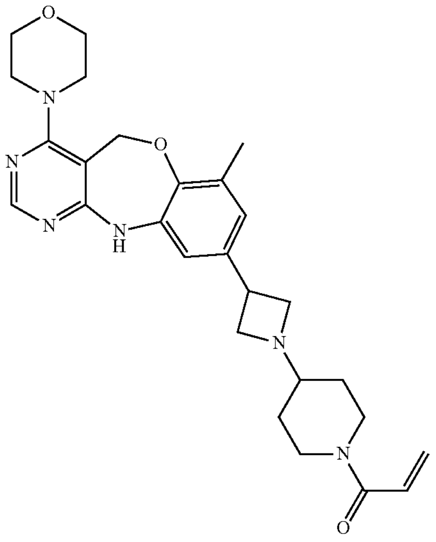 | 17 | 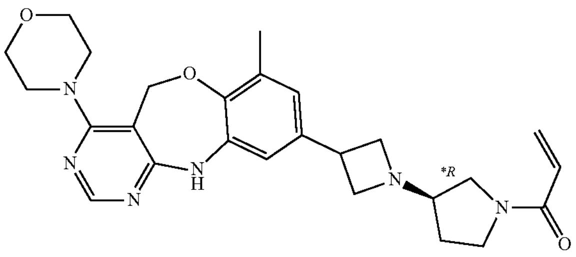 [SMILES: C=CC(=O)N1CC[C@@H](N2CC(c3cc(C)c4c(c3)Nc3ncnc(N5CCOCC5)c3CO4)C2)C1] |
| 15 | 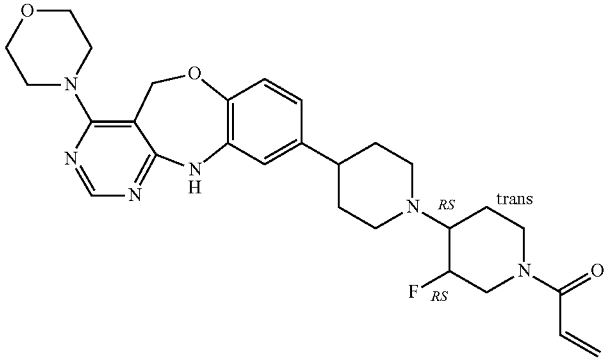 | 18 | 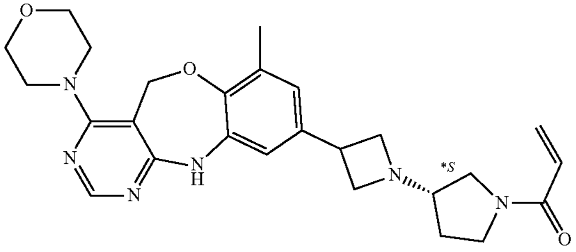 [SMILES: C=CC(=O)N1CC[C@H](N2CC(c3cc(C)c4c(c3)Nc3ncnc(N5CCOCC5)c3CO4)C2)C1] |

-continued
| Cpd # | Structure | Cpd # | Structure |
|---|---|---|---|
| 19 | 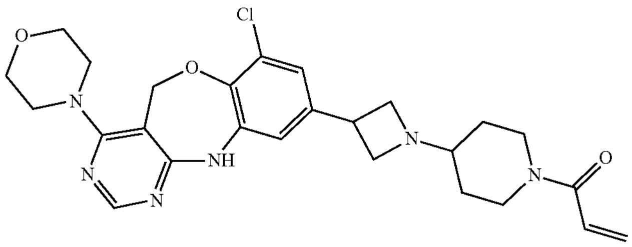 [SMILES: C=CC(=O)N1CCC(N2CC(c3cc(Cl)c4c(c3)Nc3ncnc(N5CCOCC5)c3CO4)C2)CC1] | 22 | 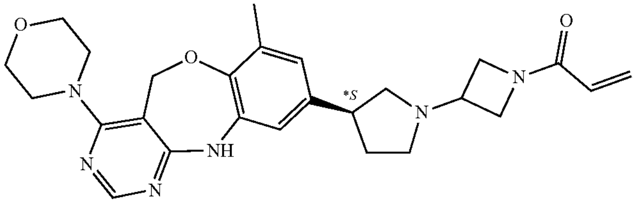 [SMILES: C=CC(=O)N1CC(N2CC[C@@H](c3cc(C)c4c(c3)Nc3ncnc(N5CCOCC5)c3CO4)C2)C1] |
| 20 | 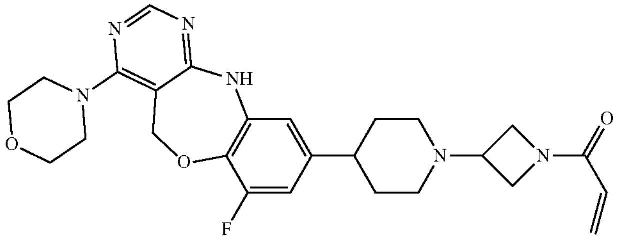 [SMILES: C=CC(=O)N1CC(N2CCC(c3cc(F)c4c(c3)Nc3ncnc(N5CCOCC5)c3CO4)CC2)C1] | 23 | 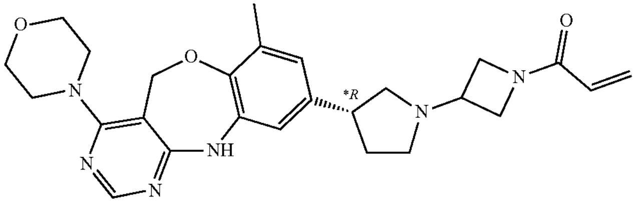 [SMILES: C=CC(=O)N1CC(N2CC[C@H](c3cc(C)c4c(c3)Nc3ncnc(N5CCOCC5)c3CO4)C2)C1] |
| 21 | 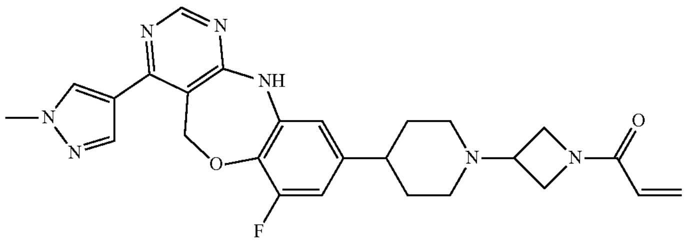 [SMILES: C=CC(=O)N1CC(N2CCC(c3cc(F)c4c(c3)Nc3ncnc(-c5cnn(C)c5)c3CO4)CC2)C1] | 24 | 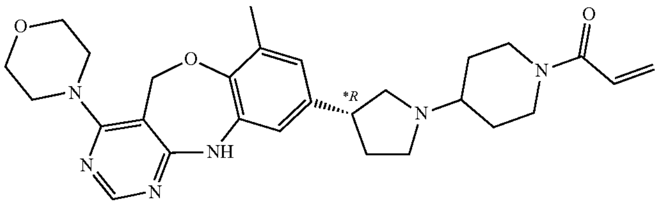 [SMILES: C=CC(=O)N1CCC(N2CC[C@H](c3cc(C)c4c(c3)Nc3ncnc(N5CCOCC5)c3CO4)C2)CC1] |

-continued
| Cpd # | Structure | Cpd # | Structure |
| --- | --- | --- | --- |
| 25 | 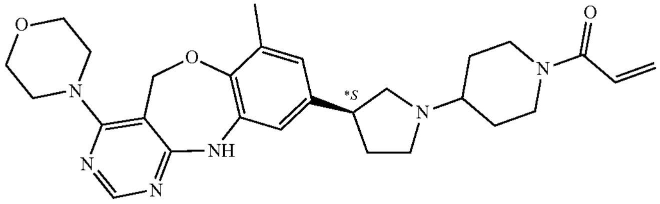 [SMILES: C=CC(=O)N1CCC(N2CC[C@@H](c3cc(C)c4c(c3)Nc3ncnc(N5CCOCC5)c3CO4)C2)CC1] | 28 | 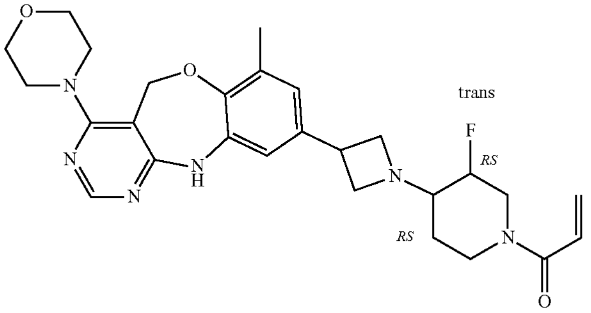 [SMILES: C=CC(=O)N1CCC(N2CC(c3cc(C)c4c(c3)Nc3ncnc(N5CCOCC5)c3CO4)C2)C(F)C1] |
| 26 | 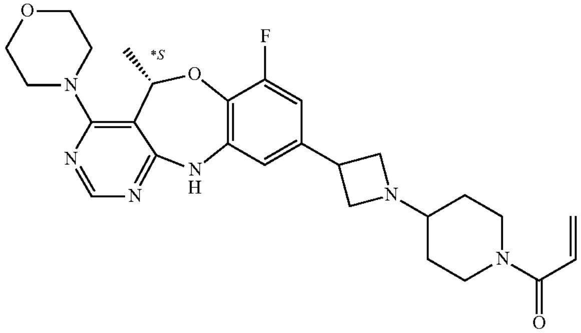 | 29 | 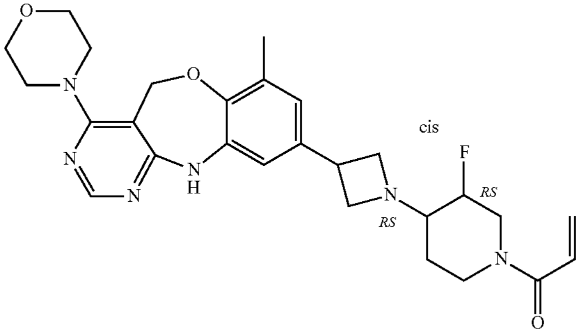 |

-continued
| Cpd # | Structure | Cpd # | Structure |
|---|---|---|---|
| 27 | 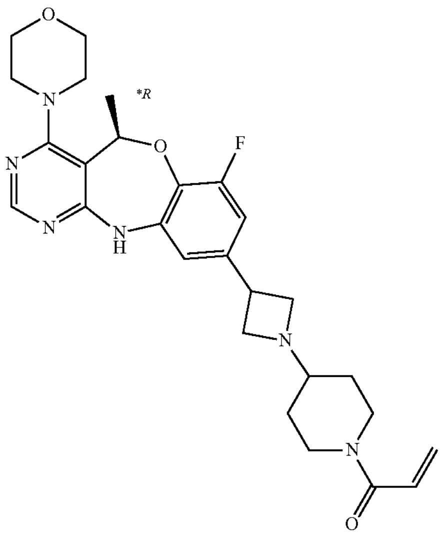 [SMILES: C=CC(=O)N1CCC(N2CC(c3cc(F)c4c(c3)Nc3ncnc(N5CCOCC5)c3[C@@H](C)O4)C2)CC1] | 30 | 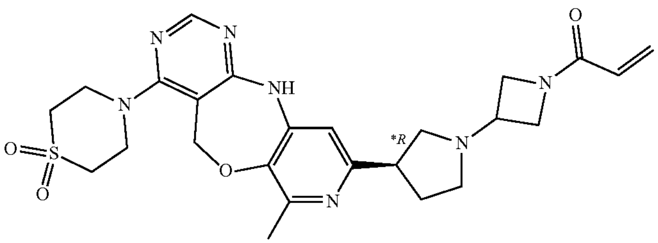 [SMILES: C=CC(=O)N1CC(N2CC[C@@H](c3cc4c(c(C)n3)OCc3c(ncnc3N3CCS(=O)(=O)CC3)N4)C2)C1] |
| 31 | 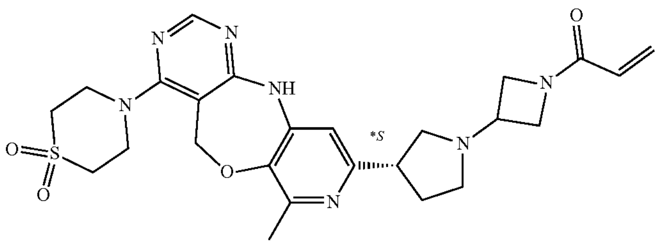 [SMILES: C=CC(=O)N1CC(N2CC[C@H](c3cc4c(c(C)n3)OCc3c(ncnc3N3CCS(=O)(=O)CC3)N4)C2)C1] | 34 | 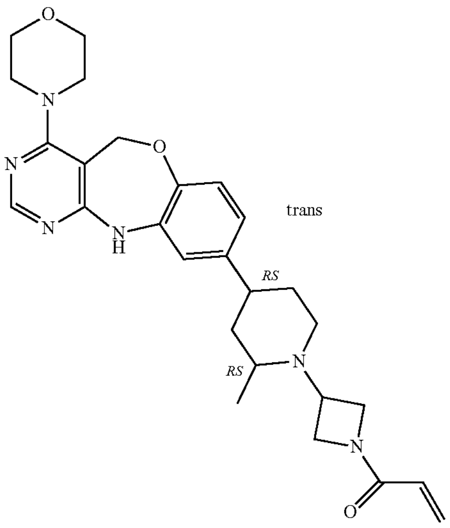 [SMILES: C=CC(=O)N1CC(N2CCC(c3ccc4c(c3)Nc3ncnc(N5CCOCC5)c3CO4)CC2C)C1] |

-continued
| Cpd # | Structure | Cpd # | Structure |
| --- | --- | --- | --- |
| 32 | 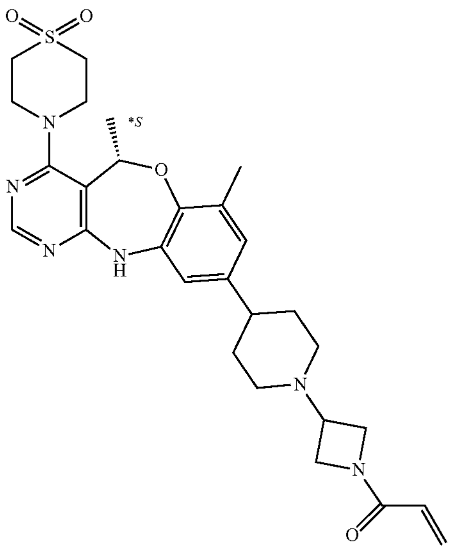 [SMILES: C=CC(=O)N1CC(N2CCC(c3cc(C)c4c(c3)Nc3ncnc(N5CCS(=O)(=O)CC5)c3[C@H](C)O4)CC2)C1] | 35 | 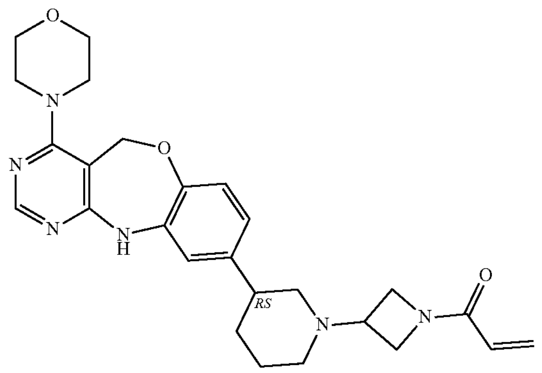 [SMILES: C=CC(=O)N1CC(N2CCCC(c3ccc4c(c3)Nc3ncnc(N5CCOCC5)c3CO4)C2)C1] |

-continued
| Cpd # | Structure | Cpd # | Structure |
| --- | --- | --- | --- |
| 33 | 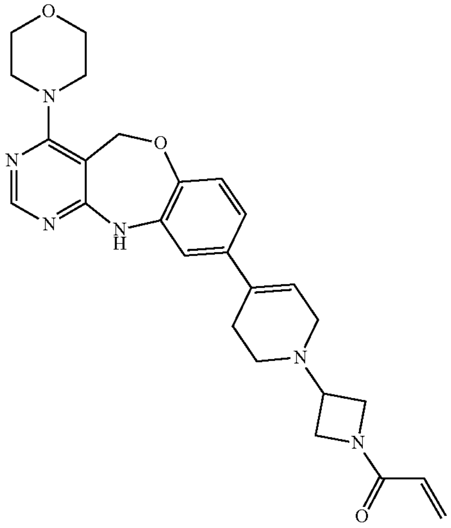 [SMILES: C=CC(=O)N1CC(N2CC=C(c3ccc4c(c3)Nc3ncnc(N5CCOCC5)c3CO4)CC2)C1] | 36 | 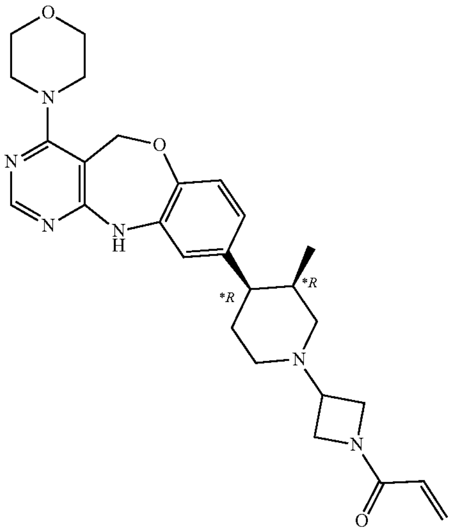 [SMILES: C=CC(=O)N1CC(N2CC[C@@H](c3ccc4c(c3)Nc3ncnc(N5CCOCC5)c3CO4)[C@@H](C)C2)C1] |

-continued
| Cpd # | Structure | Cpd # | Structure |
|---|---|---|---|
| 37 | 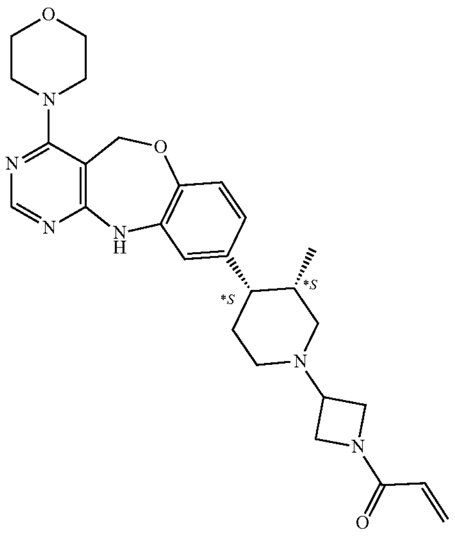 [SMILES: C=CC(=O)N1CC(N2CC[C@H](c3ccc4c(c3)Nc3ncnc(N5CCOCC5)c3CO4)[C@H](C)C2)C1] | 40 | 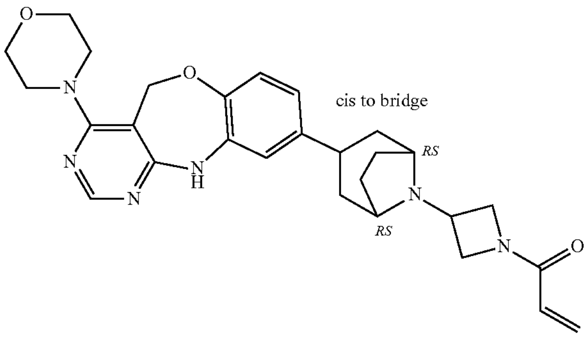 [SMILES: C=CC(=O)N1CC(N2C3CCC2CC(c2ccc4c(c2)Nc2ncnc(N5CCOCC5)c2CO4)C3)C1] |

-continued
| Cpd # | Structure | Cpd # | Structure |
|---|---|---|---|
| 38 | 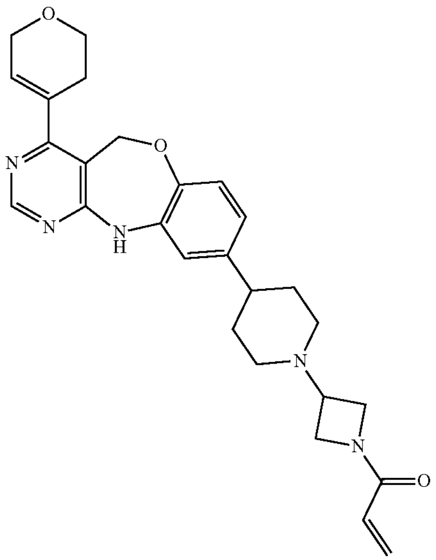 [SMILES: C=CC(=O)N1CC(N2CCC(c3ccc4c(c3)Nc3ncnc(C5=CCOCC5)c3CO4)CC2)C1] | 41 | 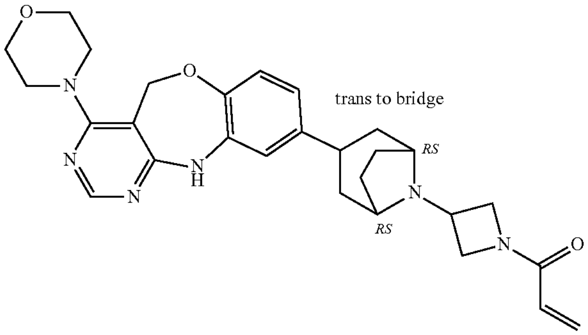 [SMILES: C=CC(=O)N1CC(N2C3CCC2CC(c2ccc4c(c2)Nc2ncnc(N5CCOCC5)c2CO4)C3)C1] |

-continued
| Cpd # | Structure | Cpd # | Structure |
|---|---|---|---|
| 39 | 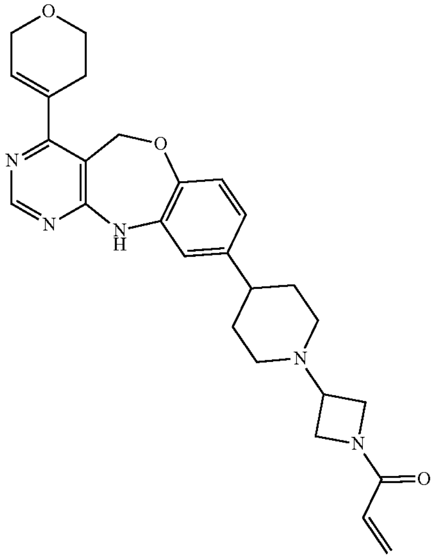 [SMILES: C=CC(=O)N1CC(N2CCC(c3ccc4c(c3)Nc3ncnc(C5=CCOCC5)c3CO4)CC2)C1] | 42 | 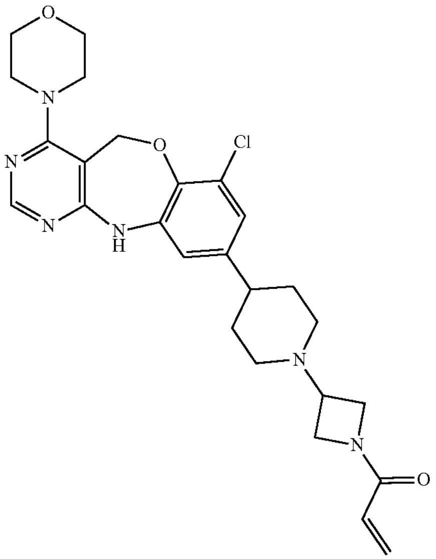 [SMILES: C=CC(=O)N1CC(N2CCC(c3cc(Cl)c4c(c3)Nc3ncnc(N5CCOCC5)c3CO4)CC2)C1] |

-continued
| Cpd # | Structure | Cpd # | Structure |
|---|---|---|---|
| 43 | 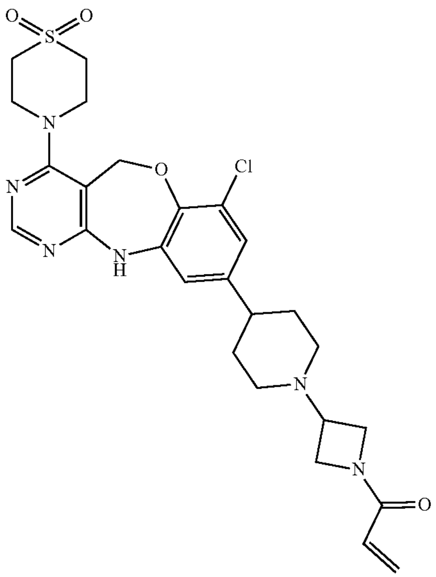 [SMILES: C=CC(=O)N1CC(N2CCC(c3cc(Cl)c4c(c3)Nc3ncnc(N5CCS(=O)(=O)CC5)c3CO4)CC2)C1] | 46 | 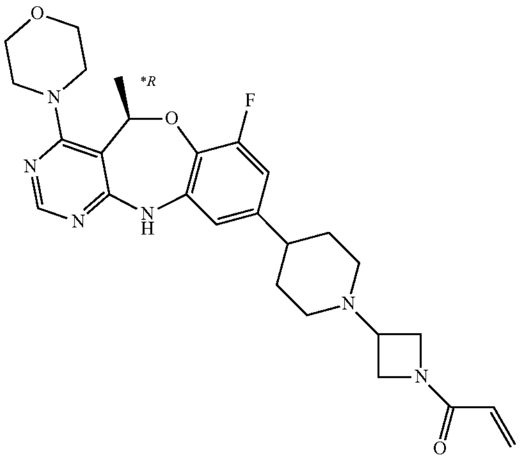 [SMILES: C=CC(=O)N1CC(N2CCC(c3cc(F)c4c(c3)Nc3ncnc(N5CCOCC5)c3[C@@H](C)O4)CC2)C1] |
| 44 | 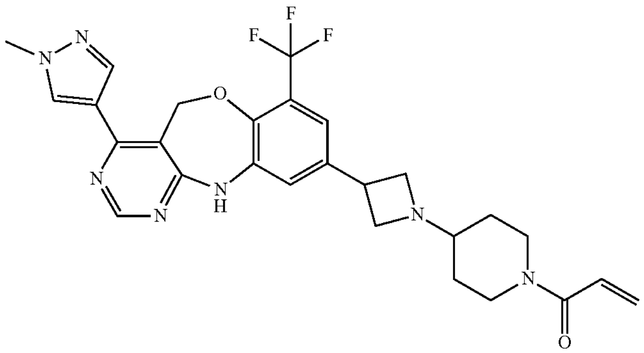 | 47 | 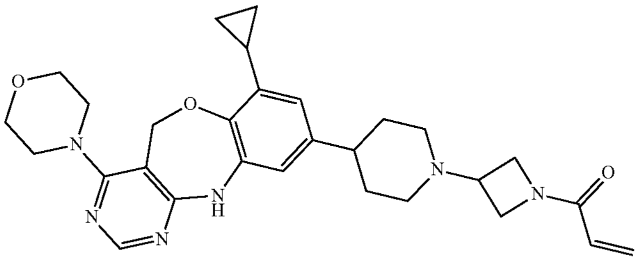 [SMILES: C=CC(=O)N1CC(N2CCC(c3cc4c(c(C5CC5)c3)OCc3c(ncnc3N3CCOCC3)N4)CC2)C1] |

-continued
| Cpd # | Structure | Cpd # | Structure |
|---|---|---|---|
| 45 | 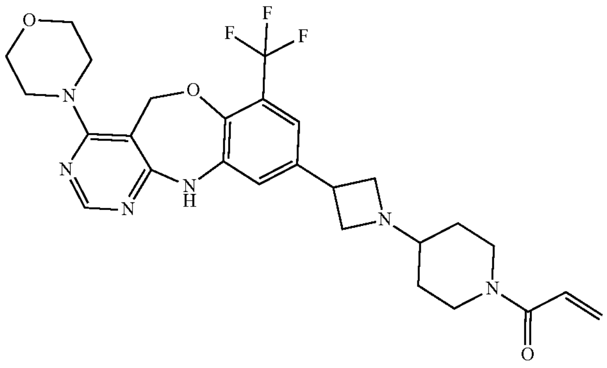 [SMILES: C=CC(=O)N1CCC(N2CC(c3cc4c(c(C(F)(F)F)c3)OCc3c(ncnc3N3CCOCC3)N4)C2)CC1] | 48 | 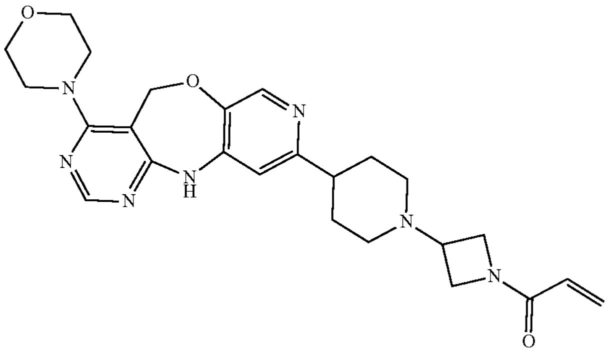 [SMILES: C=CC(=O)N1CC(N2CCC(c3cc4c(cn3)OCc3c(ncnc3N3CCOCC3)N4)CC2)C1] |
| 49 | 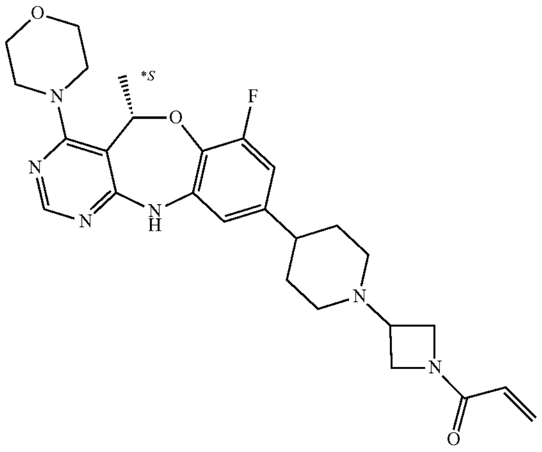 [SMILES: C=CC(=O)N1CC(N2CCC(c3cc(F)c4c(c3)Nc3ncnc(N5CCOCC5)c3[C@H](C)O4)CC2)C1] | 52 | 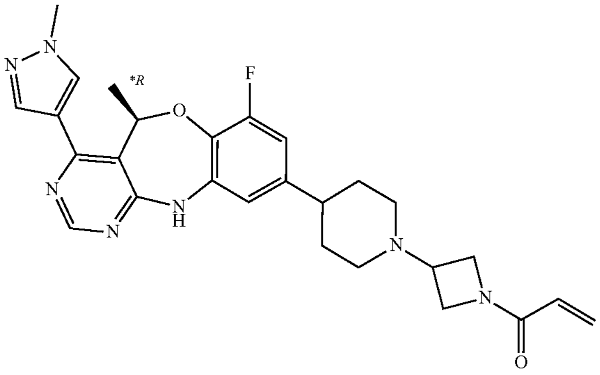 [SMILES: C=CC(=O)N1CC(N2CCC(c3cc(F)c4c(c3)Nc3ncnc(-c5cnn(C)c5)c3[C@@H](C)O4)CC2)C1] |

-continued
| Cpd # | Structure | Cpd # | Structure |
|---|---|---|---|
| 50 | 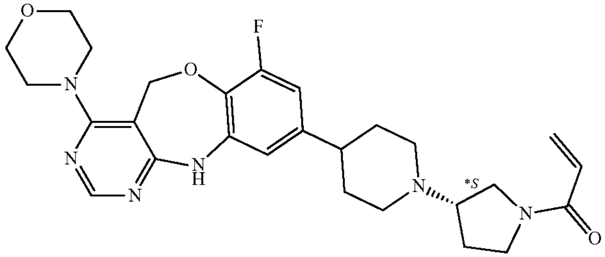 [SMILES: C=CC(=O)N1CC[C@H](N2CCC(c3cc(F)c4c(c3)Nc3ncnc(N5CCOCC5)c3CO4)CC2)C1] | 53 | 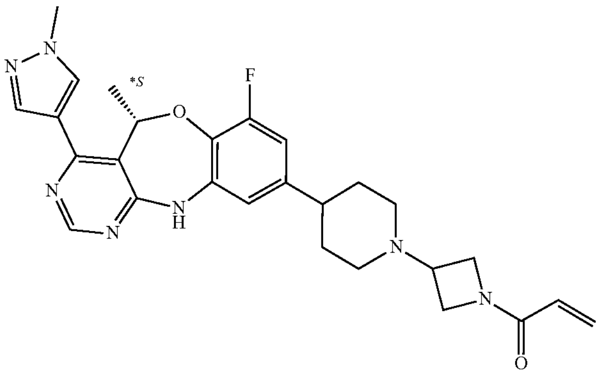 [SMILES: C=CC(=O)N1CC(N2CCC(c3cc(F)c4c(c3)Nc3ncnc(-c5cnn(C)c5)c3[C@H](C)O4)CC2)C1] |
| 51 | 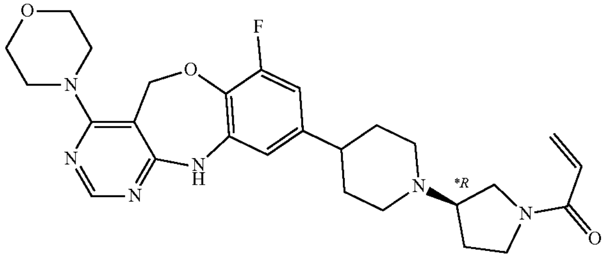 [SMILES: C=CC(=O)N1CC[C@@H](N2CCC(c3cc(F)c4c(c3)Nc3ncnc(N5CCOCC5)c3CO4)CC2)C1] | 54 | 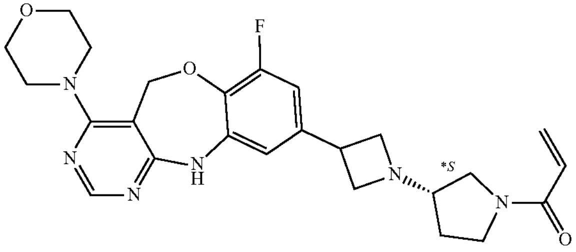 [SMILES: C=CC(=O)N1CC[C@H](N2CC(c3cc(F)c4c(c3)Nc3ncnc(N5CCOCC5)c3CO4)C2)C1] |
| 55 | 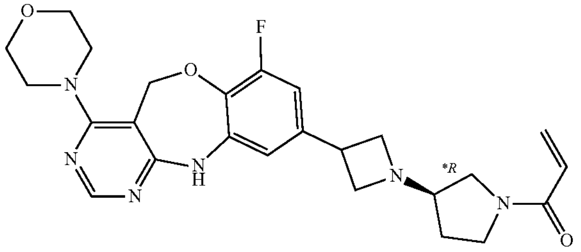 [SMILES: C=CC(=O)N1CC[C@@H](N2CC(c3cc(F)c4c(c3)Nc3ncnc(N5CCOCC5)c3CO4)C2)C1] | 58 | 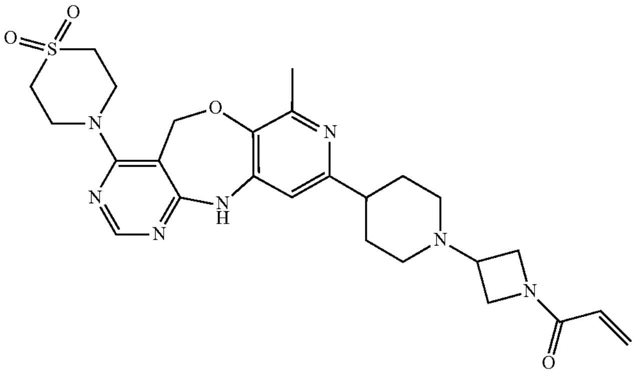 [SMILES: C=CC(=O)N1CC(N2CCC(c3cc4c(c(C)n3)OCc3c(ncnc3N3CCS(=O)(=O)CC3)N4)CC2)C1] |

-continued
| Cpd # | Structure | Cpd # | Structure |
|---|---|---|---|
| 56 | 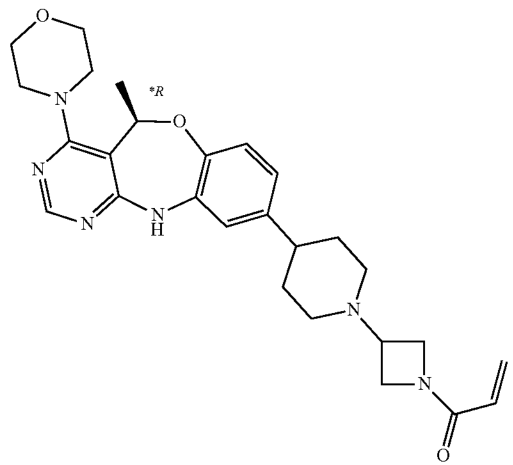 | 59 | 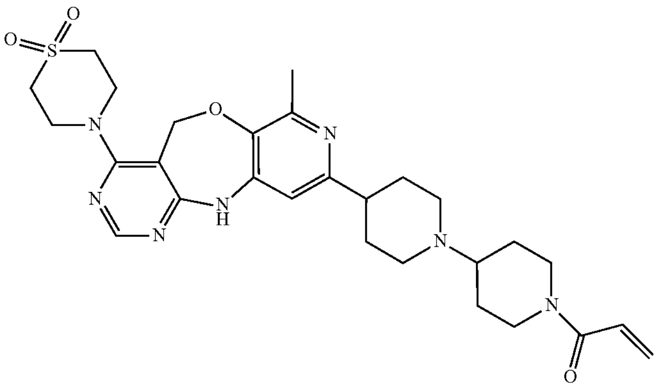 [SMILES: C=CC(=O)N1CCC(N2CCC(c3cc4c(c(C)n3)OCc3c(ncnc3N3CCS(=O)(=O)CC3)N4)CC2)CC1] |
| 57 | 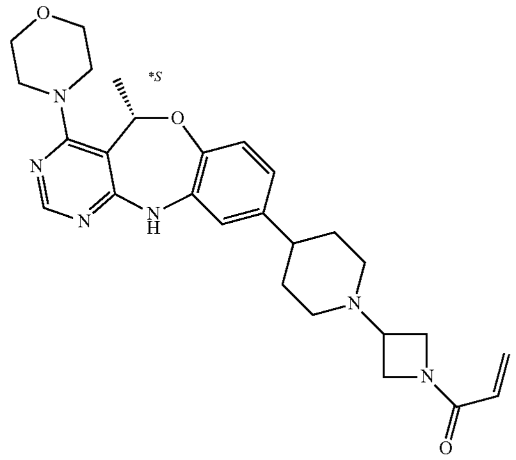 [SMILES: C=CC(=O)N1CC(N2CCC(c3ccc4c(c3)Nc3ncnc(N5CCOCC5)c3[C@H](C)O4)CC2)C1] | 60 | 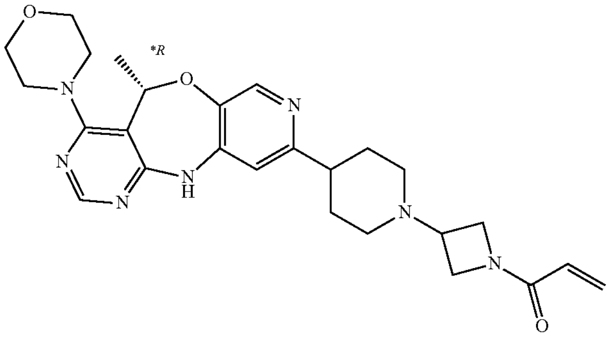 [SMILES: C=CC(=O)N1CC(N2CCC(c3cc4c(cn3)O[C@@H](C)c3c(ncnc3N3CCOCC3)N4)CC2)C1] |

-continued
| Cpd # | Structure | Cpd # | Structure |
|---|---|---|---|
| 61 | 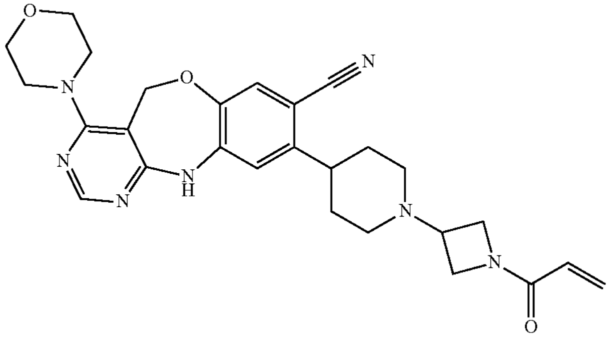 [SMILES: C=CC(=O)N1CC(N2CCC(c3cc4c(cc3C#N)OCc3c(ncnc3N3CCOCC3)N4)CC2)C1] | 64 | 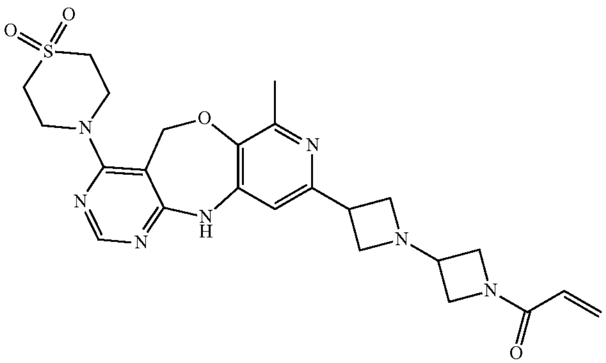 [SMILES: C=CC(=O)N1CC(N2CC(c3cc4c(c(C)n3)OCc3c(ncnc3N3CCS(=O)(=O)CC3)N4)C2)C1] |
| 62 | 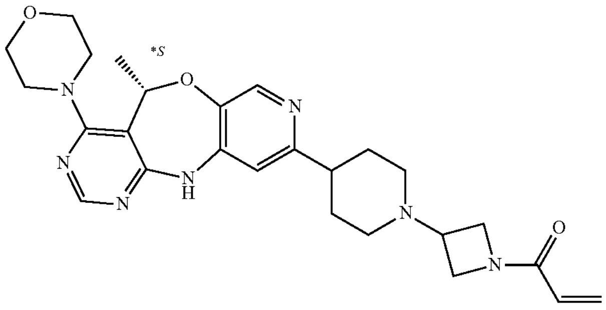 [SMILES: C=CC(=O)N1CC(N2CCC(c3cc4c(cn3)O[C@@H](C)c3c(ncnc3N3CCOCC3)N4)CC2)C1] | 65 | 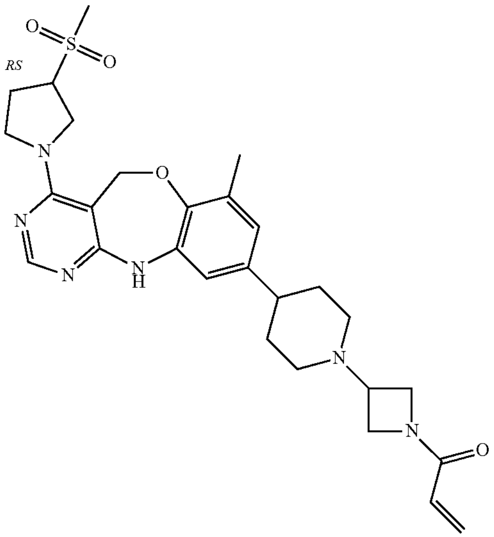 |

-continued
| Cpd # | Structure | Cpd # | Structure |
|---|---|---|---|
| 63 | 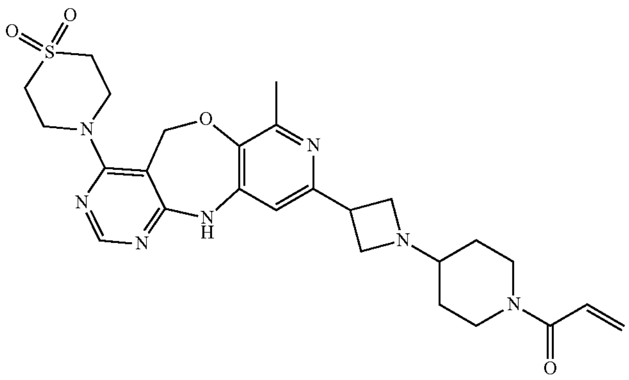 [SMILES: C=CC(=O)N1CCC(N2CC(c3cc4c(c(C)n3)OCc3c(ncnc3N3CCS(=O)(=O)CC3)N4)C2)CC1] | 66 | 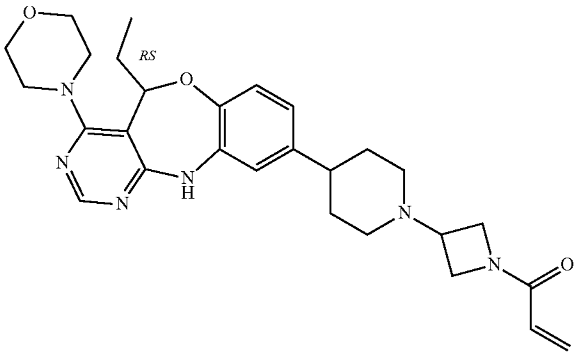 [SMILES: C=CC(=O)N1CC(N2CCC(c3ccc4c(c3)Nc3ncnc(N5CCOCC5)c3C(CC)O4)CC2)C1] |
| 67 | 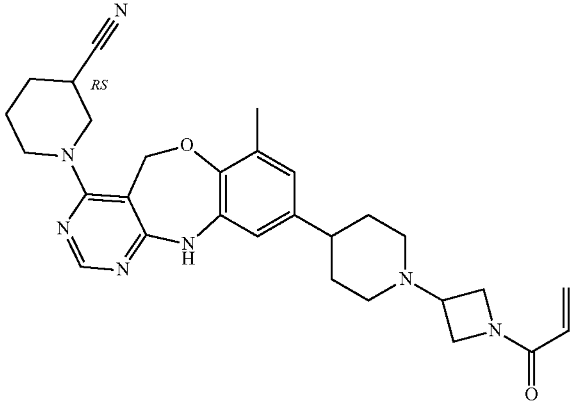 [SMILES: C=CC(=O)N1CC(N2CCC(c3cc(C)c4c(c3)Nc3ncnc(N5CCCC(C#N)C5)c3CO4)CC2)C1] | 70 | 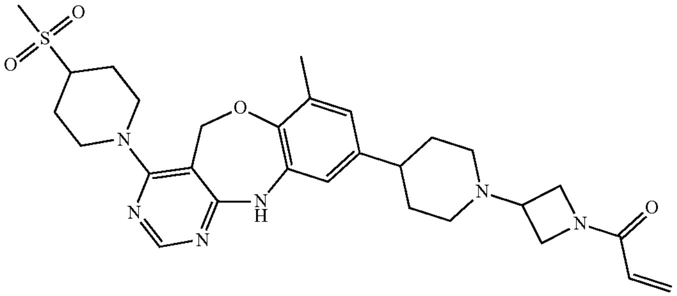 [SMILES: C=CC(=O)N1CC(N2CCC(c3cc(C)c4c(c3)Nc3ncnc(N5CCC(S(C)(=O)=O)CC5)c3CO4)CC2)C1] |

-continued
| Cpd # | Structure | Cpd # | Structure |
|---|---|---|---|
| 68 | 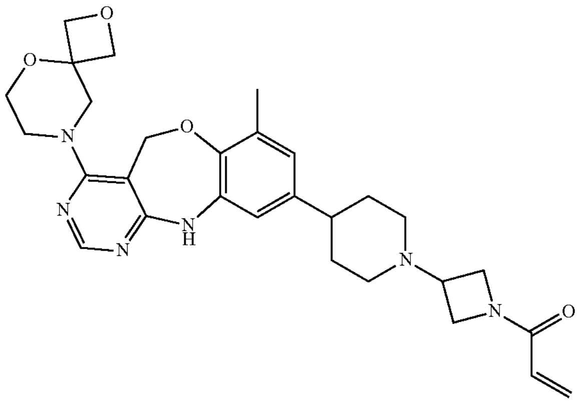 | 71 | 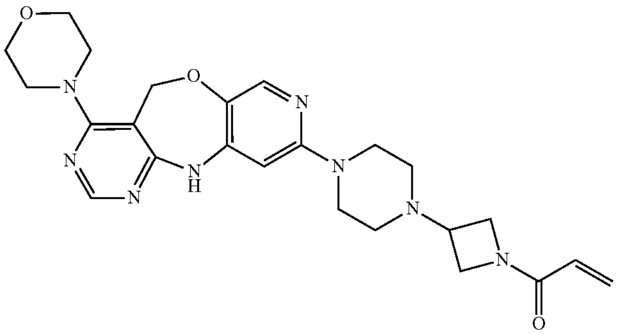 [SMILES: C=CC(=O)N1CC(N2CCN(c3cc4c(cn3)OCc3c(ncnc3N3CCOCC3)N4)CC2)C1] |
| 69 | 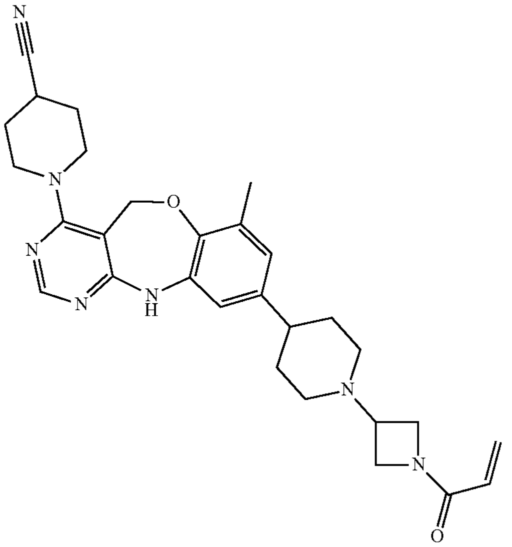 | 72 | 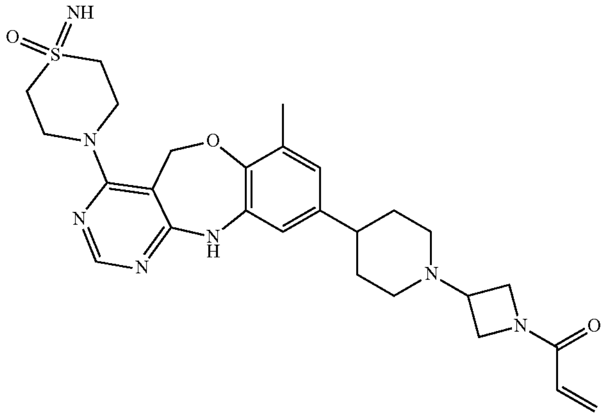 [SMILES: C=CC(=O)N1CC(N2CCC(c3cc(C)c4c(c3)Nc3ncnc(N5CCS(=N)(=O)CC5)c3CO4)CC2)C1] |

-continued
| Cpd # | Structure | Cpd # | Structure |
|---|---|---|---|
| 73 | 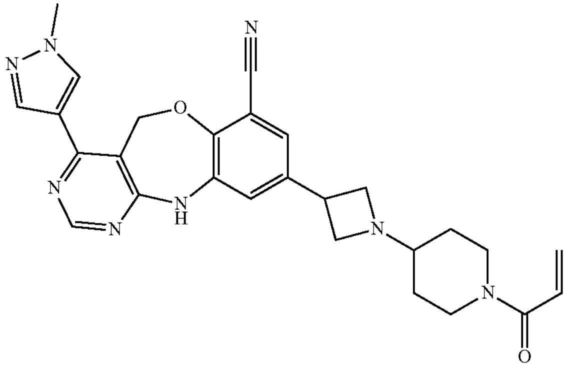 [SMILES: C=CC(=O)N1CCC(N2CC(c3cc(C#N)c4c(c3)Nc3ncnc(-c5cnn(C)c5)c3CO4)C2)CC1] | 76 | 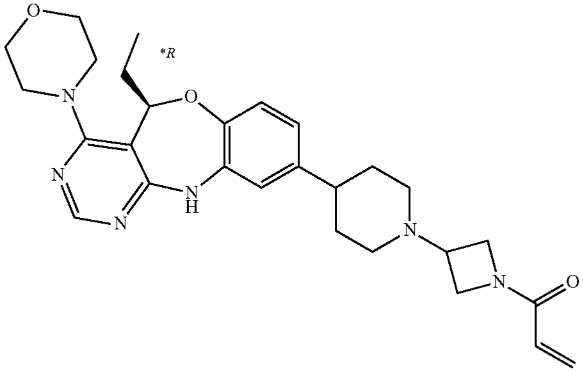 [SMILES: C=CC(=O)N1CC(N2CCC(c3ccc4c(c3)Nc3ncnc(N5CCOCC5)c3[C@@H](CC)O4)CC2)C1] |
| 74 | 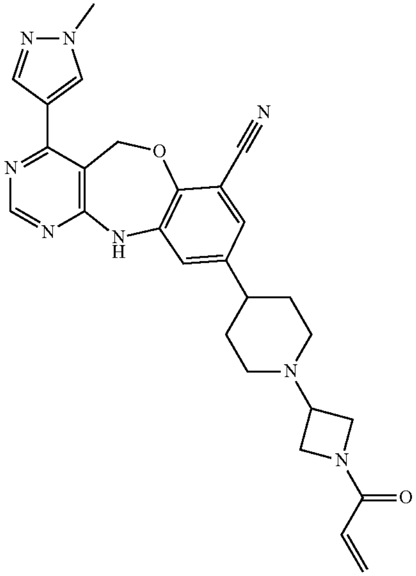 [SMILES: C=CC(=O)N1CC(N2CCC(c3cc(C#N)c4c(c3)Nc3ncnc(-c5cnn(C)c5)c3CO4)CC2)C1] | 77 | 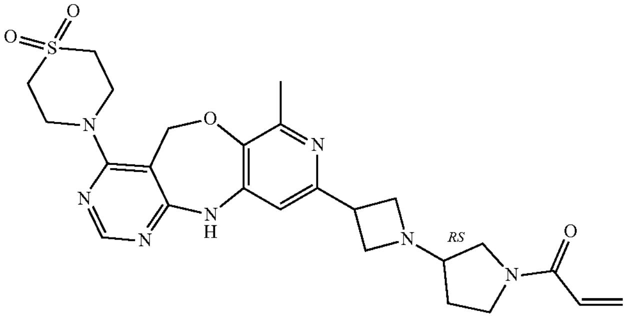 |

-continued
| Cpd # | Structure | Cpd # | Structure |
| --- | --- | --- | --- |
| 75 | 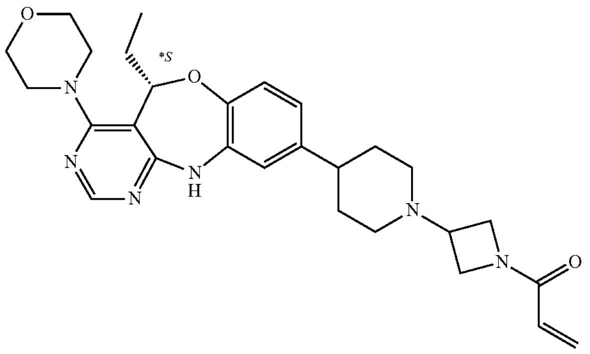 | 78 | 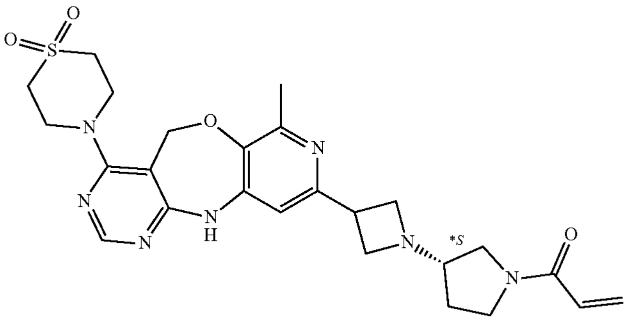 |
| 79 | 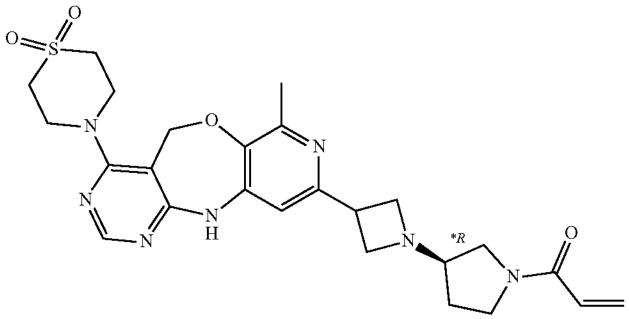 | 82 | 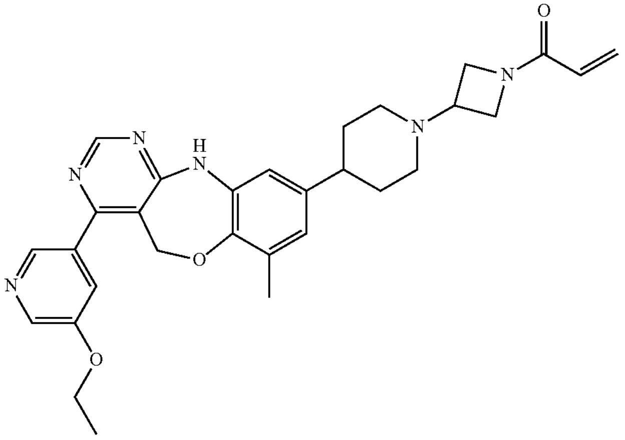 |

-continued
| Cpd # | Structure | Cpd # | Structure |
|---|---|---|---|
| 80 | 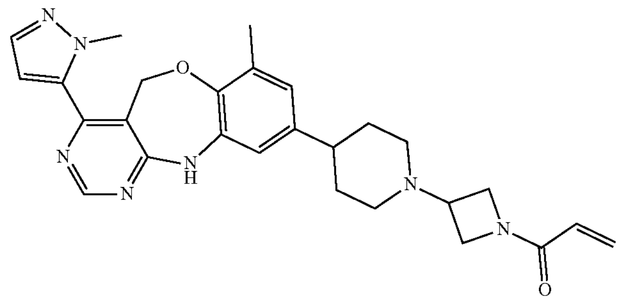 [SMILES: C=CC(=O)N1CC(N2CCC(c3cc(C)c4c(c3)Nc3ncnc(-c5ccnn5C)c3CO4)CC2)C1] | 83 | 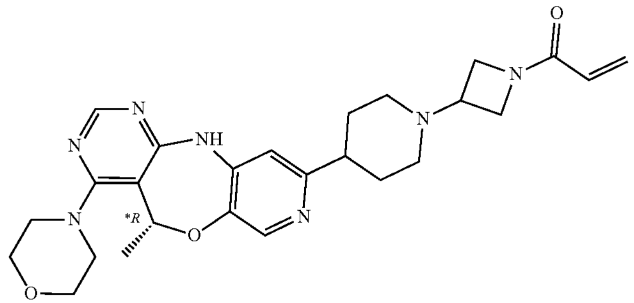 [SMILES: C=CC(=O)N1CC(N2CCC(c3cc4c(cn3)O[C@H](C)c3c(ncnc3N3CCOCC3)N4)CC2)C1] |
| 81 | 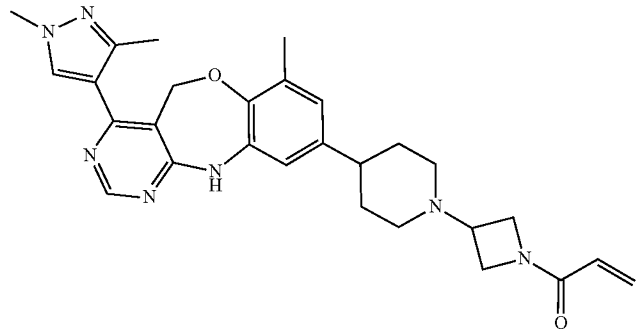 [SMILES: C=CC(=O)N1CC(N2CCC(c3cc(C)c4c(c3)Nc3ncnc(-c5cn(C)nc5C)c3CO4)CC2)C1] | 84 | 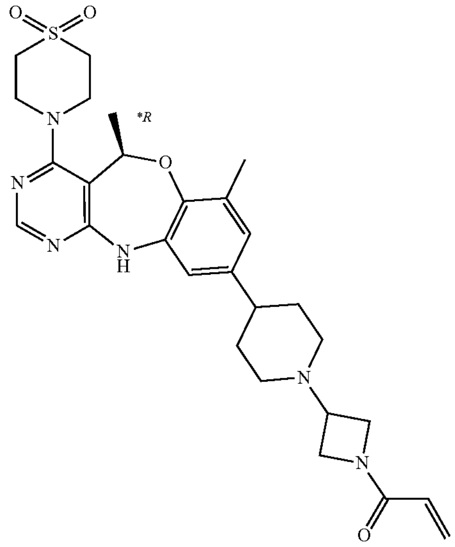 [SMILES: C=CC(=O)N1CC(N2CCC(c3cc(C)c4c(c3)Nc3ncnc(N5CCS(=O)(=O)CC5)c3[C@@H](C)O4)CC2)C1] |

-continued
| Cpd # | Structure | Cpd # | Structure |
| --- | --- | --- | --- |
| 85 | 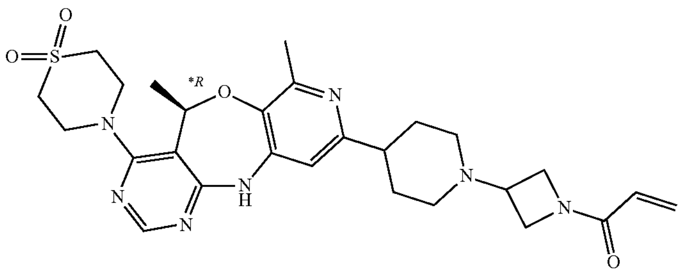 [SMILES: C=CC(=O)N1CC(N2CCC(c3cc4c(c(C)n3)O[C@H](C)c3c(ncnc3N3CCS(=O)(=O)CC3)N4)CC2)C1] | 88 | 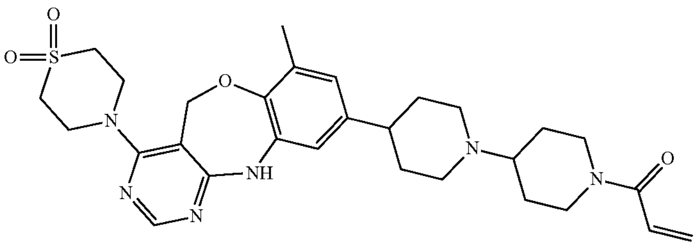 [SMILES: C=CC(=O)N1CCC(N2CCC(c3cc(C)c4c(c3)Nc3ncnc(N5CCS(=O)(=O)CC5)c3CO4)CC2)CC1] |
| 86 | 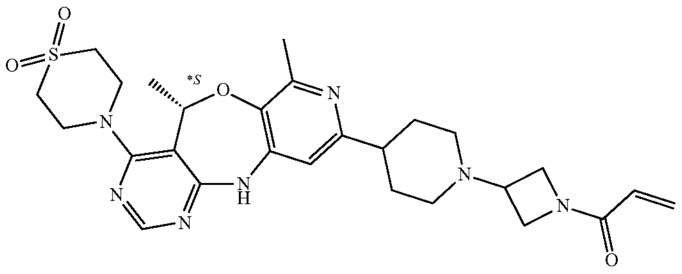 [SMILES: C=CC(=O)N1CC(N2CCC(c3cc4c(c(C)n3)O[C@@H](C)c3c(ncnc3N3CCS(=O)(=O)CC3)N4)CC2)C1] | 89 | 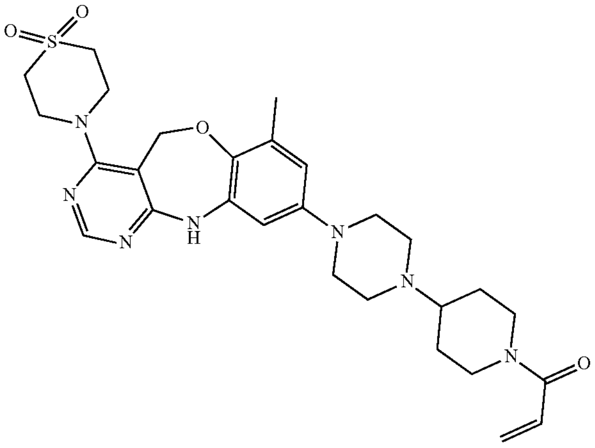 [SMILES: C=CC(=O)N1CCC(N2CCN(c3cc(C)c4c(c3)Nc3ncnc(N5CCS(=O)(=O)CC5)c3CO4)CC2)CC1] |

-continued
| Cpd # | Structure | Cpd # | Structure |
| --- | --- | --- | --- |
| 87 | 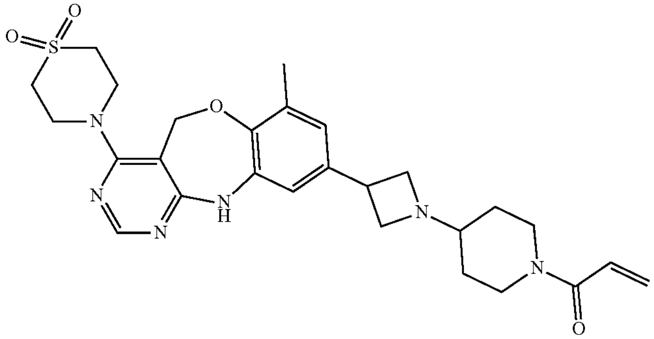 [SMILES: C=CC(=O)N1CCC(N2CC(c3cc(C)c4c(c3)Nc3ncnc(N5CCS(=O)(=O)CC5)c3CO4)C2)CC1] | 90 | 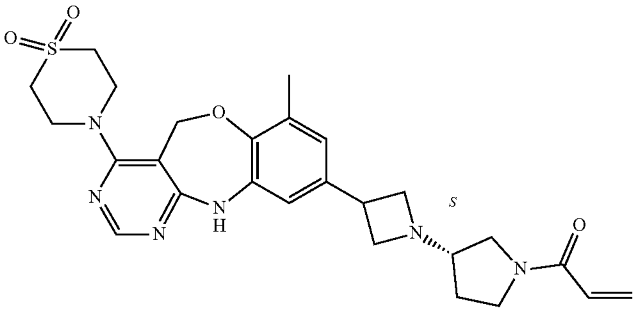 |
| 91 | 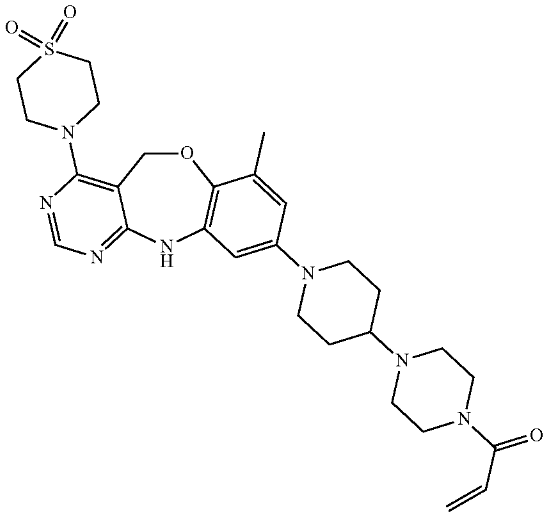 [SMILES: C=CC(=O)N1CCN(C2CCN(c3cc(C)c4c(c3)Nc3ncnc(N5CCS(=O)(=O)CC5)c3CO4)CC2)CC1] | 94 | 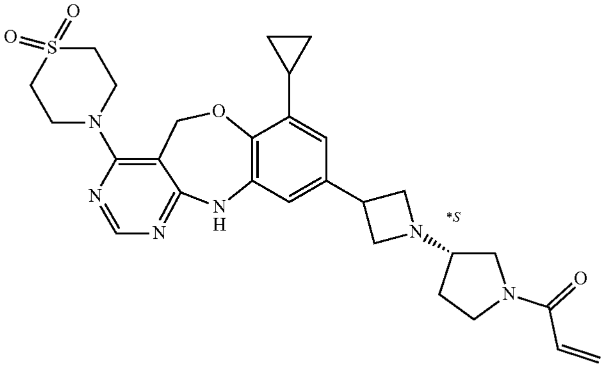 |

-continued
| Cpd # | Structure | Cpd # | Structure |
|---|---|---|---|
| 82 | 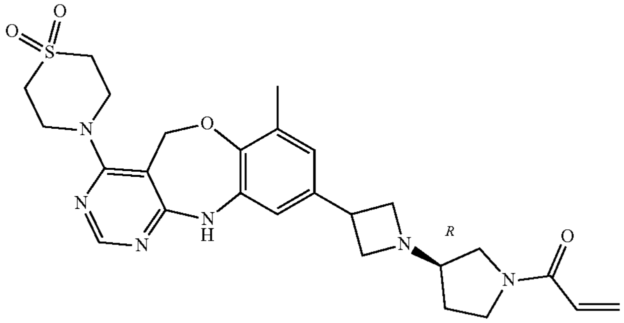 | 95 | 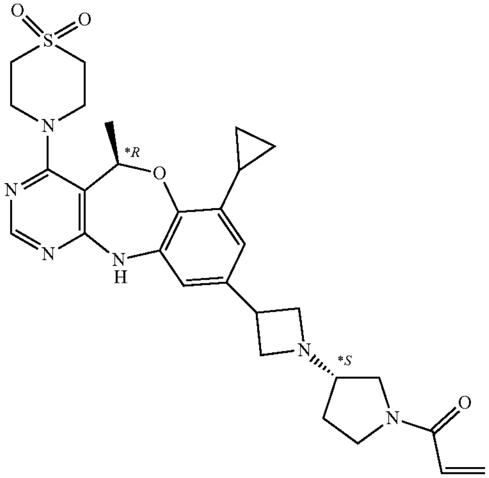 |
| 93 | 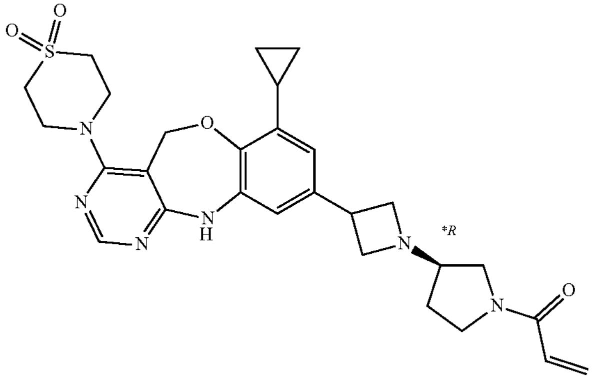 | 96 | 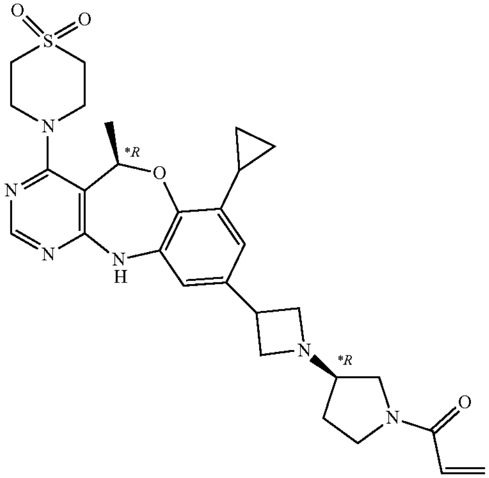 |

-continued
| Cpd # | Structure | Cpd # | Structure |
|---|---|---|---|
| 97 | 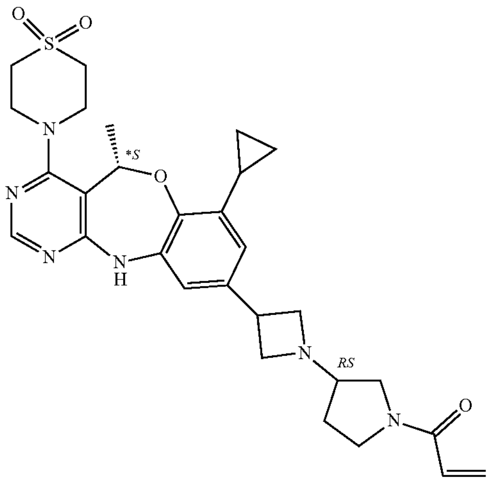 | 100 | 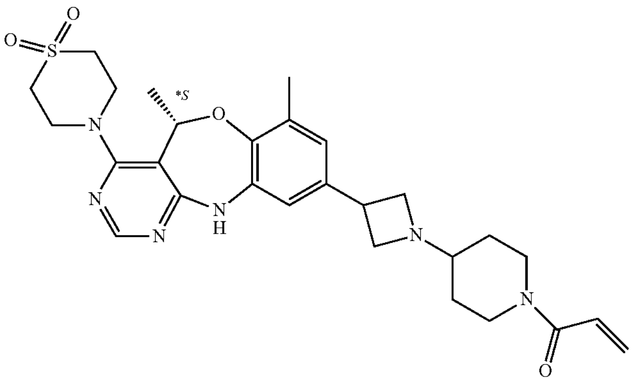 |

-continued
| Cpd # | Structure | Cpd # | Structure |
|---|---|---|---|
| 98 | 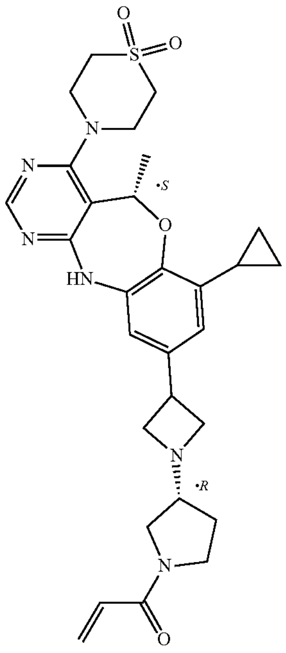 | 101 | 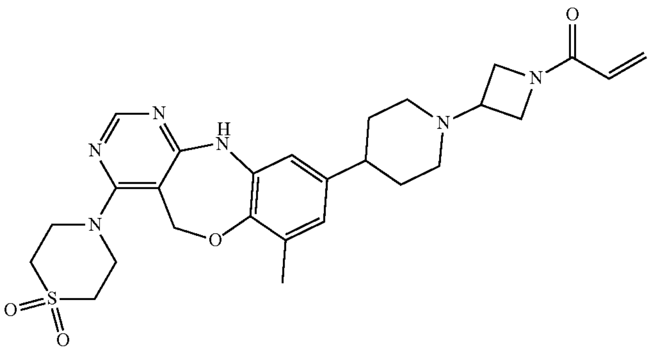 |

-continued
| Cpd # | Structure | Cpd # | Structure |
|---|---|---|---|
| 99 | 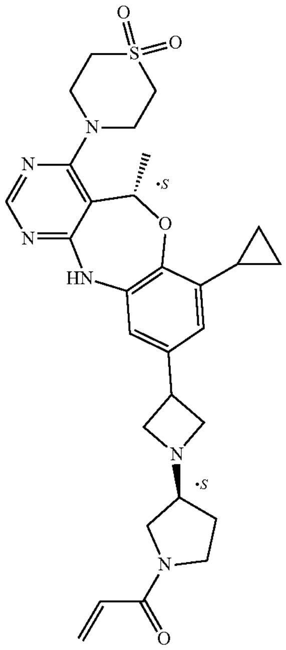 | 102 | 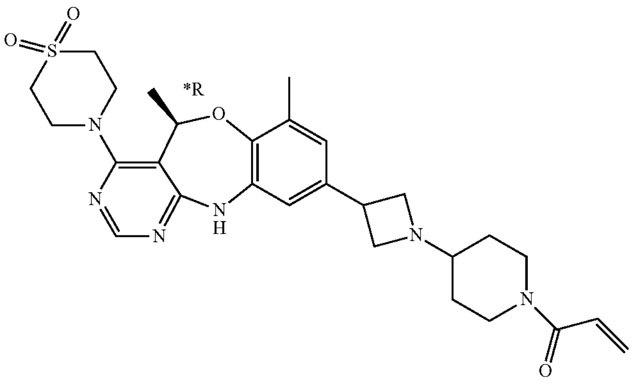 |

-continued
| Cpd # | Structure | Cpd # | Structure |
|---|---|---|---|
| 103 | 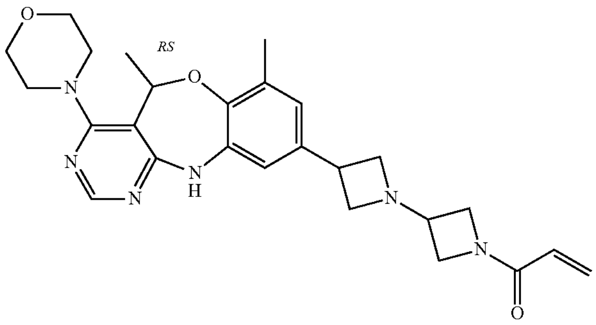 | 106 | 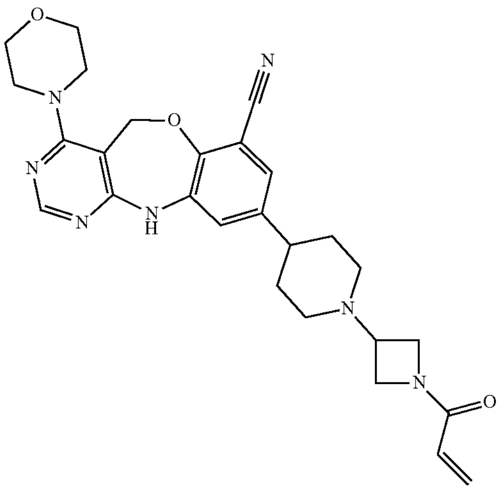 |
| 104 | 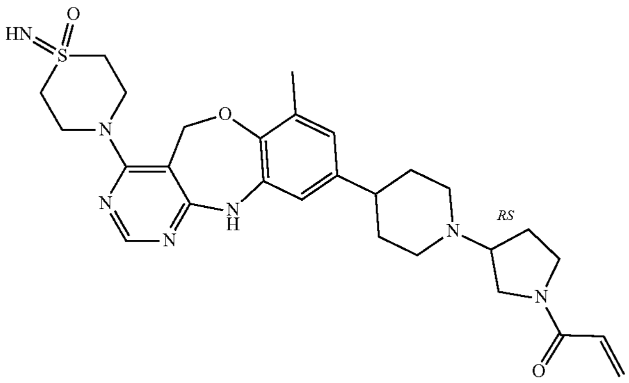 [SMILES: C=CC(=O)N1CCC(N2CCC(c3cc(C)c4c(c3)Nc3ncnc(N5CCS(=N)(=O)CC5)c3CO4)CC2)C1] | 107 | 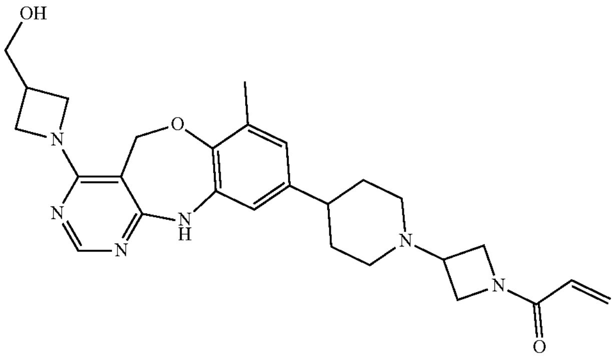 [SMILES: C=CC(=O)N1CC(N2CCC(c3cc(C)c4c(c3)Nc3ncnc(N5CC(CO)C5)c3CO4)CC2)C1] |

-continued
| Cpd # | Structure | Cpd # | Structure |
|---|---|---|---|
| 105 | 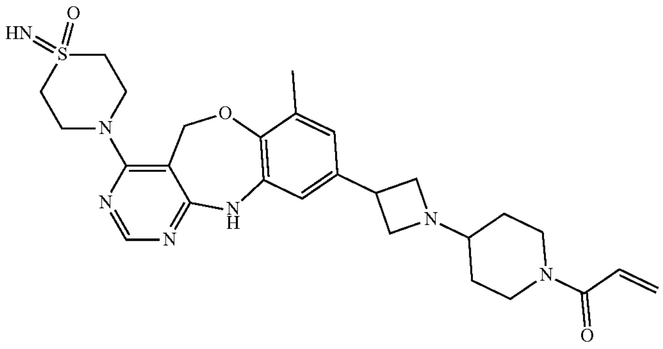 [SMILES: C=CC(=O)N1CCC(N2CC(c3cc(C)c4c(c3)Nc3ncnc(N5CCS(=N)(=O)CC5)c3CO4)C2)CC1] | 108 | 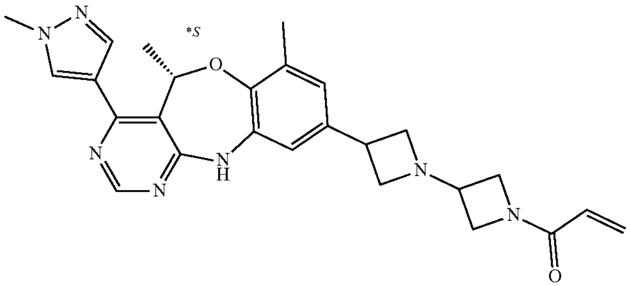 [SMILES: C=CC(=O)N1CC(N2CC(c3cc(C)c4c(c3)Nc3ncnc(-c5cnn(C)c5)c3[C@H](C)O4)C2)C1] |
| 109 | 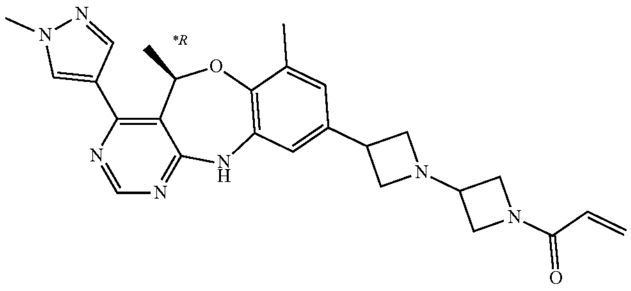 [SMILES: C=CC(=O)N1CC(N2CC(c3cc(C)c4c(c3)Nc3ncnc(-c5cnn(C)c5)c3[C@@H](C)O4)C2)C1] | 112 | 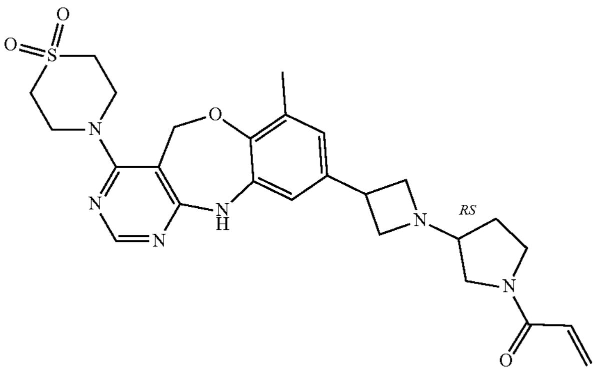 [SMILES: C=CC(=O)N1CCC(N2CC(c3cc(C)c4c(c3)Nc3ncnc(N5CCS(=O)(=O)CC5)c3CO4)C2)C1] |

-continued
| Cpd # | Structure | Cpd # | Structure |
|---|---|---|---|
| 110 | 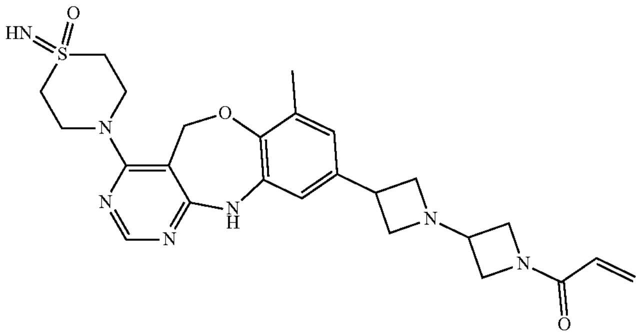 [SMILES: C=CC(=O)N1CC(N2CC(c3cc(C)c4c(c3)Nc3ncnc(N5CCS(=N)(=O)CC5)c3CO4)C2)C1] | 113 | 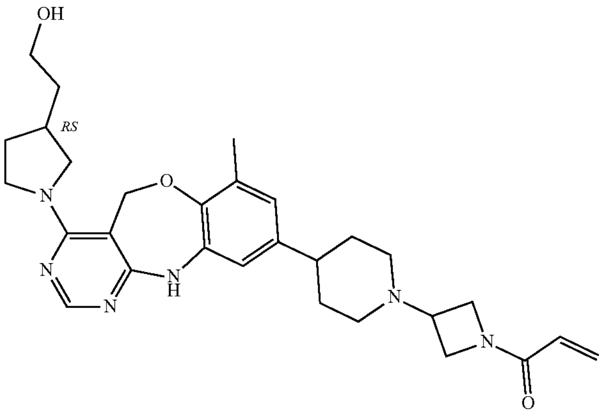 [SMILES: C=CC(=O)N1CC(N2CCC(c3cc(C)c4c(c3)Nc3ncnc(N5CCC(CCO)C5)c3CO4)CC2)C1] |
| 111 | 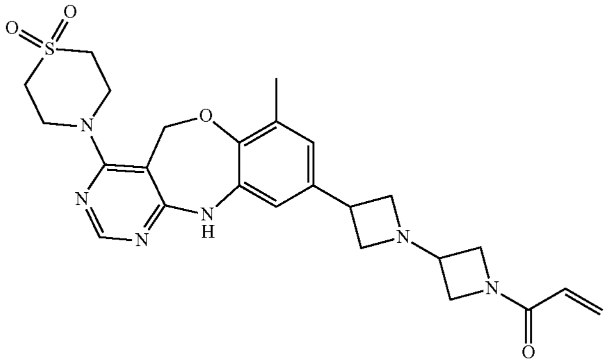 | 114 | 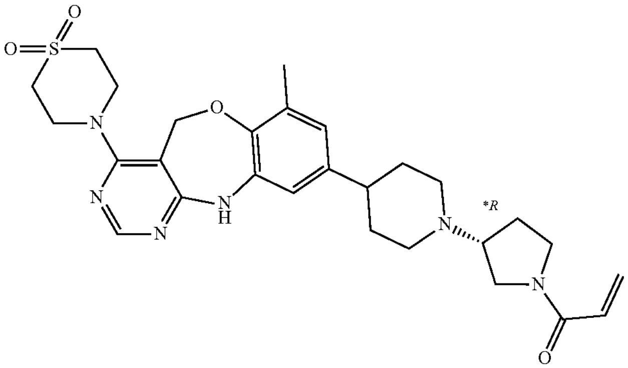 [SMILES: C=CC(=O)N1CC[C@@H](N2CCC(c3cc(C)c4c(c3)Nc3ncnc(N5CCS(=O)(=O)CC5)c3CO4)CC2)C1] |

-continued
| Cpd # | Structure | Cpd # | Structure |
|---|---|---|---|
| 115 | 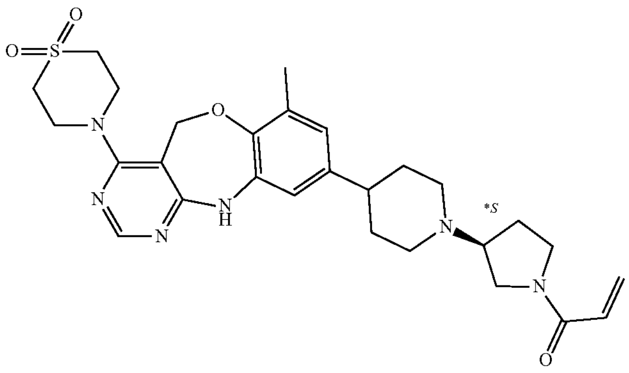 [SMILES: C=CC(=O)N1CC[C@H](N2CCC(c3cc(C)c4c(c3)Nc3ncnc(N5CCS(=O)(=O)CC5)c3CO4)CC2)C1] | 118 | 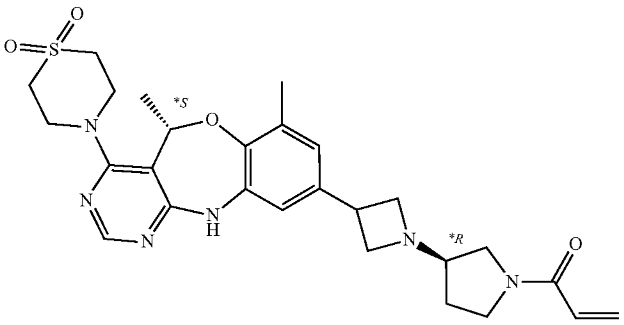 [SMILES: C=CC(=O)N1CC[C@@H](N2CC(c3cc(C)c4c(c3)Nc3ncnc(N5CCS(=O)(=O)CC5)c3[C@H](C)O4)C2)C1] |
| 116 | 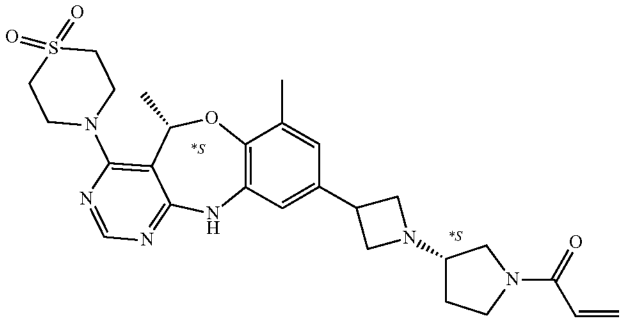 [SMILES: C=CC(=O)N1CC[C@H](N2CC(c3cc(C)c4c(c3)Nc3ncnc(N5CCS(=O)(=O)CC5)c3[C@H](C)O4)C2)C1] | 119 | 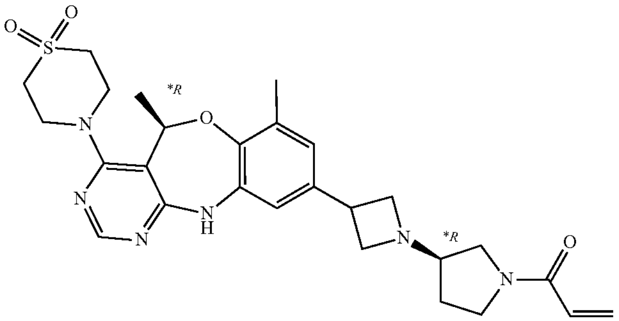 [SMILES: C=CC(=O)N1CC[C@@H](N2CC(c3cc(C)c4c(c3)Nc3ncnc(N5CCS(=O)(=O)CC5)c3[C@@H](C)O4)C2)C1] |

-continued
| Cpd # | Structure | Cpd # | Structure |
|---|---|---|---|
| 117 | 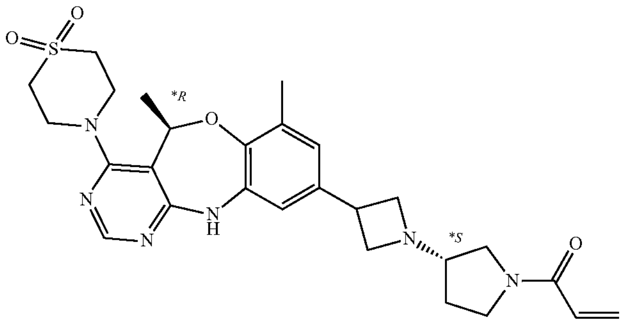 [SMILES: C=CC(=O)N1CC[C@H](N2CC(c3cc(C)c4c(c3)Nc3ncnc(N5CCS(=O)(=O)CC5)c3[C@@H](C)O4)C2)C1] | 120 | 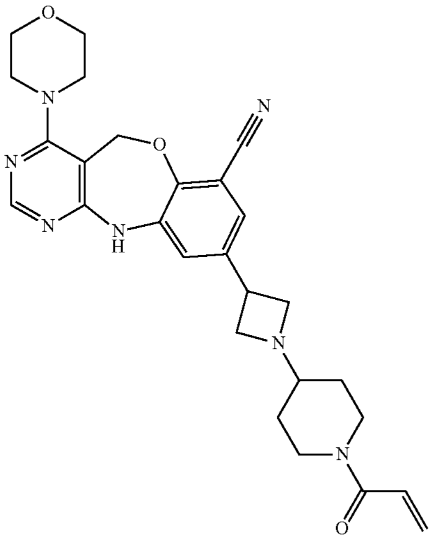 |
| 121 | 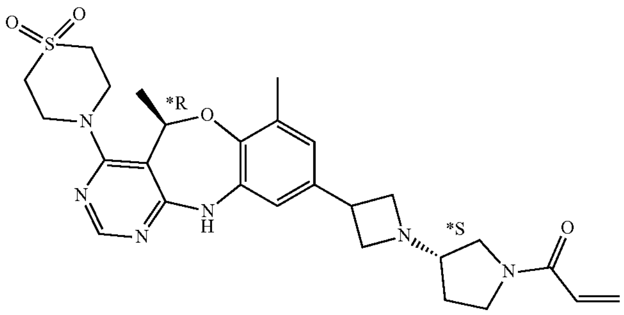 | 124 | 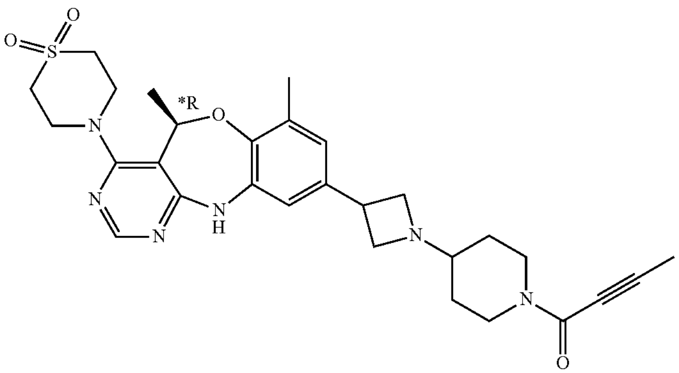 |

-continued
| Cpd # | Structure | Cpd # | Structure |
| --- | --- | --- | --- |
| 122 | 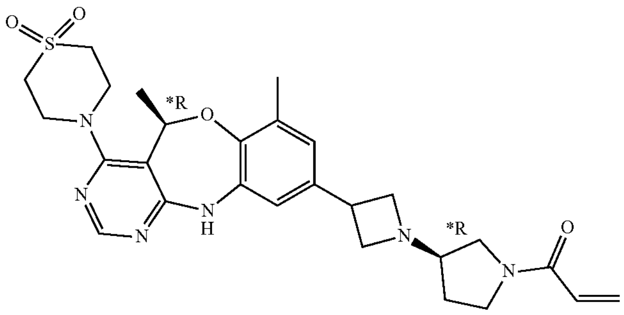 | 125 | 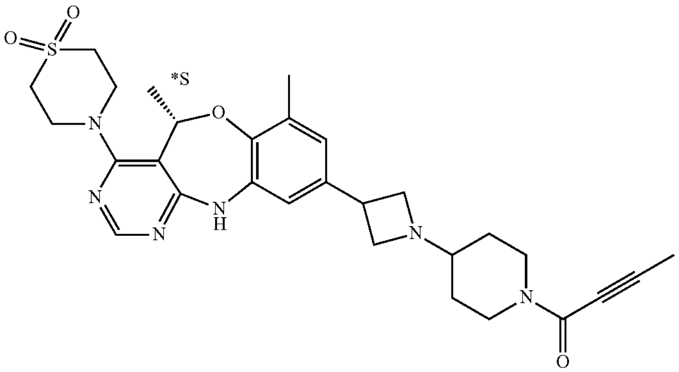 |
| 123 | 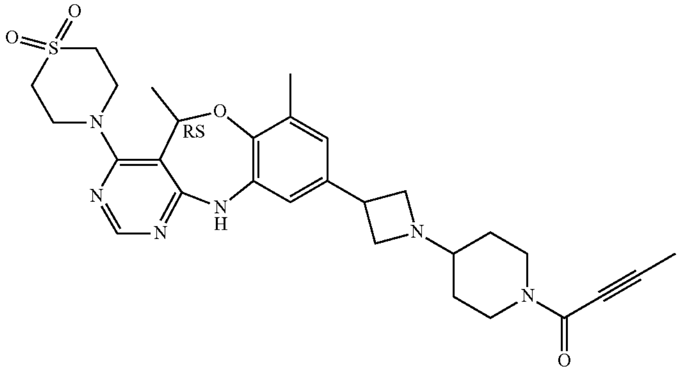 | 126 | 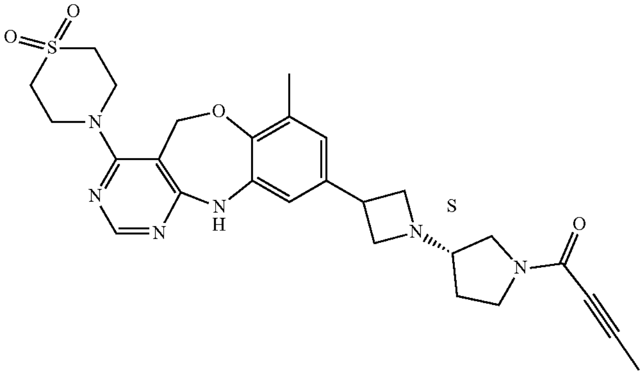 |

-continued
| Cpd # | Structure | Cpd # | Structure |
|---|---|---|---|
| 127 | 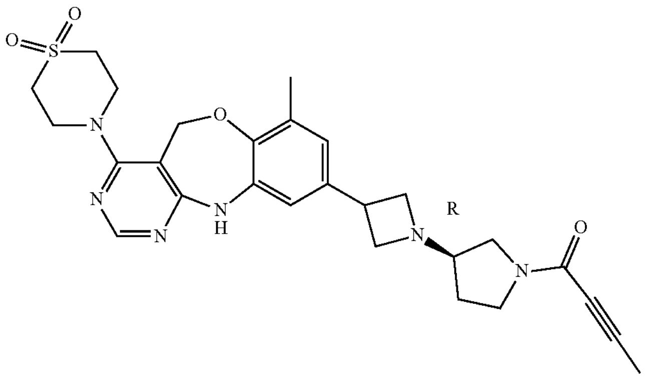 | 130 | 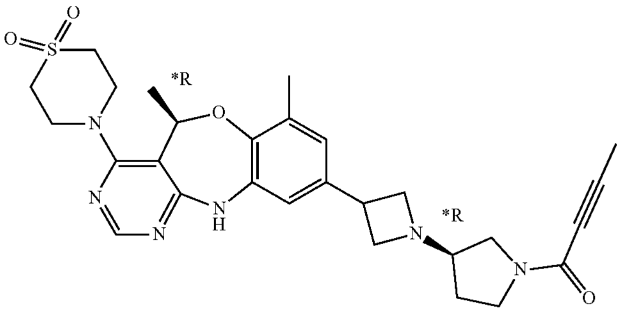 |
| 128 | 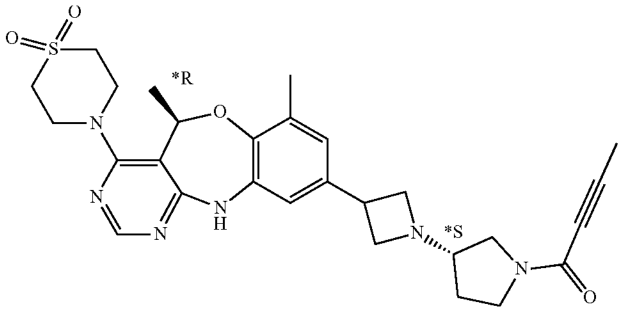 | 131 | 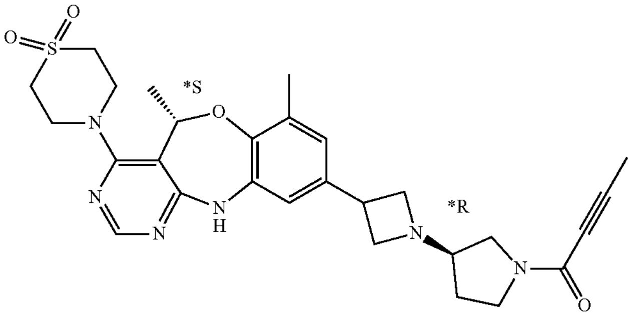 |

-continued
| Cpd # | Structure | Cpd # | Structure |
|---|---|---|---|
| 129 | 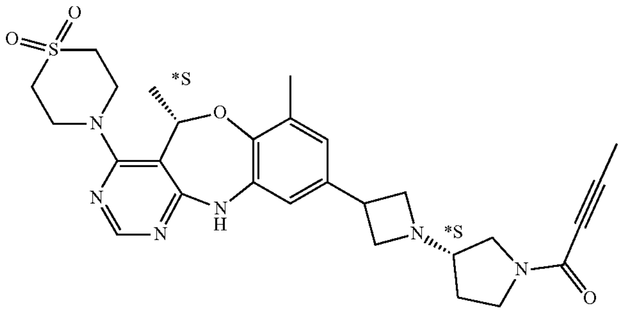 | 132 | 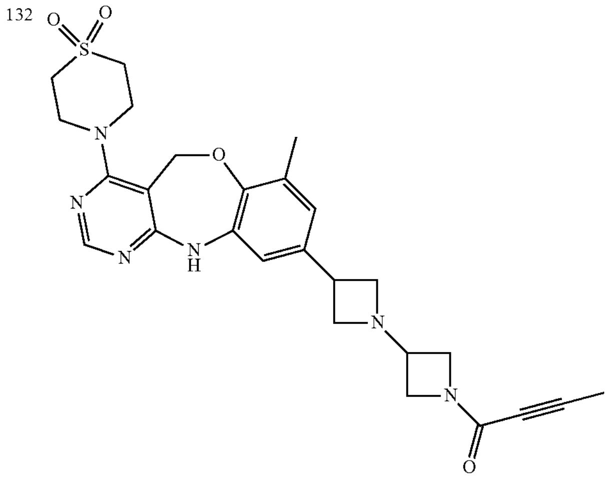 |
| 133 | 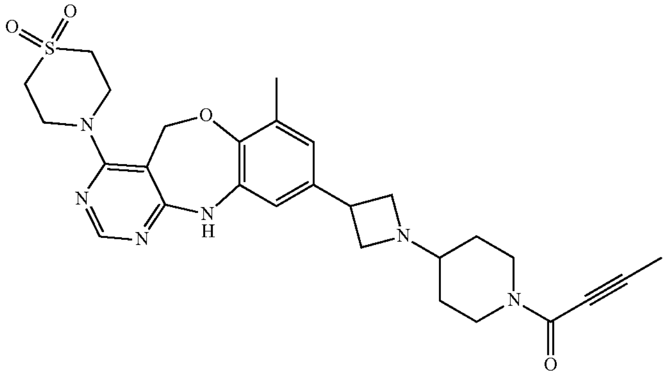 | 136 | 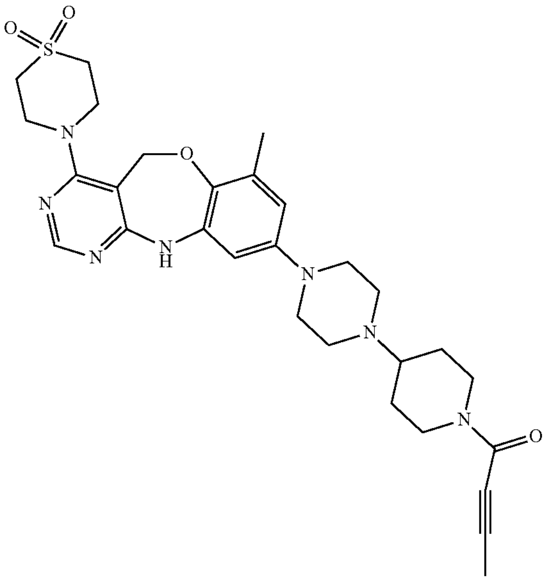 [SMILES: CC#CC(=O)N1CCC(N2CCN(c3cc(C)c4c(c3)Nc3ncnc(N5CCS(=O)(=O)CC5)c3CO4)CC2)CC1] |

-continued
| Cpd # | Structure | Cpd # | Structure |
| --- | --- | --- | --- |
| 134 | 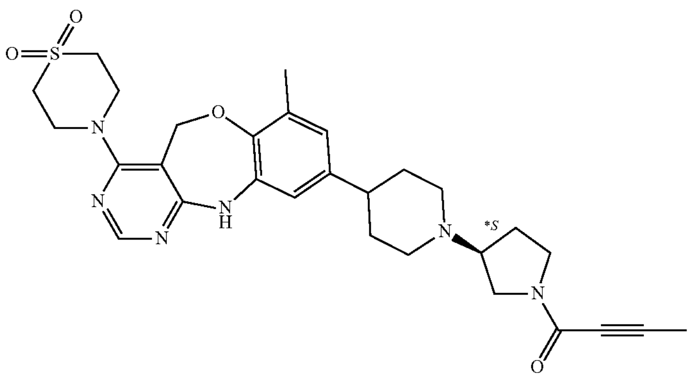 [SMILES: CC#CC(=O)N1CC[C@H](N2CCC(c3cc(C)c4c(c3)Nc3ncnc(N5CCS(=O)(=O)CC5)c3CO4)CC2)C1] | 137 | 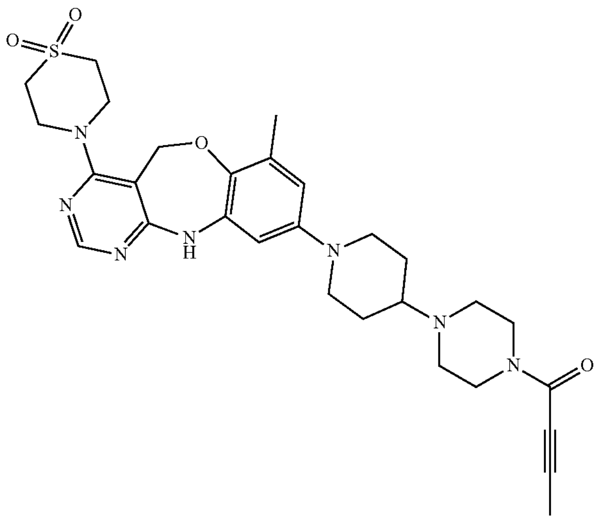 [SMILES: CC#CC(=O)N1CCN(C2CCN(c3cc(C)c4c(c3)Nc3ncnc(N5CCS(=O)(=O)CC5)c3CO4)CC2)CC1] |

-continued
| Cpd # | Structure | Cpd # | Structure |
|---|---|---|---|
| 135 | 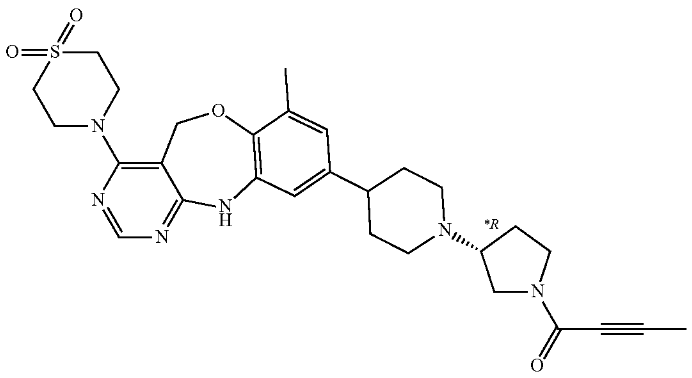 [SMILES: CC#CC(=O)N1CC[C@@H](N2CCC(c3cc(C)c4c(c3)Nc3ncnc(N5CCS(=O)(=O)CC5)c3CO4)CC2)C1] | 138 | 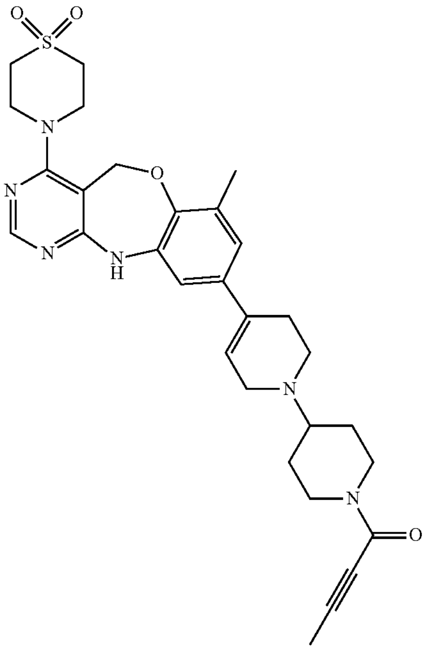 [SMILES: CC#CC(=O)N1CCC(N2CC=C(c3cc(C)c4c(c3)Nc3ncnc(N5CCS(=O)(=O)CC5)c3CO4)CC2)CC1] |

-continued
| Cpd # | Structure | Cpd # | Structure |
| --- | --- | --- | --- |
| 139 | 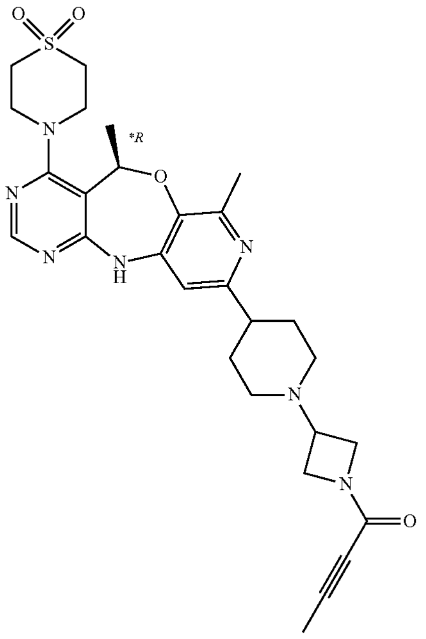 | 142 | 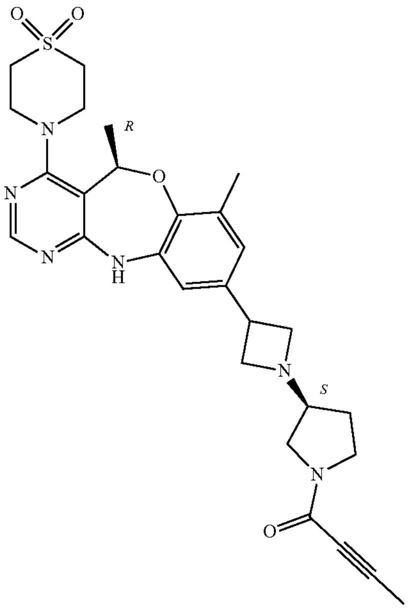 |

-continued
| Cpd # | Structure | Cpd # | Structure |
|---|---|---|---|
| 140 | 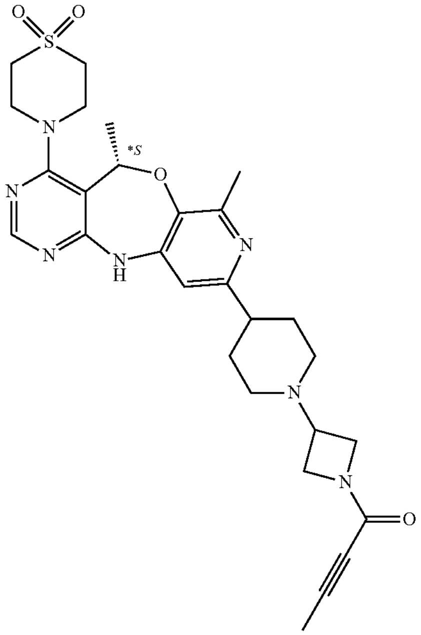 | 143 | 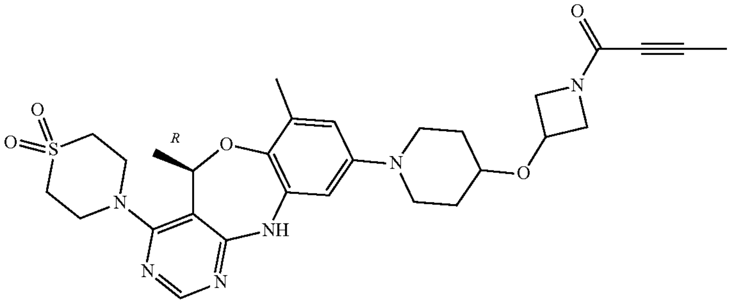 |

-continued
| Cpd # | Structure | Cpd # | Structure |
|---|---|---|---|
| 141 | 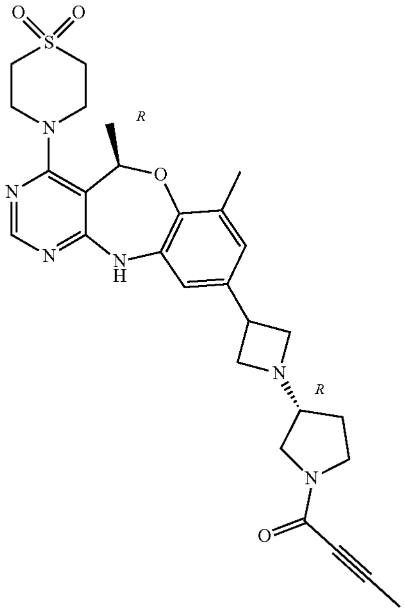 | 144 | 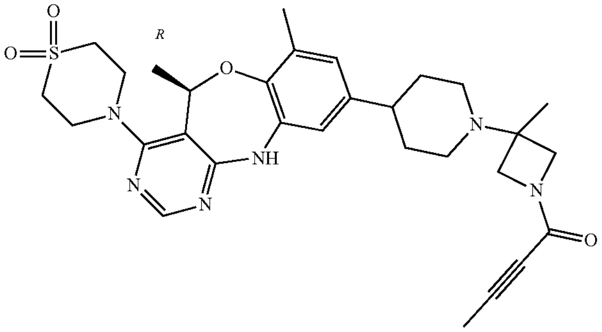 |

-continued
| Cpd # | Structure | Cpd # | Structure |
| --- | --- | --- | --- |
| 145 | 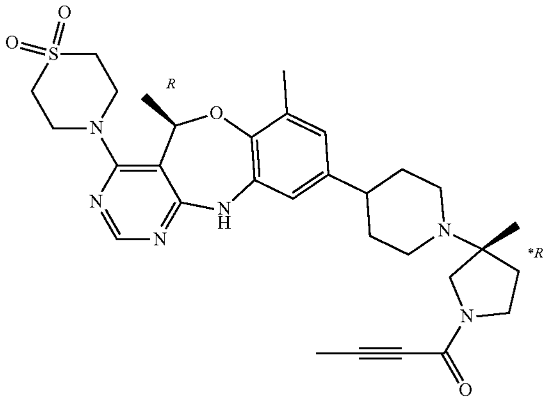 | 148 | 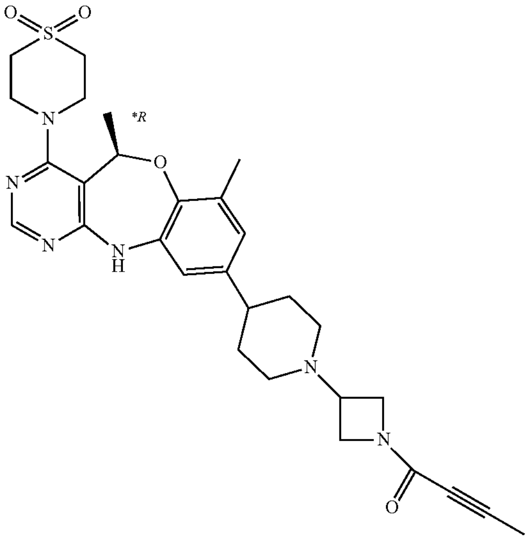 [SMILES: CC#CC(=O)N1CC(N2CCC(c3cc(C)c4c(c3)Nc3ncnc(N5CCS(=O)(=O)CC5)c3[C@@H](C)O4)CC2)C1] |

-continued
| Cpd # | Structure | Cpd # | Structure |
|---|---|---|---|
| 146 | 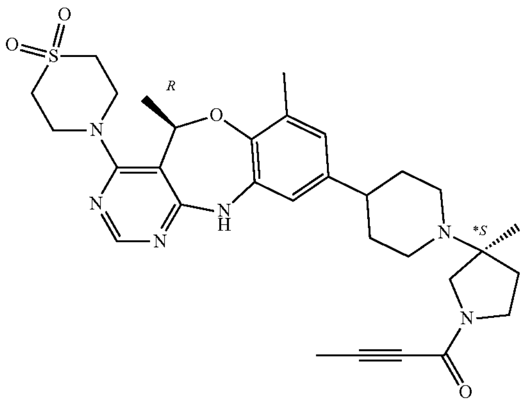 | 150 | 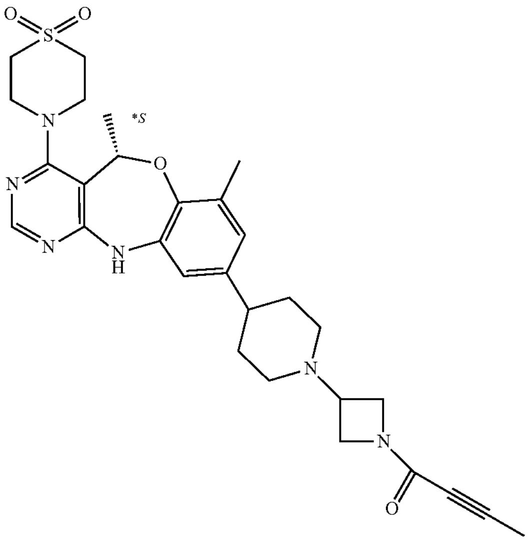 [SMILES: CC#CC(=O)N1CC(N2CCC(c3cc(C)c4c(c3)Nc3ncnc(N5CCS(=O)(=O)CC5)c3[C@H](C)O4)CC2)C1] |
| 147 | 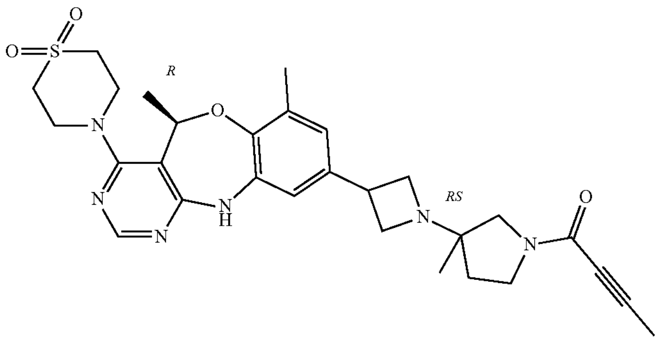 | 151 | 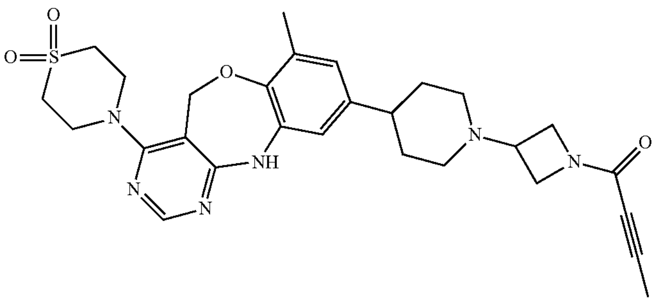 [SMILES: CC#CC(=O)N1CC(N2CCC(c3cc(C)c4c(c3)Nc3ncnc(N5CCS(=O)(=O)CC5)c3CO4)CC2)C1] |

-continued
| Cpd # | Structure | Cpd # | Structure |
| --- | --- | --- | --- |
| 152 | 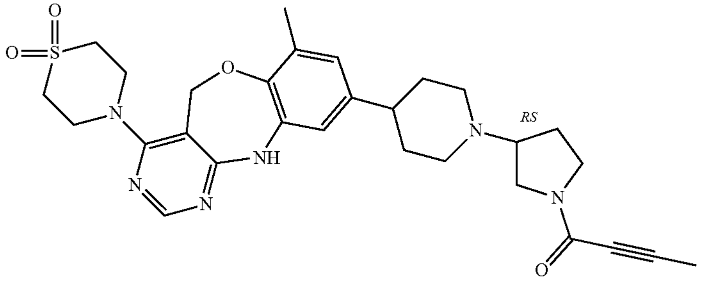 [SMILES: CC#CC(=O)N1CCC(N2CCC(c3cc(C)c4c(c3)Nc3ncnc(N5CCS(=O)(=O)CC5)c3CO4)CC2)C1] | 155 | 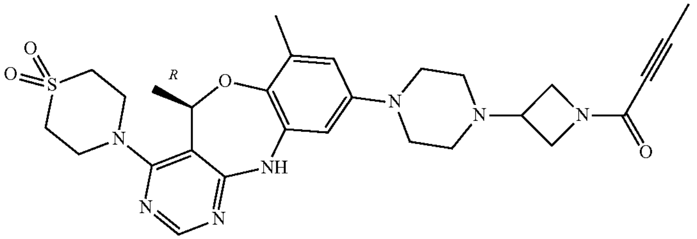 |
| 154 | 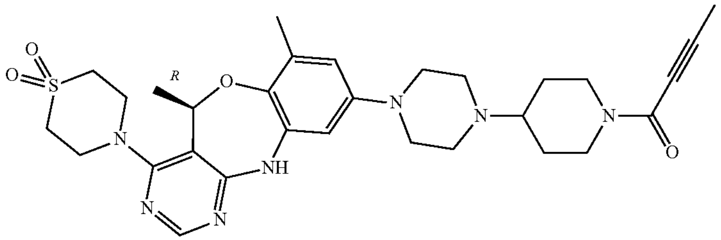 | 156 | 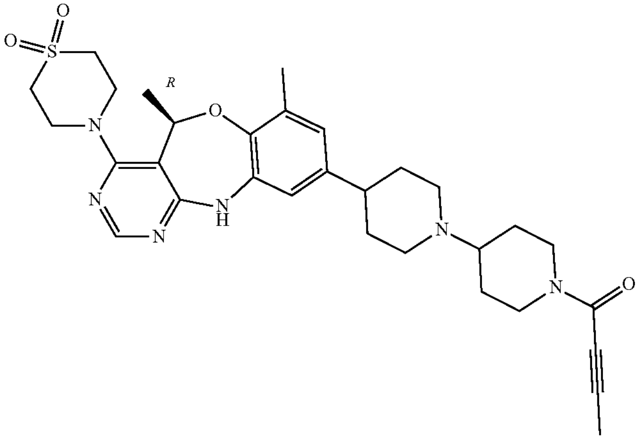 |

-continued
| Cpd # | Structure | Cpd # | Structure |
|---|---|---|---|
| 157 AKA | 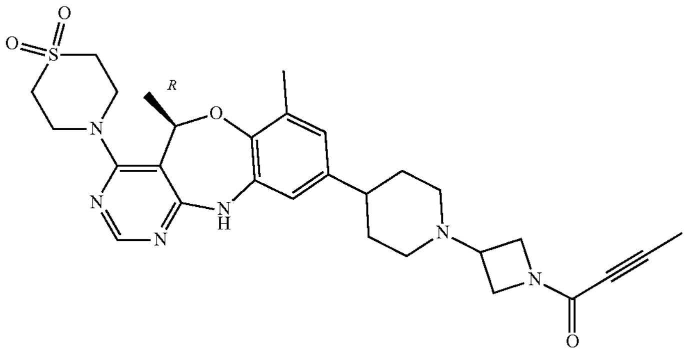 | 160 | 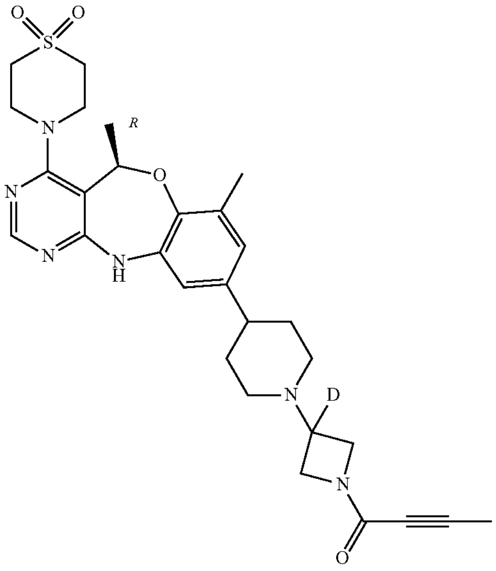 |
| 158 AAC chiral | 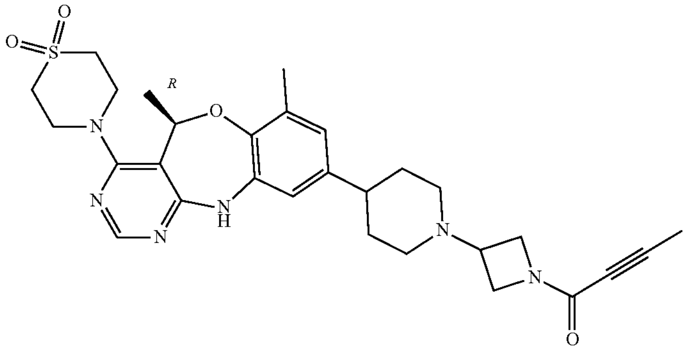 | 161 | 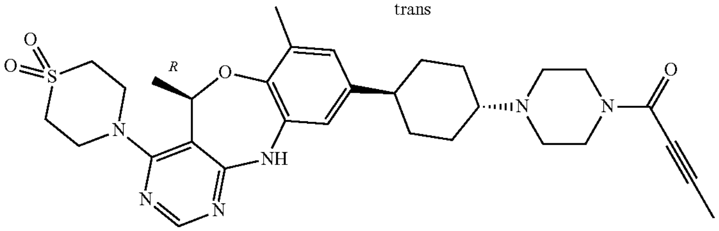 trans |

-continued
| Cpd # | Structure | Cpd # | Structure |
|---|---|---|---|
| 159 | 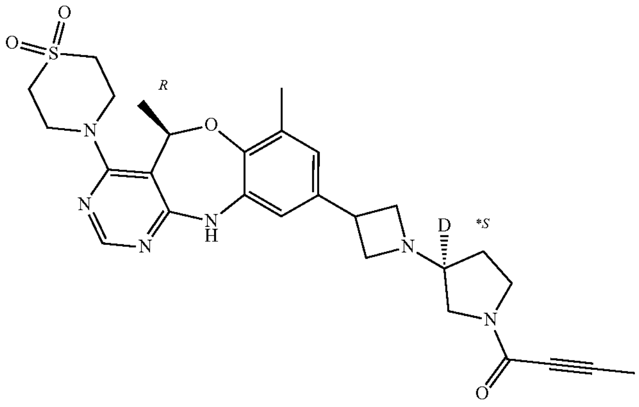 | 162 | cis 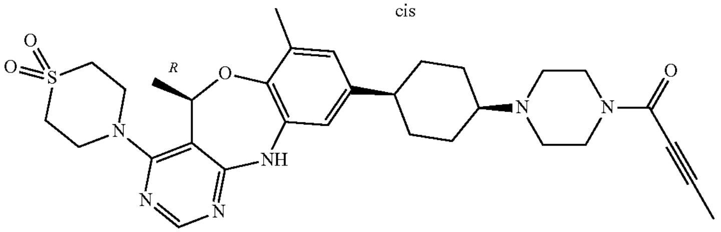 |

-continued
| Cpd # | Structure | Cpd # | Structure |
| --- | --- | --- | --- |
| 163 | 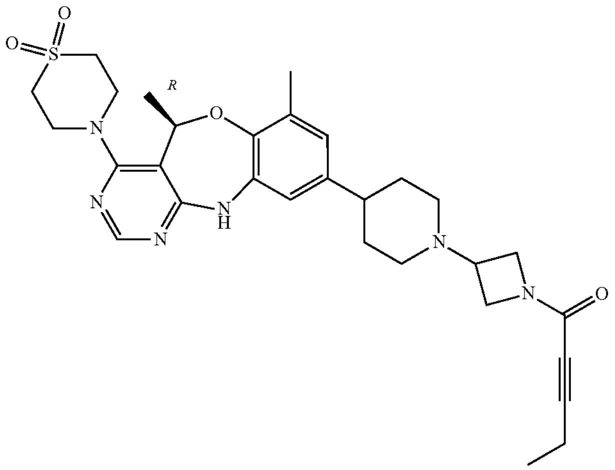 | 166 | 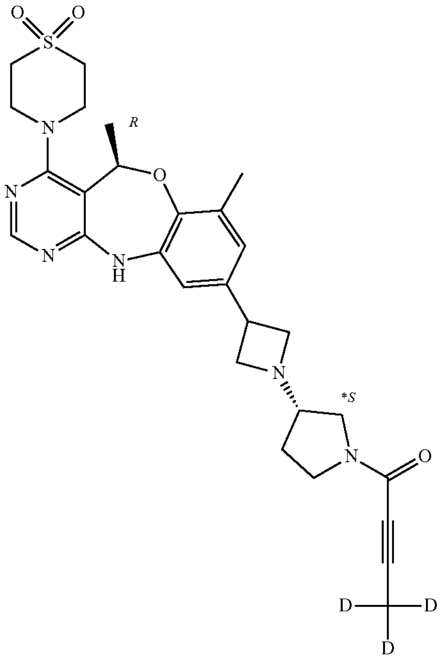 |

-continued
| Cpd # | Structure | Cpd # | Structure |
|---|---|---|---|
| 164 | 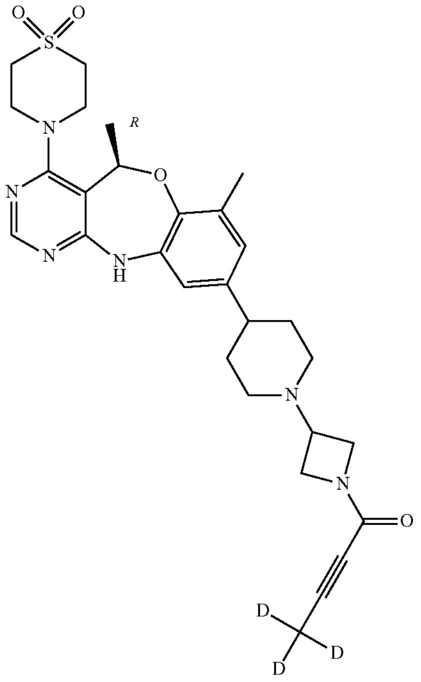 | 167 | 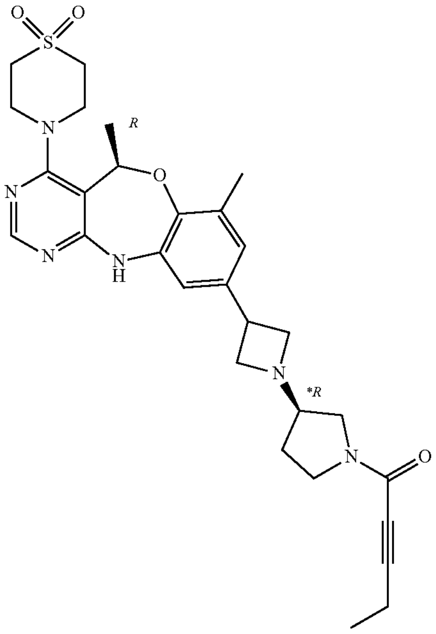 |

-continued
| Cpd # | Structure | Cpd # | Structure |
| --- | --- | --- | --- |
| 165 | 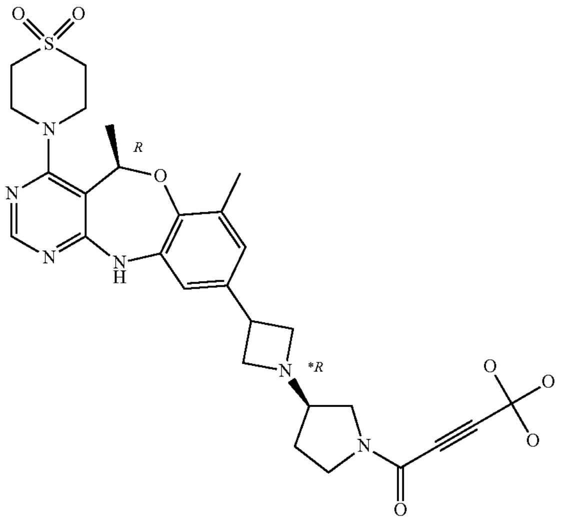 | 168 | 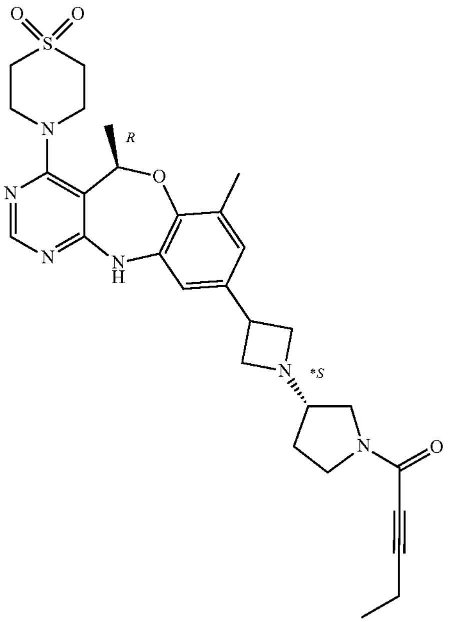 |

-continued
| Cpd # | Structure | Cpd # | Structure |
|---|---|---|---|
| 169 | 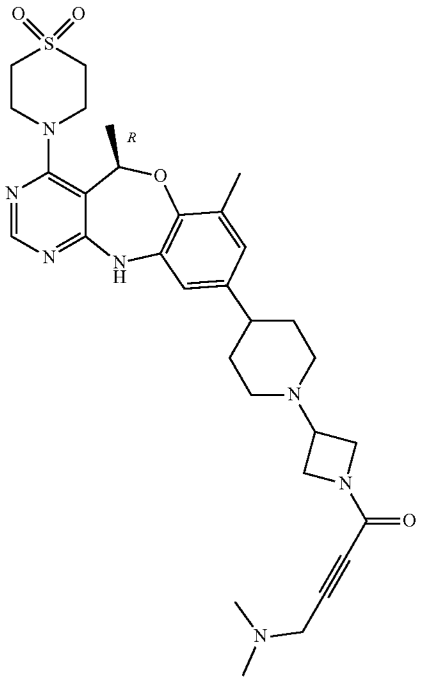 | 172 | 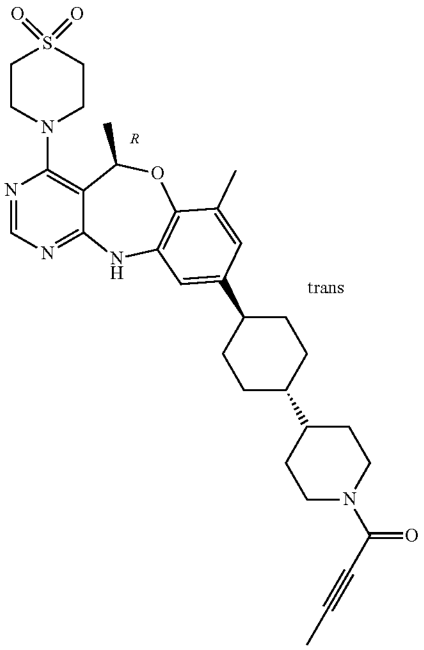 |

-continued
| Cpd # | Structure | Cpd # | Structure |
| --- | --- | --- | --- |
| 170 | 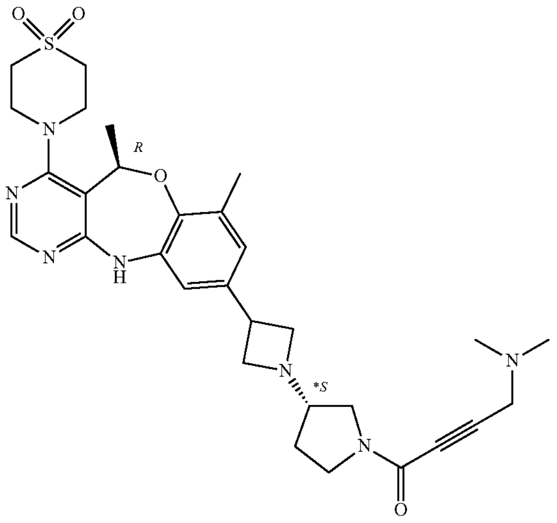 | 173 | 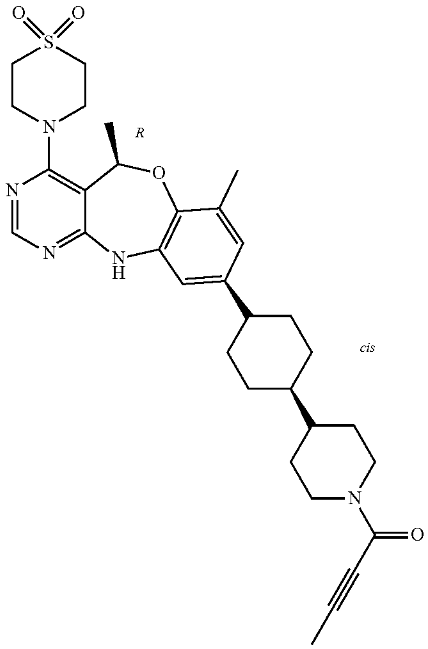 |

-continued
| Cpd # | Structure | Cpd # | Structure |
|---|---|---|---|
| 171 | 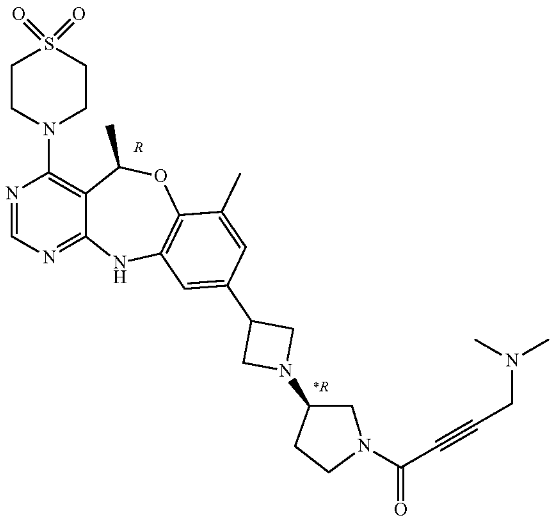 | 174 | 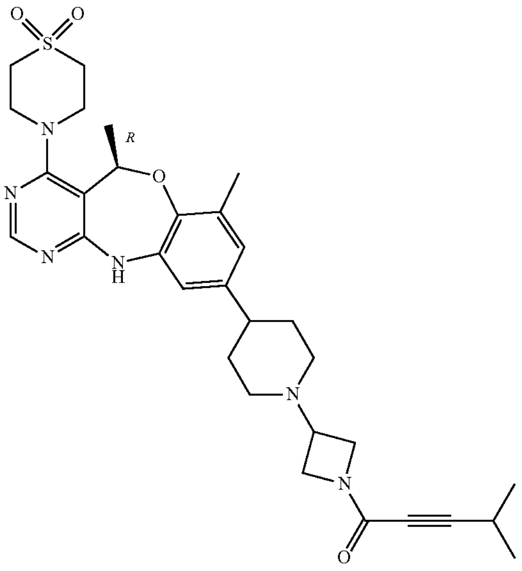 |

-continued
| Cpd # | Structure | Cpd # | Structure |
|---|---|---|---|
| 175 | 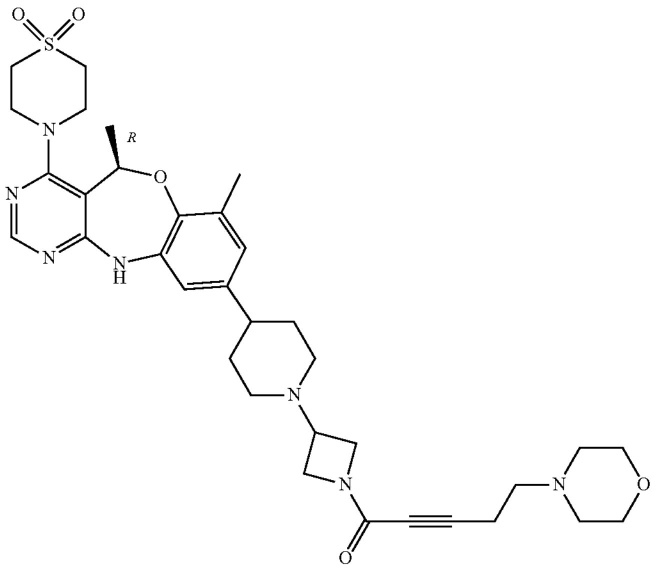 | 178 | 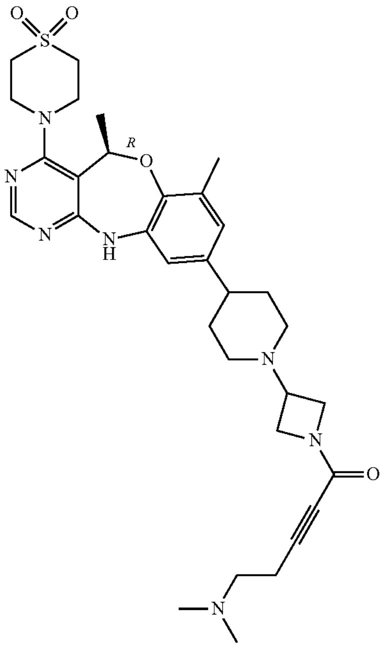 |

-continued
| Cpd # | Structure | Cpd # | Structure |
|---|---|---|---|
| 176 | 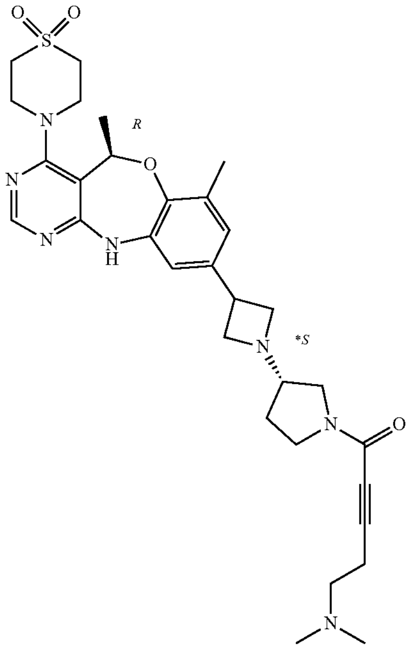 | 179 | 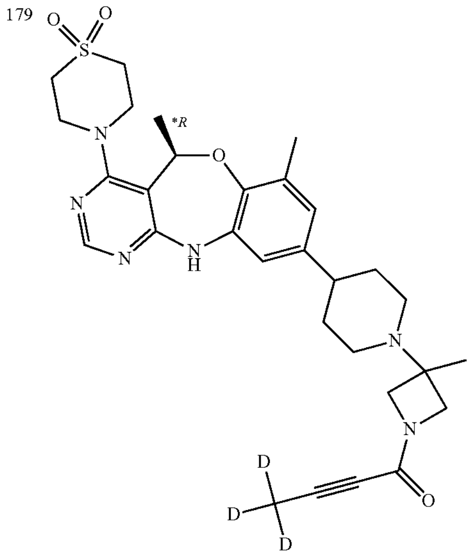 |

-continued
| Cpd # | Structure | Cpd # | Structure |
| --- | --- | --- | --- |
| 177 | 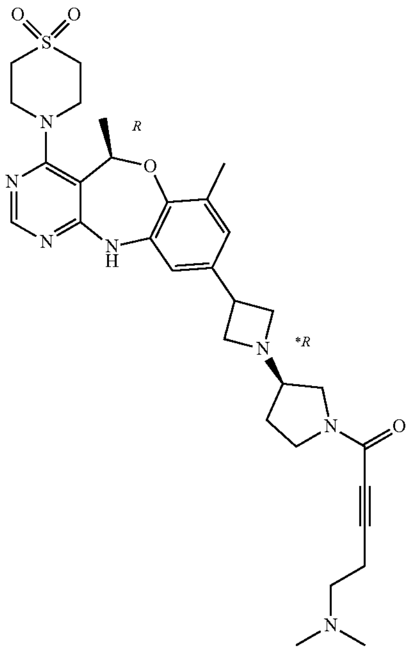 | 180 | 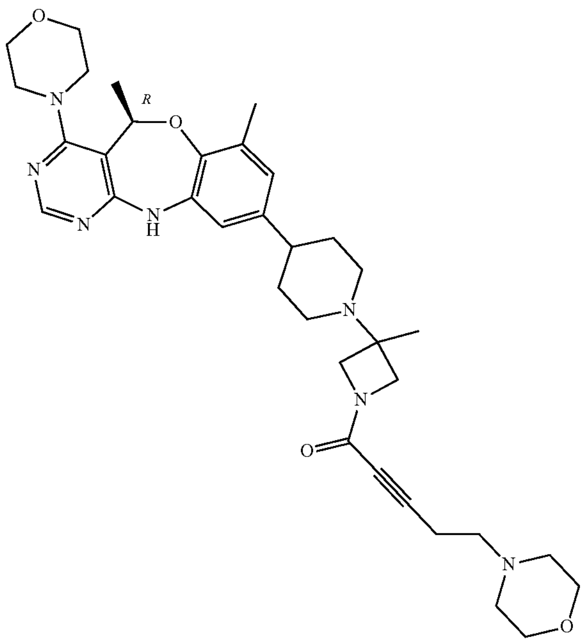 |

-continued
| Cpd # | Structure | Cpd # | Structure |
|---|---|---|---|
| 181 | 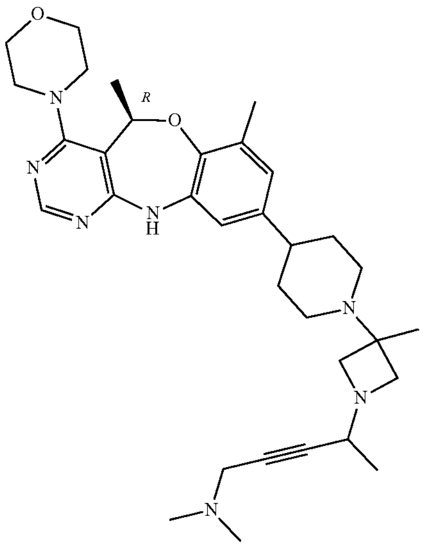 | 184 | 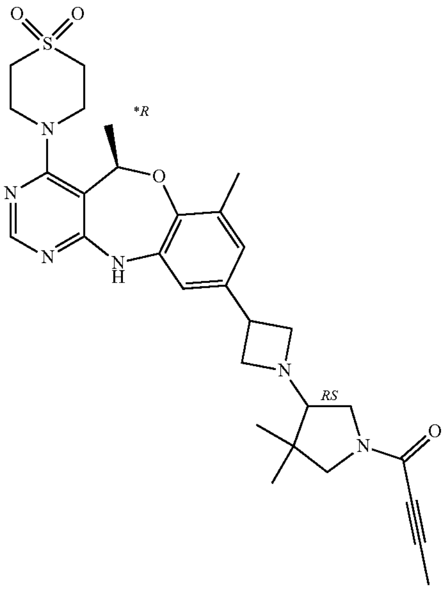 |

-continued
| Cpd # | Structure | Cpd # | Structure |
|---|---|---|---|
| 182 | 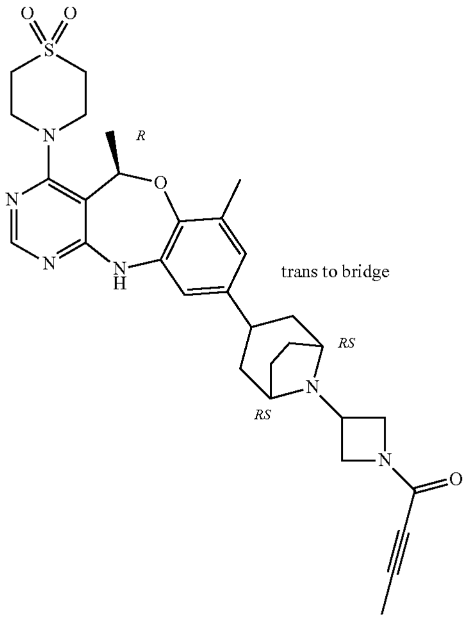 | 185 | 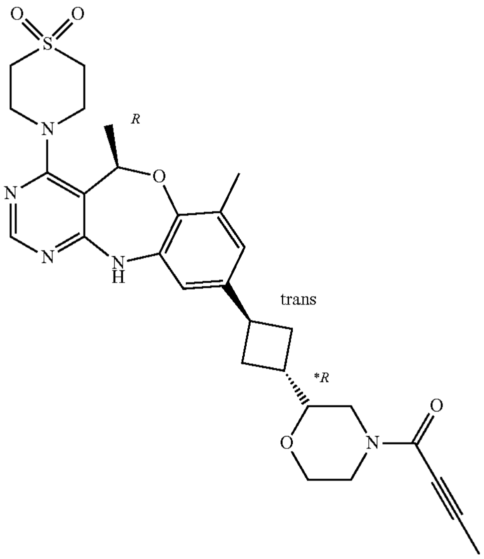 |

-continued
| Cpd # | Structure | Cpd # | Structure |
| --- | --- | --- | --- |
| 183 | 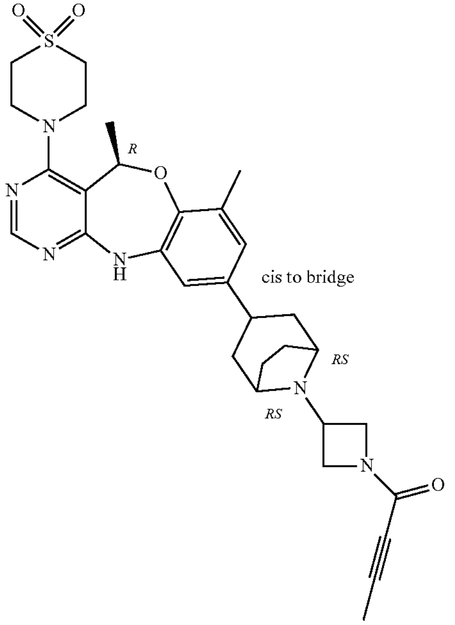 | 186 | 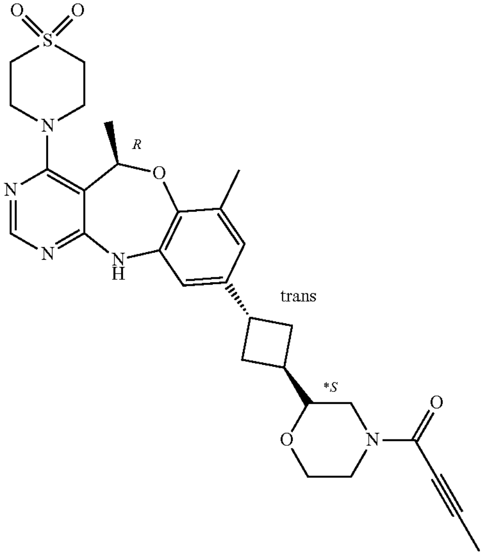 |

-continued
| Cpd # | Structure | Cpd # | Structure |
| --- | --- | --- | --- |
| 187 | 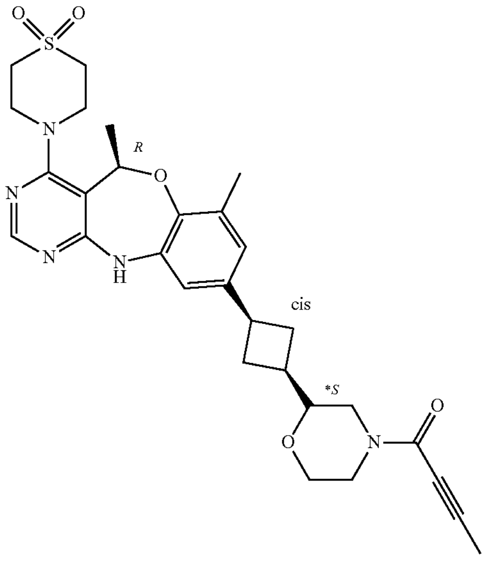 | 190 | 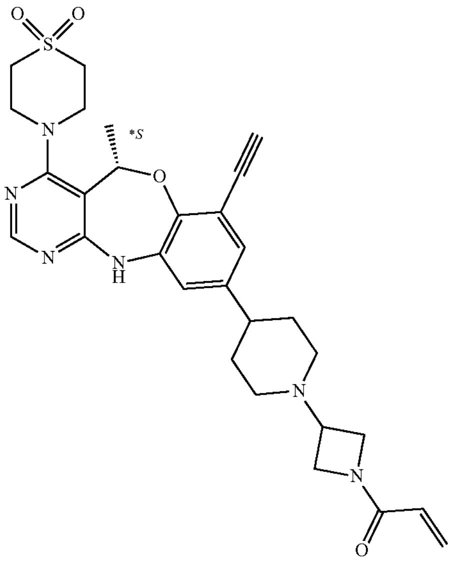 |

-continued
| Cpd # | Structure | Cpd # | Structure |
| --- | --- | --- | --- |
| 188 | 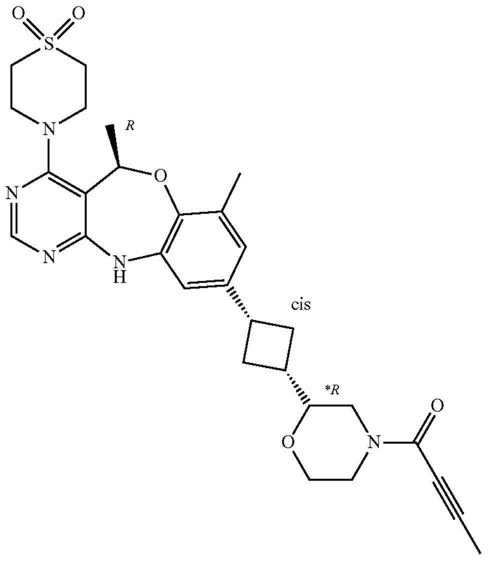 | 191 | 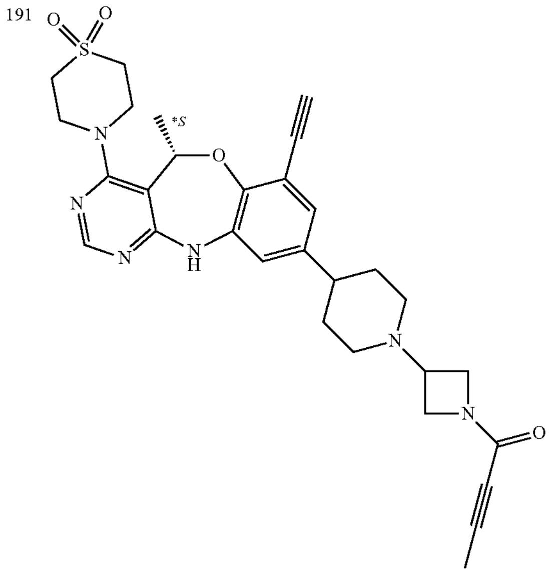 |

-continued
| Cpd # | Structure | Cpd # | Structure |
| --- | --- | --- | --- |
| 189 | 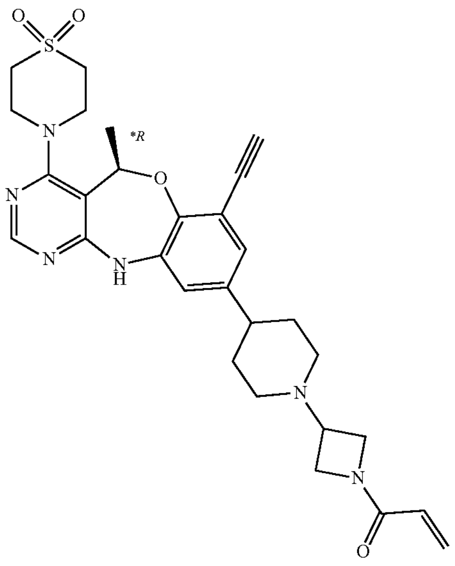 | 192 | 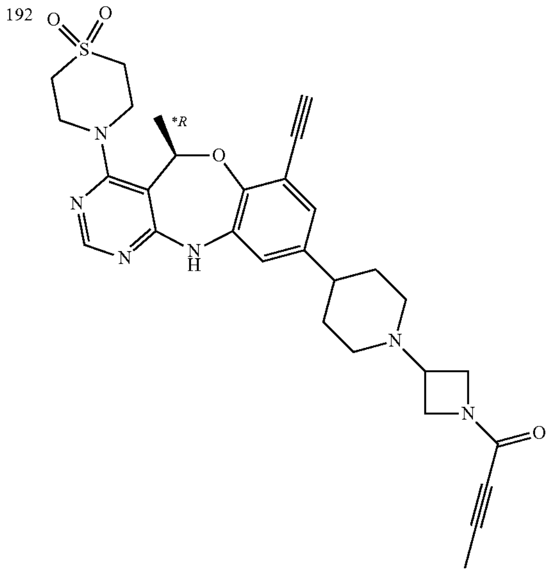 |

-continued
| Cpd # | Structure | Cpd # | Structure |
|---|---|---|---|
| 193 | 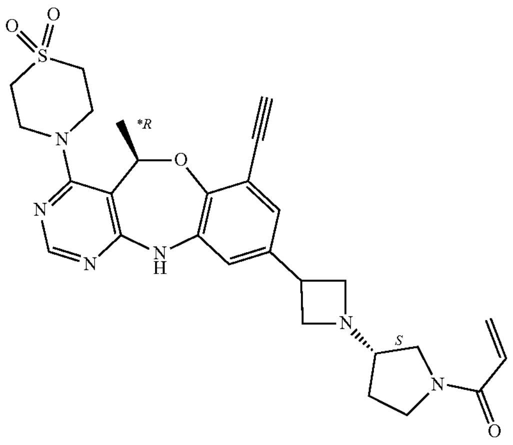 | 195 | 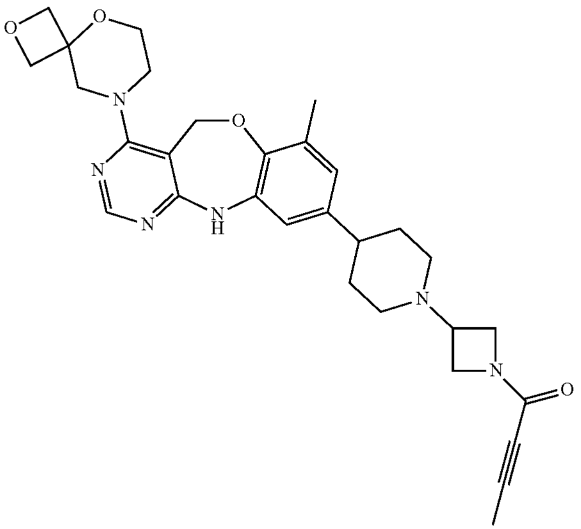 [SMILES: CC#CC(=O)N1CC(N2CCC(c3cc(C)c4c(c3)Nc3ncnc(N5CCOC6(COC6)C5)c3CO4)CC2)C1] |

-continued
| Cpd # | Structure | Cpd # | Structure |
|---|---|---|---|
| 194 | 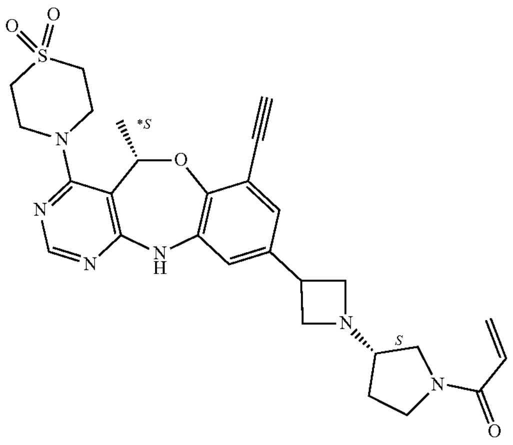 | 149 | 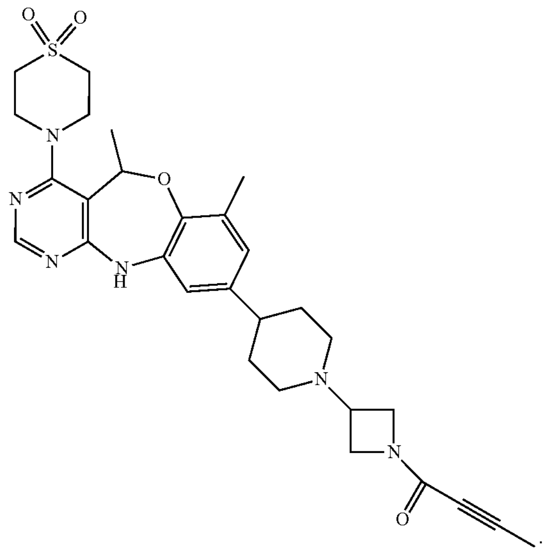 |

17. A pharmaceutical composition comprising a compound according to claim 1 and a pharmaceutically acceptable carrier.

18. A method for treatment of a disease state or condition mediated by a CDK7, which method comprises administering to a subject in need thereof an effective amount of a compound according to claim 1;

wherein the disease or condition is selected from a proliferative disease, cancer, leukemia, acute myeloid leukemia (AML), chronic myelogenous leukemia (CML), lymphoma, B cell lymphoma, chronic lymphocytic leukemia (CLL), acute lymphoblastic leukemia (ALL), T-cell acute lymphoblastic leukemia (T-ALL), Hodgkin's lymphoma, non-Hodgkin's lymphoma, melanoma, multiple myeloma, bone cancer, osteosarcoma, Ewing's sarcoma, breast cancer, triple-negative breast cancer (TNBC), brain cancer, neuroblastoma, lung cancer, small cell lung cancer (SCLC), large cell lung cancer, benign neoplasm, angiogenesis, an inflammatory disease, rheumatoid arthritis, an autoinflammatory disease, or an autoimmune disease.

19. The method of claim 18, wherein the subject is a mammal.

20. An in vitro method of modulating CDK7 activity comprising contacting the CDK7 protein, or a portion thereof, with a compound according to claim 1.

* * * * *